US012171203B2

(12) United States Patent
Hopkins et al.

(10) Patent No.: US 12,171,203 B2
(45) **Date of Patent: *Dec. 24, 2024**

(54) TRANSGENIC BIOSENSOR

(71) Applicant: KDT, Inc., Murray, UT (US)

(72) Inventors: Christopher E. Hopkins, Salt Lake City, UT (US); Miluka Gunaratna, Salt Lake City, UT (US)

(73) Assignee: NemaMetrix Inc., Eugene, OR (US)

( * ) Notice: Subject to any disclaimer, the term of this patent is extended or adjusted under 35 U.S.C. 154(b) by 203 days.

This patent is subject to a terminal disclaimer.

(21) Appl. No.: 15/934,981

(22) Filed: Mar. 24, 2018

(65) Prior Publication Data

US 2020/0064335 A1 Feb. 27, 2020

Related U.S. Application Data

(63) Continuation of application No. 14/564,144, filed on Dec. 9, 2014, now Pat. No. 9,933,412, which is a continuation of application No. 13/476,790, filed on May 21, 2012, now Pat. No. 8,937,213.

(60) Provisional application No. 61/488,720, filed on May 21, 2011.

(51) Int. Cl.
*A01K 67/00* (2006.01)
*A01K 67/033* (2006.01)
*C12N 15/85* (2006.01)
*G01N 33/50* (2006.01)

(52) U.S. Cl.
CPC ...... *A01K 67/0336* (2013.01); *C12N 15/8509* (2013.01); *G01N 33/5014* (2013.01); *G01N 33/5085* (2013.01); *A01K 2217/15* (2013.01); *A01K 2217/203* (2013.01); *A01K 2267/03* (2013.01); *A01K 2267/0393* (2013.01); *G01N 2520/00* (2013.01)

(58) Field of Classification Search
CPC .......... A01K 67/0336; A01K 2217/203; A01K 2267/0393
See application file for complete search history.

(56) References Cited

U.S. PATENT DOCUMENTS 5,877,398 A * 3/1999 Candido ............ A01K 67/0336 424/9.2
6,461,814 B1 10/2002 Spinella
6,852,541 B2 2/2005 Obayan et al.
6,953,668 B1 10/2005 Israeli et al.
7,288,374 B2 10/2007 Pincemail et al.
7,306,905 B2 12/2007 Ron et al.
7,853,406 B2 12/2010 Michelson et al.
7,915,402 B2 3/2011 Anderson et al.
7,964,177 B2 6/2011 Soga et al.
7,993,859 B2 8/2011 Rosiers et al.
2002/0192671 A1 12/2002 Castle et al.
2004/0171107 A1 9/2004 Nelson et al.
2005/0221280 A1 10/2005 Westwick et al.
2006/0040338 A1 2/2006 Westwick et al.
2006/0076921 A1 4/2006 Kubota et al.
2007/0172871 A1 7/2007 Dishaw et al.
2011/0021369 A1 1/2011 Mhlanga et al.
2011/0206615 A1 8/2011 Miyawaki et al.
2011/0262025 A1 10/2011 Jarrold et al.
2011/0262570 A1 10/2011 Finlay et al.
2012/0184460 A1 7/2012 Liang et al.

OTHER PUBLICATIONS

Naito et al. J Reprod Fert 113:137-143, 1998 (Year: 1998).*
Raina et al. Gene 96-100, 2015 (Year: 2015).*
Frokjaer-Jensen et al. Nature Genetics 2008 40(11):1375-1383. Printed document pp. 1-22 (Year: 2008).*
Shyu et al. Nature Protocols 3(4):588-596, 2008 (Year: 2008).*
Anbalagan et al., "Transgenic nematodes as biosensors for metal stress in soil pore water samples." Ecotoxicology (London, England) 21, No. 2 (Mar. 2012): 439-455.
Boyd et al., "Caenorhabditis elegans as a model in developmental toxicology." Methods in Molecular Biology (Clifton, N.J.) 889 (2012): 15-24.
Caito et al., "Genome-wide analyses of metal responsive genes in Caenorhabditis elegans." Frontiers in Genetics 3 (2012): 52.
Candido and Jones, "Transgenic Caenorhabditis elegans strains as biosensors." Trends in Biotechnology 12, No. 4 (Apr. 1996): 125-129.
Frokjaer-Jensen et al., "Single copy insertion of transgenes in C. elegans." Nature Genetics, 40(11): 1375-1383. 2008.
Hasegawa et al., "A Rapid and Inexpensive method to screen for common foods that reduce the action of acrylamide, a harmful substance in food." Toxicology Letters 175, No. 1-3 (Dec. 10, 2007): 82-88.
Hasegawa et al., "Acrylamide-responsive genes in the nematode Caenorhabditis elegans" Toxicological Sciences 101(2), 215-225 (2008). advance access publication Nov. 7, 2007.
Hasegawa et al., "Allyl isothiocyanate that induces GST and UGT expression confers oxidative stress resistance on C. elegans, as demonstrated by nematode biosensor." PLoS One 5, No. 2(2010): e9267.
Hasegawa et al., "Extremely low dose of acrylamide decreases lifespan in Caenorhabditis elegans." Toxicology Letters 152(2004) 183-189. Jun. 15, 2004.
Hasegawa et al., "Genetic and Cellular Characterization of Caenorhabditis elegans mutants abnormal in the regulation of many Phase II Enzymes" PLoS One 5(6): e11194, 2010.
Hong et al., "Differential hypoxia response of hsp-16 genes in the nematode" J Molecular Biology 344:369-381, 2004.
Hunt et al., "Toxicity ranking of heavy metals with screening method using adult Caenorhabditis elegans and propidium iodide replicates toxicity ranking in rat." Food and chemical Toxicology: An international Journal Published for the British Industrial Biological Research Association 50, No. 9 (Sep. 2012): 3280-3290.

(Continued)

*Primary Examiner* — Marcia S Noble
(74) *Attorney, Agent, or Firm* — Koren Anderson

(57) ABSTRACT

Systems and methods relate to transgenic organisms and their use as biosensors are described. In some embodiments, the systems and methods include a first population of transgenic organisms that includes a first constitutively expressed reporter gene, and a first transgene that includes a first inducible promoter from a response pathway gene, wherein the first inducible promoter is coupled to a first reporter gene. Other embodiments are described.

16 Claims, 7 Drawing Sheets

Specification includes a Sequence Listing.

(56) References Cited

OTHER PUBLICATIONS

Lagido et al., "Deveopment and application of bioluminescent caenorhabditis elegans as multicellular eukaryotic biosensors." FEBS Letters 493, No. 1 (Mar. 23, 2001): 36-39.
Lagido et al., "Rapid sublethal toxicity assessment using bioluminescent Caenorhabditis elegans, a novel whole-animal metabolic biosensor." Toxicological Sciences: An Official Journal of the Society of Toxicology 109, No. 1 (May 2009): 88-95.
Leung et al., "High-throughput screening and biosensing with fluorescent <em>C. Elegans</em> Strains." Journal of Visualized Experiments: JoVE No. 51 (2011).
Mclaggan et al., "Impact of sublethal levels of environmental pollutants found in sewage sludge on a novel Caenorhabditis elegans model biosensor." PLoS One 7, No. 10 (2012): e46503.
Naito et al., "Expression of exogenous DNA in the gonads of chimaeric chicken embryos produced by transfer of primordial germ cells transfected in vitro and subsequent fate of the introduced DNA." Journal of Reproduction and Fertility 113, 137-143. 1998.
Raina et al., "Testis mediated gene transfer: In vitro transfection in goat testis by electoporation." Gene 96-100, 2015.
Roberts et al., "Targeted transgene integration overcomes variability of position effects in zebrafish" Development 141:715-724, 2014.
Roh et al., "Assessment of Stress-related Gene expression in the heavy metal-exposed nematode Caenorhabditis elegans: a potential biomarker for metal-induced toxicity monitoring and environmental risk assessment." Environmental Toxicology and Chemistry/ SETAC 25, No. 11 (Nov. 2006): 2946-2956.
Semple et al., "Rapid selection of transgenic C. elegans using antibiotic resistance." Nature Methods 7(9) Sep. 2010: 725-729.
Shyu et al., "Visualization of protein interactions in living Caenorhabditis elegans using bimolecular fluorescence complementation analysis." Nature Protocols 3(4): 588-596, 2008.
Swain et al., "Linking toxicant physiological mode of action with induces gene expression changes in Caenorhabditis elegans." BMC Systems Biology 4 (2010): 32.
Tsyusko et al., "Toxicogenomic Responses of the Model Organism Caenorhabditis elegans to gold nanoparticles." Environmental Science & Technology 46, No. 7 (Apr. 3, 2012): 4115-4124.
Zeiser et al., "MosSCI and gateway compatible plasmid toolkit for constitutive and inducible expression of transgenes in the C. elegans Germline." PLoS One 6(5): e20082 (May 26, 2011).

* cited by examiner

SEQUENCE LISTING

```
<160> NUMBER OF SEQ ID NOS: 162

<210> SEQ ID NO 1
<211> LENGTH: 346
<212> TYPE: DNA
<213> ORGANISM: Caenorhabditis elegans

<400> SEQUENCE: 1

gattatagtt tgaagatttc taatttcaca attagagcaa atgttgttcg gtatttattt     60

tcaacggtat ttatactatt ttccaccttt ttctagaaca ttcgagctgc ttgttgcaaa    120

aggagggcga ctcacattcg gtacatggaa aagtagtgta cacaataaag agacccagat    180

acattttccg tctgcgtctc tttgcaccca ccgggagtat tttcaaacga atgcatctag    240

gaccttctag aacattctgt aaggctgcag aatgcgggta tataaggaaa gcgggctcag    300

aggaagccaa cacgctttgt tctagtgcat ctaaaaaact tcgaaa                   346


<210> SEQ ID NO 2
<211> LENGTH: 346
<212> TYPE: DNA
<213> ORGANISM: Caenorhabditis elegans

<400> SEQUENCE: 2

tttcgaagtt ttttagatgc actagaacaa agcgtgttgg cttcctctga gcccgctttc     60

cttatatacc cgcattctgc agccttacag aatgttctag aaggtcctag atgcattcgt    120

ttgaaaatac tcccggtggg tgcaaagaga cgcagacgga aaatgtatct gggtctcttt    180

attgtgtaca ctacttttcc atgtaccgaa tgtgagtcgc cctccttttg caacaagcag    240

ctcgaatgtt ctagaaaaag gtggaaaata gtataaatac cgttgaaaat aaataccgaa    300

caacatttgc tctaattgtg aaattagaaa tcttcaaact ataatc                   346


<210> SEQ ID NO 3
<211> LENGTH: 348
<212> TYPE: DNA
<213> ORGANISM: Caenorhabditis elegans
```

<400> SEQUENCE: 3

```
tcttgaagtt tagagaatga acagtaagca cttgaacaaa gtgtattggt ttcctctgaa     60
cacgattggc ttatataccc gtatcctgca gccgtttaga atgttctaga aggtcctaga    120
tgcattcatt tcaaaataca ccccataggt gcaaagagac gcagattgaa aaagtatctg    180
ggtttcttca gtacgcacac tatttctcaa tgttctgaat gtgagtcgcc ctccttttgc    240
aagaagcagc tcgaatgttc tagaaaaagg tggaaatgag tataaataca gtgacaaaac    300
cgaaccaaac aacattcact ctaattgtga aatcttcaaa ctacaatc                 348
```

<210> SEQ ID NO 4
<211> LENGTH: 348
<212> TYPE: DNA
<213> ORGANISM: Caenorhabditis elegans

<400> SEQUENCE: 4

```
tcttgaagtt tagagaatga acagtaagca cttgaacaaa gtgtattggt ttcctctgaa     60
cacgattggc ttatataccc gtatcctgca gccgtttaga atgttctaga aggtcctaga    120
tgcattcatt tcaaaataca ccccataggt gcaaagagac gcagattgaa aaagtatctg    180
ggtttcttca gtacgcacac tatttctcaa tgttctgaat gtgagtcgcc ctccttttgc    240
aagaagcagc tcgaatgttc tagaaaaagg tggaaatgag tataaataca gtgacaaaac    300
cgaaccaaac aacattcact ctaattgtga aatcttcaaa ctacaatc                 348
```

<210> SEQ ID NO 5
<211> LENGTH: 348
<212> TYPE: DNA
<213> ORGANISM: Caenorhabditis elegans

<400> SEQUENCE: 5

```
gattgtagtt tgaagatttc acaattagag tgaatgttgt ttggttcggt tttgtcactg     60
tatttatact catttccacc tttttctaga acattcgagc tgcttcttgc aaaaggaggg    120
cgactcacat tcagaacatt gagaaatagt gtgcgtactg aagaaaccca gatacttttt    180
caatctgcgt ctctttgcac ctatggggtg tattttgaaa tgaatgcatc taggaccttc    240
tagaacattc taaacggctg caggatacgg gtatataagc caatcgtgtt cagaggaaac    300
caatacactt tgttcaagtg cttactgttc attctctaaa cttcaaga                 348
```

<210> SEQ ID NO 6
<211> LENGTH: 348
<212> TYPE: DNA
<213> ORGANISM: Caenorhabditis elegans

<400> SEQUENCE: 6

```
gattgtagtt tgaagatttc acaattagag tgaatgttgt ttggttcggt tttgtcactg     60
tatttatact catttccacc tttttctaga acattcgagc tgcttcttgc aaaaggaggg    120
cgactcacat tcagaacatt gagaaatagt gtgcgtactg aagaaaccca gatacttttt    180
caatctgcgt ctctttgcac ctatggggtg tattttgaaa tgaatgcatc taggaccttc    240
tagaacattc taaacggctg caggatacgg gtatataagc caatcgtgtt cagaggaaac    300
caatacactt tgttcaagtg cttactgttc attctctaaa cttcaaga                 348
```

<210> SEQ ID NO 7
<211> LENGTH: 1716
<212> TYPE: DNA

<213> ORGANISM: Caenorhabditis elegans

<400> SEQUENCE: 7
acaattcaga aggagcaata attctgtgat atttaaacta atttctcttt gtttctttgt 60
tatgagtatt tatttttagt tcttgttcat catgcttttt ttgtcacttt tccctcccca 120
atcccatatt cctctgcttt tctctcattt tcggttacgt gtattaattg aatgtatacg 180
acgacgacag tcactagttt cgaaataact attttacgag gatgaataaa cacactgatc 240
gctgagcgac gctccgagca cttttcgaga agtttctaag aagccacttg accgagagag 300
agggagaaag aaaagcttgg catagaaatg tgcttgtgtt tatttgaact gttaaaagtg 360
tttgacgggg gcgaagtcac tggggaaacc tcgagatcaa taggacacgt ggcaatttga 420
atttttggat aattggaaaa gcagtacccg actaaagatc cgaatttgat tttcagacat 480
tttactgcaa acttgattac acacggtaat tttccaaaag ttttgtgcat tgaatcccga 540
aaaacttcac aaacgcataa tattacaacc cgatctatga gcaaagtaaa tagagagaat 600
caggctgaaa gcttattgtg attaatgaac attaggaaca atgctgattt caatttgaaa 660
catttttttt tcagatcgaa aatcagtttt ttcagatcga aaatcacatt ggatcttgac 720
attttcaaga gaattattaa aatttaaatg gctatttgaa aagtattgat tttctgaaag 780
ataataacta cttaccatct atgtcgtacc tgactatgcc aattattttc aacaattgtt 840
tattttaaaa aatttttgaa gtaagcttaa aacaaaccca ggacctctga aatgtaccaa 900
gtttggaaac taattccaag tactggtaat aacaaaaatt ttgaattcga ggcggataag 960
cgccagttgg gagttttctg attataatta tattaataga attgccaaaa atcatgataa 1020
acccctccaa tcattttttg attttcgaaa aagtttcaat gtaggttttg gtgagctgcg 1080
aagttttcca aaaatgtcta aaaactaaat tcatatggtt caatttttgt caaaaacgtt 1140
cagctcatga ggagcttgaa actaaccaat aaattttggt cattaaattg gtcagttaaa 1200
ttgataattg aaattaaccg gatatgtttg gaaaaataaa tgcaaaagtt catgatcatc 1260
agatcaaaaa ccaaaaactt cccctacatt tctatttcca aattgaagat ttcttgaagc 1320
ctacaaatag tacagtttac aaatatctct ccttctttct ctcgtccctt cttgcgcatc 1380
ctcagagctc ggagctccta tccgtcaata taaacaatca ttgtttcttt tcttctcctc 1440
gtaccttttt tcttcttcaa atccattttt cctccgcccc cttatcctac agtccaattc 1500
ctttcactct ccactttctg agcttcttct ccaactcgca aaagcttcaa agctcacaga 1560
gcattttacg atagtgcatt gtaatgttct ccaccctaga gtgcatctcc aacctgcgca 1620
tatgttttcg ctctttgaca ttacattttc ttccgattca cattttattc atccacccga 1680
taaatatatt ttcacacttt taattttcta gagaaa 1716

<210> SEQ ID NO 8
<211> LENGTH: 1859
<212> TYPE: DNA
<213> ORGANISM: Caenorhabditis elegans

<400> SEQUENCE: 8
tattctacgt caataggaat tgtcagaatt atcagttttg atatcaaaaa ttgccagctt 60
tagtacagta gaataactat gcgattcatg ctgcttatta tttattcaaa atttaaattt 120
taaccaactg tgagtttatt ttatagaaca tttttcgaaa taaaattcaa aaaaataaaa 180
attgttattt ttcaaaatct taatcttaat ttagcaccat taccgacagg caatgataga 240
acaccaaacc ggactgacca agtgtcgtac cagtttcgag caatcaagta ttgagagact 300

-continued

```
gatattcttg ctgatactat actcttaaga tatgaaacga tatctacccc tctagccccc    360
tactcgtgcg ccctcagtta cctacctacc ccgttaccta ccctacccta cctacctact    420
cagtctccta cctaccccga ccgtatcata tctttagaat atagtatcaa caagaatacc    480
aatcacccaa ccccaatcac tcgaaaccgt taggcaccag gttagccagt ctggattaat    540
cgagagtaaa ccacttgact ccagacaact acatcttata cttacttacg tctgggggac    600
aatcttggga ttctcaagat gacttccatt acgaagtctc ttgcaataac caattaccac    660
aattttggag cagaattaaa ctcacccacc agtacaggat caaagatgaa taatgaatga    720
gaggccctcc tctcattgtt gtgggcgggg tcaaggggtc aaagtttttt gaatttcgaa    780
attttgaaat tttggaattg ttaaattttt ggaaatctaa tttttgaaag aaccacattt    840
tccgtttaca atttgagttc aattccgcaa ccccgtcaaa tttaagaaga gaaagaaaaa    900
aaacacaacg tgtttgcacc tgtaaggtag tttttttttg ttgccttcgg cgttttgatt    960
cacatgaaag tttctacgga aaaactttca ttgcataacg atcttcatat cttgtttctg   1020
gaaacgaaaa tttccaacat gaaagaaacc cgacgctatt tattctcgca acacaaaaat   1080
ttcacattta aataaccgcg gtttttctcg aacagcatat ttgacgcgca ttgctcgtca   1140
agtttgatgc gtgcacacta ttttgctgtt gtttttttct tttttctcta aatttttcttt   1200
acgctttcgt agtttctata gaaacgattc tccactcccg gttttcttcc gattctcaaa   1260
attaattaaa atttagttat taaaaatcct ttttcttgaa ataatcgttc aatttcgagt   1320
tttcaagagt ggagacgttg aatttgtgag ccgcttattt tttctgtgtt tttgttttgt   1380
ggtttttaat cagtgtcata atcatacttt ccattgtttc tttattattc aaagttgtag   1440
attcagtatt ttagatcggt gatgtttatg aatcttctca ctcaggtctc caacgcgatt   1500
tttccgcagg tcagtgctta tccgaaacat tcgtcattcg caacttgggc ctatttgatc   1560
tatggcgttg tgttgttgcc tttaccttaa ttatcatcat tttcatcaga aacccacaaa   1620
aactagagac atagctacaa aattctgcga ccgagaggcg ggtacacaca caatgttgtc   1680
tatttcatct cgctccacct tctctctctc tctctcgtgt ttaccatttc ttttttaatt   1740
ttgcatctat cgactgtgat ctgcctgttt ttttctaatt ctaaactttt tgccgtgata   1800
ttccttagag tgttccctag aaaattcgtt gaatttacag gtcgaagccg ctcaaaaag    1859
```

```
<210> SEQ ID NO 9
<211> LENGTH: 1703
<212> TYPE: DNA
<213> ORGANISM: Caenorhabditis elegans

<400> SEQUENCE: 9

aaaaacttga tccgatcgaa gaaaaaaccg aaaaaaaatt cgaattgttg tgttgttcgt     60
cagttggatg gaatgatgat gaaggaagtt gattaatgga tatgactgat gattagtggt    120
ggaatatgga ataattattt atttgattta ttctgattat tctgaattag aatgtatttt    180
catatttcag gaaaaatgat tttatttcga aacgaacttg ttctagatta aaaaaattga    240
aatttaatat ttagtgctat acaattacag taccccatgg aaatacacaa atatcataaa    300
tacaagaatt atcttcctgg aagttaaact tatattttcg atgtaagtga aaaagtttaa    360
aagagaaatg atgtttgttg atcttcctgt aagtggaaac tggagaattc ataagcttaa    420
aaattccaaa atattaaaac ttgcgtgttt tttctgaaaa tcgattaaaa cagcaatatt    480
cagcatgttt ccagagccaa aaaaacctgc aagcatggga tacttttgca gttaaaaaat    540
```

-continued gtttcaggaa cttgaatgaa gttaggatgc atttgaacag agtaatgaaa ttatatgaaa 600
ttcatatgta gactctccta ctcagttgtt tgtatgtgag ttttgtatat tataacttat 660
tttgaaatta tctttaatta cttgtaatgt tttttgtatg agttaaataa taatcttttg 720
aaaattcttt ttcaaataac cattttctgt ttaaaaaaac agtgagccca atataaactt 780
gttttccatc aaaccgagct tctaccaaag ttaacttaaa ttccataatt ttcacaaacc 840
attcatagtt tgtctacgta gccttatcct tttttgaaca ttgaaaaagt gaggagaaag 900
tgcgaaaaac gagttttttt ctttctcttc ttcttggtcg tcacgtcaag acactctgaa 960
cgttggaatg ggaaaagcat cgaagatcga aaaattctga ttttttctaa agtacacaac 1020
ttatattgat attgcattgg gatttaaaaa agctctactc gaacattttg attaatttta 1080
atatctcatt tattcatctt tcgataacag atatatcaca ttgttcggta ggataaaagg 1140
gctaaaatca agttttgagg aatgttcatt tgtttggaag gtgatattat agtctgcgat 1200
aactacataa gtttggaaac cgaacacatg ttttttggc actttgctaa aaagttgtct 1260
gaaaacgttg gaaatcaata tttggtcatt tatttaggtc attttcggac cattataagt 1320
gttttctaat acaaaactgg cgctgctccg ctatttaaaa gactgaaagt gacataaatg 1380
atctaatttc cagatctctt ataacttttt ttatagcggt tccactccta atttgatgtg 1440
tttacttgtt gcatcagatc atttttcact tcttgtaatt cttatcagtt ttctatattt 1500
tctttcttat caatttttca gcttttcaac attttccagt tagttattca atttttattc 1560
cgcacgatca ctgctgtttg aattcaaata ttggagtatt aaaattatac atttataacc 1620
attctaatgt ctaccttcta cacaaattac ccttcctagt agaaaatata tttttggctt 1680
gaaatttgtt ctgtactgtc caa 1703

<210> SEQ ID NO 10
<211> LENGTH: 1851
<212> TYPE: DNA
<213> ORGANISM: Caenorhabditis elegans

<400> SEQUENCE: 10
tttctaagtt cgcacattcc tcgatttcca cttgccgtta cctttcatta tctcctttta 60
ctttaatcta tcacagtttc atagatatca aacgttaatt ttttgttgcg agctagtttg 120
ttttttttcc tcttgttcgg tccattcgct ttaacttgtc acctattttt tgtttctct 180 acagtcctct tggttcatga tcctgttaat tatcaatgct cttttctgtg atattcgata 240
ttcgaatcaa caatgtgtat gattagtgtc aaagtaactt atcggatttt gaatataatt 300
caattattcg tgtaataaat aactattttt tagtttactc atgtttgcca caaactagaa 360
ggtttattta ttcataacta cttgcaattt cacatttgaa ttctaactgt atgattgctt 420
caactctctg cgattttttg cgctaaaata cggtacccgg tctcggcgcg acaaaaaatt 480
tctagatttt tagaaaattt tacagattta ttgcaacagc tgttaccttt ttcacaaaaa 540
aatcgactga atttcgcgaa gttatgatat ctcaagcggc cgcttgcggg aaaagccata 600 tttttttca aattttcgta gctgcacaat ttttcataat tttttcattt gttaaaaata 660
aatgtatttt aaataattgt cctatttcag tttttcaata aattttttta acgaaaaact 720
ataaaaatag atgaattcta gagccacgta atttcagaat tacagtactc tttcaaggcg 780
catacccttt taacataaat tttcgcgtcg agaccgggta ccgtactttg acgcaaattt 840
tgcatctggg taattcttgt ttttgggttc ttcactttcc accacttttt tttcgaaagc 900
atcaaatttc acatattcac gtcacaatcc tagcaaagcc caatagctca ttcaagtcat 960
atttgtctct ttctttctca ttctcctgat tagcaacact gtcttatcaa ccactaggtt 1020
ccgtcttaat cgtccaaata ttgatccgct cgctcgtgtt ttctcaactt ctttatttgc 1080
tgtgtttttc tgtttctata gttctccatt ttccatctcc tcttcgcttg ttgaatggac 1140
tttattttga taagttcatt ttaatttttc taacaatctc atcactagct catgatgaca 1200
attgcaaaga aattcgtcat atagagggga aaaatgctga caaatattga aaagccttca 1260
ggagagatgt agagacgtag gagtagagac agaacataaa tttgagaagc ttgtagggag 1320
aatagacata gagttaccat gggaaaaacg ctcgcatttt ccatttaacg agattttcta 1380
gatcacaaca ttttgtgatc cgttgtgcga aaatcaagct ttttatcaaa cttttatcgt 1440
ctgttcattc tttctgacaa tctttattat cttattaaac ttgactaatt gtattgaaag 1500 tatttttta gatgcgaacg aagttccatt tttcatgact taacatctct taacgttagt 1560 gaaattttg aattccaatt aggactacgg taggagttct gtagttgatt tcctgaacac 1620
ttgttttgta acctttctga acggatttta atatttctaa aattttaaat tgcaaatctg 1680
agtcctatta aaagatgttt catccgtaaa accaacaaac aaaatatcac tttatcatca 1740
tgagatttaa tgtttccttt tgattttctg aattgttgta ctttccttca aacgacttat 1800
tgaactgatg taactttcct tctaatgtta tcatttgtat tttttgcag a 1851

<210> SEQ ID NO 11
<211> LENGTH: 1614
<212> TYPE: DNA
<213> ORGANISM: Caenorhabditis elegans

<400> SEQUENCE: 11
aaaccaaatt tactactttt actatatttt tagttgaaaa taaaaagaga aaaacattta 60
ttttctaaaa acagtaattt tcctttagtc agtttatttc tcattgagat attgtgaact 120
cctgttttaa aatcaaatga gaaaaattga acacaaattt taaatttaca taaatcccca 180
aaaactatca atatttccaa cctagacaca ctataattga ataagattct cgtgaccttc 240
ggacatacag tttgtcaaag acaagcactc ccacatttgc cggttaattg tgataaccct 300
atcaacttgg ctccgtcttc actctcactt gcaattgcac aacttctttc tttttggatg 360
taagtagcaa cattttatca tcactctatt gggaaatttt taaaacaaaa tttcttcaat 420
acgattgccg gtctcgccac gataaattgt aggtacatgc gaaaaaaataa tgcccattta 480 aagagtactg taatttccat ctctctttgt tgcaggattt tttgtcgatt tttttagttg 540
ttcaatacaa ataaattcat tcgaaaactg tcatgtcacg ataaacaaac aaattttggt 600
atttaacaaa aatttgtcgt gtcgagacct aagctagaat agtactataa tttttgagct 660
ttaatttttt caagtttttt acaaaatttt tttttctgtt gattaattga tgtattttta 720
tcggagatct ataaaaaaat caatgaaatt ttcgaagaag ccaaaaaaagt actgttgata 780 ctacagtaat cttcaaaggc gcacaccttt cggcatttaa caaaaatttg tcgtgttaag 840
accgggtaat ttgttaggca aatatttgaa aaaaaactgc ttaaatattt catgaaaatt 900
ctgttatctt taatcagatt tttaaaaaat tattatcaaa tttcaaaaaa ttacctaaaa 960
taatgtctga aattcttctt tactcacgcg aactgcaact tccagacatt aattgaggaa 1020
atttcaaatt aatcaataac aatgaatacg attttcagat taaacgagta ttttcctaca 1080
tttttattaa tttttttgat taatattaat ttttaaaatg aaatttttgg ataatcctac 1140
taaaataagc atgtcccgca aggccctatt tcaaaagttt agtgcctgaa aaatcaatat 1200

-continued

```
ttcgcaagaa cagtctacca atttttccaa tttatacttc cggcaattgc caccaattcg   1260

gtgatctaga aaatacccat ataggctcta cagtaccttc ccttatcacc cacatccaat   1320

tttgctatca gttagtcttc aatcacactt agtctttgaa caaatgaact cataactctc   1380

acaagatgtt tgcaactatc atattgatgt cattcagttc tcatatgaga aggcgggcac   1440

attgttgtat attgataaac cacccccatt ttcctcttct tccagcaaaa aaaaataaaa   1500

ttaatattgt ctcagacgct tgtgaaactg gtgctctcaa ttgaaaagca ccattgactt   1560

cgcagaaact ggcagttcat ttggctttcg gatacttaca accatacgct caca         1614


<210> SEQ ID NO 12
<211> LENGTH: 388
<212> TYPE: DNA
<213> ORGANISM: Caenorhabditis elegans

<400> SEQUENCE: 12

tctgtatata tgcaaaagga aaattaaata ttatctatcg atggaaatgt tagaaaagcg     60

aattacttgg cacggcagca ggtgccacaa agcctgcagc tgaataaagt taagatacga    120

ttgcttgctg acaaatagga cactaaattg gaaaatacac accacatttt gatttttaat    180

cagatctttt ttaattttaa ttttagtcac atctagacta ctctgactac tattctcaca    240

cgtgtggcca acaatcattc ggactacgct gtaggcagtc aggagttttc aaatgataag    300

gtgttcaaca gtgtagtctt atttgtatca ttttcacata aaacgcaatt tcaaaaactc    360

ccaattttct tcagactgcg gtaaaata                                       388


<210> SEQ ID NO 13
<211> LENGTH: 681
<212> TYPE: DNA
<213> ORGANISM: Caenorhabditis elegans

<400> SEQUENCE: 13

ccagttaccg agatctaatt tttttctatt ttctttttct acttttcatg aaatacgcat     60

ttttgaaaac gaataataaa gtatgatatg ctgtcaaaaa atttcctgca ttcttgcaaa    120

accggacgtc gaacaccaat ttgccacttt gatctacgta gatctacaaa aaatgcggga    180

gaagatcttc tcgagacgca gaattctcaa ctgatttcaa atcgttaaga acgtgctgac    240

gtcacatatt tttgggcaaa aaattcccgc attttttgta gatcaaaccc tattgggaca    300

tcctggcatc acgtgatttg cctaaaacca aaaataatgc gcattcagag aacatgccta    360

ttgtgcctac ctatttatta actttgacag tagataggca ggcggctgct tagagcctat    420

aagctagcct acctaggcaa cccacatagc ctacctttca acttttcaaa agatcattgg    480

atcactaaca caatgtgact agttgtggtt tgttacaaat tgcctcattg tcaccctaaa    540

ctccctatta tttcccgtaa atgatgacga ttttgatctt ttgtagggtt atcttgaagt    600

gaaagatcac taagtaccca gactgcactc tagtcttttt ccccttttaaa tagtctcgag   660

aatgagtttg agaaactaaa a                                              681


<210> SEQ ID NO 14
<211> LENGTH: 1390
<212> TYPE: DNA
<213> ORGANISM: Caenorhabditis elegans

<400> SEQUENCE: 14

tataattttt tttcttaatt ttcatatgtt tacattaaaa atttgagaaa ataaagtagt     60

tcaagacaaa atcaaatatg gtagagactg tggtttaagt ttgggtttac tagggaatgg    120
```

tcagcttagg ggtgaggtac ctagagacgc cacatatgcc aaacggaagc tgagatcatt 180
ggctacaaga atatgctttc aaattctgca acggacctct gggagtctgg aaattcttgt 240
ctgaaattat gcttttgaat gctcgaaagt ggtaagaatt tagaatttat tacagaaaaa 300
cgtttaatta ataaaattag ttttatactt gaaacaagta ttgtatgcac tgtatcaaaa 360
cacattttca tctttctagg tattcaactt cacgtttttc tgtaataaat tctaaattct 420
taccactttc gagcattcaa aagcataatt tcagacaaga atttccagac tcccagaggt 480
ccgttgcaga atttgaacgc atattcttgt agccaatgat ctcagcttcc gtttggcata 540
tgtggcgtct ctaggtacct cacccctaag ctgaccattc cctagttagg cttaggcttc 600
ggcttaggct tacgattaag cttaggatta agcctaggct taggctttgt ctgagttcaa 660
ctctccacca cgggaaaatt tttttgcaaa ttttttcgtc ccaaaaaaaa aaggaaaaaa 720
aaactttatt tttacttgat ttttttcact ttttttcga gttcaactct ccaccacggg 780
aaaatttttt tgcaaatttt ttcgtcccaa aaaaaaaagg aaaaaaaaac tttatttttta 840 cttgattttt tcactttttt ttcgagctca gctcgaccgt ccctcaatga aaacaagcaa 900
cctgatgtat tccagatact cccgtaccaa aggtcatttc tcgttagtca caaaatattc 960
tgattgaaaa tggtgaaaaa taacgagaga gttgaaaatt ctacagacta tggcctaaac 1020
gcagcaggtg agacacagta gagaacaaga ggcagaagag agagcagaag gcagaggaag 1080
aactaaaggg tatataaaaa gtgttttgtt gatcagtggg atcaaatagt gtgcttttta 1140
aaagtttttt tttccataaa tgtattgata tctagaattt ttttcgagtt cactgttgtt 1200
taacagtgtc acatggtgtc aggctgtctc aatacagttt gatctacaaa aaatgcggaa 1260
atcttaacca tgcaaaatca gttgaaaact cttcgtattt tctcccgcat tttttataga 1320
tctacgtaga tcaaaccgaa atgagatact ttgatacacc gtgcagtgtt aaaaaaaaata 1380 cagttacagc 1390

<210> SEQ ID NO 15
<211> LENGTH: 395
<212> TYPE: DNA
<213> ORGANISM: Caenorhabditis elegans

<400> SEQUENCE: 15
tctcattctc ttcaagacat aacacaacgg gctgacgacc atatcatcaa cgacgatttt 60
ttaggaactg tactttatct gtgtctgacc aacacgtgtg aatgaagttt caactggaaa 120
atttgtttga aacactgcaa agaatttcga attttgatga taattttaaa tgccattatc 180
agttttaata cgccactcta gtctttgatt ctttgcacac acacacacac acacacacac 240
acacacactc acaaacacgc ctgaaatttc gcaatatgct gatttaacga gaaaacattt 300
gatgacaata aacttggcgt attaatataa aagggaaaat tcaattcaga ttctcaacgg 360
tttattttct gtcacaactc ttcctaatat tcacc 395

<210> SEQ ID NO 16
<211> LENGTH: 741
<212> TYPE: DNA
<213> ORGANISM: Caenorhabditis elegans

<400> SEQUENCE: 16
tacacagcca agtctcataa ccaaaataat attgatagta aaaacatgag tgaacacgtt 60
tcaaaacaac atgtcattga aaatcaattt taatgttcac gggaattttt ttccaaaaca 120

```
gttttactca aacatatttt ccatttgaaa gtttgggaaa ctatccctgg cacgttttca    180

ctgcattggt ctttccagtt gattcagcca gagttggaaa gcctgtactt ttttcccaac    240

aaccgtttct actgctcaac ttgtaacctc aaatttgcct aattgactcc gaagcttcaa    300

aacttgcttt aaagaacttt gatgaaaatc gctgcggcga aagaatcatt gcggaatttt    360

tgccccaggg atctaaattt ccaacctact ccactgaacc aaattttttc aaacttcacc    420

aatttttttta ttttattttc acatgtcatt aaaacactaa gaattcaata catgtatgaa    480

aactgcaaac accaaagtac ggtttggact tgtaagcaaa acaccggtag tctctttgac    540

ttatcatgta ttgtcatcct atttcgtcag acggtcttgt aagttcacat tgacttactc    600

tgcgtctctc ataggacaca tactccgcat ctttctcaat agatcaaata tattttgtca    660

tcacctatta tttaaactgg ttggtttttc acaatgtcac aactaattga actctccact    720

tattgaactt gacttgaaat c                                               741


<210> SEQ ID NO 17
<211> LENGTH: 330
<212> TYPE: DNA
<213> ORGANISM: Caenorhabditis elegans

<400> SEQUENCE: 17

accgccgagt tacgacatca gattcaagcc tttgaaagtt tgaatcttta ataattaaat     60

gaataattaa ttgggagaaa catgtacata aataaaattt ccattaaaca atgttcattt    120

gtttaagctg gcacagacca caaaagctga aaccacaaag ttttttaaac cttgttcttt    180

tcttaaattt tgtagtttct tatcttatca ctcgtgtttc ttgtcctcca aataattgtg    240

aaaattgtag ttaatgtgtc aaaaaagtca catataagaa gacgaacaac ttgatttttt    300

gttgacttca tttgaaaaaa aatagaaaac                                      330


<210> SEQ ID NO 18
<211> LENGTH: 953
<212> TYPE: DNA
<213> ORGANISM: Caenorhabditis elegans

<400> SEQUENCE: 18

agaacccatt tttacaaatt gtgttcttgt ggtgttcgcg tattaacttt ttatagctgt     60

tttttactta taggatgatt aagaaaaaag ttccggcttt ctcaaagtaa ggtaaatatt    120

ttgaaaataa agaacttgta aaaggataca gctaactgat taaaaacaaa agacccatgt    180

tagttcacgc tcggatttgg agttcagctg gaggggaaag aattcagcgt tgaaatattt    240

cagttggaat ttcacctgat attatttaaa aaatgttata cgaaaattga aaaagcgcct    300

cttacccccct cttcgcccgc tttcctcttg cctactgtgc agttttttgt ctttacggag    360

ttaacaagtt gataacctgt ttaaggacaa cagataaaaa cagagaaaat taaaaaccac    420

tattggcgat ttgaaatttc cgttcccatt tttcactttt caatttcaaa tatgtactta    480

acggtttccg atcattaaca cgtaatccat catttctaga caacaagtca caccaatgcc    540

aatcaaaagt gcaaacatgc tataacgaat cttttttttc aattaaactg tttacgatgg    600

aaattaggat agtgtcatag cattaatttt cattgttcaa aaacagaaag aagtcacaaa    660

atcttcacgt gaacatgttt cgtttccata aacaaattgt attttcaaag acagccggga    720

attttcagac caattcaggt gacaactatg ggctaccacc cacctaactg tttgttcgcg    780

attattctga ctcacatcat gttttcaaaa gtgactgtat aattggagtg tagcataatc    840
```

aacacaaact acagaatggg aaatttgtga cagtatcaat cacattaaca gatctataaa 900
agagactggg aaagttgttc agagacacaa attcgttgtc tacttatcaa atc 953

<210> SEQ ID NO 19
<211> LENGTH: 607
<212> TYPE: DNA
<213> ORGANISM: Caenorhabditis elegans

<400> SEQUENCE: 19
aattttaaag tttatggatt atttagaatt tatgaatatt ttaaatatag cttgtaatag 60
tagcattggc tttttttatta gttagaatgc agtatttata tagattgtag ttgtgtgcgt 120
gctaagatta ttggagtatt ggtgttgtca cgtcttcagt ctctctgccg tgcgctcacg 180
agaatggggc aagcgaagtt gcggctgacg cgttattgga tgctggcgcg tttcgcgacc 240
agcgttggtt ttatcgagaa ttttctctgc agtacaaagt cccaaattcg gtggtttttt 300
atcgatttga cgcgcgtttg ctcaatttct cgattttccg cgttttttat tcagttctca 360
ttaattaacg ttcgatgctt gttcacaaaa ttcagttttt gttttcactt gctcgttggt 420
gtcgttcgtt gtgtaagaaa attgatttct aaatattttg tttaaattgc taaaaaataa 480
ttcaataatt tacattattg aattattaaa agttgtattt ttcaaacatc tcgcgcattc 540
tccgtccgtt tctctcaatt tttcactgtc atgtccgcat tttaatattc attttttttc 600
aggtaat 607

<210> SEQ ID NO 20
<211> LENGTH: 1723
<212> TYPE: DNA
<213> ORGANISM: Caenorhabditis elegans

<400> SEQUENCE: 20
ttggttatag gaatatcctc ctaggataga cgtttttttc tagtaatttt tgttgttttt 60
gttcgttaca ataaatctca tttttatttt ctggattaat ttgattacca atcgtttcca 120
gcgattttca catatttttc cagaatttaa tacagattaa tattttcgaa aaatttaaac 180
attttctttt cacattttaa ttcatctcta ttcattatgc aatactcttt tggttttcaa 240
gcatccgaca ttcctccgtt tcatttatgt ttgcatttct gctggcatga atgcatttca 300
ttgtgtctcg atgagaaaaa ggacaatttc atgagcttat cagttacttc gttttcaaaa 360
ttttaatgtt gaccagccat tgatgtcata ttttgtctaa gaagctcaag aactattatt 420
ttttgaagct taatttcgaa gagcaacatt ttttttcatt aaaattcagc agtcattgtt 480
ctttaaaaag ttttgattct cgtttttaaa cgatttttaa ttcagtcgag aattgaataa 540
cttcccgatt tcccggccac catcgtttaa taccttttct ttatgagact aacttccaag 600
tatgcaaatt gcaaatcgac gcaaggggaa tacactcgct cacttctcat cgaaattcga 660 aacctttttcc catttttcttt catgtctttt tcgcttttct cctctctgcc catttccatt 720
tatttctcaa acaccgttca gtgaacacga aaacccttac ggaaattgtg ttgtaagaat 780
acaaaaactt ccgtagcata gcgagaaaga gtcaccattt tgtagtgttt gcccccggtg 840
gtatagtttg cacaagtttc tgaaagaaga agaagacaca tttgaggtct tatgcacata 900
aaaatcaatg ttagactatc tttttcacgt agttttcttt tgcaaagtgg aaacttctca 960
ttaaacactt tttgcttttc aattgtctga acaagttttc gattaaacag ctgtaaagct 1020
tttgcaagtt tcatggttta tgaactattt cgaatcggtt acattgctga agttttagtg 1080

-continued

```
tttcttgaat atgtcgtcac taccaggact ggaccaaaaa tcaaaaagaa tttaaagtga   1140
aataccaaaa aaaaaatcgt cgatttgcga tttttgaagg actgtaagtg actttttttgg   1200
cttcatttag gtcccaaaaa acctttttt tctcaaaaaa tgtgactcaa aataccaaaa   1260
aagtcttaac ctgatcactt cgccttctca actcaagcca tttttgctgt ttagttcgaa   1320
tatggaacaa atcataagaa tcttgagtac ctatatgcga tacccgattc attttcctct   1380
cttctaaata acatcatttc ctctcttttt ccctctctct ctctctctgt ttttgtttgt   1440
gactcacttt gtccacaacg cgcgcggaac cggcttgttg ccacacacac actgtgatga   1500
aatatgcggg aggaaagctt ttcgcctaat agttgactta cttttcatct atattcctca   1560
attttgcaac taatagattg atttgtcatg gttttgattt cagggttttg aatattcttt   1620
gaaattggaa tttttaacaa aaatgcaaat tatgtgccaa gtcatatctc ctcctcacac   1680
tttttctatc acatgccccc aaaaaaatta atttttttca gga                     1723
```

<210> SEQ ID NO 21
<211> LENGTH: 2546
<212> TYPE: DNA
<213> ORGANISM: Caenorhabditis elegans

<400> SEQUENCE: 21

```
gaatgcagga tataaatcac gattttcgtt ttcgaacaca actttaaact tcaatttttc     60
ctttgtttct ctgaaaactt tgcagtcatt ttcaagcttc cacagaactt tacaaaaaaa    120
ctagattttc tccaacgtgg cgatattccc gagtttcgag aagaatccag cttgtcaatg    180
ctgtataaaa cctttacttt tctatcgttt ccattatttc tttcactgca cctgttactg    240
ccaggtgctt tatttcgcct atcgtctatt ttgttttcct cctaccaaat ttgacaaccc    300
tccgcaaaca ctcattccta ttttagcccg gtgaaatttc gatatggaga aaaacaaaaa    360
caagtgtgag cttccacttc ggaataattt ccggagaatg agaattgtac aattttctcc    420
tataagacca tacaataaaa ttttatcaga aacatgaagc tttggtcatt atcatttttt    480
gttaccttg aaatttgatc acaaggcttt aatttttcat gagacgtcaa tttttctga     540
tgataaataa catagttcaa agtattgcgt aatgtttcaa ttttaacatg acacataata    600
aatcagaaac tcgaaaaacg tatttaaata tagattttgt cgggaagttt aatgtgcaac    660
tgtctcgata tctttctttg aaaacattta atttttatta tattttccaa actggattcg    720
agaattctcg tattcttaaa caaatttaca atgaaaatat aaataattaa tttaaaggaa    780
catgttctgc aatcctccct gggtcccgcc acgaaaccgc cacgcactac catgaaaggc    840
gcgttcgcat tcgttctgcc gctcgtttct gttttccaga tctttccatc attttcttca    900
ttcattcgcg ctctctcatt atcttgagtt gccggctatt ttcgctgctc tctgcttttt    960
cgtatcgctt tttcactctt tccagcattc agaaaattgc attatttcgg ttttcattta   1020
aaaaactcat agcaaagtat tttgttattg atttcgcaat actttcgaaa agtatcggaa   1080
aattttaatg tttagtctgt gcgttcctca ttccctgttc tcgttgtact cttaactgat   1140
gtttttaaat ttagttttcc ggggctctct tgaaaagacc caatagtcgt attgaacctt   1200
cgcctgatcg ccactagctc atcttttagt cttatgacgg gctcacatga ttctccccag   1260
tgtcctcccg ttttctcact gcacttgttt tgtcgttcgt tcatcagtac aaagtacaag   1320
cactttcgcg tctgtctgaa aattggttcg ggtgccgtta ggacattatt catactttcc   1380
tgctagtcgc agattataaa aaaatgtcct tgaccgtctg ctctttctta tgttctccct   1440
atatatgcgt caaacgaaca actgaccctg ttcacttttc ctattcttcg tttcatcatt   1500
```

```
ttctgtaaca aaaatggaaa caatacttta cacagacgtc actattattc aggcctatga   1560
tttctctatc gtttagttaa agatgaaaag aaactggtcg acccagttgc atgacgagaa   1620
aaaagaacac cccgttcgat tttcgttgta ttccctctgc acacattgtc cccttcttcc   1680
tcatcatttc tttccctaca cagcactcta gaatgttctt cttgtgcaga aagagtgccg   1740
tttgagtcag cgacccccccc cccccccctc ctttctcttg ctcttcctca ctggttctcg   1800
taataggcga cttcttgcta acagaaagtg agcatagcaa catttttttac tttgtggcct   1860
tcaataatac gtgcgtcgtt taattagaat gtttgagtaa agttcaacgt gtagattcaa   1920
tattcacgtt ttgggcgctc tttaatttat tactgtcaag aatcagttta ccaaacggtg   1980
agtttctttt tttttgtcta attgtaagat ttagcggggt aaaaccaaca gaaatgtcat   2040
gctttttga ataatctcaa tcagttgtta tatgaattat tttcccattt tagcaatact   2100
gcttggtagt tattttcggt cagagaaacg aggacatcag ctgaacatct gcgtctctaa   2160
caacactcgg ggaaggcgga gtcagtgtgc gcgtgcgttg gggggttttat cgatcgttga   2220
ggcgggcata cagcagtcat acaccccatt cgaccagaac gctccgctcg cgtgccacct   2280
tgtctccatt ctcatttcac ttgtctctac tcggacatta ctcctcatcg attagctctt   2340
tactaccatt ttacttttat gcctttcttt tttcgtttga cttgcctatg acgagtgggg   2400
atgaagtttg ctttgttagt cttactagtg tatcgatttt ttgggtaata tttcgcaact   2460
ttctaggact ttctttcata atcacctctt ctctcgcctc ctcattccag ttttattcgc   2520
actcattttc tattttttca gcaatc                                        2546
```

<210> SEQ ID NO 22
<211> LENGTH: 580
<212> TYPE: DNA
<213> ORGANISM: Caenorhabditis elegans

<400> SEQUENCE: 22

```
aatcaataaa aaaacgttcg aaaaacgttt gaaacaaaaa aataatattc gaattcttct     60
ccccccttccc gtaaatcctg cagctctcta ccgtactttc gccgtctctc aatttcgcgg    120
cgagacccat caccacggca atcctccatt tgtgtcgctg ggcctaaatt ttttccgttt    180
ttttgctcga ttttcgccgt ttctctgcga aatttttcca aatttctgtt caatttaatc    240
aaaatattgt tctggacgct tgttcagcat agaaagtgga gattctgttg tattttaagc    300
ttggaaaacg aatttattat gaaatttcat ttttttgcta aataatttct ctattcttga    360
atttttacag ctttttaacg caaaatattc tttcctcttt gttctaaatg ggtagttaca    420
cacattatgc ggtctataac gtcttttgtc acctttgaaa ctagtctcta aagaaaaatc    480
aataattttt gcccctacgc tctcctccaa atgtttcgct ctcgccgtca ttttctgaca    540
attttactcg gtttcttttc aaattatata atttcagtcg                           580
```

<210> SEQ ID NO 23
<211> LENGTH: 1037
<212> TYPE: DNA
<213> ORGANISM: Caenorhabditis elegans

<400> SEQUENCE: 23

```
tgtaaacatt tgttattata tttttaaact ttgtgttgtg gatgtgaata tgtggaattt     60
aataaaacat ttctcgatat aataatgatt ttgttgaatt agaaaaatta gaaaagtgga    120
cgattctaaa aacaaaagtt acaacgaaaa tcatcgaagg aaaaaacaac tgaattccaa    180
```

-continued

```
aatagttttc agaggtgatc acaaaatgtt ctcaaacgat atatattcta ccatcaataa    240
ttttattggc actatatcac agtccataat tcctgtgctt taattatact tttcagtata    300
gaacaatatg ctatattatc aagttatgcg tccaataaac acaatttatt tttcagactg    360
aatttaagcc atattgagaa tagcgaaata aaaacgtaga ggaaatttgt gatcgccatt    420
cacaattaat tcttagatcg caatgataac aaacttcgat tcaaaagtca tcatgcaaat    480
tcaccgttct cgtgtgtgtg tgtttttgga ggaaataaca caattttgtg actgattttt    540
ttacaacatg tggtttgtag catagttcaa agtcattcta gaggggggctc agagggagtt   600
ctttcgctat gtcatcgttt gtttttgcac accaagaaaa atgaaaataa atgctctagg    660
atgtcatgga tcgtttccat tcttaataag tagaagctag gatttcctat acaaaaataa    720
gtaatcttcg tttctacgtc tatcaactta aatttttgta tacaatccac tttggtaata    780
ttcaaggcct tcctgtaaaa tgttttatga tcaatccgtt acaccaagaa aacaagtgca    840
atttgtcatc atgtaggctt ccgcctgtgt ttacttcctt cccccagcac aacactgact    900
atttatacca aattaataat gcagcattcc tcatgtgata actcgtttga cttttatatc    960
tttctacgtg catctttcaa gctcgaaaat taattttaaa aatttacatt gcagaacaat   1020
tgcggaacga agaagcg                                                  1037
```

<210> SEQ ID NO 24
<211> LENGTH: 2502
<212> TYPE: DNA
<213> ORGANISM: Caenorhabditis elegans

<400> SEQUENCE: 24

```
attaatgaag aatccgaggt tcctcactaa agattctcgc tttatgatag agtcctcaag     60
cttgtatatt agagttttgg ggtgtttacc taaacttatg caaacggttt tatcatggtt    120
taactaaagt agtgaattgt tggaccaatt taaaataaca tcgatcgctt cctgcagatc    180
atttgtggaa ttagtttttt caaaagagca atatagtttg aggtcatcag cgtactgcat    240
atatttaaca gtttttggaa tgtttgcacc aagatcattt gcaaatatgc cgaaaagtat    300
aggtgaaagt acgctccctt gggggacacc acatggggcg ttcctaacag aagatagaga    360
attgttcact tttactttga acgtacggtt ggagaggaat gagtccaccc agcctatgag    420
catagaattg aacccggcct ttattaattt ttgcattaag agtgaatggt ttactttgtc    480
aaatgcctta ctgtaatcaa aaaatacaac atctacttga ttattgaaat taaaattttc    540
tatataggaa cttgatatac ccaatttcta ttaaaaaatt gaattcgcgc cgagcaaaat    600
gtgatgtcaa tttcagtttt ccaattttct caattttttt gaccactaac taaaattttg    660
ataccaaagg atttttgctc aaatttcgaa ataattgcgg taaaattggc tctaaacact    720
agtttttgac ctagcgaatt ttgatgtcaa tttcaattta tttacatttt atttggaaat    780
tttcttcact gcggatccct agcaaaattt gttaaacatc acttttccga gcaatttgtg    840
atgtcgattt ccgtgtcttt acacggtttt tgcctttttg cttaaatttt tcaaaaattt    900
cagtaaaccc caaccaaaat gaattttact cacaaatttc gctcttcaat tattttttta    960
gtgaaattca caaaatctga cctcacccta aattcccact gagcacattt ggatgtcgat   1020
gtttgttcaa gtttttggcc aagttttaaa caattgcagt caaattcaac caaatcacgt   1080
ggtgtcagtt tgtcccatta cggtttgatc tacaatgcgg gcattttttg cccaatcaat   1140
tgagaactct gcatcacagc taccacattt tttgtagata tacgtagatc aaacggaaat   1200
tagacactct ggcaccactt gccaaatcat atgcaaaact gctcaatggt agaatttgac   1260
```

```
aacccaaatt gctcatcaag tttttgtgtc attttccgcg caaacaggga ttcaaatttc   1320

tgccatcaaa aactcatttt ctacaaaaga actacaaata ttatttcaaa aaggcggcag   1380

tggtggtcaa agaacaaaca tctgaacata ttgaagaagg tgtctctctc tctctctctg   1440

tctttccctg ctcacacaaa tctgtgtgtc tctctccaga aaataacaac acttgaggtt   1500

cacgggagga cggggggagc tcccgcctgt gctccaactc tcttgtcatg ccactttatg   1560

ttgctccagt gtttttgtct ctctaaatct ccagctagct gttctttcat gttcccttag   1620

ccccaatacc gccgcctttc gatcttttgg ctgtttttttg ggggatataa gaagtttcga   1680

ggaggaagac tagatctatt catcctaaaa taaatttttt ttcttttttt ttaggcttta   1740

tcagactcta aaatgctcgt acgacaccaa attccagatt tcagttttct atattttcgg   1800

tcctataata ctatattcaa aaaattagcg tcttcgaagg aatctgacat ctaaaagttc   1860

tattggtctt ttttccggca aatcggcaga ttgccgaaat caaaaatttc cggcaaattg   1920

gcaaaacggc aaattgagag attgccggaa ttgaaaattt ccggcacaga ggcaaaccgg   1980

caaattgctg atttctcaga aaaactgcaa ttgccgaaaa ttttcggcta attgaggttt   2040

tgcattttat ttttggcaaa ttgcctgaat tggaaatttc tggcaaacca gcaatttgcc   2100

aaaaatgaaa atttccggca aattgccgat ttgccgaatt tgctagaaaa aaaattaatc   2160

ggcaaaattt tacgcatcta ttttgaaaag aaagcaaatt ctatgaaaat atctaaagaa   2220

aatcttttaa aaaaatgcac agttttaaat gtttcattcc tttcaaaaat ccctctaacc   2280

gcttccggca aattaatatc cggcaaaggg caaatcacca aaccggcaaa ttgccaattt   2340

gccgaacaaa aacaactgaa ttatgctatt aataattcct ggttcctgat ttccaatttt   2400

tgattatttc ttactcactt cagtatcgga aaacgttcac aactttggaa agaatttgat   2460

gcccgtaatt tgctgaataa atttaatttt ttcaatgtcc ag                      2502
```

<210> SEQ ID NO 25
<211> LENGTH: 609
<212> TYPE: DNA
<213> ORGANISM: Caenorhabditis elegans

<400> SEQUENCE: 25

```
gttttctgca aaataatcat tgattttaac acctcgtaaa ataattttaa aaaaagaagt     60

taaaatttta attgcaaccc tatttgtaaa aagaaaactc attttcgcca aaaataaagc    120

aaaaataatt caagagaaaa acgcgccgcg tgttgcgatt ggggcgtaac tgcaatgtgt    180

gcgcacacaa tctcaacaag cgctgcgaga cccgccgcct gaccgtaatg tgaaatgggc    240

ggagacgaga agtttttttc tgtttgaaag ttgatgcaaa agcccgtgat tctttttttc    300

gagaaatttc tcgagttttt tccaacgaaa aattcattaa atttaaacct tttagctctc    360

ctttccaata ttttgcatca ttattctcct aaaacttggc atattcagtg gaaatgatgc    420

aaaatgccct gacttttgtt atcaaaaata caagaaattg tcccgtttaa cggttgaaaa    480

gcaaattttg tgtcattttg tttaggaaat gtcaaaataa gctcaaaaac cgattacaaa    540

ttatatttta ctgcttttta tcctattttc tcgcgttttc gttcatgatg caattttctt    600

tcaggcact                                                            609
```

<210> SEQ ID NO 26
<211> LENGTH: 836
<212> TYPE: DNA
<213> ORGANISM: Caenorhabditis elegans

<400> SEQUENCE: 26
ttttcggctg aaaaattggt tttttgagtt ttaaaattta tttttagcgg gaaattacat 60
gaaaacaacg aaaaaacccg aagaaacccg cgaaaattca gaaaatgatc aaaaaaccaa 120
aagaagcttc gagaaaaaaa gcagaaaata aatgtgcggc gcgaaaaatc tcgtgcggca 180
aacttgcaaa tctaggcgtg tcgggccaat ggcagacacc gcgccgcaaa ttcagccaat 240
cagcgcgctc agctccacct agaaaagtgt gcgcaccttg caaaactggg cggagcgagt 300
gaaatgatgc aaaagtctat tctgatgtaa attagccatt ttacatcaaa atttgcgtca 360
ttttcgttat ttttctctca tttttcatat tttgaacgaa aaattgaggt tttttgcttc 420
tattttcatc agaaaccatt gaaaaatgct tatttttggg ccatttttcg tcgaaattag 480
gggaaaaaac tattctacag ttttcccagc tattttctca tttattcctg tatttttcag 540
tcattacctg cttcccagac gataatgcaa ggcttctcgc ttcattttca taaaaaacga 600
ttgaaaaatg cttatttata ggccatttat cgtctaaatt aggggaaata tctgttttac 660
cgttttccca gccgatttct catccattct cgttattttt cactcctttt ctgcttctca 720
gacgataatg caaggcttct cgcttcattt tcgatgagaa actctgattt tgctcgcatt 780
ttcgcctttc cgctgcagat tttcacacaa ttttcgtagt tttcagacaa caaaag 836

<210> SEQ ID NO 27
<211> LENGTH: 580
<212> TYPE: DNA
<213> ORGANISM: Caenorhabditis elegans

<400> SEQUENCE: 27
agagaataca aaaagagacg aaaatggttc agtggaacga aacaaacgtg ggatgtaacc 60
atggaagtga gaataattga tggaatagct aatgagctga agctgagtag atcagagact 120
actttattct aaaaagtaca gtagttggaa aattacatgt ttcatttcta attttcaagg 180
aaaagctagt aattaccgta atcttgtttg tacctgaaat tttatgtact gcaggtgacc 240
aagtatgttt gaggcatgac ttcacacacc taactgataa aggcctctat cacaaactag 300
agttgtgacg gaaaattcaa cttctcagaa tatagctcaa aatctatcaa attttatttt 360
caaaaatcca aataattgtg cacgcaatgt acttactgct tcataaagtt cagaagaatt 420
ggataaattt gaatgaagtt ttcaaagctt ttatcagtga ctgtacattg tgataggctt 480
gtgctgttat cagctgcctc aaataggttg tcgcttgaaa atttatataa aaggcctacc 540
agcagacatg agaatcaagc ttcaaaggct ctactcaaaa 580

<210> SEQ ID NO 28
<211> LENGTH: 584
<212> TYPE: DNA
<213> ORGANISM: Caenorhabditis elegans

<400> SEQUENCE: 28
ctgcgaggaa gagaaaaaat cgtgctgtga aggaaaaacc gagaagactg agcaaaagaa 60
ataaccaatg agcaagtgaa cttttcccac gtctactact aaattattgt cgatctataa 120
ttctttcgct tatcaatctt gtcaattgaa ataaaacaat atttttctaa ttctttttgg 180
aacgaacaca cgtgtttaaa tgaatgttgt gctaaaaacg tcacatcaat ggtacgtgaa 240
tgttgcaaac accttgtcaa taactgataa aatcagaaac tagagctgtg actgaatcgt 300
atactagaac ggagtctctc taaaaacgtt ctaaaaacaa acaaaaaatt gtgcaaagga 360
ttagagtgct caagatcaat gagcaaactc acaatcaact atctgttatt gttttgggtc 420
tcttctatat ctctattctt ttagtatcat aagtttgtac attgtgacag ggccaccctc 480
ttttatcaca tatttgaagt ggtaaacagc cagcaaaaac caaataaaaa ggcagtgaga 540
aaaagaagaa ggcagctcaa tttgactgct gaaattaaga aatc 584

<210> SEQ ID NO 29
<211> LENGTH: 1031
<212> TYPE: DNA
<213> ORGANISM: Caenorhabditis elegans

<400> SEQUENCE: 29
tctgctgatt tatttgagct tctctgtgtg accaagacga gagccgaaga gtgaagtttc 60
cactgtcaca ccatgtattt tatactagtt cagagtatct ttgaacacct gttttaaaaa 120
ggtacaatac caaaaggcgc tcttaatgca cccggttaca tttgtatttg tttgatcaga 180
tggatgtctg tctgacaaac gtcggccaaa gaatgcactt gcagacttta ctttaatttt 240
ttgtctagtt tgaaaattct tcggatttgt tagtttcaag aactttcaat gaaaccgaaa 300
gtttgttgag ttagcgagaa ttacttctga ttacctgaaa attaatttga ctcaatcttt 360
tacctactta gaaagactaa agtttctgca caaatttgtt tgaacaggtg cttcaaaatg 420
ttacagaatt ttcattttca tccacataaa aagttgattg acaaatagtg tgggcgacat 480
gatttcttga acaatttgtt tcgcttttca atttggactc agttcttcga aatttagtta 540
ttatccatat tattactgtt ttgagtttta tcgcagtagg aaatactggt gtatatacat 600
attatatttt tccgttttgt ttacccagaa agcttaaaat tcaagttggt cagaaaaata 660
aaaaaacaac ttttgcaaga aataccattt tttcatcgtg cggaaagaac aattgaaaac 720
taagtatttt ttgctaaact gcagtactgc tacaatacta atactgtacc acgatagtca 780
cccaacagta cgaactccta ctaaaaattt attaaaaaaa gttttattat tcaaattttg 840
aaaatccata agttctaaat actttgttca gtatgctata cttaacacaa atggtattct 900
gcaattgaaa cagaaactac aataatttta tcacaaaaca cagttctccc tactttctta 960
tcacattatg tcatcggggt ggcaagtata taaaggaatg ctgtaaaaag atatgtacta 1020
ctgtctcaag t 1031

<210> SEQ ID NO 30
<211> LENGTH: 1084
<212> TYPE: DNA
<213> ORGANISM: Caenorhabditis elegans

<400> SEQUENCE: 30
agaatttgca aaacgagcag gaaagtcata ttcgcagaaa aaagtcgttg caaacattcg 60
tttttatatg tttttctttg agaaagcgtg gttcattttt gaaagtgaaa aatatttgct 120
taaaacttcc aaatttaaat ctgcagtgat tcagagaggt tgagaattat tttcaaaaac 180
attcaatgtt ttcccttgga gtgactatgc aaatatgaaa atgttttcca aaaatatttg 240
gatgccctga taaaaagtag gtgaaatttc gcaggggaac atcatattaa aatgttgaat 300
ttttagaaga aatggaaatg tttgtcggtg gtatgctcga atatttgaga tattatatat 360
ttactgttaa atccgaaatt tttgacaaac ggaaaaaatt tgtgtcgaaa tactacattt 420
tcgataacac aaaggtactt ccataacact tataaaaact gtttgactat cttatttcag 480
gaaaaaaaaa tccaagaata aacatttttc agaatttgaa ctttctaatg gctgattaat 540
aaaacaaagt tatacaacta ttcaaagcag ttgctcaatc tggcattttc ttgtgttttt 600

-continued

```
ttttgaatat ttcatcagca agatgttgat aattttgtgt taattctaat tgttttctac    660

aatttttcaa accgaaaatt gacctttgac tttgtttact ttgttctcgt gggttaactg    720

ttcactgatt tctattgctg ttgatgaggt ctttgatcaa atttgtattg tttttatact    780

gcatattgct tcaattctaa atcatctaat atattgtcaa acaacttctt gttttttttt    840

tcattcaaaa cttctgcaaa aacgttctct taacaaaggt tcacacaaca actctcctct    900

ccatctcttt ctctcaacaa caatgtgctg gccttgcatg tttgccagtg cgggttgttt    960

acgcgttttc aagattttg gtctcctatc taacgtcccg aaatgcattt tttcctttca   1020

tttggttttt ttctgttcga gaaaagtgac cgtttgtcaa atcttctaat tttcagtgaa   1080

taaa                                                                1084
```

<210> SEQ ID NO 31
<211> LENGTH: 1929
<212> TYPE: DNA
<213> ORGANISM: Caenorhabditis elegans

<400> SEQUENCE: 31

```
caattattat aagaaaataa atttaaagtt atccgagcaa caattatcaa taaatattac     60

ttttttaaat gaaaaccttt ttaatttcag cagaaatctt agaaatcaga tgatcaataa    120

ataaaaacgg ctgacttttt aaaggcgcat agaattttct tggtggcggg tcccgcaccg    180

aagagccgtt ttctaaataa tatacactaa tgattatttt tattaaattt tttcacggtt    240

ttcgagagta ttctttatat aaattcaatt ttaaagcatt ctcgtcgagt ttgaatccga    300

aattatcgat tttcgttttt ctctgctttc tctaccgctg ttttctctcc tccgctgtct    360

tcgcaagatt atagagctct tttgaatcaa tttgtttcat gtttccgctt ttgacgttat    420

tttaaacata tactgatata aataaattaa gaatagagta gaaaatctag ttcaagtaaa    480

gatgcaacat ttctttctgc aaaatttctc gaaaacacct gttttccaaa acttttcaat    540

tacacaatta gaatttcgga aaagttaaca tatataagaa catattatat atatatatat    600

atatatatat atatagatta actctcacag ttaaagaaat ctgaatagta atattgcgaa    660

atagttttgc ataagtttgt ttgattaaat taaatgtgaa gcactaacgc tattgaatcc    720

aggaaaaact cgaattattt gtttgatttt tattaaacac actttgtgaa caattttcgg    780

ttaagaggct ttgttgtagt aaaaatccta aatctacgat tatcttctta aaatttgaca    840

tacttcttac gtatgttaca ggataaatcg agttttgatg tatttcgtaa atagttttta    900

atcatgttat ctttttattt cccatctcta tgttttaatg ttgtctttac actaattcac    960

ccgtaatgtc cgtgcacaaa agaatttaac attcagatat tatggaaaca aaatcatccc   1020

aaacttcaca tccgtggctt gttctactca ttttcgccac ttttgcggtc tcaatttttg   1080

ctgtatacag caattttcct gaagtctcgg cagatgagaa ggttcatttg aaatatccca   1140

ggaatctgga agacgctaag cagctgggca gagttctctc gaagtacaag gagaacaact   1200

attcagtagt tctgtgcggt gtaattgtcg tctacgtatt tctacagtcc ttcgctatcc   1260

ctggatctat ttttctaaca attctatcag gatacctgtt tccattctat gtggcaattg   1320

tgttggtgtg ctcctgctct gcaactggag ccgccatctg ctacaccatt tctaaacttt   1380

ttggacgatc atttgttttg caaaagtttc ccgaaagaat cgcaaaatgg caggatgatc   1440

tgagcaagca tcgtgatgac tttctgaact atatgatttt ccttcgagta actccaattg   1500

ttccaaattg gctaatcaac attgccagtc ctgttctaga tgttccactg gctccattct   1560

tctggggaac atttctaggc gttgctccac caagtttcct gtatattcaa gctggctcaa   1620
```

```
cactggaaca attgagccat accagtgtag catggagttg gagttctatc gttttactta   1680

cgggttcggc gattttgtcg ctggctccta ttttgctcaa gaagaagctc aaatcggatt   1740

aattttctct cttatttcct ctttcgatct catttttttt ccattgcttt ctgtgcaaaa   1800

cttgtgatat ttagagaata tagccgataa ctcatttcta tactattttt atttattttt   1860

cgcctccttt tttgtcataa taatcatatt ttcttcacta ataaacaatt tttaggtgat   1920

gaaacaatg                                                           1929
```

<210> SEQ ID NO 32
<211> LENGTH: 1091
<212> TYPE: DNA
<213> ORGANISM: Caenorhabditis elegans

<400> SEQUENCE: 32

```
gaaactctcc tggatttttc tagattcttt tccagttaca tttcacatag aatctctaac     60

taccggtgca tttgccaatc ttcttactga aattctgtgc cttgttttgt cattaaaatt    120

ttacaccgaa taaattattt gtctttgtaa tagcttatga ctttaacaag gtcatttttt    180

ctaactggct cattcgcgct gaagtttaaa agaagtttgc ttttttgtcg gttaagccgt    240

tcatacattt tttggcaatc ttggtacaac catctactac atttatatca aaacgaaaaa    300

atgtataaat tttccctcgt cttcatctac ccgcaatcat aaaggaatct cattccgtcc    360

cactcgccct ttctttcttc aaccgaaatt ttttttcccg cggcgcaaac cctcatgtgc    420

cgtcgatagc tcagttggta gagcggagga ctgtagagtc agcaggtatc cttaggtcac    480

tggttcgaat ccggttggac ggatttcttt tttattttct gtatcaagtg taactcttca    540

gaaaatcatc gggagcagtc gtacgaaatt ttaattataa aaattaaaca ttccagcatt    600

tttctttggg aggtgaagta gagtcagcgc ggatttaccg gatttacagt tagtttgata    660

cacattcaac attcaatatt accgaatttc aaaacaaaac atttttacct aagtctttta    720

gattattgga aaattacagg taaagttttg gtgaaatgcc aaagtcataa tgcgagatgg    780

tttttttttt tgaaaaattc agatcaaaac tacgtgtttg gtttgtgata aaatattatg    840

atgaaaaaaa ctcgaagaaa tcataaccca aatgatattc agttcacaaa cataagtatc    900

atgatgcaaa atacaaagct gaatgtattt tttcaagacc gcagatcaca attaagacat    960

ggtaaacaca aactctactg cgtaccgcag tgaaatgtgg tttgtagtat gactggtaga   1020

gacacatcga cctatataaa catcaaaaaa ttgtttaaaa aaatattcca tcgagaattg   1080

cttcatttca a                                                        1091
```

<210> SEQ ID NO 33
<211> LENGTH: 1769
<212> TYPE: DNA
<213> ORGANISM: Caenorhabditis elegans

<400> SEQUENCE: 33

```
atattggaag tcaatgagaa ggaggaattc tggattgcaa acgagaattt ggaagtgagt     60

ttggagatag tagcaagcct aagcctgggc ctgagctgag tcaaagccaa agccgaagcc    120

taagcctaaa tctaagcctg agcctaagca taagcctcag tctaagatta agcctaagcc    180

tgagcctgag cctgagcctg agcctaagcc taagcctaag ccaaagccaa aacctaagct    240

taaacctaag cctgagaata agcctaagtc tatgccaaag ccaaagccaa agcctaaagc    300

taagcctatg cataaaccta agcataagcc ttaacctaag ccttaaccta aacctataag    360
```

```
cctaagccta aattttcagg cactcactac cgaaaatttt ccattaatgt tcaactcaat    420
gctgtcgacc gtcctgaaac caattgacac cctcattgaa tgtttcaaaa aagaaggacc    480
ctacggcctg gattactcgg cctattcgga ttttgaagaa atgcagcaaa aattcactaa    540
aatcgttcac gagaagcata tcattccgga tttggttcca gccattggaa acgggatcaa    600
ggagaagctg gaagctggtg ggatccgagt gttggatgtc gggtgtgggg gtggattcca    660
ttcgggcttg ctcgcggagc actatccgaa atctcagttt gttggattag atatcaccga    720
gaaagctatc aaagcagcga ggctcaagaa gaaatctgat ggcactgatt ttgaaaactt    780
ggaatttgta gtagctgacg ctgcaataat gccaagttca tggaccgact cattcgattt    840
agtcatcctg tttgggtctt gccacgatca aatgagacct gacttggtaa tttttgtatt    900
cagtttcaga gaggtatccc aatcatttac agtgccttct cgaagttcac cgtgtggtga    960
agccagatgg tttagtcgcg gtcaccgacg ttgatggatc tagcaatgtg ttcaccgatc   1020
gtgagaccta cgggaagatg gctgcgatga agtatggtgg atcgatgctt cattgtcttc   1080
cggttgggag caataggcca gatgcactat gttgcggctc aatgtgggga aggaagagag   1140
cagttgagat aatgaataag tgtggttttg ataatatcga cattattccg actgactact   1200
tccctggaac tgtttttgtat ttgatgaaaa aataaataaa ctgtagctag tgttttttta   1260
taattgtaat actttttttct atttattcaa tcttttttcc cgattttcac tgctttgttg   1320
tgactgtatc attatgatcc tgatgaataa atatcaataa acaaatacag tttttttttt   1380
atttgacatt gatttttgat tctgagaata taatacatat ctatgagaaa ttaattaatt   1440
aataattaat aagaattaat aaatttaata agaattaaag taaaatatag tgggaatata   1500
gtggaaaaat tgttttgtaa ttgtatgcaa tatgtttata attttcaaaa tcaaagagca   1560
gcacgacgga gcccaatatc aaaagttcaa gcgacacact caaaatacga ctcatacctg   1620
cgtctcctcc ctctcccaat ttcgcaacat attttcgtat tttgtggttt cttcagtcgt   1680
ctatttctcg cacatacttc cacctgatgc aatttcgagt cctcaccaaa taaatagccg   1740
gcaatgtttg ccatttctca gttttcatc                                      1769
```

<210> SEQ ID NO 34
<211> LENGTH: 1406
<212> TYPE: DNA
<213> ORGANISM: Caenorhabditis elegans

<400> SEQUENCE: 34

```
ttttttttt ttttggattt tcgactttaa aattagccta aatttatcct aaaattatcc     60
taaaaattaa aatttcacat ggttgacaaa tttgcagtgg agcgcatttg cagaattttt    120
tttttgaatt ttttttcat aaaaagcgta acattttcca aattaatggg atttttaaag    180
gaaaaaatta tcccaaaaat tttaattttc taattgaaaa aagtgttatt agcccaattt    240
ttaaaggttt tttttgcaat tttcatcaga aaaagcgtta aaaatatcaa tttttcgtga    300
aaagttgatg aattctctca aaaactcggc aaaaagtacc gccaaaaatt caaattctcc    360
aatttttcat ctctaccagc aaattcgcga tggagcgcat ttgcagagtt ttttcagaaa    420
aatcgtaaaa ttttccgaat taacgagttt tttttaagt aaaagtgatc ccaaaaattc    480
aaaattttcc gatttttgaa attttttgg tgcaaaaaaa ctaattttca aattaaaaaa    540
aagtgatttg tctaaaataa aaagcgttta aaaaaacctt ttaaaaattt tttttcccaa    600
aattcacgtg gtgccagggg ctgtcccatc gacggtttga tctacaaaaa atgcgggagt    660
ttttcgccca aaaatgttgt gacgtcagcg ctttcttaac catgcgaaat cagtccccgc    720
```

```
gcattttttg tagatcaaag tagatcaaat cgaaatgagg cattctgaca ccacgtgaaa    780
atttcaaatt ctccaatttt tcatctctac catcaaattt gcgatgaagc gcatttgcaa    840
ggcctttttt taaatttttt aaaaactcct taaagttaaa aaaaatcatt tagctttaga    900
aagcccaaaa attaaaaaaa aatttttttt taatcgaata tcaaaaaatgc atttgtgctc    960
caccgcacgg cggtaatttc gaaatttctt taaaattttt tttataaatt tctgtatttc   1020
acaactgtat tttttcccga attttcctcg cctaataaca ctatttgtca tgattcttac   1080
gtcattgtcg ccgccgtttc tctttttctc tcgccactct ctcatttcca tacactattt   1140
ccactctcat ttttatcatc attttcttca gtttttgctg cttttaaagc ctatgttttc   1200
cctttttata taatatcgca gaattttgtt tttgtaaatt taatatatat atatatatat   1260
tatttatttg atgataatgt gatttctaat ttttttttcc ccaatttttt tcaaattcaa   1320
attgtctcta cgcttttctt atacttcatt gccttttttt ttcaacaaaa atttgagaaa   1380
aaacaccaaa aaatttcaga aaaacc                                        1406
```

<210> SEQ ID NO 35
<211> LENGTH: 1051
<212> TYPE: DNA
<213> ORGANISM: Caenorhabditis elegans

<400> SEQUENCE: 35

```
gcacgtgtat ttttttcggc acgtgaaaat tttttttcaa catgtatata tatatttttt     60
caaatttgga atgtcttatg aaaaacgtcg aaaaggagga actcatttag attaattgtt    120
atgcaaagtg cagattttta acaacgaatt tttgagatca aattgtcaca gttagctgat    180
gttttcgaac tctacacatg tgtgaaggtt cactcagtct gattggttca aaagtggcgg    240
tacgagtcgc tgatcggtct tgcagttctc aatttcgagg aaaatcaaac aagaagatta    300
gccaaaatta aaaatttacg tttttgaaca gtgttttcat tgttattctc atttatgtta    360
tgaaaacatt ttcaaacgtt ttttcctgga tggtaccatt cattacatca agaacttcct    420
gtcactttaa tgatcttttg tttttttgta gtttgaatta aaatgatgat atccattgaa    480
attgagtgta ggcgtatcat gatgacaatt aattaatttt gatcttttgc tacagggttt    540
tccataggtc agttagtaag tgaaatctat aaatttggat tgtaaacgtt ttttcaacct    600
tgattttgtg ttttttttca gtttttttatt tattttagat atttaacatt taaactattg    660
aagcttttaa aaatcatagt tttatgtaaa attgaaaatt gtggtaaatg acgttttagg    720
ccgaattagt ttttcattta agactacatt ttatttcaac atctaagaac tttttgacat    780
ttttcgagcc attgttcaaa aaacatcatt gaacactaca cggttcaaaa tgtttacact    840
agatacacaa accaatagag acactctttt aagaggcaaa tggtcagaga attagacaat    900
gagacattct tttcttctgt gaatttgtat gttatagtga ttagacagtt aggatgacat    960
atatttgtca gcacaatttc tcttataaat acaagaaaat tttcagagat tctcatatcc   1020
atttctattt cattgaaaag ttttttcaaa c                                  1051
```

<210> SEQ ID NO 36
<211> LENGTH: 1121
<212> TYPE: DNA
<213> ORGANISM: Caenorhabditis elegans

<400> SEQUENCE: 36

```
tgactaacaa tatgaaatgt gtataaagct tcatgatttc acaaaattga agtctaaaaa     60
atataagctt taatttttg ctgtatgagc ccctcaaatt ctcttatata ctttttcctg    120
ctaatggcta cttctttgat cgaagatttg gccaaccggt taagtttgcc gacaccagca    180
taaagaaatt ccgttcatcg cattcaattg agttatagga gcaaacatta aaaattgatg    240
gtataacttc ttacaataac atgtgaacaa acagcacgtg ggcataatca agaaaagaag    300
cttttgattt tgaagttgat aagggaaacg atcaaggtgt tcaagaccga aaataatatt    360
ttcagtttga gtaagttgaa aattatatta tttttgaata ctttttaaac agctaacaga    420
tattgcaata gagtgcttga agttgtatgt caatatagtt ttcgtgaata gacattaatt    480
acagtgcggc tcataataaa ttttattgtt ttttttagta ttctacaatt ccatcgagta    540
gctcctgaaa atgtgaatag cctagatagt aaccgattga gaaagtaaac gtgcgcttat    600
gagttacgtt tcgtattttc acaaaatcgc agtataattt ttagtcattt cttcaaaaac    660
caaaaatcta ctgtaccctt attgtaatca aaaatgtgac ggaatctcgc atgaaaccaa    720
agattgttta caatcccaaa aataatccaa aaattgccct gtttctctca attcactgta    780
cattttcaaa gttttccaca gatacatttt cattcatctg tgaaatcgaa tcttttagac    840
tatgtatttg tcataaaatt ttgtgattct tttttgttct gttcactctc tgtcccttat    900
cgttcgtatc tctatttctc tattctctcg ttaccatctt atctattgtt attccatttt    960
tttggtcatt tgtttattga actcccttta ctcaactgca cacaaacatt tctttttatt   1020
ttcttttgaa tatatgctcc atgctaacca gaactgacct gttgattctt tttttttccc   1080
aatatactag tccttttctt aagttttacc aatgttttta g                       1121
```

<210> SEQ ID NO 37
<211> LENGTH: 854
<212> TYPE: DNA
<213> ORGANISM: Caenorhabditis elegans

<400> SEQUENCE: 37

```
tcagcgatga gcacaccgtt caaagatttt ctgaagcatt gggcttacat gtgaaacaag     60
cagcactcga tattagtgaa ggaaaaatac cgaaagcaat aattgcattc aactaaatac    120
tgtatttgca cttggtatta cagaaacgca aagttctgag aatgcgtact gggtaacata    180
tttgacgcgc aaaatatctc gtagcgaaaa ctaaaataat ttaaaaaata attcgctttc    240
gattagaaat tcatttcgaa attcgagtat gtaaatcgac tacagtagtc aataaaagta    300
ttactgtagt tttcgttacg aaatattttg cgcgtcaaat atgttgccca atacgcattc    360
tcagcatgtt gtgttcccgt aacatttaac ctattttaca taatctaggt gttttaaact    420
ttttataaaa ctttctcgta atgctatctt tgcctcttag aaaacttatt cagcgacgtg    480
tatcataacc aattctaatc ggcttgttag aaagaagaaa tataatactt cggcgtctcc    540
actttgtgac tgggcacaaa atgcaattca gattctactt tcgaaatagc cataaaatca    600
taagatcaca gatctttctt cgtttctcag gcaaccaggt gcacaattgt catcactcga    660
ccagtgagac cacaatagaa cagcaaacgt tgtcatcttt ttggttagac actttctttc    720
tgcctctgcg tcttttcata aggtgtgcat actcttgttt gcccaacaac ctagccgatc    780
agaaaacgca ctatatttga cctgcgtgta cactgctata aaagtaacat tttgttcttt    840
catttcttcg aaaa                                                      854
```

<210> SEQ ID NO 38
<211> LENGTH: 1616
<212> TYPE: DNA
<213> ORGANISM: Caenorhabditis elegans

<400> SEQUENCE: 38
aatgcaaaaa aataagcctt tccgaaaaaa cgggcccttg ggcctttaaa ggacacaaaa 60
acaggaaagc ataagacacc aaagagtaat tggatttcta cactttggtt cctagaatta 120
tttataaggt gttattgcgt ttttgtgaga ttgttctatt tatccagtca aaaattgcat 180
tttctttgtt tttgcttcaa aaaaatacat tttcagtgga aatttcagct gaaaagcaga 240
attttgaggt tttcgagtaa ataacgtaaa acactaaatt acaaatattg atttttgatg 300
tcttagacca aattttcgta aacatgtttg tatttttgga aaaaataggt tttttgtcga 360
ttttaactta atttttcgaa caaaaaatga ttttttctcc gatttaccaa agttttgact 420
taaaattccg attttctggg tcatttttcc cctaaaaata cgattttaat tcaaaaaatc 480
tatattttca aagaccaaag taccataacc ttcaaaaaac aaccactttc tctattgcat 540
cagcgaattg tcatcacccc tctcaaaata tacaaaacgt catcattttt ctgtgttttc 600
tctaattctc ctgaaaaatt ctataaaacc aacagttttt atcatcaaaa atgccttttg 660
accgactttt tttaaagttg aaaatcgtac agttttagca gaaattccag agtttcattt 720
tgaagtatgc tggaaataat aaaattattc taacatttat taatattttg taaaactaat 780
tctatacaat aaaaaagtaa aatttaatat taaaaaaacc ggtttttctc aaatttccat 840
tccccaatgt cctgttctat tatttgttcc gattcggcca cagaacgcgc acacacacac 900
tttttgctga ttctctgcct cctttctttg atttgaccgc attttatatt gatttcggc 960 cacaattcca ctatttgttc agtttgtcga tttgttggaa atttcaattc cggcaattcg 1020
ccgatttgcc ggaaatttaa attcagacaa tttgccggtt tgccggaaat tttcagttcc 1080
ggcaattttt taatttgccg gaagtttcca tttcggcaac ttgccaattt gccggaaatt 1140
cgccgttttg ccggaaattt tcaattccga caacttgcct atttcccgga aattacaatt 1200
ccgccgattt accaatttgc cagaaatttt taattccggc aatttgccga tttgtcggag 1260
atttcaatcc ggcattttgc cgaaaatttc aatttcggca gttcgccgat ttgtggaaaa 1320
taacaattct ggtcattcgc caatttgccg aaaatttcaa ttccggcaat tcgccgattt 1380
gccggaaatt ttcaattccg gcgattttcc tatttggcga atatttttaa ttccgccggt 1440
ttgccgcttt gccggaaatt tcaattccgg aactttgccg atttgccgat ttgccggaaa 1500
aaatcttttg ccgcccaccc ctaataaaga cttcaaaata tgcgtttttt tttgctttta 1560
acacgctaaa actctctaaa aatccccaat ttttcagctt aaaaaacccc aaaaaa 1616

<210> SEQ ID NO 39
<211> LENGTH: 726
<212> TYPE: DNA
<213> ORGANISM: Caenorhabditis elegans

<400> SEQUENCE: 39
ttttgcagac taaaaataac tactctgcca gtgtttaatt tatagatgca atttgtcact 60
attttcattt tatatcgacc aacccattca cacttcacta atcgtgttaa aactcaatta 120
gtggaaaatt tgaaattcta tgaaactttc atttgcgaca aaagattgtt gttttcttca 180
aaccaaaaat ttatcaatgg gaaaatgaga tagacaagaa ctgggaaaaa agtcgaggtt 240
aataatttaa agaaatattg aatattcggc gccataatat taacgaaaat aaccaaaata 300

-continued tgcccaatta ttatccaaaa agattagaag ttggcaaacc ttgggcaaga atttccagag 360
attgcactaa agttgtagcc aagtttgatc caactttatc caatctttta ctaaaattat 420
ccttaagact atttaaattt tagatagaga attggcgaga gttagatccc acttggatat 480
gacttatagt tagcctaacc tgaagctatt gcttgcttga tcatttggtt tatcgctttg 540
ctacttggat aaccagctcc aatagttgtt atttttgctt ttgtcatcat ttttccacga 600
tttacactct caagtgaaac caactgttct ttgatgccag acgatgacat tacacttgat 660
aagaaaatat atataaactg gaattaaaaa caattgatac atcgattcaa ttactgaatt 720
ctaatt 726

<210> SEQ ID NO 40
<211> LENGTH: 1283
<212> TYPE: DNA
<213> ORGANISM: Caenorhabditis elegans

<400> SEQUENCE: 40
atttcatttc ttttttataa atacttcggc tctattactg aatgaataaa tgtataatga 60
tgctctccaa atcctcttat tattcgctcg aaccgcccgt tcccatagat accgtctagt 120
tttgacaggt gttcaaccat ctgccgggaa ttacgagaag agtcgaatta attgagatcc 180
tcgtctaaat aaatctgaag tttaaaataa agccagaaat acctgaaaag agagaaaaag 240
tgtgtccacg atgtctttgt ttatgaccag tggtgtgtta tcgagaaaaa ctccaatgaa 300
tcacacacca gagaagaatc gagaaaggtc gggaaattag gaatgagaaa taataaatgt 360
gaggaagtaa taaaagaatc ttcgagaact cattccactt ttagatataa aacaagcagc 420
aaacgggttt gtaggtatta tatttatcta ttttaagttt aataaactat ttttgctaaa 480
cttaaacggt tcaggtgttg aaaaagtcct aaaatttttg atattatcaa attcttttag 540
cgtggcggtt ttcttttttt tcgaaatatt gagtttttca tctgaaaaat gcactattcg 600
tgtccttcaa aagttcatgt gtcatcagta gccactcgaa agatcgatca gtccattttg 660
atttcgaaag taagaagaga tcattactat tcaagagacg caggcacgga gcctgttgcg 720
ccgcgaatct tccaggcatt cttggcgctc cgcccaaaaa attgcaaaaa taaaagttgc 780
ttgaatcatg ttgaatgtca cttaatcgtg tggctttcaa tgttctcttt cagaaaatgt 840
atttttattt tgataatgtt aagaattcgc cgagttattc ttcctcaaaa tgtggtgcgc 900
gctctctctc cccctttttcg tcgcgaacat tctctgcgga ggcatctctt cttttaattc 960
acaattctca acacttttct gtaggcaaaa ctctctaata ttgctccttt ttcagatttt 1020
tgttcaaact ttttttgtat ttatcttgtt caagtgtttt ccattcagca gttacagact 1080
atttaaggaa attttaggtt tttagcacat ttttctaatt ttttgacgaa attcgaattt 1140
tctagaatcc cgccacgccc agtcatctag taaatttgtt gaacttcatt tctctatttt 1200
taatcattgt tctcgacgtc ctaatttttt atctccattt gagtgactat ttcttgattt 1260
ttaaattatt ttttacagta aaa 1283

<210> SEQ ID NO 41
<211> LENGTH: 1622
<212> TYPE: DNA
<213> ORGANISM: Caenorhabditis elegans

<400> SEQUENCE: 41
gctctgccag aagaagcatt aaattgtttg atattcaaac ttttgtatat agaatctcgt 60
tatttataaa ctctttttt tgtatttctt ctggtttttg atgataagaa attttatgtg 120
cacataaatc aaaaaagccg gaaattaaat agcgttttat caggcagaaa attggccacg 180
tgacgtcatc attttcctgt ttgaagaaaa tctggaaaat tttttgtttc agtcaatttt 240
taaagatgaa aacttaagtt agactgtaaa agcaattttc gcgccaaaat tacggtatcg 300
ggtctcgaaa cgacagtttt ttatctattg cgaaaatatg tgcgccttta aagagtactg 360
tagttgcaaa cttttgtcgc tgtggagttt ttatcgattt tttatatttt ttcgatgaaa 420
acaactcaaa tataacaata aaaacacaaa attaaaaaaa aaatcgataa aaaatccgcg 480
tcaacgaaag tttaaagtta cagtatttgt cgtttcgaga ccgggtaccg tagtttttgg 540
tgaaaacatt gcaaaatttg gtcaacaatt tcatcgctgc gagaccgaca caacacttta 600
ttttattttt gggtttccct tatcgcttat cataaacatg tgacgtcatc atctcttgta 660
cagagcaccg cgactgggag tataagaatc gccggaaaac atcaataatc agttcggtag 720
aagtgaaaat tgagcgtaaa atatgatcat ttttcgatgc accatatttg acgcgcaata 780
cttctacaag ccgctgtgta ctgctcgtgg acaactttgg attattttt gtttttaaaa 840
ttcaaaatag tcaatatatt gcttatttat agcgcgcctt tttgacagta agtttgtcaa 900
atttgcgcgt aagttatggt gtttgcacat atgcaccata cagcaacacc ccgcggcccg 960
gctagtggta catccatgca aatgcgctct actgataatt tgagtttaac caggtttagg 1020
cgcaagataa gaaaaaagct ttggaccaaa aaatttagag tttatttttt tcggacattt 1080
tttatataca tcacaaaaat attgggccac tcgtttttga taaaaacgac aagcccaaaa 1140
gttcaggtat acggtagaca aattgcgtac aggtaccact tttccacgta gtgccaggtt 1200
gtcccattac gctttgatct atgaaaaatg cgggaatttt tcgtccagaa aaatgtgacg 1260
tcagcacgtt ctcaaccatg cgaaatcagt tgaaaactct gcgtctattc tcccgcattt 1320
tttgtagatc tgtagatttg tagatcaatc cattccccgt ataccctgac ccataatcaa 1380
tacctaccta atttttgtct ttccccctac ttttttgcct gtccaaaata agcgagacta 1440
tgccgtagtc tggtgtccaa caacatgttc cttatcagtg ataacgctac aatcttcttt 1500
ctttttctc tgtttctctt gtctctccca acccatattc cgtattacac ctcgtcgtgg 1560
tcattttttt gttcagagtt ttatttaatt ctaaatttcc taactaaaat ttcagaacca 1620
aa 1622

<210> SEQ ID NO 42
<211> LENGTH: 1555
<212> TYPE: DNA
<213> ORGANISM: Caenorhabditis elegans

<400> SEQUENCE: 42
aaactctttt ttttgtattt cttctggttt ttgatgataa gaaattttat gtgcacataa 60
atcaaaaaag ccggaaatta aatagcgttt tatcaggcag aaaattggcc acgtgacgtc 120
atcattttcc tgtttgaaga aaatctggaa aattttttgt ttcagtcaat tttaaagat 180
gaaaacttaa gttagactgt aaaagcaatt ttcgcgccaa aattacggta tcgggtctcg 240
aaacgacagt tttttatcta ttgcgaaaat atgtgcgcct ttaaagagta ctgtagttgc 300
aaacttttgt cgctgtggag tttttatcga ttttttatat tttttcgatg aaaacaactc 360

-continued

```
aaatataaca ataaaaacac aaaattaaaa aaaaaatcga taaaaaatcc gcgtcaacga    420

aagtttaaag ttacagtatt tgtcgtttcg agaccgggta ccgtagtttt tggtgaaaac    480

attgcaaaat ttggtcaaca atttcatcgc tgcgagaccg acacaacact ttattttatt    540

tttgggtttc ccttatcgct tatcataaac atgtgacgtc atcatctctt gtacagagca    600

ccgcgactgg gagtataaga atcgccggaa aacatcaata atcagttcgg tagaagtgaa    660

aattgagcgt aaaatatgat catttttcga tgcaccatat ttgacgcgca atacttctac    720

aagccgctgt gtactgctcg tggacaactt tggattattt tttgttttta aaattcaaaa    780

tagtcaatat attgcttatt tatagcgcgc ctttttgaca gtaagtttgt caaatttgcg    840

cgtaagttat ggtgtttgca catatgcacc atacagcaac accccgcggc ccggctagtg    900

gtacatccat gcaaatgcgc tctactgata atttgagttt aaccaggttt aggcgcaaga    960

taagaaaaaa gctttggacc aaaaaattta gagtttattt ttttcggaca tttttttatat   1020

acatcacaaa aatattgggc cactcgtttt tgataaaaac gacaagccca aaagttcagg   1080

tatacggtag acaaattgcg tacaggtacc acttttccac gtagtgccag gttgtcccat   1140

tacgctttga tctatgaaaa atgcgggaat ttttcgtcca gaaaaatgtg acgtcagcac   1200

gttctcaacc atgcgaaatc agttgaaaac tctgcgtcta ttctcccgca tttttttgtag   1260

atctgtagat ttgtagatca atccattccc cgtataccct gacccataat caatacctac   1320

ctaatttttg tctttccccc tacttttttg cctgtccaaa ataagcgaga ctatgccgta   1380

gtctggtgtc caacaacatg ttccttatca gtgataacgc tacaatcttc tttctttttt   1440

ctctgtttct cttgtctctc ccaacccata ttccgtatta cacctcgtcg tggtcatttt   1500

tttgttcaga gttttattta attctaaatt tcctaactaa aatttcagaa ccaaa         1555
```

<210> SEQ ID NO 43
<211> LENGTH: 2432
<212> TYPE: DNA
<213> ORGANISM: Caenorhabditis elegans

<400> SEQUENCE: 43

```
ttttattctg aactatatac aaaatgtgct caatataacg agttttgtaa ttttgtgaga     60

aagtcgtatt gaaaattagt ttaaatgtga tttaatattt cgaaaaagta gtctaatttt    120

agctaaattc tacaattttg acaacttttc cgtgtcgcaa aacgaatttt tgtagaggag    180

tgtacctaag cgagtcggag aaacgtgcat tcttccattt ttttccccccg gggagcccat    240

agccagtttc cggacgggcg gtcttgttcc aaacgttttt aaaatttaat attgcaattt    300

aattatctat tcagcatccg tagcccagcc gcattgtgga tctcagattg gcgaatgctt    360

gtgcgctcca ttggactccg gagccattcc gtctgttgat ttcctgattt ctgcggaatt    420

gtccggatcg acgagctctg taaaaaatta atttaggaaa aatcaacatt ttttcgataa    480

gcaaacctta attccttcgt cacacttcta tggaatccag ctgacggcgg cggctgaaat    540

atttttgcaa aaaaactcac ttttcgactt ttcctctttc tgcgatcggt tttcgcctcg    600

atttgcgttg attagcttaa aatagttttt atattttaac taataataaa gaaaaacaaa    660

aaaaaatgag aaaaaacaat caaaaactcg aaaaaaacat tacgaaatca gcaaagaaaa    720

tgaagaaaaa atatatacag taattttaaa ggcgcacaca caaaagtttc ggtacgcgtg    780

ccgagaccac tcagcagaag tgtgctcctt tgaatctgga gtacggtcaa tggggattta    840

tttttgaaaa tgcaaatgcc aaaatacaag aaaaataaca aattgcatta attttagtga    900

attttctgaa aatgagattt tttgtgcttt ttttggaatt gtgcaacttt tagtgcattt    960
```

```
tcatcgtcct tttttctgaa ttcttgaagt ttctggaatt tttgttcccc cccccccccc   1020
aatctaagac taaacctaag gctgagtcta ggcctacgcc taagcctaag cctaagacta   1080
agcctattgg tgtatgtgca cataaatcaa ttttttaaa aattattatt atttttgca   1140
aaacacaaac gttttttttc agatttttta tttttcaccc tttcaacctg caaaacccat   1200
ttttcttcca ccaaaacaca gctgttcttg ccaccatttg cctgatggaa aatttatata   1260
aattggctgt cctttgtgag aaaactagaa caataatgat gacattaagt actagagtat   1320
aaatatattt ttttttgctg acaattcctg gcgtcccccg ttgacattga aaatgtataa   1380
aagaggcggc cagacaccat ccccgcaaat gtgtttttgt tgttcacttt tcttttttt   1440
tccactctct ctctctcagc tgtttgcatg ttgtttttat ggtgatctat ggtctctaag   1500
aatttgttta taagctaaga actgctcgct gagaaggttt tttttggttc gtagctagtt   1560
tttttacgt ttatcgaaaa aaaattgaaa aaagtcgaaa tttccatctt aaaaaaattag   1620
tgaattttaa tatttttgtt aaataatcgc cattgtttcg tgcttttctc gctctgtaaa   1680
attgaaaatc tataaatttt gggtaatttc gagtattacg ggagcacaaa attttgagaa   1740
tgcgttttgc acaacctatt tgacgcgcaa aatatctcgt agcgaaagct acagtaattc   1800
tgtagcgctg gtgtcgattt acgggctcaa gttttcgaat taattttttt tcgaaaagtt   1860
acatcgatat ttcattttcc ttcgtgctat tttcaaaaat cgagcccgta aatcgacaca   1920
agcggtacag taatcattta aaggattact gtagttttcg ctatgagata ttttgcgcgt   1980
caaatatgtt ttgtgtcccc gtaatatttt tttaaatcaa atttcacatt ttaaccataa   2040
aaaactcttt caaaagtgta attttctacg caaaaatgcc gttcggatga aaaattactt   2100
ttgaaaaaca aactcgaaac tacggtacgc aaaaaagtac atcggtgttt gcacataagt   2160
gaaaacaatg ttgtttttt gtaattaaaa tcgattaatt tttttcccg gaaaacaaaa   2220
acgttttcag cgtggatttc tattgtttct tgcgtaaaaa aaaattattt accaatttta   2280
aacgataatt tccacgaatt ttcgccatta atctctcgat tttgttgatt cttgactccg   2340
agcaatctct ccggttttcg caaacgatta tattatttat ttgttttcct tttcagtgcc   2400
gattctcgga aattcaacag taaatcttca aa                                 2432
```

<210> SEQ ID NO 44
<211> LENGTH: 2150
<212> TYPE: DNA
<213> ORGANISM: Caenorhabditis elegans

<400> SEQUENCE: 44

```
tttgagaatt ttctcgggaa attaaacctg tgtttttcat taaatttgat gcaagcaaca     60
agtcattata caataaaatt ggtgaaaata tgattttttt gaaatatttg gggcgaggct    120
tttagttttt tgaagagctt acaaaaatta gaatttaaga aattttcgaa cacaaatttg    180
agagaacttt tgactttttt caaaaaattg ttttcaaaaa ttttaatatt ttcaaagacg    240
aaagaatttg ttttttgtc taaatttacc taatcattat ttttcaatca aataattgca    300
tctctgaaaa cctgggaact ttgaaaatga cgtcattctt ttttccctcc ttttcttttc    360
catttggtta ttgacgtttt ccaccccctc ttgcaaaaaa aactaaacaa aaaagaaacc    420
attggcaact actaacgcca attttgtgtt gcttcatcgg gtttctttta gttttttttc    480
tgagagcgct gagattattt ggaaatttgc attttctcac gttctagctc agaaagagat    540
cagctttctg aaattgaaat ttaaaaaatc gctctaaatt gaaacagctg tttttatgt    600
```

cgattgtctc tgcaaatata tttttttcag aatatataag tatgtgtttg tttaagtttt 660
attttaaatt ttcttgaatt ttatgaacga cattagagct tatgttagtc caaatatttc 720
aaaatttatt aacttgaatc ttgcgcaaaa ttatttgaaa aatcaatttc cagccaaaat 780
cttctttaaa attttatttg aattgtcaaa aacaaatgcc tcattattaa ttttatgcca 840
atattaaaaa aaaattaatt ctcgataatc ttaaaataag atttttagaa aaacaacttt 900
caaaagcttc tatgcgaaaa aaattgtttt tattcgaatt aaaaaaaatg ttttcttcaa 960
aaaaaacaaa tttcttaaat catagatccg tgttgctcaa ctgctcaatg tttcccatga 1020
caaaaagtcc atgtctctct ctatcatttc tcatctctct tttttctcta gccatcataa 1080
aaataaacac atgtttcaac aatcattcct tggtttttta tctctcgatt gctatatcat 1140
ttttattttt tttactattg ggtaaatttt gaagagggta ctgatttttt ttcaaaattt 1200
ttccaatcca aaagtctttt gaattgcgtt aaatcatgtc tattgtacca caatgaccaa 1260
atgccatagt aaaacttttc aaaaaaatgt ttgaattttt ttttgagcgt cagaaagtgg 1320
caattacaga gtttttttta gcactatgaa aattgaaaat tttcggagtt tttcaaaatg 1380 atttttttgaa attggaaaaa ttacagaaaa caattttttg ccattttttt ggaagttgcc 1440
gataaaaaaa aatttctttg gattttatgg ttttattttg ttgaaaatat taatattcaa 1500
accaggggtg tgcggcaaat ctcaaaactt gccgagctcg gcaaattcgg caaatctctt 1560
ttttcaatat ttgccgagca cggcaaattc ggcaaatttg cctagctagg caaattcggc 1620
aaattcggca aatttgccgt gcttaacaaa ctcggaaaaa tttgatactt tttgatgttt 1680
tttggagcac caaaactact gaaatcttaa cactcatctg gtttctgaat aagttccgtg 1740
tagtatgtct gcttaagcat caaaataacg caattttgtg tcattttact aaatttttgg 1800
cgaaaaaatc aatggtttta gtcaaaattg cattgtcaaa tttatgacgt gtgcggcaaa 1860
tttcgaaatt tgccgagctc ggcaaattcc gcaaatctac tgttttgaaa tttgccgtgc 1920
tcggcaaatt cggcaaattt gccgcacacc cctgattcaa acattgtaag ggtttgaaca 1980
tgttcttaaa atgtgacaaa aactcagtaa taaaacattt aaattttttg aacactttta 2040
ccatgatatt tggtcatttt ggcacagcct taaggttaaa gctttaacaa tttccccact 2100
gacgctactc caccataatt ttgaaaatct aaaatattca gaaattcgaa 2150

<210> SEQ ID NO 45
<211> LENGTH: 1845
<212> TYPE: DNA
<213> ORGANISM: Caenorhabditis elegans

<400> SEQUENCE: 45
tttttaagaa aatgaccaaa agaatattaa aattttgaat tatggtaaag aatacaagcc 60
agcaaagaat ctagttattg ttggaaaact atgaacatca tgtcctcagt tttcaagaaa 120
acattaagat ttcaaaacta tgtattctgc atggcaatgt tgcaacaaac catttcctca 180
taaaactagc caactaacac agttattcct aataaccaca atgttctctt ttcatatgtt 240
gcctatgtaa ttctttctca gaaacattat catgaccata aaatagacaa tgtattggtt 300
tctatgtttc ttcttcctgc cagtgtcctc tcgcgttgtt tgagtactat tgttccccac 360
tctccccccc cggcgtgcgt attatcgctg aaaatgtcat attatctaat cgaacaatgc 420
ccattttttg ggatgtttaa tagcaaacat attccgattg gaattgcaaa attgagttat 480
catcttttta ttgttggtct tgtgactgtg agtttatgtt tggaatatag ttttgataag 540
tttgaaacta ttgtgaactt ggaattttttg attctccaag tttttaaaac gctatgcacc 600

```
taaacttggt attttttttc aatttaacaa aattctactt tcaaaaaaca ctactcttat    660

ttgcatgttc catagtatgt atttcttggc agtgtttttc aaaaatagaa ctccttccga    720

tttaaacaca taatgttgtg ctttttaagc ctagacacga cttccgatgt gatttttctt    780

cgaattctcc ctgtctgtaa gaaactcaca tgctgactgc aaagaatgtg cctattgcgg    840

acctcaatca gtgtcggcta cacttttttta gtgtcgtccc gaaagttgtg gtgttctgag    900

aaaacataat ttttattgat ttttaatgca gcaaaatttc aaataactga tacccggttc    960

accctaattt tcccatggat actccaaata tgttcagaaa tgcatatttt tgtacaaaat   1020

ataacgtttt ctaaagtgtt tgctaaaatg ttattgttct aaaatctttt gaaagaacca   1080

gaaaatctca aattcttaaa acatttttca tcgaaatgtg atatttgacc agccagtggc   1140

gcctaacttc tgaactttgc ttcacgcaat ctctgctttg atttctgtcg tttctctact   1200

gatttttgtt cactttcacg taagcgttca actcgcggaa ccaaagcctc cgttcatatc   1260

atattaggct ttcatatcta ccatttttct actaatcatt gttgttacaa tcgtttttttc   1320

tctgtttcga agaggcactc tacttatgac tacaacataa aagtagtatg gaattcgcgt   1380

ccttggtgac cagaggcgtt cctatttcga atctctattc gggtggaggc attatccgaa   1440

tcccgagaaa cattcttgtt tgtgtaatct gtctaatcaa tccccccttcc tatttttctc   1500

tgttcccttc cttgtcttca acatcgccct tcgatcatct gaattcagtt cgttttcgct   1560

ccgcccatga agttgggcta cataaaaaga ggaactgaaa tgacatcagg ggaagttgga   1620

tatatatttc attaagttgt actatcattt ttttcttttt tctcttttttt tcggtttgat   1680

tctatctttt caagatggcc tcgcttattt ctacgattgt caagtcaacg gtcaaagttt   1740

ttgaattgtt gcatttttct ggttctttga ttttgttcct ttttaattcc agttgtagtt   1800

taaattattt tcaggaaaga aaaccgagaa aaaagatatt acaaa                   1845
```

<210> SEQ ID NO 46
<211> LENGTH: 2272
<212> TYPE: DNA
<213> ORGANISM: Caenorhabditis elegans

<400> SEQUENCE: 46

```
agtttggcca atacctgtga ataaaaaaata atttattatt ttaggaagtt tttataaatgc     60

aaaaaaagga gtagaggaat tgtattagaa tattattaaa tggaaatatg aaatagcaat    120

tggttgatat tatacttcga atctcagaat cactaaaatg aaaaccagaa ctgcttctgc    180

ttgattttta acatactttt atgttatttg caatgattaa aaaatatata taatacgcga    240

gaaatttgaa actggtttgg ctcgataaaa aattggtgag aaacccaaaa tatcgtgaaa    300

gaagcggtgg aattaaaatg atttgagaaa gtaaattttg ataatacgaa ttataattcg    360

aaaaaatggt ggtacttaaa atatagcaaa taaaacaggt gagaaaaagt tttgaggttt    420

ttactatatt ttaatcaaac cgtttgtttt atttattttc aggcatcgaa attttatgta    480

ctcaagctta tagtaaaaat acaaatattt gatatattaa acagagataa aacataaata    540

acgagctcta aaaaattagc atattttggg aattaagaaa accagtgaaa gccgtaaaaa    600

tgatctgaag ctatgaataa gtttggttag agactctatt tctagtagat tactttatta    660

taataatgag cagaaacaga tattttttta gcatttttttc acttcatcat taaattaaaa    720

tcattacaaa aaatcgatag tccttgagaa gagagacacc aatttacaag caggcaacaa    780

acgagagaga gcgtattatc gtgtaaacgg tatatacggg agaagagtac gggagaccga    840
```

```
cggaagaaaa gcaatgggag gtgtataggg tggtggctgt gttgtgccta ggaggcagga    900
aaatataacg ttaaaaagtg cagacgcaga cacaccaatt gcccctcaga ctccaattca    960
gctgtctccg tctcttcctc gtcctcatcg cacaccctta gaccggttgc ttaaaaggag   1020
gagaagcaag tacgcaagca ttacaaacga cgacattact gacctcttat aattaaagta   1080
ataaattgtg aaaatgtaca ccgtttttta tgaattgcat aaagcgaatt tatttataaa   1140
aagttaatat atataaaagc tacatgttca ctgatctaca atttttggtt tcagattttt   1200
ttgaaatgtt gttatcaaca gtcgaacttt aaatttttct tgaaaacttg atacataaat   1260
taaaaattga acgataacat ttggctaact ttttccatgt ttgcctttgt gcaaaggtta   1320
tcacttgatt atttattttt ttgaaatctg gagcaataaa aaaaaatagt aaggatagag   1380
ataaatacaa actgaagccc ttatgtttat tacaagttat gacaatttca gtgtagtttt   1440
gaaaatatca agtattgcag ttaaatttac aatgccaaaa aatctaagaa acattacgaa   1500
gttttcatga aaatacctcg aaaactatga aaatagatca aagaatatcc ttaaatatga   1560
aagaattcag acttcattgg gttttgaaaa aaaatggaag ggaaaaggaa tctgattaaa   1620
atcagttttt ggcattgtag aagtatactt caataagttt gttttcaatg atagagctta   1680
gtcagttaac attcaagtta acttgtaatt gtaacctggt aataaaaaat caaaagataa   1740
acaaaaaata ttgtggaatt atcaaataca actaatcgga aaaagttgat tttgaggcaa   1800
acatagcttc atctgctgta cattatgaaa attttattga agaggagtta atgaagtggt   1860
acaaaacacg atgaaatgat aaaacatgaa caaaatcgag ttggtcacta tacactaaac   1920
aggacacgta ataagaaaag tcaataggca cggagagaca aaaaggtcat cctacaattg   1980
cggtggctaa ctgcatctta actacgtcgt agcattaaaa aagattgata agacagtgcg   2040
tgtatgaacg cacaaaaaga aaaacctagc aggacatcat gaggttttat tttagcgttt   2100
ttttgcatat catttttat tcattttgtt tcagtaaaat aagtttagat tcattttttta   2160
aagcgaaagt taatagaata atttgatctt gaagttgaaa attgttgtta atttttaaaa   2220
actttgtttt caaattgcct aatatttttt tgaaaacaga acataaaata ac           2272
```

<210> SEQ ID NO 47
<211> LENGTH: 1075
<212> TYPE: DNA
<213> ORGANISM: Caenorhabditis elegans

<400> SEQUENCE: 47

```
cttctacgtg gaattctgga ggttgaagct tctggtctaa ccatcatcag taagaatgta     60
aagaccattt cgtgtttcat atttatgccg tcaattgtca gtacaagggg ccgcccgttt    120
tcgtttcgtt tcgtttaaat tatagggaat acattataaa atcacacctt ttgtgtatat    180
cttcgtagtt ttattggaca ttttaatagg ccttgtttat aaaagaaaat ataataatga    240
tgacattata caaaaaagta ttcaaggaat gttttatagt tacaaaacct ataggtatac    300
agaatatgtc aaaatagggg aaaaaactga atgtatgcag tcgacgaata aggttgtctt    360
gacatttttt tggttaataa tgtttttcct gccagtttcg atatctttga aattttgatc    420
cagatgacat caatcctagc tatggaataa tgggggaact ctctttaaat tcacaacttc    480
attcgagcaa aatttgtctt ttgcacacga aaaattatta ttattattgc acaatcaaat    540
atttttcccc cgtgcaagtg tgcaatgggg cgacgggtcg agccagaaac ccgtgttgtt    600
gaaaatcaaa ccaagtgcaa aatatccatt ttgcttaatt taaaacgatc taggataact    660
ccactagcaa ctagaatatc taattgaagg attgaaattt ggaaacttac aataaggtat    720
```

```
tctattttat tacgttttca atcttgctag gaaaacttgg aaaaaaaatc cataaacgtt    780
tcccggttat ttcagaaatc gatagtcgac ctccgttgtt ccttatctaa atttcatcaa    840
ttgtatcctt tttgataaga caatactatc tttttatcac tacgtctcct tcactctaaa    900
tcctaatgta gtatcaatca atttgatgaa aagactacac tggggcccac ttattttctt    960
tttcaatcaa aattcacact ttattttata tatttcttgt aaattgtatt tttcttcatt   1020
tttaattcta ctttttttca acaattaact ctcgaattct tcaatttttt acaga        1075
```

<210> SEQ ID NO 48
<211> LENGTH: 645
<212> TYPE: DNA
<213> ORGANISM: Caenorhabditis elegans

<400> SEQUENCE: 48

```
aattttcagg agaatcaatc gacgagcttg aagatttcga caccggtcta ctatcttccg     60
gaggatccga ttattctttt taaaattttc ttcttttaaa aaatttcttt tgaaataaat    120
aaattctcac ctaggaattt caacaattca acttgaaaaa agttcgcgca aactacgaac    180
aaatgtgtgt cgagcgggcg gagccactga gaaagaggag caaaatgtac acaaaaccat    240
atttgagtgt aatttttcaa agtttggcgc cgattttctg tgagagatga gttttctcaa    300
tttatatttg gttattttta ttttagttct tactggtaaa tttctgggta agtcctgatg    360
actttgaaaa cgaaaaaaac tctttcattg atgctagtgc gattgctagg aaagcaactt    420
ttcagttacc aagaaaaagt ccaaggccat agggattagc tgcgtggcat aacaactcat    480
ccatcctcgc agatgcaaat ccgctctatt ggcaaataac atggaagagt ataaacattt    540
tctcttccac acggaaacct agtccccttg gggagcggta gtgcccacaa ccccgcatgt    600
ttaccaaact acacagacag cgctattgtc tgcaagtggc aaaaa                    645
```

<210> SEQ ID NO 49
<211> LENGTH: 1825
<212> TYPE: DNA
<213> ORGANISM: Caenorhabditis elegans

<400> SEQUENCE: 49

```
agcgtttcgt tttagaatcg ccagtgtatt ttttgtgata gtcctatgtg ctttaaatta     60
tttattttga aaggttcaat aaattatatt ttatgaccga acacattata ttctcagttg    120
ttatcttata tatccacacc ggaatgttga atatctgacc atatatattt agaatgttgc    180
ggtaattttt ttgttgctgt ggaattttat tttattttta tttttcatag tttcaacatt    240
ttacaattta ttgaaattta tgggttttaa ttgttatatt tggcgttttt cgtttacttt    300
ttcgataaaa ataaattcag ttaaaaacta agttataaca atgaaaacac ataaatttga    360
acaaatcgta gaaaaatcac tacaaatttg acagatttta tgggttctat cgcgatttat    420
tgaaattaac gtcttttaat tgttttattt tagtttttta gataaatact gttttcaaac    480
gaaaaacttt gaaaaatcga taaatctcgc agtactcctg aaaggcacac actcgtttgt    540
acttaagaaa aattgtcgcg acgagaccaa ctgtccaact acggtagttt tcaaaatacg    600
cggttcaccg caaagtcaaa ttgcggacct gaacattttt ttatttttcc cgcaaacttt    660
ttttttcaat tttgcctaaa gcgctcgaat aaacatgaaa gtctcgtgtt tccttccatc    720
cagacctctc atttttcaat tttaaaacta aaagcacttt ttgacctact ttttgtcgca    780
accgccaaaa ctcgcttcca gaattattcc ctttttagga ttttcgacgc aacatctcca    840
```

```
accggttagt tttttcgcag attttctcgc attcgcgtag tttcacttgt ttacttcgtg    900

gcgcctcgtt tttttccgct ctctcgtctg accaccttca tatttattga tctgcgccta    960

gcggcgcccg ttgaaatact ccacattttt ttgcaatctt gtctgcgagt tcaggttatt   1020

ttcgactttt atgaaagctt gctaggaagc catagcaacc ggggaagaat acgctagcca   1080

aatgagagat agaatcgatc agctaaattt aagataaata gtgaattcga attctaagac   1140

ctgctcgacc agctgaaatt ctaaaactct gcgccaagat gtatagacag gtaataatat   1200

ttgaattttc tttaaaagtg accttgaacc ctaagatttt cgctcctcct aaacgttgta   1260

gtctgttact ccctgccgcg acaattgtca gcaaaaatcg cgtcacatga tgatgaaagt   1320

ttgtggcaat gttataaaaa gactgacctt atttcgtttc ttggaagatg caaagaaatg   1380

tttattaaaa attgcagtgt gaaatcatgt ctctcgctcc aaaggtgcat ttcttatttg   1440

tttttaaaa atatatttgg ttacttagat attaatttaa atcacggaaa agtttaaacc   1500

cctcgatttc tgttatttaa catgatcact cacttttata acaattaatt tggtttttca   1560

aagatgttcc cagaatgttt tattagttct catttcgtcc tccgattttt tttctttcgt   1620

cgctctccaa ttttgccaat gtatttcatt cccattagat aagcaccgcc cgtcacctta   1680

ttctccttct tttcacattg caaacaaatt cgttgccgtt gggtttcaat atccttttca   1740

ttttttgtcg tattgttgtt cttgtgattg tggttgttat tttatcgcgg tattattttt   1800

ttttgttaaa ctaattaatt tttag                                         1825
```

```
<210> SEQ ID NO 50
<211> LENGTH: 2300
<212> TYPE: DNA
<213> ORGANISM: Caenorhabditis elegans

<400> SEQUENCE: 50

tatcaaagtt ttgttgttac ccacccaaac tttgttttag ttgcaacaag ctcacttaga     60

aggaaattga ttttcagtat ttattgaaca cagcaagaaa aatcagcaaa cgtggtactt    120

gtgtgttgca tgcgctcatt ttaataataa tgttgttgaa ttataacaaa taaaaacatg    180

tagcatattt ttgtattttc aggcttaaat aaccatttct aagcctaaag agaaaaaaaa    240

atgtacaaca cgttaaattt aaatggagaa agaaattaac aacatttgat tggatttaga    300

aataagggca cgtaatacac aagtaccaaa cgtgaacttt aaaaatttgc gtacctacca    360

tataatacaa aaccgtgaaa ggtggaatag ttttgaatgg caaattgttt gaattcattt    420

ctatagtgct aaactgaaca aatattagtt tcagttttaa aaaaagtgtt tgaaattctt    480

catttgcagt caagcagtgg caattactca gcttttgaca ttcaagacaa ccaagaaata    540

tgttttcaaa aagtttttcc gtattcagtc aagttctatt ttcctctgaa ctatagctaa    600

taatttataa ttgtacatat caggaaaaat tatgtggttt aagaatctct gaaatttttt    660

ggaaattggg aggtgaaaga atacagtaca cttttgtaat tttagctaat acgttcgaga    720

gttattatca ttatggcagc acacttgttg gtgatttcta ttttttgaca tgatatgttt    780

gaatatgatt ttcctcgtta tgtggaaaat tttgtagagg cagatgctaa acgacaagct    840

agacttttta gtgaattttt gaatcaatta tttataatgg catcaaacaa atcgaaagga    900

tctgtgcctt ttgatatttt tggttttgca acaatttgtc tttgttgttc aaacacgtat    960

acatcaaaaa ctattgttta tttcaacatt ttcagtgtat cttttaaaga tcacatcagg   1020

ttgttactaa aattagtttt gaattcaaaa ataaccaatt aaatgttcca aacatataaa   1080

aaatatttca aatatgtatc agcttcatga gtagtccata acaaaaccca gaagttcatc   1140
```

```
ggaggttgta tatctctgag agtgtcaacc cacttcttat ttttgcgata aaactaatta   1200

aaaactaaaa taggaacaaa acattaattt tatgcttcga gtgaaaattc gtatttattc   1260

actttttagg gagtttctca attattttaa tacatagata catagatatt actttttaaa   1320

taatatttac gttcaatcca aataagattt taaaacgatt cagtaaaagt tcttgcaaaa   1380

caatcaatta gcaactgagt ttggttttta aactgtttaa atctgaaaac atttttaaga   1440

aaatgaaatc cgtctaaatt cattatattt agcaggaaca tgttaaaatt tagtttctga   1500

aatttaccaa ttatttggaa ctaatgtgaa ataataagaa tattattatt caatcatttt   1560

cttgcagaca aagggaatta gaggcgtctg gtcagcattt gtcgtggctc aactgttccg   1620

caagatacat tcgtcgagtt gcgggtctcg tttgatattc acaaaaggag gggttcatct   1680

gcgaagttac acacttcttc tatcaaacca cattgcctca ttttcccaat aactgtctca   1740

tttttgaaga agatgcgatc aatcaccgtc taaaactgat tgcgttgcaa caaatctgtg   1800

atgatatgat atgatggaac ggacggaaag gttaaatttc gagtgaagaa aaaatataga   1860

agtaatatga atgagtagat gaaagaaaaa gacaaaagag aaattgatat gaccgcgcag   1920

cagacagggg catctggtgt gagcgtgcgg ttttttctgt tacctctaac gcagtccgta   1980

cacttgtcgg cgtttatttg tggctgtggg cccattgcgt tgatgacggt ccctctagct   2040

ggctttcatt gtgatccaat tgcaccattt ggtttttgag ttttattcta tttctatcgt   2100

cttttgtgat aaattaattg agtgaatgaa taatgtataa gagcctcatt atattctatt   2160

tactaaacaa aactcaatta tttcttttga aaagataatg aaatttccag tcatcattcc   2220

ataaatataa ttattatttt gccttcgcaa taatcctaaa gatttttat atccttcaag   2280

tttatcaaaa ttgtttaggt                                                2300
```

<210> SEQ ID NO 51
<211> LENGTH: 2931
<212> TYPE: DNA
<213> ORGANISM: Caenorhabditis elegans

<400> SEQUENCE: 51

```
attccaattt cccagccatc cggaaattcg ctgtaaaaat tggaaagtag gacaaataga     60

gaatataata caaagattaa acacttttta cgacaatgtt gacttcgtca tggtacattc    120

agaagtgtct gggaaatgtt cagcaggaaa acattgcaga agagaaaaac aactcggaat    180

gtttgctgaa aagttctgct tggaggtatt tttaaacttg gagaagatat cattgctcta    240

ctttggcggc ttctatcgcg gtagtcttta gtttgatcaa aaatttatca actggcaaaa    300

tacgtacaaa atagttatat acattttgct agttgacaaa tttctgataa agttgaaggg    360

aactgagagg ttataacctg tcaatcaagg agcattatgt ttttaggcgc acctacttac    420

ttcatgcctg cttggctact tacctgccta ttacctgcag tttatatgta ggcactgatg    480

taggcacgta gccatcaagt aggccgcctt ttgaggctca tttgacccat agaccttaaa    540

ataggccgtt ctagaaccct tcttatctga aacaacaatc tttcagacat tttcgaatgg    600

tcaacaactt aagtttttat tttgcaaaaa caaaaaaacaa caagttttca atgttttttt    660

gccagtggaa attattgttg ttggataggt acagatgcta ccgggttacc gagatcgtgc    720

ctaccaggcc tacctattgc ctgcctgcca tgtgcctacc tacacttcat ttcggcaaaa    780

ggtcaggggc caatgaaaaa ggagcatgaa tagattcgca tcagaaattg atgtcggtgt    840

aaggcaggtg caggtaaaat gaaggcaggc ctgtggcagg caaaggtcag catggcaagc    900
```

```
attttgggaa taccaaccag tagttttcat cagagcacga ttgcatcgac gaaaaatttg    960
aatttttgtg tattttgaag agtgccgtga aaagtctaaa tcttttgcta ttgcctctga   1020
ttccttctcg aacctgaact ataaaactga tgtaaagaaa aaaagtttcc aacttaagag   1080
atatcttatc aatttaaact ttaccgagtg attctgtgat atctcaaatt tcagtcgaaa   1140
atcacatgtg gttttccctt ttaattccga gagagagaga gagagaaagg aatttcacct   1200
ccacaacaac ccataatcat tcaattaggt tctaaacaca tacaagaaga agacaggaaa   1260
atgttagcct tttagtcata ggtgctgctc gatcatgatg ttgatgaacc aaacatcgca   1320
ttttgtagga ggggaagagg acaggagact gtccatttga aagtgactac tttgtcggat   1380
atttagagag tgacttactt acgaaagtta taaagtttgg ttagcaggaa atctggtttt   1440
tactgagaaa actctctgag ggaaaagctc ggggtgggtc atatacccgc gagatatctg   1500
ccggtcatta tttaagaatg tacagctcta ctttggcaga tcatatctcg gttattccag   1560
tacatatcaa aaattgactg aatatgaaaa taaaggaaaa tgttcaacct gtattttacc   1620
agttgaacat tttttgataa aaccaaaaat aatcgaaatt gtgcttaacg gaaaagaagt   1680
tagattaaga ttccaggctg ggtcccgcca cgataagctg caaaattatt ttttggagct   1740
gtctgttcag aatcgtcgtt attagaaggt ggaagtgctg aaatctgaaa aaaagaactc   1800
aagaatctat agaatctctc atatatgaga gatcggctcc gtgaaaggca ctaatctgga   1860
atacttcaga aattcggcga aatcttggaa attgaaaact ttgagatttt tttcttgtag   1920
atcgaaaccc gcgagatgtc agatgcttct gaattcagat ttacaaaatg agctcttcag   1980
acactcctga aagatcagct gaccagaata tgcccaccta aggcaggcgt gacttacctg   2040
aaaggtgacc tacgcctatt ctcttgccag aactcgaaac tattttctag gaaaaacttt   2100
tttgtagatc gcattccatg ggagctatac cttccctgta ggcacgcagg cactagtttc   2160
cgtgcctacc tggaatccac ataaccggag cacggagcag caacttcacc ttcagaaatg   2220
attcagagct ttacatatag tttcctgttc ctgaaaagca tgttctacga tgccatgatt   2280
ctcatttcga tgccacttct caaccaactt ttgccgagct tctgaacttg tcgagggagt   2340
ctgaataccc cccaccgccc acactaaact tttttcctct gatccgtgag aatatcctca   2400
ttatctcaca atcagtaatg tccaaatcag gcgggggagg aggggtaaaa aaacacggaa   2460
acgaggaggc gaaaagcgtc tctgggttcc cgcccttcct cccacacgtc ttctctatgc   2520
gtctctctga caatctctcg ttaaagttgc cttttttggg aaaagcttct gtctctgttt   2580
ctctctgtca acgtgtttct cagcttgcgg gcgccaaacc accaccacca tcactgactg   2640
tcgattcgcg gtgtgttgtg tttcaattgc gtaaagagtg agagagagga aaagatagag   2700
agagagagag accccaaggt tatacgtctg ttatacttgt tacccatata ctcttctaca   2760
cctttacctt caacctttcc ccacattgac tccgcctctc tctctcttac ttcttggaag   2820
acactcccca ccccctctta tctatttttt cgaaattctc gacccttcac cctcccccct   2880
tacccgcacc ggtcatcatt ctgactctgc gaactactgg agaggaacac c            2931
```

<210> SEQ ID NO 52
<211> LENGTH: 1860
<212> TYPE: DNA
<213> ORGANISM: Caenorhabditis elegans

<400> SEQUENCE: 52

```
catgaaggcg accgaaaagt gtccagtgaa gattttctaa aaatctcgaa tctggaatca     60
tgatgtgaaa tatatgaata aagaatcttt ttaaaatatt ttgaaaattc tatacatctc    120
```

-continued

```
taaaaaaatg caatctcgtt attacaaaaa gcaaaatctt tcaccttaag cctagatgta    180
ggtaatgttt gatgaacagt aaattttgaa acagtaaatt tttgaattac aaattgaaat    240
tttttaaaa tctattcaga atccctatat ccgcatgcat cagggaacgt gccaaatttg     300
aaaaatgtgt gtttctcaat ctctaatcat ttatcatatg gtcatgacaa caactggtgt    360
caaggtgtac gataacggta cactgtggca attgacactc tttttttctt tatttctcta    420
ttcaacaaga cttgtattta ttaagaaaat gcaatgagag agcgtggtga taagacgggt    480
aattccctcg cttttctcat tttttgcggt gttgtgttcg tgtcatttga gataatccat    540
gttgattcca cttttattgt tgatttgata gatgttccaa gtttttactg cttcctgaaa    600
gcataattct taaaaataat gcttcatagc agttgtggct tcatacaatt ttcaaaaaaa    660
aattcactgt ttcaaaaaaa ttgaattcaa tttcctgcat tatgacgtac gtgttaaaaa    720
aatatgttca cctaaaaatt ccgctcgaac tgtcgcgaaa tctgtgtttc agtgaaataa    780
aataaaaaca tctagacaaa atacagttct cctcaaaaat tgctgtttca aaataataat    840
ttaaaaaaaa acaccaaagt gtcgtattta aatttaaaaa aaaactatcg tttcaacaaa    900
acaggttcaa atctatttta gtattaaaat ctataacttt ataaaatttg ctatttaggt    960
tttacgaatt gttgtttttt actctgaatt gtaaaattac cgtttcaaat atattcttct   1020
aaattcaaaa atttagtata caatttttct agaaacattg aagtattacc aggaattttt   1080
ggatatttcc tataaattct attttgatca atttgtagtt gtcttatcat atattgcatt   1140
ggatgataat aggaaatgat ccgattctct ttcctgttcc aaaactaggt aaatgtacct   1200
catatatttt gttaattttg tagtcacaat aacatgttat gataataata tcgataaaaa   1260
atatcgtgat gtttaaacat taagtttcat ttttttcggt actgttctaa ttgttcaaaa   1320
caatttaaaa aatttcggtc aatttataga caataccgat tttaataatg aatgtaaaat   1380
tttcactgtt tcactaattt tataacaatt ttcattcctt ccaattcaca ttgtgttagt   1440
gtagtgatca ttacttatat attttaaaaa aatagggtgt tagttttttc cgtttgtctg   1500
tttgtttccg tgacgtcaca acgcatgaga cccattttgg cgcaaattca aatttcttca   1560
gaaaaatttt ggtgcaaact caaatttctt cagaaaaatt ttagcgggaa ttcaaatttc   1620
ttctgaaaat tttggtggga tttcaaattt gttcagaaaa attttggtgc aaattcaaat   1680
ttcttcagaa atattttggt ggttttttct tccgcgccgg aggcgcgatc agcagctagt   1740
tttcaaataa atttactgtt tcaaaaatac gatatttttt gcctaatttt tgagaatatc   1800
actatgacgt ctaaacgtaa agcgattcca taatctactt caaaattcca ggctccccaa   1860
```

<210> SEQ ID NO 53
<211> LENGTH: 2793
<212> TYPE: DNA
<213> ORGANISM: Caenorhabditis elegans

<400> SEQUENCE: 53

```
cagtgtaggc cgtcttgctc atagagacaa ataaactttt tgagatggtt ttttaataga     60
aaatacattt tatagaaatg agaaaaataa agttttacta ttagaaaagc gtaacaaaaa    120
gcttccgtaa ttatttatat gaatgttccg atatttttag cgatgtgtgc atcgtgcact    180
cacaatacta atgttatgag cttccttgca ataaacggtg gggctggaaa ctgacaggaa    240
gtgggtttat tcgatgatta caataccaca ggactgatga cacgcgtaat caaaagttga    300
aactagaaaa cataaacacg cggctttcat ctgaatcaga gacgaatatc cataaatcac    360
```

-continued

```
ggcccccaaa tagaaaccag tttattttat gtcacttctt ttccccatta actttcctgt    420
cacaatcata caacagagtt cgatcataca ggtccaaagg ttttgggtat atcttgtgga    480
catgtatgct gtgaaatgtt gaacatttca tataaaattt taaaatcaga ctattagatc    540
gaatagttct acgaaatttg taaacagttt ccatcgaaat acctattttt tgtaacacga    600
agtcgacctc tctcccggag acgctgctac agaaaggttt gaattttgag caaagttacg    660
gtattaggtc tcgaatgaaa agtttcgaaa gtacgcaaaa ctctacaata gggttaagaa    720
tcgataattt tctagattgt ccaaaaaagt agactaattt tgccattccg ttcagtgcct    780
tcaagaagta cttgaagtct atacctcacc tacttgtctg atatggtaat ttactatcga    840
gcttattagc aattttcttc acgggaaagg agttgtaggt taacttcaag tcgcgaggta    900
ggcatatttg tgcctggcga taacaagaga cgttccacaa acatcttact cagtttctat    960
ttgaaacttg gcgaagtaga catgaagttg aaccttcgga acgtcagtcc aaaggtttga   1020
aggaggggtt ccccgaactg tcatacactt catttcatcg tcagctgtct gagatcaaac   1080
attcaataag catgaagatc tctgaacgac cgaaaagata tcgataaagt gatgataaag   1140
gtctgcagca gaatggtttt gcagacattt cttcagaagt taaaacaacg ttgtcgtacc   1200
caagtatctt atcaagggag aaaaagagtc aaaagataaa ttccgccatt tgcccctccg   1260
gtccgtaata acgagtattt cttatcacgt gtgctgatct tttttcttaa cacacataca   1320
atcaatcgat ttgtcagaca tgggaaagaa taagacgtga tggatgaatg gaataatgtg   1380
aacgatgaac gagatacgtg acagtcagaa agttcactgt gaatagagta tggtataaat   1440
ggttgagaga cgacggatta cggaaagatc gaattatcac aacgtttttg atgtatctgg   1500
accgttcaca tggaatttag taattgttac ttcttgggcg acagagaaaa ttcggccagt   1560
ctcatcaaat agagagtttt tttgaaaatc tgcattgcag ggcgaacaaa atcaatttcc   1620
acattatttt aggccggttt taaagagaaa tggagagatt ttgagaactg tgaaataagg   1680
ctggttaata aattgtgcat aaaaaatcta gagagattgg aaagccatgc ctatttcact   1740
gcagcttcac caacaatcta atcataattt tgaaaatgaa aattacatta gcatggtcct   1800
ttactcacat ttttttagga tgtcgacact tttttcattt gaggtcgcta caactgttgc   1860
tcaaagttgg agcatgtgcg acctatttcc actcctcctc cacagacccc gtttgattgg   1920
tgcaaaagtg ggcagagcga aaagctgatt ggtcttgcag ttttcatttt gaagggaatt   1980
aaaaaacgga gttagtaaca attgagaatt accgttttta aatgtataac ttttcaaatc   2040
ttccgtttct gaatttatta tatacatata ttatatagac tcaattacaa attatataaa   2100
tttaatttat atattatata gccttaatta ttaaactttt tattttgaga tatttttaaa   2160
tttcaaactt tttttcagta tttaagtaag cttcctattc acgctactcc acttttagtg   2220
tgtttcaaat gaatggacgt tataccaaaa ttcaattgaa atatccagct tcataaatat   2280
attggcatgg gaatgagcct cgtcacgaac attttagaaa aacatcagga caaacttata   2340
ttgtactata acttgcaaac ctgcagcagc agaactttga acacccaaat ccatttccga   2400
cggaagtatt ctacatcttg tggccgcgta tacccatgac tactgtaccc aaactgggga   2460
aaacccaaat tgctagtaaa cgcccactaa ataaactgtt agcattgaaa gtgtgaacac   2520
gtgaatcgta tgtcaagtga taggaagtgt gacgttttgt aattaatctt aacttccaag   2580
tgtttgtttc cttgaaataa gatgcctaca cacggcggcg aaatggatac tttttatgtc   2640
```

tgcgcttatt ctctttgtcc cccatcatca tacaatcttc aacgccttca catatcagac 2700
agtccgtcgg gcactgacca accattcagg ctgcctgtct gtcatttata ggctgtctag 2760
ttatcttcaa ttaatgtttg aaaattcaga agc 2793

<210> SEQ ID NO 54
<211> LENGTH: 2016
<212> TYPE: DNA
<213> ORGANISM: Caenorhabditis elegans

<400> SEQUENCE: 54
aattaattat tttcacattt tttcgaattt tgtcgattta taggcgaaat tttacgttaa 60
cctaacggaa atatgagttt ataatgcatt tttaatcgaa aattcggttt tttcaataaa 120
atttgctatg aaatccgcaa aaacgcctgg aaattgtctg aaaacgaaga aaaataaaaa 180
taaaaatccg aattctgtgc attgtgacgt ggcggtgttt gcgtacccga catttaattt 240
cacgacactt gtttttatgt ttttattgtt ttctcgattt ctgcaagttt tccacttaaa 300
acgtgcggaa aaaatccaga aactgtaaat aatactaaaa aaatataaat tttccacaaa 360
aaaggcatga aaactaacaa ttacctcaaa tatcgtgaaa aatgcaaaaa aataagcctt 420
tccgaaaaaa cgggcccttg ggcctttaaa ggacacaaaa acaggaaagc ataagacacc 480
aaagagtaat tggatttcta cactttggtt cctagaatta tttataaggt gttattgcgt 540
ttttgtgaga ttgttctatt tatccagtca aaaattgcat tttctttgtt tttgcttcaa 600
aaaaatacat tttcagtgga aatttcagct gaaaagcaga attttgaggt tttcgagtaa 660
ataacgtaaa acactaaatt acaaatattg atttttgatg tcttagacca aattttcgta 720
aacatgtttg tatttttgga aaaaataggt tttttgtcga ttttaactta atttttcgaa 780
caaaaaatga ttttttctcc gatttaccaa agttttgact taaaattccg attttctggg 840
tcatttttcc cctaaaaata cgatttttaat tcaaaaaatc tatattttca aagaccaaag 900
taccataacc ttcaaaaaac aaccactttc tctattgcat cagcgaattg tcatcacccc 960
tctcaaaata tacaaaacgt catcattttt ctgtgttttc tctaattctc ctgaaaaatt 1020
ctataaaacc aacagttttt atcatcaaaa atgccttttg accgactttt tttaaagttg 1080
aaaatcgtac agttttagca gaaattccag agtttcattt tgaagtatgc tggaaataat 1140
aaaattattc taacatttat taatattttg taaaactaat tctatacaat aaaaaagtaa 1200
aatttaatat taaaaaaacc ggtttttctc aaatttccat tccccaatgt cctgttctat 1260
tatttgttcc gattcggcca cagaacgcgc acacacacac tttttgctga ttctctgcct 1320
cctttctttg atttgaccgc attttatatt gattttcggc cacaattcca ctatttgttc 1380
agtttgtcga tttgttggaa atttcaattc cggcaattcg ccgatttgcc ggaaatttaa 1440
attcagacaa tttgccggtt tgccggaaat tttcagttcc ggcaattttt taatttgccg 1500
gaagtttcca tttcggcaac ttgccaattt gccggaaatt cgccgttttg ccggaaattt 1560
tcaattccga caacttgcct atttcccgga aattacaatt ccgccgattt accaatttgc 1620
cagaaatttt taattccggc aatttgccga tttgtcggag atttcaatcc ggcattttgc 1680
cgaaaatttc aatttcggca gttcgccgat ttgtggaaaa taacaattct ggtcattcgc 1740
caatttgccg aaaatttcaa ttccggcaat tcgccgattt gccggaaatt ttcaattccg 1800
gcgattttcc tatttggcga atatttttaa ttccgccggt ttgccgcttt gccggaaatt 1860
tcaattccgg aactttgccg atttgccgat ttgccggaaa aaatcttttg ccgcccaccc 1920

-continued ctaataaaga cttcaaaata tgcgtttttt tttgctttta acacgctaaa actctctaaa 1980
aatccccaat tttcagctt aaaaaacccc aaaaaa 2016

<210> SEQ ID NO 55
<211> LENGTH: 1336
<212> TYPE: DNA
<213> ORGANISM: Caenorhabditis elegans

<400> SEQUENCE: 55
atccatttat ttatgtccag tacaagacga ccgttcatat cttcttagtc attttctttc 60
agccggtgta ctctttgttc aattttctct ttcttggtgc aacctttatt cacgtgtatc 120
ttctccgagc ttgtttgcat attttttttt tgaaatttca tgtgctaatt tattcatgtc 180
atttttgaag ttaaactctt cacatttcat aataaatatt tattgaaccc gtttgactac 240
tccaaattca cgaagttacc aaaataaaag tgatatttga ctttcagaaa taccatttca 300
aattccctaa gacgctcggg aaatattaat tactgcaatt tatattctgc ttgtattttt 360
cgaagttggg tccaactgtg tgaagtattg taagaatcat atccttctcc ttcacattct 420
acataaacaa ttcatttcta ttctgtaaat tttttctgat gatttacggt aaaaacgagc 480
gaaattcggt ccgggacaag ggtttctacg acgagtccat cgtggtgccg ctcgcttgtt 540
tgaattcccg cgtgccgcat tcctcgtgtc gagacccgat gtccaactgg ggggattacc 600
aactcggggg attggccccg cccacagaac cgtggcttgc aatttttttct tgttaattct 660 cgctctattg agaaaaaata attttaaaac cgtgcggcag tttcaaaaat gggcgtattg 720
caagccacgg ttctgtgggc ggggccaatc ccccgagttc ttcgggtctc taaggaaagg 780
attcgtacat tctggtcctt tttatttatt tttaacctct ttttattttt ttaaaccgca 840
atccattacc agttccattt tctccgtact cgtcagtgta gcgagtgacg agtgaaattg 900
accccatttc ttatcttatc gaaaacaatc taaatagttt ccgcattcgc ataaccagaa 960
aattcttcgg tagtcgttct catttgtttt tatttcatga acataaagta acgccatagt 1020
ctttttatga aacgtggcgt taagaaagct ctcgaaaagt ctcgatttct ccagcactaa 1080
tacacgtcat ctccgataag tacacgttgc ataggcggtc ctaataaaag cgaccgcgga 1140
cgttcacatt cagttctttg ttttcttttt gtcgtctgca ctccttcttt gcgacgtgta 1200
ttttgtgttc ttctctgtgt ttccacttct cgttagtatt ctcgcgcttc tactctgaaa 1260
ggtttttctt cttaaatgtt ctcatttttc agccactcag cgaacagttg aactgaccgc 1320
tcatcaagag aaaaat 1336

<210> SEQ ID NO 56
<211> LENGTH: 2797
<212> TYPE: DNA
<213> ORGANISM: Caenorhabditis elegans

<400> SEQUENCE: 56
aaatttcaac ttccggagcc cgatacctat aggccacgtg agaactttct caggagagac 60
gcagagagac acaaattgac tgacgaggag ccaggagaaa tgagcagaaa taaatcaaat 120
tgaagagttt ctgaggagtt cttttttctc tcttccactt catcctaccc gcctgagcca 180
ccgggggaac tgacaaaaga gagctgtcac gtggttccag actgtcccat tacggtttga 240
tctacaaaaa atgcgggaat ttttttccca aaaaaaatgt gacgttagca cctatcggtt 300
agccatacga aatcagttga gaagtctgcc gcattttttg tagatctacg tagatcaagc 360
cgaaatgaga cactctgaca ccacgtgaga tgtgctcatt gtggccgcga gagtggtgtc 420

-continued

```
aaggaatatg agagtacata tggtaattgg tgtataccat aattagatgg gaatttgaga    480
gcttttggag gaaggagagg gtttttcggc gaaaaattag tgtccgaaat gagaaaaatt    540
gaaaaaaaat gcaagttttc actaaaaaac tacacttttt ggagaaaaat tggaaaatct    600
gccagttttc agtgaaatcg agtttgaaaa aataaaaaat tcgagaattt ttttttttaa    660
tgaaagattt gtgctcgaaa tagctgtaaa atcagcttaa tttccgaaaa aaagatcgtg    720
attttctcga aattcatttt ttttaatttg taattttgat ttttccacac aatttcaagc    780
tttaaaaatg ttaaaagtca cctaaaaagt cgattttcat aacaaaatac ctagaaaatt    840
gtcgaaaacc ggcaaatttc ggcctaaatc tacttttagg cagattttaa gttgaaaaat    900
gcacaaatat ttctaaaacc tgacaattca acgatttttt cctagaaaaa atcgtcgaaa    960
tcgacttttt cgacttttca gtatttttc agtagaaaag ttcacaaaaa tgtccgaatt   1020
cgacggaaaa ttcaaatttt tttttccag aaaaagtgct gattttagcc gaaattgggt   1080
ggaaaaatcg aaatttcgac gaaaaaaatc caattgcaat tgaaaaacat tgattttcgt   1140
tcatcgaagt atcctctttt gttattttcc actttttcc cgcaggtatt ctctcgccat   1200
tcaccaagac atcacacgaa tcccggagac gcagacaact gaagagaccc actttttgtg   1260
tgattcaaag gggtcaacgc atatagccgg ccgattcgtg atgactcatc tctgtgttat   1320
tctataaatc tcttgatttt tttgaggatt taactctttt ttttcgaaaa aaacgtgttt   1380
ttccgaattt tgtatggtta aaagtatcgg aatcaccgtt ttttgttgat tttttttctca   1440
attttctttt ttgtttgagt aatgattaag aaataagaac ggaaagaaga gaagaaactg   1500
tgaaaaatga gagaaaatat ttcaaaatca ggaaaaaaaa tcattttcca aattttcagg   1560
atattatgcg gattattagg gttagaacac attttaaatt ataattttaa ttatttttaa   1620
cattgaaaaa acaaaaaatc atccgaaaac tactcttctt tcacaaaaat cggtcaaaaa   1680
taaaaaattg cgaaaaaaaa acaaaacaaa ttaaatgtag caagcgcgct ccattgacaa   1740
aatgccgaaa tttttgcgag cgaagtttga atttcgttgc aacatggggc atttttcgtg   1800
aaaaacaaga tttaaaagaa tttatacttt attcttgctc aagaaaatta atttttccat   1860
aaattctatt aaaagtggca gttaaaacaa caatttctaa gattttttca cttttttttt   1920
ggcgtttgct tgtttttcag agtttggaat agttttatgt caaattttga tttcttctca   1980
ttactttctt cataaaaaaa aatgcaaaaa agcaaatttt atcactaaat cgttcaattt   2040
ccacctagaa aagacgaatt taacgcaatt ttccgattag agcgcatttg cattgtgcgg   2100
gaaattcaaa ttattcaaaa attctcctct agtttccagt tctagtacaa tcggtggccg   2160
agtttttttc ttttttttc cagcggccac atagcaagag ccaacctgta tacttttgca   2220
gttcttgtgc aaatctgagc tccgccgagc acaaacaagt ttggacagtc cacttctctg   2280
cgtctctcgt gatgagtgtg ctctctcgtc taacctctaa tccttcccag atatttgcac   2340
atctacccca gttccacata gccataaaga cttgggtcat ttttatcgat tttttcggtt   2400
tgctcacaat attgtgagtt tcttaattag gtcttggtag ctttttggag cattttgtga   2460
ctttttatgc ctaaaaacca gtttaaatat acttttttaa tgcttaacta gatccaaaca   2520
cctttgaaaa ttgtccaaaa aaattatttt ttggccgaaa atttcagtcg aaaaaagcat   2580
tttttcggcc taaaaaaaat tccaaaaaaa tccctaattt tttctgtatc tccagagcca   2640
ctttttaagg tataaatcag caaaattttc cgatcaaaat tccatttccc tatatctttt   2700
```

-continued ccctctctct atctcaccct atctcgtgcg ttagccgacg tttactaagt cccagtcagt 2760
ttaattctat caaattcttc acttttactt acagaaa 2797

<210> SEQ ID NO 57
<211> LENGTH: 2737
<212> TYPE: DNA
<213> ORGANISM: Caenorhabditis elegans

<400> SEQUENCE: 57
atcacacggt tgaaaaaagt cgaaatgaat gaaaacaagg gcattttgga attttttttaa 60 aagaagaagt aaggtgagtt aaaagaatga aaagcggcgt gcttgagatc taatgaaaca 120
agggaccgcc cttgtttgtg atttgctaac aaccgctatc gtttgaaata ttccgggcgg 180
agttctagct gatttctact tggagtatca tagaattgga aacggaacga aattgccata 240
gtatgaaact tttaatttgt atatacaaat ataatcgacc catttaatag gcctactgcg 300
gattaatttc agtgctcctt ctaaaggcag acaatgaaac agttgtgtag taaaaacaat 360
gttcacaaga cctgaaacaa ttttctgaaa attgtttgat aatattgttc aataaacata 420
aaagatggtt cacaaaatta aaactaaatt aaaaattaat aagaaaacca gttgtcacaa 480
acgcattcgc aaccaaaacc gctaaacgct attccaacta aagttataat tgcatttttt 540
gcaattaact gttttaccac aaaacaaaac aaaattccag tttaacaaat tatcaaaatt 600
ccaataagat cctttttttaa attaaaaagg tgagattttt ctagagagtc cgaatagaaa 660
atggtaacca aaccgatgac gatgacaatg gtaatcggat caatgcagaa gttgttttga 720
aattattttc aaagtcgtta attttgagaa tatttgattt tttttagagt atgtactaga 780
tttgttctct acctcaaatg atcaaattct ttgactgcat taaaacaaaa ttttggcaaa 840
attatcgaaa atctcagaga aaataaacaa acagtctatc acatttcaaa tgaagaggaa 900
gccaaatttg aatatagacg gtccgatgaa gaatttttttg acaatttatt ttaactcgga 960
atggttatta aatttgattt ttttaaattt atatttccca ttattttaat tttttaattt 1020
atgaaacttt ttatgtgaaa aaaaaattta tgtgtttttg attataacag attttacgtc 1080
agaagccgaa ccatctttaa taaaaaattt gaaaaaaaaa atcacttcta caattttcat 1140
ttttcaaatt tgagccatca aagtcaatta ggaaaattaa ttctttcaat cgttgcagtt 1200
acagtgctat ttcaggatct ttgagagctc gccgtgagct tggttctgga gattcgcaga 1260
taaaaattca tgagtaaccg tttcaagaca tgggctatca aatggcatag gtctcatatg 1320
caagtccgat tggcatcttc tgatggttcc ctagtgagtt tattaattca caagagcatt 1380
gtatcggaat tttggcaaac tgttaaaacg gaattatatg ctttgttcag ttttgtttca 1440
gtgtgttaca cagttaattg ttttagaaac cattgcaagc aattataact ttggtgttga 1500
agtttagttg tgaatgagtt cgtgacaact ggttttctta ttagtgtgta tattaatctt 1560
gtagatcatc tcacatgctt attaggcagt ggtcatttct atttaatttt gtttgaaagg 1620
gttttaattt tttgattttt tttgttttgt tttagcgaac tcaaattgaa actaatcgcc 1680
aaattttata ataaggcctt ttcaaaacat ttgatcaaac ggaaaagttt tttcaaaaaa 1740
taaaattttg cagcggctta ggcacacgaa catccgacag gcgattcaat tgtatcaaat 1800
acttagtgct tctaggcaaa atgtagattt tagatataaa ttaagccctt tttcacagtt 1860
tgtaacgcca gggaaaacat ttttgagcaa attttgaaaa atcttatcag aaaaatgttt 1920
tgattgggtt aaaaaaaacac ctagaaactc tactcctctt taatgaaagc ttgtgtttca 1980

-continued

```
aactcttttt gtgcttaaat aaatttttat gcaaattcat aattttacca actttttttcc   2040

cactgaaaca tttcaaacat aatgtcaagt cgtacaaaat cttataacta acgattttct   2100

aatcgtatct cctgttatcg ttatctttac aatcgaagat aaacggctga gaaattttag   2160

gtccgaggta caccactacg cacaattgcg gattttgcac tatttggaga gttgagccaa   2220

aactgtctta ctttttatga aactgtggaa tgttgtaaac aattggtgaa tatatttatt   2280

gtaaaatttt tatttgaaaa tcatattctt ttgtatcgaa ttttggaatt ccacgtttga   2340

aaactgcaag agcgccttat gctgacgtgt gttagttaga ttgagagact cgcacggagt   2400

agacgcagac acaccacaca gcacaaacag acgtcgacgt ccgcaattct cgttggttat   2460

cgactctttt gtcccattcc accaccaaaa cttgccacga tttgatgttg ctaggacata   2520

aaggtccagt gggaaactgc aaattctttg ttttcactgg ttttttttcca tttgttagtt   2580

actagcttga taatttaaaa atgaaacgtc tcaaaactag ttcacttgac ctacttcgaa   2640

caccaatttg tatcgtgcgt catattcctt gccgttgcaa tttcacgtgc acttttatga   2700

atttcataga ttttttttca gataattaac cgacaaa                           2737


<210> SEQ ID NO 58
<211> LENGTH: 500
<212> TYPE: DNA
<213> ORGANISM: Caenorhabditis elegans

<400> SEQUENCE: 58

ctgttgcggc gcacctcgaa gaatagctcc tgttgggaca ttttgtgatg gctgaagtag     60

gaaattatat taaatttaca ttaaaactaa agaaaaaata cgaaaaatta tgggaaatca    120

gtggtaaatg cgaaaaaatg atttaaaaaa ccgataaacg ttgaaaacgc gacggtctcc    180

aaaataatgc aagcgtgctc cactgcgaat cccctgctca tttgcgcgcg cattcaaatt    240

tagatttccc cgatttatcg tgaaaatcgc tgccatctga caccgcattg caccgaagat    300

ggccaaagat aaccaaaaaa ccaatgaatc attggtctat cgaaaataca ttatattttg    360

ttgggagcag ccccacgaaa gccacgagag cccgcaaaaa ggtaaatatt gacttaatat    420

ttgtggcggt ctcttacttg gttccactta cttttaccaa taggcagtta tttttgcgtt    480

ttgtcgaaaa aatcgatata                                                500


<210> SEQ ID NO 59
<211> LENGTH: 502
<212> TYPE: DNA
<213> ORGANISM: Caenorhabditis elegans

<400> SEQUENCE: 59

atcgccaacc aaggaaagta gtgatctaca agttttctct gcaaaaaaaa caatcgtaat     60

tgcataacat ctatcgaact cgagagtctc ccaaaaaatc cctccaaatc tttactgcat    120

ttgcatgtaa agattttacc tatttttcta aactgctgtg ttcctgtatt ttcactctac    180

ctgtttcgtt tatttattta tttaagcatc aagtttattg aactctaata aattctcggg    240

aaattcgtgt cttaattatt cttgccaggg aaagttacgt ttccttatcg aacacctgtt    300

gcgaaaccag aaaagggcgg gtctgactaa gtgaacaaat atttcgtaat aactttcttc    360

caacagaaat taaaacacgc aaaaaacggc caactcacta gctggaacgt ggagccatgg    420

agatggataa aataactctg attgtcgaca tagcttcaag aatatcgtat tctgcatttt    480

caaaaagtct ttttcgttca aa                                             502
```

<210> SEQ ID NO 60
<211> LENGTH: 1200
<212> TYPE: DNA
<213> ORGANISM: Caenorhabditis elegans

<400> SEQUENCE: 60
gcataaaatg tttgaacttg gcatattata atacaaaaac aaaaattgaa agagccaaga 60
aatgggcgga gcctattatt gattatcctt gtattttgca aaaattgttg acagatgatt 120
ttttttccac actaactcta ttgggagttt ttcaacaatt tgatatccaa aaaaaagagg 180
aaaatccgct aacaatgtga aaaactagca tcataatttg aattgccgcg cagtttcctg 240
gcgttccaga atgatctatt tgtatttgaa agaagacctt tgaaataggc atctcaaaat 300
ttgccgagct tggcaaattc ggcaaatttc tgtttccaat aattgccgag cacggcaaac 360
tcggcataat cggcaaattt gcctggcttc gcaaactcgg aaaaatctaa gaattttgat 420
attttttgga gcacaaaaat tactgttaca ctaagaacac gtttgcttgg ttggaaatgt 480
ccgtgtggtt caatttcatg ccagtttact agatttttgg agccgaatca agagttttag 540
taattgtttt tctgttcaac ttttggtgta cgcggcaaat cccgaaattt gccgaactcg 600
gcaaacagca aaatatgaaa cgtttatcac agaacttgtt aggggatttt tcaaatatat 660
atatattttt ttaattcttg gaaaaagctt gtctacctcg aaataccta aaatcattca 720 aaaattttaa atattaccat tgagagcaaa tttacgggcc tctgaaatag tggaaaaatg 780
aaaaattaac tgaaagttaa tacgaaaatt ttcaagcttg taaaagattt ttggttgttc 840
cggaaatcgg ataatcggaa aacagccacc cttgtttctg actaatgagc taagaaattg 900
attggtactt ccatagttga tgaatgttat cagtaaaatg ggtttggcaa tgcttttgtt 960
attccaccgt gatataaact gaaaagcaca actgataaga tgaggcacct gagtgtctag 1020
acatggcaac ggaagtgggc gggattggaa tttttgagac gtggcttaag ttgtataaaa 1080
ctgaccggct aaattttaat ttcagtgagt ttttgagttt tccaattctc acccaaattc 1140
cacattttat gcatcgccta agtttttttt ttaattttaa tttttttttc cagatcccga 1200

<210> SEQ ID NO 61
<211> LENGTH: 1994
<212> TYPE: DNA
<213> ORGANISM: Caenorhabditis elegans

<400> SEQUENCE: 61
gcttggagag catctatggc gtcttttcgg aatatcaagt cagtcacgaa gtcttgtgcc 60
aattccttta ccaatcgttc gaatctggat cgaggaatga gcagttcagt agactgttgt 120
tgttttcgga tttctcgcag agcaactgta ccagaatgaa aaggatatga tcgtactggc 180
tgagtgcacg atttgcggca tactcccgaa aggttctttt tgccagccat tgtttggtag 240
atgtggtgtg aaatggagag attgtaaacc cttctatagg tgccaaaggt gagtgggcgt 300
agcttcgaag tcaactgcgg tgaagggggc gtggtttctt actattagag aaactgtatc 360
agactaactc cgataaagcc atagtcagtg aactctcaac atagttagga agagttactc 420
agattaaata aaatcgtcaa agaacaatca ggccaattct gggctaggca tagttcatag 480
gcagaacttg gtagaggaaa tcagagtaaa gtaacgatga ttttaatttt tccgtctgaa 540
aaaagatatt gaaagcattt tgccgatcga acaagacacc caaagtctca tgacgacatc 600
ccagaaagag tttcagccaa attcccaaca acagcctaaa ggaaaatctg aaaagaacaa 660
aacatttgaa cgtgctagag cgtacttgca catacttgca catactgtaa gtcaacatag 720
aactctactc ataagtgtga caaatttgtt acaccaacag tacgaagcca agatttgatt 780
aaagacaatt gttgtttaaa ctgcttgata aaaggtcaca tggttgcaaa gattgccaga 840
gcgaacgcaa aaattgctct cgctgtgaag gtggtgaaca ctgactcagc aaagtcggaa 900
aacatgatat gatttgtctt agtttattgg ttacctttat ccgaaggtgc atcaagttgc 960
ctattggcgt tatgttgaag atgactgata taatacattg taacgatttc gggaaaaata 1020
catatttaac aagataatta tttttttcga ttttccgaaa aaatggaata aaagaaaaac 1080
ggacattttc gatatttttc aaaatccaat aaagatcagc atttttttgt atttcaattt 1140
caaaaaaaaa atcgaaatta attttttaaa attggaactc gagttcctgc tcaatcctgg 1200
tcaatgatta aattaaatta tgctcgtaca gtaacttgtt atttctgtgt ttaattaaag 1260
gcgcattact gatgcgattt gggtctctcc acgattgcac tctgttgtgt tatttacttt 1320
tatttttaaa tattttattt gttattttaa ttcattttcc gcatcatttt ttcaaggaat 1380
ttcattgata tttatgccat tcgatttaaa tttaattttt tgtcgttatt ttacgtcgaa 1440
caatgagtca aacacctaat tctggttatg caacgtgggg ttacaccctt actatagtat 1500
atatatagaa tacttgcaaa aattgttata tttacacttc gaaaatcagt ccgaaaaaga 1560
cgtaaagcaa ctttgcctaa tgaacttttt ttaattaata atttcacaaa aattgtgaaa 1620
cttgttattt ctcttgtttt ttgcctttga attttaaata tgtcgaattt ttccaactat 1680
tcagctgttc ttgtcgattt ttgttaattt cgaaactagt tcagtaagaa gtgcgaattc 1740
agaaagaaaa acaaatcaag agtatttttt atttcgtttt tctctcaatt tctcttcact 1800
tctctcccat tttagtgcat gtattttcct cttctctctt cttgttgtct agtttagaca 1860
acgcggtcac tgttagagag tgcagacggt tagcgtaaca aacaaaaaag tagaattcat 1920
ttttggcgtt ggaaaccgca ttaaatactg tcctcacagt ttccgttcgt cttaatttca 1980
aatctttgct cttg 1994

<210> SEQ ID NO 62
<211> LENGTH: 2995
<212> TYPE: DNA
<213> ORGANISM: Caenorhabditis elegans

<400> SEQUENCE: 62
ctcgttttca ttgttggctt cgattattgg attttataaa ttatggtgat gtagttttga 60
atgtagacaa taaattggaa atgaaatcga tgaaatgctc aagtttataa atagcaaaaa 120
aaaaaacatc ggtagacttt atttgatcta ctgtgaaaat gttttccggc aaatcggcaa 180
attgccagaa ttgaaaattt ccggcaaatc ggcaaaatgc cagaattgaa atttccggcg 240
aatcggcaaa atgccaaaat tgaaatttcc ggcgaatcgg caaaatgcca gatttgaaat 300
ttccgacaat tcggcaaatt accacaattg aaaatttccg gcaaatcggc aaattgtcag 360
aattgaaaat ttcggcaaat cggcaaattg ccagaattga aaatttcggc aaatcggcga 420
attgccagaa ttggaattcc cggcaaaatg ctagaattta aattttcggc aaatcggcaa 480
attaccagaa ttgaaaattt cggcaaatcg gcgaattgcc agaattgaaa tttccggcaa 540
atcgcaaaat aagcaaattc tataaaaaat atatagcgaa aaaatttcaa aaaggcactg 600
ttttaagtgt ttccgtctta taaaaaatcc cttgaaacat tttcggcaaa tctgatggca 660
aaccggcaat ttgccgaaaa tgaaaatttc cggcaaatcg gcaacatgcc gaatttgtcg 720
acaaaaaatt tgccaaaagg caattgattt aactagtttt aactaaattt gagtttttca 780
tcgatttcat ctcatttccc atcttcctga gttgtattag gcttcacatt accccttca 840

-continued

```
aagtacggta gctttgaaga ccattttcat tgacacatag ctccgggtcg aataatgtat    900
cgttttccac cacctttcgt caataaatca tttacgtcat atcgtttttt gcaagcttat    960
acatatttct gtgtaggcgg caactgagac tgataaaaaa cgcattttct aaatggtttt   1020
ttgatgttgt tggactgtgg gaatggacta tggaattata acaatctgga gagaaaagag   1080
tgcccgagag aagcagagaa acaagatgaa cgtggcatac gtacacttcc acaacagcag   1140
ccgtcttgtg gcctatataa atgaccagat tcaagcggcc atttatactt ttcgatcttc   1200
ttcttttttc ctttgtcttg agattgaaat ttgagagata acgaatccaa atagacaata   1260
tgcacttaat ttacttgaaa atgagcttaa aactcacaaa aaaaacaaat aatttggact   1320
tttttgcaca tttcctgcaa aatttgatgt ttatccagct tgtgatgaat aatttttgca   1380
cagcaaaatg aattttgtgg caattttaat ttcaatcttc catccattag ttttcctgga   1440
atttttttgt tgaaaattct gatgacttgg agatttaata taagcttttt agtcgaattc   1500
ctccgtttta gacgtctaac tagttaaaaa tcgttcaaat ccttttaaat taattagtga   1560
gtaaaattca aaaagttcca gaaacttttt atagttcatt aaaaatgtat tttttcacac   1620
ctagttttaa tttaaaactc acgtggtgtc aggatgtctc ataagggttt gatctacaaa   1680
aaaatgcggg aatttttttg gaatcagttg agatctgaac tcccgcattt tttgtagatc   1740
tacgtagata aagccgatat agcacactct gacaccacgt gaaaacctat aaattctcct   1800
aattcatttt gttaatctga tcccagtgac ctctaatctt gatcatttta tcaccacgcg   1860
tacttctatt ttgcaaagac ctatgatatc agttgtctga cggtcagaaa gtctcggaaa   1920
aaggcgttga ccgagtaatt acaataaaaa aattaacgat ataaaacgtc gaatagccaa   1980
ataggtagat agcgtcagaa aaaccaatca gtgatttgct ccgcccactt ttcaaccaat   2040
cagaagggtt tactgggcgg agctatacgt tctcaatttg gaaaaagttc aaatagtgag   2100
attttatctt tttttttttg tagattcatg aataaatttc agactaattc gtgttttcat   2160
tctcgctaat ttagctttat tacgcgaaca ctaggttctg agaatgcgta ttgcacaaca   2220
tatttgacgc gcataatatc tcgtagcgaa aactacagta ataattcgaa tgattactgt   2280
agcgtttgtc acgatttacg ggtcgatta tcgaaacgga ttaaaatcat ttagttatct    2340
ataaaattaa gcaagaaaat gaggaaataa aatggaaaat atattcattt aaataatcaa   2400
ccccgtaaat cgacacaaca gagctacagt agtcatttaa agggttactg tagttttcgc   2460
tatgagatat tttgcgcgtc aaatatgttg tgcaatactc aaaaattgtg tgactataat   2520
aattagctat acaattctgt ggttttttttg agcaaaaccg aaaaacgaaa aaatttcgtt  2580
tttggcaaaa cactccaaaa tcggtatttt tcattcaaaa aaccatattt tttacggttt   2640
acgccctatt tcctacaaac aacagaaatt gaacgtggtg tcagagtgtc tcattttggt   2700
ttgatctacg ttgatctaca aaaaatgcgg gagaagagac gcagagttct caactgattt   2760
agcatggtta agagtgtgct gacgtcacat ttttgagcaa aaaattcccg cattttttttg  2820
tagatcaaac cgtaatggga gagcctggca tcacgtggca ttagactttt tgagcaagtt   2880
tgaccaaaat ctttttttctt cgatttttcg gttttccaaa aaaataacgc caggcttagc  2940
ctccacctca atattcttat gtgattgttt ccagaacctc ttccccacta aaaca        2995
```

<210> SEQ ID NO 63
<211> LENGTH: 648
<212> TYPE: DNA
<213> ORGANISM: Caenorhabditis elegans

<400> SEQUENCE: 63
ttactggcat ttaaaggaaa gaactcggaa aatttatgaa gatttgaaga aaggcacttg 60
ttaattgatg ggttttcatt gtgttttatt aaatatgaag ttgtgatagt tttaatgtga 120
ttaaaataaa atttaaatca actatcgtga aaagtttaac tacaaaactg tattaaatct 180
gagaacacat actttataag ttgggaaatt gttgatcaag tctaagttga actaatatat 240
tcttgatgga atcggaccga aaaaatcaat ttatcttatt cagaaaccat cttgagaatg 300
cctacatttt ggcgcgagaa tagcggcaga agagagagct agaacggtag gcattctcat 360
gatctcatgg tttttcttat acattttctt tttttctgcc gtttagttta ttgatctcaa 420
ttggtttgtt ggtctccccc tccccctgtc tgcggtcatt tagtccaata agtcaacgtg 480
tactaactgc acctggactt tgttcacttc ctctataaaa tgactttttg attgtcttct 540
ttcttattct atatctactt tttgaatttg taaattttat agctacaatt tcactttgaa 600
actgtttggt tttttttca gaaaccatac aattttgttt ctccaaac 648

<210> SEQ ID NO 64
<211> LENGTH: 1443
<212> TYPE: DNA
<213> ORGANISM: Caenorhabditis elegans

<400> SEQUENCE: 64
tggaatggga atgagaagat tcggatacgg gtacccaatg tggggataag ctgtgcaatc 60
actactgtgt agttatgtat aaactatgta aaattgaaga aaataaatat tttgactacc 120
tcaatccatg ttgtcacact gtaacaagaa aattaaaatc tgataagctt cagctaaaaa 180
ctcaaaacta agattctcag gaagatattt gggtatttga actaattttg accgcttttc 240
atgcacacgc aatggatttc taagtatcca agtatgatta tttcatattt cgccacttag 300
aatccagaaa tttcaggagc atatttttgt gatacaaaat aacgtatttc tgttgcatta 360
aacttctgtc taaaactgtt cggatctgaa attgaaatta gcatttaact ttttgttcca 420
actgaaataa tgtattactg gacaaaaaaa tattaccatg acatcttgct tcttttggag 480
aataataaaa taccttcagt tatagatttt aggtaacaaa taccatattt attcacacaa 540
gttgatgaaa ctcgttcgat attttaaatt aaactgcctt taaatatcta ttagccagtt 600
gttgtatggt cctatgcaca cactatcttg tatctatagt ttaatatatg cggcctatat 660
tgtgacatat attcttcccg tttgctctgt tgttctcccc ttcctgtata atgggagatt 720
gtaaatgaga gttgttctgg tcccaatacc tagccactga gaaccctcct cttctatcta 780
ctactcattt atattatcgt cattattttt atttttattt atacatatag tgggcttatc 840
aacatatatg agggtaaaat acttataatt aatcagcagt tcagaagaaa aaacaatgaa 900
tgataaggaa atttttagag aacggataga aaagggatct tttgatttct tcagtgacac 960
tgttatcatt ttcgaaaatt gggtatgaca atggagacgc cccacaatgg aaataacttc 1020
aaggttatcc atatatactg catacatatc cacaatatta tgaggtttct ctaggaaact 1080
gaaagaatcc tagtgtttga atgtgttgag catattaatt ttaagaagcc aagaaaccat 1140
aacttctgat aatgactgat atctaggctg tcacgagggt tgcttaaagt gttacagttg 1200
tgccagtaat attaatagct caatttctac aacatacaaa ccattatggt accctacaaa 1260
cactacaaat ggtttgaaac cttgttgttt attgttttta ctgaactctt atccacctga 1320
tacctaaaaa acgtcatgtt aagagaacaa caccgcccat tttgaatcct ttataaccac 1380
tgggagatga ccggatttcc aagtactcgt agttctaaaa acctttaaaa acccaaaaaa 1440
aag 1443

<210> SEQ ID NO 65
<211> LENGTH: 494
<212> TYPE: DNA
<213> ORGANISM: Caenorhabditis elegans

<400> SEQUENCE: 65
catgttttct ctgcaaaaaa acaatcgtaa ttgcataaca tctttcgaac tcgatagtct 60
cccaaaaaat tcctccaaat ctttactgca tttgcttgta aagattttac ctatttttct 120
aaactgctgt gttcctgtat tttcactcta cctgtttcgt ttatttattt atttaagcat 180
caagtttatt gatctctaat aaattctcgg gaaattcgtg tcttaattat taatattata 240
gttattcttg ccagggaaag ttacgtttcc ttatcaaaca cctgttgcga aaccagaaaa 300
gggcgggtct gactaagtga acaaatattt cgtaataact ttcttccaac agaaattaaa 360
acacgcaaaa aacggccaac tcactagctg gaacgtggag ccccatgata actccatgat 420
aaaataactc tgattgtcga catagcttca agaatatcgt attctgcatt ttcaaaaagt 480
atttttcgtt caaa 494

<210> SEQ ID NO 66
<211> LENGTH: 1683
<212> TYPE: DNA
<213> ORGANISM: Caenorhabditis elegans

<400> SEQUENCE: 66
gcacaagccg ccgtgagact cgacgatacc acaaatttca acgatttctt cacaagcttc 60
aataatgacc tcgggctcga tcaggaatgg atggttttca tcaaagcttt ctacgcagaa 120
ctcaatctca aagtcgaata atttttattt cattgttttt ttgtttgata cctgttttga 180
ttaccatttt ttatcactat atttctgact tctttctcat ttttttaaa tttccggtcg 240 atctttcaca gacacgattg tatccgtgca gtatttgaaa ataacaaatt tttctgattt 300
ctgtgggttt cacgtgaaga tcttcttcaa gaagaggtca tcagattgcg gaagatctat 360
attaccgatc tgacgcaaga ctaccatgta tatttggaaa ggaaaaattt tctgtgcaga 420
ggttgatggt ttaaattttg atttagatat tttcttcatt taatttgaaa atttccatgc 480
ctgaaaatat cctcagtgag gattctcacc taccgtatac ttaaaggcgc acacctgtct 540
caaccggagc gttgcgagac ccgcggcatc aaactacaca ctgtgttttg atgatctttc 600
gatcgttctc gaaaaaagaa agagcagagt tcattaaaac aaatggcggc aaaatgtcta 660
taaaggcgag tcgttctctt cattatcttt tgattttcga tgtgttctcc ttattgtttt 720
gttcgttgac cccttatctg cattctcacc gctacgcaac gtatatttaa cgtcagcttt 780
ttcgcagaaa atttttctat attctcatgc aaatttactg ttctcaatgc tggacgtgtc 840
gcttgtgctt tgatctcaaa tctaacattt tcccttcaaa tattttatat ctgcaacggt 900
ggggcagaaa tttaaaagtt gacctttgtc agccaactgc tatcagttat cagttggccg 960
gagatctttc tattttcact ttcttgcaac gtattcagac attttttgat gaatcggttc 1020
acagaatttt cgtcctgatg ttggtcagtg atgcgccagc cggaaattag aaccgtatgc 1080
cgttatcaat ttttcaaagg ctaaaaagtt atgaggtgta tttattgttt taacacctga 1140

-continued

```
cctgctagta ggaaggaaat taattttatg tttaaattga aatgaaagag tcgagctcca   1200

cgtgtcgtct ccctagtttc tctattcctc ttcttctccg cctatctctc ggcttctctc   1260

ctttcgcgct cctctcacaa ttcctcctaa tcgtgctgtt tttggggtgg tccaacacgg   1320

caaaaaaggc agcaaaaagt gtctgccgtc tcgtgcctct ttcttattga aagggcacga   1380

gagaatagta tcaagaggct cctcgttcgg gccgttgaag atggtatctg gtgcttcggc   1440

ggagacggga ggagcggccg tttctcgggt catcacagcc cattccttct aatgtttaca   1500

ctgaacttgt cgcaatccct cctctaaatc tcattcatcc attcattcat attcgtgtta   1560

tgtgttcgct tttacataat ttccattttc accacgtttc tcctcaaatt tgcattattt   1620

aaatctctgc cttttcataa acatttataa ttttcagggt atcacctata ctaaccatcc   1680

aaa                                                                 1683
```

<210> SEQ ID NO 67
<211> LENGTH: 2110
<212> TYPE: DNA
<213> ORGANISM: Caenorhabditis elegans

<400> SEQUENCE: 67

```
aggcaaacat cacgtttccg atatcaaaag acattgaata aaagaaaacc aatagaatgt     60

aaactattaa agtgacaatt tcagtgaaat ttatcaaaat acgaaaataa taaaattaaa    120

aattagcgcc agctaactat ttagcagagc aaatacgttt tgacccaata taaaaacaat    180

aatatgaaaa aaaaaattaa aataaagttt taccaaatcg atattggcaa aacatcttgt    240

ttttgaggct ccatatctct gcaggaaaaa atcgcactaa aaagtgatca actagaaact    300

tgttaaacac aatgtaatct aaaacttttc agttgaacac tattttgtaa aaaatttcgt    360

tgccaagata tagatcttta actatttaga atattcaaaa ataatgaagc tcaaatcaat    420

tggttccaac tcggcaacga aatttttttac aaaaaaagtgt tcaactgaaa tgttttagat    480

cacattgtgt ttaacaagtt tctagttgat cactttttag tgcgattttt tcctgcagag    540

atatggagcc tcaaaaacaa gatgttttgc caatatcgat ttggtaaaac gtcttgataa    600

ggcatcagaa tcaatgattc ggtcattgaa aataatgaaa aataggttat ttgtgacact    660

ctaaaatatt tcatgcattt tttaaaaaat ttcaaaaaaa aatttttcga tcaaattttc    720

tcatggtgga gaaaaaagtg acaattttcg aaaaaaatta aaatttctga aaagtttcca    780

gggtaattat ggttcaatta aaaagcaaaa aaattatgta aaaccctcaa aaaaatgttc    840

taaatacttg tttcccgttc tgaaaatttt gtataaaaaa ggccaaaagt taaaccatgt    900

atgggaaccg aacccacaaa cttctgctca agaggcgaac gcgttcacca ctcgaccacc    960

gaaccgatgt tttcgccctt ccaccattgt ggtgagactt ctgttggcgc cagagacaaa   1020

aatccactgt taaccatagg aaatgcactg atttcagtgt agaatttcag acgtaaaaat   1080

ttcagatttc cagcccgaac gggcaaaaat ttcagtcata ttcttatagt agagaatgtc   1140

agctttccga tacaatattt ttttttgaat atcgctccat ttattctggt cattccctag   1200

tcagttgcct gcccgtggcg gaggaagaac ataataggag gatacgcaga gatgcagaaa   1260

aaaaacttcc gtttgttggt aggtagtaat ttctcctttt gatctccaaa gatgttggga   1320

aattcgcctt ttggaatgtt ttatggcgca ctttttaaca gttaaataca tagccacact   1380

ttctatagac taaacaagta ctcttgacat atgtcattca tcatgtactc tttagatttt   1440

ccagccttac caacctcctc cacagtttat ctcattgatt gtactctttg aaggaggacc   1500

attggttctg actttttttga ccttatactg attcaaaatg tcatcaaaga cacgagcttc   1560
```

```
gtaatgagac ttcagaaaaa aatttctgaa catttttata gcggttcaaa aattctagga   1620

aatttagcaa attttagcta tagctatagg ctttacaaaa ccttcaattt atttttttg    1680

gtcagataca cgatctcatt tcattttgct gattaagatt catttgaagc tgagaggtaa   1740

acaaaaatcg ccggaaattg taaaaatgcc agaaccttta tacaacctgt atgaaggttc   1800

accttacaat tatatctgtg tttttcactt gtttagagga gtggtaggtg gaagacatta   1860

aagtgtcgtt ctcgtagaac tgttgtttgg actgatagct tttaaatacg actttttaa    1920

aaacttttg agattataca actaattgca ccatcattta tttttgccg atgtgcaact     1980

ttcatattgt tttttctcct cactttctcc gttgtccttg ttcataacac aatttgcaaa   2040

tcacattgaa atttcagatt tccgattctc gaagctttac taacatctcc accactaacc   2100

aagcctcaac                                                          2110
```

<210> SEQ ID NO 68
<211> LENGTH: 884
<212> TYPE: DNA
<213> ORGANISM: Caenorhabditis elegans

<400> SEQUENCE: 68

```
aactttttgc aattcctaaa tacttaccat tatttttgcc caatcaggtt aatgatctct     60

atcgtgtagt tttccccttt tagttccagt tctgctgtga tatttattta tttttgcgaa    120

tacatttcaa ttcctaactt ttttcggaat acaaaccagt aactcataaa atgttcgatt    180

tatactcaca tccgcgcgaa cacttcagtg ccgggtgtta taacacgtca gcgtttcgcc    240

agatgatgca attggcgttt ttccttggag aacaaatagc ctcgtagaga cgcattttat    300

ttccacactg cattggactc aattggtggt gtatttgctt tgaaggtgaa tttaaattca    360

gacttttttt tcgaaacttg cgcagaaaat tgtgaatttt tcgattttta tagtggaaaa    420

taggtttttt tcaaaatatt tttattgaaa attaaaatgt ttgctttcta tgctctatta    480

ttgccgaaga aatcaatttt aatgaaatat tcaaagaaat cgcggaaaat tttcaaaaaa    540

tttccacgat tttattttgt acgcaatcgc atctgcatac cgtacccggt ttcgaatttc    600

gaacttttcg aagcttttct tgaatttttt tctgctttcc aattagaatt aaaagtgtaa    660

tttaatcaaa ttctagtaaa tttcaaacaa atttgggatt aaatgttaaa ttttattaac    720

attttcaggc tttaaaaaaa tatttcaaag ttttgtgtca aagtctgcaa acactctcga    780

ataccgtaac cttgcatctt ttttaatttt ttgttttctt tatttttatc actcctatac    840

tttttctata atttaaagca attttataat atatttttac agaa                     884
```

<210> SEQ ID NO 69
<211> LENGTH: 1475
<212> TYPE: DNA
<213> ORGANISM: Caenorhabditis elegans

<400> SEQUENCE: 69

```
tgctagcggt caccactatc gactgagcta tctgccccta agaaagttta aaaaacttac     60

cgattttgag ttccaacatc attttctcgc tatttttgat aacgttttgg ttagcattgt    120

actccggcag tattggtagg tcattctcgt tgtttggagt ctttatttca gactccacga    180

cggctggagc aacattctga attatatttt ttaattattg ttatactttt tagcaaaaaa    240

ctgacatttg aaatagatct actgttgcaa ataatgtctg gcaacggatc ccatctctca    300

cttggcctgc ctgagcctac atccaatctt gcaattgctt gctcacaatc tctcactaat    360
```

-continued

```
ttcaccaatc cgtaaaatct ggcttcccgg agcaactgat gtcgggttct gaaagtttta    420
tttaatttat aaaactttaa acttctagct taaaacatct accatttcct gaatttcagg    480
caaattcttg aagtatccat cgaactttgt tagagtcgct ttagaagtga caaattcctt    540
gccacctaca ttgagccgga gcatttactt tcagaaacaa taacagtttg agtttatctg    600
gaatttgtta gataacttta ggtagatttg aaatttttgg tagatcggtt tcatcaaatt    660
tatcaatgtc ataaataaac tttgtagcta taaattttaa aatagctttt tttacacttt    720
attcaaggaa acactgagaa atagctgcga aaacaaaaaa aaacatttga ggggagaacc    780
tagacgcagg agagaaagaa cgtagaatct actagaaaaa gtgtctgcgt ctcttcaaaa    840
aacaaattta aacttagcaa gatgaccacc acagcaaaaa tgaaaaagag gaacgcggag    900
ggacagggac agggttcagt gagaaaaaaa ttagaaattt tggaaaaatg agataatttt    960
taaacttttt gcagtattcc aaagtttttc ggaaaattga gacaaaaatt ttaatcaaac   1020
ttcccatgaa aatgacagaa aattttaaaa ttgaaattaa atgaaatttc tttattttct   1080
ggatttttag gagtttctgg aaatttctta gcataagcat aagcctaact acaaactaaa   1140
aacttcaaac taccaactga atacaattaa ttacctcatg attttgttcc cagcagccgt   1200
aacatgttaa aaactctatg ggtcctgtga gatgtcggcc gctctaactc tgcacattgc   1260
agagattttc agacagtgtg tgaccaattt taggctgaaa atctgccgac tgtactcttt   1320
ttggaaatgt tttgtttcga aatttttac tcactctcac tataactcca actcacctgg    1380
ttgcgaaatt cagcgctttt caacgtaatc taaaatgaaa aatattcatt ccatcactcc   1440
tccaactccc catttttgtt tgaaattctc tgaaa                               1475
```

<210> SEQ ID NO 70
<211> LENGTH: 2811
<212> TYPE: DNA
<213> ORGANISM: Caenorhabditis elegans

<400> SEQUENCE: 70

```
aagaacgccg acgacaacaa caaacatttt catcgggagc cctggaaaat gacgaatgta     60
tgcattacca ttgttgaaat ttggactgga agcgcaatgg atgaaaaaac cacgctattt    120
cgaagctcat ttctgatgct ggggcacaac acaaaattaa atgagacgag gagggggaga    180
agggatggag agcatgcatg ttttgttgtt cactttcgaa aaaatgtatc gattttttct    240
agcaaatgtt tgaagtaaat aacaactttc aaatgtgata attagttatc aattcagtca    300
gtttatcaaa aaaaagtacg tcattagcat aactttgccg tatttgcatg tctaggaaat    360
tttagaaact agaattgcta aaaagtggtt taaaagttgc gggacgccga aaattggctg    420
agaaattgtc aaaaatttcc aagtgacgga aaaccgtatg ttattgtgat tagtaagacg    480
atttcgcaat tttatatata ttttgtcaca aatctgaaat cactcgtgct attttaggtg    540
taaaagtcac atgttattgc acaaacacga gcagaaaatg aattaaaatt accttctcgg    600
tttttcagac attgtcttca actttgtcta ggtatttcga aatttcaaaa aaactccacc    660
tgacccacaa atcaatacta gtaagttagt aaacacaaca gtatgggaat tggttgatat    720
gtacgttgcg agacttgttt gtgcttatct ttttcccctc tctacttaac aatcaaataa    780
cctgcaaaac actatggatt tttctcttca gtttggggca attcttccag aaaaccacca    840
aaaaagaccg caattttgct aacggtcttg ttcacactgg tagataagat aacattgcgt    900
aggtcgatcc taccgatcaa acgggagata tatgggggga gtaggagaga aattacggga    960
agaaggctat cgagcggcct tgacacggtg cttgactttt tggcgaaacg tatcagttga   1020
```

-continued cctctattat ttgggctata cagagatgag gtatgatgga cagaaacaga aaaacacaca 1080
caaagggtat tgatgagaat catagacggt gacaacgcca attcaatgag cagtagatgt 1140
gcaggagacg tgtctcgttc agttggaaac gaaggcgaga cgtgaaaaga gtgcgtggtt 1200
gcgagagacg cagtgataga gacaaactgg ataggttatg agaacgagaa ccactcggac 1260
tgaggccatt cgtagaatga agaatggaag ttgtatctgt cttttaatag actcaaatga 1320
aactgaagaa aaaaagtaca aaacataaga cactatatat ttttttcat attgaaaaag 1380 agtttgcaaa ttttcttgaa attcaaaaat tctgtttttc gtgacaacac tttttgctta 1440
ctcattttgt aaaattttaa cgtgggctat tgtttttgtg tttaaatatt tatactacat 1500
ttttgaaaat tattattttc acattgccac gtgaactcaa aatttattca tgcaaattta 1560
gaataaaatc tgttcaacta agcctatacg cctcgtgcag aagtccaaat ttgaaaggta 1620
aacctaaacc taaatttgat catgaacact gagcctgaaa gcctgtaaac cataggcaaa 1680
gcctaaaaac agcttacaaa cctttctctg aaattatgtc tgaatacgta agtttattat 1740
atgaactaag ctttacagct aaatctatgt ttgcaggctc agttttgaac gttaataact 1800
ttcgaatcca catggaaatt tagatataat tgaataaaaa agtcctcgtt aatatttgaa 1860
aaaaaatgtt gtcaatttac gaatcctttt ttttcgccta aaaaggagaa tgtcaaaagt 1920
actaaataaa aaaacaaaac attcaagagc aactaagcag tttttccgaa attttttcca 1980
aagttccaaa gtcaacctta accttaagct gcagaatttc tgatgtttac cagctactac 2040
gaaacaaaaa cgattctcat agatgatttc ccattttcgc acacaaaatg ttggcatcac 2100
aaacaaagtg agcacaagta tggagagaga tttgagagca cagacatcaa agaataaact 2160
atgttctttg ttctttttaa actactttga aaaaaaacaa atgaatttac atatttaaaa 2220
tgttgcaatt gcaatttcat gatggaaata ttggaaaatg tctataaaat aacgcagaca 2280
gtgccaatca aaagcttttc tcatctaccc agtcggttga gtgaatgaaa ggaaacatat 2340
aatatcaaag ctggcgtgcc aattcctttt tgtgctcggc tgcattattt acactgccgg 2400
tgtttccgcg ctccttctca tcgacataat ttccctcatt tcctctcagt cttccgcgca 2460
gttccatcca tcgcaatccg ccttcttgcc taaatttgtc tgacccaata ctctaactaa 2520
ctttcattta tgtccaatgc attattctct ctgtaggtga cccagtgtcc ttcctttttt 2580
ctctctcaag atgtgagacc cccccccct tttctcctca acggcgaggg gctacgtgag 2640
tttccgctgt gtgcgacgcg tccttgcccg ctcttcccaa actgcacggc caatggggtg 2700
ccgggaggcg gggtaggggc gggccaatcg acgcgttcca cgactaagta agcgtggaca 2760
ccccatcgtc tgcagaagag gacactctcg atccattcgc tattcatcgt g 2811

<210> SEQ ID NO 71
<211> LENGTH: 1113
<212> TYPE: DNA
<213> ORGANISM: Caenorhabditis elegans

<400> SEQUENCE: 71
gaacacgttg catcgataaa tcgagaatat tctcgaagcg caaaaagaaa tttcgcaact 60
atttcagacc gaataatgta ataatgtaat gggtctcttc gatagaaaat aaacgaagat 120
aaacgaagac acaattcttc ctgacgcgcg agcttcaata tgcacgtgat gactaatttg 180
gtttccatgg tgatcttttt gttcctttta tcgattcaaa tttacaataa aaataagaaa 240
ttaaagttct aaatggcgct ccaatcaatt tgccttccaa tttaacgtcg attccttcta 300

-continued

```
tatcaggtca taaaatgaat aaaaaacaat gatcaataaa atgatgcggt agttgcgtaa    360
atcgacacat gatggtcgcc tcttccgtgc gagacccatt gggcggagtt ctcacaagaa    420
tgaggccaat cggcacacaa cacgcgtgcg acaggcagtg aacgacgtgt ttttggctca    480
gttcctacca atccctggtg tacacacgag cgccacgtgg accttaacaa ttcgggtcta    540
tttttatgct tctgctctgc attttctgga ttattagtaa taatatcatt aaaagtgata    600
taacgctccc cgagtctata taaaatttct cctccataca acacatgttt tttggctttc    660
ttcttctaag cttaaaattt atagttattt actaactgta ttttccactt attaaagata    720
atttttgaaa agtgtttgta aatacttaaa attgaacccg aaacaatctg tatttgtcca    780
ttcacatgtg attcacagaa aagaatgaaa ataaatgcga aaaaaaaata aataaagtaa    840
aggcgcattg attttaccgc tcgcggtatc tcgccacgaa aacacgtttc gcgtcaagcg    900
gctcacgttt tcgatgcgat cgcggtttgt taattgcgaa aacaccttcc cttctcttca    960
atcgttcgct caatttctag aaaatatttc tgaataatct gaaaacctct aatcttgttt   1020
cttagttttt aactttttgt cggtgttccc gataatctct cgccctctaa actcactcga   1080
tcgattgtcg tttataggta aagtttttag gta                                1113
```

<210> SEQ ID NO 72
<211> LENGTH: 2263
<212> TYPE: DNA
<213> ORGANISM: Caenorhabditis elegans

<400> SEQUENCE: 72

```
aataaaagat gtgatggtca atttaggata gtaaaagatg acaggtggat tgagggaaaa     60
gagacaggtt acttctgttg agtggacaca ttgcaacccc cggccaccac cgccacggac    120
acgccgccca cttttgcggt gtgaggtgcg aaactgtctt ccgacagatt tgtaaatatt    180
acgaggaagt tgatgtaata cggaagaggt ccactggatt tatgtgaatg aagaatcaaa    240
agattgtaaa atgtttagat atgatgagct acagggtcaa aggtgatttg atacacgatt    300
ttcgagcaga aatgctgact tttcgaaatc tcattgttgt ttaatcaatc acgggatgta    360
cgaaagggat cttggtttg gatttttgaa aatcaaaata ttacaggaaa atataatgca    420
aaactagtac agactgtgaa aatgtttcta accttgattt ctgctccgtc caactgtgaa    480
attacattgt gtgtcaattt caaaaacggt acgtgatttt ttagttctgg tttttaagtg    540
aactttatgt atatgagctc tgaaaacagg aaaataaggg aaaattaata aggtagtcag    600
aatgaaatat tgcaattcga acataagcat ttagtttgaa acaacccgta tttcccttat    660
tagttttgta gcttctagtt tgtcatgcac tgattttccg acagaccggc tatactctgt    720
gggaatttcc gcaaaaatta aatttaaaat taatagatga gatgtggtat gtagttttaa    780
aaaagtcgat ggattcagaa aatgctcaga aaaatccgcg cattaatttc caaaactatc    840
acatttcaga aaagtatcaa acatcatatt tttggagtcc aatactactt cttcatttct    900
ttttttttt tcttttccac tagttttaca ataaaatata ttgttttgtc ctaatgaagc    960
acatttcatt ttgtaatgtt ttttaacttt ctactgtagg atattctatt ccgtaatcgt   1020
acaaatcttc tttctctccc aaatttaggc tgcgccctgt ttcaaagctc tgctaatagt   1080
acgcaaaaca aatgtattcg ctaactcttt cgctcatttc ggtataagtg tcacttggag   1140
atctcttcgt ctctcgcaac ccgtatttgt attgtttatc ttccaaaatg gtagtcgact   1200
gctcatatga attgaattac tagcgggata tgaaagagac atgagattta taaaaagtaa   1260
ctgaatattt caacttttga aattgaactt gtatcatttt cgaaactaaa atggaaaaac   1320
```

-continued

```
aggaacgata ttacttcatt tttccactta aagatggagt agcaaaattt gggtgattgt   1380
ttttagaatc aaaattgatc ctaaatacct attgagacaa cttgaaaatg tctcaaaaat   1440
tattgtatta ggttagtcat tctctaaaag aaaacgggca acccttcaag tattaaatca   1500
ttttgagctt gaaaagagag aacattgttc attaaaattc atgtttgggc tcctaaatct   1560
acaaaaaata tcacatttat attttcggca attctgattt cctgtaatcg acaatttcag   1620
cgattgccga aatcgtcgaa aagtcgatta ccgaacggca attgctgcat gctatgtatc   1680
acaccgtttc agcgttgtgt atcgtatttg ttcaaagata attttcttgt aaatctcgat   1740
gttattgact actgcagcta atacatttga attcccatta attcctttaa tttgataagt   1800
gtgacttggt tcccgttgcc caccatcttt tgttcctttc ctcctatctt caaatcaaac   1860
gcatctggaa tctatttttt tcattgttgt ctgtctaccg atgccaacga tctgaccttt   1920
cttaattggt attcgcgctc attttgacat tgtgtcaact tcaactattt gcgcgggttt   1980
acctgcaaaa aagtaaacaa gaaaaatgga gatgaaatga aagaatttcc aatagaaatt   2040
tgttgttgaa aactctctga accatgagac cgtccaagac gttaacatca aatcttttca   2100
attcagaaac gtttcctctt tttctccttt tgtgacacgt ttcctccgtt cttttttgga   2160
gagtcactat atttttaata cgattttgct ttacaatttc tttttaaac ttttattgat   2220
tttgtgcttc ttattttcca tttttcataa aaagtattcc aga                     2263
```

<210> SEQ ID NO 73
<211> LENGTH: 850
<212> TYPE: DNA
<213> ORGANISM: Caenorhabditis elegans

<400> SEQUENCE: 73

```
gtcgcgaaag gtttgaattc ccaactggaa aaactgagat taagaaatgg aggtatattg     60
cctgattgag atgagaaacc ggtttatgag acggataaac aagtaagttt gctgagtaac    120
gatcacaaat ttcacaaatt ctcaagacaa gtgagatgat taatttctat aaggattaat    180
ttagatgatc cgaacattac ttgagtgact gttataatag aaagactgaa aaatcgtctt    240
ttaaattaac atattccata ttgctggatc cggcaaacaa aaacaatgtt ccaggacact    300
cactccacgt gttctgagct gtcgtctcgg tcgttgattg gctgattccg cctctgtttg    360
caactagtaa cgcgccgcag tttgcagttt tcagtgaagg acaacgtgtt tgcaagagac    420
gcagacactg tgcggcactt gcaaattggg gcgggacttt tagggacacg tcgagaaggg    480
gtgagccccg gcgaaagaaa gcaaacaagc ggagagaaaa ggggagtaat tgaccgttgg    540
aaagacacct cattccattt attctcggtc gttaggaaga gacggcgatg agattccttt    600
tggtgggctt cgtcgccctt ctggctgttt caggtatgtc tttttattga ttttcagagc    660
ttagtgagct ttaaatagaa aaccgtagtt ttgaaattgt aaaaaaaatt tttaagctta    720
aatgtacgct gaaaatatta aaactgtgtt cacagaataa aaacattagg ctttattttt    780
tcattctgtg catacacgcc acgcagtttt tgaattcacg tttttattcc caacaatcat    840
cacttttcag                                                           850
```

<210> SEQ ID NO 74
<211> LENGTH: 2171
<212> TYPE: DNA
<213> ORGANISM: Caenorhabditis elegans

<400> SEQUENCE: 74

```
tctgcggttc tgaaaatatt aaaaccaatg atggaaaaga atttattcgg gataaggatt      60
tttgacaaac ggacatatgg catatcctaa tgtgagcaga ggagctgtgg tcggagcaac     120
cgaccgcacc ggctcacttc tgctgtgatt cggctcggcg ccacgaaaag agtaagagag     180
acgtgacgac ggcaatagat gaatcgaaat ctatggatgc aagaaacctc ttttcaaatc     240
attcgaacgg ttagaattgt gcaaacacgg cgacgcacaa acgcacatat cgtggggaca     300
cgtgaacgat ggccgacttg agaagaggaa gaataacaga cggcgggaga gacgaggaaa     360
gggcacaaaa ctgagatgat ggtggtcgca ggcgctgagc gtgatctctt ctgttctatt     420
tcagacacca cgggattgta ttcaacaaca ttttgttgtt tctactgatc ggatgggatg     480
attgtaatta accactattt atgtttctca cgaattgtga cactaaatgt gaaaaccaat     540
agaaaacata atcgtatttc ttcaaatctg atattaaacg ggtagttcta attatgaaaa     600
tattgcccca cgacgaagaa ttaatattaa taatatttct tatttttcac ctgcacagac     660
actatagtta tcgatgatcc cagttttatt tggtctaaaa ataaaatttg aacttctgag     720
ggattgttga gcgacattga tatggaagaa gcgctatcga taaaaatttc tatcgttcca     780
tgacaaccaa tcacatgttc aaatgactga atgccaaaga aaacctcgaa agcgaaccgg     840
tttttcttcc ggtgaccgtt tagattttta taaaatcttt tagttagctg aaaatgaaat     900
ttattgcagc tccgtgagaa aaataatcag atatacgcag aaatgactga gggacgatac     960
gaaaatgcga agaatctgcc ttgcaagagg acagatgtcg gtactcaaca cgtacccaac    1020
acagtctcct ataggattga caatttatct tcagagcaga ccggaatagt attaacaaca    1080
aaaagctaaa cttaaaaacc gaaacgaaag caattcaaac ttaaaatgaa aactaaaata    1140
aaaagcaaaa accgaatgct gaaaaaaaaa ttgtctaccg tacacctaca gtaagattct    1200
gcatatttgc gtgacagtgt ttgcacatgt ttattcgaaa aatgtcattg ttttttttc     1260
gtttttactt ttttcgccaa tcatttagct ttaccctaga ttttcattct tattttgttt    1320
tccaaatcaa tcaataaaca ataaattttg tgaaaattta cctgcaaacc tccattaaaa    1380
tttgcaaacc cggcaaactg tcacagagag aatgaaaaat tgattgaaaa taataaaact    1440
gcttggccag tttgaaccga ttttaacaat taagcttaat ttttttgaag tatttgcata    1500
cacaccatgc agtttttttt taaagtttta ccgtaaatcc ctactgagct aataaattaa    1560
aaaatttcga ttaaaacaag catttatcac gagttctaaa ctgatatgag acatatttaa    1620
tttattccga ttcacttcaa ctgatgaaaa cttttgttca aattctcaaa tatatttcaa    1680
tcgtatcaca ttttttttcg gcagctgcag cgaatttttc ctttcatgag ccatgggcaa    1740
cggcttaatt acaccaacag ccgttgtcgg tgtttggatg tattgcccta aatgaccgcc    1800
cgtacgttgt cctctccatg caacgacgct gaatattctt ctgctctcac actcgtatac    1860
tagttgtggt tgaggcgcct cgatggacag catgagagag agtgtatcct ataataagac    1920
gtagacagac gcgctctagc aaattcttta ccgcagcact ccacagcgtt cgtcagtccg    1980
ccttgtttca cgttgtcgat tgcagacaca atgcccctca ttttctattc acttctcatt    2040
gtattctatc tgtatgtgca tagtaacttg ttttacagcg agtaatctca aaaatcgata    2100
tatttttcct tttcataata ttgttctgtt accttggtac cctcattatt attttttgaa    2160
tttaggtaac c                                                         2171
```

<210> SEQ ID NO 75

<211> LENGTH: 4107
<212> TYPE: DNA
<213> ORGANISM: Caenorhabditis elegans

<400> SEQUENCE: 75
aagtgatgtt ttggcaattg gaaaagctag actaggaatg aggataaatt atgacatcat 60
taggacttgt aatttagaaa ttacacggag gcaaaccgta atgcgttttt ttaaaataat 120 atttcttaa tttttcctt ttaatttctg ctcaagtttg tttgttggca aaataaatta 180
tttaaaactt ctcaaaacta tttaaatagg ttttttgaaa ggatgtgaaa ttccttatgg 240
aattttagat gatcttcaat ttgaaaactg ttggcagagt atcgccagtg aaaaattttt 300
ctaaacaaaa taactcaaaa aaaatcagat ctttcaaagt tgtcagtaga agtttttggt 360
aaattgccaa atgttccaaa aatgtggacg ttttgaaaat gttgagcatt tcagatttaa 420
gctactgcaa tcttcaaata aaaatatttg aaacatagct agaatatatg aatcgcaaaa 480
agagttttgg taaattggta tatttttcac aactgtggta ttggtctcat tcagttatac 540
atctttattc ttaactttga tataccgtac tctaaataaa ctttcctatt acaaccacac 600
ttttaaattt catatgtttt cactcttcag aggtcaaaaa ttggaagaaa ttattaacga 660
aaaaaataaa aaattagaaa ttaattatta tgtttttatg ttcaatttac gtttcaattt 720
ttcgtatttg aaacttggca atttaccaaa gctttcacta taaatttttt tactttttct 780
acaaaatttt agtgtgtttt actacgttat cctgtcattt tagactataa taagtgagta 840
cagtattgtt ttcatttagt tcatatttct atgttctatt ataattgtct gtatctgata 900
ttcgattttt ttgaatgaac atgagtttta aagtatatca aagttaaaat acggatgtat 960
agctaaagga ggcagtaaca catatttgaa aactttgatt tcatgttctc ttccttcttt 1020
tcccacggcg ttatgtttga ccacagaagc atctattttt ggaatcaata taattttttt 1080
cggtgctttt agcaaataat ataaagtttg ggaactacct ctaatgttca ttttcatttt 1140
tgatattctc ccttgacata tcaaaatatt tcgagcagta tgcatttcct tatcattttt 1200
caactgtatt tcctgatttt agcttttcat attaatcaag taggttcatg gtttcaataa 1260
attgtgggtt aattatagat ctgcctaatc ttcaagccaa tgccttctac ggagtattgc 1320
cagtgtggat ttagtttgaa aagtattcta ataaaatact ccaaaatttt aagttagttt 1380
tggcaaattg ccaacatttg gactttttga gctatttcca gcattgccac aggaactgtc 1440
agaatgtttg aatacaaaca gttgaaaata taaaaattgt agaaaattgt tttaggtcta 1500
ctttcaaaat ttttataggt tttattataa ctaaaattat tatgactaat ttttcaccat 1560
aaaaaattaa ttgcaaataa aaaatttcaa aaatgttttg aaacgtttta ctattttatt 1620
tggacattta agcactaacg tgttcaaagc tgaaatttca aaacgtcata actttgctga 1680
aacttgactt gggcagctaa atttttcgga gagatcataa ctaacagtct tctatcggat 1740
attcaacatg agaaccccaa acctacgggc cccttcaaag atttcccttg tgaatgggca 1800
attttaaata atctctccat ttacgatatt tcaccttcaa ataaacaatg aattattcta 1860
gattacttgt tgtcattcag tcaagatatt ctcaagtatt ccaagttctc cattgtttaa 1920
tgattttgct ccaattctat ccaatttccc tttgttcgct gctttagtcc cgccaccacc 1980
ccctgtgcaa agagataacg tgtgagtgaa tctaatagcc agaatctgga aatatatata 2040
tgtttagaat cacaaaagga aaatgtgcag gcggggagat caaaatcgaa actgtatttg 2100
tgtggaacaa tgcaactatt gagagaaaca tgaagcatat ggactacgag ttgagtaggc 2160
ttcaaaagta ttcaggaatc tcaaccaacg agttttgccc agaaattacc aagaaaccag 2220
tgtaagtttc attttatttt ttggatttag ttagattttt taaataatca aaaaccgatt 2280
tcttgccgat gtcatactgt agacactgtg agaagtagga ctacctcaat attgataagt 2340
gcctacctat gtgcctagaa ggcaggtgtg gcttgcattg aacttaacag tagacgtagg 2400
tctcttgaag ttttgcttcc aggcaggcag gtaggcattt gaataattta aagctatagt 2460
aaggagtacg gtaaattaca atatcatttc gtgataaatt tcaggcaaga tcgaaatcat 2520
tttgcaatgc tctacacctt tccttatatt acgtcaactt gtgatcgtgt cagacttttt 2580
gttcgaaatg cagtttcctg gagttcagag gtctaaaaat attcctgaaa aaattataat 2640
tctagatgtt caggtgaacc gagcccgagt agcatgcgaa tgtgaaaaaa ttgtggaaat 2700
gacgcgtggc taacgaggta cttctcgtcg ccgatctttc tcttgaccag gaccgaataa 2760
atatttgaaa atgcacttat tgtttgttct caatgccgaa ttgtttacaa tgtacctttt 2820
ggtaaagagg aactcgtttg tactggccag ctaataaaat attcacatta ttcttcatac 2880
tatgttttca tatagaattt atcaatttta taatttagat gataacgagt gctgtactcc 2940
tggagtccac caggacttga taagagaatt gaagcaccac ttttataatg agcagtacta 3000
atttcgaatc tggaaatgat atttcagaaa caatccagga aacaccagaa aaatatcacc 3060
actttgaaaa atatgtgcat ttattcaatt atgctcaaat ttcagctttg gctcacgagt 3120
gatacggtca accacaattt tctccagagt acgcaattta cgcaaacacc aaacgatggc 3180
gccaaagcgc cattcaaatt ttattcatcc gtttcagcct ttttcagtct tcttgtctct 3240
cattttcgcc attttcattg ttttatttac acaaacggtc gtttaaaatg tagtttccat 3300
ctttttccga tggttcatca tttttgtcat gcgtcttttg tgaaactggt tttgcaaaac 3360
gaagcaaaaa atggataact gtgtcaaggg cgatttttcg attcgtcatg tccacataaa 3420
cgcgataatg tgtttttatc gttggtttca ttcagaaatt ggttgataaa tacattctac 3480
tacattctgg ctgtgtgatc caatttttaa atccgaaagt ctagaaattt agtgcaaaat 3540
aagcatggaa agttctaaac cccttaaaga atactgatct cagctgtttc tgttcttttc 3600
aatcagattc ccaattgcga taatatcaaa aagccctctg ctggactgct gtccacccgc 3660
aagggcatta tttccttatc ccaaaatgct ctccgtctgc atctcttcaa ctcactcact 3720
ctctcgctct cttcgcagtg cgaggccgac acgcaacgtg gcctctcatc agacacgctc 3780
cgcctattct caatgtgtgg cgaccgccga ttggccagtc gctgacgtgg accaatagat 3840
acgcggcacc tcgagccgtg tcagccacgc aagacacacg tcgacttact ccattgtcgt 3900
agcagacgag ctcagttcaa catcatcagt ttcagttttg ctcttgttcg gtttcatttc 3960
tagtctttct tctctgaaat tctcgaattt tattctttgg tatattctca ttcaatttat 4020
ctcttctttt tccgattcat atgtttaatt gttatattta ctttttaatt tcagattcaa 4080
cttggtgtcg ttttatcgaa aaacgaa 4107

<210> SEQ ID NO 76
<211> LENGTH: 1524
<212> TYPE: DNA
<213> ORGANISM: Caenorhabditis elegans

<400> SEQUENCE: 76
ttcactcctt gtctgcaaca aacgaataat agaatcaata gatggcaaaa atttgaaaac 60
agcgtacagt caagataagg gtaatgtatg tttttgtcgt caacctctaa acgtcaaact 120
gaaaacttaa agggcggcgg ttggttaaat ggcgggcgtg tagtactaaa aacaaaggtt 180

-continued

```
tgagtaagtg cgccccattg ataacaagga tctgaagaag tcttcttcgg ataatggagg    240
tcagttctga tgggaaaatc gagaaatcga gttttttttta tttgattgca agctaatcac    300
atttaaaacg cttacatggg aaagttggcg tttgaaaatc gaatgtaata tacatttttt    360
tgattttctg attacttttg agctagcatt ttaccattta tatgaaaaat aaaaaaactaa   420
gttgcgattt ggatgtggtc aattacccat ttataaaact gaaaagtatg tttatttcag    480
ttcaaaaaca ttagaatttt agaacccttc tagctaattc gacccttctc caagccatgc    540
aataaccttt gatgaatctt atctcaacca attcacattg cagagattct tatctccagc    600
ataacgtatc tccaatcgct ttctccccca tcgtccaaca cagccgctat tatcggccaa    660
agtactacgt gtctcgagtc cgatcctgac ctacttttta tgtgtacttt agttcaattg    720
cgtctggttg gatttgaatt tgttgattcc caaataggag agattctgga taatttcttc    780
gaaagcgtta caaaatgcgc agaattttgt gtatttttaa aacagttgat tttagttttt    840
tggtttaaat atctagtgta tctgctttta gcaacaaaaa atgattctaa aactcgtttc    900
tttctaaatc atgtcaccac ttatacactt ggccttttcc gatttttctt tctctctttc    960
tatagctctt tcttactctc acctgccgtt tccataacag tgctctctaa atttggtata   1020
aaacacgcag cgcaaccgca acgcaaccta gtaactgacg tgtcccacgg acaccctcca   1080
ctcacgacac tctcgcacac aaacgcgcac acagggccac acgcggcgct cgccgattgg   1140
ccgaatgact ctgcgtctct gcgcgctgca cacggtgagc cttcgctgtg ctgacgttgc   1200
cttgtcctat cgtcctaggc cacgtcgacg attcggcagt tcgttccttc gctctctccc   1260
tctcgatgcg ctcgtcgatc cgtcagtttg ctctcccttc accactccca tcggttgacg   1320
gtaccatttc ggcctacagt cgaccttgag cattcgggcg gtctatcggg agagacgacc   1380
tacaaacaga agcagtccta ggttttcctg cattccattt ctctcaccga ctggccttgt   1440
ttcggttctt tctttatctc tttcttctca gcaattcaac aagtcgtttc atattttagg   1500
cctaataata atttttattt ttac                                          1524
```

<210> SEQ ID NO 77
<211> LENGTH: 1560
<212> TYPE: DNA
<213> ORGANISM: Caenorhabditis elegans

<400> SEQUENCE: 77

```
gccatttggt ttgacaccac acttcacaaa accaaagtca caaatcatag aagttgaggg     60
aaatctttct attcgatggc tttcagatct agtcttaaat agcgacaata tttgttcaaa    120
aagaaacaga atcgttcgaa attctgatat ttatcttaaa tcaaagcgtt atttggcttt    180
tttttttaaa gatctctatt aacagaaaca ccacgatgac gcgtgagttt ataacttaca    240
attggcaaca agaatagtga ataaaactga caaggctaca cttgacgggc agaccatctc    300
ggaagacgac gaaacggaca gaatgatcta gaagagtctc gtctgcggga tttcgactca    360
gcgtcgtcat cccttccgga acctccatat caaatagcac cgtttctcgc ttctccgcct    420
ccccaggcac tattatgagc tgttgtgtgt gtgcaagctc acatcataca agaaatctcg    480
aattcccact aataatagac aatgagactg atgttttgat tgagttgaga tcgtttgatt    540
agtcagaata gacggaaatt ggatggacca acagaaaaag agaggaacgc gaatcgaaaa    600
atataactgt ggaaatcggc aaaaaaaaag aatgataaca aaagggaaaa gcgcgtggca    660
tattcttcca acaaaatatg tgtttttttg gcgaccgact gtgcaactct ctcatcattt    720
atattctaca caaaaataat tcggaatatc caaaaacatg cataaagtcg cggaaatgtt    780
```

acgaatgtca atccgaaaac agaattgtga gtttacatga atatatactc aaatctactt 840
gaataatgct gaaatgtgta ttccaataca ctttttttaat ctcacaaaat tcagtaaata 900
atctcacact ggagagtcaa agagttctac agctaaattt ctcatttacg aatcaaatta 960
gagttttaaa gcgttccttc gtattaatat cagtgtaaaa aaataattaa gacaaaaaat 1020
atttcaaaaa accagaaaaa gcgaaaaaat gaaaaaaaaa aaagaatgac aaaaacaaag 1080
cgaaactttt ttctcagact acggtagatc ttgttgtgtg cagcgtgttt gcacagattg 1140
tcgaccgtac ccggaacttt tttatttgaa atattttcaa aaaaatatat tttctctttc 1200
caaattattc acatttttcg atattttaat cgtttcttca tggttttgct gtttggaaaa 1260
agacgttcat cacagggtaa gatttataat tgtttaattc tcagcaatta atttccatga 1320
gcagcgaacg actaattgtc aaaattgagc gtgttttata ttgattctgt ctctgtgcta 1380
ttccatcttt cctgcctaaa atgtatggct tttctcgtta catttctcca atactttcca 1440
aagagacgca gacataaacg aatgtttgcc ctattgcgaa agaagtaaat gaatcaccct 1500
tccttttccc ttttttccac tattttttat tttttatttt ttgaagcaac atcggcgacc 1560

<210> SEQ ID NO 78
<211> LENGTH: 784
<212> TYPE: DNA
<213> ORGANISM: Caenorhabditis elegans

<400> SEQUENCE: 78
tccattaatc tatttgttta atttattcta attctcgatc gggaataaat aatttggaaa 60
ttattcaact tattaaattc atagatctgg gaaactatca agaatcaaaa tcttaagact 120
attctcctct cgtctcgttt cacatctctt cgttctccgt ctatcgatcg ggtgatgctg 180
caaatcattt ttatcgatct acaaagtgct gcatttacta acggcatatc gtttcgagac 240
ccaaacgctg atgtgcgtta ttgcaaataa cagttatttt tccaaaccag cattacatta 300
cagtccactt tttttccttt tcatattttc atcctggacc cagctacata cattaccgca 360
aacgtgcaaa cggtagattt tatttactag ttcctttttt ccgaaaaatt tcaaaaaatt 420
gtaaactgcg tttccgtttt caaagaactt ttttgaagtt tcaacgcttt tcatcgcaaa 480
tatttacaaa tacgtctcgt tatttagaaa ttttaaaatt ttttgaacag tgaaaatcct 540
tttcaaactt cgcgctaaaa ttataaagca accgcgccct aacgtcagaa tcaccaaaca 600
ctttttgcgt acacttgttg aaaacacgct tctatatgcg tggatgatga caattttcaa 660
atctgtgtcg tttttagaaa taatttcgtg aactttttta aaatctcaat tttcttttat 720
agtttcgttc ccactatcat tttggacact cattcttctt attttaggtc ttaaattgta 780
cata 784

<210> SEQ ID NO 79
<211> LENGTH: 1487
<212> TYPE: DNA
<213> ORGANISM: Caenorhabditis elegans

<400> SEQUENCE: 79
atattcaatt cattccaaaa acgatttttt taaagttttt ttcaccagac acactttatt 60
tctctcaatt ttcaacagac acgatagttc tgtccaacct ccattcgatt tgtgtagtcc 120
ttttccggca ttcgtacttc aagctcatac aacgtgtcgt ctgtttcatt tcgatgagcc 180
atcataaacg cacgtctgta aatgtgttca ttatttcatg tcataaatta tttgcaatat 240

```
ataccgttcg tttctttgtt gaaccgatcg tttgatatac tccaaatctt ctggagtcaa    300
ttgatgacga acatttggtc ctgaatggat tccaattctt atttctatta ttaatttatt    360
atctcaccat tgataactgg cttttcattc tgatctttct ttctcttctt ttcatcagta    420
ttatcaactt ttcttgccgg ttttgctttt tctggtgatt tttgtttttc tccaattgtg    480
ggcattgggt agtaagtaga tgtggcgaac tgtttttgtt ggtaagtagg tgcaatagct    540
gtatgaggat ctgatcccat tctttcaata ggaatttcag atgcttgtct gaaatattca    600
aataattatt ttgttagttc ggatgtttcg ataagatatt attcagatgc aaaattttta    660
ttctgcccga aaactacggt actgtactat aattttctcg cgaaaatcac aaaatattgc    720
atccaaataa catccaatac gccttcaaat ttatgaaaaa ttacggtagc ttatgagtag    780
gttttggcac atgtacattc gtgtgaacga ctgtggttgt ttcatgcttt ttgacttctt    840
gcttgacttc tgaaataaaa aaaaactttc ataagatgct ttgttcattc aacaaaagcc    900
gtttaccttg cttcttgata cttttctctg gaacgtgtgc actagtcttc tgatgagttg    960
gctccacagt atcgttgagc aaagttttcg agtaatgctt cacatttagt tcttctgatt   1020
caacacttgt cgattgactt gttggctgac tgaatcatag aataattgat aatctgaata   1080
tattaaaaag ttaactcacg tttcgtcgaa atgtgcaact cgattgtgat gaatcgatcg   1140
ttccaatgga tgctctttct tcagtatcgc tgatttggac tttgagtttt tgtttttact   1200
atgactacag cccattcttg aatctttctc tcttattgca cacgatacga tttcctggta   1260
ttttgtcggc ggaagaatat atgagtaaaa tcagaaatga atcttttttt atctaaagtt   1320
ttttattcga agaaagaatc ttcgcgaaac atgtttctgt cacagtttat ctgaactaca   1380
aatcttaggt tcacgaactt acttacttgc ttcgttaatt aaaaaaaaat tatattcttt   1440
tgctttcgtt tgcatgcaat ttccaaaact ataactccta ttttcag                  1487
```

<210> SEQ ID NO 80
<211> LENGTH: 1659
<212> TYPE: DNA
<213> ORGANISM: Caenorhabditis elegans

<400> SEQUENCE: 80

```
gcaaatgtga atggaaccaa gaagagaacg agcaaaaatg ccaccgggaa actcattata     60
tcattctgga aacaattata cttcaaaaaa tggaagcaaa atataaaaca ggagttgtga    120
atagagaaaa cgacgcttta tatcatcagt tttggcattg aaatgaatca ataacataaa    180
ttgagcgaga aaaagagaaa cagcaaaata gtgaaaaacg aatgattgac cgagagaacg    240
ggggaaggtt ggaatttttg taaacaaacg agggaaacat catgttgaaa acatatatat    300
acacattttt tatttaatgc gtcggaatat tcagaaaatc gttcagatca tcgataattt    360
ttattgataa aagaccaaaa atccagttta catgaggaaa acaatacact gtgaatttta    420
aagaaaatta aatattccaa aaaaatttaa tttaatttgt aatttgggaa actgaaacaa    480
taaaacacta tcgaaaactt aaaaaaaaac atggattgaa gctcaaaaaa actgttttaa    540
tgtttcgttt tgtagaactt tagatttttg taaagcggga gacaccacga atccgcaaga    600
agtttcttcc agaagcagat tcgctgaaaa aaaatgaagt tgtcttaaac ctgatgcttt    660
tttttgataa tttttataca ttatgtggtt tcctggttgg ccattttgtt aaaatcatta    720
tttcctgtaa taaaagtcag gcgttctcag ttatttccag atatcggatt cctaaaatag    780
ctgaactcca aaaaacggtc aagtctctga acaccaaacg cgctccttcg aacaaaaaaa    840
gcagcgcgta cgtttaacga acagtttttt cttctagaaa ttgttttctc attgcgcaat    900
```

gcattgctca ttataaataa ttatgtttta aacagttgct gggaggtttt cgctatctca 960
gtcgttgtta aacaattacc agagtgtgtt atcgtattta tctttgccgt ataatatctt 1020
ttccatattt atgcgattgc ggaaatttac cactgactct gcggaaactg cggaaattta 1080
ccactgaaat atcactcata tcgtacgttt ctttgaattc gtctccttgt tattcaaatt 1140
atgtcttcgt ttttgaacga gatatttacc tctagctttc tagatcgtca catcacttag 1200
gttcgccttg aacttctgtt ccgctaaaga cggctggttc acatatattt ttaacaatgt 1260
aattattact tatgacccga ataaaacggt agaacgcttt gtgaaattat tcgaaagcaa 1320
atgcgcccca aggagagagt gtgaatgaga ggctgcgttt tgtcatcatg tagaggcagc 1380
attggggtgt tctgtagaga acttagtcta cgtgtctcat cttccatatt tcttaatttt 1440
gttctattgg ctctttttgc atctcttctt tgattcgatt ctttaactga attagatcag 1500
aaattatact tgaagtttta tcttgaaaac ctactgtaga aaagtttgtc cgtgttctac 1560
tttcttatta gactttcgcg tttcggcctt tcctatgttc taccccccatc ttccgttctt 1620 ttttattatt ccaagatttt acagagaagt cgtttaacc 1659

<210> SEQ ID NO 81
<211> LENGTH: 747
<212> TYPE: DNA
<213> ORGANISM: Caenorhabditis elegans

<400> SEQUENCE: 81
ccgggctcga acaagacatg gacgagccat tcgatatgtg atcatctgtt atcacaaaaa 60
tgatcaattt tcttcataat ttatcaaagt ttctgttttc cttccatttc atctgatgaa 120
ttcctacttt cttgttcctt ttcactaact ttattattat aattataatt attcataatg 180
ttctttcttt cccatcatca tatccatcct tctatacatt ttgtttccat ttgttgttga 240
aattttatat gctatttcat tttttgtcgt cctttttttc cgttcttcat tttattgact 300
tctcttcatg atttctggca ttcagctcga taattcattt ataccctgtt ctttctagtg 360
ttttttcgcg ttgtttgtga cggttaaatt cttccctcta catctttgcg cgtttccaca 420
caaaaatctg tacacgacat tcggttttct cgttgttcca tttctttttt gttcaacgga 480
gcgcgtttgt cgttgcagga atcggtttta atatcatcat ccattcacgc attctctttt 540
tcatgttgtt cattgtgttt ttcttcaatt tttgtcaagt ttccttcaca cgtgcatttt 600
agtaatttct ttctataata aattgcagtt tgttaaatat ttaaatgatc aatgagctct 660
cttttcttgg ttggctcatc ctctttgtat tttttgaatt atagttgaag aaaacgttaa 720
taacttttca gaaaaccaaa aataaaa 747

<210> SEQ ID NO 82
<211> LENGTH: 2141
<212> TYPE: DNA
<213> ORGANISM: Caenorhabditis elegans

<400> SEQUENCE: 82
atatagaaaa acggtctctt aatttcaaaa aaactaaatc aaataatgtg atagactctc 60
tcaattgaaa tagataaaat tgagagagac cgtggctatt acatttgtaa attaattttc 120
ttaaactcta cttctatctc cagtgagcca tactcgtgaa ttgatcgcat tgaattcttc 180
tcttcaatat caccttgtcc aataattaca tcgtctcgtg agcacatctt ctattaaaca 240
aaattagcac taggctagtt ctcttctaaa gtgagaaatg agaagaaatg tgagttgtag 300

-continued agacgtgtat aataaaatcc ataaaaatta aaaatattgt gagttcttct gagattacgt 360
gaaggccgaa taagaggtga cggtgataat cacaagaatt taaaaataat ttttccatag 420
aacgaatata taattgcgta aatggtcgtg gttgctcaga atctcgagag actgtggcaa 480
attgtcgaag ttttggcatt ttgccaaaat ttggtaaatt gccaaatcat cgaaaatgta 540
tattttcaaa gtgatttcga gcagttttgg aaacttttac tataatattt gagcacttga 600
gaaaccgatt tcaactattt ccataccgtg gaaaaattat gttttaagtt ttggcattct 660
gccaaagttt tgacattttg ccaaaatttg gtaaattgcc aattagttca aggtgtgtac 720
ttttaaagtg attttgaaca gttttggaaa ctattactgt gatattttag cactttagga 780
actgatttta actatttcaa tactgtataa taattctttc gacaacattc tcatcgggcc 840
acatgcgatc acggaagaat ctgaaattaa aagataaata gaaaacaatt tgagattatt 900
aaatattacc tctcggtgag atctggaaaa gcttgatcgt agagagtcaa aatttccggc 960
acattttgtt cgtcaaccat gcgggaaaag tagaccaggt agtcggcgac ctcatttgga 1020
actccatcct catcggctga agctgttaaa aattaagaaa tgagataagt ttgtgttgtt 1080
aacaagcacc taaataacta ccataaatat gtttatagaa ttactctatt gattgattat 1140
caatttttct tttgaaaaga tttcacaatg cacgatcatt gatcctctga tactcaactt 1200
ctctctcggg cttttaaatg attaacttct tatgaactct tatgaacacc ttttcattta 1260
ttatttcttt caaatgaata aagctgtgat tcatttaatc tgagatttga ggatattcga 1320
caccgaaaaa cactgaaaat gacaaaagta gtcattttca tatacaatga gggagttctg 1380
agaattggca ttgattcttc actgtaacag tatttggaaa atttggtttt tctgaatttt 1440
atgtattttg ctcatggaat gttaatctgc agtttttatg caaaattatt tcagaccaaa 1500
ttctccaaat gtctgtttgc cgaattaaaa taaatcggtt aatcaaaaaa ggaccgagtc 1560
ttcagtcttt tcgaactgtt tcaaatttta acatttttca actcatttta ctcttattca 1620
tcaattctga aaaatagcat tctgtgaact tacaagaaaa ggtgttggtg cgacgacgat 1680
cagagtgatc ttcagtggat aaatcgaatt ccacgcgtcg agacattact gaaagaaggt 1740
ttttatattg atattattta aatgtcaaac taaattcgaa aaggtacgct aaaattaaga 1800
gaaaacattt ttttaattgt aaaatttgat gaaaggaatt ggaaaatgtg atggaaaaaa 1860
gaaaattgca agcgttgcat gggatttcgc aagagtgccg cacggttttt tgtgtacgca 1920
tttgctcgtc attcatgttg tctaggcagt tttgatgaca ttttttattc taaaaacaaa 1980
atgttttatt tcatttgctg tttaatgttt gaatatgtat ggaaactaat ttgataccct 2040
ttccgctgca ttatttttgc aaaatctcaa aattatatat cttcaattca ctacctagaa 2100
ggcatatctt cctgcattta aaaatctatt ttatttcaga t 2141

<210> SEQ ID NO 83
<211> LENGTH: 1463
<212> TYPE: DNA
<213> ORGANISM: Caenorhabditis elegans

<400> SEQUENCE: 83
agatcaatgg cactgaaaac gctcatttaa atgcaaaaga tcgtgtcccg taaaaatttt 60
ctgtataatt ccgtgattat tttcactcgg gaatcgctcg cccactatgg gggagtctac 120
gcaaggacaa cgcaaggaca aggacaacat tctaatggaa tggaaacgat tgcccgactg 180
caccaattct agttcaagtg aacaatgata acttttgtat tctgtattcc ttcacgtctc 240
ccagcgagcg taataaatta ttattattat tataaaagga gagttttgat cagataaatt 300
tattatcgtt gaatatccac tttctctgtt tctcgtttca ttctctaaac gacgtatgga 360
taatacatat gatgaaggtc taaaaacttc aaagaaatgt ctcctagttt tgcaaatttc 420
caccgaaaaa aaatttggtc ggttctcgga ccatttatgt attgtatttt atttggctta 480
tgttttactc aggaaagtaa ataacttttg ctaaatgtac ataaaatcag caatgttttc 540
aaaaatgttt tgaggtaatc cggcttctat gtgatatatt aattcaatcc taactgataa 600
gataattata aatttaaaac ttactgctac ctccaacttc tggaacagca taagaattgg 660
ttggtggaat ggtaacatat cttggctgcc catatccatg acgtggtggt aatttgattc 720
tatagactgc ccgtttttct ctaattgatt cagttatcaa attccacgca tcatcggaat 780
atttctacaa aacattgaat taaaaacttg aaaaattaat tatggaccaa cttcaaatgt 840
tttcagatct tcaagggaag taatttcaaa gttttcaatt tcattaaaaa ccgaaaaaat 900
tgaagcgaga atcgtaagaa ctgcaaaaac aatgagcaga atagtagcga atagaaaatt 960
tgtgtgcttc atttttgttt tcagtttcag acaggtgtct atattttata cttttcaaca 1020
caatagatat taattatttt agagagaaaa aaacaggaaa cagctacata gtgtgaagtg 1080
aaaatagaaa tatgaaaaat gaaataacaa tgactttgac gaatttatcc ctcttaccct 1140
aaattttcaa taaaatcaaa atacaacaaa agctccaaac tctaaaatta ctaaattgta 1200
tttttgtacc aaaactagct tcccgacatt gataagtaac gcactggcac aaactctaat 1260
tttttagtga acacaaaaac agtaatctgc aaaactttct ttctcgtatt ctctgtttct 1320
ctacataccg tacttaatat ttcactatct tatctctctg tgtctcttgc cgaccaaaaa 1380
actaatggtg gatcgctata taaagaaatg ttaggtaagg agttgaatgt cagttatttc 1440
tgtaaaaact agaagtttct aaa 1463

<210> SEQ ID NO 84
<211> LENGTH: 628
<212> TYPE: DNA
<213> ORGANISM: Caenorhabditis elegans

<400> SEQUENCE: 84
attattatgt tcctatttct tttatcaaat aaatgcagtt ttaaaatttt ggacttttct 60
gagaacgtac agcaataaat aaaaatctaa aaccaatcac attcaaaagg tcggagcaag 120
ttcggagctc cgggattcaa ggtcacaata atgaaattgt ttttttattg cttgacattg 180
atcgaaatta atttgttatt ttttgcaaaa tcgaaaatga atatttttga attagaaatg 240
tttttacaaa attttgaacc gccataaaaa atgttgaaaa gttaaagttt tattacgaaa 300
ttcgtacatt tgaaaacctt ttgggtctac atgttcaaaa tcgcccgaac cgttagtctt 360
cctttaaagt cagttatgac tgtgttctgt gtctcctcga ctctgttttc tgaattgtca 420
tcacaccaaa agaccaatct ttagatcttt gtatttcttt tcattacttg ctatcaaatt 480
agccatgaaa aacatatgtc atcatattac tcactcaaaa tactacaaac tacactgacg 540
aggttaccgt ttgatcttat catctcttaa attagtcggg gtatataaga agaacaaatc 600
gagtacattg tttcaagaaa aattccca 628

<210> SEQ ID NO 85
<211> LENGTH: 1441
<212> TYPE: DNA
<213> ORGANISM: Caenorhabditis elegans

<400> SEQUENCE: 85

```
gattattttc ttatgctaaa ctggcagaca gcagatcttt ttatatctgc acaaggggcg     60
gtgggattta tagaaactta agtttactac gcctgccgcc taatccgtga aaccttattt    120
ttatattttt ccgcctcccg aaacagttga tacgtgaaaa agcacggaag agaaaaaagc    180
ttcttttgga cttgattaat ctgttggtca tgagaaagcg tgacacaagg taggttacgg    240
tagcaattgc gtaattaatc ggatcagtct atgcgcattt ctgaaacatt ggggatttca    300
aatctagttt atcaaacaga tacaaatcac attgacatct cgtggaaaca gtctgtaaag    360
taccgcaaat tttacaattt ttgatattat tgtcgttaaa caagttccat ttcaaatttt    420
ttattgaata cggtaaaaaa acaagagagg cagctggttg aagtgagtca ctcttgttga    480
gttttcgtta ctggaaacct gaatgaagat agtttttaac tttagcatta cgcctcatta    540
ttttcctatt tcctttttac tattttactt gtatttttaa actttgttta gcacattgag    600
cacataaaac caaatgttat aaatatcctt atcatcaacc catcggtttc tttttaactt    660
ttttctttct cgaatttcaa tgacccggaa aaccaccaca tcatatgaaa atcgaatcta    720
aaaatttgca gatacgcatc tgtcctgctg cgctcttttt ttatttttga atgttttttt    780
ttctgcaaac gttgggaaca gtcatccaat ccttcaaccg ttcgtctcgt tttgaatgac    840
aaacgttctc tttccgtcct ctgtttgagt atatttacat tgctaattca aaaaaaaata    900
gtatagaata taatgatact tagagatagt tctggcataa agtttaaact tgaatgaaat    960
catcaatgcc attaataact gtgtcactgc attagtttat cagcaagtgt gccagcaaaa   1020
aaaacgtttc gagacgattc gatacattcc tgaaaaactt cgataaaagg gaagtatcca   1080
aacaaccaca cccaactttc atcattgact cgctgttttg ctttttattt ttgttaatct   1140
tccttacaat tagttttaaa gtttaaaaca aatattacat gttagaaaga actgtatttt   1200
ggtcagtttg ttcgaataat ttcgaaatct aaaacctttt ctttttgatg attcgtcgga   1260
gtagatgttt ctcgaaggag gtaaaaaaaa ccgtgggcga ttcttgtttg cattgaggat   1320
aatagagcag tagtagaaaa gcagggagtg tcaactcagt tttgtcttct tcttccccta   1380
tttctgtctt actttcgttt tgtttctttg aaataattag attttcagaa actattataa   1440
a                                                                   1441
```

<210> SEQ ID NO 86
<211> LENGTH: 537
<212> TYPE: DNA
<213> ORGANISM: Caenorhabditis elegans

<400> SEQUENCE: 86

```
aggaaattta tccaaatgat tttactattt gagaatgtat tatgcggtaa ctttttttgaa     60
ataaactaat cgtgacactc aaaaacttag aatctatttt aaaagaatag ataattccag    120
tttttgatat ccgggaattt atgatttttt ggaagaacgc aagaaatcga tacatttggg    180
tacgcataat aggtactctt gcacttggat caaattccta gagaacgatt agatgcttta    240
gacgcagaaa caaaaaaatg tgaccgatac aaaatcgacc acaatctcaa gaaaaataag    300
tgcgcaacac aatccgaggt caatctagac atttatgctc ttcctgcgag acaaaaatgc    360
attgtatttt ttcattcaga ttcattcagg tgtcttgaag agatatcaaa tcacatgtga    420
caaaattttg atcgaaaaat aagttgcatc ataataaaat catcttatga tcttcctata    480
taatctttct tcaatttcgg aaactacgat tcgaatatat gtttatttt aggcgaa       537
```

<210> SEQ ID NO 87
<211> LENGTH: 2201
<212> TYPE: DNA
<213> ORGANISM: Caenorhabditis elegans

<400> SEQUENCE: 87
aaccttaggg taaagtttat tttatttttt tttctttacg atagggttat ccaggctttc 60
taagccgtaa ataaacttcc attttaaatt ttaaaatatt ttaaagctca agcttatagt 120
atagggaaca aagctttctg atagtttaga actaacaaag agcttatgtt ctacaaaaac 180
agggacgttt ttatttatag ggggggaggt gtaaggattc taaccgtctc tacacttctc 240
ccacttccct tttccccagt gatagaaggc taagagtgta tagggattaa tgcttttatt 300
tacaggatca ccggccagaa agtcagtcac gccatggatc aacccttcgc tcttctccga 360
atacagctct gcaattgatc catccgtgca cagtgccaaa cgctccttac gcgttcgatc 420
cctgagataa ttgcaataat tcccacacac tcgatttatt ccaagcctct aaacttcctg 480
gctaccgtaa ccctgtgtgt gtgtgcgcac acttgtgtgc gcgcaccttg tttacgtctt 540
ctggaccttt ctgcggagga atccagggct ccgccctgcc accgcagagg ggtatataag 600
acgtggattc tatcactcca gatcttctct tacttttctg ttccccttta cttgttccct 660
ttgtctcatt tcttacttgt acccattcca ttggggttat taattcataa taaatctatt 720
ccttagcaca taccttgttc tgttgtagta tgggatgcaa caacttcggt tgtcataatg 780
ataattgagg ggaacactta aacaattacc ggtatacgct taaacattta ctatatgttc 840
attcaatcaa tcacatatcg acacaacaat taacacaatc cacaagtttt tgcgcaatac 900
tccttcttct gttcctttgt gattcgtgga tccgcacaga agccacgtcc tgcccagaga 960
tggcagctgt aatttttatg aatttttatt atcaaattcg aattccccgt catttttttgt 1020 tcataatcct atattttcaa agatctagct caaaattgcg tgaaattcca tgtttgcgga 1080
cttttggcgc tacagtaacc cggattattt ttgaaaatcg agatggagct ctgaaaatat 1140
gggagaaaag gtagaaaatc atggaaaact cgaatttggc attgaatttt ttaaagaaaa 1200
aataaaatct gaaatttaaa aaattgaaaa tttcacccaa agtttcaagc aaaattatcg 1260
aacaaaaata tcgattttta tccgttttgt aatatcaaat tcgaattccc cttcattttt 1320
tgcccccaac cagagatcta gctaaaaatc gcgtgagatt cggtgtttgc gtacttttgg 1380
cgctacagta atccggtaat tttctgaaaa ttaagctatt tagagctcta aaattttcgg 1440
tttcgggcaa aaaatggcag ggaactcgaa aatttttaat aaatttttaa aataaagtgc 1500
aggaaaaaag ttacgaacgc cccaaaactt actcaatatt atcgtgacat gacggagtgg 1560
tctgagcact ttcaaattca ttcgggtgga aatttggaat actcatggca aaattggtgc 1620
cgaagagcac ataaagagca gtaataatca gaaagaatcg cattctggaa gcttctgacc 1680
tgaaaatgct ccagtgggga gattttatac tggaaaattt ttaagtattt agataattaa 1740
ttgttcgtat ttcggaactg tgttttatca aaaagcactg tgttttgtgc tcttaattct 1800
gtaatagtag attttttttcc ctaaaaatta gagtttttca ttatcaaact ttgatttttt 1860
catgattttt ttctaaacat gcggttcaac aattccatga actcaaaaca agccgaaatt 1920
tgaagtaaat tctgtgaaaa atgatatttt ttctaatatt attcaataaa tctattttct 1980
tgtcctatat ttggagcatt tcaattgaag tttgctccat tttctgcccg cggcctagaa 2040
acctccgtgg ccgaacaaca agcgcgctct actgcactct ttttattttc gtattttcaa 2100
tttaatttca ataattttta tcggttttct tcgatttttt cgcacttccc cccagtattt 2160
tttcaatttt tccgataaaa atacaaattt tccagctaac a 2201

<210> SEQ ID NO 88
<211> LENGTH: 942
<212> TYPE: DNA
<213> ORGANISM: Caenorhabditis elegans

<400> SEQUENCE: 88
ttttatacga aaaatacttt aaaatcagag gaaaatactt tgggaccggt gaaaaagcat 60
ggaggttcgc acaaacttgt ttaggaaaac agaaatatgt ctccgtggca ggaccatact 120
gtgcgccgtt gatgtccctt tgatacagta ctcttcgcat tatttatttt ttttcggcgc 180
gcctaggggt tttcgagcgc agagttcagg aggccttctg gattatggat agaggcttga 240
tttttaaaat tgtttaattc aatacagttt tattaaagtt ttttctaaaa atcttttcta 300
aaaataatat ctgattgctg tttatacacg agaacaaaac taatttcatg gaaacaattt 360
tttctcttta ttttctcttc gaataattta aattttaaca attcaggttt taaataatca 420
atttttaaat aagcaagtga attttaagca taacttttct tcctagtgta cgtaaatcat 480
tctttccaac aaacatattt tttcgtgacg aaacttcgcc ttccagaata ttcttttttc 540
agaaaataaa taccaaaaag cacaatttct tatctcttgc tcattctttt ctttgtatcg 600
tgctcatgct tttattcatt cctcattttt atcttgcgaa accaatgtat tttcaataaa 660
aaaaacgagt gatgcatgtg cgctccaccg gccgacggaa gatcgaacat gcactgcgct 720
tcgcgagtaa atagaacgct ctggaaagtt ccgcactctt ctctctcatg attcggcgca 780
ctctctcttc catttctccg tgtttcctct tctgatgttg acccatattt attctgccgg 840
gtgtattctt tttatctatc tgttgcttca tttattccgt taacctgtta ctggttaata 900
tttcaaaaat tcatatgatt tcttttcaga ttactttcca ca 942

<210> SEQ ID NO 89
<211> LENGTH: 1311
<212> TYPE: DNA
<213> ORGANISM: Caenorhabditis elegans

<400> SEQUENCE: 89
aactaaacat tgaaatttct gcacttcttt attgtaatga tgcttctgtg tctgacttgg 60
cattttcaaa aataatggaa tggtggagaa ttgacagcgc agaccattgt taagactatg 120
actgtgcagt ttatttgcac agcactgtct ggcacactct cttcatatca catggactct 180
ctcttgctca ccctttgaca cggattaggt tagaggcata ccagtgggag tcagagtgct 240
cagaaaagta gttgccatcg tggtaagagt tctgaaaagc atcgaaggtt ttttagggac 300
caaggaaata tgaatggagc atgtaaaaat acttgtaaaa ctgtaaaaaa taactcagcc 360
caaaactgag ggaaccgtac tttctgaaag aaatatgtat gaataccgat gtttttaggt 420
tcaatcaaac aatttattcg gatttttcac gaaatattac agagagtgtg acgttacata 480
ataatgttca ctgtttgacg cagtcacgag cttccaaaca attttatatt atcgagacgc 540
aaagattcac aattttcgcg ccagaatagc acaacctggt ctcgacatga caagttttag 600
ttaaatgcga aaagatgtgc gcctttaaag agtactgtaa cttcgaattt ttcttgttgc 660
ggaatttgtg aattttcatc gctttctcat tgtatttcga atgaaaaatt ggcttttttg 720
acaaacttag acacaaaaat aatgctcatt aaattttaac aaatcgagga aaaaaaatat 780

-continued

```
tgtgaaatgt gaaaaattcc gcagaaatga gacgctttcc ggtggcaact ttcccacaat    840

ttttcactga tagaatgtaa atttttgaat taatatcact ttcagaagtt tttatacatt    900

attttctcct tataaagttt gtgtgaatca cattttcggc cgaaaaaacc ggttttccat    960

ggaatgcatg cttccgatgc ttttcgcttt tattggcgga tggttacgca acctcaccga   1020

ttttatctct attttccgca cttttcttct ctatttccaa aattttcagc ctagtttatt   1080

tttgaaattt cagcaaaata attaatttcc tcacaaaact ggcgaaaggg cttttcgttt   1140

ctctgccgtc tctcttttcg cacgctctat aagcaagtgt ccgtgaagcg cacttgcacc   1200

cgtttatttt cacaacacgt tttcagataa ttttagctat ttttcattga ttttcagtag   1260

tttttacagc tattataatg gtattttttta gtaatttcca gtataaatcc g           1311
```

<210> SEQ ID NO 90
<211> LENGTH: 550
<212> TYPE: DNA
<213> ORGANISM: Caenorhabditis elegans

<400> SEQUENCE: 90

```
tttctctgca aaaaattgga gatttttttca gtctctttca actaatgtaa atacgctctc     60

ttgtgactaa gcgcgcgcgt ttgaaccaga ggacaatttt tttcctcagc gctagtagcc    120

cctgaaagag ttattcatac ttgaaaaaag aaacttttct atagatttct gcatgaaaaa    180

tcaatcctca gcgcttcttc tcttgctttt cctgattgta atgaaatttt agagttttta    240

aattgtaaaa aaaaaactaa acaagttctt tttgaaggga aaattcgttt ttaaatgctt    300

aaaatgcttc aaaaaaaaaa caaataaaaa aaattgtttc tgtgcataca ccgtcacgac    360

aaaatgcaga cttgccattg gtctcgccgc gaaaaaacat gtttcttttg aaagattgtc    420

ttaatttttt gatttcaatc atgatttcaa tcagaatttt gcgatctttc agcattttta    480

tctattttaa agctttataa attaaaaatt aaatttttaa aaatcttcca gattgtcata    540

cgggtcccgg                                                           550
```

<210> SEQ ID NO 91
<211> LENGTH: 836
<212> TYPE: DNA
<213> ORGANISM: Caenorhabditis elegans

<400> SEQUENCE: 91

```
aaattattat ataattttca aaattactgg ttgatgaggt tagattagtg ataccttgga     60

agtggtctat gtaataacaa tttttgcaca aaaggagatg agatttgata tggaagattg    120

gcaacacaaa cgtcaaagaa tggccattcc attttcatta catctcctcc attaacttgt    180

aatttgtttt gtagaggtct gaaatatatt tattttaaat tcgaaaatat ttttcaaaaa    240

atacgtacgt tcccataact cttttcttga cttcagcaat cattctagga tcgatttcac    300

atgcaattac agtttttgcc acctccagca ttttaaccgt caagtttcct gttcctggtc    360

cgacttcaag cactgtatcg gtggctttaa gagctgattt ctcaacgatt gcattcacaa    420

ctccaggatt tttgagaata tgttgtcctt tgtcggtgtt aaatggaagt gctataaaat    480

caatgttatg aatagaaatt ttgcaaaaat aacatacatt gaacatttcc agttgatgat    540

cctgctttcg tctttttaac tttactcgtt tttcccattt tgagtttttt taaatctgaa    600

aatgaacgaa aaataatagt atttctgaaa ataggaaaat aatgaaaaga aataaaggta    660

gaatgatttg tccacgtgaa gtacaaaacg tgggactaaa aaacaattct agtccgcgcg    720
```

tcgtgtactc ctctcagaca aacagaagtt gcacaatttt ttgaaatcga tccccttttaa 780 tcactttttc ctattcttct agcgtttaat tattttctat tgattttatt tacaca 836

<210> SEQ ID NO 92
<211> LENGTH: 2115
<212> TYPE: DNA
<213> ORGANISM: Caenorhabditis elegans

<400> SEQUENCE: 92
aaaaaaaccg gctggtttgc tgaacggcaa ttgctgttca tccctatacc tgcctaccta 60
ccgccaattc agataatgtg gtgaaaaatt tcacgaaaaa aagagcaaaa agaaactata 120
attttaaaac cggagtttga aaccgtcatc gtcgttgtca ttaataccat tatcattatt 180
gacatcagga atcacgccat tttgctccgt tatcatacac atcgtcatca tcatcatcgt 240
cgtcaacacc catcaaaaaa aatgtataaa aggtttcact caaaaagagg gttttatcat 300
tttatcaaga cttaaaaatg tcctcgtagt ttgactatga tatcattttt ccattatcac 360
catgtttgcg ttttcctttt tccaaacatt tcttttgcac ggcgatgatg cttggcattt 420
tgcactcgtg aaagtttcag cttgccagtg cgccgccgcg ttgtccatgg caatgcggca 480
tttgtattca acggcagaaa attgagagat ttgtttctct cgcgtacctc gcatgttttg 540
atttttcgac ctcggtttgt ccctcaaaca aagagaatcg tttgtcgccc tcaccgcgca 600
cgcatatacg gaaaaatgct acaatttcaa ggcgtgatag agatcagctc tcccgctgat 660
ttctatcgat tccaatagag atttattcac ctcatacggc ggcattagtt tgggcggtgt 720
tttttggtgt ttgttgtgtc caaaatacga aaacggaaaa ccttcatttc agcttagttt 780
ctaaaattga ttttctttta tataattttt ttcaataatg ctgaatgcac gtgctcgccg 840
gctgcccttt tgcaatgaga ctatgcaaac gcgcccgaat gcaaacgctg ctggtggacc 900
cctctcggac ataaaattat atttcttatt ttttcgaatc tgtttttctt tcatattttc 960
gaaaaaaaat gacaatatta tttgatgaaa aaactacgaa aattggcaaa accaaaaaca 1020
aaaccaagga aggatttctg gcttccctca taaattgaaa taaaagagtt taccgaacta 1080
ggccattttg gctcggccat atctggggta gatttacggc gcgttgcttg tcgcgtcgcg 1140
gctcgagttt agttgtaaaa ctaaatgtat ttgtccgtgt ggagtataca actttgccac 1200
gcgttgtcca gcaggagatt tgcaatagag caagaaaaat tcaatgagga aggccggacc 1260
ccgtgaaaat tcgcagaaaa gtaatgaaat cgaaacagaa aactccgaga ggactacacg 1320
gccgaggatt tttcctcgtc cgctcttttg ttaggccatt ttttgaattg gtaaacggag 1380
ttttctagtc cccgaaaata taatttagac caaccagcga gcacgtgctg ccattgtcgg 1440
accaaaaaaa aaacgccaaa aaaccgtgta tttttttttc gtttttttgat ccaaatgctc 1500 atttcgtcaa aactgatgcc tactttggct gcctacctac gcctacctac ctacgtgcct 1560
acatatcgcc tattctttgc attttggcgt ccagtacttc actttccaca gaatagataa 1620
aaaagtgtat tttgacaaaa aaatttattt gacctcggcg catttgatct cgagaaaacg 1680
tggcgatttt tgtttttacc agttccaaac tacatgtaac tttgccacgt ctgccagatt 1740
tgcgttccaa catgtcaaaa tttggaaaaa aaaaccgttg tttaccgaat gacacacaaa 1800
cacttttccc catctcattg ccctcttaat ctttgcaagg tttcacaaca ttttgagaat 1860
tctgctaaac cgtctgcgtc tctcattcct ccaccctatt gtcacggttt tgctatctgt 1920
ttctctcgtt ttttcgtggt tttttctctt tttatgacct tgcgtgtatt tgccaactat 1980

```
tttttgtttg tgggcatttt ttttggggaa aaagtttgat ttctggatga tttgaatatt   2040

cgtgtatttt ataagctttt tcctaacttt tctactttcg ttcatttctg ttgtttcagc   2100

cgtaatccga acagc                                                    2115


<210> SEQ ID NO 93
<211> LENGTH: 1106
<212> TYPE: DNA
<213> ORGANISM: Caenorhabditis elegans

<400> SEQUENCE: 93

tatttcttgt gattcgcttc gattttctga aaaaagattt aattgaatat taaaactaca     60

aagaggttaa aaatgatttc cgattttctc gattcaaatt tagagaattc cagattttag    120

ctcaattgtt gtgaaaacaa tttttagctt ttgagaatta actttttctg ccaaaaaaat    180

tacctggagg agccaattac aattagctcc aagtgtttca atacagtatt tgagagctcc    240

atttggtcca agtccaagtc gatccattac atcattcaca gtgatcattt cctaaacttt    300

agtattttaa atgaaaaata tgaccttaag tattaaaata acattgatag atgatctgta    360

ccacgtttca taattattgt cctatattca ttggaataaa atacttacag tgatatttac    420

atcaggtgcg tatgccattg tgtcattagc aggatcaaga ttgatagtga gaaatggtcg    480

tttggtttgt gagaaaatgt ccgttaatcc tgcacaaaat gtagattttc cagctccagg    540

agctccaatt acaagaactc cgtacatagt ccaatgagta ctgaaatttt ctagttgaat    600

cttaattttc tacggattgt tttgatagga aaacatttaa gaagaacaaa aatatataaa    660

tacaatttaa tttaatttaa aacaaacaaa aaagcaggat aaacgggcct ggcacagggc    720

caagtacgca tttacaccgt acatgacgac atattgcgga ccattgcatt ttgccgcgtt    780

aatttttat ttaaacggct tgcatttctc cttactatcc agctgacaat ttttagtttc     840

tttagaatta tttgcaatca aaactcgttt tttgtaaaca tatttactca ggtaatgtgt    900

tgatttctca cttttttttg aaatcaaagc agaattagtc ctatttttat tctacataaa    960

tatctaaatg tattcaatta aaaattgggc cattgaactt ctaattaatt caatttataa   1020

atttatcgtg atgttttctt ttagttaatt tgtccttaat cgtgccgtct attttatttc   1080

ttcataaaaa acttttcagt tccgac                                        1106


<210> SEQ ID NO 94
<211> LENGTH: 2241
<212> TYPE: DNA
<213> ORGANISM: Caenorhabditis elegans

<400> SEQUENCE: 94

caccagcatc aggagccaac atcagtgccg acaccatcgt cgcgaaacat gcaaagctgt     60

ggagtcgaaa gcactcaaca gccggaccgt aaacaggtga gcatacagta ctcggaggaa    120

gaaggctccg aatattttac cgatgagctt gacgatgttg atgatgagat tgatgatgct    180

gctgctgcag cccgtgcggc tgagaatatt cgtattccgg cgtgtctatt acagacggct    240

gctcaaaaat ctgaggaaga ggatgagtac gatgtaagac actcattggg ttacccattt    300

ttctttggtt ggccggagaa aaattattta ctatgctccg atatttgttg atcgaaattt    360

tccaaaaaaa gagctgtagg aaattgagat tgataaaatt aatttttatg catttttcgc    420

caccacctga tgtcatggtt tacaaaaaac caaacagtta aaatttaatt agatacaatt    480

tttgaaaaaa aaaagtgttt tgtacattta gaactaatcc ataagcgacg tgcatttcaa    540

tgaaattgtt tatttttatt tggcgtattt ctacgatttt ggacaaactt gtttgaaaca    600
```

agacaacaat tttcgaaata tcgtagcatc gtttgaactt atcatattta tttttaaaaa 660
atttctttcc gccaagaaaa atgggtaacc agcgtcgtcg aaaggctatg atcattaatt 720
tttataggtc atggagacgt atctttaatt aatactctat atactggtac gacgggtaag 780
atacattaag ttgtacaaaa attacagttt tcctccttta ttttctccaa aaaacctttt 840
gtctagaaac atctcaacat tatttagtta attttttttt agtttttcaa agtttataat 900
ttcaaaaaat tatttttctg ctttttcggt ttttcttcat gttcaaaact tcttcctctc 960
tcgtcatttt tgtataatgc atcgcggcga tataaatttg cattttatct ggttatggct 1020
tcatcatttt tttttcaaac gaattttggg aaaaaagaat gctatagtca ttttaattac 1080
atccctcata tttgtggcgt actgtttcct ttccctgcta tcccgattga tgtttttaaa 1140
ggcacaccga cgagaatttt cgattaaaat tgtaaattag agtaaaatct atgacttgtc 1200
aatcgaaaat cttgtcggcg ctctttagga actccataaa aattgaaaca aaaattattt 1260
taaaaattac caatttttttc caggtggccg ctgcgtggtc gacaaaaatc gacgtggaca 1320
cgcgcctcga acaagatcaa atggagggtg tcgatgaggc ggaatgggac aaataggcgc 1380
tactggacca tttcatatta ttttcagtca agtagtgtac aatgaacaca attttctcac 1440
ggttctgtaa aaatgttttt tctattgaaa tgtttgattt ttcgccccca tcaccaatcc 1500
atcaccacct ctccctctct cgctttttat ttgtctcatg ctttattcat catttttttat 1560 gattattatt atgagtatta ttactattgt atagtctcca atttcgtgat ttttggtttt 1620
ctagaaaatt gcgcccgctc gcccgccccc acgacttacc acctcccccct gaattttttt 1680 gtgctcccat cgcctagtcg aatttattct tttgtatttt tgtgtgtcca ctttctctct 1740
cggtcgatgt gttttaacat ccatattttc tgccccgcct cgtccccccct ctcaatcgcc 1800 cgctccccgc cccgccttta cactgtgttt cgatgaaata aacagtagag aattgtaaaa 1860
ctatgtgcgt gagaatttgg aaaattttag tttttttgtga tatcggaagc ttttttaggg 1920
gaatttgaat ttatttttaa aaattgttca aagataaatt agctccgaaa ttggaaatcg 1980
tagtggaaca tttgaatttc cgccagccag acatgtggca ttgcggttac cgtacccgca 2040
attgtgatga attttcaaaa atcggtgatc ttctggattt tcgctgtcaa gcttgagttt 2100
aagggtctcc tcactgatct atgtccattt tgcggcagga attctttttt ttttagtttc 2160
attcggatat ctctaaaata tcaagaaaaa tcgataattt cacttttcct gaaaactttc 2220
atattttcag aattttcact a 2241

<210> SEQ ID NO 95
<211> LENGTH: 661
<212> TYPE: DNA
<213> ORGANISM: Caenorhabditis elegans

<400> SEQUENCE: 95
tttcatagat tttttaataa tcagtctgct cactgataaa cacgtcgatt gccgcagtat 60
cttggagaag agaactgaac ttcattgttt gaaacctaga aaatagtgaa aattagttag 120
aaagagaagg agacggagaa tgaaaaaggg aaaatcgcgc gcgatggaag aaatttgaaa 180
aaagacttta cttttgatat ttttcgaaat tttttaaaat aattatgttt agagttaaaa 240
ttgcaaggaa aaatgaaaca aaaattagtt taaaaataaa aaccaccgta tctctttccc 300
tgcgaaacca attcaccgta ttattgtatg tgcctttaat ctttaacagt aagcataaca 360
tgtgattttc gccttctttt tattaaaatc taaattatta cagaactttt aaataatttg 420

```
attatattct ttgtttaatt tttaatcatt taaattcaat ttagaaatgc taaaaatccc    480

aaaacaatga gacactattt ccctgcagga ccattttaca gaaatactgt atgcaccttt    540

aatttctttt caaaagtaag cggcctttct gtcgaatcat tttcgttga tgaactcttt    600

tttcttcact tttactctat attatcacaa aaattcgaat ttttcagcga aaaaatcgaa    660

a                                                                    661
```

<210> SEQ ID NO 96
<211> LENGTH: 1207
<212> TYPE: DNA
<213> ORGANISM: Caenorhabditis elegans

<400> SEQUENCE: 96

```
agaatgtctg gtctccgaat cgtcaactcc cttgcatatt ctttagctcc aggacagctc     60

ggtgtagctg caatttgcaa cggaggagga gaagccacag cagtgctcat caaaaaactg    120

taatatgaac ctcttgccta aatgttttct ggtcttctat tcatcattcc ttgattcact    180

tttacaacaa atttcgatta cgtatttata aatagttaag gttcttgtca cataaatgtt    240

tattctcaaa tggtgcatac gtgttattga ttgggaaatg aattaaggtt aatatgtaca    300

ttatcaggaa tggttttgag ccatctcaaa agagatatac tggaaaaatc ggaaaagcat    360

ttttcttttg agatatatca ttcattcacg tcttcaaggc aaaacatata aggggagatc    420

gtatacaaat aatcacaggg aagaattggt ggatgataaa atgatcccat aaaccattat    480

tagtttgaga gatcaagttg ggggaatgag aatattaagg ggggaagaat ttaaccggga    540

agcaaacata gagcgattta atttttccgg gatttgcttt gctaggcggt tccaggtggc    600

gaggttggct ctgaggaatc ctttgtttgt ttcgccaaca gatctgagca tgtaggggta    660

tcttggagtt acagctttct tcaccgacga tgacacattt gggtagtgga agtttccagt    720

tatgatgttg tggtaggtgc gaaggatctg caagacccgc ctatattgca ctgacttcaa    780

attggcttgg gccaaacgat cctcgtatga agaatacttt atgttgcagc gttggaagac    840

gagcctggtg aagaaatgag atgaatcaat aaaggctatg aacgggtaac tcaataaagt    900

atcttcctgg actgggatga ttccgagaaa acaatcacaa acgatacggt aatgaatagg    960

aatccattga tttcatttta tctgtaattt cagtgtctga caagagatcg tcgtttcgga   1020

attattacag gcccaaatat ggctggaaag tcaacatatc tgaaacaagc tgcccaacta   1080

gcaatcatgg cataggtagg atgcttcatt ccagcaaact atgcttcgtt gccaagtaac   1140

ctaaaagttt tgatttgcta ttttctatcg tcgaattaat ttcagttttt aatcgtatct   1200

tctccag                                                             1207
```

<210> SEQ ID NO 97
<211> LENGTH: 475
<212> TYPE: DNA
<213> ORGANISM: Caenorhabditis elegans

<400> SEQUENCE: 97

```
gatggtactg agaagaagac cgatttcgat gctccaacaa cacttgctta attattcacg     60

gagatgtcat aattacagct ttggttttca ttatttgttt ggttattatt tatatcacaa    120

atttcgctaa tcggcgagac ccctctattg cttttctctc ctatctcgtt tttgttaacc    180

cagtttcttt tgaatgaacc cttgttatga cgattttatg gttttccaac ggtaattcaa    240

taaatgatat tatatgtgga aatcttgaat ctgatttgat cgatttagtc tcgaaacgtt    300

catgaaggca acaaacaaac aaccgttgat taaattagtt ttttgaattt cgcgcaccta    360
```

atattccaga ggagcgggct tgcattatct tttttacacg aatttcttat ttacagtatg 420
cactattctt tctcctctcc cattaatttc ttgtcaatcc catccctttt tgtag 475

<210> SEQ ID NO 98
<211> LENGTH: 1109
<212> TYPE: DNA
<213> ORGANISM: Caenorhabditis elegans

<400> SEQUENCE: 98
gcgagccgtt tttttgagac cctgaaattc ggaatttctt tttattttat atttttaaat 60
tcatttaaat ataaaaatag agcacaaacc tcatcaaatg tgctcactag aaaattacac 120
gtcctgcatt tttcgttttt gatggtgact tctttttgtg acgtggcacc aattaataca 180
gcaagcagga gcagtatccg gctcattttc accctgaaaa atggaaaaaa ttggattttt 240
atgtagcttt aagacacgac aaaccgttat tttagagaaa ttacacgcag aataagcgaa 300
tgagcgcggc cgaatgcact gcaaattgtc tacgttgtcc agtttctcgg ccctgtgagc 360
ggagaaaaga gagggagaaa agaaaaatga acaaatattg gctttgaccg ggattactag 420
caaaagaggt gactgatgga agagggaaca attaaatatt agaaaaattc gaaaaagtta 480
attattttcg ctggaaatca ccttaatttg gggagtttcg aaagaaattt tgataaaaat 540
agaattatcc actttttatt tcgtgaaaaa aacaacaatt tcgactgaaa atccagcttt 600
aattcgagaa ataacaaata tttatttatt taattaaatt aaattaaatt aaagaaaata 660
attgaattac tgtagtgatc gttgcgggac ccgatgaacc gaaatcggta tgcgccttgt 720
agttacggta agaaaaacgg gcggtgtcga gaatttaatt taaattgcat ttccaaaaca 780
attttcctcg tttgaaaata aattttacga gtttttggtt agtttaaatg ctaaaaactt 840
gatttaattt aataaaacgt acctaaaaat tcagtttcgt agcagaaaac acgaaaattt 900
cagtttttag taaaatttc ggaatttcta ttttcaagtc ttgtttatag ttacttttta 960
tggtgttcaa tcaacttttt gaagtttaaa atgtttaaaa cgtttaaaat tactttacaa 1020
gaaccgaaaa aaaccgaaaa tatttcaatt tttagttttt cagcaacctt ttcttaaatc 1080
agaaataatt ttatgaaatt ttggttcaa 1109

<210> SEQ ID NO 99
<211> LENGTH: 1049
<212> TYPE: DNA
<213> ORGANISM: Caenorhabditis elegans

<400> SEQUENCE: 99
cgagaaacat caaccatcga agagcagctt ccttggccag agtgtcgtct gataggtcga 60
tgtagtcgag caggcacacg actgctctgc acagttctcc gttgtaaaag tagaaaaagc 120
agagtttcgc gggaatactc gcgaaaatct ctcgatcttt gctccgacac tccatcgcct 180
cctttcgtag agtttgccac gtgatgaaca ttttgcatgc ggttcgttga tacttcgcaa 240
gtccttgaaa gtattcggac gaggcgtagt atgaggtgat tcgagccaat ttgctcagcg 300
agttcatgtc aatcggtcca ttgacgccga attcggcgat aaaaagctcg gaaatctcct 360
gttgcaactc ggcagtttgt tcggcaaacc cgatcaccgt gcagctcaca tttttgcgta 420
gctcatctag tttttcgatg tgctgcttgt caactgactt gtttgtgatc ttcatgaaag 480
tttatctaga aaaattaaaa ttaaactgtt ttaatggaat taacattatt acatacataa 540
aaagcaagtt ttttgattga ttttcattaa aaatcgagga aaaattgaaa atgaaagggt 600

-continued

```
ttcaacgcac gttatcttct aaaaaattta aaaaattttc ttctagatga tacgcttcac    660

atacgcgacg cgtaacattg gagcaacgtt gtcacttttt cttaaaaatc tcttataaga    720

gttggcacgg tgccagatcc ggaattccac cagatcttga attaaaataa gttttttgc    780

aagttttagc aagttgaagc aagttttttt attgattttc accggaaatc gaggaaaatt    840

gaaaatgaaa cgattttcga ggcaaaaata aaaaatttcc ctccgatttt gaagtccgtg    900

aatgcgcgtg cggtgcaact gcgtacaaaa caccaaactt tacgacagtg cggtaaattc    960

tacttttcaa agtttgagcc ccaaaattcg tttaattttt gtttaaaact tttcttgttt   1020

attgaattat ttacattttt tcagtcgac                                      1049
```

```
<210> SEQ ID NO 100
<211> LENGTH: 282
<212> TYPE: DNA
<213> ORGANISM: Caenorhabditis elegans

<400> SEQUENCE: 100

ttgaccaaga tactttgaaa tcatccgcgg atcatacaca attagtacaa cgtttgacat     60

ttctcctgaa aaatggaatt tcagttctaa aaacacaaaa ataaagttag aaattgttaa    120

aaacaaaaaa gtttatttga attcgccgaa gagcgcgcca aaacatgtga catttctcgg    180

ccgtgaaaac taggccaccg cggccacaaa caaattttag ttttcttcgc tgaaaaaaac    240

atgtttttca gtctgaaatc agagttttta gtatgaaaca ag                       282
```

```
<210> SEQ ID NO 101
<211> LENGTH: 1275
<212> TYPE: DNA
<213> ORGANISM: Caenorhabditis elegans

<400> SEQUENCE: 101

ccctaaatat attcacaata tctcatattt ctagatatgc agtttcttct tctggaacta     60

cacatcgttg gccattatgc ttcgcccatt tggtaatgat ttggatactt gcgttgcacc    120

ttgggtcttc tatctaactc atccggtttt tcggaagaaa gttgttcaga gaatatttat    180

ttttaggcct gactcatgat aataaagttt cgatttattt tctataagtc cgcagagatt    240

gaaaagtggc aaatttgatt ttgcttattc cataaaagtt atctctactt aattaatttt    300

atcatgtttt atgcaatttt caaagtaatg ttggtgcgcc aaaaaattct acttaagctt    360

gaaaatttga gatgaaactc taaattgtat gcagttattt tggtaataca gctttcaaaa    420

cacagaactt gcatcttttg atcatttcta acaatgtagc cttcacctaa ttttagttcc    480

cagaagttaa ctcagacgga taatgagcgt tttaaatttt tgaatttctg gttttgccgc    540

caatacttaa caagagcaca cgctatcttg aggaaaacaa ctacctgaaa aggggcgtag    600

tcatttagtt cacacttctc tgtgcgtttt tttaaataat gttagtttcc aaaaattttt    660

agagacccga agaactcggg ggatgtccaa ttggggggat taccaactcg gggg acacgg    720

ttttaaaatt atttttcttt gttaattctc gctctattga gaaaaataca gttttaaaac    780

cgtgcggcag ttgcagaaat gggcgtattg caagccacgg ttctgtgggc ggggccaatc    840

ccccgagttg gtaatccccc caattgggca tcccccgagt tcttcgggtc tcaattttta    900

gaattgttta aaaataataa tgccaaccca aagcacaaaa tccctgcctc ttaagtgaca    960

gtcttcattc tccgagtttt gaattccagg cgtgtgtgac gactcattca aattattgtt   1020

tttgtttttt tttcagattc tcactcaatt ttgaaatttt ctgcgtttca aaaggttttt   1080

tcggaatatt ttttaattct aaagcttcaa aaactgaatt aaaagaattt tctcctaaaa   1140
```

agtcgccgaa gaaacgcaga gaaaatcggc aaaaggcggc aaacatttta ttttcaaatt 1200
ttatccgctt tcccttgtgt ttatctttat tttccctcaa tttgcttaac cgaaacgtct 1260
gttttcagaa tataa 1275

<210> SEQ ID NO 102
<211> LENGTH: 1549
<212> TYPE: DNA
<213> ORGANISM: Caenorhabditis elegans

<400> SEQUENCE: 102
ggacgtgcgg cgaattgcac caattggtgc atgttcaaaa aggaacggag aagagccacc 60
ctgtgaccac tcgagcacta atttgaatga atcaacctcc ccaagtagta acatactaac 120
cgagaatagt ttgaagttct gggggtataa acaagaatgg agatagcaaa actaacgccc 180
gagagtaagt aaatacttat atggtgagcc taagtctcgc gtcgatttat tgttttctgt 240
tcagaacaca acgtgcatat ctagaaattt tcgatgattc atgcaaaaat gttttcaaat 300
aatttttcaa aaactgaaga aagtttgaga aataatataa atttaggctt tccttcagat 360
aaatttaaat ataaaaaatc atatatattt tcaagatgcg agaaaaatat ggaagcggcc 420
agcagagata cgctatagcg ctaaacaatg tgtgcgattc acaagagctt ctgaaagata 480
aaaattgtga ctacgattca ataattgatt caaagtttga taagtcaatc gatttcaagt 540
gaaaagaaag agcttgagaa catgatgagt agcaggtgta gaaaacgcat cgacgcgatt 600
ttttgttttg tttggcgcca ctaaacacac agacattcgg tcatacactc ttccaaatat 660
agtcaatata cagtgtgttc gagtgagaga gaatggaaca tgtcgaaata tagtgtctga 720
agacgagaca ctggattatt ttgacgggaa agcgtgttcc ttccggttgc aggatgctgg 780
tgcagcaaag tgtcaaaatc gatgggaaca gggaaggacc ccaaggataa ttgaaagatg 840
agcgaggaga aagagagcga ctgaatgagt tattacgagc ggcagatagc cggaatagct 900
ggcctatttt acattgcggt cgtcgctttt tgcggaacgg gtcgaacggt tttcaatgca 960
attagacgat tcgtcatctt tttgacattt tttagataca aaaaatactt atcaataaaa 1020
aagtttttta gaaaaactta aaatatcgaa tttatcttta gaaaatgaat taaagaagat 1080
gaaaaataaa atgaaaatct aaaacagatt ccataccgta gtttcacaca aagggacatt 1140
tatagttctc aaatttgtgt cccgccgcga aatcaaaaca aaagaaagtt agtccgtgta 1200
ctccactcgg acaacattgt ttcgcaacac ttttttctgc gaacattaaa aaatataaat 1260
ttgttcaact tccatttttt aatgttatca aatgtttcaa tttttcttaa tttttatgat 1320
attttcagct gaaatttttg tttcgattag atcacaaact ttttttgat gtttaattga 1380 aattttagag atgtattaga aagtttttta atcttcaaac aaaaaacatt tttgtcaaat 1440
cgagacctca aaataattta tcttttcaat acaatttagt ttccttgctt ttaacgttca 1500
aatcttgatc atttcttttt ttttgtttat aaacgattgt ttcagataa 1549

<210> SEQ ID NO 103
<211> LENGTH: 2228
<212> TYPE: DNA
<213> ORGANISM: Caenorhabditis elegans

<400> SEQUENCE: 103
actgggtcga cgagaagttt tggaagtgag aatttactaa aaaaaagaat taaaattaga 60
ataattctgt agacatccac aaatcacctg tttttcagtc gatgaaaact tgaaagttta 120

-continued

```
taatcgtcta ctttatcctc cttcttttca aagtcaatta gaacaccatc agctcctgaa    180
catcgatttt ttatatatcg atcactggga aagaatctga aatcactgat ataatagaga    240
cattgcattg ttgacatacc ttgtcagtcg aactcgaatc aacgatctga tcttcatttt    300
ttgtgttagt tggttagtcg ttagtagatt ataaattcgg taataaattt atagtggtag    360
aaattaatga gaattatatc cacgaatccg cgtgtactgc ggaaatattc attttatatt    420
tataaaaaat gttacaagtg agatcaaatt ttttttaat gtatcataga agagaagcgc    480
caaatcaata gaatgctgca cattttaccg catccaatcg ttccattttc tgaatttgaa    540
ataattattc atagctccat aacggttgag taacgtgaat gataattctg ttttaaatta    600
ttaagactaa ttcccctatt tgaattccct ccaaaataag aactgcaaga ctagcgattt    660
gatttgagca atttgcatcg cctactttcc aaccaatcaa attaagtgtg cgaagttcga    720
agtcgcctac ctaccatata cttcccatcg ggtctcttaa caatcattgg cttgaacgaa    780
acttctctac aaactctcgt tggtggcgac agaaaccgtc ttgtcatttt gccacgtagc    840
aatagatccg ccaatgcttc aggaatctga tttgatttca gtgcttctga tggaatactt    900
ccaaagcatc gatgaaatgc ctgtgggact ccatcaatgt cttcgaattg gaacttccat    960
agacaacatg gttgttctct gaattttaaa aaaatgatta tgattaatga ttgagtataa   1020
gttcctgagc cagttgggca acctacattc caagagaagg atcgcactcc tttccaaatg   1080
tgatccttgg aagtatggac tttgtgtcaa ggattgctcg agcatccaga ttccgtggta   1140
gaagatatcg attgttccaa aaatcatcga gaaccactag aatctctctg atcctagacc   1200
tctcattata tgaatttacg atagaagttg tccgaaatct ggcattttct ccccaatcca   1260
tcggttttgt ttcaattggg tgaattttta gaaacgtctc acctgaatca agaggatgtg   1320
atgaagatct taaatctctg cagttcacct tcataacata cgtacatcag tggagaccta   1380
cttccagggt ctctgaacca tcgatcagga atatgaattg ttaaactgaa cacgtgggtt   1440
actgtagtta tatttatatt tctcacttaa caacaggaat cggtatctgt ttgatagggt   1500
tgaagtgtat tccatctcga aaatgaatcg gaacatggaa gaattgtttc ctggctagag   1560
atccacaaaa gttcgagacg ttgtcaccgg taatccgatc tccgagaaga acaatctgta   1620
agaggtctca tctgggagaa gcttatttca gtagttacct tctgttcaga ctctgcgatt   1680
ccttgactat aatagtcgat cccttcaaga ttctgatgaa ttgcatccga aaatgcttct   1740
ttaacaactt cgtgcaaatg aaaacgtaat tcgttttgat catcatactg aaacttcgga   1800
aagattttaa gtattacccc gatccaaatg tttcgaatta aagttataaa tacggtaccc   1860
ggtttcgaca cgatttttgt caaactcgag gaaactacag tagtccttaa aggcgcatac   1920
taatagcgca aaatctcaac cttcgcttac caacttaccc gcacaccttc ctttctctgc   1980
gaatcaataa taaaattcga aatcggcgtc atcattctat aaccagtaca atgaataatc   2040
aaactaaata gaaaggcagc ttgaaacatt tctttaatct tctcgcaacg aaatgtgctc   2100
cggctctcca ggcttatcag tgttagaaga gaagagaagg ataaaacaac aataaaaaca   2160
gttttcattt gtctcgtttc ttgcttcttc ccccacgatc tgctgatctg aaaatgcatt   2220
ctttcagt                                                            2228
```

<210> SEQ ID NO 104
<211> LENGTH: 1895
<212> TYPE: DNA
<213> ORGANISM: Caenorhabditis elegans

<400> SEQUENCE: 104
caagtggtat gccaactcat ttgagagatc taaacatcga agcccatcct ctacttcgac 60
agcccgtaga agttgtgtag cacattttga acatgtgagc ctgtacaaaa gccataatac 120
ttctcaacta ctatcatcgt catctctccg tcaccaatga tctctactca aaacggttat 180
ggacggtttt tttgcataag gattcaacta gccctacacg attgctttga tctctgtaca 240
tttttgcgtt taatatggat atttgctttt taatggattt tcgatcttct acttttattg 300
ttgatttttc tggttttgtg ggggttgtgt acaaattttg tttatttgtt gtcggtaacc 360
acgggtacca tattatgtga atcgtttatc atcgtattaa atcatgtata catgcattgt 420
acagagtttt tgaatataat aaatgaacat gacgtcattt gcacctactt tgtgcttttg 480
aactttcact gtttcagata ttttttattt atgaaaaaag gtatctatga acaagctttt 540
caatacatta taactttgtt gtatctggtc tgatcctcaa tatttttgag tcttcaaaag 600
aaacaattat aaattgcaat acatctcaac actgttttat ggcgtctcaa attttgaaaa 660
aaaaaattat tttataaaaa ttgatttgca gcagacatgt tgaaaacggt gcttttcttt 720
taaattattt ttgttgtgat aatgtaatta actacaactt tacataaatt gaactgaata 780
tacgggtcat tcatttttac aaaccttatc tattctatca ataccatgac tttttcgcg 840 aaaagtcagc cgacatgaca tgactcttat ctcttttttt tttgttaatt ctttttttgt 900
tgcgacaaat tagtgtcaaa aaacgtgaac ccattcgatc acataacatt ttgaacttca 960
agaaaatcac acaatcgata aatgatgaag tatggtaagt caaaattttc taatattcca 1020
actgattaat agttagtgtg tttgagtttt actttttcaa attaatgttt acattaaaac 1080
aactataaca atcctcaatt gaaatattgt acacgaaata aaaatcaaaa catatgtatg 1140
aacatatttc tcttatcttt ttgtattctg tcaaaggggt ctaatttttt tgaccatttt 1200
tttgtcagtt agaaccaaat aaaatcatgc cgcatgtctg tgaaaaatca ccttattctt 1260
tctctttgag attgataaaa acgttctgta ggttttccaa aatgttaact aaaaaatcaa 1320
atttaagccg tcggtatagt attacaggct aggtatagga tgctcggata atattaattt 1380
taaaaattcg aaaatgcatc atacataaaa ctttttaata caaaatatag atgttttctt 1440
tttatttatt tattaatata acgtatctat ataattttca attaagcaat aaatattttt 1500
gaagatttga ggataaaact aagcaaattc taaaactgca atgttcaatg aaattgcgtt 1560
attcagtgtt acctataaag atttttcaaa acgttactct cttattcttc tcccattcac 1620
gtgttgcact ttctgccagc cgccttctcg gagaaactag gaaatatctg tgactttctc 1680
tagccactct ctactctctc gtcagtgcaa atagagcgcg aatgctttaa aatgacgcat 1740
caatcactct gtcggtcatt tgattttaca cttttcactg atagcttaaa gctcggaagc 1800
ggaactatag tgaaacattt tataaattac gatttagatt tttttgaatt ctgtatcatg 1860
ctgcctaatt tttaataatt tgaatatttt taggc 1895

<210> SEQ ID NO 105
<211> LENGTH: 1302
<212> TYPE: DNA
<213> ORGANISM: Caenorhabditis elegans

<400> SEQUENCE: 105
tgcccagaga gccgtcgacc aattcaacgg agtcgatttc aacggaagag ctctacgcgt 60
caacttggct caaaacagaa acaactaatt ttcatatcgg tactttgtta cttgtttgat 120

```
ctttaatgat ctcaataata ataaacccat gaaatcgtta tcataaatat atatgctcta    180
tttttttatt tcgaatcttc atttggggtc aatctgatgg caagcgttga ggctagaagc    240
ttgaaggaac ggcttcggtt cgagcaagtt ttgaatcctg ggctatgcgc agcccaatgt    300
gagcttacaa ctgaaaattc aagtttcaac actcttcgcg gtcttatttt ggactaattc    360
ctcatatttt cagcttgaaa tggaaaaaat ctgtcgaaat cgatgctatt cgaggggcgg    420
ggccaaaacg caaccctggc acggttttta cgcaactgcc gcacgttttc tccaaggcag    480
ggtgagcgga aaaattaaac cgtcataaat tttctgctac ggcctaaaat cgtcatgtct    540
ggaatcttct ctgtttacgg ttagtttttt aataatttat tttaagtatt aaacaatcgg    600
aaactggtta aaatagccaa taaaactcga tattgtcctg aaattttggg atttttcgga    660
aaaatcgaat tcgcgaagtt ttccctaata ttttcatttg aaaaggcaat tttaagtgtt    720
tagattcaaa tttggttgcg aaatatttaa atcaattaaa attttccttt tttttagttg    780
gaaacgctcc attccagacc accgaggagg agcttggaaa cttcttcagc agcatcggac    840
aaatcaacaa cgtcaggtaa ctctcccagc cagcccgagc ttcatgattt ctaacgcaat    900
atctctttca gaatcgtctg tgatcgcgaa accggacgtc cacgtggatt cgccttcatc    960
gagttcgccg aggaaggatc cgcacagaga gccgtcgagc agatgaatgg agccgagttc   1020
aatggaagac cactccgcgt caacctcgcc aacaaataag ttgatcttca tatcgggttt   1080
ttgttacttt tttgctcttc actgatctca ttattaataa caatccaatg aaactatcga   1140
tttaattatt taattcaatt tcaactattc tctaactaat ctgttcaaca ttcggggaag   1200
tttctctatt tgtcatcctt ccatccgccg acctgattca actttcttct tccccagctg   1260
ctccgttcaa gagcctactc gactactaac ctgttgctga aa                      1302
```

<210> SEQ ID NO 106
<211> LENGTH: 2410
<212> TYPE: DNA
<213> ORGANISM: Caenorhabditis elegans

<400> SEQUENCE: 106

```
tccggcaaat cggcacattt ccggaattga aaatttccgg cgaatcggca aattgccgga     60
attgaaaatt ttctgcgaat cggaaaatag tgggaaattg aaaatttccg gcgaatcggc    120
aagtttgccg gagtcgtaaa tttctggcaa ctcagcaaat tggaggaata aaacatttgc    180
agaccggaaa ttgtcgccca cccctgtttt gcactacgct ttgacaagtg tgaatttatt    240
cgcttttttt atttgcctga attttgccga taaagaagat ttccggcaaa gtggaaaatt    300
gccggaattt aaaaatttcc ggcaaatcgg caaaatgccc aatttgccgc ccacgcctgc    360
ttcacaaatt gattaattgc agcctcttcc gtagctgaac ctctggaaga agccactaca    420
acgagtgtgc cagagccaac agagtttcaa ttgtcacggg acatttatag cactgtaaag    480
ccgactgatg aggctcatag cccgccgatt caagcccaac cgaagaaaaa agccacgcca    540
agacggaaga aagcagatga cgtggaaact gtagtagctg acggaacagc gacgatcccg    600
aagccgaaga gaaaaaggcc gccgaggaag aagcctgagc cgaagccgaa tatcgttttt    660
gaaacaacgc cgaatcctcc gacagaaagc ttcgcagcca acaacaattt ccagcagttc    720
cagtttcaaa atcagcctgg tagttggacc tacaacaatg gattcggcaa tggatatggg    780
tacggcggtg gaaccactgg atacatggat aatcttgttg gcagagggtt tgacacggtt    840
tctcagcagc ctggatttca gaatcaaggt acattttta aaaggaattg agaaaaatgt    900
gccaaaaaat tttaaaggtg gactacgctt tgtggggaaa ttgctttaaa atacgcctat    960
```

ggtaccacaa tgaccgaata tcatgattaa aaaattcaaa aatttttct aaattttata 1020 tgatttttg aaaattggaa aaatcacagt tttccctaa ttcctatttg aattaccgcc 1080
aattgaattt gttcgatggg gcgcgcttgc acgtttttaa atttatttat tttattttt 1140 gttattttcc accgattttt aatgttttcg gtgtattttt gctcgaattt tagagaaaaa 1200
gtcaaaataa atgcaaattt tcgattaaaa agtgcgctta caggcgtaaa tcagtgaaat 1260
taattaattc aggttcgaaa tcgtttaaaa gcgttacttt ttcattttta cgcctgtaag 1320
cgtgcttttt aatcgaaaat ttgcatttat gttgattttt tctctaaaat tcgagcaaaa 1380
atacaccgaa aacattaaaa atcggtggaa aataacaaaa aataaaataa ataaatttaa 1440
aaacgtgcaa gcgcgcccca tcgaacaaat tcaattggcg gtaattcaaa taggaattag 1500
gggaaaactg tgatttttc aattttcaaa aaatcatata aaatttataa attttttt 1560 gaatttttta tcatgaaatt cggtcattgt ggtaccatag gcatgtttta aagcaatttc 1620
cccactagcg ctaccccacc tttaaaggaa ttgtgaaaat tgtgaaaaaa aaaatcaaaa 1680
tttcgaaaaa aaaagcgcta attttaacta aaatctctaa ttttggccac ttttccgtgc 1740
tgcagcgtcc gaaagtgcac tttttttgaa ttattattct tattattata cattaaaaac 1800
ccccgtactc ctccaataac gccaatatta tcgaccatct ggacgtgacc gcgtgcaacc 1860
acggcctagc tgccgccacc ccattcaaac gagacatttc ggcgggagag tcctttttt 1920 cgataattcg gatttttttg tctgtttcaa gtaattttcg ccataaaaat taccattttc 1980
ttcttcggtg ccatttctaa tgattttcca gtgcgttttg agtctgaaag tttgaaaata 2040 agagttttg cacaaaaatg tgtgagaaaa gttcaagaaa atcgtcgaaa aattcaataa 2100
attaatttta aaatttaaaa aaaaattaat tttttttaaa aatcaattct gtgcatacac 2160
cgccacgcaa aagtgcacac aattacctac cgtagtcaat gcgaaattaa atgattttta 2220
tcgattttct tcattttcag gttacgaatt caccggtttg cctgcaaata actcgaataa 2280
tttcccattt ttgtgattta atttttcaaa tatccttatc tatgccctca ggtttatttt 2340
atctcatttc cactcgtgtt ttttgaataa aaattctttt tttttcttct agatttccgt 2400
ttatttcaga 2410

<210> SEQ ID NO 107
<211> LENGTH: 2249
<212> TYPE: DNA
<213> ORGANISM: Caenorhabditis elegans

<400> SEQUENCE: 107
atttttcgaa tattttgtct gaaagtttca cgtgatgtca gagtgtctca tttcggcttg 60
atctacgtag atctacgaaa atgcgggagt tgagacgcag agttttcaac tgatttcgca 120
tggttaagaa cgtgctgacg tcacattttg ttgggcaaaa aatgcccgcg tttttgtaga 180
tcaaaccgta atgggacagc ctggcaccac gtgaaattcc agaaaaaatg tctgaaccta 240
ctgtagttca caatttaaag gcgcatacca aaaaattata gcgggaatta aatttttatt 300
taataatttt ttcagttaca gagcaattaa aaaattcaat ttcatcaaaa ttttatagac 360
caattttctc gctttatagc tgagctccgc gagccaaaat aggaagggga gcacgaaaaa 420
aaaacagaaa aatgagctcg acagagccca tagcctcaag cgctaacgaa ccaaaaaatg 480
cacacacaca caggaggcgg agtcgtggaa atttcgaaaa aaaaaacaag attttcttct 540
ctctcggctc aaatttgaat gcggagcaag aatattacgg gaacaaaaaa ttctgagaat 600

```
gcgtactgca caacatattt gacgcgcaaa atatctcgtt gcgaaaagca aactacagtg    660
attctttaaa tgacatttgt agtgtcgatt tacgggatct cgattttcga aatgaattca    720
tttatcattg atcgagcccg taaatcgaca cacgcactac agtagtaatt taaagggtta    780
ctgtagtttt gttttcgcta cgagatattt tgtgcgtcaa atatgttgcc caatacgcat    840
tctcaggatt ttttgttagc gtaataaaat aacagaaaac acagaaaaag gcatgaaatt    900
taatttgaaa taccgcgctg agttttctag gccacgtgtc gtgtactccc cgtggacaag    960
cggtttttgc cttatttttc tgaagtacaa attctcaagt acaagtaaaa aagtacaaat   1020
tttaccaaat ttgaggaaaa gaactagcat gacaaaaata gaattagaaa aattctagag   1080
aaaaactacg gatttctggc ttccctcata aaatgaaatg gaagagtttg ccgaactagg   1140
ccattttggc tcagccatat ctggagtaga tttacggcgc gttccgtgtc gcggctcgat   1200
tttagttgta aaactaaatg aatttgtccg tgtggagtac acgactttac cacgcgttgt   1260
ccggcaggcg attgtcaatg gagcgcgaaa aattcaatgc accagatttg acgcgcaaaa   1320
tttgaatttt caagttgtaa atccctttttt tcttcccatt gtcccatcaa atatccttct   1380
tcaaaaaaac ccctgcgtct ctcaggccat atctgcggta gatttacggc gcgttgcgtg   1440
tcgcgtcgcg gctcgatttt agttgtctgg cgggcgatta tcaatgaagc gcgaataaat   1500
caatgaggaa ggccagaacc ccgtgaagat ccaagaaaag ttttctaggc cacgttccgt   1560
gtactccacg tggaaaatgt cctttccggc aggagattgt caatggagcg cgaaaaattc   1620
aatgcaccag atttgaccac gcgtcgtgta ctccacgtgg aaaatgtgga cactagggat   1680
ctactaaatg cctggaaaat cgtaaaaatc tcgaaacttc ctaaagaaaa aaaaagcaaa   1740
tacacaaaaa cgcattgatg tatgaacaaa ttgccctccc cgtctcccac caaaaactcc   1800
caaaaattgc tctttttttca tgtttatatg ggggaccgcg ggatttcata atagctccgt   1860
ggtccgctca gctcatccgg agccaaaaag agcacacaca cacacgcaca cataaaagtt   1920
gtaaactagt ttcgagcaaa aatgatacga cggatgagtg tgtcacgcaa tcagtgagct   1980
tctctcgctt tcgaaagaaa aatctttttc gcaaaaagaa aaagtacttt acactggcca   2040
cagtgtaaaa taagggtgaa aagatcgaaa atcggaggtt tcaaatttga atttccgcgc   2100
aaatgagagg gacgaggtgc gatggcctac aaaactccgc aggtgtactc ctctcggaaa   2160
acggtgcgag aattaatttt ttaatttata tttaattttc agcgattttt ctcagttttc   2220
cggttaaaat ttaaattttt tcaggaaaa                                     2249
```

<210> SEQ ID NO 108
<211> LENGTH: 1234
<212> TYPE: DNA
<213> ORGANISM: Caenorhabditis elegans

<400> SEQUENCE: 108

```
aaactgcaat ttcgtaaacg attgaaaatt gagaaagatc aggtatctga acaaaaactt     60
gtacatttga aatctcaact tcatttattc caggatacct acaaatatga atcctatgtg    120
cttcaatgaa ttctacagga aaatattcaa taaatgacca aatcgaaaaa ctttatttat    180
gatcccaatt atgttttctt tgattatgct acaaattcaa gaatcggcaa ataatgggaa    240
aatacgattt ttttttcaca atcaatatat actgcttgat ctctctgtta gaatttcctc    300
caaaatctga actgtatgac caaaaatcaa tttttttgaa aatgcatttg tcccaatatt    360
tcctttctac cattctgctt tgatcttttt taaccttttt attcgaataa aaatatattc    420
cgaattaaat acaattaatg tgtttccacc aactttacac ataaaaaattc attttctgat    480
```

gtaaagattt tttctaacat acatgcatta acttatttct ggagaaatat ttctctggtt 540
taaaaaaaaa aacttctatt tagttatgat ttttcctttt cacaacgtga aaagttgcaa 600
aacttctgcg aacgacgcca cttctccacg gtgttgtttc tccggaacat ttttccccag 660
tgggacgcca cgcgcaactg cgctctactg ccaattttca aaaacggaat tctttcgctg 720
aaattttctt taattttctt tcgtttttca acgtttttca ttctctaaac ttaaataatc 780
gaaatatttc gaaatgatta atgaagaaag gtaggcgtta taatatttat aatcaaaatt 840
tctcaatatc atgttagata ttcatttttg gcgaatattc aacaattgaa aatcaaaata 900
ccattattta tcgactggcg ttatttttat tgtttcagaa aagctgaaat aaagcgaatg 960
ttggaaaaat gccgtaaaac ggaaaaccga cagaaatttt ggcgatggtt gcccaatttt 1020
cagttgaaca gctggcagac tcctgttgtc attggtgttg cagctgtttc tgctgcaatt 1080
atctatcact atttttccta attaccctta ttcctattgt tcaatttttc ttcatcctga 1140
ttttgtgatc tacctcatgt aataatttc tcttcttctt tattattttc tgcgctctgt 1200
actttcttaa aactgtataa attaaaattg caga 1234

<210> SEQ ID NO 109
<211> LENGTH: 435
<212> TYPE: DNA
<213> ORGANISM: Caenorhabditis elegans

<400> SEQUENCE: 109
cccacacagc cagaagattt ttatgggcgg cagacatttt cttaaatcca ataatgtttt 60
aatttgataa aatcgaagat aaaagttcac gataaacaca agtgaagtta aaaaataaaa 120
ataaaacatt caaaaaagaa ataaacgcat tctccgtaaa tcgacacaat gacaattctg 180
gcaggtctcg ccacgaagag tgttcaaatc atgtgcgcct ttaagacgcc aagccatttt 240
ctcttctgtt ttttaccact tattttgttc ttcaaaatgg ttttttttgtt ttgttctttt 300 attaataatc aaatgtttgt ttattttata catatatact gcttgttttg cattaatatc 360
aatctgttat cgatatttat ttctttttct ttcaatacat gactctattc gtaacatttc 420
acaatttttt gcagg 435

<210> SEQ ID NO 110
<211> LENGTH: 1559
<212> TYPE: DNA
<213> ORGANISM: Caenorhabditis elegans

<400> SEQUENCE: 110
gaacgtccga catgatgaga tgcaataacc tgaaaatgag gcactttatg ataagaaaat 60
gcggtaaaac atgcgaaata tggcaccata aaccgtgagc aggacaaaga acaaacactt 120
ggaaaagaaa agaaaataga aagaaaaaaa ggaaaactgg agaaaacaaa ctcaataaca 180
caacgcgaga aatacaattt cgtttcgttt tttcttctat ttattagatt tctcacaatt 240
tgttaccagt aaagtcacgt tctatatttc aaactactcc taaaattcgg tttgaacagt 300
tctctgataa acgaatttcg aagaacgatc agaaaacaaa tctacggttg tgtgtgatca 360
atggggtcaa acggtggacg aaaggggacg gcggagagag gaaaaagtga gagaaaataa 420
ataaaattga ccttcgagtg cagagttttg ctggtatttt ggtcagaatt gattatgaaa 480
atctgaaaat taccgccggg aaagttgaaa atttgacgtg gaaacgttta aaaaaataag 540
atgagaaagt tagtactgta gatgtcgtcg gatcaagtgc acagtacgca agcaccgtta 600

-continued

```
cgaaaaattg cactaattgc tcaattaaat ttttttaaaa aattaatttt tatagtgtgt    660

tttgtgtttt ttttctgctt ttttaatgat ttttaaaggc ttgattatgt ttttttctca    720

aaatttgaat aatcaataac attaattaat tactttatta aaaaaccaca tttggcattt    780

taataaagca agttatcgcg acaaacggca aaaatgtctc tttttataaa aattgttttt    840

ttttgagtta agagaagatg tggagttttt tgaactacat tagttttcta aaaattttat    900

catctagatt ttgaggaaaa aagcagatta tatatcttta atcttggttt taaaattttt    960

ttaaaaagca gaatattaaa gtaaaatatt ataaaaagaa aaattcgtgt ttgcaaaatt   1020

tgtttgaacg gaaccttgca aaaatgatat ttagcagcta aactaactga aaactactgc   1080

ataaagcttt cccaaaaaga gctaccatcc agaaaatgtt ttttttttca aagccgaaaa   1140

agaagaaaaa aagatagaaa accgaaaaag cagcatcgtt ttcgcgcact ctttcttctt   1200

tttttctttc tttttctaaa aaaaaatatt ctccgtagct tgaagtctca ggatttccaa   1260

agggaatttc cttgatagaa tatggaaaaa caagagagtc atcagagaag ggagaggaaa   1320

agcggggatg ctggcgaaga ccgggggcac cgactgaaat ataggcaccg gcggggaggc   1380

ggggcgctct ctcctctccg ctttactccg ccccgattgt cagtggagca ggtttgcaat   1440

gagtgttctc tgatgccccc tcagcgcggg agttttgaaa tcaaatattt tgtattttaa   1500

cctactttat tgatttttca attaaaatga aatgttattt gtttaaaatt taatttcag    1559
```

```
<210> SEQ ID NO 111
<211> LENGTH: 1476
<212> TYPE: DNA
<213> ORGANISM: Caenorhabditis elegans

<400> SEQUENCE: 111

tgtaggtcta aaaatatttg tttgagaata aatattcgaa atcaatctaa cgtttttcca     60

atctacaggt ggcacgacac gctcacaacc aataagtttc ttgccacgct cgtcgatttt    120

ttgtagaatt cccatttctg agagtgtttc ttcgctttct gcttgctctg gaacttctga    180

aataactttc ccgcgattat ttggatttct atatattttc aaactactta cctattttcg    240

ttttccaaag tctcgaattg tgtacttgtc gacgttggtt ccagatttga gcattatgaa    300

gaattccaat tttaaaatca caaactggct caaaatctat acgctcgaat agagaattgt    360

gtgatgtaag agcctgaaaa ttatatttga ttttctttcc atcttttttt attttcggga    420

ataataaaac attcaaaaag ggctgagatc tatctatttt tcacatgcga cccatttcta    480

tttcacgtga agcacatgat tctgaagggc aatggaaatg aaaacccgga aaaacaaaat    540

ctttcagttt aaattgtatc aaaacaagtt tttctagatt acaaatgtac ctgaatagtg    600

atccatgaat tgggacagac cacatcgaaa taacatttca cacgtggcaa tggagccatt    660

ttgaagtttg gctgaaatta aatttatgtc gagaaattaa aaaaaatcag agcgtcatca    720

tgagaaaata ggaaaggttt agactgtaaa atcaggtttt catggcggga atgacattaa    780

aatggtgata aggtgattat tttatcaaaa gaattttttg aatgattgca cctaaaatcg    840

agtgcttttt ctttaatttg attatcaaaa gaaaataccc aagaaatgga aaatgaaaat    900

ttaagagatg aaaggaaaaa gcgacccgga aaaacatcaa gctgggaaga aatctcaact    960

agttagacca aagcttcgaa ctctgcgagc atgtattttt tttcctcact ttctcctttt   1020

cttctctatt tctctagatc tttattactg cgggggcaaa aagagtaaga gatagaaaag   1080

aatgacgcaa aaaatacacg gatttaatat ttgctttgct tttttattca gagaggaaag   1140

gtcaattggg ggtttcccct cgttttatga atgaaaaccg cacataaata taattatttc   1200
```

cacagtttta aacggcagaa acggttcgtg ttataatttg tgagataatt gattttgcat 1260
tacgaaatta gaagaaaagg cggaaataaa taaattagtg tcgcaatttt tttctcaaaa 1320
aggaaataat gcaattacgc tccaccggac agtaaaattc tcagtttatt tgaaaaacaa 1380
aaatttaatt ttttcccttt ttttcaattg aaatctcaaa tttctgaact caaaatgaaa 1440
ttttcagact ttaccagaat attgtgacat cgaccg 1476

<210> SEQ ID NO 112
<211> LENGTH: 1697
<212> TYPE: DNA
<213> ORGANISM: Caenorhabditis elegans

<400> SEQUENCE: 112
atcgcagaaa tgtgaaatca taaaatccat agtgagattg agttgtttat tattttatga 60
aatgagataa tcagttggat aactactgct cacgccgtat tcgatctatc attcgattct 120
ccgattctgg aacatcaaat tttaatcata gggagagagg ttcgggtact tgagaaaaaa 180
atgtcgtgtt tcgagaggtt ttgaaaagtc agttgttaac tggttcggtc aacatgtaga 240
gattgtagag aaatatgaga acttagagaa ttgacgtatg aagagaaaaa agtgggaaag 300
gggagccgct gttgttttcg aaagaagaaa ataagacaga aaaaatcgga gaggaacata 360
acaacaagtt aagttgactt ttgaactgga aatttgtcaa tattgaaaaa aggaacagtg 420
agaaatatcg atttccacgt cgctcgattc tatgaaaaga aattatgcac acacaagctt 480
cacagtgagc atgctgaatg attgagcaaa tacatgagag aataagagag gaatgagatg 540
aaaagaagcg ttcaaatcaa aagaaaccag acaaaatggc gatttttttac gggaatatga 600 acctactgat tggcagtgga cagctggaag aataagaaga tactgaagga aggttgaagt 660
tgaagcttgg aagacagatg atgagagaga ggaaaacctg tttctttttg attacgatcg 720
gacggaaatg agaaggaagt aagtgttttc acacgtaggt gggcattgag atctttgaag 780
gtgcattcga caggttaata atcattctaa ataccaggtg acaatggagg atacttttaa 840
acagtaaata tattggaata aaacataaaa gttagtctta ctcagaattt ctaaaatttc 900
agccttctgg aacgaaaggt aaaatcataa taataataca agtggggctg ttagtagccc 960
taaatacaag taaaatgacc gaacacagcc gttaaagaat gttgcagaaa attgcgaaat 1020
atttccttac tcttaagaac aacattcgat gtgacgcaat atgatgcatt tccttagaca 1080
aaaacgttca gttcaaaata aacaacaata aaaccgtttg tacgatttct agaatacgag 1140
tttatcagtt gttcggaaaa tatcttatca atcgtttgac tgatgttttt taaccatgtg 1200
agaatttgaa aaaaaatttc atgattgcca aaaattaaaa taaacaggaa gcttttaccg 1260
agttttcgtg attttcagaa tgaagaaatt aatatgaagc tcaaaatcaa aagcagaggg 1320
aaaagaaaaa atcgaaatct tctttcggtt aaacaacacg cgcttgcgga acttcggagc 1380
atcgtatttt gtttttgcgc tctatttttg aatcggaaac tgttttttttg tcagttttcg 1440 aaattgtttt ttttctgttt ttttacttca tgcaagagtt taactttacg caaaaattaa 1500
ttaaaaatac gcagaaggcc cactttacac aggaattaat tgaaaatact caggaatttc 1560
actttactta gtcctttttc cagagtttcc aacggaatca atatattaat ttaatttcgc 1620
aacatttttc tttgaataaa cctatttgca aatgagaatg tttcagatat ttgcttatcg 1680
aagcctggga attgctt 1697

<210> SEQ ID NO 113

<211> LENGTH: 849
<212> TYPE: DNA
<213> ORGANISM: Caenorhabditis elegans

<400> SEQUENCE: 113
gcgtaaattg gtttctataa attcttgaca aactcattcc gaacggctga aaatattgat 60
tgaactgaat tcacattatt cattaaaaaa aataggttag cctgttatgt agagaaattt 120
agtgaataaa aaactgaata tgtatttatt taatagattt ctcggcacac aggaattagg 180
aataactccc aaaaaataga tatttggcag gagggccgaa cagctgtgtt ttccgtgacg 240
tcatacaggt caatggacac aggatgtagt catattacgg gaacacacaa ttctgagaat 300
gcgcactggg gcatttgatt tgacgcgcaa tatctcttag cgaaaactat ttacagtaag 360
aatttaaatt ctaccgtagc gggctcaatt ttcgaaaata tattttctta tcgaattttg 420
agagcagttt ttcagttttc catgcttgat tttattattt tatctttaaa taaatttttt 480
tcattgaaaa aacgggaaaa acaccgggag aaattgatct ggtgagaaaa ttataatatt 540
tctgctgttt tcctgttgac aactttagaa atgtcaatta aacaactata ttttaaaata 600
atcatttatt tttttaatta cgtcaactag aaaacattaa ctttttgcga aaattcactt 660
ctaccacact catcatcccg aaaacagcga ggtctcatga aattgcaagc gcgctctact 720
gcaaggaaag gcagcgcgcg aagcaaattt tcaaacaatt ttttgaacgt tttaccgcat 780
tttctcactt tctcgcttaa ttttgctatg ttttttgcga ttttttttgta atttttcttc 840 gtttttcag 849

<210> SEQ ID NO 114
<211> LENGTH: 828
<212> TYPE: DNA
<213> ORGANISM: Caenorhabditis elegans

<400> SEQUENCE: 114
tcactaaaca aaaaacatat atttgtaaaa taccattttt cttttcatca acagcttcaa 60
aactatctga agtgctggat tttcgttcag ctccgtcgat cagctcgaag tcttgctcct 120
gttctggagt atcgctcatt ctggaaagat ttaaatacaa ccgaggaacc agaagagcgc 180
atgaaaatat agagcgtgta atttaacgtc agttattgac agagaaaata gaattacgaa 240
agaccaaatc gggcaacgag gaaaacgttt aacacaaaca caacactgaa aataagcaag 300
aaaaggagga agttatcgga aaaccgaaga actttcaact tcggaaagaa ccgtttaatt 360
tatgtttaaa atcaaacaaa aaattcccga aacatccctt ttaaactttg attttcacga 420
aaaacaacga atgaccgaaa aatgtgatca atctctgaga gtgtgcactt ttgcgtgacg 480
gtgaactgtc cgcgtgcacc agattcgacg cgcaaaataa tcggcgcgag gttcgaacga 540
acgttcgtga atttgtggga gcggttttta atgtttaaaa atcagttttg gtttatttta 600
tttgaaaaaa aaaacgataa aagctatatt ccagcagtat ctaaaatgat cttcttttaa 660
tattctaatt ttaatgtttt aaaattcatt tttcgctgca gcaaaaagtt ggtgtttgcg 720
tacaaaaccc gcgccagtct tgaaaaacgc acgcattatt tattcacatg tttcgcaata 780
tttccatatg aacttctcaa catcaccaat ttaaattaag ttacagga 828

<210> SEQ ID NO 115
<211> LENGTH: 222
<212> TYPE: DNA
<213> ORGANISM: Caenorhabditis elegans

<400> SEQUENCE: 115
cttgtttcat actaaaaact ctgatttcag actgaaaaac atgttttttt cagcgaagaa 60
aactaaaatt tgtttgtggc cgcggtggcc tagttttcac ggccgagaaa tgtcacatgt 120
tttggcgcgc tcttcggcga attcaaataa actttttgt ttttaacaat ttctaacttt 180
atttttgtgt ttttagaact gaaattccat ttttcaggag aa 222

<210> SEQ ID NO 116
<211> LENGTH: 222
<212> TYPE: DNA
<213> ORGANISM: Caenorhabditis elegans

<400> SEQUENCE: 116
ttctcctgaa aaatggaatt tcagttctaa aaacacaaaa ataaagttag aaattgttaa 60
aaacaaaaaa gtttatttga attcgccgaa gagcgcgcca aaacatgtga catttctcgg 120
ccgtgaaaac taggccaccg cggccacaaa caaattttag ttttcttcgc tgaaaaaaac 180
atgtttttca gtctgaaatc agagttttta gtatgaaaca ag 222

<210> SEQ ID NO 117
<211> LENGTH: 633
<212> TYPE: DNA
<213> ORGANISM: Caenorhabditis elegans

<400> SEQUENCE: 117
ctcttctttt actaatccat caagcgactt ttcacggagt aatctgaatt aataatattt 60
atcagtgcat atctctgaaa actaacttga cgacaaatgc ttcgacatca aaatccggct 120
ttgtgacgtc caaaacacta gacattttac attcaatact gaaaaattaa agaaaattca 180
ggaaaactcg agaatgaaaa aaaacagatt tgagacacca tcaatacaaa gggaacgaaa 240
tttgggggaa atgctggttg ccgaaaaaat aagtagaagg taagatgtgt tcaactggaa 300
catacatttt ctgaattgca aactcgattt ctctcacatt cacaattttt aatcacattt 360
aatgcttcag ttttagaaag ttctgaagta tcctcttctt cctattcagt ttctcaaaat 420
cgatggtgtc tccaggacgt gcacaaatgc gctctattgc gaattgtgga acatcattgc 480
gcgcgcgact agaaaaaaat gagcgcgttc ttgaaaatta ttttgctttc tctaatttta 540
aacgatttcg attacatttt atctgaactt tcttgggttt aatcgaataa aaaacacaaa 600
aatattcttc agactggtaa aaacttcttc aat 633

<210> SEQ ID NO 118
<211> LENGTH: 898
<212> TYPE: DNA
<213> ORGANISM: Caenorhabditis elegans

<400> SEQUENCE: 118
gtctagtttc aaaaaaaatt aaattaaatt aaattgtgta atatgtggca ttatttatat 60
acttttttgt cgatcatctg ttaagttagt ttttagtctt atcttcttgt cgcacaaaac 120
attatggttt gtgtttaata gaacaagaaa gtgggtgaca agaatcgtat gatttggaga 180
aacccagcaa tcaagaagat tttgtttcaa aattcgtagt ctggatactt tagaatgtat 240
tctcaatttt cgaataaagt ttagaggatg ttttttcaaa cttttatcaa tttttgaaaa 300
ctatctgatg gttttataat tattacagtc acatatttgt agcttgtgaa tctaaaccta 360
ttatgtatat tctcgtttta aaaaaattaa ttgccgaaaa aaagcaaaaa atttttaatct 420 tacgaaaaaa agttttttt ttggatttat cagcttcagt gctcattttc atccctaact 480
ttctttcaag aaattttaga tatgaagaac aattttaaaa ttctagatca accaaatctc 540
tgaaacaaaa ctagttttct attgtttcta catattgata tttttttaa actccattat 600 catttttaat tttttaaaaa gttttctaac taccatctgc tctccatcac ctctttatgt 660
tttttgcatt tgagcagtga aaagtttgaa gaatattggt acaactttta taccttccaa 720
aaagtgcttg ccccattctc tatgttctct tatcagtaca ctatatctca acagtcgaca 780
catttgtgtg gaaaagtgtt gtttgtgtct gactgttgtt tctaccaccg atactattta 840
taaggtggtc taccgaaaaa catcaatacg tttctttttt attcctgaaa ataaaaac 898

<210> SEQ ID NO 119
<211> LENGTH: 898
<212> TYPE: DNA
<213> ORGANISM: Caenorhabditis elegans

<400> SEQUENCE: 119
gtttttattt tcaggaataa aaaagaaacg tattgatgtt tttcggtaga ccaccttata 60
aatagtatcg gtggtagaaa caacagtcag acacaaacaa cacttttcca cacaaatgtg 120
tcgactgttg agatatagtg tactgataag agaacataga gaatggggca agcacttttt 180
ggaaggtata aaagttgtac caatattctt caaacttttc actgctcaaa tgcaaaaaac 240
ataaagaggt gatggagagc agatggtagt tagaaaactt tttaaaaaat taaaaatgat 300
aatggagttt aaaaaaaata tcaatatgta gaaacaatag aaaactagtt ttgtttcaga 360
gatttggttg atctagaatt ttaaaattgt tcttcatatc taaaatttct tgaaagaaag 420
ttagggatga aaatgagcac tgaagctgat aaatccaaaa aaaaaacttt ttttcgtaag 480
attaaaattt tttgcttttt ttcggcaatt aatttttta aaacgagaat atacataata 540
ggtttagatt cacaagctac aaatatgtga ctgtaataat tataaaacca tcagatagtt 600
ttcaaaaatt gataaaagtt tgaaaaaaca tcctctaaac tttattcgaa aattgagaat 660
acattctaaa gtatccagac tacgaatttt gaaacaaaat cttcttgatt gctgggtttc 720
tccaaatcat acgattcttg tcacccactt tcttgttcta ttaaacacaa accataatgt 780
tttgtgcgac aagaagataa gactaaaaac taacttaaca gatgatcgac aaaaaagtat 840
ataaataatg ccacatatta cacaatttaa tttaatttaa tttttttga aactagac 898

<210> SEQ ID NO 120
<211> LENGTH: 890
<212> TYPE: DNA
<213> ORGANISM: Caenorhabditis elegans

<400> SEQUENCE: 120
gaatcttcga tgttcattgt gaattttgta tcactgcctt gcctttattc acttcaggaa 60
ttttatgttt tacttgtaat ctcaataaaa atgaactttc aaattaataa taacaaacta 120
attttctagt tttacatcag atatctgctg agcttctgct cctcttccgt caaaattaaa 180
tcaaattggc tgagcagcgg cccagtcaac tagcgaagtt aggacatagg ttttcttttt 240 ttttttgtt gaaatgggca aattgccgga attgaaattt ctggcaaatt ggcaaattgc 300
cggaattgaa catttgccca aatctgcaaa ttgccggaat tgaaatttct ggcaaatggg 360
caaatcgcca gaattgaaat ttccgccaaa ttgtgatttt gcactttttt ctggaaattt 420
cagaatttca atttcaatcg gcaaatttgt acgcatccta ttttgaaaag taagcaaatt 480
ctatgaaaat atctaaagaa aacgggaaaa aaactcaaaa agacactgtt tttagtgttt 540
ccgttttata aaaaatgcct ctaaacattt ccgacaaatt tgatgatccg gcaaacgaca 600
caccggcaat ttgccgacga aaaaagttgc caaacggcaa ttgttactgg atcttatagt 660
gatcaaattt tggaaaactc aagtacagtc agaaaagcag tcagaaccca gggtctatta 720
aaacatcttt tacacattga aaagttacat atacttgaaa aaaggagaca tagagaaaaa 780
ctcagatact gtctctgaca atttttctgc tttgtgccac tgaatggtaa acaagctgaa 840
aggtataaaa actattgcaa tttttgacag aatggtattt gaaatcaagg 890

<210> SEQ ID NO 121
<211> LENGTH: 1116
<212> TYPE: DNA
<213> ORGANISM: Caenorhabditis elegans

<400> SEQUENCE: 121
atgtaacccc aataattttt ttttgttgca ttttactact tatatccgtt tccatttttt 60
aattttatgt tgtcacgttt tgtctaaata gtgtaatctt cttgtactaa ttattccaat 120
tattttaacc cgtaagcgat aaatgaaaca acacttttg gtttttattt gctaatttta 180
aataaattgt catcaattct gaaaaataat aaattttaaa aaaataccga agaggcaaac 240
aagacatttt ggaaattctg atccggataa atattccgtt agatttttat tagactcgaa 300
attgcctgaa acccccgatt ttataacgaa acctcttgaa aacttctcaa aaaagagaag 360
ttaccaaact ttaccaaatt tggtctccca tcgaccttca atgtacctaa ctctagttga 420
atacgcaaga taattaattg ctacaaccaa aattaaacgg cggtttcaaa aaaatattgt 480
tttcagccgc tgcaacattg acaagtggga aaaatttcaa attttaacta attttaggtc 540
attttttgag ccgccataac ttttttttgag aagttttcaa gatattttat tttgaagttc 600
ggagttttca gacaacttcg agtcaaataa aaatattttt taagtcgacg acaccacctc 660
ggagataatc tttaaaaaaa tcttttcaga aatgcaaaaa ttccaataag tgtcaaaact 720
cccgagtagc gcttaagcag tggcacgtct gtatttatgt atttttgttt ttttttttta 780
ctttattatt ttgtgcttta ttactgtttt ttttttaaat ttattttgtt tcatgaaatt 840
ttaggactaa cgtgaaactc aacataaaaa agctagaaaa gtttcgcgta ctgtattcta 900
tttttctttg attttattaa tgtaatacat cacttttata tcttgagtga ctaaactctt 960
gttaagtgtg tttcaataat gttttgattt tttgacttta cttatacgtg ctttgtagtt 1020
ttagtgacat tagtgaccga aagtgagacg ataacaaatt gggagcggta tataagtgaa 1080
ctacgaaact tctaaaaaaa caaaggctgt ttcaca 1116

<210> SEQ ID NO 122
<211> LENGTH: 1807
<212> TYPE: DNA
<213> ORGANISM: Caenorhabditis elegans

<400> SEQUENCE: 122
tgtgggaaaa gttggaggtt tttgcacatt ttaggtgagc gaatatcccg ttgaaattat 60
agaaattacc gattgccgga cagttttgga aattgtcaaa tccatctatt tttcgaaaaa 120
ttaatagaaa actacattgg ttttcagtat ttgataagtc tacgagacaa aaatgtctac 180
gagacaaatg tacacaaatt atcaaattta cacttccggc aattctgatt ttcggaaatt 240
gtccattccg gcaattttgc aaaatttgaa attttataaa aataattctc tacctgcctg 300
cctacaggca tgccgcaact aaccttgaaa actttaaaag aaactccgaa tttcttaaaa 360

```
ttttaagtcg gctggaaact tagaaatctc ttgccaagat aaaaaacatc gagaacatcg    420
taatcaattt tatttgattt gatacgttca caaagtgaaa ttccaatatt gaaaatcaaa    480
ttcaattaat caattaagag ttcagtgagt cgtccttgaa atgtaccaat ttcacttgag    540
cgctcagaat ttcgttcaaa atcatcaatt tctcgtccaa aaatcgatga aattttgcga    600
gtaggtacaa gtttgtgctg gaaattaatt tattggttgt atggatattt ttttttaatt    660
taagaattaa aaatttacca tgaaaataaa gtatgaaata ttacaactat cagggtaaac    720
caagcaacgc gagatccagt caaactgtac acgactaaac tttaaatagc aatactaatc    780
taaaaagcaa atattttttct ttaagtagaa gcaaggcaga agtttgacat tttttccgac   840
cagttgaatt gtgattctat atacatctgg ttcactcgaa tttcagacaa acaactccac    900
attcctcaat ttctgtgata gaacaataac ttattttctt cacatttctc tttcaattat    960
gcattttcat tctttaagtg tcttttttta aaatttgaca ccatttgccc gcgactcgtt   1020
gtccggaggt ttcctcttac ctcggagaaa ttccgctaaa tctaccatgc atgagtctca   1080
ccacgtggac aacgagttac tgtaacttgt gtcaatttac gggccgctat cctttttttta   1140
aatgatatgt accaattgat acaaagaaat acttgttttg ttatcaaaat agagtataaa   1200
atataaatga aataattcaa aaattattct caattgggcc agatacaata ggatagtggg   1260
gaagttcaag gatgatattg tgtcagacaa ggagcaaaaa tgcattaggc cagtttttac   1320
agaattcatt ccaagtacag aatttttcaa acattccatt aggaaatggt gaagaaaacc   1380
aatacatttc aacttccaaa tttttgaaat ggatttaaag cttccctata aaatttgttt   1440
atgaaaataa ttttaacgat ttcatttaca atcaccacat tttttagaat tctcagcaca   1500
ggttgaattg ttcagtacct tttttcaaca tctagttcac ctacatatga gttcttaatt   1560
taattacgtt ttttgaaaag taaatatgtt atttggcaag tccattcaaa caaaagacgt   1620
cgaccactta taatcaaaaa gtacacttgc ggcagacatc tcgatacttg ttttctctgc   1680
ctgttgtcac tgatcttatc gatatgtaat attgtgaaat gttgcgcagt gttgaaaaat   1740
aagatataaa attaggaaag aattgtataa aaatcagaca aaactattct gtccaacaaa   1800
gatcatt                                                             1807
```

<210> SEQ ID NO 123
<211> LENGTH: 1546
<212> TYPE: DNA
<213> ORGANISM: Caenorhabditis elegans

<400> SEQUENCE: 123

```
gatgagatgc aataacctga aaatgaggca ctttatgata agaaaatgcg gtaaaacatg     60
cgaaatatgg caccataaac cgtgagcagg acaaagaaca aacacttgga aaagaaaaga    120
aaatagaaag aaaaaaagga aaactggaga aaacaaactc aataacacaa cgcgagaaat    180
acaatttcgt ttcgtttttt cttctattta ttagatttct cacaatttgt taccagtaaa    240
gtcacgttct atatttcaaa ctactcctaa aattcggttt gaacagttct ctgataaacg    300
aatttcgaag aacgatcaga aaacaaatct acggttgtgt gtgatcaatg gggtcaaacg    360
gtggacgaaa ggggacggcg gagagaggaa aaagtgagag aaaataaata aaattgacct    420
tcgagtgcag agttttgctg gtattttggt cagaattgat tatgaaaatc tgaaaattac    480
cgccgggaaa gttgaaaatt tgacgtggaa acgtttaaaa aaataagatg agaaagttag    540
tactgtagat gtcgtcggat caagtgcaca gtacgcaagc accgttacga aaaattgcac    600
taattgctca attaaatttt tttaaaaaat taatttttat agtgtgtttt gtgttttttt    660
```

```
tctgcttttt taatgatttt taaaggcttg attatgtttt tttctcaaaa tttgaataat    720
caataacatt aattaattac tttattaaaa aaccacattt ggcattttaa taaagcaagt    780
tatcgcgaca aacggcaaaa atgtctcttt ttataaaaat tgtttttttt tgagttaaga    840
gaagatgtgg agtttttga actacattag ttttctaaaa attttatcat ctagattttg    900
aggaaaaaag cagattatat atctttaatc ttggttttaa aattttttta aaaagcagaa    960
tattaaagta aaatattata aaaagaaaaa ttcgtgtttg caaaatttgt ttgaacggaa   1020
ccttgcaaaa atgatattta gcagctaaac taactgaaaa ctactgcata aagctttccc   1080
aaaaagagct accatccaga aaatgttttt tttttcaaag ccgaaaaaga agaaaaaaag   1140
atagaaaacc gaaaaagcag catcgttttc gcgcactctt tcttcttttt ttctttcttt   1200
ttctaaaaaa aaatattctc cgtagcttga agtctcagga tttccaaagg gaatttcctt   1260
gatagaatat ggaaaaacaa gagagtcatc agagaaggga gaggaaaagc ggggatgctg   1320
gcgaagaccg ggggcaccga ctgaaatata ggcaccggcg gggaggcggg gcgctctctc   1380
ctctccgctt tactccgccc cgattgtcag tggagcaggt ttgcaatgag tgttctctga   1440
tgccccctca gcgcgggagt tttgaaatca aatattttgt attttaacct actttattga   1500
tttttcaatt aaaatgaaat gttatttgtt taaaatttaa tttcag                  1546
```

<210> SEQ ID NO 124
<211> LENGTH: 1375
<212> TYPE: DNA
<213> ORGANISM: Caenorhabditis elegans

<400> SEQUENCE: 124

```
accatgtacc caatttctcc agatgtctca aaaagtcctt cttcttgtta atatagctcg     60
cctcctcaaa ttttgatctt ccaattcctc tccgcccaat atattctagt ccgtgtctta    120
ccccttgaca aaaatgagct tttctcagat tccgactaat tccaaaaaaa ttccctacgt    180
tttgaataat tgtcgctttg tatttttttt tctcgttttc atacgggtgt tcatcattca    240
ttttactttt ttaaaaattt tcctctcgtt tcttttgaac gtcccatttt tattgcaatc    300
gttcattgtc tagggtctat ccttctaatc attcttcttc tcagaaatat cacaaaccgt    360
ctgtgttgca ttcaaatttt taagtaaaaa taataaacta aagaaccaca atgaaggtct    420
aagttggcaa aattgaaaag ccgaaagctt ttcccggaat aatagtaatt actggagtgc    480
atcccgaact gtctaaaagt agagaaaaga ttaagtggat atatattttt tatattttt    540
aatatagtaa tctgtttgaa ctgttataca aaccgaaatc gtgttagttt ggacaaagtt    600
ttgcatcaaa ttttttttga gttttagatc gaactattgt gtttttaatg taccagtcaa    660
tatttggcat tcacaagcgg tatagccaaa tgtacccaga gttgatcaga tagcgttttt    720
cttcactgtg ttccgttgtt atcaaataaa ttatgcaaaa actgcgaaaa tttgagttca    780
aacattaaaa aaaatcatat ttttctaggt tattgcgagt ttttagcaag aacaactaat    840
gttttcatgt ttaaacaaaa aaactgagtg agtgagaaaa aatctcatgt atgccatggg    900
atcaagccat atattttcca tagactaaaa ttatttagag atggaaaatt gaaaacagga    960
gacgggttac tgtaggaaga tttttttaag actattgcaa atacataaat cttttgaata   1020
tattttactt cttcgaccgc cgctttgaaa cagtgcgtta ctgtgaacgt tgaaaaccaa   1080
acatttgaac tcttcacctc acttgtccat tttgttaatt gtctagccaa ctgtagccac   1140
ctttgatcag gtagaccttt tccaatctgc gtctctcatt ctctcaaatt cacttagcca   1200
```

-continued

```
tgttttgtac ggacatcatt tctgatacat taactacgat aatagttgtg cacgctgtgg   1260

tcatttgatt aacttttttt cctgttgcag cagttcgcga gtatataacc tgtctttaac   1320

tgataaatcg tttgcattgg tcgtttgaag gaaacaacaa tacgctttcc aaaaa        1375
```

<210> SEQ ID NO 125
<211> LENGTH: 1350
<212> TYPE: DNA
<213> ORGANISM: Caenorhabditis elegans

<400> SEQUENCE: 125

```
tacagttaca attgaaataa atggaaatct ctcttatttt tacattgaaa tttcttgctg     60

gtcacttctt ccaatccacc gtagttaacc gactgggtgg tctactaccc gtttctggtt    120

ttctctgcac tctcttcgga gagagtgcag acaaaattct ccgcgttcgc agtcctggtt    180

ctgtttcgag acgttgacgt cgcccgacac cactcctaca actgttcgga cagcgtctgc    240

aattttcgat tagtaatata gttttggttg tgaatataat ataaattgtg aaaaattgca    300

ttgagaatta ggaaaagagc atgtgagaag aggaggggaa tttttagaat aactgagaat    360

ataatttaga gaaacacgat tacttcgcat caattcagaa tatcttttaa aatctgagaa    420

attttggtta aaaaataaca cagggcgctt agtttgtggt tttctcaatt ctgtttaatt    480

tttaaaacag taattcttat ttcgataaac taaaatgaat atgaaatttt cttacgatta    540

aaaaatgcat gaaaccagat ataacaaatt gaaggaaaac tgaaaaactt cagaaagtgt    600

tttttctga aaataaaagc agaaaaattc gaagctcgcg caaagaacgt aaacgcgctc    660

cattgctaac tcatttgaac attagttttt ttcattgggc tttcaatctt gtaagtgatg    720

tttaggcatc taaaagtttt ataaattgac aaaatccagc ttaaaagatg ctatcaaaaa    780

ctaacttttc agaatattta tttggctaat gtttgaccca tacgtttttt gccgaaaaga    840

atttcaaaaa tgaaaagtat cttgaaatgc atcaaaatcc gggaatattg ccgatggtca    900

gtttttcagc atttctaaat tgagagactg aaatgggaat ttatttattt ttattcatct    960

gctttttat ttcatgaata tccgcatctg aaatcagctt ttttttcag gaaaattgat   1020

tgaaagaaga caataacagc tcgttgttca acatctcgat tcttccatat gaatcgatga   1080

atggaaaaac cgtggcattt ggtaaagttt tggctggaac cgaagttgtc tcccgcatcg   1140

ccttcaataa atcaaacacg aagggttcca aggcttgcgt catcaccgac tgtggagaag   1200

ttatctgaaa ggttttatca tagattttca aattttttgg tttattatta tttctttctt   1260

tttgttccga taagtccata tatgaaattt gtccagtttt tatgaaaata aacatttatt   1320

ttatttaata ttttttatt catcatatgc                                       1350
```

<210> SEQ ID NO 126
<211> LENGTH: 632
<212> TYPE: DNA
<213> ORGANISM: Caenorhabditis elegans

<400> SEQUENCE: 126

```
tctgaaaaac gttgatttaa aattttataa aaaatttgaa gcaaaaatga aagagaaaac     60

taaaaaaaaa gtaaatgtac tgaagtgatt ggcagattaa taataattta tcgataaaac    120

catttttaa aaaacttcat cagtttttgt gagtgtcagc aaagaagaag aagattcacg    180

atcaaaaatt cgttgagcct atatgaaata gttgcgctgg tttttcgacg gggggatcaa    240

atacgtcaaa taggtcaaat agacgaagca ttcataaaaa gtacaatatt cattgaaaaa    300

tagttttgga tttgtttttt tgttttcttc attttttgt tgaaaaaata atggtaatta    360
```

aaagttttta ataattattt aaatcaagat tgaaatatca gaaaacgaca aaaattcgtt 420
cgagaacttt ctcaagacta ccgtactctt taaagacgca tgacgatttt cacatgggtc 480
tcaccacgac ttgtctgaaa tttgaatgtt cgttcaaaaa cttttttttt tgcgattttc 540
aaaaccaaag cttaacaaac aattttcctc aagttttcaa cgctttttgc tcgttttttt 600
cgctcaaata aattatttca gaaggttttg ca 632

<210> SEQ ID NO 127
<211> LENGTH: 1057
<212> TYPE: DNA
<213> ORGANISM: Caenorhabditis elegans

<400> SEQUENCE: 127
tatattcaaa aaaatatatt ttttgtaaat gttcttgaca aggtgtcagg aaatcagaat 60
aaacattcaa caggtgttta tgtttttttt gtatcattct aaaaatccta acccgtgcct 120
gattttcata aaactaaaac actaaatgtt gtcaatctgt gaccctggag cctagaataa 180
gttttccaaa atctgattat taaaaacaca acaacagatt ttaaatagat ttgagcacaa 240
gtcatgcatt gagcataagc cacaaatgaa ataacgagag tgaattttta gagtctaatt 300
gaattgcatt agcttttcta aaaacttttt ttcggctcaa aatcatttcc acaaaaaaaa 360
cagttttaaa ataataagag ttggccttca gagcggtttt gtgtttaaca aattataatt 420
cttattgtca gctcgattac gttttttttt cagtatcttt cgttttgctt tttgttttta 480
gttactcgcc acgagagagg gtttccctcc aaatttcgca aaaactagca caaattatat 540
gtatgtaccg gaactaacct ataatacttc cgggttcatg ccaaattcta atttctaaat 600
ccccagacag acacgctctc aacttcctcc ctctttttgt ttatgaatga atttagtttg 660
tgacaatcag ctaaaagtcg tgatttgaaa agttcaagaa atcgtcaagc tcgtgaccac 720
gaaaaagttc tagtcacaat acatcataga ctagaaagca tttctcgatc aactagttga 780
cagctttttg tgaataaaga ttgagaattc gagttgtttt cgaaccatga ttacatggct 840
taacaataat acatgcagct cattgagtct atacaaacac aaaatacggg tctgcgtcta 900
attatttcct acaatatttt tgttattatt cacaaaaaac gggagatagt cgacagctct 960
caaccggttg aagagttgtg tcgtgaagaa acaatataaa aacattgaaa agtaataact 1020
gataacaaca gttctcaaac aatattatag tgatcaa 1057

<210> SEQ ID NO 128
<211> LENGTH: 509
<212> TYPE: DNA
<213> ORGANISM: Caenorhabditis elegans

<400> SEQUENCE: 128
agcaaataaa ataattttat ggtttttcat ttgaaaaaaa agttattaac cttccggcgc 60
aaatgaataa aataataaaa atgattaagt tattgcacgg cccaattcat cgttgctata 120
cttattgact acagaatatt tttacttcta tcaacaatgc aagtttgaaa atttccataa 180
ataagatttt tcttatcact accttttttgc ttattttcat tttaatttcg tggtctctgc 240
tctccctttt ctgacctgct gacagtttga atcgtcttca aactaaatac tcggtatgtt 300
tgcctaaatc tcttgtaaga gagtagtctc tcattcagag aatttcactc ttgttgttag 360
aacaaacttc actggcgtgt attttgggaa aatagattat atatatttaa gagattaata 420
cgatttctaa ttttagttgt ccatcaaatt gaattttttt gtgtcgtttt tctgaataaa 480
catctgaaat tgattcacca tttttcaga 509

<210> SEQ ID NO 129
<211> LENGTH: 570
<212> TYPE: DNA
<213> ORGANISM: Caenorhabditis elegans

<400> SEQUENCE: 129
ttattaatat tattgtattt ctgaatgtac cgtattgtat ttctacatat tgaatcaata 60
aattgttttg tacaataatt ctttggctga gactggtcgg acaaattcaa tgcaagcctg 120
caaacttatt agactctaat agaaaatttt ctcaaattgg aacaattatt ctataattcc 180
ttgccggttt tgcagaaaaa atgttttttt aagaattaaa aattttaatt atgttccaat 240
taaacctaca tcaatgctct agaattctcc aaaacatcaa aaaaatttgt tgacaagatt 300
ggaaaatctg aaatattttt aattttttaa tatcaaaccc ccttcaaatg ctacacaact 360
taaaaataaa aacaaaaagt gtggtcaaca actttcaaag cgtagaacac gcattttgtg 420
ttgtgtgtct tatttctttt ctacctctta tctatcgtct cattcgcgcg cttttcaatt 480
ttgggggtag gctgagttag tataagaaaa gttaataaaa aatattagtt tctaattttc 540
gagtttctaa tctagcagta ttttaaaata 570

<210> SEQ ID NO 130
<211> LENGTH: 287
<212> TYPE: DNA
<213> ORGANISM: Caenorhabditis elegans

<400> SEQUENCE: 130
atctttaata attaaatgaa taattaattg ggagaaacat gtacataaat aaaatttcca 60
ttaaacaatg ttcatttgtt taagctggca cagaccacaa aagctgaaac cacaaagttt 120
tttaaacctt gttcttttct taaattttgt agtttcttat cttatcactc gtgtttcttg 180
tcctccaaat aattgtgaaa attgtagtta atgtgtcaaa aaagtcacat ataagaagac 240
gaacaacttg attttttgtt gacttcattt gaaaaaaaat agaaaac 287

<210> SEQ ID NO 131
<211> LENGTH: 1670
<212> TYPE: DNA
<213> ORGANISM: Caenorhabditis elegans

<400> SEQUENCE: 131
tactgaattt tgcaaaaatg aggagtatag gaaaactcgc tcagaaaatc gaaaaaaaat 60
tagttccgtt ttgtaacact cagactttac aactaccaat tagaaaaaat aataatacac 120
taaaagagaa gaatagaaat cagaagaagt cagtatcatg ggagctcatg agttaattgc 180
ctgaaatgcg tattcccaga aataaaaatg cggtttctta gctctgagat ctgaagtgta 240
agactgccaa tagattccat gagattcgtt gtgacaaggg gttctgaaaa aaggaatcgc 300
gcaaatttat ttattgcaca gttgtagatg ataaagtttc tttcagattt gaataatttt 360
taaaagcttc taaaaattat cttgcagcta attgtccaaa aattattaaa catttgaata 420
tttttctttg cttccaacag gttttatgga aattattaac aactgtaaaa cgttaacgta 480
gaataaagta aatcgatctt gaaaacccaa aagaaccggc cctatatttt tggcaggtgg 540
aaattttgaa tgaaatttaa taatatagct cctgaacttt taaacgatga tattagatgt 600

```
tgaatgatca atttccttgt agtcataacc atacggtttt tgaaacatca taattttatc    660
gaaatcactt gtaaatcccc cgggtacagc tataaccaac cctattcgac aatttcaatt    720
tcggatattg taaaaaaaaa ttttaaaggt ggtgtagtcg aatttttttt attgctttat    780
taggttcaaa attgtctgaa aaaaaccgaa tttcataatg aaacttcttg aaaacttctc    840
aaaaaaagtt atgacggctc aaaaaatgac ctaaaattag ttaaaatttg aaatttgacc    900
gacttgtcaa tgacgcagct gctggaaaca attttttttt gaaattaccg tccaatttgg    960
gtatttaagt taattatctc gcgttttcaa cttcattata aagcttataa acagcgagaa   1020
ttttaaattt tttttaccaa atctcgccgt ccatcgaatt caaaatacat aaatggtgtt   1080
gaaaacgcaa aatacataat tacatgctat actcacaatt tgacggtgat ttcaaaaaaa   1140
aattgtttcc agccgctgcg acattgacaa gtcggtcaaa tttcaaattt aaacgaattt   1200
tagaccattt tttgagccgt cataactttt ttttgttgag aagttttcaa gaaatttcat   1260
tatgaaattc ggctttttca gacacttttt agtctaataa agcaatcaaa aaattcgact   1320
tcaccacctt taacttagca attgccaaaa ttttttattg cagtacatat aaaattagaa   1380
acacacaatg tctcaaacct ggaattacta ggaattttta agaaaatgac tgaaaaaaca   1440
aactatgcca aggacaaatt taatgttttt ttcaaagtat agcatgtcga aaatactgtt   1500
tttgataatt aaactgttta atactactaa tttttcacat tctcatacga ctatgaaaat   1560
aagtgtagga aatgtaacct gtgtgatgaa cattctactt tgccttatca aattggaaaa   1620
acctcgtata aaatggtcaa caaaaaatga aactgattta acttctgatc              1670
```

<210> SEQ ID NO 132
<211> LENGTH: 648
<212> TYPE: DNA
<213> ORGANISM: Caenorhabditis elegans

<400> SEQUENCE: 132

```
aagttcacaa tttattcatt catccatgta aactgtatat tttgaatttg tgttgtaaag     60
aatttatctt cgaataaaat gtttttaaag gtttttaaat tgtattctgg tgagattgct    120
taaatagagt ccttcggcga taaaaatgct aaaaattata tgaaaaaaac tatacaaaga    180
atatgtctcg aagtgtttca ttccagatca aagtcgaaaa ttagcttaga aaaaggatct    240
tcgtcaaaac ccctgattta acaccaagac gaataggaaa aataaagtaa tttaaaataa    300
aataaattac aagtgcgctc cattgtaaaa acgctagaat ttgcaaaaac tgaacaatat    360
ttgattttcg actggaaaaa aaacttgttg gtaaattgca tgaacagttt taaaatgtca    420
ttaagaaaac tgatgccaat ttttggttgt tttctctcgt ttaggaaatt aaaattccct    480
cttatttttt tagcatgaac cgtcaacgat ttctggtcag ataaattatg gttattatag    540
tgtgtagttt tttgagttta aaccaatgtt tcgaaatttt tatcagtaaa cagaaactac    600
ggtttgctgt atataagtta attccgatag caaaagtaga aatccaaa                 648
```

<210> SEQ ID NO 133
<211> LENGTH: 1081
<212> TYPE: DNA
<213> ORGANISM: Caenorhabditis elegans

<400> SEQUENCE: 133

```
cttctgtaat aaaaaaaaat tgaaatgttt agtgaggaga gtgatagaaa ataaaaaaag     60
ccgagactaa acattttccc tgtgctgccc tgtttataaa cgtttcaaag gaaaattctg    120
aaccctgtaa caactgtcgt cgaccttcga atagctcaaa aacatttggt ctgcttgtgg    180
```

```
atcgcacgtt tgtttcacaa aattcattgt gatttgtcgt ttgagatata tcccttctat    240

caatcaacat gttgatgccg gaacttttaa tcccaagaaa tctgttacac aaagatcgga    300

aaataccttt aattgcttac aacttttatt aatagtcgat agatacactt gcttttgact    360

tgccagaaat ttaagtatga tgcttatcaa ataattacat tgattacaat tattaaataa    420

ttgaataatt gctaactaca actaaaaaat tattcgaaac ttttttgtaa aactaagaat    480

cagtccgcgg atgaatggta atattgttca aattcgtcta gaaaaaaaac caaaaaaata    540

attaaaaaat gagaaactgc gcaaaatata tatatttaaa atgaaacaca acgaggcggc    600

tctcgttaac cagcattgtg caaataaccc aaaaactctg ttcacgccaa agtgctgaaa    660

agagaaaaga ggctggcgtg aagccgacag gtataggtcc tgaaaccgcg ccccactggt    720

tactcgaatt tgcgaatcat tcttcttttt tttttttcaa agcaacttcc ctttattaat    780

ttcagattat tgaacattca attttttttt gttgtaaaaa tcaattgttt ttctccgaat    840

agttaagaaa aatgtatgtt ttgaaaatta tctgttcttg ggaaataata gagttctgca    900

aacaaactta ctatcagtcg attcgcctaa ttcgaccctt ctatcaaaaa cgttgtgctg    960

aatgtataaa ttgtgaattt ttgagtgaaa ataactgata agagcttttt tatcagtcaa   1020

ctgacagtgt gcatgttttg tataaaaaca gtccactgat ttcgaaaaat caaatcagaa   1080

t                                                                   1081
```

<210> SEQ ID NO 134
<211> LENGTH: 2047
<212> TYPE: DNA
<213> ORGANISM: Caenorhabditis elegans

<400> SEQUENCE: 134

```
ctttgtaaat tattttcaat taatttattt gcacatgtga actattagaa aagaaaaagt     60

ttacttttat atttggtgct atattggtga taaatctatg caattggtaa taaatcggaa    120

atacgtttat tttctgcaat tgaatataat aaaaggtaaa taaatgatga gtgcgagaaa    180

tttgagttcc ataattgtac aagccaggga gttttgaaaa ataacagaac cggtacctat    240

ttctcttttt ataacatata acatctgaaa ccgacatgtt aaataaaaaa ttttgagaaa    300

gaaagttgtt aattctcgtt aatttgcgat atgtctataa taaacctcgt agcatttcta    360

tcgactaaaa atttgttata atcagaaaaa accatcgaag ttttcaagtc aaatttcaaa    420

atactcttca catcaaaact tgcaaaatta aactcacaga ctggaaaagg aaattcgaaa    480

atgtctgaag aataacggtt ttggaaaccg agctgtactt ttttccagga agatcgttca    540

caaacaaaat caaatagcca taaattgaaa tacttgcaca acttaaaaaa tacgagaaca    600

ttgaagaaat atcgatgttc ttcaatacac ataaaatgtt gttgtcatat tgtttccatg    660

agcaaatggc tgaaatctgg gcaataataa tatttgataa atgtccatta ctcacttggt    720

atagcaactt tatgaactaa agaaattata aaagaattga taattataaa tgcaagacat    780

cggggtcgaa acctaacgaa tgatcgaaaa tttggaaatt tcaatgatat gactttttgt    840

attgctagta gaaacatgga aacagcgaaa atattcggga aaacggtatt ttgagaatgt    900

gctattagag ccataatgga ctgaacgata gcccaatttg taattagaat cttacgattt    960

acatttctga aaatttatag atattaactt taaaacatat atgaatggat cttacaatcc   1020

attaattaca atcaatacaa taacattgtt catattaatt aaaaataaag taatgctcat   1080

taataaagac atcaaatgat taatttttaa aatgtgacat gatttatgtc tcaaataatg   1140
```

```
tgtcttgttg tgattccatg aacggcagta aaatataaaa acgatactat ttgtagaagc   1200
aaaaaccatc aataaagtta tttcaaagtc aatatgactt gttgctaagt tctgaaaagt   1260
ctgaaatact tgcatagctt aaaagcgtaa aagtgaatta ctatgcataa gtctgtgggc   1320
gaaatgcatg tgacaacatt tgcacctgtt tggtttttaa tagcctccaa atttaagact   1380
atgaaaattc attctgcggt ccttcctgaa caatggcacg tccaaacgtc tacaacattt   1440
gaatatttat atttaataca aaagtagacc ataaaaatag aattaacatt tttttgatcg   1500
acaatttcca aaaaaataac aaaaactgag attgttccaa atttttttc caaaagttat   1560
ataaaatttt aaaaaaattt caaaactttt actatgatat atttacagcc cccccccccc   1620
acaaaaataa cggatttcat cgctttgaat ttttaataaa ttttcaatga aaatttatgg   1680
aatagacacg ggaccaggcg gaagtcttga tactttttgg tactgtgtac caaccaaaaa   1740
ttgcagatac aaaaagaata aaaacatttt ttttaaattt ttttattcaa ttttccgtat   1800
ttttgaacca cacttaaata aactctattt gaagcacagt cttatttccg tgttttcatc   1860
agagaccaca gttccttatc cttgcgttat caattttcat tacatcttta catcaaatct   1920
tttgtggcaa atgtacaaaa tgtacatttt gaagtaaata tacccgataa gaattagtta   1980
tcggtcaaga gactgtttga ttgctttata taaaatcaga tatttcaatt ttaattctca   2040
aatcgaa                                                             2047
```

<210> SEQ ID NO 135
<211> LENGTH: 2212
<212> TYPE: DNA
<213> ORGANISM: Caenorhabditis elegans

<400> SEQUENCE: 135

```
ttgtcttata ttttattaaa atcggggcga agccctgatt ttaaatccat attgtttttt     60
ttgtcttcca ctatccctac aaataggaaa gagaatgtgt tctttctgat gaagtaaaaa    120
cggcgcagcc agccgacagc cgaaattttc acgattttcg gctggtagcg ccagccgaaa    180
aattaaaaga agtcggctgg cggcgccagc cgacagccga accagctttt tgtcggctgg    240
tagctttaaa tttttttcca gttttttaca gaaaattcgt ccagttctta cagaaaattc    300
gcgtttctat gttttaaatt tgataacatt tgcagtaacg gagactgctg acccggcgtt    360
tcccatgaga aaagagagag agagagagag ggggagacag tgagatatac ggcagagaca    420
tagacagggg agacaccatt agagatcgtc tcctatagag tgctgccggc agggggcgtt    480
gtggacctgt gggaagaagg ggggagacaa ccgcacactg tgcggttgta aatgcggaat    540
aatccattta aaactaagga aaatagtggt ctaatgctta acagtgagcc gcctagataa    600
aacaaaaaaa agtcggctgg ctgcgccagc cgacagccga aattttcact attttcggct    660
ggtgccacca gccgacagcc gaaaaattga agtcaatcgg ctgtcggcgc cagccgacag    720
ccgaaaaaat cagccagccg ctcagccctg gtggggtggc gatgtgttgg cagccaaccc    780
ttcaacgaac tgtatctccc gcctgtatct cccttcaaag tgagatcctg taacagtaat    840
tagagaccat atttacagcc agcctacatg catcactgga gactctgtgg agagggagga    900
ggcaagagaa aggggaggca agagggggcg ggcgggcact gctgaacctt gaaagcgccg    960
tagctccgct cacaattgga attgaaaaat gaaaagtata tatttgaagt caacgttaaa   1020
aggagaatat gatagcattt gaaattttgg aaattggtga agaatgaaaa aaaaagcctc   1080
tggagcaagg cttgaagctc acaacttcag gaacggggct cgaggaactc atggccaaaa   1140
actttttatt tgtctcgctt ctcatagcaa aaataataag atttaaaaca taaaattgat   1200
```

tatccaacaa aaaactggtc caggaaaaga gggaaactga aaattcgagg tcaaaaatta 1260
aataaactaa aattgtgaaa aatggtcgta gagagctgtg ctttcagctg gcattcggaa 1320
tttatgcact tattacgaat ttaacataaa atcccatttg atagtggaaa aattttcatt 1380
tttccagcaa aaacgtcatt tttttgagaa aatgcagcaa tttgcgattt ctgaagttat 1440
ttttaacttt tttgaaaaaa aaaaatattt ttgaagagaa aatttcctga aaaatacgtt 1500
tttcaaaaaa tttacctcaa aaagtgccaa actgaccgac ttatggacga aaaaccatca 1560
aaaatcgcta atttgcacac caaaaaaaag gggggggggg ggaaatgcaa ttttcgattt 1620
cacactaaag agcccacttc tatagcaatt tttgagtttc actcaaaata tctcggctca 1680
atgagctcca atctttctga aaacaagaat acagaggtgg ggcaagcttt ttgaagagac 1740
agcaaaaaac tgcatcaaaa tccatccacc caccgtcaag ttacacgcgc gttttcattt 1800
accacttttg tcggattttg aagcttaata tctcggctcc tgtaaatcga aatcggctga 1860
aaattcacaa gaaaacttac ttcactacga tcctcctgtc attaaatttt cgtgagctta 1920
gaccgaaaac tgacaaaacg ccaaactttg ctaacgctcg ccactgacgc caagccttca 1980
gacacgcttt cactaaatac agtctatttt tccgtgtttt catcagagac cacagtttta 2040
aaataatgcg ttttcaattt atttgatgtg atttatacat tttcccatca gaaatgctgt 2100
gctaaatgta ttcaatgtgt ctttttgagt gaaaccactc ttaatttatc agtcaacaga 2160
taatgttgct ttgtataaaa aggattcatc gaatttgaaa ttttcaatca aa 2212

<210> SEQ ID NO 136
<211> LENGTH: 1481
<212> TYPE: DNA
<213> ORGANISM: Caenorhabditis elegans

<400> SEQUENCE: 136
ggccaaaaat agtaaaactt gatcgttttc tgccattgaa aactgcgtta ctatcatgct 60
tggtttttgg gggcgctggt atagaatatg tgctcaagga agtgccggat atcagaaaac 120
tgatagtttt gatcaaaaag ttgtgtatgc ctgtctttct gtctgtctgt tgacactccc 180
tccgagaggc agccagagcc tcagagtgac aaatgcgaac ggcagacgga atggaggaaa 240
aggatgagcg gtgctaataa cagtacacag tttgacgaaa atccaagttt attgagcagg 300
gcagctttaa gctgggaata aacaaggcaa aaacgtagag aatatttagg gaattgggca 360
cgaagatcag caacgagcag ccatggcgtt gggagaacga agaaaagaag tgaagaatgg 420
ctacatttta ggccagaatt aatatgagca agggaataaa cagcgcgcgc tacgacactc 480
cgatgtgtac aatggcgcgc gcttgcatcc ttggcggcaa attcaaatga gaattattta 540
atttaattaa tttaaatggt ggaatgatta ttaaagaacg aacaaacgga attgtgtgag 600
taaattaccg gcggatgatt atcgctggat tgtgggcaat tcttgccgat aattataatc 660
cgcaaagttg gggcggagga cctctactga ggccaagtca caacactgtc taccgtctgt 720
ctattctata tctagaagat gtcaacattc agtggttatt ttttagtaat aaaagtgtaa 780
aacaaaacaa ttcagatctg caaagctgaa aagtgatgaa aattgatatc ttcaattata 840
atttatagta ctttttttaat aattactcta attacacccc actgctttac tttgaaatct 900
catatctcgc tccattctga agtagtcaac tagaaacggt aaaaaatcca tagaaaattg 960
tttttccagg tgacaatttt taaataaaaa tggggtgcaa tagtaataga gcaattatgc 1020
taattttgtg aaactgtagt ttcaatactt taaactctat ctgtacgttg ttctctattg 1080

-continued

```
aaaaatacat accagatcag ttatcaattt catttctcat atgtcaatcg ctattaattt   1140

tactgataag aacacgctgt gtcagttgtg tcagttgtag ttgcaacgag aaatacaatt   1200

tctttttggg tttcttctta agtttctcgg cttgaataat gggaaaacta attaacagtt   1260

gactaaatta tttaatttta ttatcccgcc cttaaaaagt tacccaaaaa gatttagtga   1320

agttatgtcg ttctaatata atacttcgaa caacttgtgt cagttgtagt cagttgttaa   1380

aatctaaatt tggtgataag atagtcgtat cactagttct gcaacgttat tatttaaata   1440

gccggagatt gacaaaaata ttcattcata atttttaaaa a                       1481
```

<210> SEQ ID NO 137
<211> LENGTH: 895
<212> TYPE: DNA
<213> ORGANISM: Caenorhabditis elegans

<400> SEQUENCE: 137

```
tctttaatga taatttatgg gatctgtatt tctctttctg tcaataaaaa ttgaaaatga     60

tttttacatt ctcaatattt tctaaatcat gtttcgtgaa gctgaagagt aaaattcgac    120

atttagaagg tttcgttaga aaaatgaaaa gtgtagtgcc agaggggact ttatctaaaa    180

caggcctgaa ggttcgaccc gcgttacagt tccagtctaa agtaataaca ctaattcaaa    240

ataatatata cgaaaaaaaa acacttgaat attatttgat ttttaaagat tttcaatttt    300

gaaattatca aatttccttg aatttgggaa tttttgaaga agtttcagat gcaggtttga    360

aatcctagaa tgtgcaagta tgaaaactga aacaaaatgt atttatacga ctttttttggt    420

cactgccaaa cttataatcg gtcaaaacta tgtttgcaca aatttctaac attaaaaata    480

aacgatttta attttttttt gaaaattatg cctgtataca tttcagcatt ataagagcgt    540

ttttaagcga ttccctactg atgatactgt agcattctaa aattattgta gcttaatagc    600

tatctaattt gtaaaattaa atttaaaaaa ataaatttga agtggatcta ttagaacctt    660

catacaatat ttcctactct tttaaatttg aaatttttcg agtcagtgct agtgatagat    720

agaatacatc cattccgtag ttatctacgc tttcctcttg gaatcaacac atcaaaactc    780

aaagtacgcc tttattaaag aaccgtgctt tgtagtttta aattacttgc ttccattgtt    840

tgtagccttt ccttataaaa gatagcaggt tctgtttaac tatctcaatt tcaaa         895
```

<210> SEQ ID NO 138
<211> LENGTH: 1036
<212> TYPE: DNA
<213> ORGANISM: Caenorhabditis elegans

<400> SEQUENCE: 138

```
atttttgaac taaataatat ttcaaattgc acccgcaaat atcgtcactt ttataccgat     60

aaacaaataa agtttagtga tgacttatga taagaacctc tttgagtcta tatgtacgtg    120

aaacaaacgt taaagaataa cggctttacg tgttagtcat tcataaaatt tcataagttg    180

atctggaaat ttgtgttatg gacgttacgc cattatttct cgtcactcaa cgtctcgtca    240

atggtaattg tttttcagag acggtgaatc atgtttcagt tgatgatttt aggaaacgca    300

tgccatgttg agacaccata ataatttaaa tttttgtggg taccttttat tgggattttc    360

taacatttca gtcagaactt ttagtagaat ttttttatag atcttttttt ttcagcttaa    420

aattagtgtt ctaattactg tttaaaaaat gaaaactgaa acgtttgatg attttgtttt    480

taaaaaattt tcaatttttt tcgatatgtt tttattgatt gtaagatcaa ctcttttaaa    540

gtttactttt catttttgt taataaataa gaaaatttta ccgacttttt agaaatttaa    600
```

tttattgaaa aactgataaa cgtcttgttt tgatcaattt tccaataaag aatactttta 660
gcgttagtca caacatatac tcaaaatgtg tcaaaaaaca atgtttcgaa cagttttatt 720 gttttttta gcttcatccc gaacaactaa aaattgactt tcccgataac ttaagacgaa 780
taagtttaaa atttgaaatc tagttatttt tcacgatttt gacttttgtt ctgtccgcgc 840
cgaatctgaa acttgaacac taattcaatg tacacataag aatagacaag tagtgaatat 900
gcccattatc acacagacta catactttga ctgttccaag cgtcgcaagc gtcgcaagtg 960
tagcattttg agtcagtgat aacaatgtaa gaaagtatat aaagaacatg catttgttca 1020
tttctattgc aaaaca 1036

<210> SEQ ID NO 139
<211> LENGTH: 1435
<212> TYPE: DNA
<213> ORGANISM: Caenorhabditis elegans

<400> SEQUENCE: 139
tgattccaaa tgataattgg ctagtcttaa aacattttat attttaggga attcgaaatc 60
aaaactatgc acgtcatatc aaaatcaatt tttgttcaat attaatgtta tttattcatt 120
tgacagctat caataattat atttattaaa atagctgata gaactattta gggcattcac 180
aaacatttca gaatgtttcc gaaagttcgc aacagcggat tcgccacaat gcttcctcat 240
aacccatttg taacaccatt tttcaattgt aaacatgctt gtcaaaaatg cagtatcatt 300
gggttgcaaa acataactcg ggcatttgta tttaaatata ttgaagttag aagaacggag 360
ctttgacaaa caggcaatga atggagtttg tttcaaataa atgaaatcac atccaacaaa 420
aaccaactct gtgtatcaat cgcctcttgg caaacattta tcggagaaac tctgaaacgg 480
gtactatttc tagtttagtt ttggtatatt tcacaactga acaccttcac actgtttact 540
tatttccact atatcagcat tatttctcga gttccgataa tcgtccaaca ttctatgagc 600
tttatctcca aactggctat atcgtaaatg cttgaaaaaa taaaaaggat catagcaatc 660
cgactcatta gcaggtgttg tgggaatatt atcaagaaat gcgttgtaat tctccgtagt 720 atttctgtt tttagctttt cacaaatgtt tcttatagta tccgaaaagc atgtctttcc 780
atcttctaat tgatcactga tatcatcaat ctgaaaatat tagattgatt ttttgctgag 840
aagaacctca aaaccaacta tgaaaaaatc atttagtttg atgcagccgt cacggtagtt 900
taacaaatgt gtacaagcaa cttggacaca aggacgaggg tcattgatgt agtaagattg 960
caaaaaagga actcagaaca gtaagaaagc caaagttaaa agcattgttg tcctgaaaaa 1020
tccttattag tgtgtgataa aaataaattt cacaagttgg acagttatta tttcacaaaa 1080
taaaatatta ttttgttgtg tgtactttac aattgacgaa aagatcaaac cgacgcaaaa 1140
atgatcaata taatccgttc atatttgttt ggtaaagcat ttttctgcta atcaaaaact 1200
gttggtgcaa aataatcgca cgttttttcg tttttttttt aatttttttgg tctcaaaatt 1260 acataaattt tcggaaacat ttctaacgct gaaaaaaaca tttaattgtg tgaagtgtag 1320
ccgtgaaaat gtgttaggtg ttgctaccct cttatcttca atcttatcat gtttttgtct 1380
cctttataaa gaattgccgg tgaacttgaa gttcagatgt ataactgttt ctatc 1435

<210> SEQ ID NO 140
<211> LENGTH: 1043
<212> TYPE: DNA
<213> ORGANISM: Caenorhabditis elegans

<400> SEQUENCE: 140
tcccttgtta tttgattttt aagatttgcc cttatgtcag tgtcttctgc atgagtacat 60
gcatatttgc atattattag aatgttatgt ataaaaagaa aaagagagcc acctcttaac 120
gataatccaa tttcttgtta cgcagaaacg cctcgttttc ctgtggactt tcgatatctt 180
caacatgctg ctattatcac tcccatgacc cgtttcctat ctgtttttat ttcgattact 240
acacatctgc tagaaacaca cgtcacgtgt gatttgtact caccgttttc tcctttcata 300
ctttttagcc tacaaaccac gaattgcttt gtgacttgac tcaattttct cccgaaactt 360
tttttcgtcc tcaattccca ctacccattt tcttgcttct ccctgttgca atattttcaa 420
tttcccatcc aaaaacggcc cgagcacggg ttttcttttc ctttttgtag gttcacttct 480
tctttttctt cttcgtttct attttttttac acaatcattg ttcacctttg ggcaccccag 540
tgaaacattt gtttgataaa aattgtgtgt tccacggcac taaccacaaa atctttgcta 600
caaatactac tcgtattgtt tgtgatgact gtggtgaaag taagaagaat cgagagacat 660
taggggacaa atataaaata gaaacgataa ggcgacgaaa acgcacattc ttctcgattt 720
ccgaccgtca atcgctgagt gaataattgt tgacggcaac tgggaaaatc tgtgagaaaa 780
taatgtacca tgttttcgaa tttctaaaat tagagataat ttcttccgtt ttctctttta 840
catcttgttt tcttcatttt acaacaaatc cttcttcttt ctcttaccgc tttgtgcact 900
tgcactgtaa atgacggcaa cttacggacc tagcgttcga cgaacacagt caaggacgct 960
cacacatcgt cgacgggttc acctgctctg ttgcagtgat ttttgatgtt tttattggtg 1020
actagttttt gactttttac aaa 1043

<210> SEQ ID NO 141
<211> LENGTH: 1364
<212> TYPE: DNA
<213> ORGANISM: Caenorhabditis elegans

<400> SEQUENCE: 141
atttgaggac tgggatgtca ttaggactga aattattcta aattagataa tatattttaa 60
ggtaaaacgt ctgtttaaat tatttgtata agcaacaaaa aataaacgaa aactaaaatt 120
ctacctgaag ttcaggtcct gaacaataac ataaaaaatt tgggaaaaca cgaaaaaaata 180 aacttaaaaa attaattaaa aaattaaaga ttaaaattaa agattaaata atctctagaa 240
catagatctc taaaacactt cccgtagcgg ttcatttttg ttcgagtctg actggcgttt 300
tctatgggaa acagaaaaca acacgctgtt tgctcagttt cgagaatttt ggaattcaca 360
gacttatttt gttttgccgt atatgatctt aatcatagac atataatatt tatgacaatg 420
ctttgctata attctgtgtg gtgagcgttc gcagaaggtt ctgcacaatt ctttcaatga 480
aaaaaaaaag aaaattataa gaacttatta gaaaattata agatgtagaa agttattcat 540
aaaagttagt attcccaaga aaaatcataa agaaaggttt tttttcaagg ttttttttcag 600 atttttggcg ttgttcaact tgtattgcaa tcattattat tgcgatcatt agtaatttaa 660
tataatttgc tccagagcat ttgtaagcaa tgaaatccaa ttttccctct gtggtgtttg 720
gtttagaaac ttttgcaatt tcgtcttgat gtgccgcggc atgccgcaaa aatcataggg 780
gatttgattt cccagtagtt gaagttggca gagttaacta taaggatgac ctaaaacaag 840
ttttaggcta cttgttatag acatggactt cgatttctaa tttggacagc atccgctaca 900
gtgaaagtct gcggattgat ttcaaactct ctaaaatcga acgagttttc aattttttttt 960 tcaattttga tgcctaattt agtgaacacg gtaattatag tttcttgtat ataaaacccg 1020

-continued tttaactcct taaattactg tttacgtttc gtgttgtaat aaacgatctc ttgatcttca 1080
ttcaactatg ctggcacaaa aatagacaca attcgaagag gcgcagaggg agtaacagac 1140
acaaaaaatg ttaggacgtc tgcgatctcg ccggtaagaa acactgaaaa tactctctgc 1200
gtagtcacga aagctacaaa ctttaatgta ttcaaccaaa taatgttaac tgtataaaaa 1260
gaaacaaaga aaaaaaagta taaaaagaaa ctttaaacca aaactaatca tcagattcaa 1320
tatcttctat ctgtttgaca ttctatttct gtaagctcga aaat 1364

<210> SEQ ID NO 142
<211> LENGTH: 625
<212> TYPE: DNA
<213> ORGANISM: Caenorhabditis elegans

<400> SEQUENCE: 142
agtagagtca atatcttgaa atgtttagaa ttctcgcgta tctcacatgt tgaggtgaga 60
tatttgtaat gaatagtttc atagtctttg gccaaaatat gattatacgt taaagcaaat 120
tttgatgtta cgccgtttga agaaatgttt ttagcatgtt taacagagat tcagactaaa 180
tttattctac acagtttctg aagggatatt ttttgccaga gtcaattttc ttgtaaacca 240
gtgagcctta ggtacataga aaattttgaa aaatatccaa gaataaaatt ttttctgcat 300
gccttattct gggcttattt tttgcggttt tcaattcaat tttatcgtat ttcaaaaaat 360
taaattagaa caaatgcata ttcattttta catccttttc taattggtaa ttataatttc 420
aaaaatcttc tttgcttatc atttgtaaca acaactacaa aaactgtact cgtagtttta 480
tctaaccgta ttctttgacc gcatcctccc ttttgaccat tcaagtaaaa agatgacaat 540
cgccgtctac atattgccac gtgacgcaaa ttacttataa aaccattcgt ataaatattt 600
cattgatttc ttgaattcaa aaagc 625

<210> SEQ ID NO 143
<211> LENGTH: 2328
<212> TYPE: DNA
<213> ORGANISM: Caenorhabditis elegans

<400> SEQUENCE: 143
cccgaatttt tttatcgcag aaaaccaaga tggaataaat aaatggataa tctaattaaa 60
aattgtaatt tactatttgg aatcaaaaat aaataaacaa atcttataat atgtcagcaa 120
taaaaataat aaaagaacaa ttgaaagttc aatgtgttgt caagaaatcc attaaagtat 180
cgtcatcaac ggggtcatca atttccatgt tgttgttatt gtcttccata acatctattt 240
ccatgaagtc ttagagtact gacaatagtt tatttagtaa attaattttt gagaaagttt 300
cttgacacat tgctttgaga ctttgattaa atcacaaatg actcactatt atcataattt 360
tctatccaaa atgttgattt catttcaatt tccattgaat cagctattcc attacatcca 420
tcagttggtt tacaaaatgg gaccagtggc ctcaatatct gtattttctt cctttttttgt 480 gaaaatcgta cttttgaaaa tactaatgga ttctcgttct gatcgaaatg aggaaactgt 540
gctgttttct aagaacactt gagacgtgga ttttctttgt tgttcttaaa tacgaaaatc 600
aaatttactg acaaaatatc taaaacttac aatcacttcg ttgctgtagg gataatcaca 660
aaaatttgac atgattttct ggttttcatt ctgaaaaact gggagcattt taatttgaaa 720
aaaacgaacc gtagtctgcc ccaattgatt tgttggtaaa ggaagtgaat taaagcgaca 780
aggaatacat ttatctgttg aaagtgaatg catttttctg gaaagacgga ataaattgaa 840

```
attaaaacaa tattcagtta aagggaaact gaattatccc aaacccgggt tatttcaaaa    900
cggaatctac atcttacttt aattctgatt gtcagcccta taacaactat ttcatctatt    960
caaaaagata caaaaataaa ccaattaaca ttacttcgta gatacctcat cacatgacca   1020
ccctctcaag ttgatataat taactttcta aattgaccaa aagtgtttgc taatgtgtat   1080
agggtatagt aaataggaag gagttcggaa gttcgatgag agtaaatatc ttttgtgaaa   1140
tatctattgg aaattagcgg aaaaaagata aattttctcc tgaagtgcac aactaataac   1200
gaatatctta atgtggaaat aaatcaaatc aaatcaatat acatcccaat catgacatcc   1260
aagaacccca caaaaatatg ttcctaaaaa ctaactgata attaatttga atgtttccaa   1320
cagaaccttg ctcgcttttt gcacattttt ccactttgtt tcgctctaca cgcttgtatt   1380
tttttaatta attatatttt ttcggcctca ataaaaatta aaattccaga ttgaacacat   1440
ttaatgtcag aatataatta cagtaccttt ttatgacaaa acatatttcg gtataatctc   1500
agatttccac ttcttgtttc atggcccaag tttttctcaa tgctcacttg taacggaaaa   1560
tggagtcagt gaagctgttc aattctagat aatatgatgc tatcaaaggt cttaaaattt   1620
agataaaatg atgaaaatga cgacattaaa gtgtagcctt actgaaaaaa ccaattattg   1680
aactttaaga aaaaaaacat tttggaaaat aaaggtaatt catttttcgt acacctaaaa   1740
tttgaaaaac cgaaatttca gtgagaacgt cttcaactgc atcaaaaaaa ttgtgaagaa   1800
aatcgaattg aaaagagagg ctaaattggc ttcatatctt taatttagcc gattatacac   1860
gtcgggccag tctttttaa atgactgtca tggaggactt gatttcaaga ttggaagtga   1920
tgaactacaa aaaatatcaa acaattttta actgcataaa aacggttttt ctccgggatc   1980
aaagatgttt tcggtatcaa gtcacattca tggttcatta aaacatacta tttttctagt   2040
cttaaaatgt aatctgtata attttatgtt gttgattgaa ctcataatat gacaggattt   2100
tttttgtgat ttctgtaatg aagtacagtc ttacacgaaa actagagtaa tacaagtcat   2160
aaattttatt cgtctttttt cccgtagtcc tttcaataat gtatgaaaag catttacaaa   2220
ctacaactct ttcaaaaact agagttctta tcatacaaac cacacatttt ttgcagctct   2280
atataaacca actgataatg aggttttgtc tactctcatt actcaatt                2328
```

<210> SEQ ID NO 144
<211> LENGTH: 948
<212> TYPE: DNA
<213> ORGANISM: Caenorhabditis elegans

<400> SEQUENCE: 144

```
gtgaatacca caactgaatg tctcgaatat ggagccaatg attcggaaat ctatgaggaa     60
atggcatcga tttgcaagta tattgtacgg gattcgagag ctcacgggga ctcggttcca    120
gagtgatttt tgttgttcgc caattttatg attgtttctt gttgttaagt tttctaaaaa    180
ataaattctt tgattttaat aaatttcgaa aattcaaata ttatggggac gccgagggaa    240
tcagggtgca aaggcgctct aacgccaaat gacaaccgag cattgggtct cgttaggaaa    300
tggcggcaaa cgagacattt aaattttttta ttacgggaac acaaaattct aataatgcgt   360
attgcacaat atatcttacg cgctaagtat ctcgtagcga aaactacagt aatttttttaa   420
tgactacgct tgtgtcgatt tacgagctcg attttagaga tgaatttatt ttcgaatagt    480
gtcagcgata tttcgcttta atttcgaatc gagcccgtaa atcgacacaa acgctacagt    540
agtcatttaa agaaattact gtagttttcg ctacgagata ttttgtgcgt caaatatgat    600
gcgcaatacg cagtctcaga actttgtgtt cccataataa aaagtgagag ttttcatgcg    660
```

cccttggagc gctactgcac ctcaatttca aaaaacgcat ttttctgcgt ccccataata 720
caccgggatt ttcttttctc ttcgtctgaa aaacaatcaa tcatcattaa aatcatcatc 780
tatcaccaat acagaatcca tagatcaaac agatcaaaaa accaacttga acgcttgcag 840
gcaactacga taaaaatata ttttgtagtg tagtcatcat atcaatcatc tagctataat 900
aatgcctgcc gtataaatac aaaacacgat gatgatcttt ttgcgaaa 948

<210> SEQ ID NO 145
<211> LENGTH: 1233
<212> TYPE: DNA
<213> ORGANISM: Caenorhabditis elegans

<400> SEQUENCE: 145
attagagaac ttttcgagaa gtctaccgtt gtagttttcg aaatagtaat ttatttagtg 60
acgtttataa aggtttacat gatttggttt ggaaattttt taggagttta ttcataaaaa 120
caaagtaacc atggacattc cagaagtcta tagtacacgc gatcctaccg tacccttcag 180
tatttctatc agattgatag ctttcggtag tcaggtacag cctaaaaaat tcctgcttgc 240
ctttttgcct acatgtctgc ctaccttcag tcataatgcc tacataatga tttttttccaa 300 ttgaaacttg cagacagaaa ttcaaatggc aaaaagaaac aaacaccgaa acattaatca 360
catttctttt catatcagtt ttcctgtcaa agcacatttc tggagtctgt gtgtattttt 420
ttgtgtcttt atgtgatcgg tgttgtgaaa tttgtagttg atgttgataa catacttttt 480
tttgaaacaa aaagtgattg attaggcttg aattcagaga tatgttcgtg atactttgcg 540
attctcgagc caaaaacacg gtatccggtc tcgacacgac aactttttcg caaaatacaa 600
gctgatgtgc gccttgaaag agtactgtaa tttcaacctt tcgttgttgc ggaattttca 660
tagtttctcg ttcaaaatat atgtatttat taaacaaaaa actaaaacaa aacaattgag 720
aacacataaa ttgtgaaaaa tcaatgagac cacagcaaaa aattttgtat ctacagtact 780
ctttaaaggc gcacatccgt tcttattttc agcaaaaatg tcgcttcgag accgggtacc 840
gtattttttt ttgtgcaaaa ctttaggtct aggtaatatt aaaaaaaaat tccacaaaac 900
tagaatctag agctttccat taaatttttt gatgacattt gaaaattcat gatgattttt 960
ttccaacaat ttcgaaatat ccctcttttc acctggtcca ctgaattctc tttccgaaag 1020
accaccacaa tttcagggct ccgcccattt cgtggtttgt agccttcccg accctacgtt 1080
tttgatgaca attgtgagag aagtgagagg ttcagacaca aaaagcgacg tggtcgaatg 1140
agtataaata gagagtgaag tttccaattt ccctcacaat tgtttgtttg caatccactt 1200
tccaaaaaaa cacaacttca atcaaaaatc att 1233

<210> SEQ ID NO 146
<211> LENGTH: 656
<212> TYPE: DNA
<213> ORGANISM: Caenorhabditis elegans

<400> SEQUENCE: 146
gctaaacttt cgtattcgac tgataatgag aacgtggagg agtatcgtga ggttctcact 60
gaaaaagctg aacgtctcat ggaagactta aagcgatggc acttgtacag taaagatgtg 120
acaaaggatt tagaaacggc ggaaaagttg actttatgat aagaataccg ataaaattat 180
gaaatttctc gaaacttttg aattgtgaag caacttctta ataaagtaac tcattgactt 240
taatttttaa accacggctt agagaaaatt aaaaatcaaa cactgcagct tttttgatgc 300
gaaaattcat tgatatggaa caaacctcaa atttgataaa taatacaata atttgtcaag 360
aaatcacaaa aacgttcttt tgaaatgcaa gttataagac atacgcaaga tgttatgtcg 420
gtggctggtt ttaactataa aatacgaaac aattgacctc ctgacacaaa atttccgagc 480
ttgatttgtc tgatatcatt tgtgctttgg aattattgtt tcatgtgcat aaaatctaca 540
ctgtgttcat tcacgataag aagaatttca gacagaaacc acaggaggtt catcgatata 600
aaatgctaat catttgattt aaagaaccat actcttttta ctctcgtcgt taagaa 656

<210> SEQ ID NO 147
<211> LENGTH: 1275
<212> TYPE: DNA
<213> ORGANISM: Caenorhabditis elegans

<400> SEQUENCE: 147
cagctatccc gaattctcga gcgacatccg tcatctgaaa gagatactaa tgtcatgtga 60
agtggtatta aaaatatagt aagcacggta gaaacattaa cttataaaat tgagatttct 120
gataaataaa atttttccgg gagttctgta aaacttctta cggttttaac ttgataattc 180
catagggttt aaaatttcct tttgtttctt gagtttcttc tcggaatttg aacaaaaata 240
acgcgtttaa tctcgaatca gtacaatgat ggactacacg gcagttttaa aaaaccaatt 300
aataataata atcctaaaaa atgagaagaa tatttaagaa aatgtaaaag ttttccgcgg 360
aattccgcta aaattcgaaa attgaaagtg ttcaaattgc aagcgattgt gcattcagac 420
gtgacagtgt ctggggtgta ttgcgtactc gacattttaa ctgacgacac ttgtactttt 480
gcgccatact tccggagctc cagctccgcg gagccctgag caattatttt tttacttttt 540
atgaaaagct ttctatagat atcttttaag aagttacact ataattgtgc aaatcaaact 600
ggctccggac aacacaaatt tcgtctatac ctttatgatc tttttttgtt aaacaagtga 660
aacaattatt tccttttcaa actgctcttg tttcttctct ttattaatca attttttttt 720
ttttgctttg tgtaaattaa ttgtttgtcg cggatgagct aattctgagg tttgaccagc 780
agaaatctgt tttctgaaaa atcaataact cgccgcttaa ttttggtttt attcaagtga 840
tatgcaatta gaaggttcta atcatttata tctcgctgaa agatctcaga tttcaagcct 900
tttgctaagg atttaattcc taaaactttt tttgacctat catttttttgt gtgatctacc 960 gctgtaaata cttgttgttt tgcggctaaa ctctttcaat gtttccaaca agtgagccaa 1020
tatcaagtaa aaaaagaaaa atcgttttct attcaaccat tttattctgt aaataatatt 1080
aaattcatct tcacggtaca atcttcttct cccatctaat aaagtccacg cacactccgt 1140
tccgtcgttt ccctattcgt tatcattcat catcttgcca ttttcttctc cgccaaatcc 1200
cattgtctta tactaaattt catcctctcg tctgtagaag tgtatattat tgaaaaatta 1260
aagtatattt tcagg 1275

<210> SEQ ID NO 148
<211> LENGTH: 358
<212> TYPE: DNA
<213> ORGANISM: Caenorhabditis elegans

<400> SEQUENCE: 148
cgcttcattt tccaacaaac caagtactgg agccatttac tataagaact aaattaaata 60
ttaaatatat cgtttcaaga attcattgga atgaggcaaa agtaaatact taggattaaa 120
aaatccagct ttatattaaa aactttaaag gcgcatatga gatgttattc gggtcccgca 180
gcgctcatgc ggggtacgat agtacttcaa agaattacgc gggaatttct tttatgcggg 240
aaaacggttt tttcttgttt actagttcct ttctttcgtc taattttgat atcttgtgtt 300
tttttccaat tataaaatgt ttgtctcttc ttaaatttga aattttgaaa tttttcag 358

<210> SEQ ID NO 149
<211> LENGTH: 2636
<212> TYPE: DNA
<213> ORGANISM: Caenorhabditis elegans

<400> SEQUENCE: 149
ctctccttct ttcatattct gtgtccactt ctcactcatt gaatcataca tctctatgtt 60
ttctcatagt catcatatat tgtcagctgc agaaatctca tcatttttcc aaacgaaaag 120
ctcttaagag aaatgcttgt tttctgtggg gtacagcgaa tggcttctgt gggaatgcag 180
tttgtgaatg taaatagatt gttatgcagt cttgcaaatg tgtcggaggc caaaagtaga 240
gtagacatat ttgaaattta tagctttgag tgtccttagt ctattttgat atttcatttc 300
tgctttcctc agtctctcat tccagctgca aaaaataaaa ataagaaaaa acacgaatcc 360
cgtccattcg ccattcaaca tagatcatat tcctcagatt ttttgcagaa tatgtaattt 420
ttgctgaatg ctcgctctat tgtccttcat tggttatcaa tctttttgca ttaatagctt 480
taatttttga tgttttcgaa agattaggga aaaatttttt aatgtgtctt ttgtgacttg 540
agattatatg ctacactgaa aaaattggtc gcataacatt tcagagttca aagtgttttt 600
tctttcgatt gtgtaagcgg caaaattcta ctttatcatg catttttgtt tcaatcaaaa 660
atttgatgtg atttgtacat ggcgtcggtt tggtactagt tgtccacttc ctcagccatg 720
aaaagtgtga gtaagtgata acgtttatta tctttttttga attcattcta tgtttaagct 780
acacgtattt aactagctga ctcatttcca ccaaatatgc caaaagacct ccgagatttt 840
tttttgaaga taatttcgat ttcgcagaaa aaaaaacata taagtgatgt gggggtgtgt 900
cgccttcttc agctttccat agtgaaagtt tcgtaaaaac aagcttgcta tttcattttt 960
ccccgttcta ataccttgtc gcccagaaaa aatatttata tgatcttttt caactctttt 1020
tttgtaaaaa tggccaaaga ttagctaata tttgtatacc atcaaagttc tgccaaaatc 1080
tcgttgaaac atccatcgta gaacactcat tgggttccat caatacattt tttgtgtaac 1140
atcagtcgat tgttatcatt cgtatatgca tggtcatctc aaccgccctt acgacgtctt 1200
caaccatttt ctcttctaac tctctttctc tcaatttcac ttctcactac tctagtctat 1260
tcaattcttt gaaaaggcaa aaaaaaatgc ataaaaagat gaagaagaca ttcaacagac 1320
gggtgtcttc cttattttta ttcaaatcaa aacaaatggc gaccttctta ttcttctctt 1380
ttgcccgatg attcattttc tttttccatt aattttgtta tctattgctg aataacccgc 1440
tttactgaat gtgtggactg gcatttgcca cgttgcattt tggaaaagag ccgatgtagt 1500
tcttccgggt atatgtattc acagaacgat tcataagatc agacatatag acataaaatt 1560
cagcgcattc tgccttgtgg tttgtcaact acttccgtct tttttctgca tattcatttc 1620
ccgcttctgc tgtcttgttc atgaactctt gaactttgca ctttgccctc tttttaagtt 1680
tctctcgatt gatgcagcag cagcagactg tcattcatat ttgtctagtg atttcgtagg 1740
ttcaaacaac ttattaagcg gtttcaccta aaatttcgca tcccaaaata aaagttcaat 1800
tgcgaactag aagtacccag aagcgaaatt tttttgcttc aaaaatacgg tacccggttt 1860
tcaacaaaat cgttttcaag tgacatgagc gattttcctt tttatggaaa atttctaatt 1920
caaaaataaa tatttgaaat accttttttta gattattata tttattcttg gtattttctc 1980

-continued

```
tattcccact aaaatagact gatacgagaa cagttcttgt ttgcgcaaac tcacattttc   2040

tctctctatc tctccgtctc ttcttccgta tctctctgac ggtcccatac tctctcactc   2100

atcgtcagac accaccactt atcgatctat tttcgacgag tgagcggctg ttcgtcgcat   2160

gtttttttat aacttgattc gatcaatttc atcatatctt cttcacttat ttgaatttcc   2220

gttttgaaca tcatttttcc gtcggaaagt tgaagcattt gtttgatttt ctcggtggaa   2280

gattagattt caaaactttc gaaatttaac aatagaaaaa gagaaaaaag tgtagttatt   2340

aggaaatatt ttagacaatt ttgttggcaa ttaattgaaa ttaatttctt ctttctacat   2400

attttaaaaa tgtatctttt tttctattta tatttccttt ccggggatga gcgacaatta   2460

ttttcggcag ctctacaaaa tgactgcttg agataaaatt tctacttaaa atttattgtc   2520

gaaagataga aaaatgttgc ctcaaactgt aattttgtcg agttgcccaa aataattgtc   2580

gcacacctca gatttttttt tctattattt tttaaataat taaaattaca gtggaa       2636
```

<210> SEQ ID NO 150
<211> LENGTH: 2645
<212> TYPE: DNA
<213> ORGANISM: Caenorhabditis elegans

<400> SEQUENCE: 150

```
tattttgact tttgaatttt ggaggttttc aagaataggc aaacgttttg gcatcttttt     60

gaaaaaatct gatttttttgg tagattctat ccactttcta aaaattctac atgctctgaa   120

caaagtggaa aatacactga aaatttcaga tcgaagtttc aggtgtttga atttgtgtaa   180

tagtctgaaa aatctgaata taagctttca aatgagacat ctcgaagaaa atgaatttgt   240

gaaaaaatcc aattttttttc taattcgagc acaaaatgat gtcggtctat cacacctcct   300

tgttgttagg tgaataattg ttaaattctt aatctttatg atataacaaa gataggcttc   360

taactacgtc acgcctacat attcaatgaa attttgtagt gctactacta tttgtgcaag   420

ccggaatatg aatgtccttt cattttttttt cgtcccaaaa gtatataaaa tatctcacga   480

tatactcaga gattgggcaa caaagttcag gagaactttt gatgcacacc ggaaataaaa   540

gggcttcact gctttttttg ttgaattcat attggttttg gcgggaaata ttgaatcatt   600

attgatactt ttgaaacagg aatagacagt atttttcgta cggaaattcg ataatttccg   660

aaaatgttcg gttgcctccc tcgccccctt tgaaattaca ggagactaaa attcgaagaa   720

tgcgtattac gaaacgtata cgcgcaaaat atctcatagc gaaaactaca gtaatttttt   780

aaattactac tgtagcgctt gtgtcgattt atgggctcga ttaaaattga gcaaaaaatt   840

tagaaaatac tatgcaggcg cggaggaaaa taaaatatcg atatcactat tcggaaacaa   900

attcatttca aaaatcgagc acgtaaatcg acacaagcgc tacagtagca atttttaaaa   960

aaattactgt agttttcgct acgagatatt ttgcgcgtca aatttgctgc gcaatacgca  1020

ttctcagaat tttgcgttac cgtaatatac acggtgaaga acacgagcca ccaggagtac  1080

ggtagccctg actttaattg caaaaaaaga gaaaacagtg aaaaaaatct gtatataatt  1140

gctattattt ttaaatttcg caaaaaaaat tagaaatgac cacattaatt ttgaattcct  1200

gcgcgaatga attctatttt ttgcgtattc ctgcaatatt tattggattt tctcttagcc  1260

taaagcctaa aacgcagaaa tttcgaaata ataaattgac catttttgaa ttattggtgc  1320

aaaattgaga aaaattgtga aaaattatac catttttttga acaattacgc tcagcttact  1380

aattgtaaga ttactcagat ttatggcaaa acacgatttt tacgccttca aaaaatccta  1440

gcttttggca aaacttacag gaaattaaaa aattcagaat aaaaagtaat aagatccagg  1500
```

aagccatgac tcgaatcatt gtagttgaac tgtatgaatg atttgatccc agcttcttcc 1560
gccaccctaa acaccccata atttccgttt tccgcttgaa taggaaatgt tgtatatttc 1620
tgtactcctt cctgaagtat taaaactcgt tttcgtttat taaactgttt ctttttttcag 1680 atcactcaac ttcctcttct caacgtcaac ttcgactcgg ctaattataa ttttatttat 1740
ttttctgatt tttttaaaat tcttgttttt tctcaaattt ccaatttcaa catcatctta 1800
ttttcaaata aaaatattta ttttgcgact ttctattaat ttgaaacagc gaatattgtt 1860
aatttattaa gtaaatttaa tcattttaga tcgttttcaa ccgattttcg agggctttcc 1920
acaaattttg tacttttaaa taaatttaaa gtttattcta ccgaaaacac tatttatttt 1980
tccacgtgga caccgccaat tttctctgaa aattctaaaa ttctggttga aaattaattt 2040
ttaaagcttc ctcacgagaa aagcgccaac gcacgaggag cgcgccagca aacccgcatt 2100
gacgcagtct cggtgcactt ctgaactcca aaacacactg ttcccgttcg atttttctcg 2160
catttttcat agttttttttc gaaattgaag cttttaaagg tgttttagac ttgattcgaa 2220
gtgaaatatt gattgattga gccggaaaat aggcaaaaag ttctggaaaa acgcgcgaaa 2280
ttaaaattcc agtgactttc gagataatga tattgatttt tccgagtaat taagttgata 2340
tccagctatt tatttttgcg tgacattcta attaccggat tttcaaagtt ttttcgaaaa 2400
aaaaacaaag caaaatcgat ttatttcgaa ttactcgcga cttctcaact ttgaagctga 2460
aaatagttag ttttgttttt tctgttatca gtgcgcgctt tttctgcaat aataacattc 2520
cgcagtacga ttttttcaaa ttttttgctt ttcgagaacg gaaaatcaag tttatttcag 2580
tgtgcacgaa aaacgagcga gattctgact tgaccagttc gttcggaatc gactcatttt 2640
tggag 2645

<210> SEQ ID NO 151
<211> LENGTH: 1848
<212> TYPE: DNA
<213> ORGANISM: Caenorhabditis elegans

<400> SEQUENCE: 151
gatctgttct ttccgaaaag aagtagttaa caggtgcggc ttcactgggt ggtctcattt 60
ttcattttaa cctgttaatt tattccggct tcacctctaa tccttaatga cattaacatc 120
ttcctaatgt gtctaagctt ttcccacgga aagctaattt cctctctctt atttttctca 180
ttaccgttct ggttgagctt catcttatac cgtgaatggt ttcataatta cgtgctacat 240
aatttgttat gctggtcgag gctcaacgtt tcgaacatct ggctcttttc cttcagctaa 300
ccacaccact cttcgttaca atcccttctg cgcacacata tcctatctac cagccggaca 360
gatgctcgtt tctcggtgca aaacgttgag agttgagatc gagcagccgg ttggtagttc 420
ttaatgacaa attgccaaga ctttttctga attattttag gatttaaaac ttttctaaag 480
tattacgata gttcataatt tctttctttt ttaaaaattg gctctttttt gtaatgtatg 540
gtatctaact aaaactaggc ctcatttcca taactattct ttaaattgag ttgagctcaa 600
agagttagac agaactggtg tgaatcatag aacccacctg tgtttttact ttctttgaaa 660
aatgtcggtc acttagtcgt ctctctgtct gttccttttc ctaatcacaa gtaacaacac 720
acagtcttct ttcacatata ttatttgttg accaatcgta gggtcaacta tctagtactc 780
gagaccgcct atttgaacag agctcctcac tgtcaccaaa tgtaccgtat tgctttccgg 840
ctgttattgt tgttatcact gcttcttctt cctatcatgt tacccatcca actatacacc 900

-continued

```
ttagactagt catcttattg atatacattc ctcccatcca acacaacggt attctattta    960

tttatccaat tagtcatagt cgtaccacca tccagcacga aggtgcctct ttagtaaaga   1020

gtagaaagaa gaaccggatg ggaaatgttt ttgttacaaa aatgacacat attgtagtgg   1080

acagaaggag tgagacagac atgagcaagc caatttgttt ataatttctc ttctagaaaa   1140

aaatacattt ttccatactt cactagtcaa aacctttcac ctttctaata catctcgtaa   1200

accataatct tgatagttct gagcatttca atacgaaagc ttctcactgt ctagatctct   1260

gactgagtgc cctcatcaaa agtgcaatct gtcatctgtt tcctcataat cacggagcac   1320

taatttttct ctctgcgtct ctataatcag atatctctcg tcactaagaa ctttccgaaa   1380

tgtttatgct tctcatctga ccacttcggt tccgcacaaa aaagtacggc attccaaaag   1440

aaatctgatc cccctccgtt cattcgtggt ccgagtcggt gccaccagtc gttgcgcatt   1500

gaatatttgt ttggtccgtt ccccttcttc tccgactgct gacctcgggc actttgatga   1560

ccgggccacc acctcagtac ccctctatta caccctcttt gcctccgcgc atatgactcc   1620

accccttctc gtggaaggcg tgtatctccc ctcttttccg ctattccctc gatggatata   1680

tattcaaatg tatgtgtgtt cctgacggga gggcgtctcg cttgagagca tcgtcacatc   1740

ttttacaatt ttacttatga ttttacttca tcttcttctt cttactgcga ttttgatatg   1800

cattcttatg taaactatta ttattccagg tttcctcact cttttcaa                1848
```

<210> SEQ ID NO 152
<211> LENGTH: 1957
<212> TYPE: DNA
<213> ORGANISM: Caenorhabditis elegans

<400> SEQUENCE: 152

```
taggttaaca ctgataaatc ttgcagaact gttttatttt attaaatgag acattaccga     60

tctaaataaa tttacaatcc catcaaactt tctcctttat cctccagaat cccatcattt    120

tcatcggcac ttcttcaaaa gtttaaatgt gagtgaccgc ccgtctcgct ctactaatcg    180

tatatgcaaa ttttctttga tatcatagaa cctgtcatac ttctccaagt atatgaaaga    240

caattaaaac tactgagaga aagaagtagt tcgcgataaa aaagtacata taatacacct    300

tttcacctag aagagatgct ttcaacttct acttttctgg tcatatgtaa atagttgggt    360

tttttgacag tttgacaggt ttacggcagt caagacgaca aaaatggtta tcaaaaggag    420

ctggcataca gccaatacca ccagttctga tctttttacg attatcaaat tgtacatggg    480

gggttaagtt gaattttagt ttcatttttt caaaagttta aactcgaaaa ataactgaat    540

tgaaatatag tgaagttggc aatataccaa gggtagaaaa tcagacgagt gattttattt    600

ctagacaatc ttaaattgct caaattgtgg tcttttctat atttgaactt ttaaatgcag    660

caatttgtga aacatacaat tgaaacaaat ttcctcaaaa actgccacca gctgaggtat    720

catgaagcct tctgttcaca catgttgcca cctaatcggt cacttatcct aattaacatt    780

cttccactaa attgtcccct agtcaccccc acttgaacga tatacacacc aactgttctc    840

gttcactaat acacttcttc cggagggatt caactggtta tattctgcag ttgtcggcag    900

gtgtgtggta gacggtgacg taatattgca cagggtgtcg gggaatgatt atgaagtcga    960

gatgcgcaac agctggtaat tgaagccacg agagaaaatg gaaaagacta tgatgagggc   1020

acaaggatag aaaaattgac tgggagtgac caaacaggcg aggtcacaat gaaattggtg   1080

aaaatggaaa ccctaaaagt aactttagat tttagaaaat agttggacga tttttcgttt   1140

tcaaagttca aagcatgcat tattatcatc tgaagatgca cgatttgact tgtgtgactg   1200
```

atatctcgtc gcgatcttac cgtaacctac agtacttcca tattaactaa agttggttcg 1260
cttcgagaca tcgggaacgt gagttatgta tttggcatta ttcgtcattt tatattctag 1320
aaagatttac attctgtcaa gttggaatat tttttcttag ccgtgcaata gaacttttgt 1380
tgaatttctc agagtacaat ttttatgacc gccgatttcc tctcgataag cattacgtta 1440
tttacctatg gttttcaact atttaatgag atttatcagg acctcccgta gttttatctt 1500
ctatttttac tcaaattttg agctcaaaaa taacaggaaa gatttaatcg aaaaaaacat 1560
atttctgaaa tccaagagca atcgcgcgct attgataatc tggtttgccg catttctcgc 1620
ggcaacaaca aagagtttga atcgaaacgc ctttttattt gaaaaaaaac cttttttgtt 1680
ttaaaattta gtctatacgt gaatctaaca cacacaaact gttcactaat ttctctttgt 1740
tcgtcttttt accatttcat ttcgaaactc gctgtcgtct cgtttctctc accactcttc 1800
acacttttgc cgcctaatcg atcgatcttg ccgcggcgca ctcacatttt tctcttattt 1860
tcttaccggc aaaaaatgta cgttttaccg cacttttcgc ttacattact atttcaaatt 1920
ctcttatcaa aattatttca gaaacgaagt aacacaa 1957

<210> SEQ ID NO 153
<211> LENGTH: 791
<212> TYPE: DNA
<213> ORGANISM: Caenorhabditis elegans

<400> SEQUENCE: 153
catgaagaaa cagtggccgt attgggaaaa atgaacgatt tttcggcggg aataatttat 60 tttttatgt ttttctatgc gttttcgggt gttttcgggt tgctaagcga ttggttgcct 120
ttttgaatca ctagtcttgg tttttgttgt ttctgtgaat gaataattgg tttttcgagg 180 ttttttgtc aaacatgcct aaaaaataaa ttatgacgtt ttagttgatt tgtttgttct 240
ttaaacgtct gaaaataagg tttaaatcta atttattaat tataaaattc gtcaaaataa 300
gttgcgcgtc aaattatatg tattgtacgc agtgtcaaac tccaggcctc agttttcatg 360
aatttaccag cgatttttgt tataaatttt tttattgaaa tttaaaattt ttatttttca 420
accaatttgc ctcgaaaatt cgttatttcc ccattaaaaa ccgcttttct aaagtgttgc 480
gcgtcaaata aaatgcctgg tacgcaatgc acggagaatg cgcaaaggac gactgctggc 540
gcactttttg aatgcggtaa attgaggcgc gaagtttcat tcgaaaacgc gcgcgaaact 600
tcattcatcg cactttctcc gttcatttcg tcctattttt ttgtggtttt tcgcgatttt 660
ttcgcttttc tgagtgaaaa aataattttc cttcgttttt tcaatgaaaa tccgcggaaa 720
acccattttt tcccgtgaaa atccgcattt ttcgctgtat ttcataattt ttattcagat 780
ctcccgtcaa a 791

<210> SEQ ID NO 154
<211> LENGTH: 1005
<212> TYPE: DNA
<213> ORGANISM: Caenorhabditis elegans

<400> SEQUENCE: 154
ttgctgttct taattgattt cataaatatg tataaagcat taaatttgaa tatattttta 60
ataaagaaaa atcgatattc acattagagc gcgcttgcaa tttcacgatg agacctgacg 120
ataccgcgcg aattaaatcg atcgcttttt ggcctaaaat gctcattaac aattgttttt 180
gtagttttta gcttaaaatt atattttaaa atccagtttg ccttgttaca tattggaaaa 240

-continued

```
cggtatttt agagtttttc ctcaaaaacc aagcgaaaac cttgaatttt gttccgaaaa    300

cttgttcaaa acattttttt cgttgaaaac tcaaataatt caccaattta tctattttag    360

gccgaaatct cttatttttt cagtccaaaa agcaccaaat ttggtcaaaa acctgtccaa    420

aatctaccgt accctcgtgt tgctcgtgaa atgcggtgca ttgtgtgcaa acaccgcggc    480

gtgaacatgc acactctgca acgcgggaaa tcatttcgaa aaggttttta ggcgcgtatt    540

gcccgatttt tcggctcatt tcgtgtgttt tcatttattt ttgccttctt tctccggtcg    600

cgatgcgttt aattaagttt tgcttctaaa tttcgtcaat ttcgctgaaa aaccacgtag    660

aaaacttgat aggaactgga tatcctaaaa aaaaggattt ccttgagaaa aatgggtttt    720

ttttctgaat ttcgcagtga tattcttgaa attctcagcg cagcgctccc cagacaatcg    780

atattcctaa tttttcaagc atcttgtggc tcagccagct gttctgtaat tatcgatttt    840

atttgttaca gcgtctatat aaatacccta gaaagtcatc attctgcact cttaatacct    900

ttcactcgtg tgagttgcat tctccatagc aactctacct ctctccttct atctcttttt    960

ctcttttcaa atctaatttc gtttcagaga ctcccgctat aaacg                  1005
```

<210> SEQ ID NO 155
<211> LENGTH: 727
<212> TYPE: DNA
<213> ORGANISM: Caenorhabditis elegans

<400> SEQUENCE: 155

```
ttcgctttaa ctcctccaga agttgacggt ccgccagtgc ctccactagt cgtcgggagt     60

ttatggttca gtttcgcctt tttcatgtcc tccggcttca taatcgtatc atttaggcgt    120

ttgtgttttt tacgttccat tatttataag attctaaacg agaaactctt aagattttcc    180

ggaaaataat gataaaaacg gttgtgaaat tgaatgagaa taaaaaaacg aaacaagcac    240

gagtgaggca ggtgcgctcc aatgcgaatt tctttgcgcg gatgtttaaa tggttatttt    300

tttatgggaa tcgacaagtc acatgctacg ctagagagag ttttacattt tacagtcttt    360

ttggaattta ataatatata tattatcata aaatcgaata aaaattgttt cgaataatga    420

atagctttgt tttttcgtct tgacttctga aataatttta aatttgagaa aaatttgtgt    480

cgcaatatat aattattaat attattaata atgtaatttt tttataataa actgatttat    540

attttaaaaa caaaaaagga atgacaattc agtttagttt tatgaaaaac tttgaaaaga    600

caaaaataat tacagtaaac gcgctccgct agactcccca aatttgtttt tgttttccag    660

gcttgtgtcc aggcaaattc cagctttctt tttgtttcag aatttctagg tatttatctc    720

cgtgaaa                                                              727
```

<210> SEQ ID NO 156
<211> LENGTH: 2600
<212> TYPE: DNA
<213> ORGANISM: Caenorhabditis elegans

<400> SEQUENCE: 156

```
gaaaacttcg attcttatgg ttaaaacgag ccttgttagt aaaaattatt gagtgaataa     60

ataaattaga tcaagtattt tcacttctgc caaaattcaa ctaaatagaa atggttggaa    120

ttaagttaca agctaccagt ttacaaaaca ataattgaca ggtaatcgga gtgaagacag    180

ttttttgcct ttgataattt tacattcaca tttaatttta cattcacata aaaaaagaat    240

cacacatttt tttcaattga caagtttttg ataaagtgga agacatcgga gatatgaccc    300

gtcaaagttg ctcagcaggg tgcaaaacta aaagaggaaa tactgtgaaa cattttgaca    360
```

```
atttagagaa atacacagcg aaagaatgaa atctaaaaaa gcgtattaac tttaactaga    420
taaacatact aacttattga ggtaaatctg agcagatcct cttcctattc ccaatattta    480
cccaattagt cttctgattg cgcacctgca tatcttaagt actcaaatac aacacacatc    540
ttgagaaatg atgactccac actcagaatg caattcacac tattagaagc catgtgcaat    600
atgaaaacaa gcttatcctg aagctgcaaa cccatttacc tcatcaatta tttgcgatgt    660
gccgacctgt tgcatggctt ccgacactgt aaggggataa tctgtttgtc ggcacgcttc    720
aaccgattaa ttggcgtgtg aaacgatact aatccagtcg attctcgact aactgtaaac    780
actttgatgc taaccgacgt gccggctaat atactctctg tgttacgtca gaatccttta    840
aatatgcaaa tatggataag gtggaatgat ctcaagaggt gtgattgggt caaattggat    900
tacgtaattc ttaagtgggc taaaggtata ctgtaactgg ggtgcaattt atgtgggaag    960
tgcggcgaag ttatattggg gttttataga ttctataact tgttacattg attttgaata   1020
gatttcaatt ttcagaaaag tgggaaaact gtatttacat tttgaaagaa atttaatgca   1080
acagaaaata gtgattggct ggaaaagtgc ccctatgtta taaacttttt gttgaagctt   1140
tgaaattttt cacaaattat tcaactgaag tctcacacgt cgaaaaatgg ccaaacaaat   1200
ttttaaaaaa tagaggcctg atcatagttt ctgccatttc atggccgtct gtgacgtcac   1260
atgaggtttt tcgactattt ggcttccagg gttttacctg tttttaattt caaaattata   1320
tattcttcag taaatctctg aaagtcacag tcgtttcagc gaactttcaa ggccgcgtgt   1380
gacgtcacac tcttgcaaag aaagctgcac gtggtgtcag gttgtcccat aacggtttgc   1440
tctacgaaaa atgcgggaat tttttcatca aaaaatgtga cgtcagcacg ttcttaacca   1500
tgcgaaatca gttgagaagt ctgcgtctaa gttcccgcgt tttttgtaga tcacaacgga   1560
atgggacatt ctgacaccat gtgaagctgg ccttgagata gttttgtaga ttcaaaatat   1620
ttttaatgtc caatatttgt tttcaaaaca ttcgttaaaa tgtgcagaat atgttaaact   1680
gaaggttcct aggtttaaaa cttcaagcta aagctttccg gctcagttct caggttcagg   1740
tctgtaatct ttctgtaagc ttgtaatctt gttagttcct cagacagact tagctgctaa   1800
atttatttca tgtctaatat tacacttcaa gagctatgag tttgtcttca taaaagtttt   1860
ggctcccata taggaacttt ggaacatcat ttgatccccg tttcgaaaac gttcgaaaat   1920
tgttttgttt ctttatttaa acccgacagt tcaaattctt tatcttgatc aaaccctttt   1980
ttttcatctg tccattcctc ggccttaacc taatttatac agtttcgcaa taacctcccc   2040
cgtgcttgct ccagtaccag ctgttgcgtc acgacttctt attttcaaaa ctcaaatctt   2100
gcatcacacc tcatcaatta atcatcctca tcaagcctgc aaacttatac ccccttctct   2160
agacccctct cctgacattt gacactcctg tggtagaggg gtgtggcctt gcctgggcgg   2220
ggcgtgcaat gagaagctgt gcacgcacac cattcattca cacccaaaac attcacaccg   2280
attagtcgta ttctaacttc tcttttcaat tcagttgata tgctggtaag tctagaaatt   2340
atttattttt gatctacata cctgtccaat attgttcgtc tccccctccc cctcctgaga   2400
aacaaatttt tgtttttgtc tgctcgcctc accctcaacc tctctctctc tggatgtgtt   2460
cgtggtgtag aaacaaaaac agatttttgt ttttttgttt tttgtttctt gttttagaac   2520
ttgtatccta gtaattgtta gacatctccc tactatcttt cccctatata aaccccccttc  2580
aaaaccttac taatttccag                                               2600
```

<210> SEQ ID NO 157

<211> LENGTH: 394
<212> TYPE: DNA
<213> ORGANISM: Caenorhabditis elegans

<400> SEQUENCE: 157
aacagaactc acccgtttct agaacaacgt ttgctatcaa ctccaccccg aaagaatcca 60
ggtggttcgt ctgacattat gctgcaattt tatgagaata ttcagacgca acaacaacgt 120
gacaaacgac gagataaaaa tctatcaagg ctgaaacaat gacaaaaaag aaatcccgac 180
aaatgaaaat ggcgcctaaa acaaactttt ttaaaggacg tcgggtttca ttcacagatg 240
ggtctcggaa cgaaatcatg gagtacggta tcacacactt gaatttgaaa gtgaacttct 300
ttatttgttt ctcttgcaag tttaaactta agtttttaat tttttctgct tgtttctcaa 360
taaaataaaa atattacttg atttgtagcg caga 394

<210> SEQ ID NO 158
<211> LENGTH: 2557
<212> TYPE: DNA
<213> ORGANISM: Caenorhabditis elegans

<400> SEQUENCE: 158
ttctgcgtga aatgtgatgt ttctacagta acccgtacaa ccaaggcatc gaacttcacg 60
acatttacga attcaaattt gaattgcaaa ctttttaatt ttatcgattt tctttctttt 120
tgagctttat caatagctct aagcgattat tcaacagaat ttcacttttt tacgcctaaa 180
tgattgaaaa tttgataaaa tatcaataat ttacggttat cctcttcgta atcttcgctt 240
tcttcccaga gtagtgaaaa tatcgacttt ttgatagaaa ctggattttt taacttccct 300
gttcgaaaaa ctatttttcc ttaaatgaga tctgaaataa ggtgataaat taataaatta 360
agtgtatttc tgaggaaatt tgactgtttt agcacaatta atcttgtttc agaaaaaaag 420
tccagttttc tagatttttc cgtcttattg tcgaattaat atccctatta tcactttttc 480
atgctcatcc tcgagcggca gcgtctcaaa gaattgtgag agcaaacgcg ctccattgac 540
ctccacactc agccgccaaa aacaaacgtt cgaacattcg tgtgttgtgc ctccttttcc 600
gttatcttgc agtcatcttt tgtcgttttt ttctttgttc tttttgttga acgtgttgct 660
aagcaattat tacatcaatt gaagaaaagg ctcgccgatt tattgttgcc agaaagattc 720
tgagattctc gaagtcgatt ttataatatt taaccttggt ttttgcattg tttcgtttaa 780
aaaaaccact gtttatgtga aaaacgatta gtttactaat aaaactactt ttaaaccttt 840
acctttacct caccgctccg tgttcatggc tcatagattt tcgatactca aatccaaaaa 900
taaatttacg agggcaatta atgtgaaaca aaaacaatcc taagatttcc acatgtttga 960
cctctccggc accttcttcc ttagccccac cactccatca cctctttggc ggtgttcttc 1020
gaaacccact taggaaagca gtgtgtatct catttggtat gctcttttcg attttatagc 1080
tctttgtcgc aatttcaatg ctttaaacaa tccaaatcgc attatatttg tgcatggagg 1140
caaatgacgg ggttggaatc ttagatgaga tcaggagctt tcagggtaaa cgcccggttc 1200
attttgtacc acatttcatc attttcctgt cgtccttggt atcctcaact tgtcccggtt 1260
ttgttttcgg tacactcttc cgtgatgcca cctgctccgt ctcaattatc gtttagaaat 1320
gtgaactgtc cagatgggtg actcatattg ctgctgctac aatccacttt cttttctcat 1380
cggcatgctt acgagcccat cataaacttt tttttccgcg aaatttgcaa taaaccggcc 1440
aaaaactttc tccaaattgt tacgcaatat atacaatcca taagaatatc ttctcaatgt 1500
ttatgatttc ttcgcagcac tttctcttcg tgtgctaaca tcttattttt ataatatttc 1560
cgctaaaatt ccgatttttg agtattaatt tatcgtaaaa ttatcataat agcaccgaaa 1620
actacaaaaa atggtaaagt cttttaaatc ggctcgacat tatcgtatta aggaatcaca 1680
aaattctgag aatgcgtact gcgcaacata tttgacgcgc aaaatatctc gtagcgaaaa 1740
ctacagtaat tctttaaatg actactgtag cgcttgtgtc gatttacggg ctcaattttt 1800
gaaaataatt tttttttcg aattttgaca acccgtaaat cgtcacaagc gctacggtag 1860
tcatttaaag gattactgta gttctagcta cgagatattt tgcgcgccaa atatgatgcg 1920
taatacgcat tctctgaatt ttgtgtttcc gtaataattt cacaagattt tggcattcct 1980
ctttaaaggc gcacggattt attccaatgg gtctcggcac gcaaaaagtt tgatagactt 2040
ttaaattctc cttgcatttt taattcaatt actaaaattt tcgtgaattt ttctgttaaa 2100
atttttaaaa tcagttttct aatattttcc aggctgacaa acagaaacaa aaacacaaca 2160
aacattttaa aaatcagttt tcaaattaaa aataacgatt tctcattgaa aattgtgttt 2220
tatgtttgcg aaaataaaag agaactgatt caaaacaatt ttaacaaaaa aaaaccccaa 2280
aattcgccag aaatcaagat aaaaaattca agagggtcaa aattttccga ttttactgac 2340
tttcaccttt tttttcgtag ttcagtgcag ttgttggagt ttttgacgaa aactaggaaa 2400
aaaatcgata aaaattactc aaatcgagct gaattttgag gacaatgttt aaaaaaaaac 2460
actatttttc caataatttc actcattttc agactaaatc gaaaatcaaa tcgtactctg 2520
actacgggtc agtagagagg tcaaccatca gccgaag 2557

<210> SEQ ID NO 159
<211> LENGTH: 284
<212> TYPE: DNA
<213> ORGANISM: Caenorhabditis elegans

<400> SEQUENCE: 159
aaattcgagg aattttagat ttcatcttga aatttgcaat ggaaaaaata attattcaaa 60
gaaaatcaca gaaaatgcaa caaaaaaaac aaaaaaagaa caaaaaacaa gtcgaaaagt 120
gcgcccgggt cgtttgctga cgcatctctt caaacgagac gcgctgctgg cgcacttctc 180
gtgccctgtg cgtgcatttc cgcaacaaaa ttcaacactt gttttgaaac gcaccgccct 240
gtttcttttt tcaattttga taagaaaatc agcattgttt cagg 284

<210> SEQ ID NO 160
<211> LENGTH: 405
<212> TYPE: DNA
<213> ORGANISM: Caenorhabditis elegans

<400> SEQUENCE: 160
tagaaacatg tttcccgtaa gtgacctatc cagtgaaaca aaaacatgtt tctgtccgcc 60
ttccttccat cggtggaggt gcatgctaga ttgcctccta aactctaata cctaaaattt 120
taataattta ttgacaacat acagtttcac cgataaccga cactcttatt ttttctgatc 180
ctgactattc tgttcattat ttcagctcct atcatagaac gatctttcca gatcttggac 240
aagtcacagt tacaggtaat tttttcaaca ggtgtttgta taatgtctta gtttctgtaa 300
aattgtttta tcatgtaaaa tatttcagat tattcgaggg cagaaaaacg tgatattact 360
attggagagg aattgacaaa gttgtgtgat aaatttaatt ttgag 405

<210> SEQ ID NO 161
<211> LENGTH: 899
<212> TYPE: DNA

<213> ORGANISM: Caenorhabditis elegans

<400> SEQUENCE: 161
cgagtttctt gtgagaacca aaaactattc ctctgcaaga aaaaatttat taatccggca 60
taaaatactt tttattacaa taggaacttc acagtcgctt cctccgacgc tttgagcggt 120
acatcgatgc ttatcaccat gctgattgtt acctttctta cccgtttgac tttctgcaat 180
ttttaactgc aaagatgttt aatgcagata ctcgaaagaa acgaaaaaat gataaaaaag 240
tgaaaaaccc caaaaataaa tttgaaaact ccgcgtaagc ttgctcgatc gctgcgagac 300
cattgcatac cgtactactt ctttaaaggc gcacacatca aatctagctg tttcgtgaca 360
ggacccagca atgttcagcc gcgaagtttt gaatcgccat ttttttttaa tttctagaat 420
gtttatagtt ttgctttcga tgagattttt aagcattatg aggaacaaat ttttttaaaa 480
actttagaag ttttaaaatt taattttgcg attatgcttt gctttcgcgt gtcctttccg 540
ttgttcctcg ctccaaatat atcacagtaa ttaaccacta cttatgtagt tatcacgttt 600
ctaaaaatat aaattcattt ttatttctct attgattcgg tttgttgctc ttcttgtctc 660
aatcttgtgc tactgccgaa taccctgcta atttttcgtt ttcagtcatt cgattcactt 720
gggttgttgt ttaaaatggt aagatttttg caggttactt tctttcccat gaggtaaatg 780
catttattgc gggtgcgctc tatcgcacga cgccgcgaat cattgtattt caaattgatt 840
ttcctgttgc acttttatta gttacaattt ttattagtta tttttagttg gattcgaca 899

<210> SEQ ID NO 162
<211> LENGTH: 1290
<212> TYPE: DNA
<213> ORGANISM: Caenorhabditis elegans

<400> SEQUENCE: 162
gaaaacctaa aatgaacaaa attttttgtc attaaataac aacgcttcgg ttaacgcttg 60
aaattgatat tcggaaaata aaaagcctga tttttgttcg atttctgaaa tatatttcat 120
gctttacccg tttttaattg cgaacaattc taaatttgaa atataatttt caatcaacga 180
aaaacaattt tcaagataaa aaattattat ataaatttaa gctaagtatt aataaattaa 240
taagtaatag tattcaaaaa tcatagaatc ttgcaagaaa aaatgtttta aagatttaat 300
agttcgagtg attgaaaaac gaatagtact ttaaaaaata atgctttaag gcagaaaagt 360
gatataaaaa ttaagctcaa aagggcaaaa gataaggtta atgtccagtt ttggttttaa 420
aatggttcgg acacaatgta catagtagac atttgggtgt cctcttcctt ctcttttccc 480
cattgcgtcc actgaccctc cttgctgtat gtctgcgcat cgtctttttc tacacttttt 540
ccttttccct ggcccgttcc tatcggtgcc tttcacacac gcgagcggca gtggacgaga 600
cgggagggcg aggtgttgaa caagagtaca gcaagtgcgc gccatcgaaa aagcggaaaa 660
aaaaatttca aatggcgcta ctttgaaaat tgagaattct gtatttactg ccagttttac 720
ttgcatttaa atttccatgt tttctattct aaaacgaaaa tctatctaag aaaaccctta 780
ataaaaacct ataaatcata aattgtgatt cttaaattcg aaaatatgtt cgttcaactt 840
gacgcctaga aatatgtgga cttaatcctg ttataaatca gtagttgacg acaaaaatag 900
tagagcagca aaagcagttc taacttgtga aaaacatgaa agttcttgtt ttcgtcaagc 960
gaacgggggc tcgaggaagg acttggcacg tgtctctagg ccatgttttt ctcaattttt 1020
gttgctctag agaaagcttt tgctattgat tatgggacaa tcttggggat atgaaggtaa 1080
cattttaaaa ataagtttag gtaaatgtgt agcataattt ttgaaaaaaa aagctccact 1140

-continued

```
gttaaaaatg ccgattttag ggattgcgaa acgttcacta tgtacacata aatggctata   1200
taatttgaat ttgcattcaa taaatctttt ccttccaatt gtatgtttta acttaaaaat   1260
aattaattaa aattatctca ggagtcaaaa                                    1290
```

Transgenic biosensor production

Identification of toxin response elements

Tox Genes:
Literature based
Profiling Data

↓

Promoter Discovery:
by
ChIP-seq
And
MultiZ conserved
alignment
promoter  coding

↓

PCR Promoter Capture
Isolate Promoter

Transgene reporter plasmid

Reporter Plasmid Assembly promoter
+
targeting vector

↓ reporter

↓

Targeting Plasmid:

Unc-119 reporter

Mos1 in genome

Nematode Transgenesis

Micro-injection:
DNA inserted into
gonad tissue

↓

Genome Insertion:
Single copy insertion at
Mos1 Locus

↓

Toxicity Biosensor:
Toxin activates
fluorescent animal

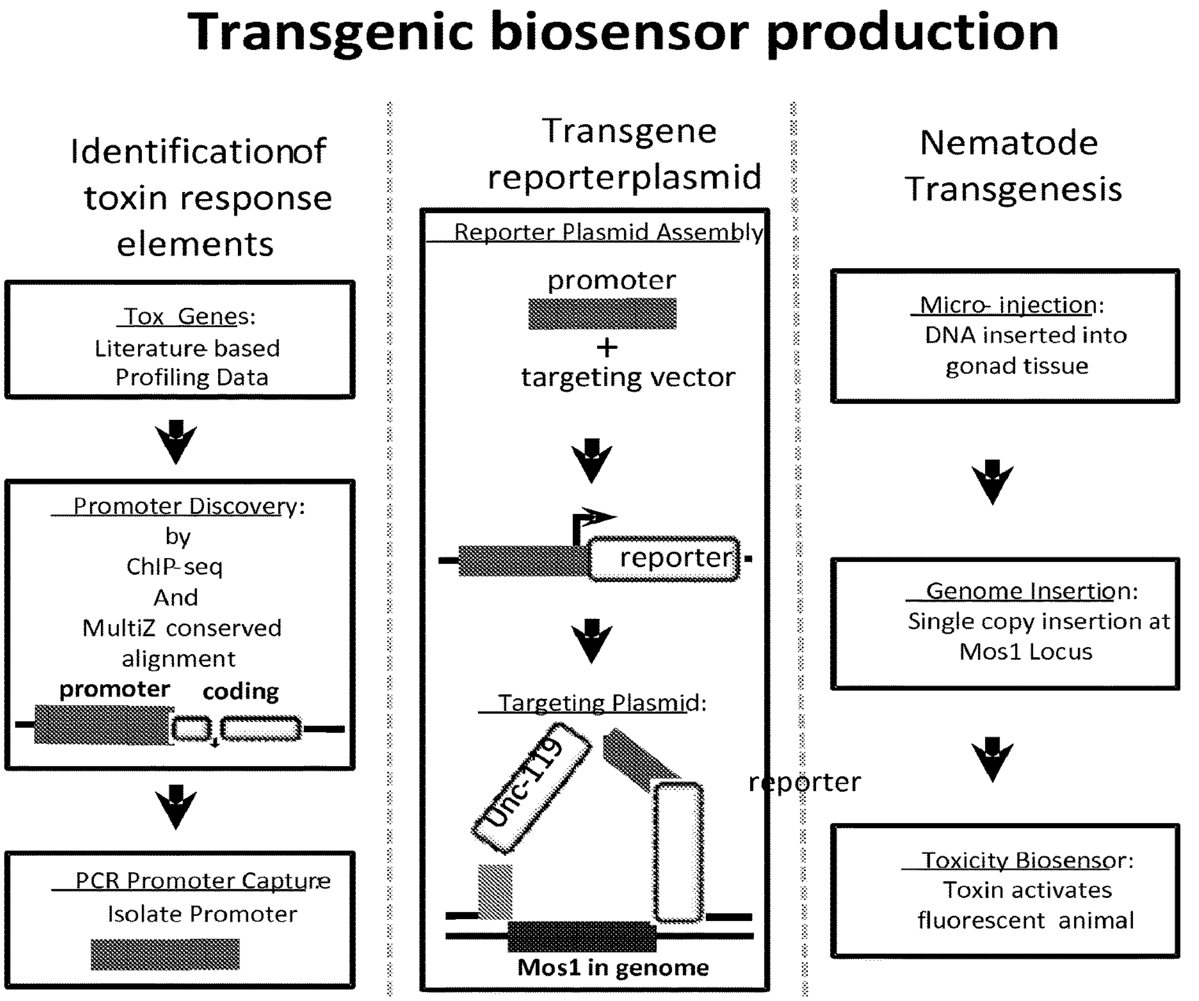

FIGURE 1A    FIGURE 1B    FIGURE 1C biosenor profiling plate concept

Sensitivity and selectivity of hsp-16.41 biosensor
FIGURE 3B
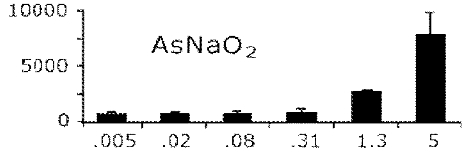
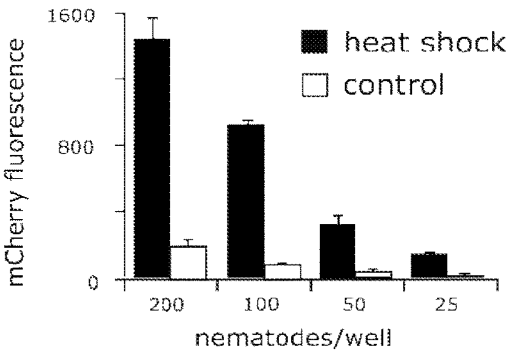
FIGURE 3A
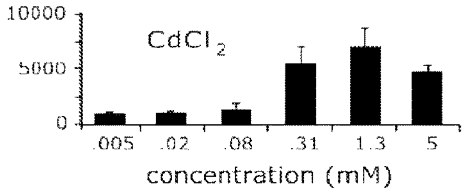
FIGURE 3C
Chronic exposure reveals need for normalization to population change
FIGURE 4B
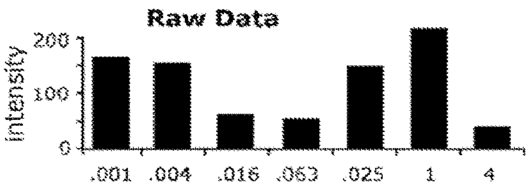
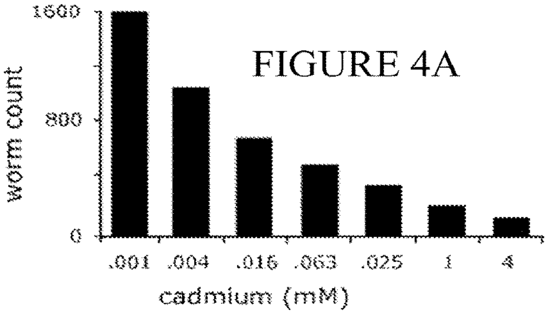
FIGURE 4A
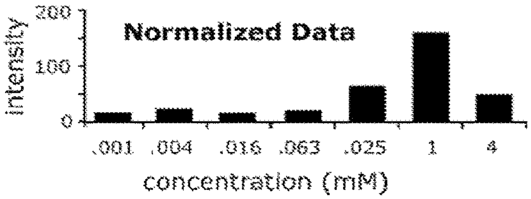
FIGURE 4C

Dual color worm normalization
FIGURE 5A
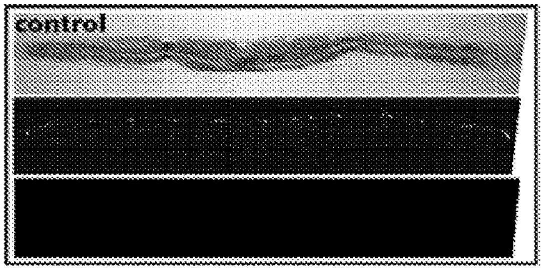
FIGURE 5B
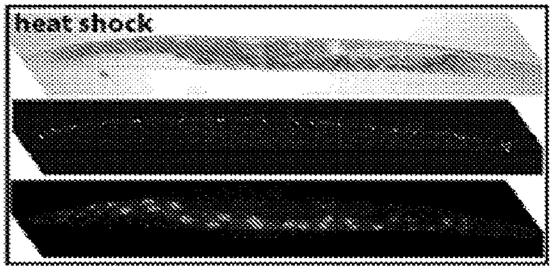
$$\text{Normalized ratio} = \frac{(R_i / G_i)}{(R_c / G_c)}$$
Copas biosort
FIGURE 6A
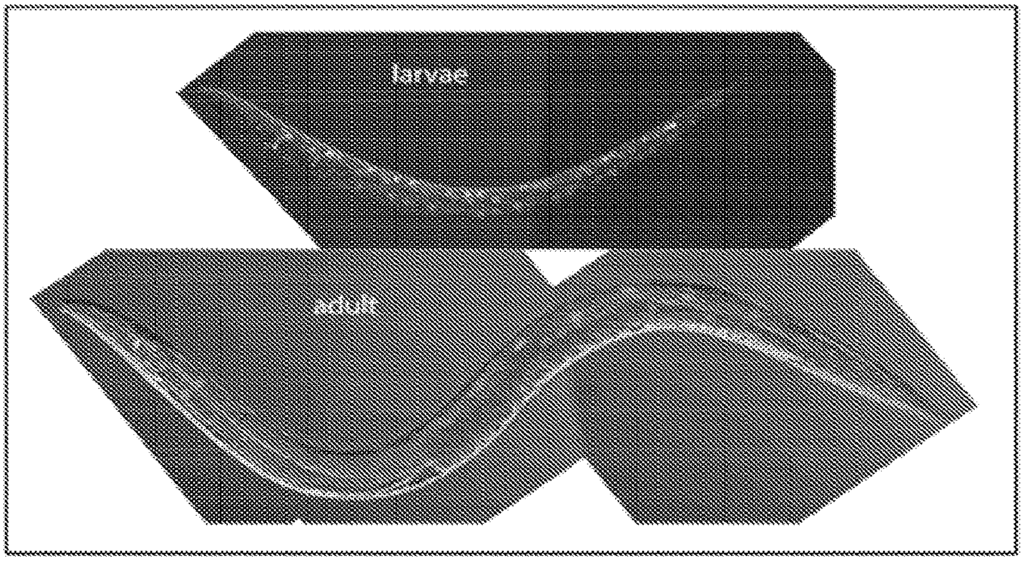
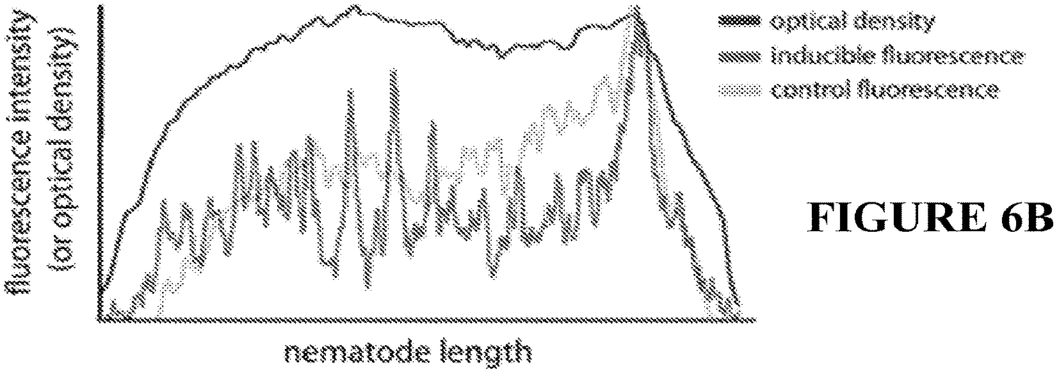
FIGURE 6B

Specific and selective biosensor response to two types of oxidative stressors

Digitized readout toxicity pathway activation

TRANSGENIC BIOSENSOR

CROSS-REFERENCE TO RELATED APPLICATIONS

This application is a continuation application of U.S. patent application Ser. No. 14/564,144 filed 9 Dec. 2014, which is a continuation of U.S. patent application Ser. No. 13/476,790 filed 21 May 2012 (now U.S. Pat. No. 8,937, 213), which claims the benefit under 35 USC 119(e) of U.S. Provisional Application No. 61/488,720 filed on 21 May 2011, the full disclosures of which are incorporated herein by reference.

The instant application contains a Sequence Listing which has been submitted electronically in ASCII format via EFS-Web and hereby incorporated by reference in its entirety. Said ASCII copy, created on 8 Aug. 2012, is named 20283_05_ST25.TXT and is 296,288 bytes in size.

BACKGROUND

One of the most difficult problems in drug discovery and toxicology is the ability to extrapolate results from early studies at the biochemical and cell-based level to effects in humans. The resulting inefficiencies in this extrapolation result in a high attrition rate in drug development and are an enormous drain of resources, effectively passing the buck on to consumers in one manner or another.

From the pollutants in the air we breathe to side-effects from drugs necessary for our health, we are surrounded by chemicals in our environment. It is important to determine which of these chemicals pose health risks and which are relatively harmless. Over 50,000 chemicals are in need of accurate toxicology assessment (Whittenberger J. Toxicity testing: strategies to determine needs and priorities. Washington DC: National Academy Press; 1984; and Kreweski D. Toxicity Testing in the 21st Century: A Vision and a Strategy. 500 Fifth Street, NW Washington, DC 20001: National Academy Press; 2007). Understanding the mechanism of action is becoming recognized as a critical parameter for accurate toxicology assessment (Lock et al. Toxicol. Lett. 2003 April; 140-141:317-322). However, there are limited choices in the marketplace for comprehensive tests to report toxicology pathway activation. The currently available methods are tedious in application or removed from a whole-organism format. As a result, toxicology researchers are in need of fast and efficient high-throughput methods to detect toxicology pathway activation.

Methods using intact cells or whole organisms are challenging to apply in high-throughput formats. Whole organism approaches are the most reliable in capturing accurate correlative toxicity data because the tests are performed in a native-context platform. Yet these approaches are costly for high-throughput implementation with classical models such as the mouse. Tissue must be harvested and either RNA extracted for transcription analysis (microarrays (Shioda J. Environ. Pathol. Toxicol. Oncol 2004; 23(1):13-31), RNA-seq (Kamb Res. Toxicol. 2011 August; 24(8):1163-1168.), rtPCR (Walker J. Biochem. Mol. Toxicol. 2001; 15(3):121-127.)) or metabolic analysis by specific biochemical assay (P450 (Guengerich Chem. Res. Toxicol. 2008 January; 21(1):70-83) and MDR (Sarkadi Physiol. Rev. 2006 October; 86(4):1179-1236.) transporter activity). Furthermore, tissue specific toxicity mandates careful dissection to allow accurate capture of toxicology data (such as sedimented-tissue lysates of liver, brain, and other tissues). As a result, intact organism toxicity approaches are difficult to implement in cost effective high-throughput strategies. In vitro analysis on cell culture systems is a method more amenable to high-throughput analysis. The common approach is to transfect primary cultures with reporter plasmids and detect gene activation as increased expression of reporter genes. These platforms are expensive, time consuming to maintain, and can be plagued with reproducibility problems. An additional drawback of cell culture transfection methods is the lack of native context. Frequently cell culture responses can give hypersensitive results and these results disappear upon whole organism analysis. Creation of transgenic immortalized lines can solve some reproducibility issues (Youdim et al. Drug Metab. Dispos. 2007 February; 35(2):275-282), but these lines are even further removed from native context and can give misleading results. Better methods are needed both in the research setting and in the market place.

Other public health related areas are also in need of improved methods for predicting effects in humans and animals including air quality, cosmetics, apparel, infant food, drinking water, environmental toxicology, food additives, nutraceuticals, manufacturing, organic foods, plastics, pesticides, industrial toxicity, toys, and waste water. Just about any area where exposure of potential toxins to humans or animals occurs is an area where improved method for detecting toxicological liabilities would be a benefit.

BRIEF SUMMARY

The described systems and methods relate to transgenic organisms and their use as biosensors. In some implementations, the described systems and methods include a first population of transgenic organisms that includes a first constitutively expressed reporter gene, and a first transgene that includes a first inducible promoter from a response pathway gene, wherein the first inducible promoter is operably coupled to a first reporter gene.

In other implementations, the population of transgenic organisms further includes a second population of transgenic organisms having a second transgene that includes a second inducible promoter that is operably coupled to a second reporter gene, wherein the second population of transgenic organisms further includes a second constitutively expressed reporter gene, and wherein the first inducible promoter and the second inducible promoter each include a promoter that is derived from a different gene.

In still other implementations, the described systems and methods comprise an object that includes a transgene, a transgenic organism, or a construct, wherein the object includes a promoter region having a promoter, a fragment of the promoter, or a homolog of either the promoter or the fragment of the promoter, wherein the homolog includes at least about a 95% identity to the promoter or the fragment of the promoter, wherein the promoter region is operably coupled to a reporter gene, wherein the reporter gene encodes a protein selected from a fluorescent protein and a luminescent protein, and wherein the promoter region includes a promoter region for a gene selected from: *C. elegans* genes cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp- 35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, WO1A11.1, WO2C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, RO5D11.6, R05F9.10, RO9H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, and Y39H10A.7; ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, KO2E11.3, KO2E11.4, KO2E11.5, KO2E11.6, KO2E11.7, KO2E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, lin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, RO5D11.6, R05D8.7, R05D8.9, R05F9.10, R07B7.4, R07B7.5, RO9H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, sink-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, WO1A11.1, WO1B11.6, WO2C12.1, W03F9.9, WO3G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, and zyg-12; and homologous genes from an organism selected from *Danio rerio* (zebrafish), *Drosophila melanogaster, Daphnia* spp., and *Xenopus laevis.*

In yet other implementations, the described systems and methods include an object selected from a transgene, a transgenic organism, and a construct, wherein the object comprises a promoter region that includes a promoter, a fragment of the promoter, or a homolog of either the promoter or the fragment of the promoter, wherein the homolog has at least about a 95% identity to the promoter or the fragment of the promoter, wherein the promoter region is operably coupled to a reporter gene of an inducible reporter, wherein the reporter gene encodes a protein selected from a fluorescent protein and a luminescent protein, and wherein the promoter region includes a sequence selected from those found in SEQ ID NO:1 to SEQ ID NO:162.

BRIEF DESCRIPTION OF THE DRAWINGS

FIGS. 1A, B, and C show a schematic representation of a transgenesis algorithm for generating transgenic organisms for use in the invention. The transgenesis algorithm involves, as shown in FIG. 1A, identifying a promoter response element, as shown in FIG. 1B, operably linking or fusing the promoter response element to a reporter gene to create a functional transgene and, as shown in FIG. 1C, inserting the functional transgene into the host organism's genome (e.g., *C. elegans*). FIG. 1A comprises (1) toxicity profiling data analyzed for genes involved in response pathways (e.g., qPCR, microarray, RNA seq, and/orRNAi screens from literature), (2) promoter discovery (e.g., bioinformatic scan using ModENCODE ChIP-seq data and bioinformatics scan with MultiZ alignment for 5' conserved elements), and (3) promoter isolation (e.g., design primers for region of interest and amplify from wild-type DNA). FIG. 1B comprises (1) reporter plasmid assembly (e.g., insert promoter into targeting vector/contruct by standard molecular biology techniques) and (2) targeting plasmid assembly (e.g, having a positive selection marker (e.g., unc-119 rescue) and a homology arm for transposition (e.g., sequence flanking Mos1 site to yield transgene of interest—toxin sensitive promoter driving reporter gene). FIG. 1C comprises (1) microinjection of targeting plasmid into worm (e.g., insert targeting plasmid mix into gonad tissue of selectable background animals (e.g., unc-119 mutants)) and (2) genome insertion (e.g., array formation, Mos1 transposon insertion, homologous gene repair, transgene insertion, and array loss) to give the desired transgenic worm.

FIG. 2A shows the initial plate layout before addition of a selected agent.

FIGS. 3A, B, and C show the fluorescence plate-reader sensitivity and toxin response. FIG. 3A shows 2-fold dilutions starting with 200 worms per well, assayed in duplicate, were exposed to heat shock (34° C. for 1 hour) and allowed to recover for 16 hr 15 C. FIG. 3B shows arsenic and FIG. 3C shows cadmium responses: 24 hr exposure, ~600 worms per well, assayed in triplicate.

FIGS. 4A, B, and C show the population effects of chronic toxin exposure. FIG. 4A shows chronic exposure was assayed for effect on population size during 72 hr exposure to cadmium at various concentrations. FIG. 4B shows raw data profiles show bimodal response in fluorescence intensity over the titration range tested. FIG. 4C shows population-normalized response curves show single-mode effect of cadmium on fluorescence intensity.

FIGS. 5A and B show the results of the dual reporter configuration for population normalization. FIG. 5A shows uninduced vs. FIG. 5B which shows induced (30° C., 1 hr) nematodes (hsp-16::hRFP, unc-47::GFP) were imaged in green and red channels. FIG. 5A is the control worms (top panel is a photograph of the worm, the middle panel is the GFP expression, and the bottom panel is the RFP expression). FIG. 5B is the heat shock treated animal (top panel is a photograph of the worm, the middle panel is the GFP expression, and the bottom panel is the RFP expression). Expression of fluorescent protein shows up as lighter shaded areas in the images. The images show significant induction of RFP in the heat shock treated animals. The equation used for normalization using values in the control animals where $R_i$ is the value measured for RFP fluorescence in the induced animal, G is the value from GFP fluorescence in the induced animal, $R_c$ is the value for RFP fluorescence in the control animal and $G_c$ is the value of GFP fluorescence in the control animal.

FIGS. 6A and B show the NIEHS findings with hsp-16::hRFP induction in unc-47::GFP background. FIG. 6A shows confirmation of heat shock responsiveness in the larvae and adults nematodes. FIG. 6B shows representative COPAS biosorting profile showing nematode size-dependent effects on observe fluorescence. The lighter shaded areas in the images indicated fluorescence of GFP or RFP.

DETAILED DESCRIPTION

Figure 2A:
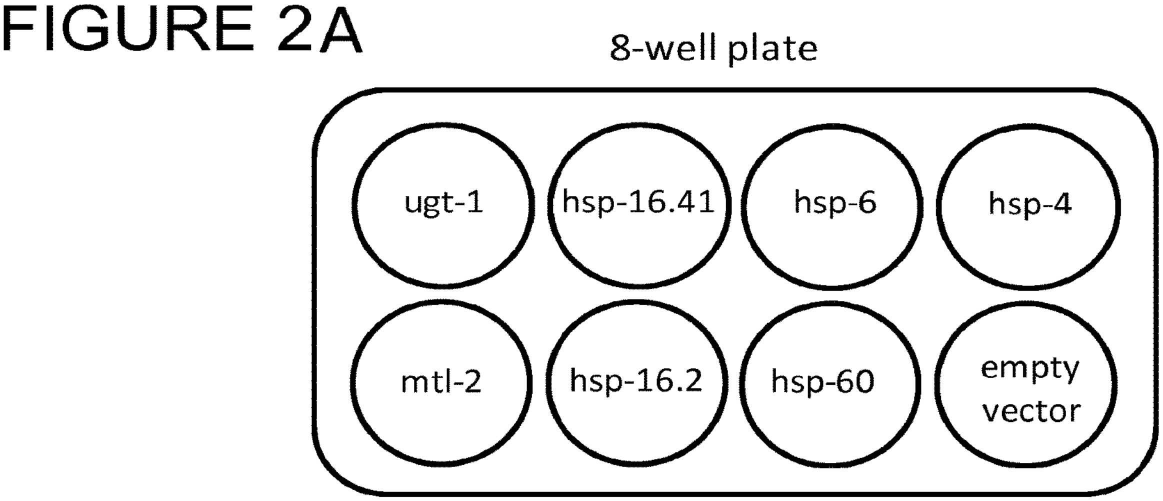
FIGS. 2A and B show a schematic representation of a plurality of representative populations of transgenic organism within the context of a multiwell plate. Each well has a population of worms from the indicated strain (as indicated by the abbreviation in the well which signifies the promoter region of the indicated gene that is fused, or operably linked, to a reporter gene).

The invention described herein is a remarkable new paradigm useful for probing the effects of exposure to a stimuli (e.g., a chemical agent or heat shock), on gene expression at the organismal level in a rapid and efficient manner. The inventors have created biosensor organisms that are easily useable and provide robust reproducible results in an out-of-the-box format for testing the effects of exposure to various stimuli on gene expression levels as measured by reporter genes. Importantly, the compositions and methods described herein are unexpectedly useful for identifying gene expression responses to stimuli at the whole organism level.

In a specific implementation of the invention, the inventors have used nematodes (e.g., *C. elegans*) as model organisms. Other organisms can be used as model systems, especially those that are translucent or partially translucent. A panel for oxidative stress response transgenic biosensor organisms was created based on the promoters of 7 genes induced by oxidative stress. Seven unique nematodes lines each corresponding to a different oxidative stress gene were created by genetic engineering technology (each line "representative" of a particular oxidative stress gene). More specifically, promoter regions for each oxidative stress response gene were identified and fused, or operably linked, to the coding region of a fluorescent protein gene to create a transgene promoter reporter construct using standard molecular biology methodology. Importantly, the promoter regions were identified/chosen to contain transcription factor response elements (e.g, transcription factor binding elements) that recruit transcription factors to help modulate transcription of genes under control of the promoter. Each transgene then was inserted into the nematode genome as a single copy (e.g., using single copy transgenesis procedures) to yield seven unique lines (also referred to as representative transgenic organisms e.g., seven representative transgenic organisms). Each line also has a constitutively expressed transgene encoding another fluorescent protein for normalization purposes which was introduced using standard techniques.

The seven different promoters used to create the lines were obtained from genes involved in oxidative stress response. Two genes used were alpha cystallins which respond to cytoplasmic heat shock (hsp-16.2 and hsp-16.41) (David et al. Environ. Toxicol. Chem 2003 January; 22(1): 111-118; Hong et al. J. Mol. Biol 2004 November; 344(2): 369-381; Candido E P M. Prog. Mol. Subcell. Biol 2002; 28:61-78; Dengg et al. J Pharmacol Toxicol Methods 2004 December; 50(3):209-214; and Strayer et al. FASEB J 2003 December; 17(15):2305-2307). A metallothionein gene was used to detect oxidative metal toxicity (mtl-2) (Sukaina Zeitoun-Ghandour et al. Aquatic Toxicology 2010 October; 100(2):140-150; Cui et al. Genome Biol 2007; 8(6):R122; Roh et al. Environ. Toxicol. Chem 2006 November; 25(11): 2946-2956; Liao et al. J. Biol. Chem 2002 November; 277(44):42049-42059; and Dong et al. J. Mol. Biol 2008 February; 376(3):621-633) as well as a uridine diphosphate-glucuronosyl/glucosyl transferases gene (ugt-1) (Cui et al. Genome Biol 2007; 8(6):R122). The remaining 3 genes were chosen for unfolded protein response (UPR) oxidative stress in the mitochondria (hsp-6 and hsp-60) (Yoneda et al. J. Cell. Sci 2004 August; 117(Pt 18):4055-4066.) and endoplasmic reticulum (hsp-4) (Vadim Kapulkin et al. FEBS Letters 2005 June; 579(14):3063-3068; and Urano et al. J. Cell Biol 2002). Promoters for these genes were selected to contain all clearly identified transcription factor binding sites and were cloned into expression vectors containing hsRFP, which is mCherry red fluorescent protein fused to the his-57 histone gene. The resulting hsRFP reporter construct expresses red fluorescence in cell nuclei. The reporter is injected into GFP expressing nematodes (unc-47::GFP) using the MosSCI method (Frokjaer-Jensen et al. Nat Genet 2008; 40(11): 1375-83), which creates single copy insertions of the transcriptional reporter genes at Mos1 loci. The result is a two-color fluorescent nematode (FIG. 5), where each strain contains both a ubiquitously-expressed GFP and hsRFP whose expression is drivenby an oxidative-stress gene promoter.

Figure 7:
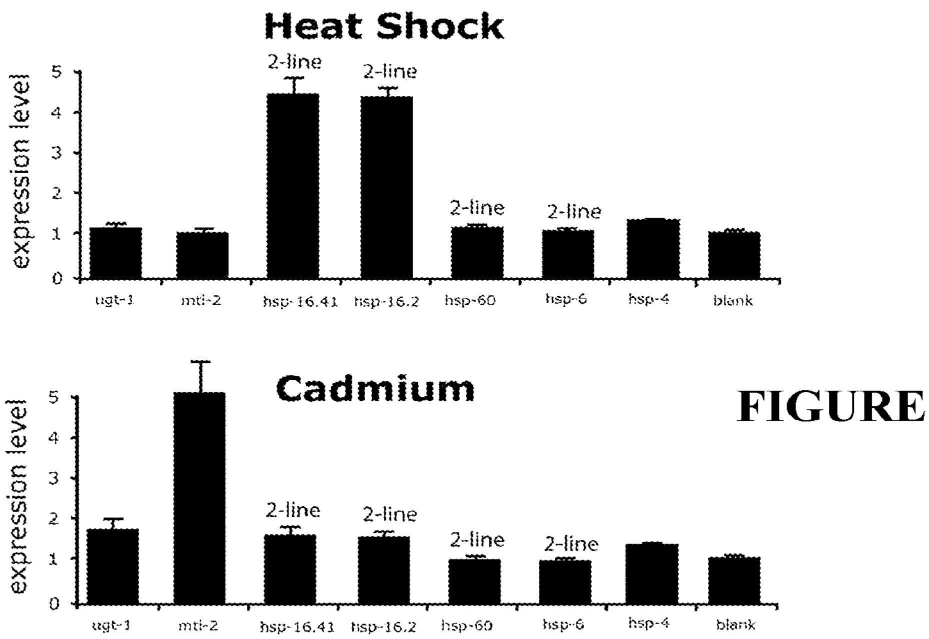
FIG. 7 shows expression response profiles using two-color nematode biosensors. The upper graph shows biosensors exposed to 34° C. for 1.5 hrs on seeded NGM plates followed by 4 hrs recovery at 20° C. The lower graph shows biosensors exposed to cadmium (1 mM, NGM plates) for 15 hrs. Responses are population-normalized changes relative to unexposed control. Error bars indicate average of 2 to 6 independent measurements. The label "2 line" indicates data derived from combining responses of two independently-derived MosSCI lines for the same reporter.

Changes in expression were quantified with a plate reader assay. The 7-member oxidative stress response biosensor panel was heat shock exposed. Significant increased expression was observed in the hsp-16.41 and hsp-16.2 reporters (FIG. 7A), in contrast to the low to non-existent expression induction of the remaining genes. Exposure to metal toxicity elicited a different response in the panel. Cadmium primarily induced metallothionein gene expression (FIG. 7B) and only mildly induced expression from ugt-1, hsp-16's, and hsp-4. Thus, the simple 7-promoter panel was capable of distinguishing different types of responses. In particular, the panel differentiated between two types of oxidative stress responses: heavy metal ion induced oxidative stress and heat shock induced oxidative stress.

In addition, these results show the inventive methods and composition have 4 remarkable features. First, the system shows induction at significant levels over background. For example, the oxidative stress response panel has strong responses occurring at greater than 4-fold over background. Second, the system shows important levels of fidelity. The panel responses are highly reproducible, where less than 10% error occurs in the assays of 2 to 6 measures done on different days and/or different populations. Third, the method of MosSCI transgenesis creates independently derived strains with similar responses as indicated. Fourth, the arrangement of reports in a plate-reader panel provides an easy-to-use format that quickly reveals which genes are important for toxicity pathway response and can identify different types of response like one response pathway versus another response pathway.

In conclusion, the oxidative response panel demonstrated the system is feasible for sensitive and selective detection of changes in gene expression at the whole organism level when the organism is exposed to external stimuli. This system has advantages over cell culture methods because it is easier to use and amazingly less costly to implement. The inventive system is a whole organism approach, which detects cellular response in a native context. The ease of assay implementation makes the system ideal for high-throughput applications. In general, application of this technology in toxicogenomics is expected to be extremely valuable in the drug discovery sector (Yang et al. Chem Biol Interact 2004 November; 150(1):71-85). With this inventive system, pharmaceutical companies will decrease their financial exposure because better toxicology capture at the front end of drug development translates to lower frequency of drugs failing in clinical trials due to unwanted side-effect toxicity. Additionally, this technology has clear utility in a variety of other sectors, including screening potential pharmaceutical effects for wanted or on-target effects, or differentiating between types of on-target effects.

Definitions

As used herein, "operably linked" and "operably fused" may refer to the association of two or more nucleic acid elements in a recombinant DNA construct, e.g. as when a promoter is operably linked with DNA that is transcribed to RNA for expressing a protein. Additionally, the term "operably coupled" may be used herein to comprise the terms "operably linked" and "operably fused."

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, the term "promoter" refers to a region of DNA which lies upstream of the transcriptional initiation site of a gene to which RNA polymerase binds to initiate transcription of RNA. An "inducible promoter" is a promoter that increases expression of its cognate gene or reporter when exposed to an inducing agent.

As used herein, the term "fluorescent protein" refers to proteins that fluoresce in response to excitation at a particular wavelength or range of wavelengths of light. As used herein, "RFP" refers to a class of proteins called red fluorescent proteins which are fluorescent proteins that fluoresce in the red region of the spectrum, generally in emitting light having a wavelength in the range of 600 to 650 nanometers. As used herein, "GFP" refers to a class of proteins called green fluorescent proteins which are fluorescent proteins that fluoresce in the green region of the spectrum, generally in emitting light having a wavelength in the range of 500 to 50 nanometers. The terms "RFP" and "GFP" are not intended to be construed based on the amino acid sequence of the underlying protein but are intended to be construed based on the wavelength of light they emit. For example, a RFP has been constructed by site-directed mutagenesis of a protein that was originally a GFP. As the term is used herein, this new protein is a RFP.

As used herein "detectably different" refers to measurements or observations that can be meaningfully distinguished from one another. In the context of "detectably different fluorescent proteins" this refers to proteins that fluorescent at different wavelengths of light such that they level of amount of the two proteins can be meaningfully determined. Detectably different can refer to no greater than 50%, 40%, 30%, 20%, or 10% of emissions.

As used herein, the term "transgene" refers to a gene in an organism that has been introduced, or is to be introduced, that is non-native. Typically transgenes according to the invention are created by genetic engineering technology and inserted into an organism to create a transgenic organism.

Figure 2B:
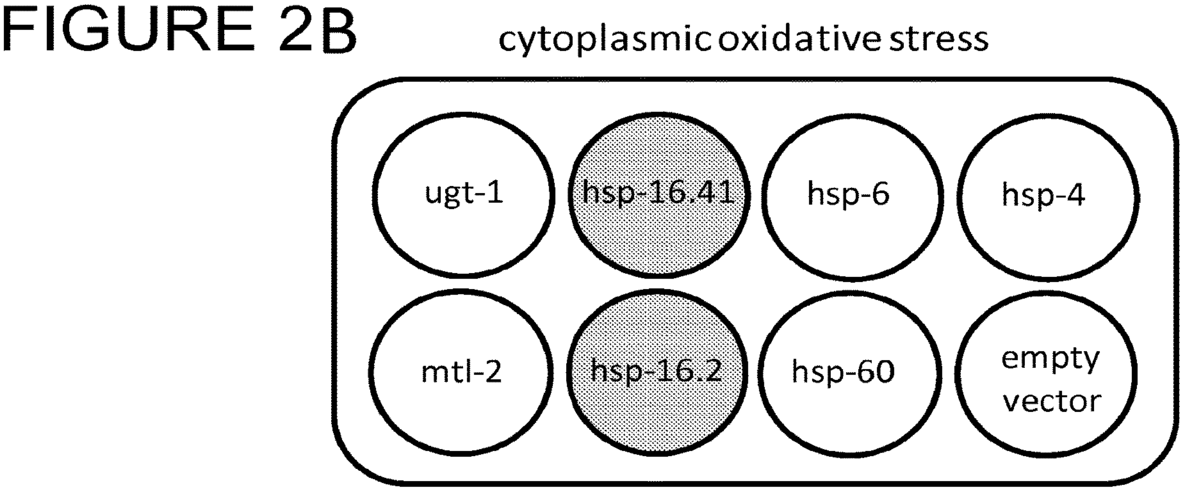
FIG. 2B shows wells highlighted in grey when the selected agent is one that selective induces cytoplasmic oxidative stress (e.g., induces promoter driven expression of reporter gene).

Thus, in one embodiment, the invention is one or more (a) representative transgenic organisms or (b) populations of representative transgenic organisms as biosensors for detecting an alteration in gene expression in response to exposure to a selected agent. Each representative transgenic organism or population of representative transgenic organisms has a transgene which is an inducible promoter of a gene operably linked, or fused, to a reporter gene. Thus, a representative transgenic organism is a biosensor having a transgene which is an inducible promoter of a gene of interest operably linked, or fused, to a reporter gene. In a specific aspect, the transgenic organisms have a second reporter transgene that is a constitutive reporter that is used to normalize the expression level of the reporter driven by the inducible promoter. A population of transgenic organisms is 1 or more transgenic organisms each organism having as a transgene the same inducible promoter operably linked or fused to a reporter gene. In one aspect, the invention is a plurality of representative transgenic organisms or population of representative transgenic organisms where each representative transgenic organism or population of representative transgenic organisms has a distinct transgene that is a distinct inducible promoter of a gene operably linked, or fused, to a reporter gene. In a specific aspect, each population of representative transgenic organisms has 10 or more, 30 or more, 50 or more, 100 or more, 150 or more, 200 or more, or 300 or more transgenic organisms. A plurality of representative populations of transgenic organisms can be envisaged in the format of e.g., microwell plate with (a) each individual well having 2 or more transgenic organisms having as a transgene the same inducible promoter operably linked or fused to a reporter gene and (b) at least 2 wells differing from one another in the identity of the inducible promoter of the transgene (e.g., the inducible promoters in the transgenic organism in the first well and the inducible promoter for the transgenic organism in the second well are different i.e., from different genes). This concept is exemplified in FIG. 2. According to a method of this embodiment, the plurality of representative transgenic organisms or population of representative transgenic organisms is contacted with or exposed to a selected agent, incubated for a time sufficient for induction of the gene driven by the inducible promoter, and expression of reporter gene is determined. In a specific aspect, the reporter gene driven by the inducible promoter encodes a fluorescent or luminescent protein. In a specific aspect, the constitutive reporter encodes a fluorescent or luminescent protein. In a specific aspect, each transgenic organism has an inducible promoter operably linked or fused to a reporter gene encoding a first fluorescent protein and a constitutive reporter encoding a second fluorescent protein wherein the first and second fluorescent protein fluoresce at detectably different wavelengths. Non-limiting examples of fluorescent proteins that fluoresce at detectably different wavelengths are GFP and RFP. Preferably, the inducible reporter expresses at least 2-fold greater, 3-fold great, or 4-fold greater than background levels (e.g., untreated organisms).

In a specific aspect of the embodiment described in the paragraph above, the invention is two or more (a) representative transgenic organisms or (b) populations of representative transgenic organisms as biosensors for detecting an alteration in gene expression as a response to exposure to a selected agent. In another specific aspect, the invention is three or more (a) representative transgenic organisms or (b) populations of representative transgenic organisms as biosensors for detecting an alteration in gene expression as a response to exposure to a selected agent. In yet another specific aspect, the invention is four or more (a) representative transgenic organisms or (b) populations of representative transgenic organisms as biosensors for detecting an alteration in gene expression as a response to exposure to a selected agent. In another specific aspect, the invention is five or more (a) representative transgenic organisms or (b) populations of representative transgenic organisms as biosensors for detecting an alteration in gene expression as a response to exposure to a selected agent. In another specific aspect, the invention is seven or more (a) representative transgenic organisms or (b) populations of representative transgenic organisms as biosensors for detecting an alteration in gene expression as a response to exposure to a selected agent. In another specific aspect, the invention is ten or more (a) representative transgenic organisms or (b) populations of representative transgenic organisms as biosensors for detecting an alteration in gene expression as a response to exposure to a selected agent. In another specific aspect, the invention is fifteen or more (a) representative transgenic organisms or (b) populations of representative transgenic organisms as biosensors for detecting an alteration in gene expression as a response to exposure to a selected agent. In another specific aspect, the invention is twenty or more (a) representative transgenic organisms or (b) populations of representative transgenic organisms as biosensors for detecting an alteration in gene expression as a response to exposure to a selected agent. Preferably, the inducible reporter is capable of expressing at least 2-fold greater, 3-fold greater, or 4-fold greater than its background expression level (e.g., untreated organisms).

The invention is a plurality of transgenic organisms for use as biosensors. The plurality of transgenic organisms includes at least two (a) representative transgenic organisms or (b) populations of representative transgenic organisms wherein the representative transgenic organisms or populations of representative transgenic organisms are distinct from one another in having transgenes comprising different inducible promoters operably linked or fused to a reporter gene (e.g., different strains) wherein the inducible promoter or promoters are chosen from SEQ ID NO:1 through SEQ ID NO:162, or a fragment thereof having 50, 100, 200, 300, 400, or 500 or more nucleotides of said promoter. For example, transgenic organism (1) has a transgene which is the inducible promoter of gene (1) operably linked or fused to a reporter gene and transgenic organism (2) has a transgene which is the inducible promoter region of gene (2) operably linked or fused to a reporter gene. The reporter genes used in the transgenic organism can be the same or different reporter genes. In a specific aspect, the reporter gene is the same gene in each transgenic organism. Typically, the inducible promoter is selected from a response pathway gene. Response pathway genes are genes from pathways that modulate an organism's response to an agent or stimuli at the gene expression level. In one specific aspect, the response pathway gene is a toxicity response pathway gene. In another specific aspect, the toxicity pathway response gene is a heavy metal, oxidative stress, endocrine disruption, xenobiotic, carcinogenic, genotoxic, neurotoxic, hepatatoxic, nephratoxic, or immunotoxic response pathway gene. In another aspect, the response pathway gene is an oxidative stress response gene, a carcinogen response pathway gene, an apoptosis pathway gene, an endocrine pathway gene, a genotoxin pathway gene, or a xenobiotic metabolism pathway. In one aspect, the response pathway gene is an oxidative stress response gene. In one aspect, the response pathway gene is a genotoxin response gene. In one aspect, the response pathway gene is a xenobiotic metabolism pathway gene. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having transgenes whose promoters are chosen from distinct oxidative stress response genes. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having representative transgenes whose promoters are chosen from distinct genotoxin stress response genes. In one aspect, the plurality of representative transgenic organisms or populations of representative transgenic organisms comprise 2 or more, 3 or more, 4 or more, or 5 or more (a) representative transgenic organisms or (b) population of representative transgenic organisms having representative transgenes whose promoters are chosen from distinct xenobiotic metabolism pathway genes. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

The invention is a transgenic organism, or a transgene, nucleic acid, or construct, comprising an inducible promoter operably linked, or fused, to a reporter gene to provide a biosensor functionality. In one specific aspect, the transgenic organism has the inducible promoter reporter transgene inserted into its genome by a single copy site specific insertion technology. In another specific aspect, the transgenic organism has a second reporter in its genome wherein said second reporter is expressed at a constitutive level. In one aspect, the constitutive reporter is inserted into the organism's genome as a single copy or using a single site insertion technology. The second reporter (constitutive) is used e.g., for normalization of the signal generated from the first reporter (inducible reporter). In one specific aspect, the transgene comprising the inducible promoter operably linked, or fused, to the reporter gene is inserted into the organism's genome in multiple copies, for example, 2 or more copies, 3 or more copies, 5 or more copies, 7 or more copies, or 10 or more copies. In one aspect, the reporter gene driven by the inducible promoter encodes a fluorescent or luminescent protein. In one aspect, the second reporter gene expressed at a constitutive level encodes a fluorescent protein or luminescent protein. In one aspect, the reporter gene driven by the inducible promoter encodes a fluorescent protein. In one aspect, the second reporter gene expressed at a constitutive level encodes a fluorescent protein. In one aspect, the reporter gene driven by the inducible promoter encodes a fluorescent protein which fluoresces at a wavelength that is detectably different than the wavelength that the fluorescent protein encoded by the constitutive reporter fluoresces. In one specific aspect, the reporter driven by the inducible promoter encodes a protein comprising a RFP and the reporter driven by the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression of a reporter gene operably linked, or fused, to an inducible promoter in a transgenic organism. According to this method, a plurality or array of representative transgenic organisms, or populations thereof, is provided wherein each representative transgenic organism, or population thereof, has an inducible promoter reporter construct integrated into its genome. A representative transgenic organism is one that has one type of inducible promoter reporter construct as a transgene e.g., a promoter from a specific gene. For example, a plurality of representative transgenic organisms can refer to e.g., a representative transgenic organism or population thereof (a) which has a transgene which is inducible promoter (a) operably linked or fused to a reporter; and representative transgenic organism or a population thereof (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. Each different representative transgenic organism can be present as multiple organisms to give a population of representative transgenic organisms (e.g., 3, 5, 10, 50, 100, 200 or 300 or more organisms) or as a single organism. The representative transgenic organism or population of transgenic organisms are exposed to or contacted with a selected agent and incubated with reagent and time sufficient to allow expression of the reporter gene. The reporter gene is detected or quantified. Optionally, the quantity of reporter can be normalized against the value for a second reporter gene, e.g., the constitutive reporter gene. Preferably, the reporter or reporters are fluorescents proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression in a transgenic organism a first reporter gene operably linked or fused to an inducible promoter and a second reporter expressed at constitutive levels. According to this method, a plurality or array of representative transgenic organisms, or populations thereof, is provided wherein each representative transgenic organism, or population thereof, has an inducible promoter reporter construct and a constitutively expressed reporter integrated into its genome wherein the inducible promoter or promoters are chosen from SEQ ID NO:1 through SEQ ID NO:162, or a fragment thereof having 50, 100, 200, 300, 400, or 500 or more nucleotides of said promoter. A representative transgenic organism is one that has one type of inducible promoter reporter construct as a transgene. For example, a plurality of representative transgenic organisms can refer to e.g., a representative transgenic organism (a) which has a transgene which is inducible promoter (a) operably linked or fused to a reporter; and representative transgenic organism (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. The representative transgenic organism or population of transgenic organisms are exposed to or contacted with a selected agent and incubated with reagents and time sufficient to allow expression of the reporter genes. The level of the reporter gene is then detected or quantified. The quantity or level of the inducible reporter can be normalized against the quantity or level of a second reporter gene, e.g., the constitutive reporter gene. Preferably, the reporter or reporters encode a fluorescent proteins or proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than background its level (e.g., untreated transgenic organism or identical transgenic organism except for not having the inducible promoter reporter construct).

The combination of use of single site insertion technology for the inducible promoter reporter transgene and the use of second constitutive reporter for normalization in the invention has produced remarkable unprecedented results for whole organism biosensors. In one aspect, the transgene is inserted into a single site of the host organisms's genome using single site insertion technology and is present as one copy. In one aspect, the transgene is inserted into multiple sites in the host organism's genome using a site-specific insertion technology and is present in from 2 to 50 copies, more preferably 2 to 20 copies and even more preferably from 2 to 10 copies.

In an alternative aspect, the transgene is inserted into the organism's genome as multiple copies. For example, ballistic genes guns can be used to insert the transgene into the organism's genome in the range of 1 copy to about 50 copies. In another aspect, the transgene is inserted into the extra-chromosomal array of a *C. elegans* host organism. In this aspect, the host organism typically has from about 100 to about 1000 copies of the transgene.

According to one aspect of the invention, the transgenic organism is translucent or at least partially translucent. More specifically, the transgenic organism of this aspect is translucent or at least partially translucent to allow for spectrophotometric detection of one or more reporter genes in a medium or high-throughput fashion. In one specific aspect, medium or high throughput format refers to the ability detect the expression level of the reporter gene in a multi-well plate format using a plate reader that is capable of detecting and quantitating the level of fluorescence or bioluminescence of the respective reporter. In another specific aspect, the transgenic organism is a nematode, *Danio rerio* (zebrafish), *Drosophila melanogaster, Daphnia* spp., or *Xenopus laevis*. In one specific aspect, the organism is a nematode. In another specific aspect, the organism is *C. elegans*. The ordinary skilled artisan is capable of identify promoters in organisms such *Danio rerio, Drosophila melanogaster, Daphnia* spp., or *Xenopus laevis* to create the transgenic organisms in a manner similar to that described herein for *C. elegans*.

In one embodiment, the invention involves transgenesis of DNA into the worm genome (e.g., *C. elegans*). This DNA is a transgene that contains an inducible promoter operably linked or fused to a gene encoding a reporter protein. The inserted DNA then allows reporter protein expression in the transgenic organism upon exposure to a selected agent or toxin that activates or induces its expression. The genetically engineered animal serves as a biosensor (e.g., for toxicity). According to one aspect of this embodiment, the transgene is inserted into the genome using MosSCI technology. The method involves (a) providing a strain of an organism having an insertion element site and a marker for positive selection (b) injecting the organisms with a vector having a transgene comprising (1) an inducible promoter reporter construct, (2) a marker for selection, and (3) sequence elements (e.g., homology arms) sufficient for effectuating insertion into the insertion element site or sites of the strain, a vector for producing a transposase compatible with the transposon and insertion element site, and one or more plasmids acting as markers for tracking the presence of extrachromosal arrays. Injected animals are transferred to plates, allowed to grow or incubate for a time sufficient to allow for transformation and recovery, and are then screened for insertion events by use of the selection markers in the strain, the transgene, and the markers for tracking the presence of extrachromosomal markers

Inducible Promoters

Figure 8:
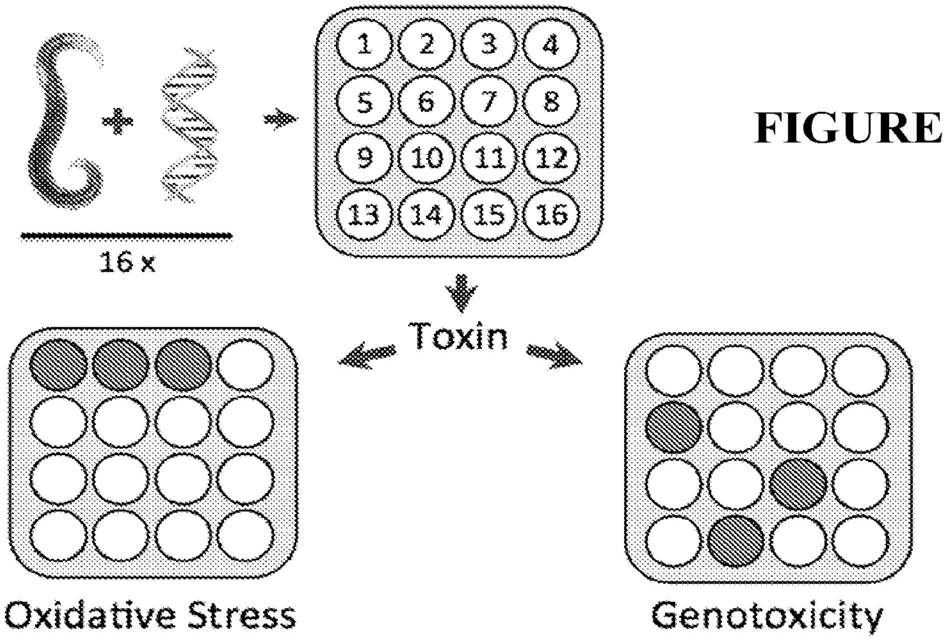
FIG. 8 shows a predicted set of results related to a panel or array of biosensors involved in oxidative stress and genotoxic stress. A 16 well microwell plate having populations of representative transgenic organisms for both oxidative stress and genotoxin stress are seeded into the wells of the plates. Exposure of organisms in the wells of the plates to a selected agent that induces oxidative stress or genotoxic stress gives digitized read-outs indicative of which toxicity pathway is being activated by the selected agent. The lower left plate shows activation of an oxidative stress pathway whereas the lower right plate shows activation of a genotoxin pathway.
Figure 9:
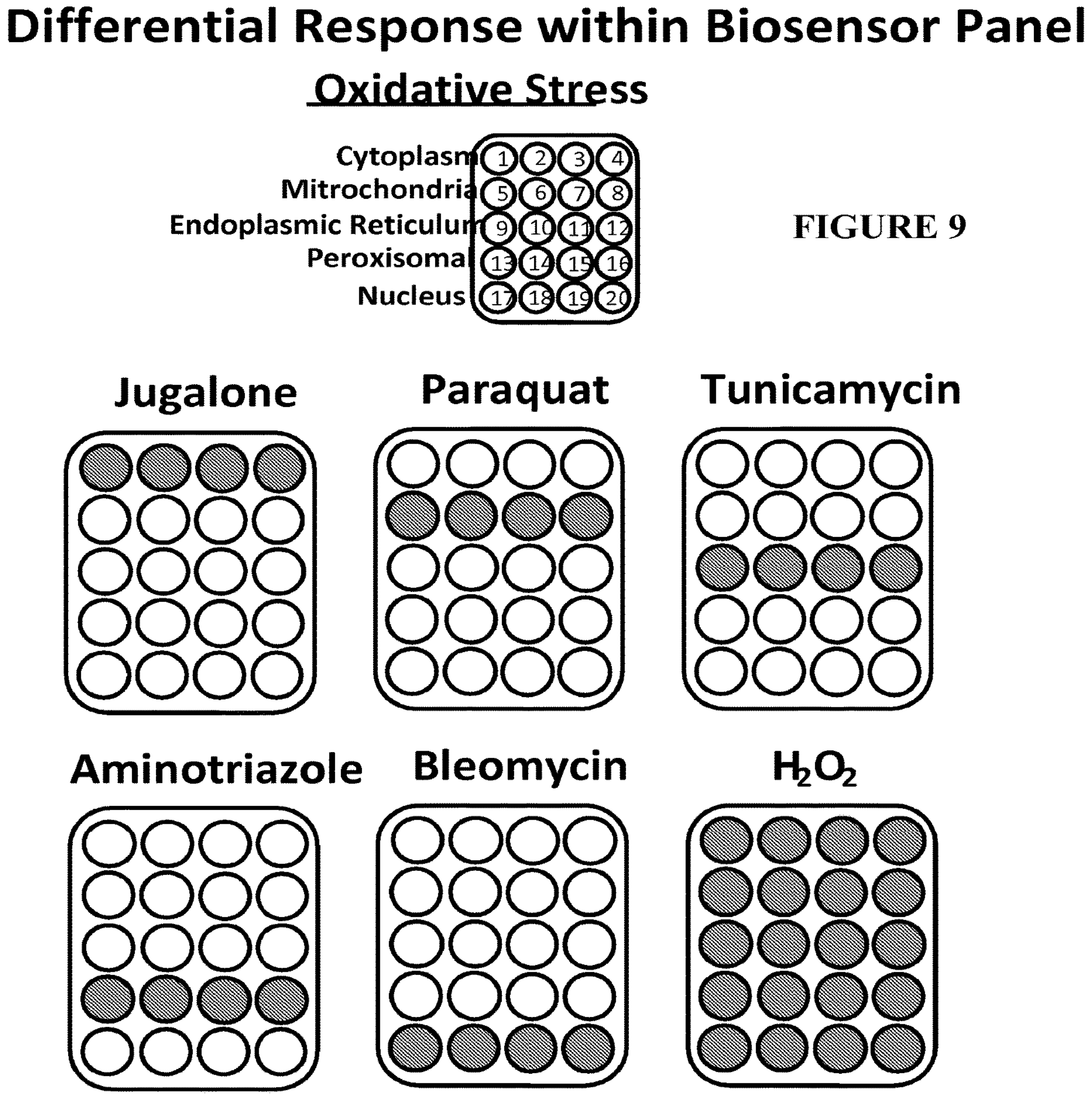
FIG. 9 shows a predicted set of results related to a panel or array of biosensors involved in oxidative stress. A 16 well microwell plate having populations of representative transgenic organisms for both oxidative stress are seeded into the wells of the plates. Exposure of the wells in the plate with a selected agent that induces oxidative stress give digitized read-outs indicative of which oxidative stress toxicity pathway is being activated by the selected agent. The plates show activation of the indicated oxidative stress pathway by induction of the reporters in the highlighted rows.
Figure 10:
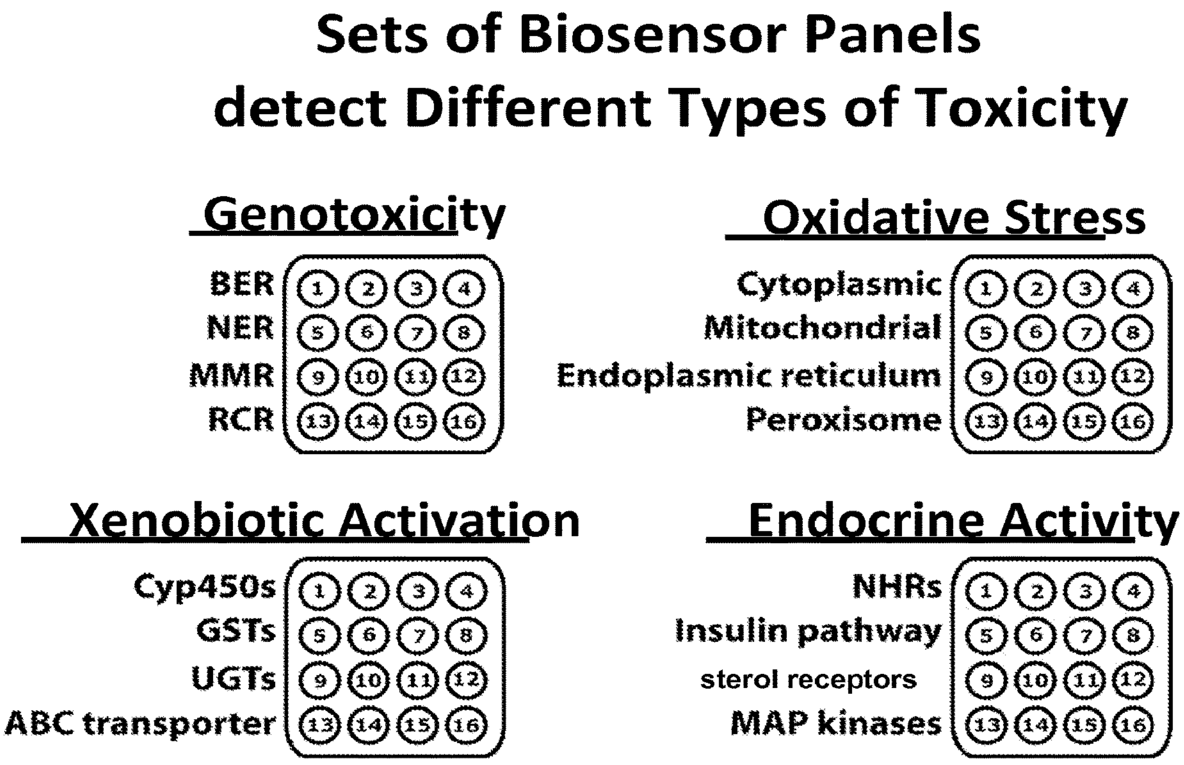
FIG. 10 shows sets/formats of arrays or panels for different types of stress response biosensors and specific subgroups.

A variety of inducible promoters are used to make different transgenic biosensors organisms of the invention. Inducible promoters are chosen from different genes that are selected for being activated or modulated in response to stimuli or conditions, e.g., like toxins or a drug or drug candidate. The promoters are chosen to include transcription factor response elements which are DNA sequences that enhance or drive transcription of a gene involved in a response pathway by serving as a template for the transcriptional machinery (transcription factors) associated with the response pathway. In one embodiment of the invention, the resulting transgenic biosensor organisms are arranged into a panel. A test compound (selected agent) is exposed to members of the panel and specific types of response (e.g., toxicities) are detected (see e.g., FIG. 8 or FIG. 9). In an alternative embodiment, the same representative transgenic strain, or population thereof, is duplicated in all wells of the panel and a population of molecules, like a library, are screened for one type of toxicity. In one specific example, a library of molecules designed to inhibit or modulate a specific target or that inhibited or modulated a specific target are counter-screened against one or more representative transgenic organisms, or populations thereof, to identify a molecule or molecules that have the least toxicology liabilities or have a desirable toxicity profile.

The inducible promoters used in the invention can be any promoter element or region that is involved in regulating gene expression. Promoter regions typically lie upstream of a gene, anywhere from about 1 to 10,000 or more base pairs (bp) upstream of the start site. In general, regions ranging from 1 to 4,000 bp upstream of start codon are chosen for promoter selection. In one aspect, the region ranges from about 1 to 2500 bp upstream from the start site. In one aspect, the region ranges from about 1 to 2000 bp upstream from the start site. In one aspect, the region ranges from about 1 to 1000 bp upstream from the start site. In one aspect, the promoter is within about 500 bp upstream of the transcription start site. See e.g., Gerstein et al. Science. 2010 Dec. 24; 330(6012):1775-87.

The genes chosen for the exemplary oxidative stress response panel are the following oxidative response genes (hsp-16.41, hsp16.2, hsp-6 and hsp-60, hsp-4, mlt-2, and ugt-1). To choose the oxidative-response gene promoters and any other promoters for use in the invention, a combination of modENCODE's TF-GFP ChIP-seq data (Niu et al. Genome Res. 2011 February; 21(2):245-254) and multi-z 6-species alignment (Niu et al. Genome Research 2004; 14(4):708-715.) can be used to find the extent of conserved genomic regions containing TF (transcription factor) sites in front of the oxidative-response gene's start codon (or other response pathway genes). Promoter-reporter fusion constructs can be designed for Gibson (Gibson et al. Nat. Methods 2009 May; 6(5):343-345) reaction cloning using APE plasmid editor (biologylabs.utah.edu/jorgensen/wayned/ape). In general, regions ranging from 300 to 4,000 bp upstream of start codon were chosen for promoter selection. Other techniques for identifying, selecting and cloning inducible promoter regions for use in the compositions and methods of the invention are known to the skilled artisan.

Reporter Genes

Reporter genes for use in the invention include any reporter that can be expressed and quantified. Preferably, the reporter gene encodes a protein that can be detected spectrophotometrically. Some examples include fluorescent proteins (e.g., green fluorescent protein (GFP), cyan fluorescent protein (CFP), red fluorescent protein (RFP), mCherry, Tag-RFP, etc.), luciferase which is a luminescent reporter (Ranella, Firefly, etc.), chomogenic (beta-Gal, etc.), etc. See e.g., Pollock et al., Trends in Cell Biology 9:57 (1999). Useful fluorescent proteins also include mutants and spectral variants of these proteins which retain the ability to fluoresce. See e.g., Shaner et al., Nat. Biotech. 22:1567 (2004), Tag-RFP (Shaner, N. C. et al., 2008 Nature Methods, 5(6), 545-551), fluorescent proteins fused to e.g., his-GFP or his-RFP which is histone H2B fused to the indicated fluorescent protein Essex et al. Mol. Biol. Cell 2009 February; 20(4):1252-1267). Other fluorescent proteins that can be used in the invention include, but are not limited to, AcGFP, AcGFP1, AmCyan, AmCyanl, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRedl, JRed, Katuska, Kusabira Orange, Kusabira Orange2, mApple, mBanana, mCerulean, mCFP, mCherry, mCitrine, mECFP, mEmerald, mGrapel, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1 which are described in the literature or otherwise commercially available. hRFP and hsRFP are RFP's fused to e.g., a histone protein like H2B from *C. elegans.*

Isolated Nucleic Acids, Transgenes, Constructs, Transgenic Organisms and Transgenic *C. elegans* Organisms The invention is nucleic acids and constructs and transgenic organisms comprising those nucleic acids as described herein.

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, WO1A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, RO5D11.6, R05F9.10, RO9H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, cm-1, crn-2, crn-3, crn-4, cm-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, mh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, sink-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans.*

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio* (zebrafish), *Drosophila melanogaster, Daphnia* spp., or *Xenopus laevis* and the promoter is for gene that organism that is homologous to the gene in *C. elegans* corresponding to cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, WO1A11.1, WO2C12.1, WO3G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, RO5D11.6, R05F9.10, RO9H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, cm-1, crn-2, crn-3, crn-4, cm-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, mh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, sink-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans.*

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, lin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, RO5D11.6, R05D8.7, R05D8.9, R05F9.10, R07B7.4, R07B7.5, RO9H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, srnk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, WO1A11.1, WO1B11.6, WO2C12.1, W03F9.9, WO3G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans.*

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio, Drosophila melanogaster, Daphnia* spp., or *Xenopus laevis* and the promoter is for gene that organism that is homologous to the gene in *C. elegans* corresponding to ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, lin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, RO5D11.6, R05D8.7, R05D8.9, R05F9.10, R07B7.4, R07B7.5, RO9H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, WO1A11.1, WO1B11.6, WO2C12.1, W03F9.9, WO3G1.5, W1008.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans.*

Examples of preferred nucleic acids corresponding to promoters that are used in the compositions and methods of the invention are given below in reference to the pathways and gene abbreviations in SEQ ID NO: 1 through SEQ ID NO: 162.

Cytoplasmic Oxidative Stress Toxicity hsp-16.41

SEQ ID NO: 1 gattatagtttgaagatttctaatttcacaattagagcaaatgttgttcggtatttattttcaacggtatttatactattttccacctttttctagaacatt cgagctgcttgttgcaaaaggagggcgactcacattcggtacatggaaaagtagtgtacacaataaagagacccagatacattttccgtctg cgtctctttgcacccaccgggagtattttcaaacgaatgcatctaggaccttctagaacattctgtaaggctgcagaatgcgggtatataagg aaagcgggctcagaggaagccaacacgctttgttctagtgcatctaaaaaacttcgaaa hsp-16.2

SEQ ID NO: 2 tttcgaagtttttagatgcactagaacaaagcgtgttggcttcctctgagcccgctttccttatatacccgcattctgcagccttacagaatgttc tagaaggtcctagatgcattcgtttgaaaatactcccggtgggtgcaaagagacgcagacggaaaatgtatctgggtctctttattgtgtaca ctacttttccatgtaccgaatgtgagtcgccctccttttgcaacaagcagctcgaatgttctagaaaaaggtggaaaatagtataaataccgtt gaaaataaataccgaacaacatttgctctaattgtgaaattagaaatcttcaaactataatc hsp-16.1

SEQ ID NO: 3 tcttgaagtttagagaatgaacagtaagcacttgaacaaagtgtattggtttcctctgaacacgattggcttatatacccgtatcctgcagccgt ttagaatgttctagaaggtcctagatgcattcatttcaaaatacaccccataggtgcaaagagacgcagattgaaaaagtatctgggtttcttc agtacgcacactatttctcaatgttctgaatgtgagtcgccctccttttgcaagaagcagctcgaatgttctagaaaaaggtggaaatgagtat aaatacagtgacaaaaccgaaccaaacaacattcactctaattgtgaaatcttcaaactacaatc hsp-16.11

SEQ ID NO: 4 tcttgaagtttagagaatgaacagtaagcacttgaacaaagtgtattggtttcctctgaacacgattggcttatatacccgtatcctgcagccgt ttagaatgttctagaaggtcctagatgcattcatttcaaaatacaccccataggtgcaaagagacgcagattgaaaaagtatctgggtttcttc agtacgcacactatttctcaatgttctgaatgtgagtcgccctccttttgcaagaagcagctcgaatgttctagaaaaaggtggaaatgagtat aaatacagtgacaaaaccgaaccaaacaacattcactctaattgtgaaatcttcaaactacaatc hsp-16.48

SEQ ID NO: 5 gattgtagtttgaagatttcacaattagagtgaatgttgtttggttcggttttgtcactgtatttatactcatttccacctttttctagaacattcgagct gcttcttgcaaaaggagggcgactcacattcagaacattgagaaatagtgtgcgtactgaagaaacccagatactttttcaatctgcgtctctt tgcacctatggggtgtattttgaaatgaatgcatctaggaccttctagaacattctaaacggctgcaggatacgggtatataagccaatcgtgt tcagaggaaaccaatacactttgttcaagtgcttactgttcattctctaaacttcaaga hsp-16.49

SEQ ID NO: 6 gattgtagtttgaagatttcacaattagagtgaatgttgtttggttcggttttgtcactgtatttatactcatttccacctttttctagaacattcgagct gcttcttgcaaaaggagggcgactcacattcagaacattgagaaatagtgtgcgtactgaagaaacccagatactttttcaatctgcgtctctt tgcacctatggggtgtattttgaaatgaatgcatctaggaccttctagaacattctaaacggctgcaggatacgggtatataagccaatcgtgt tcagaggaaaccaatacactttgttcaagtgcttactgttcattctctaaacttcaaga -continued hsp-12.2

SEQ ID NO: 7 acaattcagaaggagcaataattctgtgatatttaaactaatttctctttgtttctttgttatgagtatttatttttagttcttgttcatcatgctttttttgtc acttttccctccccaatcccatattcctctgcttttctctcattttcggttacgtgtattaattgaatgtatacgacgacgacagtcactagtttcgaa ataactattttacgaggatgaataaacacactgatcgctgagcgacgctccgagcacttttcgagaagtttctaagaagccacttgaccgag agagagggagaaagaaaagcttggcatagaaatgtgcttgtgtttatttgaactgttaaaagtgtttgacgggggcgaagtcactggggaa acctcgagatcaataggacacgtggcaatttgaatttttggataattggaaaagcagtacccgactaaagatccgaatttgattttcagacattt tactgcaaacttgattacacacggtaattttccaaaagttttgtgcattgaatcccgaaaaacttcacaaacgcataatattacaacccgatctat gagcaaagtaaatagagagaatcaggctgaaagcttattgtgattaatgaacattaggaacaatgctgatttcaatttgaaacattatttttcag atcgaaaatcagtttttttcagatcgaaaatcacattggatcttgacattttcaagagaattattaaaatttaaatggctatttgaaaagtattgatttt ctgaaagataataactacttaccatctatgtcgtacctgactatgccaattattttcaacaattgtttattttaaaaaatttttgaagtaagcttaaaa caaacccaggacctctgaaatgtaccaagtttggaaactaattccaagtactggtaataacaaaaattttgaattcgaggcggataagcgcc agttgggagttttctgattataattatattaatagaattgccaaaaatcatgataaacccctccaatcatttttttgattttcgaaaaagtttcaatgta ggttttggtgagctgcgaagttttccaaaaatgtctaaaaactaaattcatatggttcaatttttgtcaaaaacgttcagctcatgaggagcttga aactaaccaataaattttggtcattaaattggtcagttaaattgataattgaaattaaccggatatgtttggaaaaataaatgcaaaagttcatgat catcagatcaaaaaccaaaaacttcccctacatttctatttccaaattgaagatttcttgaagcctacaaatagtacagtttacaaatatctctcct tctttctctcgtcccttcttgcgcatcctcagagctcggagctcctatccgtcaatataaacaatcattgtttcttttcttctcctcgtaccttttttctt cttcaaatccattttcctccgccccttatcctacagtccaattcctttcactctccactttctgagcttcttctccaactcgcaaaagcttcaaag ctcacagagcattttacgatagtgcattgtaatgttctccaccctagagtgcatctccaacctgcgcatatgttttcgctctttgacattacattttc ttccgattcacattttattcatccacccgataaatatattttcacacttttaattttctagagaaa sod-1

SEQ ID NO: 8 tattctacgtcaataggaattgtcagaattatcagttttgatatcaaaaattgccagctttagtacagtagaataactatgcgattcatgctgcttat tatttattcaaaatttaaattttaaccaactgtgagtttattttatagaacatttttcgaaataaaattcaaaaaaataaaaattgttatttttcaaaatct taatcttaatttagcaccattaccgacaggcaatgatagaacaccaaaccggactgaccaagtgtcgtaccagtttcgagcaatcaagtattg agagactgatattcttgctgatactatactcttaagatatgaaacgatatctacccctctagcccccctactcgtgcgccctcagttacctacctac cccgttacctaccctaccctacctacctactcagtctcctacctaccccgaccgtatcatatctttagaatatagtatcaacaagaataccaatc acccaaccccaatcactcgaaaccgttaggcaccaggttagccagtctggattaatcgagagtaaaccacttgactccagacaactacatct tatacttacttacgtctgggggacaatcttgggattctcaagatgacttccattacgaagtctcttgcaataaccaattaccacaattttggagca gaattaaactcacccaccagtacaggatcaaagatgaataatgaatgagaggccctcctctcattgttgtgggcggggtcaaggggtcaaa gtttttgaatttcgaaatttgaaattttggaattgttaaatttttggaaatctaattttgaaagaaccacatttccgtttacaatttgagttcaattcc gcaaccccgtcaaatttaagaagagaaagaaaaaaaacacaacgtgtttgcacctgtaaggtagtttttttttgttgccttcggcgttttgattca catgaaagtttctacggaaaaactttcattgcataacgatcttcatatcttgtttctggaaacgaaaatttccaacatgaaagaaacccgacgct atttattctcgcaacacaaaaatttcacatttaaataaccgcggtttttctcgaacagcatatttgacgcgcattgctcgtcaagtttgatgcgtgc acactattttgctgttgatttttcttattctctaaattttctttacgctttcgtagtttctatagaaacgattctccactcccggttttcttccgattctcaa aattaattaaaatttagttattaaaaatccttttttcttgaaataatcgttcaatttcgagttttcaagagtggagacgttgaatttgtgagccgcttatt ttttctgtgatttgattgtggtttttaatcagtgtcataatcatactttccattgtttctttattattcaaagttgtagattcagtattttagatcggtgatg tttatgaatcttctcactcaggtctccaacgcgatttttccgcaggtcagtgcttatccgaaacattcgtcattcgcaacttgggcctatttgatct atggcgttgtgttgttgcctttaccttaattatcatcattttcatcagaaacccacaaaaactagagacatagctacaaaattctgcgaccgaga ggcgggtacacacacaatgttgtctatttcatctcgctccaccttctctctctctctctcgtgtttaccatttctttttttaattttgcatctatcgactgt gatctgcctgtttttttctaattctaaactttttgccgtgatattccttagagtgttccctagaaaattcgttgaatttacaggtcgaagccgctcaaa aag -continued sto-1

SEQ ID NO: 9 aaaaacttgatccgatcgaagaaaaaaccgaaaaaaaattcgaattgttgtgttgttcgtcagttggatggaatgatgatgaaggaagttgatt aatggatatgactgatgattagtggtggaatatggaataattatttatttgatttattctgattattctgaattagaatgtattttcatatttcaggaaa aatgattttatttcgaaacgaacttgttctagattaaaaaaattgaaatttaatatttagtgctatacaattacagtaccccatggaaatacacaaat atcataaatacaagaattatcttcctggaagttaaacttatattttcgatgtaagtgaaaaagtttaaaagagaaatgatgtttgttgatcttcctgt aagtggaaactggagaattcataagcttaaaaattccaaaatattaaaacttgcgtgtttttttctgaaaatcgattaaaacagcaatattcagcat gtttccagagccaaaaaaacctgcaagcatgggatacttttgcagttaaaaaatgtttcaggaacttgaatgaagttaggatgcatttgaaca gagtaatgaaattatatgaaattcatatgtagactctcctactcagttgtttgtatgtgagttttgtatattataacttattttgaaattatctttaattact tgtaatgtttttttgtatgagttaaataataatcttttgaaaattctttttcaaataaccattttctgtttaaaaaaacagtgagcccaatataaacttgttt tccatcaaaccgagcttctaccaaagttaacttaaattccataattttcacaaaccattcatagtttgtctacgtagccttatcctttttttgaacattg aaaaagtgaggagaaagtgcgaaaaacgagtttttttctttctcttcttcttggtcgtcacgtcaagacactctgaacgttggaatgggaaaag catcgaagatcgaaaaattctgatatactaaagtacacaacttatattgatattgcattgggatttaaaaaagctctactcgaacattagattaat tttaatatctcatttattcatctttcgataacagatatatcacattgttcggtaggataaaagggctaaaatcaagttttgaggaatgttcatttgtttg gaaggtgatattatagtctgcgataactacataagtttggaaaccgaacacatgttttttttggcactttgctaaaaagttgtctgaaaacgttgga aatcaatataggtcatttatttaggtcattacggaccattataagtgattctaatacaaaactggcgctgctccgctatttaaaagactgaaagt gacataaatgatctaatttccagatctcttataacttttttttatagcggttccactcctaatttgatgtgtttacttgttgcatcagatcatttttcacttc agtaattcttatcagattctatattactacttatcaattatcagcattcaacattaccagttagttattcaattatattccgcacgatcactgctga tgaattcaaatattggagtattaaaattatacatttataaccattctaatgtctaccttctacacaaattacccttcctagtagaaaatatatttttggc ttgaaatttgttctgtactgtccaa gcs-1

SEQ ID NO: 10 tttctaagttcgcacattcctcgatttccacttgccgttacctttcattatctccttttactttaatctatcacagtttcatagatatcaaacgttaatttttt tgagcgagctagatgattattcctatgacggtccattcgattaacttgtcacctattattgattctctacagtcctcaggacatgatcctga aattatcaatgctatactgtgatattcgatattcgaatcaacaatgtgtatgattagtgtcaaagtaacttatcggattagaatataattcaattatt cgtgtaataaataactatttttttagtttactcatgtttgccacaaactagaaggtttatttattcataactacttgcaatttcacatttgaattctaactg tatgattgcttcaactctctgcgattattgcgctaaaatacggtacccggtctcggcgcgacaaaaaatttctagattatagaaaatatacaga atattgcaacagctgaaccatttcacaaaaaaatcgactgaatttcgcgaagttatgatatctcaagcggccgcttgcgggaaaagccatat attatcaaattacgtagctgcacaattatcataattattcatagttaaaaataaatgtatataaataattgtcctatacagatacaataaaattat aacgaaaaactataaaaatagatgaattctagagccacgtaatttcagaattacagtactattcaaggcgcatacccattaacataaattacg cgtcgagaccgggtaccgtactagacgcaaattagcatctgggtaattcttgatagggacttcactaccaccactattatcgaaagcatca aatttcacatattcacgtcacaatcctagcaaagcccaatagctcattcaagtcatatagtctattattctcattctcctgattagcaacactgtc ttatcaaccactaggaccgtcttaatcgtccaaatattgatccgctcgctcgtgattctcaacttattatagctgtgatactgtactatagactc cattttccatctcctcttcgcttgttgaatggactttattttgataagttcattttaatttttctaacaatctcatcactagctcatgatgacaattgcaa agaaattcgtcatatagaggggaaaaatgctgacaaatattgaaaagccttcaggagagatgtagagacgtaggagtagagacagaacat aaatttgagaagcttgtagggagaatagacatagagttaccatgggaaaaacgctcgcattttccatttaacgagattttctagatcacaacat tttgtgatccgttgtgcgaaaatcaagctttttatcaaacttttatcgtctgttcattctttctgacaatctttattatcttattaaacttgactaattgtatt gaaagtatttttttagatgcgaacgaagttccatttttcatgacttaacatctcttaacgttagtgaaatttttgaattccaattaggactacggtag gagttctgtagttgatttcctgaacacttgttttgtaacctttctgaacggattttaatatttctaaaattttaaattgcaaatctgagtcctattaaaag atgtttcatccgtaaaaccaacaaacaaaatatcactttatcatcatgagatttaatgtttccttttgattttctgaattgttgtactttccttcaaacg acttattgaactgatgtaactttccttctaatgttatcatttgtattttttttgcaga -continued hpo-15

SEQ ID NO: 11 aaaccaaatttactacttttactatatttttagttgaaaataaaaagagaaaaacatttattttctaaaaacagtaattttcctttagtcagtttatttctc attgagatattgtgaactcctgttttaaaatcaaatgagaaaaattgaacacaaattttaaatttacataaatccccaaaaactatcaatatttcca acctagacacactataattgaataagattctcgtgaccttcggacatacagtttgtcaaagacaagcactcccacatttgccggttaattgtgat aaccctatcaacttggctccgtcttcactctcacttgcaattgcacaacttctttctttttggatgtaagtagcaacattttatcatcactctattggg aaatttttaaaacaaaatttcttcaatacgattgccggtctcgccacgataaattgtaggtacatgcgaaaaaataatgcccatttaaagagtac tgtaatttccatctctctttgttgcaggatttttttgtcgatttattagttgttcaatacaaataaattcattcgaaaactgtcatgtcacgataaacaaa caaattttggtatttaacaaaaatttgtcgtgtcgagacctaagctagaatagtactataattttttgagctttaatttttttcaagtttttttacaaaatttttt ttttctgttgattaattgatgtatttttttatcggagatctataaaaaaatcaatgaaattttcgaagaagccaaaaaagtactgttgatactacagtaa tcttcaaaggcgcacacctttcggcatttaacaaaaatttgtcgtgttaagaccgggtaatttgttaggcaaatatttgaaaaaaaaactgcttaa atatttcatgaaaattctgttatctttaatcagattttttaaaaaattattatcaaatttcaaaaaattacctaaaataatgtctgaaattcttctttactca cgcgaactgcaacttccagacattaattgaggaaatttcaaattaatcaataacaatgaatacgattttcagattaaacgagtattttcctacattt ttattaattttttttgattaatattaatttttaaaatgaaattttttggataatcctactaaaataagcatgtcccgcaaggccctatttcaaaagtttagtg cctgaaaaatcaatatttcgcaagaacagtctaccaatttttccaatttatacttccggcaattgccaccaattcggtgatctagaaaataccat ataggctctacagtaccttcccttatcacccacatccaattttgctatcagttagtcttcaatcacacttagtctttgaacaaatgaactcataactc tcacaagatgtttgcaactatcatattgatgtcattcagttctcatatgagaaggcgggcacattgttgtatattgataaaccacccccattttcct cttcttccagcaaaaaaaaataaaattaatattgtctcagacgcttgtgaaactggtgctctcaattgaaaagcaccattgacttcgcagaaact ggcagttcatttggctttcggatacttacaaccatacgctcaca dhs-18

SEQ ID NO: 12 tctgtatatatgcaaaaggaaaattaaatattatctatcgatggaaatgttagaaaagcgaattacttggcacggcagcaggtgccacaaagc ctgcagctgaataaagttaagatacgattgcttgctgacaaataggacactaaattggaaaatacacaccacattttgatttttaatcagatcttt tttaattttaattttagtcacatctagactactctgactactattctcacacgtgtggccaacaatcattcggactacgctgtaggcagtcaggagt tttcaaatgataaggtgttcaacagtgtagtcttatttgtatcattttcacataaaacgcaatttcaaaaactcccaatttttcttcagactgcggtaa aata gst-14

SEQ ID NO: 13 ccagttaccgagatctaatttttttctatttttctttttctacttttcatgaaatacgcatttttgaaaacgaataataaagtatgatatgctgtcaaaaaa tttcctgcattcttgcaaaaccggacgtcgaacaccaatttgccactttgatctacgtagatctacaaaaaatgcgggagaagatcttctcgag acgcagaattctcaactgatttcaaatcgttaagaacgtgctgacgtcacatatttttgggcaaaaaattcccgcatttttttgtagatcaaaccct attgggacatcctggcatcacgtgatttgcctaaaaccaaaaataatgcgcattcagagaacatgcctattgtgcctacctatttattaactttga cagtagataggcaggcggctgcttagagcctataagctagcctacctaggcaacccacatagcctacctttcaacttttcaaaagatcattgg atcactaacacaatgtgactagttgtggtttgttacaaattgcctcattgtcaccctaaactccctattatttcccgtaaatgatgacgattttgatc ttttgtagggttatcttgaagtgaaagatcactaagtacccagactgcactctagtctttttcccctttaaatagtctcgagaatgagtttgagaaa ctaaaa gst-32

SEQ ID NO: 14 tataatttttttttcttaattttcatatgtttacattaaaaatttgagaaaataaagtagttcaagacaaaatcaaatatggtagagactgtggtttaagt ttgggtttactagggaatggtcagcttaggggtgaggtacctagagacgccacatatgccaaacggaagctgagatcattggctacaagaa tatgctttcaaattctgcaacggacctctgggagtctggaaattcttgtctgaaattatgcttttgaatgctcgaaagtggtaagaatttagaattt attacagaaaaacgtttaattaataaaattagttttatacttgaaacaagtattgtatgcactgtatcaaaacacattttcatctttctaggtattcaa cttcacgtttttctgtaataaattctaaattcttaccactttcgagcattcaaaagcataatttcagacaagaatttccagactcccagaggtccgtt gcagaatttgaacgcatattcttgtagccaatgatctcagcttccgtttggcatatgtggcgtctctaggtacctcacccctaagctgaccattc cctagttaggcttaggcttcggcttaggcttacgattaagcttaggattaagcctaggcttaggctttgtctgagttcaactctccaccacggga -continued aaatttttttgcaaatttttttcgtcccaaaaaaaaaaggaaaaaaaaactttatttttacttgattatttcacttattttcgagttcaactctccaccac gggaaaatttttttgcaaatttttttcgtcccaaaaaaaaaaggaaaaaaaaactttatttttacttgatttttttcactttttttttcgagctcagctcgac cgtccctcaatgaaaacaagcaacctgatgtattccagatactcccgtaccaaaggtcatttctcgttagtcacaaaatattctgattgaaaatg gtgaaaaataacgagagagttgaaaattctacagactatggcctaaacgcagcaggtgagacacagtagagaacaagaggcagaagag agagcagaaggcagaggaagaactaaagggtatataaaaagtgttttgttgatcagtgggatcaaatagtgtgcttttttaaaagtttttttttcc ataaatgtattgatatctagaatttttttcgagttcactgttgtttaacagtgtcacatggtgtcaggctgtctcaatacagtttgatctacaaaaaat gcggaaatcttaaccatgcaaaatcagttgaaaactcttcgtattttctcccgcatttttttatagatctacgtagatcaaaccgaaatgagatactt tgatacaccgtgcagtgttaaaaaaaatacagttacagc gst-38

SEQ ID NO: 15 tctcattctcttcaagacataacacaacgggctgacgaccatatcatcaacgacgatttttttaggaactgtactttatctgtgtctgaccaacac gtgtgaatgaagtttcaactggaaaatttgtttgaaacactgcaaagaatttcgaattttgatgataattttaaatgccattatcagttttaatacgc cactctagtctttgattctttgcacacacacacacacacacacacacacacactcacaaacacgcctgaaatttcgcaatatgctgatttaa cgagaaaacatttgatgacaataaacttggcgtattaatataaaagggaaaattcaattcagattctcaacggtttattttctgtcacaactcttcc taatattcacc

W06H8.2

SEQ ID NO: 16

Tacacagccaagtctcataaccaaaataatattgatagtaaaaacatgagtgaacacgtttcaaaacaacatgtcattgaaaatcaattttaat gttcacgggaatttttttccaaaacagttttactcaaacatattttccatttgaaagtttgggaaactatccctggcacgttttcactgcattggtctt tccagttgattcagccagagttggaaagcctgtactttttttcccaacaaccgtttctactgctcaacttgtaacctcaaatttgcctaattgactcc gaagcttcaaaacttgctttaaagaactttgatgaaaatcgctgcggcgaaagaatcattgcggaatttttgccccagggatctaaatttccaa cctactccactgaaccaaatttttttcaaacttcaccaatttttttatttattttcacatgtcattaaaacactaagaattcaatacatgtatgaaaact gcaaacaccaaagtacggtttggacttgtaagcaaaacaccggtagtctctttgacttatcatgtattgtcatcctatttcgtcagacggtcttgt aagttcacattgacttactctgcgtctctcataggacacatactccgcatctttctcaatagatcaaatatattttgtcatcacctattatttaaactg gttggtttttcacaatgtcacaactaattgaactctccacttattgaacttgacttgaaatc cyp-34A9

SEQ ID NO: 17 accgccgagttacgacatcagattcaagcctttgaaagtttgaatctttaataattaaatgaataattaattgggagaaacatgtacataaataa aatttccattaaacaatgttcatttgtttaagctggcacagaccacaaaagctgaaaccacaaagttttttaaaccttgttcttttcttaaattttgta gtttcttatcttatcactcgtgtttcttgtcctccaaataattgtgaaaattgtagttaatgtgtcaaaaaagtcacatataagaagacgaacaactt gatttttttgttgacttcatttgaaaaaaaatagaaaac ugt-41

SEQ ID NO: 18 agaacccatttttacaaattgtgttcttgtggtgttcgcgtattaactttttatagctgtttttttacttataggatgattaagaaaaaagttccggcttt ctcaaagtaaggtaaatattttgaaaataaagaacttgtaaaaggatacagctaactgattaaaaacaaaagacccatgttagttcacgctcg gatttggagttcagctggaggggaaagaattcagcgttgaaatatttcagttggaatttcacctgatattatttaaaaaatgttatacgaaaattg aaaaagcgcctcttacccccctcttcgcccgctttcctcttgcctactgtgcagtttttttgtctttacggagttaacaagttgataacctgtttaagg acaacagataaaaacagagaaaattaaaaaccactattggcgatttgaaatttccgttcccatttttcacttttcaatttcaaatatgtacttaacg gtttccgatcattaacacgtaatccatcatttctagacaacaagtcacaccaatgccaatcaaaagtgcaaacatgctataacgaatcttttttttt caattaaactgtttacgatggaaattaggatagtgtcatagcattaattttcattgttcaaaaacagaaagaagtcacaaaatcttcacgtgaac atgtttcgtttccataaacaaattgtattttcaaagacagccgggaattttcagaccaattcaggtgacaactatgggctaccacccacctaact gtttgttcgcgattattctgactcacatcatgttttcaaaagtgactgtataattggagtgtagcataatcaacacaaactacagaatgggaaatt tgtgacagtatcaatcacattaacagatctataaaagagactgggaaagttgttcagagacacaaattcgttgtctacttatcaaatc -continued dnj-19

SEQ ID NO: 19 aattttaaagtttatggattatttagaatttatgaatattttaaatatagcttgtaatagtagcattggctttttttattagttagaatgcagtatttatatag attgtagttgtgtgcgtgctaagattattggagtattggtgttgtcacgtcttcagtctctctgccgtgcgctcacgagaatggggcaagcgaa gttgcggctgacgcgttattggatgctggcgcgtttcgcgaccagcgttggttttatcgagaattttctctgcagtacaaagtcccaaattcgg tggtttttttatcgatttgacgcgcgtttgctcaatttctcgatttccgcgtttttttattcagttctcattaattaacgttcgatgcttgttcacaaaattc agtttttgttttcacttgctcgttggtgtcgttcgttgtgtaagaaaattgatttctaaatatttgtttaaattgctaaaaaataattcaataatttacatt attgaattattaaaagttgtatttttcaaacatctcgcgcattctccgtccgtttctctcaatttttcactgtcatgtccgcattttaatattcattttttttc aggtaat hipr-1

SEQ ID NO: 20 ttggttataggaatatcctcctaggatagacgttatttctagtaatttttgttgatttgttcgttacaataaatctcatttttattttctggattaatttgat taccaatcgtttccagcgattttcacatatttttccagaatttaatacagattaatatttcgaaaaatttaaacatttttcttttcacattttaattcatctc tattcattatgcaatactcttttggttttcaagcatccgacattcctccgtttcatttatgtttgcatttctgctggcatgaatgcatttcattgtgtctc gatgagaaaaaggacaatttcatgagcttatcagttacttcgttttcaaaattttaatgttgaccagccattgatgtcatattttgtctaagaagctc aagaactattattattgaagcttaatttcgaagagcaacattattttcattaaaattcagcagtcattgttctttaaaaagttttgattctcgtttttaa acgatttttaattcagtcgagaattgaataacttcccgatttcccggccaccatcgtttaataccttttctttatgagactaacttccaagtatgcaa attgcaaatcgacgcaaggggaatacactcgctcacttctcatcgaaattcgaaacctttttcccatttttctttcatgtctttttcgcttttctcctctc tgcccatttccatttatttctcaaacaccgttcagtgaacacgaaaacccttacggaaattgtgttgtaagaatacaaaaacttccgtagcatag cgagaaagagtcaccattttgtagtgtttgcccccggtggtatagtttgcacaagtttctgaaagaagaagaagacacatttgaggtcttatgc acataaaaaatcaatgttagactatctttttcacgtagttttcttttgcaaagtggaaacttctcattaaacactttttgcttttcaattgtctgaacaagt tttcgattaaacagctgtaaagcttttgcaagtttcatggtttatgaactatttcgaatcggttacattgctgaagttttagtgtttcttgaatatgtcg tcactaccaggactggaccaaaaatcaaaaagaatttaaagtgaaataccaaaaaaaaaatcgtcgatttgcgatttttgaaggactgtaagt gactttttttggcttcatttaggtcccaaaaaaaccttttttttctcaaaaaaatgtgactcaaaataccaaaaaaagtcttaacctgatcacttcgccttct caactcaagccatttttgctgtttagttcgaatatggaacaaatcataagaatcttgagtacctatatgcgatacccgattcattttcctctcttcta aataacatcatttcctctcttttttccctctctctctctctgtttttgtttgtgactcactttgtccacaacgcgcgcggaaccggcttgttgccaca cacacactgtgatgaaatatgcgggaggaaagcttttcgcctaatagttgacttacttttcatctatattcctcaattttgcaactaatagattgatt tgtcatggttttgatttcagggttttgaatattctttgaaattggaatttttaacaaaaatgcaaattatgtgccaagtcatatctcctcctcacactttt tctatcacatgcccccaaaaaaaattaattttttttcagga Ubq-1

SEQ ID NO: 21 gaatgcaggatataaatcacgattttcgttttcgaacacaactttaaacttcaatttttcctttgtttctctgaaaactttgcagtcattttcaagcttc cacagaactttacaaaaaaactagattttctccaacgtggcgatattcccgagtttcgagaagaatccagcttgtcaatgctgtataaaaccttt acttttctatcgtttccattatttctttcactgcacctgttactgccaggtgctttatttcgcctatcgtctattttgttttcctcctaccaaatttgacaac cctccgcaaacactcattcctatatagcccggtgaaatacgatatggagaaaaacaaaaacaagtgtgagcttccacttcggaataatttcc ggagaatgagaattgtacaattactcctataagaccatacaataaaattaatcagaaacatgaagctaggtcattatcattattgaacccag aaatttgatcacaaggcataattatcatgagacgtcaattattctgatgataaataacatagacaaagtattgcgtaatgatcaatataacatg acacataataaatcagaaactcgaaaaacgtatttaaatatagattttgtcgggaagtttaatgtgcaactgtctcgatatctttctttgaaaacat ttaatttttattatattttccaaactggattcgagaattctcgtattcttaaacaaatttacaatgaaaatataaataattaatttaaaggaacatgttct gcaatcctccctgggtcccgccacgaaaccgccacgcactaccatgaaaggcgcgttcgcattcgttctgccgctcgtttctgttttccagat ctttccatcattttcttcattcattcgcgctctctcattatcttgagttgccggctattttcgctgctctctgctttttcgtatcgctttttcactctttcca gcattcagaaaattgcattatacggattcatttaaaaaactcatagcaaagtattagttattgatacgcaatactacgaaaagtatcggaaaat ataatgatagtctgtgcgacctcattccctgactcgagtactcttaactgatgatttaaatttagattccggggctctcagaaaagacccaat -continued agtcgtattgaaccttcgcctgatcgccactagctcatcttttagtcttatgacgggctcacatgattctccccagtgtcctcccgttttctcactg cacttgattgtcgacgacatcagtacaaagtacaagcactacgcgtctgtctgaaaattggacgggtgccgttaggacattattcatactac ctgctagtcgcagattataaaaaaatgtcatgaccgtctgctctacttatgactccctatatatgcgtcaaacgaacaactgaccctgttcact tttcctattcttcgtttcatcattttctgtaacaaaaatggaaacaatactttacacagacgtcactattattcaggcctatgatttctctatcgtttagt taaagatgaaaagaaactggtcgacccagttgcatgacgagaaaaaagaacaccccgttcgattttcgttgtattccctctgcacacattgtc ccatcacctcatcatactaccctacacagcactctagaatgacttcagtgcagaaagagtgccgatgagtcagcgacccccccccccc ccctcctttctcttgctcttcctcactggttctcgtaataggcgacttcttgctaacagaaagtgagcatagcaacatttttttactttgtggccttca ataatacgtgcgtcgataattagaatgatgagtaaagacaacgtgtagattcaatattcacgattgggcgctattaatttattactgtcaagaa tcagtttaccaaacggtgagtactattattgtctaattgtaagatttagcggggtaaaaccaacagaaatgtcatgatattgaataatctcaat cagagttatatgaattattacccatatagcaatactgatggtagttatatcggtcagagaaacgaggacatcagctgaacatctgcgtctct aacaacactcggggaaggcggagtcagtgtgcgcgtgcgaggggggattatcgatcgagaggcgggcatacagcagtcatacaccccca ttcgaccagaacgctccgctcgcgtgccaccttgtctccattctcatttcacttgtctctactcggacattactcctcatcgattagctctttacta ccattaactatatgccatcattacgtagacttgcctatgacgagtggggatgaagtttgctttgttagtcttactagtgtatcgatttttttgggta atatttcgcaactactaggactactacataatcacctcactctcgcctcctcattccagattattcgcactcattactattattcagcaatc Ubq-2

SEQ ID NO: 22 aatcaataaaaaaacgttcgaaaaacgtttgaaacaaaaaaataatattcgaattcttctccccccttcccgtaaatcctgcagctctctaccgta catcgccgtctctcaatttcgcggcgagacccatcaccacggcaatcctccatagtgtcgctgggcctaaattattccgtattagctcgattt tcgccgtttctctgcgaaatttttccaaatttctgttcaatttaatcaaaatattgttctggacgcttgttcagcatagaaagtggagattctgttgta ttttaagcttggaaaacgaatttattatgaaatttcattttttttgctaaataatttctctattcttgaatttttacagctttttaacgcaaaatattctttcct ctttgttctaaatgggtagttacacacattatgcggtctataacgtcttttgtcacctttgaaactagtctctaaagaaaaatcaataatttttgccc ctacgctctcctccaaatgtttcgctctcgccgtcattttctgacaattttactcggtttcttttcaaattatataatttcagtcg sto-2

SEQ ID NO: 23 tgtaaacatttgttattatatttttaaactttgtgttgtggatgtgaatatgtggaatttaataaaacatttctcgatataataatgattttgttgaattag aaaaattagaaaagtggacgattctaaaaacaaaagttacaacgaaaatcatcgaaggaaaaaacaactgaattccaaaatagttttcagag gtgatcacaaaatgttctcaaacgatatatattctaccatcaataattttattggcactatatcacagtccataattcctgtgctttaattatacttttc agtatagaacaatatgctatattatcaagttatgcgtccaataaacacaatttatttttcagactgaatttaagccatattgagaatagcgaaataa aaacgtagaggaaatttgtgatcgccattcacaattaattcttagatcgcaatgataacaaacttcgattcaaaagtcatcatgcaaattcaccg ttctcgtgtgtgtgtgtttttggaggaaataacacaattttgtgactgatttttttacaacatgtggtttgtagcatagttcaaagtcattctagaggg ggctcagagggagttctttcgctatgtcatcgtttgtttttgcacaccaagaaaaatgaaaataaatgctctaggatgtcatggatcgtttccatt cttaataagtagaagctaggatttcctatacaaaaataagtaatcttcgtttctacgtctatcaacttaaatttttgtatacaatccactttggtaatat tcaaggccttcctgtaaaatgttttatgatcaatccgttacaccaagaaaacaagtgcaatttgtcatcatgtaggcttccgcctgtgtttacttcc ttcccccagcacaacactgactatttataccaaattaataatgcagcattcctcatgtgataactcgtttgacttttatatctttctacgtgcatcttt caagctcgaaaattaattttaaaaatttacattgcagaacaattgcggaacgaagaagcg sto-3

SEQ ID NO: 24 attaatgaagaatccgaggttcctcactaaagattctcgctttatgatagagtcctcaagcttgtatattagagttttggggtgtttacctaaactt atgcaaacggttttatcatggtttaactaaagtagtgaattgttggaccaatttaaaataacatcgatcgcttcctgcagatcatttgtggaattag ttttttcaaaagagcaatatagtttgaggtcatcagcgtactgcatatatttaacagtttttggaatgtttgcaccaagatcatttgcaaatatgccg aaaagtataggtgaaagtacgctcccttgggggacaccacatggggcgttcctaacagaagatagagaattgttcacttttactttgaacgta cggttggagaggaatgagtccacccagcctatgagcatagaattgaacccggcctttattaatttttgcattaagagtgaatggtttactttgtc aaatgccttactgtaatcaaaaaatacaacatctacttgattattgaaattaaaattttctatataggaacttgatatacccaatttctattaaaaaat tgaattcgcgccgagcaaaatgtgatgtcaatttcagttttccaattttctcaattttttttgaccactaactaaaatttgataccaaaggatttttgct -continued caaatttcgaaataattgcggtaaaattggctctaaacactagtttttgacctagcgaattttgatgtcaatttcaatttatttacattttatttggaaa ttttcttcactgcggatccctagcaaaatttgttaaacatcacttttccgagcaatttgtgatgtcgatttccgtgtctttacacggtttttgcctttttg cttaaattttcaaaaatttcagtaaaccccaaccaaaatgaattttactcacaaatttcgctcttcaattatttttttagtgaaattcacaaaatctga cctcaccctaaattcccactgagcacatttggatgtcgatgtttgttcaagtttttggccaagttttaaacaattgcagtcaaattcaaccaaatca cgtggtgtcagtttgtcccattacggtttgatctacaatgcgggcatttttttgcccaatcaattgagaactctgcatcacagctaccacatttttttg tagatatacgtagatcaaacggaaattagacactctggcaccacttgccaaatcatatgcaaaactgctcaatggtagaatttgacaacccaa attgctcatcaagttttgtgtcattttccgcgcaaacagggattcaaatttctgccatcaaaaactcattttctacaaaagaactacaaatattatt tcaaaaaggcggcagtggtggtcaaagaacaaacatctgaacatattgaagaaggtgtctctctctctctctgtctttccctgctcacacaa atctgtgtgtctctctccagaaaataacaacacttgaggttcacgggaggacggggggagctcccgcctgtgctccaactctcttgtcatgc cactttatgttgctccagtgtttttgtctctctaaatctccagctagctgttctttcatgttcccttagccccaataccgccgcctttcgatcttttggc tgtttttttggggatataagaagtttcgaggaggaagactagatctattcatcctaaaataaattattttcttttttttttaggctttatcagactctaa aatgctcgtacgacaccaaattccagatttcagttttctatattttcggtcctataatactatattcaaaaaattagcgtcttcgaaggaatctgac atctaaaagttctattggtctttttttccggcaaatcggcagattgccgaaatcaaaaatttccggcaaattggcaaaacggcaaattgagagat tgccggaattgaaaatttccggcacagaggcaaaccggcaaattgctgatttctcagaaaaactgcaattgccgaaaattttcggctaattga ggttttgcatttttatttttggcaaattgcctgaattggaaatttctggcaaaccagcaatttgccaaaaatgaaaatttccggcaaattgccgattt gccgaatttgctagaaaaaaaattaatcggcaaaattttacgcatctattttgaaaagaaagcaaattctatgaaaatatctaaagaaaatctttt aaaaaaatgcacagttttaaatgtttcattcctttcaaaaatccctctaaccgcttccggcaaattaatatccggcaaagggcaaatcaccaaa ccggcaaattgccaatttgccgaacaaaaacaactgaattatgctattaataattcctggttcctgatttccaattttttgattatttcttactcacttc agtatcggaaaacgttcacaactttggaaagaatttgatgcccgtaatttgctgaataaatttaatttttttcaatgtccag Mitochondrial Oxidative Stress Toxicity hsp-6

SEQ ID NO: 25 gttttctgcaaaataatcattgattttaacacctcgtaaaataatttaaaaaaagaagttaaaattttaattgcaaccctatttgtaaaaagaaaac tcattttcgccaaaaataaagcaaaaataattcaagagaaaaacgcgccgcgtgttgcgattggggcgtaactgcaatgtgtgcgcacaca atctcaacaagcgctgcgagacccgccgcctgaccgtaatgtgaaatgggcggagacgagaagtttttttctgtttgaaagttgatgcaaaa gcccgtgattctttttttcgagaaatttctcgagtttttccaacgaaaaattcattaaatttaaaccttttagctctcctttccaatattttgcatcatta ttctcctaaaacttggcatattcagtggaaatgatgcaaaatgccctgacttttgttatcaaaaatacaagaaattgtcccgtttaacggttgaaa agcaaattttgtgtcattttgtttaggaaatgtcaaaataagctcaaaaaccgattacaaattatattttactgctttttatcctattttctcgcgttttc gttcatgatgcaattttctttcaggcact hps-60

SEQ ID NO: 26 ttttcggctgaaaaattggtttttttgagttttaaaatttatttttagcgggaaattacatgaaaacaacgaaaaaacccgaagaaacccgcgaaa attcagaaaatgatcaaaaaaccaaaagaagcttcgagaaaaaaagcagaaaataaatgtgcggcgcgaaaaatctcgtgcggcaaactt gcaaatctaggcgtgtcgggccaatggcagacaccgcgccgcaaattcagccaatcagcgcgctcagctccacctagaaaagtgtgcgc accttgcaaaactgggcggagcgagtgaaatgatgcaaaagtctattctgatgtaaattagccattttacatcaaaatttgcgtcattttcgttat ttttctctcatttttcatattttgaacgaaaaattgaggtttttttgcttctattttcatcagaaaccattgaaaaatgcttatttttgggccatttttcgtcg aaattaggggaaaaaactattctacagttttcccagctattttctcatttattcctgtatttttcagtcattacctgcttcccagacgataatgcaag gcttctcgcttcattttcataaaaaacgattgaaaaatgcttatttataggccatttatcgtctaaattaggggaaatatctgttttaccgttttccca gccgatttctcatccattctcgttatttttcactccttttctgcttctcagacgataatgcaaggcttctcgcttcattttcgatgagaaactctgatttt gctcgcattttcgcctttccgctgcagattttcacacaattttcgtagtttttcagacacaaaag -continued mtl-2

SEQ ID NO: 27 agagaatacaaaaagagacgaaaatggttcagtggaacgaaacaaacgtgggatgtaaccatggaagtgagaataattgatggaatagct aatgagctgaagctgagtagatcagagactactttattctaaaaagtacagtagttggaaaattacatgtttcatttctaattttcaaggaaaagc tagtaattaccgtaatcttgtttgtacctgaaattttatgtactgcaggtgaccaagtatgtttgaggcatgacttcacacacctaactgataaag gcctctatcacaaactagagttgtgacggaaaattcaacttctcagaatatagctcaaaatctatcaaattttattttcaaaaatccaaataattgt gcacgcaatgtacttactgcttcataaagttcagaagaattggataaatttgaatgaagttttcaaagcttttatcagtgactgtacattgtgatag gcttgtgctgttatcagctgcctcaaataggttgtcgcttgaaaatttatataaaaggcctaccagcagacatgagaatcaagcttcaaaggct ctactcaaaa mtl-1

SEQ ID NO: 28 ctgcgaggaagagagaaaaaatcgtgctgtgaaggaaaaaccgagaagactgagcaaaagaaataaccaatgagcaagtgaacttttccca cgtctactactaaattattgtcgatctataattctttcgcttatcaatcttgtcaattgaaataaaacaatatttttctaattctttttggaacgaacaca cgtgtttaaatgaatgttgtgctaaaaacgtcacatcaatggtacgtgaatgttgcaaacaccttgtcaataactgataaaatcagaaactaga gctgtgactgaatcgtatactagaacggagtctctctaaaaacgttctaaaaacaaacaaaaaaattgtgcaaaggattagagtgctcaagatc aatgagcaaactcacaatcaactatctgttattgttttgggtctcttctatatctctattcttttagtatcataagtttgtacattgtgacagggccac cctcttttatcacatatttgaagtggtaaacagccagcaaaaaccaaataaaaaggcagtgagaaaaagaagaaggcagctcaatttgactg ctgaaattaagaaatc cdr-1

SEQ ID NO: 29 tctgctgatttatttgagcttctctgtgtgaccaagacgagagccgaagagtgaagtttccactgtcacaccatgtattttatactagttcagagt atctttgaacacctgttttaaaaaggtacaataccaaaaggcgctcttaatgcacccggttacatttgtatttgtttgatcagatggatgtctgtct gacaaacgtcggccaaagaatgcacttgcagactttactttaatttttttgtctagtttgaaaattcttcggatttgttagtttcaagaactttcaatg aaaccgaaagtttgttgagttagcgagaattacttctgattacctgaaaattaatttgactcaatcttttacctacttagaaagactaaagtttctgc acaaatttgtttgaacaggtgcttcaaaatgttacagaattttcattttcatccacataaaaagttgattgacaaatagtgtgggcgacatgatttc ttgaacaatttgtttcgcttttcaatttggactcagttcttcgaaatttagttattatccatattattactgttttgagttttatcgcagtaggaaatactg gtgtatatacatattatatttttccgttttgtttacccagaaagcttaaaattcaagttggtcagaaaaataaaaaaacaacttttgcaagaaatacc attttttcatcgtgcggaaagaacaattgaaaactaagtatttttttgctaaactgcagtactgctacaatactaatactgtaccacgatagtcacc caacagtacgaactcctactaaaaatttattaaaaaaagttttattattcaaattttgaaaatccataagttctaaatactttgttcagtatgctatact taacacaaatggtattctgcaattgaaacagaaactacaataattttatcacaaaacacagttctccctactttcttatcacattatgtcatcgggg tggcaagtatataaaggaatgctgtaaaaagatatgtactactgtctcaagt sod-3

SEQ ID NO: 30 agaatttgcaaaacgagcaggaaagtcatattcgcagaaaaaaagtcgttgcaaacattcgtttttatatgtttttctttgagaaagcgtggttcat ttttgaaagtgaaaaatatttgcttaaaacttccaaatttaaatctgcagtgattcagagaggttgagaattattttcaaaaacattcaatgttttcc cttggagtgactatgcaaatatgaaaatgttttccaaaaatatttggatgccctgataaaaagtaggtgaaatttcgcaggggaacatcatatta aaatgttgaatttttagaagaaatggaaatgtttgtcggtggtatgctcgaatatttgagatattatatatttactgttaaatccgaaatttttgacaa acggaaaaaaatttgtgtcgaaatactacattttcgataacacaaaggtacttccataacacttataaaaactgtttgactatcttatttcaggaaa aaaaaatccaagaataaacatttttcagaatttgaactttctaatggctgattaataaaacaaagttatacaactattcaaagcagttgctcaatct ggcattttcttgtgtttttttttgaatatttcatcagcaagatgttgataattttgtgttaattctaattgttttctacaattttttcaaaccgaaaattgacct ttgactttgtttactttgttctcgtgggttaactgttcactgatttctattgctgttgatgaggtctttgatcaaatttgtattgtttttatactgcatattgc ttcaattctaaatcatctaatatattgtcaaacaacttcttgatttttttttcattcaaaacttctgcaaaaacgttctcttaacaaaggttcacacaaca actctcctctccatctctttctctcaacaacaatgtgctggccttgcatgtttgccagtgcgggttgtttacgcgttttcaagatttttggtctcctat ctaacgtcccgaaatgcatttttttcctttcatttggtttttttctgttcgagaaaagtgaccgtttgtcaaatcttctaattttcagtgaataaa -continued eat-3

SEQ ID NO: 31 caattattataagaaaataaatttaaagttatccgagcaacaattatcaataaatattactttttaaatgaaaacctttttaatttcagcagaaatctt agaaatcagatgatcaataaataaaaacggctgactttttaaaggcgcatagaattttcttggtggcgggtcccgcaccgaagagccgttttc taaataatatacactaatgattatttttattaaatttttcacggttttcgagagtattctttatataaattcaattttaaagcattctcgtcgagtttgaat ccgaaattatcgattttcgtttttctctgctttctctaccgctgttttctctcctccgctgtcttcgcaagattatagagctcttttgaatcaatttgtttc atgtttccgcttttgacgttattttaaacatatactgatataaataaattaagaatagagtagaaaatctagttcaagtaaagatgcaacatttctttc tgcaaaatttctcgaaaacacctgttttccaaaacttttcaattacacaattagaatttcggaaaagttaacatatataagaacatattatatatata tatatatatatatatatagattaactctcacagttaaagaaatctgaatagtaatattgcgaaatagttttgcataagtttgtttgattaaattaaat gtgaagcactaacgctattgaatccaggaaaaactcgaattatttgtttgatttttattaaacacactttgtgaacaattttcggttaagaggctttg ttgtagtaaaaatcctaaatctacgattatcttcttaaaatttgacatacttcttacgtatgttacaggataaatcgagttttgatgtatttcgtaaata gtattaatcatgttatctttttatttcccatctctatgattaatgttgtctttacactaattcacccgtaatgtccgtgcacaaaagaatttaacattca gatattatggaaacaaaatcatcccaaacttcacatccgtggcttgttctactcattttcgccacttttgcggtctcaattttttgctgtatacagcaa ttttcctgaagtctcggcagatgagaaggttcatttgaaatatcccaggaatctggaagacgctaagcagctgggcagagttctctcgaagta caaggagaacaactattcagtagttctgtgcggtgtaattgtcgtctacgtatttctacagtccttcgctatccctggatctatttttctaacaattc tatcaggatacctgtttccattctatgtggcaattgtgttggtgtgctcctgctctgcaactggagccgccatctgctacaccatttctaaactttttt ggacgatcatttgttttgcaaaagtttcccgaaagaatcgcaaaatggcaggatgatctgagcaagcatcgtgatgactttctgaactatatga ttttccttcgagtaactccaattgttccaaattggctaatcaacattgccagtcctgttctagatgttccactggctccattcttctggggaacattt ctaggcgttgctccaccaagtttcctgtatattcaagctggctcaacactggaacaattgagccataccagtgtagcatggagttggagttcta tcgttttacttacgggttcggcgattttgtcgctggctcctatttgctcaagaagaagctcaaatcggattaatttctctcttatttcctctttcgat ctcatttttttttccattgctttctgtgcaaaacttgtgatatttagagaatatagccgataactcatttctatactatttttatttatttttcgcctcctttttt gtcataataatcatatttcttcactaataaacaattttttaggtgatgaaacaatg cyp-14A4

SEQ ID NO: 32 gaaactctcctggatttttctagattcttttccagttacatttcacatagaatctctaactaccggtgcatttgccaatcttcttactgaaattctgtgc cttgttttgtcattaaaatttacaccgaataaattatttgtctttgtaatagcttatgactttaacaaggtcatttttttctaactggctcattcgcgctg aagtttaaaagaagtttgcttttttgtcggttaagccgttcatacatttttggcaatcttggtacaaccatctactacatttatatcaaaacgaaaa aatgtataaattttccctcgtcttcatctacccgcaatcataaaggaatctcattccgtcccactcgccctttctttcttcaaccgaaatttttttcccc gcggcgcaaaccctcatgtgccgtcgatagctcagttggtagagcggaggactgtagagtcagcaggtatccttaggtcactggttcgaat ccggttggacggatttctttttttattttctgtatcaagtgtaactcttcagaaaatcatcgggagcagtcgtacgaaattttaattataaaaattaaa cattccagcattttttctttgggaggtgaagtagagtcagcgcggatttaccggatttacagttagtttgatacacattcaacattcaatattaccg aatttcaaaacaaaacatttttacctaagtcttttagattattggaaaattacaggtaaagttttggtgaaatgccaaagtcataatgcgagatggt tttttttttgaaaaattcagatcaaaactacgtgtttggtttgtgataaaatattatgatgaaaaaaaactcgaagaaatcataacccaaatgatatt cagttcacaaacataagtatcatgatgcaaaatacaaagctgaatgtattttttcaagaccgcagatcacaattaagacatggtaaacacaaa ctctactgcgtaccgcagtgaaatgtggtttgtagtatgactggtagagacacatcgacctatataaacatcaaaaaattgtttaaaaaaatatt ccatcgagaattgcttcatttcaa cyp-33C8

SEQ ID NO: 33 atattggaagtcaatgagaaggaggaattctggattgcaaacgagaatttggaagtgagtttggagatagtagcaagcctaagcctgggcc tgagctgagtcaaagccaaagccgaagcctaagcctaaatctaagcctgagcctaagcataagcctcagtctaagattaagcctaagcctg agcctgagcctgagcctgagcctaagcctaagcctaagccaaagccaaaacctaagcttaaacctaagcctgagaataagcctaagtctat gccaaagccaaagccaaagcctaaagctaagcctatgcataaacctaagcataagccttaacctaagccttaacctaaacctataagccta agcctaaattttcaggcactcactaccgaaaattttccattaatgttcaactcaatgctgtcgaccgtcctgaaaccaattgacaccctcattga -continued atgtttcaaaaaagaaggaccctacggcctggattactcggcctattcggattttgaagaaatgcagcaaaaattcactaaaatcgttcacga gaagcatatcattccggatttggttccagccattggaaacgggatcaaggagaagctggaagctggtgggatccgagtgttggatgtcgg gtgtgggggtggattccattcgggcttgctcgcggagcactatccgaaatctcagtttgttggattagatatcaccgagaaagctatcaaagc agcgaggctcaagaagaaatctgatggcactgattttgaaaacttggaatttgtagtagctgacgctgcaataatgccaagttcatggaccg actcattcgatttagtcatcctgtttgggtcttgccacgatcaaatgagacctgacttggtaatttttgtattcagtttcagagaggtatcccaatc atttacagtgccttctcgaagttcaccgtgtggtgaagccagatggtttagtcgcggtcaccgacgttgatggatctagcaatgtgttcaccga tcgtgagacctacgggaagatggctgcgatgaagtatggtggatcgatgcttcattgtcttccggttgggagcaataggccagatgcactat gttgcggctcaatgtggggaaggaagagagcagttgagataatgaataagtgtggttttgataatatcgacattattccgactgactacttccc tggaactgttttgtatttgatgaaaaaataaataaactgtagctagtgatttttataattgtaatacttattctatttattcaatctttttcccgattttca ctgctttgttgtgactgtatcattatgatcctgatgaataaatatcaataaacaaatacagtttttttttatttgacattgatttttgattctgagaatat aatacatatctatgagaaattaattaattaataattaataagaattaataaatttaataagaattaaagtaaaatatagtgggaatatagtggaaaa attgttttgtaattgtatgcaatatgtttataattttcaaaatcaaagagcagcacgacggagcccaatatcaaaagttcaagcgacacactcaa aatacgactcatacctgcgtctcctccctctcccaatttcgcaacatattttcgtattttgtggtttcttcagtcgtctatttctcgcacatacttccac ctgatgcaatttcgagtcctcaccaaataaatagccggcaatgtttgccatttctcagttttcatc glrx-10

SEQ ID NO: 34 ttttttttttttggattttcgactttaaaattagcctaaatttatcctaaaattatcctaaaaattaaaatttcacatggttgacaaatttgcagtggag cgcatttgcagaattatttttgaatttttttttcataaaaagcgtaacattttccaaattaatgggattttaaaggaaaaaattatcccaaaaatttt aattttctaattgaaaaaagtgttattagcccaatttttaaaggtttttttgcaattttcatcagaaaaagcgttaaaaatatcaattttcgtgaaaa gttgatgaattctctcaaaaactcggcaaaaagtaccgccaaaaattcaaattctccaatttttcatctctaccagcaaattcgcgatggagcg catttgcagagttattcagaaaaatcgtaaaattttccgaattaacgagttattttaagtaaaagtgatcccaaaaattcaaaattttccgattttt gaaatttttttggtgcaaaaaaactaattttcaaattaaaaaaaagtgatttgtctaaaataaaaagcgtttaaaaaaaccttttaaaaattttttttc ccaaaattcacgtggtgccaggggctgtcccatcgacggtttgatctacaaaaaatgcgggagtttttcgcccaaaaatgttgtgacgtcag cgctttcttaaccatgcgaaatcagtccccgcgcatttttttgtagatcaaagtagatcaaatcgaaatgaggcattctgacaccacgtgaaaat ttcaaattctccaatttttcatctctaccatcaaatttgcgatgaagcgcatttgcaaggcctttttttaaatttttttaaaaactccttaaagttaaaaa aaatcatttagctttagaaagcccaaaaattaaaaaaaaattttttttttaatcgaatatcaaaaatgcatttgtgctccaccgcacggcggtaattt cgaaatttctttaaaatttttttttataaatttctgtatttcacaactgtatttttttcccgaattttcctcgcctaataacactatttgtcatgattcttacgtc attgtcgccgccgtttctctttttctctcgccactctctcatttccatacactatttccactctcatttttatcatcatttcttcagtttttgctgcttttaa agcctatgttttccctttttatataatatcgcagaattttgtttttgtaaatttaatatatatatatatattatttatttgatgataatgtgatttctaattt ttttttccccaatttttttcaaattcaaattgtctctacgcttttcttatacttcattgcctttttttttcaacaaaaatttgagaaaaaacaccaaaaaatttc agaaaaacc

F56D5.3

SEQ ID NO: 35

Gcacgtgtatttttttcggcacgtgaaaatttttttcaacatgtatatatatatttttttcaaatttggaatgtcttatgaaaaacgtcgaaaaggagg aactcatttagattaattgttatgcaaagtgcagatttttaacaacgaatttttgagatcaaattgtcacagttagctgatgttttcgaactctacac atgtgtgaaggttcactcagtctgattggttcaaaagtggcggtacgagtcgctgatcggtcttgcagttctcaatttcgaggaaaatcaaaca agaagattagccaaaattaaaaatttacgtttttgaacagtgttttcattgttattctcatttatgttatgaaaacattttcaaacgtttttttcctggatg gtaccattcattacatcaagaacttcctgtcactttaatgatcttttgatttttgtagtttgaattaaaatgatgatatccattgaaattgagtgtagg cgtatcatgatgacaattaattaatttttgatcttttgctacagggttttccataggtcagttagtaagtgaaatctataaatttggattgtaaacgtttt ttcaaccttgatttttgtgattttttcagtttttttatttattttagatatttaacatttaaactattgaagcttttaaaaatcatagttttatgtaaaattgaaaa ttgtggtaaatgacgttttaggccgaattagtttttcatttaagactacattttatttcaacatctaagaactttttgacatttttcgagccattgttcaa aaaacatcattgaacactacacggttcaaaatgtttacactagatacacaaaccaatagagacactcttttaagaggcaaatggtcagagaat -continued tagacaatgagacattcttttcttctgtgaatttgtatgttatagtgattagacagttaggatgacatatatttgtcagcacaatttctcttataaatac aagaaaattttcagagattctcatatccatttctatttcattgaaaagtttttcaaac gad-3

SEQ ID NO: 36 tgactaacaatatgaaatgtgtataaagcttcatgatttcacaaaattgaagtctaaaaaatataagctttaatttttttgctgtatgagcccctcaa attctcttatatactttttcctgctaatggctacttctttgatcgaagatttggccaaccggttaagtttgccgacaccagcataaagaaattccgtt catcgcattcaattgagttataggagcaaacattaaaaattgatggtataacttcttacaataacatgtgaacaaacagcacgtgggcataatc aagaaaagaagcttttgattttgaagttgataagggaaacgatcaaggtgttcaagaccgaaaataatattttcagtttgagtaagttgaaaatt atattatttttgaatactttttaaacagctaacagatattgcaatagagtgcttgaagttgtatgtcaatatagttttcgtgaatagacattaattaca gtgcggctcataataaattttattgtttttttagtattctacaattccatcgagtagctcctgaaaatgtgaatagcctagatagtaaccgattgag aaagtaaacgtgcgcttatgagttacgtttcgtattttcacaaaatcgcagtataatttttagtcatttcttcaaaaaccaaaaatctactgtaccct tattgtaatcaaaaatgtgacggaatctcgcatgaaaccaaagattgtttacaatcccaaaaataatccaaaaattgccctgtttctctcaattca ctgtacattttcaaagttttccacagatacattttcattcatctgtgaaatcgaatcttttagactatgtatttgtcataaaatttttgtgattctttttgttc tgttcactctctgtcccttatcgttcgtatctctatttctctattctctcgttaccatcttatctattgttattccatttttttggtcatttgtttattgaactc cctttactcaactgcacacaaacatttcttttttattttcttttgaatatatgctccatgctaaccagaactgacctgttgattctttttttttcccaatatact agtccttttcttaagttttaccaatgtttttag

F17A9.4

SEQ ID NO: 37

Tcagcgatgagcacaccgttcaaagattttctgaagcattgggcttacatgtgaaacaagcagcactcgatattagtgaaggaaaaatacc gaaagcaataattgcattcaactaaatactgtatttgcacttggtattacagaaacgcaaagttctgagaatgcgtactgggtaacatatttgac gcgcaaaatatctcgtagcgaaaactaaaataatttaaaaaataattcgctttcgattagaaattcatttcgaaattcgagtatgtaaatcgacta cagtagtcaataaaagtattactgtagttttcgttacgaaatattttgcgcgtcaaatatgttgcccaatacgcattctcagcatgttgtgttcccgt aacatttaacctattttacataatctaggtgttttaaacttttttataaaactttctcgtaatgctatctttgcctcttagaaaacttattcagcgacgtgt atcataaccaattctaatcggcttgttagaaagaagaaatataatacttcggcgtctccactttgtgactgggcacaaaatgcaattcagattct actttcgaaatagccataaaatcataagatcacagatctttcttcgtttctcaggcaaccaggtgcacaattgtcatcactcgaccagtgagac cacaatagaacagcaaacgttgtcatctttttggttagacactttctttctgcctctgcgtcttttcataaggtgtgcatactcttgtttgcccaaca acctagccgatcagaaaacgcactatatttgacctgcgtgtacactgctataaaagtaacattttgttctttcatttcttcgaaaa

C35B1.5

SEQ ID NO: 38 aatgcaaaaaaataagcctttccgaaaaaacgggcccttgggcctttaaaggacacaaaaacaggaaagcataagacaccaaagagtaa ttggatttctacactttggttcctagaattatttataaggtgttattgcgtttttgtgagattgttctatttatccagtcaaaaattgcatttctttgttttt gcttcaaaaaaatacattttcagtggaaatttcagctgaaaagcagaattttgaggttttcgagtaaataacgtaaaacactaaattacaaatatt gatttttgatgtcttagaccaaattttcgtaaacatgtttgtatttttggaaaaaaataggttttttgtcgattttaacttaatttttcgaacaaaaaatgat tttttctccgatttaccaaagttttgacttaaaattccgattttctgggtcatttttcccctaaaaatacgattttaattcaaaaaatctatattttcaaag accaaagtaccataaccttcaaaaaacaaccactttctctattgcatcagcgaattgtcatcacccctctcaaaatatacaaaacgtcatcatttt tctgtgttttctctaattctcctgaaaaattctataaaaccaacagtttttatcatcaaaaatgccttttgaccgactttttttaaagttgaaaatcgta cagttttagcagaaattccagagtttcattttgaagtatgctggaaataataaaattattctaacatttattaatattttgtaaaactaattctatacaa taaaaaagtaaaatttaatattaaaaaaaccggtttttctcaaatttccattccccaatgtcctgttctattatttgttccgattcggccacagaacg cgcacacacacactttttgctgattctctgcctcctttctttgatttgaccgcattttatattgattttcggccacaattccactatttgttcagtttgtc gatttgttggaaatttcaattccggcaattcgccgatttgccggaaatttaaattcagacaatttgccggtttgccggaaattttcagttccggca atttttttaatttgccggaagtttccatttcggcaacttgccaatttgccggaaattcgccgttttgccggaaattttcaattccgacaacttgcctat ttcccggaaattacaattccgccgatttaccaatttgccagaaatttttaattccggcaatttgccgatttgtcggagatttcaatccggcattttg ccgaaaatttcaatttcggcagttcgccgatttgtggaaaataacaattctggtcattcgccaatttgccgaaaatttcaattccggcaattcgc -continued cgatttgccggaaattttcaattccggcgattttcctatttggcgaatatttttaattccgccggtttgccgctttgccggaaatttcaattccggaa ctttgccgatttgccgatttgccggaaaaaatcttttgccgcccacccctaataaagacttcaaaatatgcgtttifitttgcttttaacacgctaaa actctctaaaaatccccaatttttcagcttaaaaaaccccaaaaaa gst-4

SEQ ID NO: 39 ttttgcagactaaaaataactactctgccagtgtttaatttatagatgcaatttgtcactattttcattttatatcgaccaacccattcacacttcacta atcgtgttaaaactcaattagtggaaaatttgaaattctatgaaactttcatttgcgacaaaagattgttgttttcttcaaaccaaaaatttatcaatg ggaaaatgagatagacaagaactgggaaaaaagtcgaggttaataatttaaagaaatattgaatattcggcgccataatattaacgaaaata accaaaatatgcccaattattatccaaaaagattagaagttggcaaaccttgggcaagaatttccagagattgcactaaagttgtagccaagtt tgatccaactttatccaatcttttactaaaattatccttaagactatttaaattttagatagagaattggcgagagttagatcccacttggatatgac ttatagttagcctaacctgaagctattgcttgcttgatcatttggtttatcgctttgctacttggataaccagctccaatagttgttatttttgcttttgt catcatttttccacgatttacactctcaagtgaaaccaactgttctttgatgccagacgatgacattacacttgataagaaaatatatataaactg gaattaaaaacaattgatacatcgattcaattactgaattctaatt Peroxisomal Oxidative Stress Toxicity hps-1

SEQ ID NO: 40 atttcatttctttttttataaatacttcggctctattactgaatgaataaatgtataatgatgctctccaaatcctcttattattcgctcgaaccgcccgtt cccatagataccgtctagttttgacaggtgttcaaccatctgccgggaattacgagaagagtcgaattaattgagatcctcgtctaaataaatc tgaagtttaaaataaagccagaaatacctgaaaagagagaaaaagtgtgtccacgatgtctttgtttatgaccagtggtgtgttatcgagaaa aactccaatgaatcacacaccagagaagaatcgagaaaggtcgggaaattaggaatgagaaataataaatgtgaggaagtaataaaaga atcttcgagaactcattccacttttagatataaaacaagcagcaaacgggtttgtaggtattatatttatctattttaagtttaataaactatttttgct aaacttaaacggttcaggtgttgaaaaagtcctaaaatttttgatattatcaaattcttttagcgtggcggttttcttttttttcgaaatattgagttttt catctgaaaaatgcactattcgtgtccttcaaaagttcatgtgtcatcagtagccactcgaaagatcgatcagtccattttgatttcgaaagtaa gaagagatcattactattcaagagacgcaggcacggagcctgttgcgccgcgaatcttccaggcattcttggcgctccgcccaaaaaaattg caaaaataaaagttgcttgaatcatgttgaatgtcacttaatcgtgtggctttcaatgttctctttcagaaaatgtatttttttatttgataatgttaaga attcgccgagttattcttcctcaaaatgtggtgcgcgctctctctccccctttttcgtcgcgaacattctctgcggaggcatctcttcttttaattcac aattctcaacacttttctgtaggcaaaactctctaatattgctccttttttcagatttttgttcaaactttttttgtatttatcttgttcaagtgttttccattca gcagttacagactatttaaggaaattttaggtttttagcacatttttctaatttttttgacgaaattcgaatttttctagaatcccgcccacgcccagtcat ctagtaaatttgttgaacttcatttctctatttttaatcattgttctcgacgtcctaat-
tttttatctccatttgagtgactatttcttgatttttaaattatttt ttacagtaaaa ctl-1

SEQ ID NO: 41 gctctgccagaagaagcattaaattgtttgatattcaaacttttgtatatagaatctcgttatttataaactcttttttttgtatttcttctggtttttgatg ataagaaattttatgtgcacataaatcaaaaaagccggaaattaaatagcgttttatcaggcagaaaattggccacgtgacgtcatcattttcct gtttgaagaaaatctggaaaatttttttgtttcagtcaattttttaaagatgaaaacttaagttagactgtaaaagcaattttcgcgccaaaattacgg tatcgggtctcgaaacgacagtttttttatctattgcgaaaatatgtgcgcctttaaagagtactgtagttgcaaacttttgtcgctgtggagtttttta tcgatttttttatatttttttcgatgaaaacaactcaaatataacaataaaaacacaaaattaaaaaaaaaatcgataaaaaatccgcgtcaacgaa agtttaaagttacagtatttgtcgtttcgagaccgggtaccgtagtttttggtgaaaacattgcaaaatttggtcaacaatttcatcgctgcgaga ccgacacaacactttattttatttttgggtttcccttatcgcttatcataaacatgtgacgtcatcatctcttgtacagagcaccgcgactgggagt ataagaatcgccggaaaacatcaataatcagttcggtagaagtgaaaattgagcgtaaaatatgatcatttttcgatgcaccatatttgacgcg caatacttctacaagccgctgtgtactgctcgtggacaactttggattatttttttgtttttaaaattcaaaatagtcaatatattgcttatttatagcgc gcattttgacagtaagtttgtcaaatttgcgcgtaagttatggtgtttgcacatatgcaccatacagcaacaccccgcggcccggctagtggt -continued acatccatgcaaatgcgctctactgataatttgagtttaaccaggtttaggcgcaagataagaaaaaaagctttggaccaaaaaatttagagttt
atttttttcggacatttttatatacatcacaaaaatattgggccactcgtttttgataaaaacgacaagcccaaaagttcaggtatacggtagac
aaattgcgtacaggtaccacttttccacgtagtgccaggttgtcccattacgctttgatctatgaaaaatgcgggaatttttcgtccagaaaaat
gtgacgtcagcacgttctcaaccatgcgaaatcagttgaaaactctgcgtctattctcccgcatttttttgtagatctgtagatttgtagatcaatc
cattccccgtataccctgacccataatcaatacctacctaattttttgtctttcccccctactttttttgcctgtccaaaataagcgagactatgccgta
gtctggtgtccaacaacatgttccttatcagtgataacgctacaatcttctttcttttttctctgtttctcttgtctctcccaacccatattccgtattac
acctcgtcgtggtcatttttttgttcagagttttatttaattctaaatttcctaactaaaatttcagaaccaaa ct1-2

SEQ ID NO: 42 aaactctttttttgtatttcttctggtttttgatgataagaaattttatgtgcacataaatcaaaaaagccggaaattaaatagcgttttatcaggca
gaaaattggccacgtgacgtcatcattttcctgtttgaagaaaatctggaaaatttttttgtttcagtcaattttttaaagatgaaaacttaagttagac
tgtaaaagcaattttcgcgccaaaattacggtatcgggtctcgaaacgacagtttttttatctattgcgaaaatatgtgcgcctttaaagagtact
gtagttgcaaacttttgtcgctgtggagtattatcgattattatattattcgatgaaaacaactcaaatataacaataaaaacacaaaattaaaaa
aaaaatcgataaaaaatccgcgtcaacgaaagtttaaagttacagtatttgtcgtttcgagaccgggtaccgtagtttttggtgaaaacattgc
aaaatttggtcaacaatttcatcgctgcgagaccgacacaacactttattttatttttgggtttcccttatcgcttatcataaacatgtgacgtcatc
atctcttgtacagagcaccgcgactgggagtataagaatcgccggaaaacatcaataatcagttcggtagaagtgaaaattgagcgtaaaa
tatgatcatttttcgatgcaccatatttgacgcgcaatacttctacaagccgctgtgtactgctcgtggacaactttggattattattgtattaaaat
tcaaaatagtcaatatattgcttatttatagcgcgcctttttgacagtaagtttgtcaaatttgcgcgtaagttatggtgtttgcacatatgcaccat
acagcaacaccccgcggcccggctagtggtacatccatgcaaatgcgctctactgataatttgagtttaaccaggtttaggcgcaagataa
gaaaaaaagctttggaccaaaaaatttagagtttattttttttcggacatttttatatacatcacaaaaatattgggccactcgtttttgataaaaacg
acaagcccaaaagttcaggtatacggtagacaaattgcgtacaggtaccacttttccacgtagtgccaggttgtcccattacgctttgatctat
gaaaaatgcgggaatttttcgtccagaaaaatgtgacgtcagcacgttctcaaccatgcgaaatcagttgaaaactctgcgtctattctcccg
catttttttgtagatctgtagatttgtagatcaatccattccccgtataccctgacccataatcaatacctacctaattttttgtctttcccccctactttttt
gcctgtccaaaataagcgagactatgccgtagtctggtgtccaacaacatgttccttatcagtgataacgctacaatcttctttcttttttctctgtt
tctcttgtctctcccaacccatattccgtattacacctcgtcgtggtcatttttttgttcagagttttatttaattctaaatttcctaactaaaatttcaga
accaaa ctl-3

SEQ ID NO: 43 ttttattctgaactatatacaaaatgtgctcaatataacgagttttgtaattttgtgagaaagtcgtattgaaaattagtttaaatgtgatttaatatttc
gaaaaagtagtctaattttagctaaattctacaattttgacaacttttccgtgtcgcaaaacgaatttttgtagaggagtgtacctaagcgagtcg
gagaaacgtgcattcttccatttttttcccccggggagcccatagccagtttccggacgggcggtcttgttccaaacgtttttaaaatttaatatt
gcaatttaattatctattcagcatccgtagcccagccgcattgtggatctcagattggcgaatgcttgtgcgctccattggactccggagccat
tccgtctgttgatttcctgatttctgcggaattgtccggatcgacgagctctgtaaaaaattaatttaggaaaaatcaacatttttttcgataagcaa
accttaattccttcgtcacacttctatggaatccagctgacggcggcggctgaaatatttttgcaaaaaaaactcacttttcgacttttcctctttctg
cgatcggttttcgcctcgatttgcgttgattagcttaaaatagtttttatatttaactaataataaagaaaaacaaaaaaaaatgagaaaaaaaca
atcaaaaactcgaaaaaaacattacgaaatcagcaaagaaaatgaagaaaaaatatatacagtaattttaaaggcgcacacacaaaagtttc
ggtacgcgtgccgagaccactcagcagaagtgtgctcctttgaatctggagtacggtcaatggggatttatttttgaaaatgcaaatgccaaa
atacaagaaaaataacaaattgcattaattttagtgaattttctgaaaatgagattattgtgcttatttggaattgtgcaacttttagtgcattttcat
cgtcctttttttctgaattcttgaagtttctggaatttttgttcccccccccccccaatctaagactaaacctaaggctgagtctaggcctacgcct
aagcctaagcctaagactaagcctattggtgtatgtgcacataaatcaattatttaaaaattattattattattgcaaaacacaaacgtatttttca
gattttttatttttcaccctttcaacctgcaaaacccatttttcttccaccaaaacacagctgttcttgccaccatttgcctgatggaaaatttatata
aattggctgtcctttgtgagaaaactagaacaataatgatgacattaagtactagagtataaatatattatttttgctgacaattcctggcgtccc -continued ccgttgacattgaaaatgtataaaagaggcggccagacaccatccccgcaaatgtgtttttgttgttcacttttcttttttttccactctctctctct cagctgtttgcatgttgtttttatggtgatctatggtctctaagaatttgtttataagctaagaactgctcgctgagaaggtttttttggttcgtagct agttattttacgtttatcgaaaaaaaattgaaaaaagtcgaaatttccatcttaaaaaattagtgaattttaatatttttgttaaataatcgccattgtt tcgtgcttttctcgctctgtaaaattgaaaatctataaattttgggtaatttcgagtattacgggagcacaaaattttgagaatgcgttttgcacaa cctatttgacgcgcaaaatatctcgtagcgaaagctacagtaattctgtagcgctggtgtcgatttacgggctcaagttttcgaattaattatttt cgaaaagttacatcgatatttcattttccttcgtgctattttcaaaaatcgagcccgtaaatcgacacaagcggtacagtaatcatttaaaggatt actgtagttttcgctatgagatattttgcgcgtcaaatatgattgtgtccccgtaatattatttaaatcaaatttcacattttaaccataaaaaactct ttcaaaagtgtaattttctacgcaaaaatgccgttcggatgaaaaattacttttgaaaaacaaactcgaaactacggtacgcaaaaaagtacat cggtgtttgcacataagtgaaaacaatgttgatttttgtaattaaaatcgattaattattttcccggaaaacaaaaacgttttcagcgtggatttct attgtttcttgcgtaaaaaaaaattatttaccaattttaaacgataatttccacgaattttcgccattaatctctcgatttgttgattcttgactccgag caatctctccggattcgcaaacgattatattatttatttgattccttttcagtgccgattctcggaaattcaacagtaaatcttcaaa

W01B11.6

SEQ ID NO: 44 tttgagaattttctcgggaaattaaacctgtgatttcattaaatttgatgcaagcaacaagtcattatacaataaaattggtgaaaatatgattattt gaaatatttggggcgaggcttttagtttttgaagagcttacaaaaattagaatttaagaaattttcgaacacaaatttgagagaacttttgactttt ttcaaaaaattgattcaaaaattttaatattttcaaagacgaaagaatttgattttgtctaaatttacctaatcattattttcaatcaaataattgcat ctctgaaaacctgggaactttgaaaatgacgtcattctttttccctccttttcttttccatttggttattgacgttttccacccccctcttgcaaaaaaa actaaacaaaaaagaaaccattggcaactactaacgccaattttgtgttgcttcatcgggtttcttttagttattttctgagagcgctgagattatt tggaaatttgcattttctcacgttctagctcagaaagagatcagctttctgaaattgaaatttaaaaaatcgctctaaattgaaacagctgatttta tgtcgattgtctctgcaaatatattatttcagaatatataagtatgtgtttgtttaagttttatttaaattttcttgaattttatgaacgacattagagctt atgttagtccaaatatttcaaaatttattaacttgaatcttgcgcaaaattatttgaaaaatcaatttccagccaaaatcttctttaaaattttatttgaa ttgtcaaaaacaaatgcctcattattaattttatgccaatattaaaaaaaaattaattctcgataatcttaaaataagattttttagaaaaacaactttc aaaagcttctatgcgaaaaaaattgtttttattcgaattaaaaaaaatgttttcttcaaaaaaaacaaatttcttaaatcatagatccgtgttgctca actgctcaatgtttcccatgacaaaaagtccatgtctctctctatcatttctcatctctctttttttctctagccatcataaaaataaacacatgtttcaa caatcattccttggtttttatctctcgattgctatatcattttatttttttttactattgggtaaattttgaagagggtactgatttttttcaaaattttc caatccaaaagtcttttgaattgcgttaaatcatgtctattgtaccacaatgaccaaatgccatagtaaaacttttcaaaaaaatgtttgaatttttttt gagcgtcagaaagtggcaattacagagttttttttagcactatgaaaattgaaaattttcggagtttttcaaaatgatttttttgaaattggaaaaatt acagaaaacaattattgccattatttggaagttgccgataaaaaaaaatttctttggattttatggttttattttgttgaaaatattaatattcaaacc aggggtgtgcggcaaatctcaaaacttgccgagctcggcaaattcggcaaatctctttttttcaatatttgccgagcacggcaaattcggcaaa tttgcctagctaggcaaattcggcaaattcggcaaatttgccgtgcttaacaaactcggaaaaatttgatactttttgatgtttttttggagcacca aaactactgaaatcttaacactcatctggtttctgaataagttccgtgtagtatgtctgcttaagcatcaaaataacgcaattttgtgtcattttact aaatttttggcgaaaaaatcaatggttttagtcaaaattgcattgtcaaatttatgacgtgtgcggcaaatttcgaaatttgccgagctcggcaa attccgcaaatctactgttttgaaatttgccgtgctcggcaaattcggcaaatttgccgcacacccctgattcaaacattgtaagggtttgaaca tgttcttaaaatgtgacaaaaactcagtaataaaacatttaaatttttttgaacacttttaccatgatatttggtcattttggcacagccttaaggttaa agctttaacaatttccccactgacgctactccaccataattttgaaaatctaaaatattcagaaattcgaa

F10D7.3

SEQ ID NO: 45 ttttggaaatggtatcagaattgtttaaatatcttatctgaagtttatttaagtttgttacttaaaagtttgtcggtttcgcacaaaactttatttaagtta ggggcacgaaaaaagtaaaatcacaaattatcaataattttaaaatcaaaccatcaaccagaaaccagaaaactaaaccttgtattttgaaat gtgcccgtttgaagatctatgcaataaaaaaattacatttgaactgctatcaatttttttaaaaccggcaattttgacatttgccggtttagtacattt ttgaccgatctagataaattaaaaagctgataaatttgttaagtattcaacttttgagattcaaaatttaagaagcttttcggcattttgaaaacat atgtgacgtatgtcaagtttgatttgccgttcaaccgatgagcctgtatgaacatttgactaatgattatttcaatatcagatcattttaattgttta aatttgataaacgaaattgaaaattttcgaaaatatatgtttcgaagttgtatacatttttaagagttttcactttgtggcagatttttctcttttcaattt -continued gaaagtgtcacgtaccttgaaatagtttgtttttttaagaaaatgaccaaaagaatattaaaattttgaattatggtaaagaatacaagccagca aagaatctagttattgttggaaaactatgaacatcatgtcctcagttttcaagaaaacattaagatttcaaaactatgtattctgcatggcaatgtt gcaacaaaccatttcctcataaaactagccaactaacacagttattcctaataaccacaatgttctcttttcatatgttgcctatgtaattctttctca gaaacattatcatgaccataaaatagacaatgtattggtttctatgtttcttcttcctgccagtgtcctctcgcgttgtttgagtactattgttcccca ctctcccccccggcgtgcgtattatcgctgaaaatgtcatattatctaatcgaacaatgcccatttttttgggatgtttaatagcaaacatattcc gattggaattgcaaaattgagttatcatctttttattgttggtcttgtgactgtgagtttatgtttggaatatagttttgataagtttgaaactattgtga acttggaattttttgattctccaagtttttaaaacgctatgcacctaaacttggtatttttttttcaatttaacaaaattctactttcaaaaaacactactct tatttgcatgttccatagtatgtatttcttggcagtgtttttcaaaaatagaactccttccgatttaaacacataatgttgtgctttttaagcctagaca cgacttccgatgtgatttttcttcgaattctccctgtctgtaagaaactcacatgctgactgcaaagaatgtgcctattgcggacctcaatcagtg tcggctacactttttagtgtcgtcccgaaagttgtggtgttctgagaaaacataatttttattgatttttaatgcagcaaaatttcaaataactgata cccggttcaccctaattacccatggatactccaaatatgacagaaatgcatatttagtacaaaatataacgattctaaagtgatgctaaaatgt tattgttctaaaatcttttgaaagaaccagaaaatctcaaattcttaaaacatttttcatcgaaatgtgatatttgaccagccagtggcgcctaact tctgaactttgcttcacgcaatctctgctttgatttctgtcgtttctctactgatttttgttcactttcacgtaagcgttcaactcgcggaaccaaagc ctccgttcatatcatattaggcatcatatctaccatttactactaatcattgagttacaatcgattactctgatcgaagaggcactctacttatga ctacaacataaaagtagtatggaattcgcgtccaggtgaccagaggcgacctatacgaatctctattcgggtggaggcattatccgaatcc cgagaaacattcttgtttgtgtaatctgtctaatcaatccccttcctatttttctctgttcccttccttgtcttcaacatcgcccttcgatcatctgaat tcagacgattcgctccgcccatgaagttgggctacataaaaagaggaactgaaatgacatcaggggaagaggatatatatacattaaga gtactatcattatactatactcatattcggatgattctatcattcaagatggcctcgcttatactacgattgtcaagtcaacggtcaaagtattg aattgagcatttactggactagattagaccatttaattccagagtagataaattattacaggaaagaaaaccgagaaaaaagatattacaa a prx-1

SEQ ID NO: 46 agtttggccaatacctgtgaataaaaaataatttattattttaggaagttttataaatgcaaaaaaaggagtagaggaattgtattagaatattatt aaatggaaatatgaaatagcaattggttgatattatacttcgaatctcagaatcactaaaatgaaaaccagaactgcttctgcttgatttttaacat acttttatgttatttgcaatgattaaaaaatatatataatacgcgagaaatttgaaactggtttggctcgataaaaaattggtgagaaacccaaaa tatcgtgaaagaagcggtggaattaaaatgatttgagaaagtaaattttgataatacgaattataattcgaaaaaatggtggtacttaaaatata gcaaataaaacaggtgagaaaaagttttgaggtttttactatattttaatcaaaccgtttgttttatttattttcaggcatcgaaattttatgtactcaa gcttatagtaaaaatacaaatatttgatatattaaacagagataaaacataaataacgagctctaaaaaattagcatattttgggaattaagaaa accagtgaaagccgtaaaaatgatctgaagctatgaataagtttggttagagactctatttctagtagattactttattataataatgagcagaaa cagatatttttttagcatttttttcacttcatcattaaattaaaatcattacaaaaaatcgatagtccttgagaagagagacaccaatttacaagcag gcaacaaacgagagagagcgtattatcgtgtaaacggtatatacgggagaagagtacgggagaccgacggaagaaaagcaatgggag gtgtatagggtggtggctgtgttgtgcctaggaggcaggaaaatataacgttaaaaagtgcagacgcagacacaccaattgcccctcaga ctccaattcagctgtctccgtctcacctcgtcctcatcgcacacccttagaccggagcttaaaaggaggagaagcaagtacgcaagcatta caaacgacgacattactgacctcttataattaaagtaataaattgtgaaaatgtacaccgtttttttatgaattgcataaagcgaatttatttataaaa agttaatatatataaaagctacatgttcactgatctacaattttttggtttcagatttttttgaaatgttgttatcaacagtcgaactttaaatttttcttga aaacttgatacataaattaaaaattgaacgataacatttggctaacttttttccatgtttgcctttgtgcaaaggttatcacttgattatttattttttttga aatctggagcaataaaaaaaaaatagtaaggatagagataaatacaaactgaagcccttatgtttattacaagttatgacaatttcagtgtagtttt gaaaatatcaagtattgcagttaaatttacaatgccaaaaaatctaagaaacattacgaagttttcatgaaaatacctcgaaaactatgaaaata gatcaaagaatatccttaaatatgaaagaattcagacttcattgggttttgaaaaaaaatggaagggaaaaggaatctgattaaaatcagttttt ggcattgtagaagtatacttcaataagatgattcaatgatagagcttagtcagttaacattcaagttaacttgtaattgtaacctggtaataaaaa atcaaaagataaacaaaaaatattgtggaattatcaaatacaactaatcggaaaaagttgattttgaggcaaacatagcttcatctgctgtacat -continued tatgaaaattttattgaagaggagttaatgaagtggtacaaaacacgatgaaatgataaaacatgaacaaaatcgagttggtcactatacact aaacaggacacgtaataagaaaagtcaataggcacggagagacaaaaaggtcatcctacaattgcggtggctaactgcatcttaactacgt cgtagcattaaaaaagattgataagacagtgcgtgtatgaacgcacaaaaagaaaaacctagcaggacatcatgaggttttattttagcgtttt tttgcatatcatttttttattcattttgtttcagtaaaataagtttagattcatttttttaaagcgaaagttaatagaataatttgatcttgaagttgaaaattg ttgttaatttttaaaaactttgttttcaaattgcctaatattttttttgaaaacagaacataaaataac prx-5

SEQ ID NO: 47 cttctacgtggaattctggaggttgaagcttctggtctaaccatcatcagtaagaatgtaaagaccatttcgtgtttcatatttatgccgtcaattg tcagtacaaggggccgcccgttttcgtttcgtttcgtttaaattatagggaatacattataaaatcacaccttttgtgtatatcttcgtagttttattg gacattttaataggccttgtttataaaagaaaatataataatgatgacattatacaaaaaagtattcaaggaatgttttatagttacaaaacctata ggtatacagaatatgtcaaaatagggggaaaaaactgaatgtatgcagtcgacgaataaggttgtcttgacattttttttggttaataatgtttttcct gccagtttcgatatctttgaaattttgatccagatgacatcaatcctagctatggaataatgggggaactctctttaaattcacaacttcattcgag caaaatttgtcttttgcacacgaaaaattattattattattgcacaatcaaatatttttcccccgtgcaagtgtgcaatggggcgacgggtcgagc cagaaacccgtgttgttgaaaatcaaaccaagtgcaaaatatccattttgcttaatttaaaacgatctaggataactccactagcaactagaat atctaattgaaggattgaaatttggaaacttacaataaggtattctattttattacgttttcaatcttgctaggaaaacttggaaaaaaaatccataa acgtttcccggttatttcagaaatcgatagtcgacctccgttgttccttatctaaatttcatcaattgtatcctttttgataagacaatactatcttttta tcactacgtctccttcactctaaatcctaatgtagtatcaatcaatttgatgaaaagactacactggggcccacttattttctttttcaatcaaaattc acactttattttatatatttcttgtaaattgtatttttcttcatttttaattctacttatttcaacaattaactctcgaattcttcaatttttttacaga duox-2

SEQ ID NO: 48 aattttcaggagaatcaatcgacgagcttgaagatttcgacaccggtctactatcttccggaggatccgattattctttttaaaatttttcttcttttaa aaaatttcttttgaaataaataaattctcacctaggaatttcaacaattcaacttgaaaaaagttcgcgcaaactacgaacaaatgtgtgtcgag cgggcggagccactgagaaagaggagcaaaatgtacacaaaaccatatttgagtgtaattttttcaaagtttggcgccgattttctgtgagag atgagttttctcaatttatatttggttatttttattttagttcttactggtaaatttctgggtaagtcctgatgactttgaaaacgaaaaaaactctttcat tgatgctagtgcgattgctaggaaagcaacttttcagttaccaagaaaaagtccaaggccatagggattagctgcgtggcataacaactcat ccatcctcgcagatgcaaatccgctctattggcaaataacatggaagagtataaacattttctcttccacacggaaacctagtccccttgggg agcggtagtgcccacaaccccgcatgtttaccaaactacacagacagcgctattgtctgcaagtggcaaaaa prdx-2

SEQ ID NO: 49 agcgtttcgttttagaatcgccagtgtatttttttgtgatagtcctatgtgctttaaattatttattttgaaaggttcaataaattatattttatgaccgaa cacattatattctcagttgttatcttatatatccacaccggaatgttgaatatctgaccatatatatttagaatgttgcggtaattttttttgttgctgtgg aattttattttatttttatttttcatagtttcaacattttacaatttattgaaatttatgggttttaattgttatatttggcgtttttcgtttactttttcgata aaaataaattcagttaaaaactaagttataacaatgaaaacacataaatttgaacaaatcgtagaaaaatcactacaaatttgacagattttatgggtt ctatcgcgatttattgaaattaacgtatttaattgattattttagttattagataaatactgattcaaacgaaaaactttgaaaaatcgataaatctc gcagtactcctgaaaggcacacactcgtttgtacttaagaaaaattgtcgcgacgagaccaactgtccaactacggtagttttcaaaatacgc ggttcaccgcaaagtcaaattgcggacctgaacatttttttattttcccgcaaacttttttttttcaattttgcctaaagcgctcgaataaacatgaa agtctcgtgtttccttccatccagacctctcatttttcaattttaaaactaaaagcacttttttgacctactttttgtcgcaaccgccaaaactcgcttc cagaattattcccttttttaggattttcgacgcaacatctccaaccggttagtttttttcgcagattttctcgcattcgcgtagtttcacttgtttacttcg tggcgcctcgtttttttccgctctctcgtctgaccaccttcatatttattgatctgcgcctagcggcgcccgttgaaatactccacatttttttgcaa tcttgtctgcgagttcaggttattttcgacttttatgaaagcttgctaggaagccatagcaaccggggaagaatacgctagccaaatgagaga tagaatcgatcagctaaatttaagataaatagtgaattcgaattctaagacctgctcgaccagctgaaattctaaaactctgcgccaagatgta tagacaggtaataatatttgaattttctttaaaagtgaccttgaaccctaagattttcgctcctcctaaacgttgtagtctgttactccctgccgcg acaattgtcagcaaaaatcgcgtcacatgatgatgaaagtttgtggcaatgttataaaaagactgaccttatttcgtttcttggaagatgcaaag aaatgtttattaaaaattgcagtgtgaaatcatgtctctcgctccaaaggtgcatttcttatttgtttttttaaaaatatatttggttacttagatattaatt -continued taaatcacggaaaagtttaaacccctcgatttctgttatttaacatgatcactcacttttataacaattaatttggtttttcaaagatgttcccagaat gattattagttctcatttcgtcctccgattattttctttcgtcgctctccaattttgccaatgtatttcattcccattagataagcaccgcccgtcacct tattctccttcttttcacattgcaaacaaattcgttgccgttgggtttcaatatcatttcatttttttgtcgtattgttgttcttgtgattgtggttgttatttt atcgcggtattattttttttttgttaaactaattaatttttag pxn-2

SEQ ID NO: 50 tatcaaagttttgttgttacccacccaaactttgttttagttgcaacaagctcacttagaaggaaattgattttcagtatttattgaacacagcaaga aaaatcagcaaacgtggtacttgtgtgttgcatgcgctcattttaataataatgttgttgaattataacaaataaaaacatgtagcatatttttgtatt ttcaggcttaaataaccatttctaagcctaaagagaaaaaaaaaatgtacaacacgttaaatttaaatggagaaagaaattaacaacatttgatt ggatttagaaataagggcacgtaatacacaagtaccaaacgtgaactttaaaaatttgcgtacctaccatataatacaaaaccgtgaaaggt ggaatagttttgaatggcaaattgtttgaattcatttctatagtgctaaactgaacaaatattagtttcagttttaaaaaaagtgtttgaaattcttcat ttgcagtcaagcagtggcaattactcagcttttgacattcaagacaaccaagaaatatgttttcaaaaagtttttccgtattcagtcaagttctattt tcctctgaactatagctaataatttataattgtacatatcaggaaaaattatgtggtttaagaatctctgaaatttttttggaaattgggaggtgaaa gaatacagtacacttttgtaattttagctaatacgttcgagagttattatcattatggcagcacacttgttggtgatttctatttttttgacatgatatgt ttgaatatgattttcctcgttatgtggaaaattttgtagaggcagatgctaaacgacaagctagactttttagtgaatttttgaatcaattatttataa tggcatcaaacaaatcgaaaggatctgtgccttttgatattttttggttttgcaacaatttgtctttgttgttcaaacacgtatacatcaaaaactattg tttatttcaacattttcagtgtatcttttaaagatcacatcaggttgttactaaaattagttttgaattcaaaaataaccaattaaatgttccaaacatat aaaaaatatttcaaatatgtatcagcttcatgagtagtccataacaaaacccagaagttcatcggaggttgtatatctctgagagtgtcaaccc acttcttatttttgcgataaaactaattaaaaactaaaataggaacaaaacattaattttatgcttcgagtgaaaattcgtatttattcactttttagg gagtttctcaattattttaatacatagatacatagatattactttttaaataatatttacgttcaatccaaataagattttaaaacgattcagtaaaagtt cttgcaaaacaatcaattagcaactgagtttggtttttaaactgtttaaatctgaaaacatttttaagaaaatgaaatccgtctaaattcattatattt agcaggaacatgttaaaatttagtttctgaaatttaccaattatttggaactaatgtgaaataataagaatattattattcaatcatttttcttgcagac aaagggaattagaggcgtctggtcagcatttgtcgtggctcaactgttccgcaagatacattcgtcgagttgcgggtctcgtttgatattcaca aaaggaggggttcatctgcgaagttacacacttcttctatcaaaccacattgcctcattttcccaataactgtctcatttttgaagaagatgcgat caatcaccgtctaaaactgattgcgttgcaacaaatctgtgatgatatgatatgatggaacggacggaaaggttaaatttcgagtgaagaaaa aatatagaagtaatatgaatgagtagatgaaagaaaaagacaaaagagaaattgatatgaccgcgcagcagacaggggcatctggtgtga gcgtgcggtttttttctgttacctctaacgcagtccgtacacttgtcggcgtttatttgtggctgtgggcccattgcgttgatgacggtccctctag ctggctttcattgtgatccaattgcaccatttggtttttgagttttattctatttctatcgtcttttgtgataaattaattgagtgaatgaataatgtataa gagcctcattatattctatttactaaacaaaactcaattatttcttttgaaaagataatgaaatttccagtcatcattccataaatataattattattttg ccttcgcaataatcctaaagatttttttatatccttcaagtttatcaaaattgtttaggt mlt-7

SEQ ID NO: 51 attccaatttcccagccatccggaaattcgctgtaaaaattggaaagtaggacaaatagagaatataatacaaagattaaacactttttacgac aatgttgacttcgtcatggtacattcagaagtgtctgggaaatgttcagcaggaaaacattgcagaagagaaaaacaactcggaatgtttgct gaaaagttctgcttggaggtatttttaaacttggagaagatatcattgctctactttggcggcttctatcgcggtagtctttagtttgatcaaaaatt tatcaactggcaaaatacgtacaaaatagttatatacattttgctagttgacaaatttctgataaagttgaagggaactgagaggttataacctgt caatcaaggagcattatgatttaggcgcacctacttacttcatgcctgcttggctacttacctgcctattacctgcagtttatatgtaggcactga tgtaggcacgtagccatcaagtaggccgccttttgaggctcatttgacccatagaccttaaaataggccgttctagaacccttcttatctgaaa caacaatctttcagacattttcgaatggtcaacaacttaagtttttattttgcaaaaacaaaaaacaacaagttttcaatgtttttttgccagtggaa attattgttgttggataggtacagatgctaccgggttaccgagatcgtgcctaccaggcctacctattgcctgcctgccatgtgcctacctaca cttcatttcggcaaaaggtcaggggccaatgaaaaaggagcatgaatagattcgcatcagaaattgatgtcggtgtaaggcaggtgcaggt aaaatgaaggcaggcctgtggcaggcaaaggtcagcatggcaagcatttgggaataccaaccagtagttttcatcagagcacgattgcat -continued cgacgaaaaatttgaattttttgtgtattttgaagagtgccgtgaaaagtctaaatcttttgctattgcctctgattccttctcgaacctgaactataa aactgatgtaaagaaaaaaagtttccaacttaagagatatcttatcaatttaaactttaccgagtgattctgtgatatctcaaatttcagtcgaaaa tcacatgtggttttcccttttaattccgagagagagagagagagaaaggaatttcacctccacaacaacccataatcattcaattaggttctaa acacatacaagaagaagacaggaaaatgttagccttttagtcataggtgctgctcgatcatgatgttgatgaaccaaacatcgcattttgtag gaggggaagaggacaggagactgtccatttgaaagtgactactttgtcggatatttagagagtgacttacttacgaaagttataaagtttggtt agcaggaaatctggtttttactgagaaaactctctgagggaaaagctcggggtgggtcatatacccgcgagatatctgccggtcattatttaa gaatgtacagctctactttggcagatcatatctcggttattccagtacatatcaaaaattgactgaatatgaaaataaaggaaaatgttcaacct gtattttaccagttgaacatttttttgataaaaccaaaaataatcgaaattgtgcttaacggaaaagaagttagattaagattccaggctgggtcc cgccacgataagctgcaaaattatttttttggagctgtctgttcagaatcgtcgttattagaaggtggaagtgctgaaatctgaaaaaaagaact caagaatctatagaatctctcatatatgagagatcggctccgtgaaaggcactaatctggaatacttcagaaattcggcgaaatcttggaaatt gaaaactttgagatttttttcttgtagatcgaaacccgcgagatgtcagatgcttctgaattcagatttacaaaatgagctcttcagacactcctg aaagatcagctgaccagaatatgcccacctaaggcaggcgtgacttacctgaaaggtgacctacgcctattctcttgccagaactcgaaac tattttctaggaaaaactttttttgtagatcgcattccatgggagctataccttccctgtaggcacgcaggcactagtttccgtgcctacctggaat ccacataaccggagcacggagcagcaacttcaccttcagaaatgattcagagctttacatatagtttcctgttcctgaaaagcatgttctacga tgccatgattctcatttcgatgccacttctcaaccaacttttgccgagcttctgaacttgtcgagggagtctgaatacccccccaccgcccacac taaactttttttcctctgatccgtgagaatatcctcattatctcacaatcagtaatgtccaaatcaggcgggggaggaggggtaaaaaaacacg gaaacgaggaggcgaaaagcgtctctgggttcccgcccttcctcccacacgtcttctctatgcgtctctctgacaatctctcgttaaagttgcc ttttttgggaaaagcttctgtctctgtttctctctgtcaacgtgtttctcagcttgcgggcgccaaaccaccaccaccatcactgactgtcgattc gcggtgtgttgtgtttcaattgcgtaaagagtgagagagaggaaaagatagagagagagagagaccccaaggttatacgtctgttatactt gttacccatatactcttctacacctttaccttcaacctttccccacattgactccgcctctctctctcttacttcttggaagacactccccacccccct cttatctatttttttcgaaattctcgacccttcaccctcccccccttacccgcaccggtcatcattctgactctgcgaactactggagaggaacacc

ZK550.6

SEQ ID NO: 52 catgaaggcgaccgaaaagtgtccagtgaagattttctaaaaatctcgaatctggaatcatgatgtgaaatatatgaataaagaatctttttaaa atattttgaaaattctatacatctctaaaaaaatgcaatctcgttattacaaaaagcaaaatctttcaccttaagcctagatgtaggtaatgtttgat gaacagtaaattttgaaacagtaaatttttgaattacaaattgaaattttttaaaatctattcagaatccctatatccgcatgcatcagggaacgt gccaaatttgaaaaatgtgtgtttctcaatctctaatcatttatcatatggtcatgacaacaactggtgtcaaggtgtacgataacggtacactgt ggcaattgacactcttttttttctttatttctctattcaacaagacttgtatttattaagaaaatgcaatgagagagcgtggtgataagacgggtaatt ccctcgcttttctcatttttttgcggtgttgtgttcgtgtcatttgagataatccatgttgattccacttttattgttgatttgatagatgttccaagtttttta ctgcttcctgaaagcataattcttaaaaataatgcttcatagcagttgtggcttcatacaattttcaaaaaaaaattcactgtttcaaaaaaattga attcaatttcctgcattatgacgtacgtgttaaaaaaatatgttcacctaaaaattccgctcgaactgtcgcgaaatctgtgtttcagtgaaataa aataaaaacatctagacaaaatacagttctcctcaaaaattgctgtttcaaaataataatttaaaaaaaaacaccaaagtgtcgtatttaaattta aaaaaaaactatcgtttcaacaaaacaggttcaaatctattttagtattaaaatctataactttataaaatttgctatttaggttttacgaattgttgttt tttactctgaattgtaaaattaccgtttcaaatatattcttctaaattcaaaaatttagtatacaattttttctagaaacattgaagtattaccaggaattt ttggatatttcctataaattctattttgatcaatttgtagttgtcttatcatatattgcattggatgataataggaaatgatccgattctctttcctgttcc aaaactaggtaaatgtacctcatatattttgttaattttgtagtcacaataacatgttatgataataatatcgataaaaaatatcgtgatgtttaaaca ttaagtttcatttttttcggtactgttctaattgttcaaaacaatttaaaaaatttcggtcaatttatagacaataccgattttaataatgaatgtaaaat tttcactgtttcactaattttataacaattttcattccttccaattcacattgtgttagtgtagtgatcattacttatatattttaaaaaaatagggtgtta gtttttttccgtttgtctgtttgtttccgtgacgtcacaacgcatgagacccattttggcgcaaattcaaatttcttcagaaaattttggtgcaaact caaatttcttcagaaaaattttagcgggaattcaaatttcttctgaaaattttggtgggatttcaaatttgttcagaaaaattttggtgcaaattcaaa tttcttcagaaatattttggtggtttttttcttccgcgccggaggcgcgatcagcagctagttttcaaataaatttactgtttcaaaaatacgatatttt ttgcctaatttttgagaatatcactatgacgtctaaacgtaaagcgattccataatctacttcaaaattccaggctccccaa -continued

C28H8.11

SEQ ID NO: 53 cagtgtaggccgtcttgctcatagagacaaataaactattgagatggattttaatagaaaatacattttatagaaatgagaaaaataaagtttta ctattagaaaagcgtaacaaaaagcttccgtaattatttatatgaatgttccgatatttttagcgatgtgtgcatcgtgcactcacaatactaatgt tatgagcttccttgcaataaacggtggggctggaaactgacaggaagtgggtttattcgatgattacaataccacaggactgatgacacgcg taatcaaaagttgaaactagaaaacataaacacgcggctttcatctgaatcagagacgaatatccataaatcacggcccccaaatagaaac cagtttattttatgtcacttcttttccccattaactttcctgtcacaatcatacaacagagttcgatcatacaggtccaaaggttttgggtatatcttgt ggacatgtatgctgtgaaatgttgaacatttcatataaaattttaaaatcagactattagatcgaatagttctacgaaatttgtaaacagtttccatc gaaatacctatttttttgtaacacgaagtcgacctctctcccggagacgctgctacagaaaggtttgaattttgagcaaagttacggtattaggtc tcgaatgaaaagtttcgaaagtacgcaaaactctacaatagggttaagaatcgataattttctagattgtccaaaaaagtagactaattttgcca ttccgttcagtgccttcaagaagtacttgaagtctatacctcacctacttgtctgatatggtaatttactatcgagcttattagcaattttcttcacgg gaaaggagttgtaggttaacttcaagtcgcgaggtaggcatatttgtgcctggcgataacaagagacgttccacaaacatcttactcagtttct atttgaaacttggcgaagtagacatgaagttgaaccttcggaacgtcagtccaaaggtttgaaggaggggttccccgaactgtcatacactt catttcatcgtcagctgtctgagatcaaacattcaataagcatgaagatctctgaacgaccgaaaagatatcgataaagtgatgataaaggtc tgcagcagaatggttttgcagacatttcttcagaagttaaaacaacgttgtcgtacccaagtatcttatcaagggagaaaaagagtcaaaaga taaattccgccatttgcccctccggtccgtaataacgagtatttcttatcacgtgtgctgatcttattcttaacacacatacaatcaatcgatttgtc agacatgggaaagaataagacgtgatggatgaatggaataatgtgaacgatgaacgagatacgtgacagtcagaaagttcactgtgaata gagtatggtataaatggttgagagacgacggattacggaaagatcgaattatcacaacgtttttgatgtatctggaccgttcacatggaattta gtaattgttacttcttgggcgacagagaaaattcggccagtctcatcaaatagagagtttttttgaaaatctgcattgcagggcgaacaaaatc aatttccacattattttaggccggttttaaagagaaatggagagattttgagaactgtgaaataaggctggttaataaattgtgcataaaaaatct agagagattggaaagccatgcctatttcactgcagcttcaccaacaatctaatcataattttgaaaatgaaaattacattagcatggtcctttact cacattatttaggatgtcgacactatttcatttgaggtcgctacaactgttgctcaaagttggagcatgtgcgacctatttccactcctcctccac agaccccgtttgattggtgcaaaagtgggcagagcgaaaagctgattggtcttgcagttttcattttgaagggaattaaaaaacggagttagt aacaattgagaattaccgtttttaaatgtataacttttcaaatcttccgtttctgaatttattatatacatatattatatagactcaattacaaattatata aatttaatttatatattatatagccttaattattaaactattattttgagatatttttaaatttcaaacttatttcagtatttaagtaagcttcctattcacgc tactccacttttagtgtgtttcaaatgaatggacgttataccaaaattcaattgaaatatccagcttcataaatatattggcatgggaatgagcctc gtcacgaacattttagaaaaacatcaggacaaacttatattgtactataacttgcaaacctgcagcagcagaactttgaacacccaaatccatt tccgacggaagtattctacatcttgtggccgcgtatacccatgactactgtacccaaactggggaaaacccaaattgctagtaaacgcccac taaataaactgttagcattgaaagtgtgaacacgtgaatcgtatgtcaagtgataggaagtgtgacgttttgtaattaatcttaacttccaagtgt ttgtttccttgaaataagatgcctacacacggcggcgaaatggatactttttatgtctgcgcttattctctttgtcccccatcatcatacaatcttca acgccttcacatatcagacagtccgtcgggcactgaccaaccattcaggctgcctgtctgtcatttataggctgtctagttatcttcaattaatgt ttgaaaattcagaagc

C35B1.5

SEQ ID NO: 54 aattaattattttcacatttttttcgaattttgtcgatttataggcgaaattttacgttaacctaacggaaatatgagtttataatgcattttttaatcgaaa attcggtttttttcaataaaatttgctatgaaatccgcaaaaacgcctggaaattgtctgaaaacgaagaaaaataaaaataaaaatccgaattct gtgcattgtgacgtggcggtgtagcgtacccgacatttaatttcacgacacttgatttatgatttattgattctcgatactgcaagattccactt aaaacgtgcggaaaaaatccagaaactgtaaataatactaaaaaaatataaattttccacaaaaaaggcatgaaaactaacaattacctcaa atatcgtgaaaaatgcaaaaaaaataagcctttccgaaaaaacgggcccttgggcctttaaaggacacaaaaacaggaaagcataagacac caaagagtaattggatttctacactttggttcctagaattatttataaggtgttattgcgtttttgtgagattgttctatttatccagtcaaaaattgca ttttctttgtttttgcttcaaaaaaatacattttcagtggaaatttcagctgaaaagcagaattttgaggttttcgagtaaataacgtaaaacactaa attacaaatattgatattgatgtcttagaccaaattacgtaaacatgtagtatattggaaaaaataggattagtcgatataacttaattatcgaa -continued caaaaaatgatttttttctccgatttaccaaagttttgacttaaaattccgattttctgggtcatttttcccctaaaaatacgattttaattcaaaaaatct atattacaaagaccaaagtaccataaccttcaaaaaacaaccactactctattgcatcagcgaattgtcatcacccctctcaaaatatacaaa acgtcatcatttttctgtgttttctctaattctcctgaaaaattctataaaaccaacagtttttatcatcaaaaatgccttttgaccgactttttttaaagt tgaaaatcgtacagattagcagaaattccagagatcattagaagtatgctggaaataataaaattattctaacatttattaatattagtaaaact aattctatacaataaaaaagtaaaatttaatattaaaaaaaccggtttttctcaaatttccattccccaatgtcctgttctattatttgttccgattcgg ccacagaacgcgcacacacacactttttgctgattctctgcctcctttctttgatttgaccgcatttttatattgattttcggccacaattccactattt gttcagtagtcgatttgttggaaatttcaattccggcaattcgccgatttgccggaaatttaaattcagacaatttgccggtagccggaaattac agttccggcaatttttttaatttgccggaagtttccatttcggcaacttgccaatttgccggaaattcgccgttttgccggaaattttcaattccgac aacttgcctatttcccggaaattacaattccgccgatttaccaatttgccagaaatttttaattccggcaatttgccgatttgtcggagatttcaatc cggcattttgccgaaaatttcaatttcggcagttcgccgatttgtggaaaataacaattctggtcattcgccaatttgccgaaaatttcaattccg gcaattcgccgatttgccggaaattttcaattccggcgattttcctatttggcgaatatttttaattccgccggtttgccgctttgccggaaatttca attccggaactttgccgatttgccgatttgccggaaaaaatcattgccgcccacccctaataaagacttcaaaatatgcgtattattgcattaa cacgctaaaactctctaaaaatccccaatttttcagcttaaaaaaccccaaaaaa Endoplasmic Reticulum Oxidative Stress Toxicity hsp-4

SEQ ID NO: 55 atccatttatttatgtccagtacaagacgaccgttcatatcttcttagtcattttctttcagccggtgtactctttgttcaatttt ctctttcttggtgcaacctttattcacgtgtatcttctccgagcttgtttgcatattttttttttgaaatttcatgtgctaattta ttcatgtcatttttgaagttaaactcttcacatttcataataaatatttattgaacccgtttgactactccaaattcacgaagtta ccaaaataaaagtgatatttgactttcagaaataccatttcaaattccctaagacgctcgggaaatattaattactgcaatttata ttctgcttgtatttttcgaagttgggtccaactgtgtgaagtattgtaagaatcatatccttctccttcacattctacataaacaa ttcatttctattctgtaaatttttttctgatgatttacggtaaaaacgagcgaaattcggtccgggacaagggtttctacgacgagt ccatcgtggtgccgctcgcttgtttgaattcccgcgtgccgcattcctcgtgtcgagacccgatgtccaactggggggattaccaa ctcgggggattggccccgcccacagaaccgtggcttgcaatttttttcttgttaattctcgctctattgagaaaaaaataattttaaa accgtgcggcagtttcaaaaaatgggcgtattgcaagccacggttctgtgggcggggccaatcccccgagttcttcgggtctctaag gaaaggattcgtacattctggtcattttatttatttttaacctcatttattatttaaaccgcaatccattaccagttccattttct ccgtactcgtcagtgtagcgagtgacgagtgaaattgaccccatttcttatcttatcgaaaacaatctaaatagtttccgcattcg cataaccagaaaattcttcggtagtcgttctcatttgtttttatttcatgaacataaagtaacgccatagtctttttatgaaacgt ggcgttaagaaagctctcgaaaagtctcgatttctccagcactaatacacgtcatctccgataagtacacgttgcataggcggtcc taataaaagcgaccgcggacgttcacattcagttctttgttttctttttgtcgtctgcactccttctttgcgacgtgtattttgtg ttcttctctgtgtttccacttctcgttagtattctcgcgcttctactctgaaaggtttttcttcttaaatgttctcatttttcagc cactcagcgaacagttgaactgaccgctcatcaagagaaaaat dnj-27

SEQ ID NO: 56 aaatttcaacttccggagcccgatacctataggccacgtgagaactttctcaggagagacgcagagagacacaaattgactgacga ggagccaggagaaatgagcagaaataaatcaaattgaagagtttctgaggagttcttttttctctcttccacttcatcctacccgc ctgagccaccggggggaactgacaaaagagagctgtcacgtggttccagactgtcccattacggtttgatctacaaaaaatgcggga attttttttcccaaaaaaaaatgtgacgttagcacctatcggttagccatacgaaatcagttgagaagtctgccgcatttttttgtaga tctacgtagatcaagccgaaatgagacactctgacaccacgtgagatgtgctcattgtggccgcgagagtggtgtcaaggaatatg agagtacatatggtaattggtgtataccataattagatgggaatttgagagcttttggaggaaggagagggtttttcggcgaaaaa ttagtgtccgaaatgagaaaaattgaaaaaaaaatgcaagttttcactaaaaaactacactttttggagaaaaaattggaaaatctgc -continued cagttttcagtgaaatcgagtttgaaaaaataaaaaattcgagaatttttttttttaatgaaagatttgtgctcgaaatagctgta aaatcagcttaatttccgaaaaaaagatcgtgattttctcgaaattcatttttttttaatttgtaattttgatttttccacacaatt tcaagctttaaaaatgttaaaagtcacctaaaaagtcgattttcataacaaaatacctagaaaattgtcgaaaaccggcaaatttc ggcctaaatctacttttaggcagattttaagttgaaaaatgcacaaatatttctaaaacctgacaattcaacgatttttttcctaga aaaaatcgtcgaaatcgactttttcgacttttcagtatttttttcagtagaaaagttcacaaaaatgtccgaattcgacggaaaatt caaatttttttttttccagaaaaagtgctgattttagccgaaattgggtggaaaaatcgaaatttcgacgaaaaaaatccaattgca attgaaaaacattgattttcgttcatcgaagtatcctcttttgttattttccactttttttcccgcaggtattctctcgccattcac caagacatcacacgaatcccggagacgcagacaactgaagagacccactttttgtgtgattcaaaggggtcaacgcatatagccgg ccgattcgtgatgactcatctctgtgttattctataaatctcttgatttttttgaggatttaactcttttttttcgaaaaaaacgt gtttttccgaatttttgtatggttaaaagtatcggaatcaccgtttttttgttgatttttttctcaattttctttttttgtttgagtaa tgattaagaaataagaacggaaagaagagaagaaactgtgaaaaatgagagaaaatatttcaaaatcaggaaaaaaaatcattttc caaattttcaggatattatgcggattattagggttagaacacattttaaattataattttaattatttttaacattgaaaaaacaa aaaatcatccgaaaactactcttctttcacaaaaatcggtcaaaaataaaaaattgcgaaaaaaaaacaaaacaaattaaatgtag caagcgcgctccattgacaaaatgccgaaattttttgcgagcgaagtttgaatttcgttgcaacatggggcatttttcgtgaaaaac aagatttaaaagaatttatactttattcttgctcaagaaaattaatttttccataaattctattaaaagtggcagttaaaacaaca atttctaagatttttttcactttttttttggcgtttgcttgtttttcagagtttggaatagttttatgtcaaattttgatttcttct cattactttcttcataaaaaaaaaatgcaaaaaagcaaattttatcactaaatcgttcaatttccacctagaaaagacgaatttaac gcaattttccgattagagcgcatttgcattgtgcgggaaattcaaattattcaaaaattctcctctagtttccagttctagtacaa tcggtggccgagtttttttcttttttttttccagcggccacatagcaagagccaacctgtatacttttgcagttcttgtgcaaatct gagctccgccgagcacaaacaagtttggacagtccacttctctgcgtctctcgtgatgagtgtgctctctcgtctaacctctaatc cttcccagatatttgcacatctaccccagttccacatagccataaagacttgggtcatttttatcgatttttttcggtttgctcaca atattgtgagtttcttaattaggtcttggtagctttttggagcattttgtgactttttatgcctaaaaaccagtttaaatatactt ttttaatgcttaactagatccaaacacctttgaaaattgtccaaaaaaaattatttttttggccgaaaatttcagtcgaaaaaagcat tttttcggcctaaaaaaaaattccaaaaaaaatccctaatttttttctgtatctccagagccactttttaaggtataaatcagcaaaat tttccgatcaaaattccatttccctatatcttttccctctctctatctcaccctatctcgtgcgttagccgacgtttactaagtcc cagtcagtttaattctatcaaattcttcacttttacttacagaaa dnj-7

SEQ ID NO: 57 atcacacggttgaaaaaagtcgaaatgaatgaaaacaagggcattttggaatttttttaaaagaagaagtaaggtgagttaaaaga atgaaaagcggcgtgcttgagatctaatgaaacaagggaccgcccttgtttgtgatttgctaacaaccgctatcgtttgaaatatt ccgggcggagttctagctgatttctacttggagtatcatagaattggaaacggaacgaaattgccatagtatgaaacttttaattt gtatatacaaatataatcgacccatttaataggcctactgcggattaatttcagtgctccttctaaaggcagacaatgaaacagtt gtgtagtaaaaacaatgttcacaagacctgaaacaattttctgaaaattgtttgataatattgttcaataaacataaaagatggtt cacaaaattaaaactaaattaaaaattaataagaaaaccagttgtcacaaacgcattcgcaaccaaaaccgctaaacgctattcca actaaagttataattgcatttttttgcaattaactgttttaccacaaaacaaaacaaaattccagtttaacaaattatcaaaattcc aataagatcctttttttaaattaaaaaggtgagattttttctagagagtccgaatagaaaatggtaaccaaaccgatgacgatgacaa tggtaatcggatcaatgcagaagttgttttgaaattattttcaaagtcgttaattttgagaatatttgattttttttagagtatgt actagatttgttctctacctcaaatgatcaaattctttgactgcattaaaacaaaattttggcaaaattatcgaaaatctcagaga aaataaacaaacagtctatcacatttcaaatgaagaggaagccaaatttgaatatagacggtccgatgaagaatttttttgacaatt tattttaactcggaatggttattaaatttgatttttttaaatttatatttcccattattttaattttttaatttatgaaactttttt atgtgaaaaaaaaaatttatgtgtttttgattataacagattttacgtcagaagccgaaccatctttaataaaaaatttgaaaaaaa -continued aaatcacttctacaattttcatttttcaaatttgagccatcaaagtcaattaggaaaattaattctttcaatcgttgcagttacag tgctatttcaggatctttgagagctcgccgtgagcttggttctggagattcgcagataaaaattcatgagtaaccgtttcaagaca tgggctatcaaatggcataggtctcatatgcaagtccgattggcatcttctgatggttccctagtgagtttattaattcacaagag cattgtatcggaattttggcaaactgttaaaacggaattatatgctttgttcagttttgtttcagtgtgttacacagttaattgtt ttagaaaccattgcaagcaattataactttggtgttgaagtttagttgtgaatgagttcgtgacaactggttttcttattagtgtg tatattaatcttgtagatcatctcacatgcttattaggcagtggtcatttctatttaattttgtttgaaagggttttaatttttg atttttttgttttgttttagcgaactcaaattgaaactaatcgccaaattttataataaggccttttcaaaacatttgatcaaac ggaaaagtttttcaaaaaataaaatttgcagcggcttaggcacacgaacatccgacaggcgattcaattgtatcaaatacttag tgcttctaggcaaaatgtagattttagatataaattaagcccttttcacagtttgtaacgccagggaaaacatttttgagcaaat tttgaaaaatcttatcagaaaaatgttttgattgggttaaaaaacacctagaaactctactcctctttaatgaaagcttgtgttt caaactcttttgtgcttaaataaattttatgcaaattcataattttaccaactttttcccactgaaacatttcaaacataatg tcaagtcgtacaaaatcttataactaacgattttctaatcgtatctcctgttatcgttatctttacaatcgaagataaacggctga gaaattttaggtccgaggtacaccactacgcacaattgcggattttgcactatttggagagttgagccaaaactgtcttactttt atgaaactgtggaatgttgtaaacaattggtgaatatatttattgtaaaattttatttgaaaatcatattcttttgtatcgaatt ttggaattccacgtttgaaaactgcaagagcgccttatgctgacgtgtgttagttagattgagagactcgcacggagtagacgcag acacaccacacagcacaaacagacgtcgacgtccgcaattctcgttggttatcgactcttttgtcccattccaccaccaaaacttg ccacgatttgatgttgctaggacataaaggtccagtgggaaactgcaaattctttgttttcactggtttttttccatttgttagtt actagcttgataatttaaaaatgaaacgtctcaaaactagttcacttgacctacttcgaacaccaatttgtatcgtgcgtcatatt ccttgccgttgcaatttcacgtgcacttttatgaatttcatagatttttttcagataattaaccgacaaa

Y41C4A.11

SEQ ID NO: 58

Ctgttgcggcgcacctcgaagaatagctcctgttgggacattttgtgatggctgaagtaggaaattatattaaatttacattaaaa ctaaagaaaaaatacgaaaaattatgggaaatcagtggtaaatgcgaaaaaatgatttaaaaaaccgataaacgttgaaaacgcga cggtctccaaaataatgcaagcgtgctccactgcgaatcccctgctcatttgcgcgcgcattcaaatttagatttccccgatttat cgtgaaaatcgctgccatctgacaccgcattgcaccgaagatggccaaagataaccaaaaaaccaatgaatcattggtctatcgaa aatacattatatttgttgggagcagccccacgaaagccacgagagcccgcaaaaaggtaaatattgacttaatatttgtggcggt ctcttacttggttccacttacttttaccaataggcagttatttttgcgttttgtcgaaaaaatcgatata arf-1.1

SEQ ID NO: 59 atcgccaaccaaggaaagtagtgatctacaagttttctctgcaaaaaaaacaatcgtaattgcataacatctatcgaactcgagag tctcccaaaaaatccctccaaatctttactgcatttgcatgtaaagatttacctatttttctaaactgctgtgttcctgtatttt cactctacctgtttcgtttatttatttatttaagcatcaagtttattgaactctaataaattctcgggaaattcgtgtcttaatta ttcttgccagggaaagttacgtttccttatcgaacacctgttgcgaaaccagaaaagggcgggtctgactaagtgaacaaatattt cgtaataactttcttccaacagaaattaaaacacgcaaaaaacggccaactcactagctggaacgtggagccatggagatggataa aataactctgattgtcgacatagcttcaagaatatcgtattctgcattttcaaaaagtctttttcgttcaaa lips-11

SEQ ID NO: 60 gcataaaatgtttgaacttggcatattataatacaaaaacaaaaattgaaagagccaagaaatgggcggagcctattattgattat ccttgtattttgcaaaaattgttgacagatgatttttttccacactaactctattgggagtttttcaacaatttgatatccaaaa aaaagaggaaaatccgctaacaatgtgaaaaactagcatcataatttgaattgccgcgcagtttcctggcgttccagaatgatcta tttgtatttgaaagaagacctttgaaataggcatctcaaaatttgccgagcttggcaaattcggcaaatttctgtttccaataatt gccgagcacggcaaactcggcataatcggcaaatttgcctggcttcgcaaactcggaaaaatctaagaatttttgatatttttttgga gcacaaaaattactgttacactaagaacacgtttgcttggttggaaatgtccgtgtggttcaatttcatgccagtttactagattt ttggagccgaatcaagagttttagtaattgtttttctgttcaacttttggtgtacgcggcaaatcccgaaatttgccgaactcggc -continued aaacagcaaaatatgaaacgtttatcacagaacttgttaggggatttttcaaatatatatatattttttaattcttggaaaaagc ttgtctacctcgaaatacctaaaatcattcaaaaattttaaatattaccattgagagcaaatttacgggcctctgaaatagtgga aaaatgaaaaattaactgaaagttaatacgaaaattttcaagcttgtaaaagatttttggttgttccggaaatcggataatcggaa aacagccacccttgtttctgactaatgagctaagaaattgattggtacttccatagttgatgaatgttatcagtaaaatgggtttg gcaatgcttttgttattccaccgtgatataaactgaaaagcacaactgataagatgaggcacctgagtgtctagacatggcaacgg aagtgggcgggattggaatttttgagacgtggcttaagttgtataaaactgaccggctaaattttaatttcagtgagtttttgagt tttccaattctcacccaaattccacattttatgcatcgcctaagttattttttaatttaatttttttttccagatcccga srp-7

SEQ ID NO: 61 gcttggagagcatctatggcgtcttttcggaatatcaagtcagtcacgaagtcttgtgccaattcctttaccaatcgttcgaatct ggatcgaggaatgagcagttcagtagactgttgttgttttcggatttctcgcagagcaactgtaccagaatgaaaaggatatgatc gtactggctgagtgcacgatttgcggcatactcccgaaaggttctttttgccagccattgtttggtagatgtggtgtgaaatggag agattgtaaacccttctataggtgccaaaggtgagtgggcgtagcttcgaagtcaactgcggtgaagggggcgtggtttcttacta ttagagaaactgtatcagactaactccgataaagccatagtcagtgaactctcaacatagttaggaagagttactcagattaaata aaatcgtcaaagaacaatcaggccaattctgggctaggcatagttcataggcagaacttggtagaggaaatcagagtaaagtaacg atgattttaattttttccgtctgaaaaaagatattgaaagcattttgccgatcgaacaagacacccaaagtctcatgacgacatccc agaaagagtttcagccaaattcccaacaacagcctaaaggaaaatctgaaaagaacaaaacatttgaacgtgctagagcgtacttg cacatacttgcacatactgtaagtcaacatagaactctactcataagtgtgacaaatttgttacaccaacagtacgaagccaagat ttgattaaagacaattgttgtttaaactgcttgataaaaggtcacatggttgcaaagattgccagagcgaacgcaaaaattgctct cgctgtgaaggtggtgaacactgactcagcaaagtcggaaaacatgatatgatttgtcttagtttattggttacctttatccgaag gtgcatcaagttgcctattggcgttatgttgaagatgactgatataatacattgtaacgatttcgggaaaaatacatatttaacaa gataattattttttttcgattttccgaaaaaatggaataaaagaaaaacggacattttcgatatttttcaaaatccaataaagatca gcatttttttgtatttcaatttcaaaaaaaaaatcgaaattaatttttttaaaattggaactcgagttcctgctcaatcctggtcaa tgattaaattaaattatgctcgtacagtaacttgttatttctgtgtttaattaaaggcgcattactgatgcgatttgggtctctcc acgattgcactctgttgtgttatttacttttattttaaatatttttatttgttattttaattcatttccgcatcatttttttcaag gaatttcattgatatttatgccattcgatttaaatttaatttttttgtcgttattttacgtcgaacaatgagtcaaacacctaattc tggttatgcaacgtggggttacacccttactatagtatatatatagaatacttgcaaaaattgttatatttacacttcgaaaatca gtccgaaaaaagacgtaaagcaactttgcctaatgaactttttttaattaataatttcacaaaaattgtgaaacttgttatttctct tgtttttttgcctttgaattttaaatatgtcgaatttttccaactattcagctgttcttgtcgatttttgttaatttcgaaactagt tcagtaagaagtgcgaattcagaaagaaaaacaaatcaagagtattttttatttcgtttttctctcaatttctcttcacttctctc ccattttagtgcatgtattttcctcttctctcttcttgttgtctagtttagacaacgcggtcactgttagagagtgcagacggtta gcgtaacaaacaaaaaagtagaattcatttttggcgttggaaaccgcattaaatactgtcctcacagtttccgttcgtcttaattt caaatctttgctcttg ale-1

SEQ ID NO: 62 ctcgttttcattgttggcttcgattattggattttataaattatggtgatgtagttttgaatgtagacaataaattggaaatgaaa tcgatgaaatgctcaagtttataaatagcaaaaaaaaaaacatcggtagactttatttgatctactgtgaaaatgttttccggcaa atcggcaaattgccagaattgaaaatttccggcaaatcggcaaaatgccagaattgaaatttccggcgaatcggcaaaatgccaaa attgaaatttccggcgaatcggcaaaatgccagatttgaaatttccgacaattcggcaaattaccacaattgaaaatttccggcaa atcggcaaattgtcagaattgaaaatttcggcaaatcggcaaattgccagaattgaaaatttcggcaaatcggcgaattgccagaa ttggaattcccggcaaaatgctagaatttaaattttcggcaaatcggcaaattaccagaattgaaaatttcggcaaatcggcgaat tgccagaattgaaatttccggcaaatcgcaaaataagcaaattctataaaaaatatatagcgaaaaaatttcaaaaaggcactgtt -continued ttaagtgtttccgtcttataaaaaatcccttgaaacattttcggcaaatctgatggcaaaccggcaatttgccgaaaatgaaaatt
tccggcaaatcggcaacatgccgaatttgtcgacaaaaaatttgccaaaaggcaattgatttaactagttttaactaaatttgagt
ttttcatcgatttcatctcatttcccatcttcctgagttgtattaggcttcacattaccccccttcaaagtacggtagctttgaaga
ccattttcattgacacatagctccgggtcgaataatgtatcgttttccaccacctttcgtcaataaatcatttacgtcatatcgtt
ttttgcaagcttatacatatttctgtgtaggcggcaactgagactgataaaaaacgcattttctaaatggtttttgatgttgttg
gactgtgggaatggactatggaattataacaatctggagagaaaagagtgcccgagagaagcagagaaacaagatgaacgtggcat
acgtacacttccacaacagcagccgtcttgtggcctatataaatgaccagattcaagcggccatttatacttttcgatcttcttct
tttttcctttgtcttgagattgaaatttgagagataacgaatccaaatagacaatatgcacttaatttacttgaaaatgagcttaa
aactcacaaaaaaaacaaataatttggactttttgcacatttcctgcaaaatttgatgtttatccagcttgtgatgaataatttt
tgcacagcaaaatgaattttgtggcaattttaatttcaatcttccatccattagttttcctggaatttttttgttgaaaattctga
tgacttggagatttaatataagctttttagtcgaattcctccgttttagacgtctaactagttaaaaatcgttcaaatccttttaa
attaattagtgagtaaaattcaaaaagttccagaaacttttatagttcattaaaaatgtatttttttcacacctagttttaattta
aaactcacgtggtgtcaggatgtctcataagggtttgatctacaaaaaaatgcgggaattttttggaatcagttgagatctgaac
tcccgcatttttgtagatctacgtagataaagccgatatagcacactctgacaccacgtgaaaacctataaattctcctaattca
ttttgttaatctgatcccagtgacctctaatcttgatcattttatcaccacgcgtacttctatttgcaaagacctatgatatcag
ttgtctgacggtcagaaagtctcggaaaaaggcgttgaccgagtaattacaataaaaaaattaacgatataaaacgtcgaatagcc
aaataggtagatagcgtcagaaaaaccaatcagtgatttgctccgcccactttcaaccaatcagaagggtttactgggcggagct
atacgttctcaatttggaaaaagttcaaatagtgagattttatctttttttttttgtagattcatgaataaatttcagactaattc
gtgttttcattctcgctaatttagctttattacgcgaacactaggttctgagaatgcgtattgcacaacatatttgacgcgcataa
tatctcgtagcgaaaactacagtaataattcgaatgattactgtagcgtttgtcacgatttacggggtcgattatcgaaacggatt
aaaatcatttagttatctataaaattaagcaagaaaatgaggaaataaaatggaaaatatattcatttaaataatcaaccccgtaa
atcgacacaacagagctacagtagtcatttaaagggttactgtagttttcgctatgagatattttgcgcgtcaaatatgttgtgca
atactcaaaaattgtgtgactataataattagctatacaattctgtggtttttttgagcaaaaccgaaaaacgaaaaaaatttcgtt
tttggcaaaacactccaaaatcggtatttttcattcaaaaaaccatatttttttacggtttacgccctatttcctacaaacaacaga
aattgaacgtggtgtcagagtgtctcattttggtttgatctacgttgatctacaaaaaatgcgggagaagagacgcagagttctca
actgatttagcatggttaagagtgtgctgacgtcacatttttgagcaaaaaattcccgcatttttttgtagatcaaaccgtaatgg
gagagcctggcatcacgtggcattagacttttttgagcaagtttgaccaaaatctttttttcttcgatttttcggttttccaaaaaaa
taacgccaggcttagcctccacctcaatattcttatgtgattgtttccagaacctcttc cccactaaaaca ckb-2

SEQ ID NO: 63 ttactggcatttaaaggaaagaactcggaaaatttatgaagatttgaagaaaggcacttgttaattgatgggttttcattgtgttt
tattaaatatgaagttgtgatagttttaatgtgattaaaataaaatttaaatcaactatcgtgaaaagtttaactacaaaactgta
ttaaatctgagaacacatactttataagttgggaaattgttgatcaagtctaagttgaactaatatattcttgatggaatcggacc
gaaaaaaatcaatttatcttattcagaaaccatcttgagaatgcctacattttggcgcgagaatagcggcagaagagagagctagaa
cggtaggcattctcatgatctcatggtttttcttatacatttcttttttttctgccgtttagtttattgatctcaattggtttgtt
ggtctccccctccccctgtctgcggtcatttagtccaataagtcaacgtgtactaactgcacctggactttgttcacttcctctat
aaaatgacttttttgattgtcttctttcttattctatatctacttttttgaatttgtaaattttatagctacaatttcactttgaaac
tgtttggttatttttcagaaaccatacaattttgtttctccaaac fipr-24

SEQ ID NO: 64 tggaatgggaatgagaagattcggatacgggtacccaatgtggggataagctgtgcaatcactactgtgtagttatgtataaacta
tgtaaaattgaagaaaataaatattttgactacctcaatccatgttgtcacactgtaacaagaaaattaaaatctgataagcttca -continued gctaaaaactcaaaactaagattctcaggaagatatttgggtatttgaactaattttgaccgcttttcatgcacacgcaatggatt tctaagtatccaagtatgattatttcatatttcgccacttagaatccagaaatttcaggagcatatttttgtgatacaaaataacg tatttctgttgcattaaacttctgtctaaaactgttcggatctgaaattgaaattagcatttaacttttttgttccaactgaaataa tgtattactggacaaaaaaatattaccatgacatcttgcttcttttggagaataataaaataccttcagttatagattttaggtaa caaataccatatttattcacacaagttgatgaaactcgttcgatattttaaattaaactgcctttaaatatctattagccagttgt tgtatggtcctatgcacacactatcttgtatctatagtttaatatatgcggcctatattgtgacatatattcttcccgtttgctct gttgttctccccttcctgtataatgggagattgtaaatgagagttgttctggtcccaatacctagccactgagaaccctcctcttc tatctactactcatttatattatcgtcattatttttatttttatttatacatatagtgggcttatcaacatatatgagggtaaaat acttataattaatcagcagttcagaagaaaaaacaatgaatgataaggaaatttttagagaacggatagaaaagggatcttttgat ttcttcagtgacactgttatcattttcgaaaattgggtatgacaatggagacgccccacaatggaaataacttcaaggttatccat atatactgcatacatatccacaatattatgaggtttctctaggaaactgaaagaatcctagtgtttgaatgtgttgagcatattaa ttttaagaagccaagaaaccataacttctgataatgactgatatctaggctgtcacgagggttgcttaaagtgttacagttgtgcc agtaatattaatagctcaatttctacaacatacaaaccattatggtaccctacaaacactacaaatggtttgaaaccttgttgttt attgtttttactgaactcttatccacctgatacctaaaaaacgtcatgttaagagaacaacaccgcccattttgaatcctttataa ccactgggagatgaccggatttccaagtactcgtagttctaaaaacctttaaaaacccaaaaaaaag ar1-7

SEQ ID NO: 65 catgttttctctgcaaaaaaacaatcgtaattgcataacatctttcgaactcgatagtctcccaaaaaattcctccaaatctttac tgcatttgcttgtaaagatttacctatttttctaaactgctgtgttcctgtattttcactctacctgtttcgtttatttatttat ttaagcatcaagtttattgatctctaataaattctcgggaaattcgtgtcttaattattaatattatagttattcttgccagggaa agttacgtttccttatcaaacacctgttgcgaaaccagaaaagggcgggtctgactaagtgaacaaatatttcgtaataactttct tccaacagaaattaaaacacgcaaaaaacggccaactcactagctggaacgtggagccccatgataactccatgataaaataactc tgattgtcgacatagcttcaagaatatcgtattctgcattttcaaaaagtatttttcgttcaaa

F07A11.2

SEQ ID NO: 66 gcacaagccgccgtgagactcgacgataccacaaatttcaacgatttcttcacaagcttcaataatgacctcgggctcgatcagga atggatggttttcatcaaagctttctacgcagaactcaatctcaaagtcgaataatttttatttcattgtttttttgtttgatacc tgttttgattaccatttttttatcactatatttctgacttctttctcatttttttttaaatttccggtcgatctttcacagacacgat tgtatccgtgcagtatttgaaaataacaaatttttctgatttctgtgggtttcacgtgaagatcttcttcaagaagaggtcatcag attgcggaagatctatattaccgatctgacgcaagactaccatgtatatttggaaaggaaaaattttctgtgcagaggttgatggt ttaaattttgatttagatattttcttcatttaatttgaaaatttccatgcctgaaaatatcctcagtgaggattctcacctaccgt atacttaaaggcgcacacctgtctcaaccggagcgttgcgagacccgcggcatcaaactacacactgtgttttgatgatctttcga tcgttctcgaaaaaagaaagagcagagttcattaaaacaaatggcggcaaaatgtctataaaggcgagtcgttctcttcattatct tttgattttcgatgtgttctccttattgttttgttcgttgaccccttatctgcattctcaccgctacgcaacgtatatttaacgtc agctttttcgcagaaaattttttctatattctcatgcaaatttactgttctcaatgctggacgtgtcgcttgtgctttgatctcaaa tctaacattttcccttcaaatattttatatctgcaacggtggggcagaaatttaaaagttgacctttgtcagccaactgctatcag ttatcagttggccggagatctttctattttcactttcttgcaacgtattcagacatttttttgatgaatcggttcacagaattttcg tcctgatgttggtcagtgatgcgccagccggaaattagaaccgtatgccgttatcaatttttcaaaggctaaaaagttatgaggtg tatttattgttttaacacctgacctgctagtaggaaggaaattaattttatgtttaaattgaaatgaaagagtcgagctccacgtg tcgtctccctagtttctctattcctcttcttctccgcctatctctcggcttctctcctttcgcgctcctctcacaattcctcctaa tcgtgctgtttttggggtggtccaacacggcaaaaaaggcagcaaaaagtgtctgccgtctcgtgcctctttcttattgaaagggc acgagagaatagtatcaagaggctcctcgttcgggccgttgaagatggtatctggtgcttcggcggagacgggaggagcggccgtt -continued tctcgggtcatcacagcccattccttctaatgtttacactgaacttgtcgcaatccctcctctaaatctcattcatccattcattc
atattcgtgttatgtgttcgcttttacataatttccattttcaccacgtttctcctcaaatttgcattatttaaatctctgccttt
tcataaacatttataattttcagggtatcacctatactaaccatccaaa

C04F12.1

SEQ ID NO: 67 aggcaaacatcacgtttccgatatcaaaagacattgaataaaagaaaaccaatagaatgtaaactattaaagtgacaatttcagtg
aaatttatcaaaatacgaaaataataaaattaaaaattagcgccagctaactatttagcagagcaaatacgttttgacccaatata
aaacaataatatgaaaaaaaaaattaaaataaagtttttaccaaatcgatattggcaaaacatcttgttttt gaggctccatatct
ctgcaggaaaaaatcgcactaaaaagtgatcaactagaaacttgttaaacacaatgtaatctaaaacttttcagttgaacactatt
ttgtaaaaaatttcgttgccaagatatagatctttaactatttagaatattcaaaaataatgaagctcaaatcaattggttccaac
tcggcaacgaaattttttacaaaaaagtgttcaactgaaatgttttagatcacattgtgtttaacaagtttctagttgatcacttt
ttagtgcgattttttcctgcagagatatggagcctcaaaaacaagatgttttgccaatatcgatttggtaaaacgtcttgataagg
catcagaatcaatgattcggtcattgaaaataatgaaaaataggttatttgtgacactctaaaatatttcatgcattttttaaaaa
atttcaaaaaaaatttttcgatcaaatttctcatggtggagaaaaaagtgacaattttcgaaaaaaattaaaatttctgaaaag
tttccagggtaattatggttcaattaaaaagcaaaaaaattatgtaaaaccctcaaaaaaatgttctaaatacttgtttcccgttc
tgaaaattttgtataaaaaaggccaaaagttaaaccatgtatgggaaccgaacccacaaacttctgctcaagaggcgaacgcgttc
accactcgaccaccgaaccgatgttttcgcccttccaccattgtggtgagacttctgttggcgccagagacaaaaatccactgtta
accataggaaatgcactgatttcagtgtagaatttcagacgtaaaaatttcagatttccagcccgaacgggcaaaaatttcagtca
tattcttatagtagagaatgtcagctttccgatacaatatttttttttgaatatcgctccatttattctggtcattccctagtcag
ttgcctgcccgtggcggaggaagaacataataggaggatacgcagagatgcagaaaaaaacttccgtttgttggtaggtagtaat
ttctccttttgatctccaaagatgttgggaaattcgccttttggaatgttttatggcgcacttttt aacagttaaatacatagcca
cactttctatagactaaacaagtactcttgacatatgtcattcatcatgtactctttagattttccagccttaccaacctcctcca
cagtttatctcattgattgtactctttgaaggaggaccattggttctgacttttttgacct tatactgattcaaaatgtcatcaaa
gacacgagcttcgtaatgagacttcagaaaaaaatttctgaacattttt atagcggttcaaaaattctaggaaatttagcaaattt
tagctatagctataggctttacaaaaccttcaattt atttttttggtcagatacacgatctcatttcattttgctgattaagatt
catttgaagctgagaggtaaacaaaaatcgccggaaattgtaaaaatgccagaacctttatacaacctgtatgaaggttcacctta
caattatatctgtgtttttcacttgtttagaggagtggtaggtggaagacattaaagtgtcgttctcgtagaactgttgtttggac
tgatagcttttaaatacgacttttttaaaaactttttgagattatacaactaattgcaccatcatttatttttt gccgatgtgcaa
cttt catattgttttttctcctcactttctccgttgtccttgttcataacacaatttgcaaatcacattgaaatttcagatttccg
attctcgaagctttactaacatctccaccactaaccaagcctcaac hke-4.1

SEQ ID NO: 68 aacttttt gcaattcctaaatacttaccattattttt gcccaatcaggttaatgatctctatcgtgtagttttccccttttagttc
cagttctgctgtgatatttatttatttttgcgaatacatttcaattcctaactttttt cggaatacaaaccagtaactcataaaat
gttcgatttatactcacatccgcgcgaacacttcagtgccgggtgttataacacgtcagcgtttcgccagatgatgcaattggcgt
ttttccttggagaacaaatagcctcgtagagacgcatttt atttccacactgcattggactcaattggtggtgtatttgctttgaa
ggtgaatttaaattcagacttttttttcgaaacttgcgcagaaaattgtgaatttttcgatttttatagtggaaaataggttttt
tcaaaatatttttattgaaaattaaaatgtttgctttctatgctctattattgccgaagaaatcaattttaatgaaatattcaaag
aaatcgcggaaaatttt caaaaatttccacgatttttt tttgtacgcaatcgcatctgcataccgtacccggtttcgaatttcga
acttttcgaagcttttcttgaattttttctgctttccaattagaattaaaagtgtaatttaatcaaattctagtaaatttcaaac
aaatttgggattaaatgttaaatttttattaacattttcaggctttaaaaaaatatttcaaagtttt gtgtcaaagtctgcaaacac
tctcgaataccgtaaccttgcatctttttt aattttttgttttctttattttt atcactcctatactttttctataatttaaagca
attttataatatatttttacagaa -continued

F22E5.6

SEQ ID NO: 69 tgctagcggtcaccactatcgactgagctatctgcccctaagaaagtttaaaaaacttaccgattttgagttccaacatcattttc tcgctatttttgataacgttttggttagcattgtactccggcagtattggtaggtcattctcgttgtttggagtctttatttcaga ctccacgacggctggagcaacattctgaattatatttttttaattattgttatactttttagcaaaaaactgacatttgaaatagat ctactgttgcaaataatgtctggcaacggatcccatctctcacttggcctgcctgagcctacatccaatcttgcaattgcttgctc acaatctctcactaatttcaccaatccgtaaaatctggcttcccggagcaactgatgtcgggttctgaaagttttatttaatttat aaaactttaaacttctagcttaaaacatctaccatttcctgaatttcaggcaaattcttgaagtatccatcgaactttgttagagt cgctttagaagtgacaaattccttgccacctacattgagccggagcatttactttcagaaacaataacagtttgagtttatctgga atttgttagataactttaggtagatttgaaatttttggtagatcggtttcatcaaatttatcaatgtcataaataaactttgtagc tataaattttaaaatagctttttttacactttattcaaggaaacactgagaaatagctgcgaaaacaaaaaaaaacatttgagggg agaacctagacgcaggagagaaagaacgtagaatctactagaaaaagtgtctgcgtctcttcaaaaaacaaatttaaacttagcaa gatgaccaccacagcaaaaatgaaaaagaggaacgcggagggacagggacagggttcagtgagaaaaaaattagaaattttggaaa aatgagataatttttaaactttttgcagtattccaaagtttttcggaaaattgagacaaaaatttttaatcaaacttcccatgaaaa tgacagaaaattttaaaattgaaattaaatgaaatttctttattttctggatttttaggagtttctggaaatttcttagcataagc ataagcctaactacaaactaaaaacttcaaactaccaactgaatacaattaattacctcatgattttgttcccagcagccgtaaca tgttaaaaactctatgggtcctgtgagatgtcggccgctctaactctgcacattgcagagattttcagacagtgtgtgaccaattt taggctgaaaatctgccgactgtactctttttggaaatgttttgtttcgaaatttttttactcactctcactataactccaactcac ctggttgcgaaattcagcgcttttcaacgtaatctaaaatgaaaaatattcattccatcactcctccaactccccatttttgtttg aaattctctgaaa pdi-2

SEQ ID NO: 70 aagaacgccgacgacaacaacaaacattttcatcgggagccctggaaaatgacgaatgtatgcattaccattgttgaaatttggac tggaagcgcaatggatgaaaaaaccacgctatttcgaagctcatttctgatgctggggcacaacacaaaattaaatgagacgagga gggggagaagggatggagagcatgcatgttttgttgttcactttcgaaaaaatgtatcgatttttttctagcaaatgtttgaagtaa ataacaactttcaaatgtgataattagttatcaattcagtcagtttatcaaaaaaaaagtacgtcattagcataactttgccgtatt tgcatgtctaggaaattttagaaactagaattgctaaaaagtggtttaaaagttgcgggacgccgaaaattggctgagaaattgtc aaaaatttccaagtgacggaaaaccgtatgttattgtgattagtaagacgatttcgcaattttatatatattttgtcacaaatctg aaatcactcgtgctattttaggtgtaaaagtcacatgttattgcacaaacacgagcagaaaatgaattaaaattaccttctcggtt tttcagacattgtcttcaactttgtctaggtatttcgaaatttcaaaaaaactccacctgacccacaaatcaatactagtaagtta gtaaacacaacagtatgggaattggttgatatgtacgttgcgagacttgtttgtgcttatctttttcccctctctacttaacaatc aaataacctgcaaaacactatggatttttctcttcagtttggggcaattcttccagaaaaccaccaaaaaagaccgcaattttgct aacggtcttgttcacactggtagataagataacattgcgtaggtcgatcctaccgatcaaacgggagatatatgggggggagtagga gagaaattacgggaagaaggctatcgagcggccttgacacggtgcttgactttttggcgaaacgtatcagttgacctctattattt gggctatacagagatgaggtatgatggacagaaacagaaaaacacacacaaagggtattgatgagaatcatagacggtgacaacgc caattcaatgagcagtagatgtgcaggagacgtgtctcgttcagttggaaacgaaggcgagacgtgaaaagagtgcgtggttgcga gagacgcagtgatagagacaaactggataggttatgagaacgagaaccactcggactgaggccattcgtagaatgaagaatggaag ttgtatctgtcttttaatagactcaaatgaaactgaagaaaaaaagtacaaaacataagacactatatatttttttttcatattgaa aaagagtttgcaaattttcttgaaattcaaaaattctgtattcgtgacaacactttttgcttactcattttgtaaaattttaacgt gggctattgatttgtgtttaaatatttatactacatttttgaaaattattattttcacattgccacgtgaactcaaaatttattca tgcaaatttagaataaaatctgttcaactaagcctatacgcctcgtgcagaagtccaaatttgaaaggtaaacctaaacctaaatt tgatcatgaacactgagcctgaaagcctgtaaaccataggcaaagcctaaaaacagcttacaaacctttctctgaaattatgtctg -continued aatacgtaagtttattatatgaactaagctttacagctaaatctatgtttgcaggctcagttttgaacgttaataactttcgaatc cacatggaaatttagatataattgaataaaaaagtcctcgttaatatttgaaaaaaaatgttgtcaatttacgaatcctttttttt cgcctaaaaaggagaatgtcaaaagtactaaataaaaaaacaaaacattcaagagcaactaagcagtttttccgaaatttttttcca aagttccaaagtcaaccttaaccttaagctgcagaatttctgatgtttaccagctactacgaaacaaaaacgattctcatagatga tttcccattttcgcacacaaaatgttggcatcacaaacaaagtgagcacaagtatggagagagatttgagagcacagacatcaaag aataaactatgttctttgttctttttaaactactttgaaaaaaaacaaatgaatttacatatttaaaatgttgcaattgcaatttc atgatggaaatattggaaaatgtctataaaataacgcagacagtgccaatcaaaagcttttctcatctacccagtcggttgagtga atgaaaggaaacatataatatcaaagctggcgtgccaattcctttttgtgctcggctgcattatttacactgccggtgtttccgcg ctccttctcatcgacataatttccctcatttcctctcagtcttccgcgcagttccatccatcgcaatccgccttcttgcctaaatt tgtctgacccaatactctaactaactttcatttatgtccaatgcattattctctctgtaggtgacccagtgtccttccttttttct ctctcaagatgtgagaccccccccccttttctcctcaacggcgaggggctacgtgagtttccgctgtgtgcgacgcgtccttgcc cgctcttcccaaactgcacggccaatggggtgccgggaggcggggtaggggcgggccaatcgacgcgttccacgactaagtaagcg tggacaccccatcgtctgcagaagaggacactctcgatccattcgctattcatcgtg pdi-3

SEQ ID NO: 71 gaacacgttgcatcgataaatcgagaatattctcgaagcgcaaaaagaaatttcgcaactatttcagaccgaataatgtaataatg taatgggtctcttcgatagaaaataaacgaagataaacgaagacacaattcttcctgacgcgcgagcttcaatatgcacgtgatga ctaatttggtttccatggtgatctttttgttccttttatcgattcaaatttacaataaaaataagaaattaaagttctaaatggcg ctccaatcaatttgccttccaatttaacgtcgattccttctatatcaggtcataaaatgaataaaaaacaatgatcaataaaatga tgcggtagttgcgtaaatcgacacatgatggtcgcctcttccgtgcgagacccattgggcggagttctcacaagaatgaggccaat cggcacacaacacgcgtgcgacaggcagtgaacgacgtgtttttggctcagttcctaccaatccctggtgtacacacgagcgccac gtggaccttaacaattcgggtctatttttatgcttctgctctgcattttctggattattagtaataaatatcattaaaagtgatata acgctccccgagtctatataaaatttctcctccatacaacacatgtttttggctttcttcttctaagcttaaaatttatagttat ttactaactgtattttccacttattaaagataatttttgaaaagtgtttgtaaatacttaaaattgaacccgaaacaatctgtatt tgtccattcacatgtgattcacagaaaagaatgaaaataaatgcgaaaaaaaaataaataaagtaaaggcgcattgattttaccgc tcgcggtatctcgccacgaaaacacgtttcgcgtcaagcggctcacgttttcgatgcgatcgcggtttgttaattgcgaaaacacc ttcccttctcttcaatcgttcgctcaatttctagaaaatatttctgaataatctgaaaacctctaatcttgtttcttagtttttaa ctttttgtcggtgttcccgataatctctcgccctctaaactcactcgatcgattgtcgtttataggtaaagtttttaggta itr-1

SEQ ID NO: 72 aataaaagatgtgatggtcaatttaggatagtaaaagatgacaggtggattgagggaaaagagacaggttacttctgttgagtgga cacattgcaaccccggccaccaccgccacggacacgccgcccacttttgcggtgtgaggtgcgaaactgtcttccgacagatttg taaatattacgaggaagttgatgtaatacggaagaggtccactggatttatgtgaatgaagaatcaaaagattgtaaaatgtttag atatgatgagctacagggtcaaaggtgatttgatacacgattttcgagcagaaatgctgacttttcgaaatctcattgttgtttaa tcaatcacgggatgtacgaaagggatcttggttttggatttttgaaaatcaaaatattacaggaaaatataatgcaaaactagtac agactgtgaaaatgtttctaaccttgatttctgctccgtccaactgtgaaattacattgtgtgtcaatttcaaaaacggtacgtga ttattagttctggtttttaagtgaactttatgtatatgagctctgaaaacaggaaaataagggaaaattaataaggtagtcagaat gaaatattgcaattcgaacataagcatttagtttgaaacaacccgtatttcccttattagttttgtagcttctagtttgtcatgca ctgattttccgacagaccggctatactctgtgggaatttccgcaaaaattaaatttaaaattaatagatgagatgtggtatgtagt tttaaaaaagtcgatggattcagaaaatgctcagaaaaatccgcgcattaatttccaaaactatcacatttcagaaaagtatcaaa catcatatttttggagtccaatactacttcttcatttcttttttttttttcttttccactagttttacaataaaatatattgtttt gtcctaatgaagcacatttcattttgtaatgtttttaactttctactgtaggatattctattccgtaatcgtacaaatcttcttt ctctcccaaatttaggctgcgccctgtttcaaagctctgctaatagtacgcaaaacaaatgtattcgctaactctttcgctcattt -continued cggtataagtgtcacttggagatctcttcgtctctcgcaacccgtatttgtattgtttatcttccaaaatggtagtcgactgctca tatgaattgaattactagcgggatatgaaagagacatgagatttataaaaagtaactgaatatttcaacttttgaaattgaacttg tatcattttcgaaactaaaatggaaaaacaggaacgatattacttcatttttccacttaaagatggagtagcaaaatttgggtgat tgtttttagaatcaaaattgatcctaaatacctattgagacaacttgaaaatgtctcaaaaattattgtattaggttagtcattct ctaaaagaaaacgggcaacccttcaagtattaaatcattttgagcttgaaaagagagaacattgttcattaaaattcatgtttggg ctcctaaatctacaaaaaatatcacatttatattttcggcaattctgatttcctgtaatcgacaatttcagcgattgccgaaatcg tcgaaaagtcgattaccgaacggcaattgctgcatgctatgtatcacaccgtttcagcgttgtgtatcgtatttgttcaaagataa ttttcttgtaaatctcgatgttattgactactgcagctaatacatttgaattcccattaattcctttaatttgataagtgtgactt ggttcccgttgcccaccatcttttgttcctttcctcctatcttcaaatcaaacgcatctggaatctattttttttcattgttgtctg tctaccgatgccaacgatctgacctttcttaattggtattcgcgctcattttgacattgtgtcaacttcaactatttgcgcgggtt tacctgcaaaaaagtaaacaagaaaaatggagatgaaatgaaagaatttccaatagaaatttgttgttgaaaactctctgaaccat gagaccgtccaagacgttaacatcaaatcttttcaattcagaaacgtttcctctttttctccttttgtgacacgtttcctccgttc ttttttggagagtcactatattttaatacgattttgctttacaatttctttttttaaacttttattgattttgtgcttcttatttt ccatttttcataaaaagtattccaga

T05E11.3

SEQ ID NO: 73 gtcgcgaaaggtttgaattcccaactggaaaaactgagattaagaaatggaggtatattgcctgattgagatgagaaaccggttta tgagacggataaacaagtaagtttgctgagtaacgatcacaaatttcacaaattctcaagacaagtgagatgattaatttctataa ggattaatttagatgatccgaacattacttgagtgactgttataatagaaagactgaaaaatcgtcttttaaattaacatattcca tattgctggatccggcaaacaaaaacaatgttccaggacactcactccacgtgttctgagctgtcgtctcggtcgttgattggctg attccgcctctgtttgcaactagtaacgcgccgcagtttgcagttttcagtgaaggacaacgtgtttgcaagagacgcagacactg tgcggcacttgcaaattggggcgggacttttagggacacgtcgagaaggggtgagccccggcgaaagaaagcaaacaagcggagag aaaaggggagtaattgaccgttggaaagacacctcattccatttattctcggtcgttaggaagagacggcgatgagattcctttg gtgggcttcgtcgcccttctggctgtttcaggtatgtctttttattgattttcagagcttagtgagctttaaatagaaaaccgtag ttttgaaattgtaaaaaaaatttttaagcttaaatgtacgctgaaaatattaaaactgtgttcacagaataaaaacattaggcttt attttttcattctgtgcatacacgccacgcagtttttgaattcacgtttttattcccaacaatcatcacttttcag ZK632.6 (cnx-1)

SEQ ID NO: 74 tctgcggttctgaaaatattaaaaccaatgatggaaaagaatttattcgggataaggattttgacaaacggacatatggcatatc ctaatgtgagcagaggagctgtggtcggagcaaccgaccgcaccggctcacttctgctgtgattcggctcggcgccacgaaaagag taagagagacgtgacgacggcaatagatgaatcgaaatctatggatgcaagaaacctcttttcaaatcattcgaacggttagaatt gtgcaaacacggcgacgcacaaacgcacatatcgtggggacacgtgaacgatggccgacttgagaagaggaagaataacagacggc gggagagacgaggaaagggcacaaaactgagatgatggtggtcgcaggcgctgagcgtgatctcttctgttctatttcagacacca cgggattgtattcaacaacattttgttgtttctactgatcggatgggatgattgtaattaaccactatttatgtttctcacgaatt gtgacactaaatgtgaaaaccaatagaaaacataatcgtatttcttcaaatctgatattaaacgggtagttctaattatgaaaata ttgccccacgacgaagaattaatattaataatatttcttatttttcacctgcacagacactatagttatcgatgatcccagtttta tttggtctaaaaataaaatttgaacttctgagggattgttgagcgacattgatatggaagaagcgctatcgataaaaatttctatc gttccatgacaaccaatcacatgttcaaatgactgaatgccaaagaaaacctcgaaagcgaaccggtttttcttccggtgaccgtt tagatttttataaaatcttttagttagctgaaaatgaaatttattgcagctccgtgagaaaaataatcagatatacgcagaaatga ctgagggacgatacgaaaatgcgaagaatctgccttgcaagaggacagatgtcggtactcaacacgtacccaacacagtctcctat aggattgacaatttatcttcagagcagaccggaataatattaacaacaaaaagctaaacttaaaaaccgaaacgaaagcaattcaa acttaaaatgaaaactaaaataaaaagcaaaaaccgaatgctgaaaaaaaaattgtctaccgtacacctacagtaagattctgcat -continued atttgcgtgacagtgtttgcacatgtttattcgaaaaatgtcattgattatttcgtttttactttttttcgccaatcatttagcttt
accctagattttcattcttattttgttttccaaatcaatcaataaacaataaattttgtgaaaatttacctgcaaacctccattaa
aatttgcaaacccggcaaactgtcacagagagaatgaaaaattgattgaaaataataaaactgcttggccagtttgaaccgatttt
aacaattaagcttaattatttgaagtatttgcatacacaccatgcagtttttttttaaagttttaccgtaaatccctactgagcta
ataaattaaaaaatttcgattaaaacaagcatttatcacgagttctaaactgatatgagacatatttaatttattccgattcactt
caactgatgaaaacttttgttcaaattctcaaatatatttcaatcgtatcacatttttttttcggcagctgcagcgaatttttcctt
tcatgagccatgggcaacggcttaattacaccaacagccgttgtcggtgtttggatgtattgccctaaatgaccgcccgtacgttg
tcctctccatgcaacgacgctgaatattcttctgctctcacactcgtatactagttgtggttgaggcgcctcgatggacagcatga
gagagagtgtatcctataataagacgtagacagacgcgctctagcaaattctttaccgcagcactccacagcgttcgtcagtccgc
cttgtttcacgttgtcgattgcagacacaatgcccctcatttctattcacttctcattgtattctatctgtatgtgcatagtaac
ttgttttacagcgagtaatctcaaaaatcgatatatttttccttttcataatattgttctgttaccttggtaccctcattattatt
ttttgaatttaggtaacc Y38A10A.5 (crt-1)

SEQ ID NO: 75 aagtgatgttttggcaattggaaaagctagactaggaatgaggataaattatgacatcattaggacttgtaat'ttagaaattacac
ggaggcaaaccgtaatgcgtttttttaaaataatatttcttaatttttttcctttttaatttctgctcaagtttgtttgttggcaaa
ataaattatttaaaacttctcaaaactatttaaataggtttttgaaaggatgtgaaattccttatggaattttagatgatcttca
atttgaaaactgttggcagagtatcgccagtgaaaaatttttctaaacaaaataactcaaaaaaaatcagatctttcaaagttgtc
agtagaagtttttggtaaattgccaaatgttccaaaaatgtggacgttttgaaaatgttgagcatttcagatttaagctactgcaa
tcttcaaataaaaatatttgaaacatagctagaatatatgaatcgcaaaaagagttttggtaaattggtatatttttcacaactgt
ggtattggtctcattcagttatacatctttattcttaactttgatataccgtactctaaataaactttcctattacaaccacactt
ttaaatttcatatgttttcactcttcagaggtcaaaaattggaagaaattattaacgaaaaaaaataaaaaattagaaattaattat
tatgtttttatgttcaatttacgtttcaatttttcgtatttgaaacttggcaatttaccaaagctttcactataaattttttttact
ttttctacaaaattttagtgtgttttactacgttatcctgtcattttagactataataagtgagtacagtattgttttcatttagt
tcatatttctatgttctattataattgtctgtatctgatattcgattatttgaatgaacatgagttttaaagtatatcaaagttaa
aatacggatgtatagctaaaggaggcagtaacacatatttgaaaactttgatttcatgttctcttccttcttttcccacggcgtta
tgtttgaccacagaagcatctatttttggaatcaatataatttttttcggtgcttttagcaaataatataaagtttgggaactacc
tctaatgttcattttcattttgatattctcccttgacatatcaaaatatttcgagcagtatgcatttccttatcatttttcaact
gtatttcctgattttagcttttcatattaatcaagtaggttcatggtttcaataaattgtgggttaattatagatctgcctaatct
tcaagccaatgccttctacggagtattgccagtgtggatttagtttgaaaagtattctaataaaatactccaaaattttaagttag
ttttggcaaattgccaacatttggactttttgagctatttccagcattgccacaggaactgtcagaatgtttgaatacaaacagtt
gaaaatataaaaattgtagaaaattgttttaggtctactttcaaaatttttataggttttattataactaaaattattatgactaa
tttttcaccataaaaaattaattgcaaataaaaaatttcaaaaatgttttgaaacgttttactattttatttggacatttaagcac
taacgtgttcaaagctgaaatttcaaaacgtcataactttgctgaaacttgacttgggcagctaaatttttcggagagatcataac
taacagtcttctatcggatattcaacatgagaaccccaaacctacgggccccttcaaagatttcccttgtgaatgggcaattttaa
ataatctctccatttacgatatttcaccttcaaataaacaatgaattattctagattacttgttgtcattcagtcaagatattctc
aagtattccaagttctccattgtttaatgatttttgctccaattctatccaatttccctttgttcgctgctttagtcccgccaccac
cccctgtgcaaagagataacgtgtgagtgaatctaatagccagaatctggaaatatatatatgtttagaatcacaaaaggaaaatg
tgcaggcggggagatcaaaatcgaaactgtatttgtgtggaacaatgcaactattgagagaaacatgaagcatatggactacgagt
tgagtaggcttcaaaagtattcaggaatctcaaccaacgagttttgcccagaaattaccaagaaaccagtgtaagtttcattttat
tttttggatttagttagatttttttaaataatcaaaaaccgatttcttgccgatgtcatactgtagacactgtgagaagtaggacta
cctcaatattgataagtgcctacctatgtgcctagaaggcaggtgtggcttgcattgaacttaacagtagacgtaggtctcttgaa -continued gttttgcttccaggcaggcaggtaggcatttgaataatttaaagctatagtaaggagtacggtaaattacaatatcatttcgtgat aaatttcaggcaagatcgaaatcattttgcaatgctctacacctttccttatattacgtcaacttgtgatcgtgtcagacttttttg ttcgaaatgcagtttcctggagttcagaggtctaaaaatattcctgaaaaaattataattctagatgttcaggtgaaccgagcccg agtagcatgcgaatgtgaaaaaattgtggaaatgacgcgtggctaacgaggtacttctcgtcgccgatctttctcttgaccaggac cgaataaatatttgaaaatgcacttattgtttgttctcaatgccgaattgtttacaatgtaccttttggtaaagaggaactcgttt gtactggccagctaataaaatattcacattattcttcatactatgttttcatatagaatttatcaattttataatttagatgataa cgagtgctgtactcctggagtccaccaggacttgataagagaattgaagcaccacttttataatgagcagtactaatttcgaatct ggaaatgatatttcagaaacaatccaggaaacaccagaaaaatatcaccactttgaaaaatatgtgcatttattcaattatgctca aatttcagctttggctcacgagtgatacggtcaaccacaattttctccagagtacgcaatttacgcaaacaccaaacgatggcgcc aaagcgccattcaaattttattcatccgtttcagcctttttcagtcttcttgtctctcattttcgccattttcattgttttattta cacaaacggtcgtttaaaatgtagtttccatctttttccgatggttcatcatttttgtcatgcgtcttttgtgaaactggttttgc aaaacgaagcaaaaaatggataactgtgtcaagggcgatttttcgattcgtcatgtccacataaacgcgataatgtgtttttatcg ttggtttcattcagaaattggttgataaatacattctactacattctggctgtgtgatccaatttttaaatccgaaagtctagaaa tttagtgcaaaataagcatggaaagttctaaaccccttaaagaatactgatctcagctgtttctgttcttttcaatcagattccca attgcgataatatcaaaaagccctctgctggactgctgtccacccgcaagggcattatttccttatcccaaaatgctctccgtctg catctcttcaactcactcactctctcgctctcttcgcagtgcgaggccgacacgcaacgtggcctctcatcagacacgctccgcct attctcaatgtgtggcgaccgccgattggccagtcgctgacgtggaccaatagatacgcggcacctcgagccgtgtcagccacgca agacacacgtcgacttactccattgtcgtagcagacgagctcagttcaacatcatcagtttcagttttgctcttgttcggtttcat ttctagtctttcttctctgaaattctcgaattttattctttggtatattctcattcaatttatctcttctttttccgattcatatg tttaattgttatatttacttttttaatttcagattcaacttggtgtcgttttatcgaaaaacgaa hsp-3

SEQ ID NO: 76 ttcactccttgtctgcaacaaacgaataatagaatcaatagatggcaaaaatttgaaaacagcgtacagtcaagataagggtaatg tatgtttttgtcgtcaacctctaaacgtcaaactgaaaacttaaagggcggcggttggttaaatggcgggcgtgtagtactaaaaa caaaggtttgagtaagtgcgccccattgataacaaggatctgaagaagtcttcttcggataatggaggtcagttctgatgggaaaa tcgagaaatcgagtttttttttatttgattgcaagctaatcacatttaaaacgcttacatgggaaagttggcgtttgaaaatcgaat gtaatatacattttttttgattttctgattacttttgagctagcattttaccatttatatgaaaaataaaaaactaagttgcgattt ggatgtggtcaattacccatttataaaactgaaaagtatgtttatttcagttcaaaaacattagaattttagaacccttctagcta attcgacccttctccaagccatgcaataacctttgatgaatcttatctcaaccaattcacattgcagagattcttatctccagcat aacgtatctccaatcgctttctcccccatcgtccaacacagccgctattatcggccaaagtactacgtgtctcgagtccgatcctg acctacttttttatgtgtactttagttcaattgcgtctggttggatttgaatttgttgattcccaaataggagagattctggataat ttcttcgaaagcgttacaaaatgcgcagaattttgtgtattttaaaacagttgattttagtttttttggtttaaatatctagtgta tctgcttttagcaacaaaaaaatgattctaaaactcgtttctttctaaatcatgtcaccacttatacacttggccttttccgatttt tctttctctctttctatagctctttcttactctcacctgccgtttccataacagtgctctctaaatttggtataaaacacgcagcg caaccgcaacgcaacctagtaactgacgtgtcccacggacaccctccactcacgacactctcgcacacaaacgcgcacacagggcc acacgcggcgctcgccgattggccgaatgactctgcgtctctgcgcgctgcacacggtgagccttcgctgtgctgacgttgccttg tcctatcgtcctaggccacgtcgacgattcggcagttcgttccttcgctctctccctctcgatgcgctcgtcgatccgtcagtttg ctctcccttcaccactcccatcggttgacggtaccatttcggcctacagtcgaccttgagcattcgggcggtctatcgggagagac gacctacaaacagaagcagtcctaggttttcctgcattccatttctctcaccgactggccttgtttcggttctttctttatctctt tcttctcagcaattcaacaagtcgtttcatattttaggcctaataataatttttatttttacaggaaaataaatcaaacacaaagt -continued xbp-1

SEQ ID NO: 77 gccatttggtttgacaccacacttcacaaaaccaaagtcacaaatcatagaagttgagggaaatctttctattcgatggctttcag atctagtcttaaatagcgacaatatttgttcaaaaagaaacagaatcgttcgaaattctgatatttatcttaaatcaaagcgttat ttggcttattattaaagatctctattaacagaaacaccacgatgacgcgtgagtttataacttacaattggcaacaagaatagtga ataaaactgacaaggctacacttgacgggcagaccatctcggaagacgacgaaacggacagaatgatctagaagagtctcgtctgc gggatttcgactcagcgtcgtcatcccttccggaacctccatatcaaatagcaccgtttctcgcttctccgcctccccaggcacta ttatgagctgttgtgtgtgtgcaagctcacatcatacaagaaatctcgaattcccactaataatagacaatgagactgatgttttg attgagttgagatcgtttgattagtcagaatagacggaaattggatggaccaacagaaaaagagaggaacgcgaatcgaaaaatat aactgtggaaatcggcaaaaaaaaagaatgataacaaaagggaaaagcgcgtggcatattcttccaacaaaatatgtgtttttttg gcgaccgactgtgcaactctctcatcatttatattctacacaaaaataattcggaatatccaaaaacatgcataaagtcgcggaaa tgttacgaatgtcaatccgaaaacagaattgtgagtttacatgaatatatactcaaatctacttgaataatgctgaaatgtgtatt ccaatacactttttaatctcacaaaattcagtaaataatctcacactggagagtcaaagagttctacagctaaatttctcattta cgaatcaaattagagttttaaagcgttccttcgtattaatatcagtgtaaaaaaataattaagacaaaaaatatttcaaaaaacca gaaaaagcgaaaaaatgaaaaaaaaaaaagaatgacaaaaacaaagcgaaactttttctcagactacggtagatcttgttgtgtg cagcgtgtttgcacagattgtcgaccgtacccggaactttttatttgaaatattttcaaaaaaatatattttctctttccaaatt attcacattttcgatattttaatcgtttcttcatggttttgctgtttggaaaaagacgttcatcacagggtaagatttataattg tttaattctcagcaattaatttccatgagcagcgaacgactaattgtcaaaattgagcgtgttttatattgattctgtctctgtgc tattccatctttcctgcctaaaatgtatggcttttctcgttacatttctccaatactttccaaagagacgcagacataaacgaatg tttgccctattgcgaaagaagtaaatgaatcacccttcatttcccttattccactatttttatttttatttttgaagcaacat cggcgacc cdc-48.1

SEQ ID NO: 78 tccattaatctatttgtttaatttattctaattctcgatcgggaataaataatttggaaattattcaacttattaaattcatagat ctgggaaactatcaagaatcaaaatcttaagactattctcctctcgtctcgtttcacatctcttcgttctccgtctatcgatcggg tgatgctgcaaatcatttttatcgatctacaaagtgctgcatttactaacggcatatcgtttcgagacccaaacgctgatgtgcgt tattgcaaataacagttatttttccaaaccagcattacattacagtccactttttttcctttcatattttcatcctggacccagc tacatacattaccgcaaacgtgcaaacggtagatttatttactagttcctttttccgaaaaatttcaaaaaattgtaaactgcg tttccgttttcaaagaactttttgaagtttcaacgcttttcatcgcaaatatttacaaatacgtctcgttatttagaaattttaa aatttttgaacagtgaaaatccttttcaaacttcgcgctaaaattataaagcaaccgcgccctaacgtcagaatcaccaaacact ttttgcgtacacttgttgaaaacacgcttctatatgcgtggatgatgacaattttcaaatctgtgtcgtttttagaaataatttcg tgaactttttaaaatctcaattttcttttatagtttcgttcccactatcattttggacactcattcttcttattttaggtcttaa attgtacata cdc-48.3

SEQ ID NO: 79 atattcaattcattccaaaaacgatttttttaaagtttttttcaccagacacactttatttctctcaattttcaacagacacgata gttctgtccaacctccattcgatttgtgtagtccttttccggcattcgtacttcaagctcatacaacgtgtcgtctgtttcatttc gatgagccatcataaacgcacgtctgtaaatgtgttcattatttcatgtcataaattatttgcaatatataccgttcgtttctttg ttgaaccgatcgtttgatatactccaaatcttctggagtcaattgatgacgaacatttggtcctgaatggattccaattcttattt ctattattaatttattatctcaccattgataactggcttttcattctgatctttctttctcttcttttcatcagtattatcaactt ttcttgccggttttgctttttctggtgattttttgtttttctccaattgtgggcattgggtagtaagtagatgtggcgaactgtttt tgttggtaagtaggtgcaatagctgtatgaggatctgatcccattctttcaataggaatttcagatgcttgtctgaaatattcaaa taattattttgttagttcggatgtttcgataagatattattcagatgcaaaatttttattctgcccgaaaactacggtactgtact -continued ataattttctcgcgaaaatcacaaaatattgcatccaaataacatccaatacgccttcaaatttatgaaaaattacggtagcttat gagtaggttttggcacatgtacattcgtgtgaacgactgtggttgtttcatgctttttgacttcttgcttgacttctgaaataaaa aaaaactttcataagatgctttgttcattcaacaaaagccgtttaccttgcttcttgatacttttctctggaacgtgtgcactagt cttctgatgagttggctccacagtatcgttgagcaaagttttcgagtaatgcttcacatttagttcttctgattcaacacttgtcg attgacttgttggctgactgaatcatagaataattgataatctgaatatattaaaaagttaactcacgtttcgtcgaaatgtgcaa ctcgattgtgatgaatcgatcgttccaatggatgctctttcttcagtatcgctgatttggactttgagtttttgtttttactatga ctacagcccattcttgaatctttctctcttattgcacacgatacgatttcctggtattttgtcggcggaagaatatatgagtaaaa tcagaaatgaatctttttttatctaaagtttttttattcgaagaaagaatcttcgcgaaacatgtttctgtcacagtttatctgaac tacaaatcttaggttcacgaacttacttacttgcttcgttaattaaaaaaaaattatattcttttgctttcgtttgcatgcaattt ccaaaactataactcctattttcag cdc-48.2

SEQ ID NO: 80 gcaaatgtgaatggaaccaagaagagaacgagcaaaaatgccaccgggaaactcattatatcattctggaaacaattatacttcaa aaaatggaagcaaaatataaaacaggagttgtgaatagagaaaacgacgctttatatcatcagttttggcattgaaatgaatcaat aacataaattgagcgagaaaaagagaaacagcaaaatagtgaaaaacgaatgattgaccgagagaacgggggaaggttggaatttt tgtaaacaaacgagggaaacatcatgttgaaaacatatatatacacatttttttatttaatgcgtcggaatattcagaaaatcgttc agatcatcgataatttttattgataaaagaccaaaaatccagtttacatgaggaaaacaatacactgtgaattttaaagaaaatta aatattccaaaaaaatttaatttaatttgtaatttgggaaactgaaacaataaaacactatcgaaaacttaaaaaaaaacatggat tgaagctcaaaaaaactgttttaatgtttcgttttgtagaactttagatttttgtaaagcgggagacaccacgaatccgcaagaag tttcttccagaagcagattcgctgaaaaaaaatgaagttgtcttaaacctgatgctttttttgataatttttatacattatgtgg tttcctggttggccattttgttaaaatcattatttcctgtaataaaagtcaggcgttctcagttatttccagatatcggattccta aaatagctgaactccaaaaaaacggtcaagtctctgaacaccaaacgcgctccttcgaacaaaaaaagcagcgcgtacgtttaacga acagtttttttcttctagaaattgttttctcattgcgcaatgcattgctcattataaataattatgttttaaacagttgctgggagg ttttcgctatctcagtcgttgttaaacaattaccagagtgtgttatcgtatttatctttgccgtataatatcttttccatatttat gcgattgcggaaatttaccactgactctgcggaaactgcggaaatttaccactgaaatatcactcatatcgtacgtttctttgaat tcgtctccttgttattcaaattatgtcttcgtttttgaacgagatatttacctctagctttctagatcgtcacatcacttaggttc gccttgaacttctgttccgctaaagacggctggttcacatatatttttaacaatgtaattattacttatgacccgaataaaacggt agaacgctttgtgaaattattcgaaagcaaatgcgccccaaggagagagtgtgaatgagaggctgcgttttgtcatcatgtagagg cagcattggggtgttctgtagagaacttagtctacgtgtctcatcttccatatttcttaattttgttctattggctctttttgcat ctcttctttgattcgattctttaactgaattagatcagaaattatacttgaagttttatcttgaaaacctactgtagaaaagtttg tccgtgttctactttcttattagactttcgcgtttcggcctttcctatgttctaccccatcttccgttctttttttattattccaa gattttacagagaagtcgtttaacc ufd-1

SEQ ID NO: 81 ccgggctcgaacaagacatggacgagccattcgatatgtgatcatctgttatcacaaaaatgatcaattttcttcataatttatca aagtttctgttttccttccatttcatctgatgaattcctactttcttgttcccttttcactaactttattattataattataattat tcataatgttctttctttcccatcatcatatccatccttctatacattttgtttccatttgttgttgaaattttatatgctatttc attttttgtcgtcctttttttccgttcttcattttattgacttctcttcatgatttctggcattcagctcgataattcatttatac cctgttctttctagtgattttcgcgttgtttgtgacggttaaattcttccctctacatctttgcgcgtttccacacaaaaatctgt acacgacattcggttttctcgttgttccatttctttttgttcaacggagcgcgtttgtcgttgcaggaatcggttttaatatcat catccattcacgcattctctttttcatgttgttcattgtgtttttcttcaatttttgtcaagtttccttcacacgtgcattttagt aatttctttctataataaattgcagtttgttaaatatttaaatgatcaatgagctctcttttcttggttggctcatcctctttgta ttttttgaattatagttgaagaaaacgttaataacttttcagaaaaccaaaaataaaa -continued np1-4

SEQ ID NO: 82 atatagaaaaacggtctcttaatttcaaaaaaactaaatcaaataatgtgatagactctctcaattgaaatagataaaattgagag
agaccgtggctattacatttgtaaattaattttcttaaactctacttctatctccagtgagccatactcgtgaattgatcgcattg
aattcttctcttcaatatcaccttgtccaataattacatcgtctcgtgagcacatcttctattaaacaaaattagcactaggctag
ttctcttctaaagtgagaaatgagaagaaatgtgagttgtagagacgtgtataataaaatccataaaaattaaaaatattgtgagt
tcttctgagattacgtgaaggccgaataagaggtgacggtgataatcacaagaatttaaaaataatttttccatagaacgaatata
taattgcgtaaatggtcgtggttgctcagaatctcgagagactgtggcaaattgtcgaagttttggcattttgccaaaatttggta
aattgccaaatcatcgaaaatgtatattttcaaagtgatttcgagcagttttggaaacttttactataatatttgagcacttgaga
aaccgatttcaactatttccataccgtggaaaaattatgttttaagttttggcattctgccaaagttttgacattttgccaaaatt
tggtaaattgccaattagttcaaggtgtgtacttttaaagtgattttgaacagttttggaaactattactgtgatattttagcact
ttaggaactgattttaactatttcaatactgtataataattctttcgacaacattctcatcgggccacatgcgatcacggaagaat
ctgaaattaaaagataaatagaaaacaatttgagattattaaatattacctctcggtgagatctggaaaagcttgatcgtagagag
tcaaaatttccggcacattttgttcgtcaaccatgcgggaaaagtagaccaggtagtcggcgacctcattggaactccatcctca
tcggctgaagctgttaaaaattaagaaatgagataagtttgtgttgttaacaagcacctaaataactaccataaatatgtttatag
aattactctattgattgattatcaatttttcttttgaaaagatttcacaatgcacgatcattgatcctctgatactcaacttctct
ctcgggcttttaaatgattaacttcttatgaactcttatgaacaccttttcatttattatttctttcaaatgaataaagctgtgat
tcatttaatctgagatttgaggatattcgacaccgaaaaacactgaaaatgacaaaagtagtcattttcatatacaatgagggagt
tctgagaattggcattgattcttcactgtaacagtatttggaaaatttggtttttctgaattttatgtattttgctcatggaatgt
taatctgcagtttttatgcaaaattatttcagaccaaattctccaaatgtctgtttgccgaattaaaataaatcggttaatcaaaa
aaggaccgagtcttcagtcttttcgaactgtttcaaattttaacatttttcaactcatttactcttattcatcaattctgaaaaa
tagcattctgtgaacttacaagaaaaggtgttggtgcgacgacgatcagagtgatcttcagtggataaatcgaattccacgcgtcg
agacattactgaaagaaggtttttatattgatattatttaaatgtcaaactaaattcgaaaaggtacgctaaaattaagagaaaac
atttttttaattgtaaaatttgatgaaaggaattggaaaatgtgatggaaaaaagaaaattgcaagcgttgcatgggatttcgcaa
gagtgccgcacggtttttttgtgtacgcatttgctcgtcattcatgttgtctaggcagttttgatgacatttttttattctaaaaaca
aaatgttttatttcatttgctgtttaatgtttgaatatgtatggaaactaatttgataccctttccgctgcattatttttgcaaaa
tctcaaaattatatatcttcaattcactacctagaaggcatatcttcctgcatttaaaaatctattttatttcagat Nuclear Oxidative Stress Toxicty ugt-1

SEQ ID NO: 83 agatcaatggcactgaaaacgctcatttaaatgcaaaagatcgtgtcccgtaaaaattttctgtataattccgtgattattttcac
tcgggaatcgctcgcccactatgggggagtctacgcaaggacaacgcaaggacaaggacaacattctaatggaatggaaacgattg
cccgactgcaccaattctagttcaagtgaacaatgataacttttgtattctgtattccttcacgtctcccagcgagcgtaataaat
tattattattattataaaaggagagttttgatcagataaatttattatcgttgaatatccactttctctgtttctcgtttcattct
ctaaacgacgtatggataatacatatgatgaaggtctaaaaacttcaaagaaatgtctcctagttttgcaaatttccaccgaaaaa
aaatttggtcggttctcggaccatttatgtattgtattttatttggcttatgttttactcaggaaagtaaataacttttgctaaat
gtacataaaatcagcaatgttttcaaaaatgttttgaggtaatccggcttctatgtgatatattaattcaatcctaactgataaga
taattataaatttaaaacttactgctacctccaacttctggaacagcataagaattggttggtggaatggtaacatatcttggctg
cccatatccatgacgtggtggtaatttgattctatagactgcccgtttttctctaattgattcagttatcaaattccacgcatcat
cggaatatttctacaaaacattgaattaaaaacttgaaaaattaattatggaccaacttcaaatgttttcagatcttcaaggaag -continued taatttcaaagttttcaatttcattaaaaaccgaaaaaattgaagcgagaatcgtaagaactgcaaaaacaatgagcagaatagta gcgaatagaaaatttgtgtgcttcatttttgttttcagtttcagacaggtgtctatattttatacttttcaacacaatagatatta attattttagagagaaaaaaacaggaaacagctacatagtgtgaagtgaaaatagaaatatgaaaaatgaaataacaatgactttg acgaatttatccctcttaccctaaattttcaataaaatcaaaatacaacaaaagctccaaactctaaaattactaaattgtatttt tgtaccaaaactagcttcccgacattgataagtaacgcactggcacaaactctaatttttttagtgaacacaaaaacagtaatctgc aaaactttctttctcgtattctctgtttctctacataccgtacttaatatttcactatcttatctctctgtgtctcttgccgacca aaaaactaatggtggatcgctatataaagaaatgttaggtaaggagttgaatgtcagttatttctgtaaaaactag aagtttctaaa ugt-13

SEQ ID NO: 84 attattatgttcctatttcttttatcaaataaatgcagttttaaaatttggacttttctgagaacgtacagcaataaataaaaat ctaaaaccaatcacattcaaaaggtcggagcaagttcggagctccgggattcaaggtcacaataatgaaattgtttttttattgct tgacattgatcgaaattaatttgttatttttgcaaaatcgaaaatgaatatttttgaattagaaatgtttttacaaaattttgaa ccgccataaaaaatgttgaaaagttaaagttttattacgaaattcgtacatttgaaaaccttttgggtctacatgttcaaaatcgc ccgaaccgttagtcttcctttaaagtcagttatgactgtgttctgtgtctcctcgactctgttttctgaattgtcatcacaccaaa agaccaatctttagatctttgtatttcttttcattacttgctatcaaattagccatgaaaaacatatgtcatcatattactcactc aaaatactacaaactacactgacgaggttaccgtttgatcttatcatctcttaaattagtcggggtatataagaagaacaaatcga gtacattgtttcaagaaaaattccca hsp-17

SEQ ID NO: 85 gattattttcttatgctaaactggcagacagcagatctttttatatctgcacaaggggcggtgggatttatagaaacttaagttta ctacgcctgccgcctaatccgtgaaaccttatttttatatttttccgcctcccgaaacagttgatacgtgaaaaagcacggaagag aaaaaagcttcttttggacttgattaatctgttggtcatgagaaagcgtgacacaaggtaggttacggtagcaattgcgtaattaa tcggatcagtctatgcgcatttctgaaacattggggatttcaaatctagtttatcaaacagatacaaatcacattgacatctcgtg gaaacagtctgtaaagtaccgcaaattttacaattttgatattattgtcgttaaacaagttccatttcaaatttttttattgaata cggtaaaaaaacaagagaggcagctggttgaagtgagtcactcttgttgagttttcgttactggaaacctgaatgaagatagtttt taactttagcattacgcctcattattttcctatttcctttttactattttacttgtatttttaaactttgtttagcacattgagca cataaaaccaaatgttataaatatccttatcatcaacccatcggtttctttttaactttttttctttctcgaatttcaatgacccgg aaaaccaccacatcatatgaaaatcgaatctaaaaatttgcagatacgcatctgtcctgctgcgctcttatttatttttgaatgat tttttctgcaaacgttgggaacagtcatccaatccttcaaccgttcgtctcgttttgaatgacaaacgttctctttccgtcctct gtttgagtatatttacattgctaattcaaaaaaaaatagtatagaatataatgatacttagagatagttctggcataaagtttaaa cttgaatgaaatcatcaatgccattaataactgtgtcactgcattagtttatcagcaagtgtgccagcaaaaaaaacgtttcgaga cgattcgatacattcctgaaaaacttcgataaaagggaagtatccaaacaaccacacccaactttcatcattgactcgctgttttg ctttttattttgttaatcttccttacaattagttttaaagtttaaaacaaatattacatgttagaaagaactgtattttggtcag tttgttcgaataatttcgaaatctaaaaccttttctttttgatgattcgtcggagtagatgtttctcgaaggaggtaaaaaaaacc gtgggcgattcttgtttgcattgaggataatagagcagtagtagaaaagcagggagtgtcaactcagttttgtcttcttcttcccc tatttctgtcttactttcgttttgtttctttgaaataattagattttcagaaactattataaa cdr-5

SEQ ID NO: 86 aggaaatttatccaaatgattttactatttgagaatgtattatgcggtaactttttttgaaataaactaatcgtgacactcaaaaac ttagaatctattttaaaagaatagataattccagtttttgatatccgggaatttatgatttttttggaagaacgcaagaaatcgata catttgggtacgcataataggtactcttgcacttggatcaaattcctagagaacgattagatgctttagacgcagaaacaaaaaaa tgtgaccgatacaaaatcgaccacaatctcaagaaaaataagtgcgcaacacaatccgaggtcaatctagacatttatgctcttcc tgcgagacaaaaatgcattgtatttttttcattcagattcattcaggtgtcttgaagagatatcaaatcacatgtgacaaaatttg -continued atcgaaaaataagttgcatcataataaaatcatcttatgatcttcctatataatctttcttcaatttcggaaactacgattcgaat
atatgttttattttaggcgaa rnp-2

SEQ ID NO: 87 aaccttagggtaaagtttattttattatttttctttacgatagggttatccaggctttctaagccgtaaataaacttccattttaa
attttaaaatattttaaagctcaagcttatagtatagggaacaaagctttctgatagtttagaactaacaaagagcttatgttcta
caaaaacagggacgtttttatttatagggggggaggtgtaaggattctaaccgtctctacacttctcccacttccctttttccccag
tgatagaaggctaagagtgtatagggattaatgcttttatttacaggatcaccggccagaaagtcagtcacgccatggatcaaccc
ttcgctcttctccgaatacagctctgcaattgatccatccgtgcacagtgccaaacgctccttacgcgttcgatccctgagataat
tgcaataattcccacacactcgatttattccaagcctctaaacttcctggctaccgtaaccctgtgtgtgtgtgcgcacacttgtg
tgcgcgcaccttgtttacgtcttctggacctttctgcggaggaatccagggctccgccctgccaccgcagaggggtatataagacg
tggattctatcactccagatcttctcttacttttctgttcccctttacttgttccctttgtctcatttcttacttgtacccattcc
attggggttattaattcataataaatctattccttagcacataccttgttctgttgtagtatgggatgcaacaacttcggttgtca
taatgataattgaggggaacacttaaacaattaccggtatacgcttaaacatttactatatgttcattcaatcaatcacatatcga
cacaacaattaacacaatccacaagtttttgcgcaatactccttcttctgttcctttgtgattcgtggatccgcacagaagccacg
tcctgcccagagatggcagctgtaatttttatgaatttttattatcaaattcgaattccccgtcatttttttgttcataatcctata
ttttcaaagatctagctcaaaattgcgtgaaattccatgtttgcggacttttggcgctacagtaacccggattatttttgaaaatc
gagatggagctctgaaaatatgggagaaaaggtagaaaatcatggaaaactcgaatttggcattgaatttttttaaagaaaaaataa
aatctgaaatttaaaaaattgaaaatttcacccaaagtttcaagcaaaattatcgaacaaaaaatatcgatttttatccgttttgta
atatcaaattcgaattccccttcatttttttgcccccaaccagagatctagctaaaaatcgcgtgagattcggtgtttgcgtacttt
tggcgctacagtaatccggtaattttctgaaaattaagctatttagagctctaaaattttcggtttcgggcaaaaaaatggcaggga
actcgaaaatttttaataaatttttaaaataaagtgcaggaaaaaagttacgaacgccccaaaacttactcaatattatcgtgaca
tgacggagtggtctgagcactttcaaattcattcgggtggaaatttggaatactcatggcaaaattggtgccgaagagcacataaa
gagcagtaataatcagaaagaatcgcattctggaagcttctgacctgaaaatgctccagtggggagattttatactggaaaatttt
taagtatttagataattaattgttcgtatttcggaactgtgttttatcaaaaagcactgtgttttgtgctcttaattctgtaatag
tagatttttttccctaaaaattagagtttttcattatcaaactttgatttttttcatgatttttttctaaacatgcggttcaacaat
tccatgaactcaaaacaagccgaaatttgaagtaaattctgtgaaaaatgatatttttttctaatattattcaataaatctatttc
ttgtcctatatttggagcatttcaattgaagtttgctccatttttctgcccgcggcctagaaacctccgtggccgaacaacaagcgc
gctctactgcactctttttattttcgtattttcaatttaatttcaataattttttatcggttttcttcgatttttttcgcacttcccc
ccagtatttttttcaatttttccgataaaaatacaaattttccagctaaca dnj-13

SEQ ID NO: 88 ttttatacgaaaaatactttaaaatcagaggaaaatactttgggaccggtgaaaaagcatggaggttcgcacaaacttgtttagga
aaacagaaatatgtctccgtggcaggaccatactgtgcgccgttgatgtccctttgatacagtactcttcgcattatttattttttt
ttcggcgcgcctaggggttttcgagcgcagagttcaggaggccttctggattatggatagaggcttgattttttaaaattgtttaat
tcaatacagttttattaaagtttttttctaaaaatcttttctaaaaataatatctgattgctgtttatacacgagaacaaaactaat
ttcatggaaacaattttttctctttattttctcttcgaataatttaaattttaacaattcaggttttaaataatcaatttttaaat
aagcaagtgaattttaagcataacttttcttcctagtgtacgtaaatcattctttccaacaaacatatttttttcgtgacgaaactt
cgccttccagaatattcttttttcagaaaataaataccaaaaagcacaatttcttatctcttgctcattcttttctttgtatcgtg
ctcatgcttttattcattcctcatttttatcttgcgaaaccaatgtattttcaataaaaaaaaacgagtgatgcatgtgcgctccac
cggccgacggaagatcgaacatgcactgcgcttcgcgagtaaatagaacgctctggaaagttccgcactcttctctctcatgattc -continued ggcgcactctctcttccatttctccgtgtttcctcttctgatgttgacccatatttattctgccgggtgtattctttttatctatc tgttgcttcatttattccgttaacctgttactggttaatatttcaaaaattcatatgatttcttttcagattactttccaca dnj-25

SEQ ID NO: 89 aactaaacattgaaatttctgcacttctttattgtaatgatgcttctgtgtctgacttggcattttcaaaaataatggaatggtgg agaattgacagcgcagaccattgttaagactatgactgtgcagtttatttgcacagcactgtctggcacactctcttcatatcaca tggactctctcttgctcaccctttgacacggattaggttagaggcataccagtgggagtcagagtgctcagaaaagtagttgccat cgtggtaagagttctgaaaagcatcgaaggtttttttagggaccaaggaaatatgaatggagcatgtaaaaatacttgtaaaactgt aaaaaataactcagcccaaaactgagggaaccgtactttctgaaagaaatatgtatgaataccgatgtttttaggttcaatcaaac aatttattcggatttttcacgaaatattacagagagtgtgacgttacataataatgttcactgtttgacgcagtcacgagcttcca aacaattttatattatcgagacgcaaagattcacaattttcgcgccagaatagcacaacctggtctcgacatgacaagttttagtt aaatgcgaaaagatgtgcgcctttaaagagtactgtaacttcgaatttttcttgttgcggaatttgtgaattttcatcgctttctc attgtatttcgaatgaaaaattggctttttttgacaaacttagacacaaaaataatgctcattaaattttaacaaatcgaggaaaaa aaatattgtgaaatgtgaaaaattccgcagaaatgagacgctttccggtggcaactttcccacaatttttcactgatagaatgtaa atttttgaattaatatcactttcagaagtttttatacattattttctccttataaagtttgtgtgaatcacatttcggccgaaaa aaccggttttccatggaatgcatgcttccgatgcttttcgcttttattggcggatggttacgcaacctcaccgattttatctctat tttccgcacttttcttctctatttccaaaattttcagcctagtttattttttgaaatttcagcaaaataattaatttcctcacaaaa ctggcgaaagggcttttcgtttctctgccgtctctcttttcgcacgctctataagcaagtgtccgtgaagcgcacttgcacccgtt tattttcacaacacgttttcagataattttagctatttttcattgatttcagtagtttttacagctattataatggtattttta gtaatttccagtataaatccg pme-1

SEQ ID NO: 90 tttctctgcaaaaaattggagatttttcagtctctttcaactaatgtaaatacgctctcttgtgactaagcgcgcgcgtttgaac cagaggacaattttttcctcagcgctagtagcccctgaaagagttattcatacttgaaaaaagaaacttttctatagatttctgc atgaaaaatcaatcctcagcgcttcttctcttgcttttcctgattgtaatgaaattttagagtttttaaattgtaaaaaaaaaact aaacaagttctttttgaagggaaaattcgtttttaaatgcttaaaatgcttcaaaaaaaaaacaaataaaaaaaaattgtttctgtg catacaccgtcacgacaaaatgcagacttgccattggtctcgccgcgaaaaaacatgtttcttttgaaagattgtcttaattttt gatttcaatcatgatttcaatcagaattttgcgatctttcagcatttttatctattttaaagctttataaattaaaaattaaattt ttaaaaatcttccagattgtcatacgggtcccgg tag-124

SEQ ID NO: 91 aaattattatataattttcaaaattactggttgatgaggttagattagtgataccttggaagtggtctatgtaataacaattttg cacaaaaggagatgagatttgatatggaagattggcaacacaaacgtcaaagaatggccattccattttcattacatctcctccat taacttgtaatttgttttgtagaggtctgaaatatatttattttaaattcgaaaatatttttcaaaaaatacgtacgttcccataa ctcttttcttgacttcagcaatcattctaggatcgatacacatgcaattacagtattgccacctccagcatataaccgtcaagatc ctgacctggtccgacttcaagcactgtatcggtggcataagagctgatttctcaacgattgcattcacaactccaggatattgaga atatgagtcctagtcggtgaaaatggaagtgctataaaatcaatgaatgaatagaaattttgcaaaaataacatacattgaacatt tccagttgatgatcctgctttcgtctttttaactttactcgtttttcccatttgagttttttaaatctgaaaatgaacgaaaaa taatagtatttctgaaaataggaaaataatgaaaagaaataaaggtagaatgatttgtccacgtgaagtacaaaacgtgggactaa aaaacaattctagtccgcgcgtcgtgtactcctctcagacaaacagaagttgcacaatttttttgaaatcgatcccttttaatcact ttttcctattcttctagcgtttaattattttctattgattttatttacaca -continued pme-5

SEQ ID NO: 92 aaaaaaaccggctggtttgctgaacggcaattgctgttcatccctatacctgcctacctaccgccaattcagataatgtggtgaaa
aatttcacgaaaaaaagagcaaaaagaaactataattttaaaaccggagtttgaaaccgtcatcgtcgttgtcattaataccatta
tcattattgacatcaggaatcacgccattttgctccgttatcatacacatcgtcatcatcatcatcgtcgtcaacacccatcaaaa
aaaatgtataaaaggtttcactcaaaaagagggttttatcattttatcaagacttaaaaatgtcctcgtagtttgactatgatatc
atttttccattatcaccatgtttgcgttttcctttttccaaacatttcttttgcacggcgatgatgcttggcattttgcactcgtg
aaagtttcagcttgccagtgcgccgccgcgttgtccatggcaatgcggcatttgtattcaacggcagaaaattgagagatttgttt
ctctcgcgtacctcgcatgttttgatttttcgacctcggtttgtccctcaaacaaagagaatcgtttgtcgccctcaccgcgcacg
catatacggaaaaatgctacaatttcaaggcgtgatagagatcagctctcccgctgatttctatcgattccaatagagatttattc
acctcatacggcggcattagtagggcggtgattaggtgtagagtgtccaaaatacgaaaacggaaaaccttcatttcagcttagtt
tctaaaattgatttctttatataatttttttcaataatgctgaatgcacgtgctcgccggctgcccttttgcaatgagactatg
caaacgcgcccgaatgcaaacgctgctggtggacccctctcggacataaaattatatttcttattttttcgaatctgtttttcttt
catattttcgaaaaaaaaatgacaatattatttgatgaaaaaactacgaaaattggcaaaaccaaaaacaaaaccaaggaaggattt
ctggcttccctcataaattgaaataaaagagtttaccgaactaggccattttggctcggccatatctggggtagatttacggcgcg
ttgcttgtcgcgtcgcggctcgagtttagttgtaaaactaaatgtatttgtccgtgtggagtatacaactttgccacgcgttgtcc
agcaggagatttgcaatagagcaagaaaaattcaatgaggaaggccggaccccgtgaaaattcgcagaaaagtaatgaaatcgaaa
cagaaaactccgagaggactacacggccgaggattttcctcgtccgctcttttgttaggccatttttttgaattggtaaacggagt
tttctagtccccgaaaatataatttagaccaaccagcgagcacgtgctgccattgtcggaccaaaaaaaaaaacgccaaaaaaccgt
gtattattatcgattagatccaaatgctcatacgtcaaaactgatgcctactaggctgcctacctacgcctacctacctacgtgcc
tacatatcgcctattctttgcattttggcgtccagtacttcactttccacagaatagataaaaaagtgtattagacaaaaaaattt
atttgacctcggcgcatttgatctcgagaaaacgtggcgatattgatttaccagttccaaactacatgtaactttgccacgtctgc
cagatttgcgttccaacatgtcaaaatttggaaaaaaaaaccgttgtttaccgaatgacacacaaacacttttccccatctcattg
ccctcttaatctttgcaaggtttcacaacattttgagaattctgctaaaccgtctgcgtctctcattcctccaccctattgtcacg
gttttgctatctgatctctcgattacgtggatatctatatatgaccagcgtgtatagccaactattattgatgtgggcattattag
gggaaaaagatgatttctggatgatttgaatattcgtgtattttataagctttttcctaacttttctactttcgttcatttctgtt
gtttcagccgtaatccgaacagc air-2

SEQ ID NO: 93 tatttcttgtgattcgcttcgattttctgaaaaaagatttaattgaatattaaaactacaaagaggttaaaaatgatttccgattt
tctcgattcaaatttagagaattccagatttagctcaattgttgtgaaaacaatttttagcttttgagaattaactttttctgcc
aaaaaaattacctggaggagccaattacaattagctccaagtgtttcaatacagtatttgagagctccatttggtccaagtccaag
tcgatccattacatcattcacagtgatcatttcctaaactttagtattttaaatgaaaaatatgaccttaagtattaaaataacat
tgatagatgatctgtaccacgtttcataattattgtcctatattcattggaataaaatacttacagtgatatttacatcaggtgcg
tatgccattgtgtcattagcaggatcaagattgatagtgagaaatggtcgtttggtttgtgagaaaatgtccgttaatcctgcaca
aaatgtagattttccagctccaggagctccaattacaagaactccgtacatagtccaatgagtactgaaattttctagttgaatct
taattttctacggattgttttgataggaaaacatttaagaagaacaaaaatatataaatacaatttaatttaatttaaaacaaaca
aaaaagcaggataaacgggcctggcacagggccaagtacgcatttacaccgtacatgacgacatattgcggaccattgcattttgc
cgcgttaatttttttatttaaacggcttgcatttctccttactatccagctgacaatttttagtttctttagaattatttgcaatca
aaactcgtttttttgtaaacatatttactcaggtaatgtgttgatttctcacttttttttgaaatcaaagcagaattagtcctattt
ttattctacataaatatctaaatgtattcaattaaaaattgggccattgaacttctaattaattcaatttataaatttatcgtgat
gttttcttttagttaatttgtccttaatcgtgccgtctattttatttcttcataaaaaacttttcagttccgac -continued mlh-1

SEQ ID NO: 94 caccagcatcaggagccaacatcagtgccgacaccatcgtcgcgaaacatgcaaagctgtggagtcgaaagcactcaacagccgga ccgtaaacaggtgagcatacagtactcggaggaagaaggctccgaatattttaccgatgagcttgacgatgttgatgatgagattg atgatgctgctgctgcagcccgtgcggctgagaatattcgtattccggcgtgtctattacagacggctgctcaaaaatctgaggaa gaggatgagtacgatgtaagacactcattgggttacccatttttctttggttggccggagaaaaattatttactatgctccgatat ttgttgatcgaaattttccaaaaaaagagctgtaggaaattgagattgataaaattaatttttatgcatttttcgccaccacctga tgtcatggtttacaaaaaccaaacagttaaaatttaattagatacaatttttgaaaaaaaaaagtgttttgtacatttagaacta atccataagcgacgtgcatttcaatgaaattgtttattttatttggcgtatttctacgattttggacaaacttgtttgaaacaag acaacaattttcgaaatatcgtagcatcgtttgaacttatcatatttatttttaaaaaatttctttccgccaagaaaaaatgggtaa ccagcgtcgtcgaaaggctatgatcattaatttttataggtcatggagacgtatctttaattaatactctatatactggtacgacg ggtaagatacattaagttgtacaaaaattacagttttcctcctttatttctccaaaaaacctttttgtctagaaacatctcaacat tatttagttaattatttttagtttttcaaagtttataatttcaaaaaattatttttctgctttttcggtttttcttcatgttcaaa acttcttcctctctcgtcatttttgtataatgcatcgcggcgatataaatttgcattttatctggttatggcttcatcattttttt ttcaaacgaattttgggaaaaaagaatgctatagtcattttaattacatccctcatatttgtggcgtactgtttcctttccctgct atcccgattgatgtttttaaaggcacaccgacgagaattttcgattaaaattgtaaattagagtaaaatctatgacttgtcaatcg aaaatcttgtcggcgctctttaggaactccataaaaattgaaacaaaaattattttaaaaattaccaatttttttccaggtggccgc tgcgtggtcgacaaaaatcgacgtggacacgcgcctcgaacaagatcaaatggagggtgtcgatgaggcggaatgggacaaatagg cgctactggaccatttcatattattttcagtcaagtagtgtacaatgaacacaattttctcacggttctgtaaaaatgttttttct attgaaatgtttgatttttcgcccccatcaccaatccatcaccacctctccctctctcgctttttatttgtctcatgctttattca tcatttttttatgattattattatgagtattattactattgtatagtctccaatttcgtgatttttggttttctagaaaattgcgcc cgctcgcccgcccccacgacttaccacctccccctgaatttttttgtgctcccatcgcctagtcgaatttattcttttgtattttt gtgtgtccactttctctctcggtcgatgtgttttaacatccatatttctgccccgcctcgtccccccctctcaatcgcccgctccc cgccccgcctttacactgtgtttcgatgaaataaacagtagagaattgtaaaactatgtgcgtgagaatttggaaaattttagttt tttgtgatatcggaagctttttttaggggaatttgaatttatttttaaaaattgttcaaagataaattagctccgaaattggaaatc gtagtggaacatttgaatttccgccagccagacatgtggcattgcggttaccgtacccgcaattgtgatgaattttcaaaaatcgg tgatcttctggattttcgctgtcaagcttgagtttaagggtctcctcactgatctatgtccattttgcggcaggaattcttttttt tttagtttcattcggatatctctaaaatatcaagaaaaaatcgataatttcacttttcctgaaaactttcatattttcagaatttc acta msh-2

SEQ ID NO: 95 tttcatagatttttttaataatcagtctgctcactgataaacacgtcgattgccgcagtatcttggagaagagaactgaacttcatt gtttgaaacctagaaaatagtgaaaattagttagaaagagaaggagacggagaatgaaaaagggaaaatcgcgcgcgatggaagaa atttgaaaaaagactttacttttgatatttttcgaaatttttttaaaataattatgtttagagttaaaattgcaaggaaaaatgaaa caaaaattagtttaaaaataaaaaccaccgtatctctttccctgcgaaaccaattcaccgtattattgtatgtgcctttaatcttt aacagtaagcataacatgtgattttcgccttctttttattaaaatctaaattattacagaacttttaaataatttgattatattct ttgtttaatttttaatcatttaaattcaatttagaaatgctaaaaatcccaaaacaatgagacactatttccctgcaggaccattt tacagaaatactgtatgcacctttaatttcttttcaaaagtaagcggcctttctgtcgaatcatttttcgttgatgaactcttttt tcttcacttttactctatattatcacaaaaaattcgaatttttcagcgaaaaaaatcgaaa msh-4

SEQ ID NO: 96 agaatgtctggtctccgaatcgtcaactcccttgcatattctttagctccaggacagctcggtgtagctgcaatttgcaacggagg aggagaagccacagcagtgctcatcaaaaaaactgtaatatgaacctcttgcctaaatgttttctggtcttctattcatcattcctt gattcacttttacaacaaatttcgattacgtatttataaatagttaaggttcttgtcacataaatgtttattctcaaatggtgcat -continued acgtgttattgattgggaaatgaattaaggttaatatgtacattatcaggaatggttttgagccatctcaaaagagatatactgga aaaatcggaaaagcatttttcttttgagatatatcattcattcacgtcttcaaggcaaaacatataaggggagatcgtatacaaat aatcacagggaagaattggtggatgataaaatgatcccataaaccattattagtttgagagatcaagttggggaatgagaatatt aagggggaagaatttaaccgggaagcaaacatagagcgatttaatttttccgggatttgctttgctaggcggttccaggtggcga ggttggctctgaggaatcctttgtttgtttcgccaacagatctgagcatgtaggggtatcttggagttacagctttcttcaccgac gatgacacatttgggtagtggaagtttccagttatgatgttgtggtaggtgcgaaggatctgcaagacccgcctatattgcactga cttcaaattggcttgggccaaacgatcctcgtatgaagaatactttatgttgcagcgttggaagacgagcctggtgaagaaatgag atgaatcaataaaggctatgaacgggtaactcaataaagtatcttcctggactgggatgattccgagaaaacaatcacaaacgata cggtaatgaataggaatccattgatttcattttatctgtaatttcagtgtctgacaagagatcgtcgtttcggaattattacaggc ccaaatatggctggaaagtcaacatatctgaaacaagctgcccaactagcaatcatggcataggtaggatgcttcattccagcaaa ctatgcttcgttgccaagtaacctaaaagttttgatttgctattttctatcgtcgaattaatttcagtttttaatcgtatcttctc cag ahi-14

SEQ ID NO: 97 gatggtactgagaagaagaccgatttcgatgctccaacaacacttgcttaattattcacggagatgtcataattacagctttggtt ttcattatttgtttggttattatttatatcacaaatttcgctaatcggcgagacccctctattgcttttctctcctatctcgtttt tgttaacccagtttctttgaatgaacccttgttatgacgattttatggttttccaacggtaattcaataaatgatattatatgtg gaaatcttgaatctgatttgatcgatttagtctcgaaacgttcatgaaggcaacaaacaaacaaccgttgattaaattagtttttt gaatttcgcgcacctaatattccagaggagcgggcttgcattatctttttttacacgaatttcttatttacagtatgcactattctt tctcctctcccattaatttcttgtcaatcccatcccttttttgtag msh-5

SEQ ID NO: 98 gcgagccgtttttttgagaccctgaaattcggaatttctttttatttttatattttttaaattcatttaaatataaaaaatagagcaca aacctcatcaaatgtgctcactagaaaattacacgtcctgcatttttcgtttttgatggtgacttctttttgtgacgtggcaccaa ttaatacagcaagcaggagcagtatccggctcattttcaccctgaaaaatggaaaaaaattggattttttatgtagctttaagacacg acaaaccgttattttagagaaattacacgcagaataagcgaatgagcgcggccgaatgcactgcaaattgtctacgttgtccagtt tctcggccctgtgagcggagaaaagagagggagaaaagaaaaatgaacaaatattggctttgaccgggattactagcaaaagaggt gactgatggaagagggaacaattaaatattagaaaaattcgaaaaagttaattattttcgctggaaatcaccttaatttggggagt ttcgaaagaaatttttgataaaaaatagaattatccacttttttatttcgtgaaaaaaaacaacaatttcgactgaaaatccagctttaa ttcgagaaataacaaatatttatttatttaattaaattaaattaaattaaagaaaataattgaattactgtagtgatcgttgcggg acccgatgaaccgaaatcggtatgcgccttgtagttacggtaagaaaaaacgggcggtgtcgagaatttaatttaaattgcatttcc aaaacaattttcctcgtttgaaaataaattttacgagtttttggttagtttaaatgctaaaaacttgatttaatttaataaaacgt acctaaaaaattcagtttcgtagcagaaaacacgaaaatttcagtttttagtaaaattttcggaatttctattttcaagtcttgttt atagttactttttatggtgttcaatcaactttttgaagtttaaaatgtttaaaacgtttaaaattactttacaagaaccgaaaaaa accgaaaatatttcaattttttagtttttcagcaaccttttcttaaatcagaaataattttatgaaattttggttcaa tag-63

SEQ ID NO: 99 cgagaaacatcaaccatcgaagagcagcttccttggccagagtgtcgtctgataggtcgatgtagtcgagcaggcacacgactgct ctgcacagttctccgttgtaaaagtagaaaaaagcagagtttcgcgggaatactcgcgaaaatctctcgatctttgctccgacactc catcgcctcctttcgtagagtttgccacgtgatgaacattttgcatgcggttcgttgatacttcgcaagtccttgaaagtattcgg acgaggcgtagtatgaggtgattcgagccaatttgctcagcgagttcatgtcaatcggtccattgacgccgaattcggcgataaaa agctcggaaatctcctgttgcaactcggcagtttgttcggcaaacccgatcaccgtgcagctcacatttttgcgtagctcatctag tttttcgatgtgctgcttgtcaactgacttgtttgtgatcttcatgaaagtttatctagaaaaattaaaattaaactgttttaatg -continued gaattaacattattacatacataaaaagcaagtttttgattgattttcattaaaaatcgaggaaaaattgaaaatgaaagggttt caacgcacgttatcttctaaaaaatttaaaaaatttcttctagatgatacgcttcacatacgcgacgcgtaacattggagcaacg ttgtcactttttcttaaaaatctcttataagagttggcacggtgccagatccggaattccaccagatcttgaattaaaataagttt ttttgcaagttttagcaagttgaagcaagtttttttattgattttcaccggaaatcgaggaaaattgaaaatgaaacgattttcga ggcaaaaataaaaaatttccctccgattttgaagtccgtgaatgcgcgtgcggtgcaactgcgtacaaaacaccaaactttacgac agtgcggtaaattctacttttcaaagtttgagccccaaaattcgtttaatttttgtttaaaactttttcttgtttattgaattattt acattttttcagtcgac polq-1

SEQ ID NO: 100 ttgaccaagatactttgaaatcatccgcggatcatacacaattagtacaacgtttgacatttctcctgaaaaatggaatttcagtt ctaaaaacacaaaaataaagttagaaattgttaaaaacaaaaaagtttatttgaattcgccgaagagcgcgccaaaacatgtgaca tttctcggccgtgaaaactaggccaccgcggccacaaacaaattttagttttcttcgctgaaaaaaacatgtttttcagtctgaaa tcagagtttttagtatgaaacaag him-6

SEQ ID NO: 101 ccctaaatatattcacaatatctcatatttctagatatgcagtttcttcttctggaactacacatcgttggccattatgcttcgcc catttggtaatgatttggatacttgcgttgcaccttgggtcttctatctaactcatccggtttttcggaagaaagttgttcagaga atatttatttttaggcctgactcatgataataaagtttcgatttattttctataagtccgcagagattgaaaagtggcaaatttga ttttgcttattccataaaagttatctctacttaattaattttatcatgttttatgcaattttcaaagtaatgttggtgcgccaaaa aattctacttaagcttgaaaatttgagatgaaactctaaattgtatgcagttattttggtaatacagctttcaaaacacagaactt gcatcttttgatcatttctaacaatgtagccttcacctaattttagttcccagaagttaactcagacggataatgagcgttttaaa tttttgaatttctggttttgccgccaatacttaacaagagcacacgctatcttgaggaaaacaactacctgaaaaggggcgtagtc atttagttcacacttctctgtgcgttttttaaataatgttagtttccaaaaatttttagagacccgaagaactcgggggatgtcc aattggggggattaccaactcgggggacacggttttaaaattatttttcttgttaattctcgctctattgagaaaaatacagttt taaaaccgtgcggcagttgcagaaatgggcgtattgcaagccacggttctgtgggcggggccaatcccccgagttggtaatccccc caattgggcatcccccgagttcttcgggtctcaatttttagaattgtttaaaaataataatgccaacccaaagcacaaaatccctg cctcttaagtgacagtcttcattctccgagttttgaattccaggcgtgtgtgacgactcattcaaattattgatttgattatttca gattctcactcaattttgaaattttctgcgtttcaaaaggtttttcggaatatttttaattctaaagcttcaaaaactgaatta aaagaatttctctcctaaaaagtcgccgaagaaacgcagagaaaatcggcaaaaggcggcaaacatttttattttcaaattttatccg ctttcccttgtgtttatctttattttccctcaatttgcttaaccgaaacgtctgttttcagaatataa xpa-1

SEQ ID NO: 102 ggacgtgcggcgaattgcaccaattggtgcatgttcaaaaaggaacggagaagagccaccctgtgaccactcgagcactaatttga atgaatcaacctccccaagtagtaacatactaaccgagaatagtttgaagttctgggggtataaacaagaatggagatagcaaaac taacgcccgagagtaagtaaatacttatatggtgagcctaagtctcgcgtcgatttattgttttctgttcagaacacaacgtgcat atctagaaattttcgatgattcatgcaaaaatgttttcaaataatttttcaaaaactgaagaaagtttgagaaataatataaattt aggctttccttcagataaatttaaatataaaaaatcatatatattttcaagatgcgagaaaaatatggaagcggccagcagagata cgctatagcgctaaacaatgtgtgcgattcacaagagcttctgaaagataaaaattgtgactacgattcaataattgattcaaagt ttgataagtcaatcgatttcaagtgaaaagaaagagcttgagaacatgatgagtagcaggtgtagaaaacgcatcgacgcgattat tgattgtttggcgccactaaacacacagacattcggtcatacactcttccaaatatagtcaatatacagtgtgttcgagtgagaga gaatggaacatgtcgaaatatagtgtctgaagacgagacactggattattttgacgggaaagcgtgttccttccggttgcaggatg ctggtgcagcaaagtgtcaaaatcgatgggaacagggaaggaccccaaggataattgaaagatgagcgaggagaaagagagcgact gaatgagttattacgagcggcagatagccggaatagctggcctatttacattgcggtcgtcgctttttgcggaacgggtcgaacg gttttcaatgcaattagacgattcgtcatctttttgacatttttagatacaaaaaatacttatcaataaaaaagtttttagaaa -continued aacttaaaatatcgaatttatctttagaaaatgaattaaagaagatgaaaaataaaatgaaaatctaaaacagattccataccgta
gtttcacacaaagggacatttatagttctcaaatttgtgtcccgccgcgaaatcaaaacaaaagaaagttagtccgtgtactccac
tcggacaacattgtttcgcaacactttttctgcgaacattaaaaaatataaatttgttcaacttccatttttaatgttatcaaa
tgtttcaatttttcttaatttttatgatattttcagctgaaatttttgatcgattagatcacaaacttattttgatgtttaattga
aattttagagatgtattagaaagtttttaatcttcaaacaaaaaacatttttgtcaaatcgagacctcaaaataatttatatttc
aatacaatttagtttccttgcttttaacgttcaaatcttgatcatttattattttgtttataaacgattgtttcagataa nth-1

SEQ ID NO: 103 actgggtcgacgagaagttttggaagtgagaatttactaaaaaaaagaattaaaattagaataattctgtagacatccacaaatca
cctgtttttcagtcgatgaaaacttgaaagtttataatcgtctactttatcctccttcttttcaaagtcaattagaacaccatcag
ctcctgaacatcgatttttttatatatcgatcactgggaaagaatctgaaatcactgatataatagagacattgcattgttgacata
ccttgtcagtcgaactcgaatcaacgatctgatcttcatttttttgtgttagttggttagtcgttagtagattataaattcggtaat
aaatttatagtggtagaaattaatgagaattatatccacgaatccgcgtgtactgcggaaatattcattttatatttataaaaaat
gttacaagtgagatcaaattttttttaatgtatcatagaagagaagcgccaaatcaatagaatgctgcacattttaccgcatcca
atcgttccattttctgaatttgaaataattattcatagctccataacggttgagtaacgtgaatgataattctgttttaaattatt
aagactaattcccctatttgaattccctccaaaataagaactgcaagactagcgatttgatttgagcaatttgcatcgcctacttt
ccaaccaatcaaattaagtgtgcgaagttcgaagtcgcctacctaccatatacttcccatcgggtctcttaacaatcattggcttg
aacgaaacttctctacaaactctcgttggtggcgacagaaaccgtcttgtcattttgccacgtagcaatagatccgccaatgcttc
aggaatctgatttgatttcagtgcttctgatggaatacttccaaagcatcgatgaaatgcctgtgggactccatcaatgtcttcga
attggaacttccatagacaacatggttgttctctgaattttaaaaaaatgattatgattaatgattgagtataagttcctgagcca
gttgggcaacctacattccaagagaaggatcgcactcctttccaaatgtgatccttggaagtatggactttgtgtcaaggattgct
cgagcatccagattccgtggtagaagatatcgattgttccaaaaatcatcgagaaccactagaatctctctgatcctagacctctc
attatatgaatttacgatagaagttgtccgaaatctggcattttctccccaatccatcggttttgtttcaattgggtgaattttta
gaaacgtctcacctgaatcaagaggatgtgatgaagatcttaaatctctgcagttcaccttcataacatacgtacatcagtggaga
cctacttccagggtctctgaaccatcgatcaggaatatgaattgttaaactgaacacgtgggttactgtagttatatttatatttc
tcacttaacaacaggaatcggtatctgtttgatagggttgaagtgtattccatctcgaaaatgaatcggaacatggaagaattgtt
tcctggctagagatccacaaaagttcgagacgttgtcaccggtaatccgatctccgagaagaacaatctgtaagaggtctcatctg
ggagaagcttatttcagtagttaccttctgttcagactctgcgattccttgactataatagtcgatcccttcaagattctgatgaa
ttgcatccgaaaatgcttctttaacaacttcgtgcaaatgaaaacgtaattcgttttgatcatcatactgaaacttcggaaagatt
ttaagtattaccccgatccaaatgtttcgaattaaagttataaatacggtacccggtttcgacacgatttttgtcaaactcgagga
aactacagtagtccttaaaggcgcatactaatagcgcaaaatctcaaccttcgcttaccaacttacccgcacaccttcctttctct
gcgaatcaataataaaattcgaaatcggcgtcatcattctataaccagtacaatgaataatcaaactaaatagaaaggcagcttga
aacatttctttaatcttctcgcaacgaaatgtgctccggctctccaggcttatcagtgttagaagagaagagaaggataaaacaac
aataaaaacagttttcatttgtctcgtttcttgcttcttcccccacgatctgctgatctgaaaatgcattctttcagt sir-2.2

SEQ ID NO: 104 caagtggtatgccaactcatttgagagatctaaacatcgaagcccatcctctacttcgacagcccgtagaagttgtgtagcacatt
ttgaacatgtgagcctgtacaaaagccataatacttctcaactactatcatcgtcatctctccgtcaccaatgatctctactcaaa
acggttatggacggtttttttgcataaggattcaactagccctacacgattgctttgatctctgtacatttttgcgtttaatatgg
atatttgctttttaatggattttcgatcttctacttttattgttgatttttctggttttgtgggggttgtgtacaaattttgttta
tttgttgtcggtaaccacgggtaccatattatgtgaatcgtttatcatcgtattaaatcatgtatacatgcattgtacagagtttt
tgaatataataaatgaacatgacgtcatttgcacctactttgtgcttttgaactttcactgtttcagatatttttttatttatgaaa -continued aaaggtatctatgaacaagcttttcaatacattataactttgttgtatctggtctgatcctcaatatttttgagtcttcaaaagaa acaattataaattgcaatacatctcaacactgttttatggcgtctcaaattttgaaaaaaaaaattattttataaaaattgatttg cagcagacatgttgaaaacggtgcttttcttttaaattattttgttgtgataatgtaattaactacaactttacataaattgaac tgaatatacgggtcattcatttttacaaaccttatctattctatcaataccatgactttttttcgcgaaaagtcagccgacatgaca tgactcttatctcttttttttttgttaattctttttttgttgcgacaaattagtgtcaaaaaacgtgaacccattcgatcacataa cattttgaacttcaagaaaatcacacaatcgataaatgatgaagtatggtaagtcaaaatttctaatattccaactgattaatag ttagtgtgtttgagttttactttttcaaattaatgtttacattaaaacaactataacaatcctcaattgaaatattgtacacgaaa taaaaatcaaaacatatgtatgaacatatttctcttatctttttgtattctgtcaaaggggtctaattttttgaccattttttg tcagttagaaccaaataaaatcatgccgcatgtctgtgaaaaatcaccttattctttctctttgagattgataaaaacgttctgta ggttttccaaaatgttaactaaaaaatcaaatttaagccgtcggtatagtattacaggctaggtataggatgctcggataatatta attttaaaaattcgaaaatgcatcatacataaaactttttaatacaaaatatagatgtttttctttttatttatttattaatataac gtatctatataattttcaattaagcaataaatatttttgaagatttgaggataaaactaagcaaattctaaaactgcaatgttcaa tgaaattgcgttattcagtgttacctataaagatttttcaaaacgttactctcttattcttctcccattcacgtgttgcactttct gccagccgccttctcggagaaactaggaaatatctgtgactttctctagccactctctactctctcgtcagtgcaaatagagcgcg aatgctttaaaatgacgcatcaatcactctgtcggtcatttgattttacacttttcactgatagcttaaagctcggaagcggaact atagtgaaacattttataaattacgatttagattttttgaattctgtatcatgctgcctaattttttaataatttgaatattttta ggc exo-3

SEQ ID NO: 105 tgcccagagagccgtcgaccaattcaacggagtcgatttcaacggaagagctctacgcgtcaacttggctcaaaacagaaacaact aattttcatatcggtactttgttacttgtttgatctttaatgatctcaataataataaacccatgaaatcgttatcataaatatat atgctctatttttttatttcgaatcttcatttggggtcaatctgatggcaagcgttgaggctagaagcttgaaggaacggcttcgg ttcgagcaagttttgaatcctgggctatgcgcagcccaatgtgagcttacaactgaaaattcaagtttcaacactcttcgcggtct tattttggactaattcctcatattttcagcttgaaatggaaaaaaatctgtcgaaatcgatgctattcgaggggcggggccaaaacg caaccctggcacggtttttacgcaactgccgcacgttttctccaaggcagggtgagcggaaaaaattaaaccgtcataaattttctg ctacggcctaaaatcgtcatgtctggaatcttctctgtttacggttagtttttttaataatttattttaagtattaaacaatcggaa actggttaaaatagccaataaaactcgatattgtcctgaaattttgggatttttcggaaaaatcgaattcgcgaagttttccctaa tattttcatttgaaaaggcaattttaagtgtttagattcaaatttggttgcgaaatatttaaatcaattaaaattttcctttttt tagttggaaacgctccattccagaccaccgaggaggagcttggaaacttcttcagcagcatcggacaaatcaacaacgtcaggtaa ctctcccagccagcccgagcttcatgatttctaacgcaatatctctttcagaatcgtctgtgatcgcgaaaccggacgtccacgtg gattcgccttcatcgagttcgccgaggaaggatccgcacagagagccgtcgagcagatgaatggagccgagttcaatggaagacca ctccgcgtcaacctcgccaacaaataagttgatcttcatatcgggtttttgttactttttttgctcttcactgatctcattattaat aacaatccaatgaaactatcgatttaattatttaattcaatttcaactattctctaactaatctgttcaacattcggggaagtttc tctatttgtcatccttccatccgccgacctgattcaactttcttcttccccagctgctccgttcaagagcctactcgactactaac ctgttgctgaaa ung-1

SEQ ID NO: 106 tccggcaaatcggcacatttccggaattgaaaatttccggcgaatcggcaaattgccggaattgaaaattttctgcgaatcggaaa atagtgggaaattgaaaatttccggcgaatcggcaagtttgccggagtcgtaaatttctggcaactcagcaaattggaggaataaa acatttgcagaccggaaattgtcgcccacccctgttttgcactacgctttgacaagtgtgaatttattcgctttttttatttgcct gaattttgccgataaagaagatttccggcaaagtggaaaattgccggaatttaaaaatttccggcaaatcggcaaaatgcccaatt tgccgcccacgcctgcttcacaaattgattaattgcagcctcttccgtagctgaacctctggaagaagccactacaacgagtgtgc cagagccaacagagtttcaattgtcacgggacatttatagcactgtaaagccgactgatgaggctcatagcccgccgattcaagcc -continued caaccgaagaaaaaagccacgccaagacggaagaaagcagatgacgtggaaactgtagtagctgacggaacagcgacgatcccgaa gccgaagagaaaaaggccgccgaggaagaagcctgagccgaagccgaatatcgtttttgaaacaacgccgaatcctccgacagaaa gcttcgcagccaacaacaatttccagcagttccagtttcaaaatcagcctggtagttggacctacaacaatggattcggcaatgga tatgggtacggcggtggaaccactggatacatggataatcttgttggcagagggtttgacacggtttctcagcagcctggatttca gaatcaaggtacatttttttaaaaggaattgagaaaaatgtgccaaaaaaattttaaaggtggactacgctttgtggggaaattgctt taaaatacgcctatggtaccacaatgaccgaatatcatgattaaaaaattcaaaaatttttctaaattttatatgatttttttgaa aattggaaaaatcacagttttcccctaattcctatttgaattaccgccaattgaatttgttcgatggggcgcgcttgcacgtatta aatttatttattttattattgttattttccaccgatttttaatgattcggtgtatttttgctcgaattttagagaaaaagtcaaaa taaatgcaaattttcgattaaaaagtgcgcttacaggcgtaaatcagtgaaattaattaattcaggttcgaaatcgtttaaaagcg ttactttttcatttttacgcctgtaagcgtgctttttaatcgaaaatttgcatttatgttgatttttttctctaaaattcgagcaaa aatacaccgaaaacattaaaaatcggtggaaaataacaaaaaataaaataaataaatttaaaaacgtgcaagcgcgccccatcgaa caaattcaattggcggtaattcaaataggaattaggggaaaactgtgattattcaattttcaaaaaatcatataaaatttataaat tatttttgaattattatcatgaaattcggtcattgtggtaccataggcatgttttaaagcaatttccccactagcgctaccccacc tttaaaggaattgtgaaaattgtgaaaaaaaaaatcaaaatttcgaaaaaaaaagcgctaattttaactaaaatctctaattttgg ccacttttccgtgctgcagcgtccgaaagtgcactttttttgaattattattcttattattatacattaaaaaccccccgtactcct ccaataacgccaatattatcgaccatctggacgtgaccgcgtgcaaccacggcctagctgccgccaccccattcaaacgagacatt tcggcgggagagtcctttttttcgataattcggatttttttgtctgtttcaagtaattttcgccataaaaattaccattttcttct tcggtgccatttctaatgattttccagtgcgttttgagtctgaaagtttgaaaataagagtttttgcacaaaaatgtgtgagaaaa gttcaagaaaatcgtcgaaaaattcaataaattaattttaaaatttaaaaaaaaattaattttttttaaaaatcaattctgtgcat acaccgccacgcaaaagtgcacacaattacctaccgtagtcaatgcgaaattaaatgatttttatcgatttttcttcattttcaggt tacgaattcaccggtttgcctgcaaataactcgaataatttcccattttttgtgatttaatttttcaaatatccttatctatgccct caggtttattttatctcatttccactcgtgattttgaataaaaattcttatttttcttctagatttccgtttatttcaga mrt-2

SEQ ID NO: 107 atttttcgaatattttgtctgaaagtttcacgtgatgtcagagtgtctcatttcggcttgatctacgtagatctacgaaaatgcgg gagttgagacgcagagttttcaactgatttcgcatggttaagaacgtgctgacgtcacattttgttgggcaaaaaatgcccgcgtt tttgtagatcaaaccgtaatgggacagcctggcaccacgtgaaattccagaaaaaatgtctgaacctactgtagttcacaatttaa aggcgcataccaaaaaattatagcgggaattaaatttttatttaataatttttttcagttacagagcaattaaaaaattcaatttca tcaaaattttatagaccaattttctcgctttatagctgagctccgcgagccaaaataggaaggggagcacgaaaaaaaaaacagaaa aatgagctcgacagagcccatagcctcaagcgctaacgaaccaaaaaatgcacacacacacaggaggcggagtcgtggaaatttcg aaaaaaaaaacaagattttcttctctctcggctcaaatttgaatgcggagcaagaatattacgggaacaaaaaattctgagaatgc gtactgcacaacatatttgacgcgcaaaatatctcgttgcgaaaagcaaactacagtgattctttaaatgacatttgtagtgtcga tttacgggatctcgattttcgaaatgaattcatttatcattgatcgagcccgtaaatcgacacacgcactacagtagtaatttaaa gggttactgtagttttgttttcgctacgagatattttgtgcgtcaaatatgttgcccaatacgcattctcaggatttttttgttagc gtaataaaataacagaaaacacagaaaaaggcatgaaatttaatttgaaataccgcgctgagttttctaggccacgtgtcgtgtac tccccgtggacaagcggtttttgccttatttttctgaagtacaaattctcaagtacaagtaaaaaagtacaaattttaccaaattt gaggaaaagaactagcatgacaaaaatagaattagaaaaattctagagaaaaactacggatttctggcttccctcataaaatgaaa tggaagagtttgccgaactaggccattttggctcagccatatctggagtagatttacggcgcgttccgtgtcgcggctcgatttta gttgtaaaactaaatgaatttgtccgtgtggagtacacgactttaccacgcgttgtccggcaggcgattgtcaatggagcgcgaaa aattcaatgcaccagatttgacgcgcaaaatttgaattttcaagttgtaaatccctttttttcttcccattgtcccatcaaatatcc ttcttcaaaaaaaacccctgcgtctctcaggccatatctgcggtagatttacggcgcgttgcgtgtcgcgtcgcggctcgattttag -continued ttgtctggcgggcgattatcaatgaagcgcgaataaatcaatgaggaaggccagaaccccgtgaagatccaagaaaagttttctag gccacgttccgtgtactccacgtggaaaatgtcctttccggcaggagattgtcaatggagcgcgaaaaattcaatgcaccagattt gaccacgcgtcgtgtactccacgtggaaaatgtggacactagggatctactaaatgcctggaaaatcgtaaaaatctcgaaacttc ctaaagaaaaaaaaagcaaatacacaaaaacgcattgatgtatgaacaaattgccctccccgtctcccaccaaaaactcccaaaaa ttgctctttttttcatgtttatatggggaccgcgggatttcataatagctccgtggtccgctcagctcatccggagccaaaaagag cacacacacacacgcacacataaaagttgtaaactagtttcgagcaaaaatgatacgacggatgagtgtgtcacgcaatcagtgag cttctctcgctttcgaaagaaaaatctttttcgcaaaaagaaaaagtactttacactggccacagtgtaaaataagggtgaaaaga tcgaaaatcggaggtttcaaatttgaatttccgcgcaaatgagagggacgaggtgcgatggcctacaaaactccgcaggtgtactc ctctcggaaaacggtgcgagaattaatttttttaatttatatttaattttcagcgatttttctcagttttccggttaaaatttaaat tttttcaggaaaa rae-1

SEQ ID NO: 108 aaactgcaatttcgtaaacgattgaaaattgagaaagatcaggtatctgaacaaaaacttgtacatttgaaatctcaacttcattt attccaggatacctacaaatatgaatcctatgtgcttcaatgaattctacaggaaaatattcaataaatgaccaaatcgaaaaact ttatttatgatcccaattatgttttctttgattatgctacaaattcaagaatcggcaaataatgggaaaatacgattttttttttca caatcaatatatactgcttgatctctctgttagaatttcctccaaaatctgaactgtatgaccaaaaatcaatttttttgaaaatg catttgtcccaatatttcctttctaccattctgctttgatctttttttaaccttttttattcgaataaaaatatattccgaattaaat acaattaatgtgtttccaccaactttacacataaaaattcattttctgatgtaaagatttttttctaacatacatgcattaacttat ttctggagaaatatttctctggtttaaaaaaaaaaacttctatttagttatgatttttcctttttcacaacgtgaaaagttgcaaaa cttctgcgaacgacgccacttctccacggtgttgtttctccggaacatttttccccagtgggacgccacgcgcaactgcgctctac tgccaattttcaaaaacggaattctttcgctgaaatttttctttaatttttctttcgtttttcaacgtttttcattctctaaacttaa ataatcgaaatatttcgaaatgattaatgaagaaaggtaggcgttataatatttataatcaaaatttctcaatatcatgttagata ttcatttttggcgaatattcaacaattgaaaatcaaaataccattatttatcgactggcgttatttttattgtttcagaaaagctg aaataaagcgaatgttggaaaaatgccgtaaaacggaaaaccgacagaaattttggcgatggttgcccaattttcagttgaacagc tggcagactcctgttgtcattggtgttgcagctgtttctgctgcaattatctatcactatttttcctaattacccttattcctatt gttcaatttttcttcatcctgattttgtgatctacctcatgtaataatttttctcttcttctttattatttttctgcgctctgtactt tcttaaaactgtataaattaaaattgcaga rad-23

SEQ ID NO: 109 cccacacagccagaagatttttatgggcggcagacattttcttaaatccaataatgttttaatttgataaaatcgaagataaaagt tcacgataaacacaagtgaagttaaaaaataaaaataaaacattcaaaaaagaaataaacgcattctccgtaaatcgacacaatga caattctggcaggtctcgccacgaagagtgttcaaatcatgtgcgcctttaagacgccaagccattttctcttctgtttttttacca cttattttgttcttcaaaatggttttttttgttttgttcttttattaataatcaaatgtttgtttattttatacatatatactgctt gttttgcattaatatcaatctgttatcgatatttatttcttttttctttcaatacatgactctattcgtaacatttcacaattttttt gcagg brc-1

SEQ ID NO: 110 gaacgtccgacatgatgagatgcaataacctgaaaatgaggcactttatgataagaaaatgcggtaaaacatgcgaaatatggcac cataaaccgtgagcaggacaaagaacaaacacttggaaaagaaaagaaaatagaaagaaaaaaaggaaaactggagaaaacaaact caataacacaacgcgagaaatacaatttcgtttcgttattcttctatttattagatttctcacaatttgttaccagtaaagtcacg ttctatatttcaaactactcctaaaattcggtttgaacagttctctgataaacgaatttcgaagaacgatcagaaaacaaatctac ggttgtgtgtgatcaatggggtcaaacggtggacgaaaggggacggcggagagaggaaaaagtgagagaaaataaataaaattgac cttcgagtgcagagttttgctggtattttggtcagaattgattatgaaaatctgaaaattaccgccgggaaagttgaaaatttgac gtggaaacgtttaaaaaaataagatgagaaagttagtactgtagatgtcgtcggatcaagtgcacagtacgcaagcaccgttacga -continued aaaattgcactaattgctcaattaaatttttttaaaaaattaattttttatagtgtgattgtgatttttctgctttttaatgatt tttaaaggcttgattatgattttctcaaaatttgaataatcaataacattaattaattactttattaaaaaaccacatttggcat tttaataaagcaagttatcgcgacaaacggcaaaaatgtctcttttttataaaaattgtttttttttgagttaagagaagatgtgga gtttttgaactacattagttttctaaaaattttatcatctagattttgaggaaaaaagcagattatatatctttaatcttggttt taaaatttttttaaaaagcagaatattaaagtaaaatattataaaaagaaaaattcgtgtttgcaaaatttgtttgaacggaacct tgcaaaaatgatatttagcagctaaactaactgaaaactactgcataaagctttcccaaaaagagctaccatccagaaaatgtttt ttttttcaaagccgaaaaagaagaaaaaaagatagaaaaccgaaaaagcagcatcgttttcgcgcactctttcttcttttttttctt tctttttctaaaaaaaatattctccgtagcttgaagtctcaggatttccaaagggaatttccttgatagaatatggaaaaacaag agagtcatcagagaagggagaggaaaagcggggatgctggcgaagaccgggggcaccgactgaaatataggcaccggcggggaggc ggggcgctctctcctctccgctttactccgccccgattgtcagtggagcaggtttgcaatgagtgttctctgatgccccctcagcg cgggagttttgaaatcaaatattttgtattttaacctactttattgatttttcaattaaaatgaaatgttatttgtttaaaattta atttcag brc-2

SEQ ID NO: 111 tgtaggtctaaaaatatttgtttgagaataaatattcgaaatcaatctaacgtttttccaatctacaggtggcacgacacgctcac aaccaataagtttcttgccacgctcgtcgattttttgtagaattcccatttctgagagtgtttcttcgctttctgcttgctctgga acttctgaaataactttcccgcgattatttggatttctatatattttcaaactacttacctattttcgttttccaaagtctcgaat tgtgtacttgtcgacgttggttccagatttgagcattatgaagaattccaattttaaaatcacaaactggctcaaaatctatacgc tcgaatagagaattgtgtgatgtaagagcctgaaaattatatttgattttctttccatctttttttattttcgggaataataaaac attcaaaaagggctgagatctatctatttttcacatgcgacccatttctatttcacgtgaagcacatgattctgaagggcaatgga aatgaaaacccggaaaaacaaaatctttcagtttaaattgtatcaaaacaagtttttctagattacaaatgtacctgaatagtgat ccatgaattgggacagaccacatcgaaataacatttcacacgtggcaatggagccattttgaagtttggctgaaattaaatttatg tcgagaaattaaaaaaaatcagagcgtcatcatgagaaaataggaaaggtttagactgtaaaatcaggttttcatggcgggaatga cattaaaatggtgataaggtgattattttatcaaaagaatttttttgaatgattgcacctaaaatcgagtgctttttctttaatttg attatcaaaagaaaatacccaagaaatggaaaatgaaaatttaagagatgaaaggaaaaagcgacccggaaaaacatcaagctggg aagaaatctcaactagttagaccaaagcttcgaactctgcgagcatgtatttttttttcctcactttctccttttcttctctatttc tctagatctttattactgcgggggcaaaaagagtaagagatagaaaagaatgacgcaaaaaatacacggatttaatatttgctttg cttattattcagagaggaaaggtcaattgggggtttcccctcgttttatgaatgaaaaccgcacataaatataattatttccacag ttttaaacggcagaaacggttcgtgttataatttgtgagataattgattttgcattacgaaattagaagaaaaggcggaaataaat aaattagtgtcgcaattatttctcaaaaaggaaataatgcaattacgctccaccggacagtaaaattctcagtttatttgaaaaac aaaaatttaattattccattattcaattgaaatctcaaatttctgaactcaaaatgaaattttcagactttaccagaatattgtga catcgaccg rad-50

SEQ ID NO: 112 atcgcagaaatgtgaaatcataaaatccatagtgagattgagttgtttattattttatgaaatgagataatcagttggataactac tgctcacgccgtattcgatctatcattcgattctccgattctggaacatcaaattttaatcatagggagagaggttcgggtacttg agaaaaaaaatgtcgtgtttcgagaggttttgaaaagtcagttgttaactggttcggtcaacatgtagagattgtagagaaatatga gaacttagagaattgacgtatgaagagaaaaaaagtgggaaaggggagccgctgttgttttcgaaagaagaaaataagacagaaaaa atcggagaggaacataacaacaagttaagttgacttttgaactggaaatttgtcaatattgaaaaaaggaacagtgagaaatatcg atttccacgtcgctcgattctatgaaaagaaattatgcacacacaagcttcacagtgagcatgctgaatgattgagcaaatacatg agagaataagagaggaatgagatgaaaagaagcgttcaaatcaaaagaaaccagacaaaatggcgatttttttacgggaatatgaac ctactgattggcagtggacagctggaagaataagaagatactgaaggaaggttgaagttgaagcttggaagacagatgatgagaga -continued gaggaaaacctgtttctttttgattacgatcggacggaaatgagaaggaagtaagtgttttcacacgtaggtgggcattgagatct ttgaaggtgcattcgacaggttaataatcattctaaataccaggtgacaatggaggatacttttaaacagtaaatatattggaata aaacataaaagttagtcttactcagaatttctaaaatttcagccttctggaacgaaaggtaaaatcataataataatacaagtggg gctgttagtagccctaaatacaagtaaaatgaccgaacacagccgttaaagaatgttgcagaaaattgcgaaatatttccttactc ttaagaacaacattcgatgtgacgcaatatgatgcatttccttagacaaaaacgttcagttcaaaataaacaacaataaaaccgtt tgtacgatttctagaatacgagtttatcagttgttcggaaaatatcttatcaatcgtttgactgatgtttttttaaccatgtgagaa tttgaaaaaaaaatttcatgattgccaaaaattaaaataaacaggaagcttttaccgagttttcgtgattttcagaatgaagaaatt aatatgaagctcaaaatcaaaagcagagggaaaagaaaaaatcgaaatcttctttcggttaaacaacacgcgcttgcggaacttcg gagcatcgtattttgtttttgcgctctatttttgaatcggaaactgatttttgtcagttttcgaaattgatttttttctgattttta cttcatgcaagagtttaactttacgcaaaaattaattaaaaatacgcagaaggcccactttacacaggaattaattgaaaatactc aggaatttcactttacttagtcctttttccagagtttccaacggaatcaatatattaatttaatttcgcaacatttttctttgaat aaacctatttgcaaatgagaatgtttcagatatttgcttatcgaagcctgggaattgctt

Y47D3A.29

SEQ ID NO: 113

Gcgtaaattggtttctataaattcttgacaaactcattccgaacggctgaaaatattgattgaactgaattcacattattcattaa aaaaaataggttagcctgttatgtagagaaatttagtgaataaaaaactgaatatgtatttatttaatagatttctcggcacacag gaattaggaataactcccaaaaaatagatatttggcaggagggccgaacagctgtgttttccgtgacgtcatacaggtcaatggac acaggatgtagtcatattacgggaacacacaattctgagaatgcgcactggggcatttgatttgacgcgcaatatctcttagcgaa aactatttacagtaagaatttaaattctaccgtagcgggctcaattttcgaaaatatatttttcttatcgaattttgagagcagttt ttcagttttccatgcttgattttattattttatctttaaataaatttttttcattgaaaaaacgggaaaaacaccgggagaaattg atctggtgagaaaattataatatttctgctgttttcctgttgacaactttagaaatgtcaattaaacaactatattttaaaataat catttattatttaattacgtcaactagaaaacattaactattgcgaaaattcacttctaccacactcatcatcccgaaaacagcga ggtctcatgaaattgcaagcgcgctctactgcaaggaaaggcagcgcgcgaagcaaattttcaaacaatttttttgaacgttttacc gcattttctcactttctcgcttaattttgctatgatttttgcgattatttgtaatttttcttcgtttttcag cku-80

SEQ ID NO: 114 tcactaaacaaaaaacatatatttgtaaaataccattttttcttttcatcaacagcttcaaaactatctgaagtgctggattttcgt tcagctccgtcgatcagctcgaagtcttgctcctgttctggagtatcgctcattctggaaagatttaaatacaaccgaggaaccag aagagcgcatgaaaatatagagcgtgtaatttaacgtcagttattgacagagaaaatagaattacgaaagaccaaatcgggcaacg aggaaaacgtttaacacaaacacaacactgaaaataagcaagaaaaggaggaagttatcggaaaaccgaagaactttcaacttcgg aaagaaccgtttaatttatgtttaaaatcaaacaaaaaaattcccgaaacatccctttttaaactttgattttcacgaaaaacaacga atgaccgaaaaatgtgatcaatctctgagagtgtgcacttttgcgtgacggtgaactgtccgcgtgcaccagattcgacgcgcaaa ataatcggcgcgaggttcgaacgaacgttcgtgaatttgtgggagcggtttttaatgtttaaaaatcagttttggtttattttatt tgaaaaaaaaaacgataaaagctatattccagcagtatctaaaatgatcttcttttaatattctaattttaatgttttaaaattca tttttcgctgcagcaaaaagttggtgtttgcgtacaaaacccgcgccagtcttgaaaaacgcacgcattatttattcacatgtttc gcaatatttccatatgaacttctcaacatcaccaatttaaattaagttacagga him-10

SEQ ID NO: 115 cttgtttcatactaaaaactctgatttcagactgaaaaacatgtttttttcagcgaagaaaactaaaatttgtttgtggccgcggt ggcctagttttcacggccgagaaatgtcacatgttttggcgcgctcttcggcgaattcaaataaacttattgatttaacaatttct aactttatttttgtgatttagaactgaaattccatttttcaggagaa -continued polq-1

SEQ ID NO: 116 ttctcctgaaaaatggaatttcagttctaaaaacacaaaaataaagttagaaattgttaaaaacaaaaaagtttatttgaattcgc cgaagagcgcgccaaaacatgtgacatttctcggccgtgaaaactaggccaccgcggccacaaacaaattttagttttcttcgctg aaaaaaacatgtttttcagtctgaaatcagagtttttagtatgaaacaag lin-35

SEQ ID NO: 117 ctcttcttttactaatccatcaagcgacttttcacggagtaatctgaattaataatatttatcagtgcatatctctgaaaactaac ttgacgacaaatgcttcgacatcaaaatccggctttgtgacgtccaaaacactagacattttacattcaatactgaaaaattaaag aaaattcaggaaaactcgagaatgaaaaaaaacagatttgagacaccatcaatacaaagggaacgaaatttgggggaaatgctggt tgccgaaaaaataagtagaaggtaagatgtgttcaactggaacatacattttctgaattgcaaactcgatttctctcacattcaca atttttaatcacatttaatgcttcagttttagaaagttctgaagtatcctcttcttcctattcagtttctcaaaatcgatggtgtc tccaggacgtgcacaaatgcgctctattgcgaattgtggaacatcattgcgcgcgcgactagaaaaaaatgagcgcgttcttgaaa attattttgctttctctaattttaaacgatttcgattacattttatctgaactttcttgggtttaatcgaataaaaaacacaaaaa tattcttcagactggtaaaaacttcttcaat

Xenobiotic Toxicity Genes cyp-13A6

SEQ ID NO: 118 gtctagtttcaaaaaaaattaaattaaattaaattgtgtaatatgtggcattatttatatactttttgtcgatcatctgttaagttagttttagtcttatc ttcttgtcgcacaaaacattatggtttgtgtttaatagaacaagaaagtgggtgacaagaatcgtatgatttggagaaacccagcaatcaaga agattttgtttcaaaattcgtagtctggatactttagaatgtattctcaattttcgaataaagtttagaggatgtttttcaaacttttatcaattttgaa aactatctgatggttttataattattacagtcacatatttgtagcttgtgaatctaaacctattatgtatattctcgttttaaaaaaattaattgccgaaa aaaagcaaaaaatttaatcttacgaaaaaaagtttttttttggatttatcagcttcagtgctcattttcatccctaactttctttcaagaaattttaga tatgaagaacaattttaaaattctagatcaaccaaatctctgaaacaaaactagttttctattgtttctacatattgatattttttttaaactccattatc atttttaattttttaaaaagttttctaactaccatctgctctccatcacctctttatgtttttttgcatttgagcagtgaaaagtttgaagaatattggtaca acttttataccttccaaaaagtgcttgccccattctctatgttctcttatcagtacactatatctcaacagtcgacacatttgtgtggaaaagtgttg tttgtgtctgactgttgtttctaccaccgatactatttataaggtggtctaccgaaaaacatcaatacgtttctttttttattcctgaaaataaaaac cyp-13A7

SEQ ID NO: 119 gtttttattttcaggaataaaaaagaaacgtattgatgtttttcggtagaccaccttataaatagtatcggtggtagaaacaacagtcagacaca aacaacacttttccacacaaatgtgtcgactgttgagatatagtgtactgataagagaacatagagaatggggcaagcacttttttggaaggta taaaagttgtaccaatattcttcaaacttttcactgctcaaatgcaaaaaacataaagaggtgatggagagcagatggtagttagaaaactttttt aaaaaattaaaaatgataatggagtttaaaaaaaatatcaatatgtagaaacaatagaaaactagttttgtttcagagatttggttgatctagaat tttaaaattgttcttcatatctaaaatttcttgaaagaaagttagggatgaaaatgagcactgaagctgataaatccaaaaaaaaaactttttttcg taagattaaaatttttttgctttttttcggcaattaatttttttaaaacgagaatatacataataggtttagattcacaagctacaaatatgtgactgtaa taattataaaaccatcagatagttttcaaaaattgataaaagtttgaaaaaacatcctctaaactttattcgaaaattgagaatacattctaaagtat ccagactacgaattttgaaacaaaatcttcttgattgctgggtttctccaaatcatacgattcttgtcacccactttcttgttctattaaacacaaac cataatgttttgtgcgacaagaagataagactaaaaactaacttaacagatgatcgacaaaaaagtatataaataatgccacatattacacaat ttaatttaatttaattttttttgaaactagac cyp-13A11

SEQ ID NO: 120 gaatcttcgatgttcattgtgaattttgtatcactgccttgcctttattcacttcaggaattttatgttttacttgtaatctcaataaaaatgaactttcaa attaataataacaaactaattttctagttttacatcagatatctgctgagcttctgctcctcttccgtcaaaattaaatcaaattggctgagcagcg -continued gcccagtcaactagcgaagttaggacataggttttcttttttttttttgttgaaatgggcaaattgccggaattgaaatttctggcaaattggcaaa ttgccggaattgaacatttgcccaaatctgcaaattgccggaattgaaatttctggcaaatgggcaaatcgccagaattgaaatttccgccaa attgtgattttgcactttttttctggaaatttcagaatttcaatttcaatcggcaaatttgtacgcatcctattttgaaaagtaagcaaattctatgaaaa tatctaaagaaaacgggaaaaaaactcaaaaagacactgtttttagtgtttccgttttataaaaaatgcctctaaacatttccgacaaatttgatg atccggcaaacgacacaccggcaatttgccgacgaaaaaagttgccaaacggcaattgttactggatcttatagtgatcaaattttggaaaa ctcaagtacagtcagaaaagcagtcagaacccagggtctattaaaacatcttttacacattgaaaagttacatatacttgaaaaaaggagaca tagagaaaaactcagatactgtctctgacaatttttctgctttgtgccactgaatggtaaacaagctgaaaggtataaaaactattgcaattttg acagaatggtatttgaaatcaagg cyp-14A3

SEQ ID NO: 121 atgtaaccccaataattattttgttgcattttactacttatatccgtttccatttttttaatttatgttgtcacgttttgtctaaatagtgtaatcttcttgt actaattattccaattattttaacccgtaagcgataaatgaaacaacactttttggtttttatttgctaattttaaataaattgtcatcaattctgaaaaat aataaattttaaaaaaataccgaagaggcaaacaagacatttggaaattctgatccggataaatattccgttagatttttattagactcgaaatt gcctgaaaccccgatttataacgaaacctcttgaaaacttctcaaaaaagagaagttaccaaactttaccaaatttggtctcccatcgacctt caatgtacctaactctagttgaatacgcaagataattaattgctacaaccaaaattaaacggcggtttcaaaaaaatattgttttcagccgctgc aacattgacaagtgggaaaaatttcaaattttaactaattttaggtcatttttgagccgccataacttatttgagaagttttcaagatattttattttg aagttcggagttttcagacaacttcgagtcaaataaaaatatttttaagtcgacgacaccacctcggagataatctttaaaaaaatcttttcaga aatgcaaaaattccaataagtgtcaaaactcccgagtagcgcttaagcagtggcacgtctgtatttatgtatttttgattattattactttattattt gtgctttattactgtttttttttaaatttattttgtttcatgaaattttaggactaacgtgaaactcaacataaaaaagctagaaaagtttcgcgtactg tattctatttttctttgatttattaatgtaatacatcacttttatatcttgagtgactaaactcttgttaagtgtgtttcaataatgttttgatttttgac tttacttatacgtgctttgtagttttagtgacattagtgaccgaaagtgagacgataacaaattgggagcggtatataagtgaactacgaaacttct aaaaaaacaaaggctgtttcaca cyp14A5

SEQ ID NO: 122 tgtgggaaaagttggaggtttttgcacattttaggtgagcgaatatcccgttgaaattatagaaattaccgattgccggacagttttggaaattg tcaaatccatctatttttcgaaaaattaatagaaaactacattggttttcagtatttgataagtctacgagacaaaaatgtctacgagacaaatgta cacaaattatcaaatttacacttccggcaattctgattttcggaaattgtccattccggcaatttttgcaaaatttgaaattttataaaaataattctct acctgcctgcctacaggcatgccgcaactaaccttgaaaactttaaaagaaactccgaatttcttaaaattttaagtcggctggaaacttagaa atctcttgccaagataaaaaacatcgagaacatcgtaatcaattttatttgatttgatacgttcacaaagtgaaattccaatattgaaaatcaaatt caattaatcaattaagagttcagtgagtcgtccttgaaatgtaccaatttcacttgagcgctcagaatttcgttcaaaatcatcaatttctcgtcca aaaatcgatgaaattttgcgagtaggtacaagtttgtgctggaaattaatttattggttgtatggatattatttttaatttaagaattaaaaatttacc atgaaaataaagtatgaaatattacaactatcagggtaaaccaagcaacgcgagatccagtcaaactgtacacgactaaactttaaatagca atactaatctaaaaagcaaatatttttctttaagtagaagcaaggcagaagtttgacatttttttccgaccagttgaattgtgattctatatacatctg gttcactcgaatttcagacaaacaactccacattcctcaatttctgtgatagaacaataacttattttcttcacatttctctttcaattatgcattttcat tctttaagtgtctttttttaaaatttgacaccatttgcccgcgactcgttgtccggaggtttcctcttacctcggagaaattccgctaaatctaccat gcatgagtctcaccacgtggacaacgagttactgtaacttgtgtcaatttacgggccgctatcctttttttaaatgatatgtaccaattgatacaa agaaatacttgttttgttatcaaaatagagtataaaatataaatgaaataattcaaaaattattctcaattgggccagatacaataggatagtggg gaagttcaaggatgatattgtgtcagacaaggagcaaaaatgcattaggccagtttttacagaattcattccaagtacagaatttttcaaacatt ccattaggaaatggtgaagaaaaccaatacatttcaacttccaaatttttgaaatggatttaaagcttccctataaaatttgtttatgaaaataattt taacgatttcatttacaatcaccacatttttttagaattctcagcacaggttgaattgttcagtacctttttttcaacatctagttcacctacatatgagtt cttaatttaattacgttattgaaaagtaaatatgttatttggcaagtccattcaaacaaaagacgtcgaccacttataatcaaaaagtacacttgc ggcagacatctcgatacttgttttctctgcctgttgtcactgatcttatcgatatgtaatattgtgaaatgttgcgcagtgttgaaaaataagatata aaattaggaaagaattgtataaaaatcagacaaaactattctgtccaacaaagatcatt -continued cyp-25A4

SEQ ID NO: 123 gatgagatgcaataacctgaaaatgaggcactttatgataagaaaatgcggtaaaacatgcgaaatatggcaccataaaccgtgagcagg
acaaagaacaaacacttggaaaagaaaagaaaatagaaagaaaaaaaggaaaactggagaaaacaaactcaataacacaacgcgaga
aatacaatttcgtttcgtttttcttctatttattagatttctcacaatttgttaccagtaaagtcacgttctatatttcaaactactcctaaaattcggttt
gaacagttctctgataaacgaatttcgaagaacgatcagaaaacaaatctacggttgtgtgtgatcaatggggtcaaacggtggacgaaag
gggacggcggagagaggaaaaagtgagagaaaataaataaaattgaccttcgagtgcagagttttgctggtattttggtcagaattgattat
gaaaatctgaaaattaccgccgggaaagttgaaaatttgacgtggaaacgtttaaaaaaataagatgagaaagttagtactgtagatgtcgtc
ggatcaagtgcacagtacgcaagcaccgttacgaaaaattgcactaattgctcaattaaattatttaaaaaattaatttttatagtgtgattgtgtt
ttattctgctttttaatgatttttaaaggcttgattatgatttttctcaaaatttgaataatcaataacattaattaattactttattaaaaaaccacattt
ggcattttaataaagcaagttatcgcgacaaacggcaaaaatgtctctttttataaaaattgtttttttttgagttaagagaagatgtggagtttttt
gaactacattagttttctaaaattttatcatctagattttgaggaaaaaagcagattatatatctttaatcttggttttaaaattttttaaaaagcaga
atattaaagtaaaatattataaaaagaaaaattcgtgtttgcaaaatttgtttgaacggaaccttgcaaaaatgatatttagcagctaaactaact
gaaaactactgcataaagctttcccaaaaagagctaccatccagaaaatgtttttttttcaaagccgaaaaagaagaaaaaaagatagaaaa
ccgaaaaagcagcatcgttttcgcgcactctttcttctttttttctttctttttctaaaaaaaaatattctccgtagcttgaagtctcaggatttccaaa
gggaatttccttgatagaatatggaaaaacaagagagtcatcagagaagggagaggaaaagcggggatgctggcgaagaccgggggc
accgactgaaatataggcaccggcggggaggcggggcgctctctcctctccgctttactccgccccgattgtcagtggagcaggtttgca
atgagtgttctctgatgccccctcagcgcgggagttttgaaatcaaatattttgtattttaacctactttattgatttttcaattaaaatgaaatgttat
ttgtttaaaatttaatttcag cyp-29A2

SEQ ID NO: 124 accatgtacccaatttctccagatgtctcaaaaagtccttcttcttgttaatatagctcgcctcctcaaattttgatcttccaattcctctccgccca
atatattctagtccgtgtcttaccccttgacaaaaatgagcttttctcagattccgactaattccaaaaaaattccctacgttttgaataattgtcgc
tttgtattatttttctcgttttcatacgggtgttcatcattcatttttactttttaaaaattttcctctcgtttcttttgaacgtcccatttttattgcaatcg
ttcattgtctagggtctatccttctaatcattcttcttctcagaaatatcacaaaccgtctgtgttgcattcaaattttttaagtaaaaataataaactaaa
gaaccacaatgaaggtctaagttggcaaaattgaaaagccgaaagcttttcccggaataatagtaattactggagtgcatcccgaactgtct
aaaagtagagaaaagattaagtggatatatattttttatatttttttaatatagtaatctgtttgaactgttatacaaaccgaaatcgtgttagtttgga
caaagttttgcatcaaattttttttgagttttagatcgaactattgtgtttttaatgtaccagtcaatatttggcattcacaagcggtatagccaaatgt
acccagagttgatcagatagcgtttttcttcactgtgttccgttgttatcaaataaattatgcaaaaactgcgaaaatttgagttcaaacattaaaa
aaaatcatatttttctaggttattgcgagtttttagcaagaacaactaatgttttcatgtttaaacaaaaaaactgagtgagtgagaaaaaatctca
tgtatgccatgggatcaagccatatattttccatagactaaaattatttagagatggaaaattgaaaacaggagacgggttactgtaggaagat
tttttaagactattgcaaatacataaatcttttgaatatattttacttcttcgaccgccgctttgaaacagtgcgttactgtgaacgttgaaaacca
aacatttgaactcttcacctcacttgtccattttgttaattgtctagccaactgtagccacctttgatcaggtagaccttttccaatctgcgtctctca
ttctctcaaattcacttagccatgttttgtacggacatcatttctgatacattaactacgataatagttgtgcacgctgtggtcatttgattaactttttt
tcctgttgcagcagttcgcgagtatataacctgtctttaactgataaatcgtttgcattggtcgtttgaaggaaacaacaatacgctttccaaaaa cyp-31A1

SEQ ID NO: 125 tacagttacaattgaaataaatggaaatctctcttatttttacattgaaatttcttgctggtcacttcttccaatccaccgtagttaaccgactgggt
ggtctactacccgtttctggttttctctgcactctcttcggagagagtgcagacaaaattctccgcgttcgcagtcctggttctgtttcgagacgt
tgacgtcgcccgacaccactcctacaactgttcggacagcgtctgcaattttcgattagtaatatagttttggttgtgaatataatataaattgtg
aaaaattgcattgagaattaggaaaagagcatgtgagaagaggaggggaatttttagaataactgagaatataatttagagaaacacgatta
cttcgcatcaattcagaatatcttttaaaatctgagaaattttggttaaaaaataacacagggcgcttagtttgtggttttctcaattctgtttaatttttt
aaaacagtaattcttatttcgataaactaaaatgaatatgaaattttcttacgattaaaaaatgcatgaaaccagatataacaaattgaaggaaa -continued actgaaaaacttcagaaagtgtttttttctgaaaataaaagcagaaaaaattcgaagctcgcgcaaagaacgtaaacgcgctccattgctaact catttgaacattagttttttttcattgggctttcaatcttgtaagtgatgtttaggcatctaaaagttttataaattgacaaaatccagcttaaaagatg ctatcaaaaactaacttttcagaatatttatttggctaatgtttgacccatacgtttttttgccgaaaagaatttcaaaaatgaaaagtatcttgaaat gcatcaaaatccgggaatattgccgatggtcagtttttcagcatttctaaattgagagactgaaatgggaatttatttatttttattcatctgcttttttt atttcatgaatatccgcatctgaaatcagcttttttttttcaggaaaattgattgaaagaagacaataacagctcgttgttcaacatctcgattcttcc atatgaatcgatgaatggaaaaaccgtggcatttggtaaagttttggctggaaccgaagttgtctcccgcatcgccttcaataaatcaaacac gaagggttccaaggcttgcgtcatcaccgactgtggagaagttatctgaaaggttttatcatagattttcaaatttttttggtttattattatttctttct ttttgttccgataagtccatatatgaaatttgtccagtttttatgaaaataaacatttatttttatttaatattttttttattcatcatatgc cyp-31A3

SEQ ID NO: 126 tctgaaaaacgttgatttaaaattttataaaaaatttgaagcaaaaatgaaagagaaaactaaaaaaaaagtaaatgtactgaagtgattggca gattaataataatttatcgataaaaccatttttttaaaaaacttcatcagtttttgtgagtgtcagcaaagaagaagaagattcacgatcaaaaattc gttgagcctatatgaaatagttgcgctggtttttcgacgggggggatcaaatacgtcaaataggtcaaatagacgaagcattcataaaaagtac aatattcattgaaaaatagttttggatttgatttttgattcttcatttattgttgaaaaaataatggtaattaaaagtttttaataattatttaaatcaaga ttgaaatatcagaaaacgacaaaaaattcgttcgagaactttctcaagactaccgtactctttaaagacgcatgacgattttcacatgggtctcac cacgacttgtctgaaatttgaatgttcgttcaaaaactttttttttttgcgatttttcaaaaccaaagcttaacaaacaattttcctcaagttttcaacgct ttttgctcgttttttttcgctcaaataaaattatttcagaaggttttgca cyp-33B1

SEQ ID NO: 127 tatattcaaaaaaatatatttttttgtaaatgttcttgacaaggtgtcaggaaatcagaataaacattcaacaggtgtttatgttttttttgtatcattcta aaaatcctaacccgtgcctgattttcataaaactaaaacactaaatgttgtcaatctgtgaccctggagcctagaataagttttccaaaatctgat tattaaaaacacaacaacagattttaaatagatttgagcacaagtcatgcattgagcataagccacaaatgaaataacgagagtgaatttttag agtctaattgaattgcattagcttttctaaaaacttttttttcggctcaaaatcatttccacaaaaaaaacagttttaaaataataagagttggccttc agagcggttttgtgtttaacaaattataattcttattgtcagctcgattacgttattttttcagtatctttcgttttgcttttttgatttagttactcgccacg agagagggtttccctccaaatttcgcaaaaactagcacaaattatatgtatgtaccggaactaacctataatacttccgggttcatgccaaattc taatttctaaatccccagacagacacgctctcaacttcctccctctttttgtttatgaatgaatttagtttgtgacaatcagctaaaagtcgtgattt gaaaagttcaagaaatcgtcaagctcgtgaccacgaaaaagttctagtcacaatacatcatagactagaaagcatttctcgatcaactagttg acagctttttgtgaataaagattgagaattcgagttgttttcgaaccatgattacatggcttaacaataatacatgcagctcattgagtctatacaa acacaaaatacgggtctgcgtctaattatttcctacaatatttttgttattattcacaaaaaacgggagatagtcgacagctctcaaccggttgaa gagttgtgtcgtgaagaaacaatataaaaacattgaaaagtaataactgataacaacagttctcaaacaatattatagtgatcaa cyp-33E1

SEQ ID NO: 128 agcaaataaaataattttatggtattcatttgaaaaaaaaagttattaaccttccggcgcaaatgaataaaataataaaaatgattaagttattgca cggcccaattcatcgttgctatacttattgactacagaatatttttacttctatcaacaatgcaagtttgaaaatttccataaataagatttttcttatc actaccttttttgcttattttcattttaatttcgtggtctctgctctcccttttctgacctgctgacagtttgaatcgtcttcaaactaaatactcggtatgt ttgcctaaatctcttgtaagagagtagtctctcattcagagaatttcactcttgttgttagaacaaacttcactggcgtgtattttgggaaaataga ttatatatatttaagagattaatacgatttctaattttagttgtccatcaaattgaatttttttgtgtcgtttttctgaataaacatctgaaattgattcacc atttttcaga cyp34A6

SEQ ID NO: 129 ttattaatattattgtatttctgaatgtaccgtattgtatttctacatattgaatcaataaattgttttgtacaataattctttggctgagactggtcgga caaattcaatgcaagcctgcaaacttattagactctaatagaaaattttctcaaattggaacaattattctataattccttgccggttttgcagaaa aaatgtttttttaagaattaaaaattttaattatgttccaattaaacctacatcaatgctctagaattctccaaaacatcaaaaaaaatttgttgacaag attggaaaatctgaaatatttttaatttttttaatatcaaaccccccttcaaatgctacacaacttaaaaataaaaacaaaaagtgtggtcaacaactt -continued tcaaagcgtagaacacgcattttgtgttgtgtgtcttatttcttttctacctcttatctatcgtctcattcgcgcgcttttcaattttgggggtaggctg agttagtataagaaaagttaataaaaaatattagtttctaattttcgagtttctaatctagcagtattttaaaata cyp-34A9

SEQ ID NO: 130 atctttaataattaaatgaataattaattgggagaaacatgtacataaataaaatttccattaaacaatgttcatttgtttaagctggcacagacca caaaagctgaaaccacaaagtttttaaaccttgttcttttcttaaattttgtagtttcttatcttatcactcgtgtttcttgtcctccaaataattgtgaa aattgtagttaatgtgtcaaaaaagtcacatataagaagacgaacaacttgatttttttgttgacttcatttgaaaaaaaatagaaaac cyp-34A10

SEQ ID NO: 131 tactgaattttgcaaaaatgaggagtataggaaaactcgctcagaaaatcgaaaaaaaattagttccgttttgtaacactcagactttacaacta ccaattagaaaaaataataatacactaaaagagaagaatagaaatcagaagaagtcagtatcatgggagctcatgagttaattgcctgaaat gcgtattcccagaaataaaaatgcggtttcttagctctgagatctgaagtgtaagactgccaatagattccatgagattcgttgtgacaaggg gttctgaaaaaaggaatcgcgcaaatttatttattgcacagttgtagatgataaagtttctttcagatttgaataatttttaaaagcttctaaaaatta tcttgcagctaattgtccaaaaattattaaacatttgaatatttttctttgcttccaacaggttttatggaaattattaacaactgtaaaacgttaacgt agaataaagtaaatcgatcttgaaaacccaaaagaaccggccctatatttttggcaggtggaaattttgaatgaaatttaataatatagctcctg aactttttaaacgatgatattagatgttgaatgatcaatttccttgtagtcataaccatacggtttttgaaacatcataattttatcgaaatcacttgta aatcccccgggtacagctataaccaaccctattcgacaatttcaatttcggatattgtaaaaaaaaatttttaaaggtggtgtagtcgaattttttttt attgctttattaggttcaaaattgtctgaaaaaaaccgaatttcataatgaaacttcttgaaaacttctcaaaaaaagttatgacggctcaaaaaa tgacctaaaattagttaaaatttgaaatttgaccgacttgtcaatgacgcagctgctggaaacaatttttttttgaaattaccgtccaatttgggtat ttaagttaattatctcgcgttttcaacttcattataaagcttataaacagcgagaattttaaatttttttttaccaaatctcgccgtccatcgaattcaaa atacataaatggtgttgaaaacgcaaaatacataattacatgctatactcacaatttgacggtgatttcaaaaaaaaattgtttccagccgctgc gacattgacaagtcggtcaaatttcaaatttaaacgaattttagaccatttttttgagccgtcataacttttttttttgttgagaagttttcaagaaatttc attatgaaattcggctttttcagacacttttttagtctaataaagcaatcaaaaaattcgacttcaccacctttaacttagcaattgccaaaattttttta ttgcagtacatataaaattagaaacacacaatgtctcaaacctggaattactaggaatttttaagaaaatgactgaaaaaacaaactatgccaa ggacaaatttaatgtttttttcaaagtatagcatgtcgaaaatactgtttttgataattaaactgtttaatactactaatttttcacattctcatacgact atgaaaataagtgtaggaaatgtaacctgtgtgatgaacattctactttgccttatcaaattggaaaaacctcgtataaaatggtcaacaaaaa atgaaactgatttaacttctgatc cyp-35A1

SEQ ID NO: 132 aagttcacaatttattcattcatccatgtaaactgtatattttgaatttgtgttgtaaagaatttatcttcgaataaaatgtttttaaaggtttttaaattgt attctggtgagattgcttaaatagagtccttcggcgataaaaatgctaaaaattatatgaaaaaaactatacaaagaatatgtctcgaagtgttt cattccagatcaaagtcgaaaattagcttagaaaaaggatcttcgtcaaaacccctgatttaacaccaagacgaataggaaaaataaagtaa tttaaaataaaataaattacaagtgcgctccattgtaaaaacgctagaatttgcaaaaactgaacaatatttgattttcgactggaaaaaaaactt gttggtaaattgcatgaacagttttaaaatgtcattaagaaaactgatgccaatttttggttgttttctctcgtttaggaaattaaaattccctcttatt tttttagcatgaaccgtcaacgatttctggtcagataaattatggttattatagtgtgtagtttttttgagtttaaaccaatgtttcgaaatttttatcagt aaacagaaactacggtttgctgtatataagttaattccgatagcaaaagtagaaatccaaa cyp-35A2

SEQ ID NO: 133 cttctgtaataaaaaaaaattgaaatgtttagtgaggagagtgatagaaaataaaaaaagccgagactaaacattttccctgtgctgccctgttt ataaacgtttcaaaggaaaattctgaaccctgtaacaactgtcgtcgaccttcgaatagctcaaaaacatttggtctgcttgtggatcgcacgtt tgtttcacaaaattcattgtgatttgtcgtttgagatatatcccttctatcaatcaacatgttgatgccggaacttttaatcccaagaaatctgttaca caaagatcggaaaatacctttaattgcttacaacttttattaatagtcgatagatacacttgcttttgacttgccagaaatttaagtatgatgcttat caaataattacattgattacaattattaaataattgaataattgctaactacaactaaaaaattattcgaaacttattgtaaaactaagaatcagtcc gcggatgaatggtaatattgttcaaattcgtctagaaaaaaaaccaaaaaaataattaaaaaatgagaaactgcgcaaaatatatatatttaaa -continued atgaaacacaacgaggcggctctcgttaaccagcattgtgcaaataacccaaaaactctgttcacgccaaagtgctgaaaagagaaaaga ggctggcgtgaagccgacaggtataggtcctgaaaccgcgccccactggttactcgaatttgcgaatcattcttcttttttttttttcaaagcaa cttccctttattaatttcagattattgaacattcaatttttttttgttgtaaaaatcaattgtttttctccgaatagttaagaaaaatgtatgttttgaaaat tatctgttcttgggaaataatagagttctgcaaacaaacttactatcagtcgattcgcctaattcgacccttctatcaaaaacgttgtgctgaatgt ataaattgtgaatttttgagtgaaaataactgataagagctttttttatcagtcaactgacagtgtgcatgttttgtataaaaacagtccactgatttc gaaaaatcaaatcagaat cyp-35A3

SEQ ID NO: 134 ctttgtaaattattttcaattaatttatttgcacatgtgaactattagaaaagaaaaagtttacttttatatttggtgctatattggtgataaatctatgc aattggtaataaatcggaaatacgtttattttctgcaattgaatataataaaaggtaaataaatgatgagtgcgagaaatttgagttccataattgt acaagccagggagttttgaaaaataacagaaccggtacctatttctcttttttataacatataacatctgaaaccgacatgttaaataaaaaaatttt gagaaagaaagttgttaattctcgttaatttgcgatatgtctataataaacctcgtagcatttctatcgactaaaaatttgttataatcagaaaaaa ccatcgaagttttcaagtcaaatttcaaaatactcttcacatcaaaacttgcaaaattaaactcacagactggaaaaggaaattcgaaaatgtct gaagaataacggttttggaaaccgagctgtacttttttccaggaagatcgttcacaaacaaaatcaaatagccataaattgaaatacttgcaca acttaaaaaaatacgagaacattgaagaaatatcgatgttcttcaatacacataaaatgttgttgtcatattgtttccatgagcaaatggctgaaat ctgggcaataataatatttgataaatgtccattactcacttggtatagcaactttatgaactaaagaaattataaaagaattgataattataaatgc aagacatcggggtcgaaacctaacgaatgatcgaaaatttggaaatttcaatgatatgactttttgtattgctagtagaaacatggaaacagc gaaaatattcgggaaaacggtatttgagaatgtgctattagagccataatggactgaacgatagcccaatttgtaattagaatcttacgattta catttctgaaaatttatagatattaactttaaaacatatatgaatggatcttacaatccattaattacaatcaatacaataacattgttcatattaatta aaaataaagtaatgctcattaataaagacatcaaatgattaatttttaaaatgtgacatgatttatgtctcaaataatgtgtcttgttgtgattccatg aacggcagtaaaatataaaaacgatactatttgtagaagcaaaaaccatcaataaagttatttcaaagtcaatatgacttgttgctaagttctga aaagtctgaaatacttgcatagcttaaaagcgtaaaagtgaattactatgcataagtctgtgggcgaaatgcatgtgacaacatttgcacctgt ttggtttttaatagcctccaaatttaagactatgaaaattcattctgcggtccttcctgaacaatggcacgtccaaacgtctacaacatttgaatat ttatatttaatacaaaagtagaccataaaaatagaattaacatttttttgatcgacaatttccaaaaaaataacaaaaactgagattgttccaaattt tttttccaaaagttatataaaatttaaaaaaatttcaaaactttactatgatatatttacagcccccccccccacaaaaataacggatttcatcg ctttgaattttttaataaattttcaatgaaaatttatggaatagacacgggaccaggcggaagtcttgatactttttggtactgtgtaccaaccaaa aattgcagatacaaaaagaataaaaacattattttaaatttttttattcaattttccgtatttttgaaccacacttaaataaactctatttgaagcaca gtcttatttccgtgttttcatcagagaccacagttccttatccttgcgttatcaattttcattacatctttacatcaaatcttttgtggcaaatgtacaaa atgtacattttgaagtaaatatacccgataagaattagttatcggtcaagagactgtttgattgctttatataaaatcagatatttcaattttaattctc aaatcgaa cyp-35A4

SEQ ID NO: 135 ttgtcttatattttattaaaatcggggcgaagccctgattttaaatccatattgattattgtcttccactatccctacaaataggaaagagaatgtgt tctttctgatgaagtaaaaacggcgcagccagccgacagccgaaattttcacgattttcggctggtagcgccagccgaaaaattaaaagaa gtcggctggcggcgccagccgacagccgaaccagctttttgtcggctggtagctttaaattttttttccagtttttttacagaaaattcgtccagtt cttacagaaaattcgcgtttctatgttttaaatttgataacatttgcagtaacggagactgctgacccggcgtttcccatgagaaaagagagag agagagagagggggagacagtgagatatacggcagagacatagacaggggagacaccattagagatcgtctcctatagagtgctgccg gcagggggcgttgtggacctgtgggaagaagggggggagacaaccgcacactgtgcggttgtaaatgcggaataatccatttaaaactaa ggaaaatagtggtctaatgcttaacagtgagccgcctagataaaacaaaaaaaagtcggctggctgcgccagccgacagccgaaattttc actattttcggctggtgccaccagccgacagccgaaaaaattgaagtcaatcggctgtcggcgccagccgacagccgaaaaaatcagcca gccgctcagccctggtggggtggcgatgtgttggcagccaaccccttcaacgaactgtatctcccgcctgtatctcccttcaaagtgagatcc tgtaacagtaattagagaccatatttacagccagcctacatgcatcactggagactctgtggagagggaggaggcaagagaaaggggag gcaagagggggcgggcgggcactgctgaaccttgaaagcgccgtagctccgctcacaattggaattgaaaaatgaaaagtatatatttga -continued agtcaacgttaaaaggagaatatgatagcatttgaaattttggaaattggtgaagaatgaaaaaaaaagcctctggagcaaggcttgaagct cacaacttcaggaacggggctcgaggaactcatggccaaaaacttttttatttgtctcgcttctcatagcaaaaataataagatttaaaacataa aattgattatccaacaaaaaactggtccaggaaaagagggaaactgaaaattcgaggtcaaaaattaaataaactaaaattgtgaaaaatgg tcgtagagagctgtgctttcagctggcattcggaatttatgcacttattacgaatttaacataaaatcccatttgatagtggaaaaattttcattttt ccagcaaaaacgtcatttttttgagaaaatgcagcaatttgcgatttctgaagttatttttaactttttgaaaaaaaaaaatatttttgaagagaaa atttcctgaaaaatacgtttttcaaaaaatttacctcaaaaagtgccaaactgaccgacttatggacgaaaaaccatcaaaaatcgctaatttgc acaccaaaaaaaagggggggggggggaaatgcaattttcgatttcacactaaagagcccacttctatagcaatttttgagtttcactcaaaat atctcggctcaatgagctccaatctttctgaaaacaagaatacagaggtggggcaagctttttgaagagacagcaaaaaactgcatcaaaat ccatccacccaccgtcaagttacacgcgcgttttcatttaccacttttgtcggattttgaagcttaatatctcggctcctgtaaatcgaaatcggc tgaaaattcacaagaaaacttacttcactacgatcctcctgtcattaaattttcgtgagcttagaccgaaaactgacaaaacgccaaactttgct aacgctcgccactgacgccaagccttcagacacgctttcactaaatacagtctatttttccgtgttttcatcagagaccacagttttaaaataat gcgttttcaatttatttgatgtgatttatacattttcccatcagaaatgctgtgctaaatgtattcaatgtgtctttttgagtgaaaccactcttaatttat cagtcaacagataatgttgctttgtataaaaaggattcatcgaatttgaaattttcaatcaaa cyp-35A5

SEQ ID NO: 136 ggccaaaaatagtaaaacttgatcgttttctgccattgaaaactgcgttactatcatgcttggtttttgggggcgctggtatagaatatgtgctca aggaagtgccggatatcagaaaactgatagttttgatcaaaaagttgtgtatgcctgtctttctgtctgtctgttgacactccctccgagaggca gccagagcctcagagtgacaaatgcgaacggcagacggaatggaggaaaaggatgagcggtgctaataacagtacacagtttgacgaa aatccaagtttattgagcagggcagctttaagctgggaataaacaaggcaaaaacgtagagaatatttagggaattgggcacgaagatcag caacgagcagccatggcgttgggagaacgaagaaaagaagtgaagaatggctacattttaggccagaattaatatgagcaagggaataa acagcgcgcgctacgacactccgatgtgtacaatggcgcgcgcttgcatccttggcggcaaattcaaatgagaattatttaatttaattaattt aaatggtggaatgattattaaagaacgaacaaacggaattgtgtgagtaaattaccggcggatgattatcgctggattgtgggcaattcttgc cgataattataatccgcaaagttggggcggaggacctctactgaggccaagtcacaacactgtctaccgtctgtctattctatatctagaagat gtcaacattcagtggttatttttttagtaataaaagtgtaaaacaaaacaattcagatctgcaaagctgaaaagtgatgaaaattgatatcttcaat tataatttatagtactttttttaataattactctaattacaccccactgctttactttgaaatctcatatctcgctccattctgaagtagtcaactagaaa cggtaaaaaatccatagaaaattgtttttccaggtgacaattttttaaataaaaatggggtgcaatagtaatagagcaattatgctaattttgtgaa actgtagtttcaatactttaaactctatctgtacgttgttctctattgaaaaatacataccagatcagttatcaatttcatttctcatatgtcaatcgct attaattttactgataagaacacgctgtgtcagttgtgtcagttgtagttgcaacgagaaatacaatttctttttgggtttcttcttaagtttctcggc ttgaataatgggaaaactaattaacagttgactaaattatttaattttattatcccgcccttaaaaagttacccaaaaagatttagtgaagttatgtc gttctaatataatacttcgaacaacttgtgtcagttgtagtcagttgttaaaatctaaatttggtgataagatagtcgtatcactagttctgcaacgt tattatttaaatagccggagattgacaaaaatattcattcataatttttaaaaa cyp-35B3

SEQ ID NO: 137 tctttaatgataatttatgggatctgtatttctctttctgtcaataaaaattgaaaatgatttttacattctcaatattttctaaatcatgtttcgtgaagct gaagagtaaaattcgacatttagaaggtttcgttagaaaaatgaaaagtgtagtgccagaggggactttatctaaaacaggcctgaaggttc gacccgcgttacagttccagtctaaagtaataacactaattcaaaataatatatacgaaaaaaaaacacttgaatattatttgatttttaaagattt tcaattttgaaattatcaaatttccttgaatttgggaatttttgaagaagtttcagatgcaggtttgaaatcctagaatgtgcaagtatgaaaactg aaacaaaatgtatttatacgactttttttggtcactgccaaacttataatcggtcaaaactatgtttgcacaaatttctaacattaaaaataaacgatt ttaattttttttgaaaattatgcctgtatacatttcagcattataagagcgtttttaagcgattccctactgatgatactgtagcattctaaaattattg tagcttaatagctatctaatttgtaaaattaaatttaaaaaaataaatttgaagtggatctattagaaccttcatacaatatttcctactcttttaaattt -continued gaaatttttcgagtcagtgctagtgatagatagaatacatccattccgtagttatctacgctttcctcttggaatcaacacatcaaaactcaaagt acgcctttattaaagaaccgtgctttgtagttttaaattacttgcttccattgtttgtagcctttccttataaaagatagcaggttctgtttaactatctc aatttcaaa cyp-35C1

SEQ ID NO: 138 atttttgaactaaataatatttcaaattgcacccgcaaatatcgtcacttttataccgataaacaaataaagtttagtgatgacttatgataagaac ctctttgagtctatatgtacgtgaaacaaacgttaaagaataacggctttacgtgttagtcattcataaaatttcataagttgatctggaaatttgtg ttatggacgttacgccattatttctcgtcactcaacgtctcgtcaatggtaattgtttttcagagacggtgaatcatgtttcagttgatgattttagg aaacgcatgccatgttgagacaccataataatttaaatttttgtgggtaccttttattgggatttttctaacatttcagtcagaacttttagtagaatttt tttatagatctttttttttcagcttaaaattagtgttctaattactgtttaaaaaatgaaaactgaaacgtttgatgattttgtttttaaaaaattttcaattt ttttcgatatgttttattgattgtaagatcaactcttttaaagtttacttttcatttttttgttaataaataagaaaatttttaccgactttttagaaatttaat ttattgaaaaactgataaacgtcttgttttgatcaattttccaataaagaatacttttagcgttagtcacaacatatactcaaaatgtgtcaaaaaaaca atgtttcgaacagttttattgttttttttagcttcatcccgaacaactaaaaattgactttcccgataacttaagacgaataagtttaaaatttgaaat ctagttatttttcacgattttgacttttgttctgtccgcgccgaatctgaaacttgaacactaattcaatgtacacataagaatagacaagtagtga atatgcccattatcacacagactacatactttgactgttccaagcgtcgcaagcgtcgcaagtgtagcattttgagtcagtgataacaatgtaa gaaagtatataaagaacatgcatttgttcatttctattgcaaaaca cyp-35D1

SEQ ID NO: 139 tgattccaaatgataattggctagtcttaaaacattttatattttagggaattcgaaatcaaaactatgcacgtcatatcaaaatcaatttttgttcaa tattaatgttatttattcatttgacagctatcaataattatatttattaaaatagctgatagaactatttagggcattcacaaacatttcagaatgtttcc gaaagttcgcaacagcggattcgccacaatgcttcctcataacccatttgtaacaccattttttcaattgtaaacatgcttgtcaaaaatgcagta tcattgggttgcaaaacataactcgggcatttgtatttaaatatattgaagttagaagaacggagctttgacaaacaggcaatgaatggagttt gtttcaaataaatgaaatcacatccaacaaaaaccaactctgtgtatcaatcgcctcttggcaaacatttatcggagaaactctgaaacgggta ctatttctagtttagttttggtatatttcacaactgaacaccttcacactgtttacttatttccactatatcagcattatttctcgagttccgataatcgt ccaacattctatgagctttatctccaaactggctatatcgtaaatgcttgaaaaaaataaaaaggatcatagcaatccgactcattagcaggtgtt gtgggaatattatcaagaaatgcgttgtaattctccgtagtatttttctgtttttagcttttcacaaatgtttcttatagtatccgaaaagcatgtctttc catcttctaattgatcactgatatcatcaatctgaaaatattagattgatttttttgctgagaagaacctcaaaaccaactatgaaaaaatcatttagt ttgatgcagccgtcacggtagtttaacaaatgtgtacaagcaacttggacacaaggacgagggtcattgatgtagtaagattgcaaaaaag gaactcagaacagtaagaaagccaaagttaaaagcattgttgtcctgaaaaatccttattagtgtgtgataaaaataaatttcacaagttggac agttattatttcacaaaataaaatattattttgttgtgtgtactttacaattgacgaaaagatcaaaccgacgcaaaaatgatcaatataatccgttc atatttgtttggtaaagcatttttctgctaatcaaaaactgttggtgcaaaataatcgcacgtttttttcgtttttttttttaatttttttggtctcaaaattaca taaattttcggaaacatttctaacgctgaaaaaaaacatttaattgtgtgaagtgtagccgtgaaaatgtgttaggtgttgctaccctcttatcttca atcttatcatgtttttgtctcctttataaagaattgccggtgaacttgaagttcagatgtataactgtttctatc vem-1

SEQ ID NO: 140 tcccttgttatttgatttttaagatttgcccttatgtcagtgtcttctgcatgagtacatgcatatttgcatattattagaatgttatgtataaaaagaaa aagagagccacctcttaacgataatccaatttcttgttacgcagaaacgcctcgttttcctgtggactttcgatatcttcaacatgctgctattatc actcccatgacccgtttcctatctgtttttatttcgattactacacatctgctagaaacacacgtcacgtgtgatttgtactcaccgttttctcctttc atactttttagcctacaaaccacgaattgctttgtgacttgactcaattttctcccgaaactttttttcgtcctcaattcccactacccattttcttgctt ctccctgttgcaatattttcaatttcccatccaaaaacggcccgagcacgggttttcttttccttttttgtaggttcacttcttctttttcttcttcgtttct attttttttacacaatcattgttcacctttgggcaccccagtgaaacatttgtttgataaaaattgtgtgttccacggcactaaccacaaaatctttgc tacaaatactactcgtattgtttgtgatgactgtggtgaaagtaagaagaatcgagagacattaggggacaaatataaaatagaaacgataag gcgacgaaaacgcacattcttctcgatttccgaccgtcaatcgctgagtgaataattgttgacggcaactgggaaaatctgtgagaaaataat -continued gtaccatgttttcgaatttctaaaattagagataatttcttccgttttctcttttacatcttgttttcttcattttacaacaaatccttcttctttctcttac cgctttgtgcacttgcactgtaaatgacggcaacttacggacctagcgttcgacgaacacagtcaaggacgctcacacatcgtcgacgggttc acctgctctgttgcagtgattttgatgtttttattggtgactagtttttgactttttacaaa dhs-23

SEQ ID NO: 141 atttgaggactgggatgtcattaggactgaaattattctaaattagataatatattttaaggtaaaacgtctgtttaaattatttgtataagcaacaa aaaataaacgaaaactaaaattctacctgaagttcaggtcctgaacaataacataaaaaatttgggaaaacacgaaaaaataaacttaaaaa attaattaaaaaattaaagattaaaattaaagattaaataatctctagaacatagatctctaaaacacttcccgtagcggttcatttttgttcgagtc tgactggcgttttctatgggaaacagaaaacaacacgctgtttgctcagtttcgagaattttggaattcacagacttattttgttttgccgtatatg atcttaatcatagacatataatatttatgacaatgctttgctataattctgtgtggtgagcgttcgcagaaggttctgcacaattctttcaatgaaaa aaaaaagaaaattataagaacttattagaaaattataagatgtagaaagttattcataaaagttagtattcccaagaaaaatcataaagaaagg ttttttttcaaggtttttttcagattttggcgttgttcaacttgtattgcaatcattattattgcgatcattagtaatttaatataatttgctccagagcatt tgtaagcaatgaaatccaattttccctctgtggtgtttggtttagaaacttttgcaatttcgtcttgatgtgccgcggcatgccgcaaaaatcata ggggatttgatttcccagtagttgaagttggcagagttaactataaggatgacctaaaacaagttttaggctacttgttatagacatggacttcg atttctaatttggacagcatccgctacagtgaaagtctgcggattgatttcaaactctctaaaatcgaacgagttttcaattttttttcaattttgat gcctaatttagtgaacacggtaattatagtttcttgtatataaaacccgtttaactccttaaattactgtttacgtttcgtgttgtaataaacgatctct tgatcttcattcaactatgctggcacaaaaatagacacaattcgaagaggcgcagagggagtaacagacacaaaaaatgttaggacgtctg cgatctcgccggtaagaaacactgaaaatactctctgcgtagtcacgaaagctacaaactttaatgtattcaaccaaataatgttaactgtata aaaagaaacaaagaaaaaaaagtataaaaagaaactttaaaccaaaactaatcatcagattcaatatcttctatctgtttgacattctatttctgt aagctcgaaaat sodh-2

SEQ ID NO: 142 agtagagtcaatatcttgaaatgtttagaattctcgcgtatctcacatgttgaggtgagatatttgtaatgaatagtttcatagtctttggccaaaat atgattatacgttaaagcaaattttgatgttacgccgtttgaagaaatgtttttagcatgtttaacagagattcagactaaatttattctacacagttt ctgaagggatatttttttgccagagtcaattttcttgtaaaccagtgagccttaggtacatagaaaattttgaaaaatatccaagaataaaattttt ctgcatgccttattctgggcttatttttttgcggttttcaattcaattttatcgtatttcaaaaaattaaattagaacaaatgcatattcatttttacatcctt ttctaattggtaattataatttcaaaaatcttctttgcttatcatttgtaacaacaactacaaaaactgtactcgtagttttatctaaccgtattctttga ccgcatcctcccttttgaccattcaagtaaaaagatgacaatcgccgtctacatattgccacgtgacgcaaattacttataaaaccattcgtata aatatttcattgatttcttgaattcaaaaagc ugt-16

SEQ ID NO: 143 cccgaatttttttatcgcagaaaaccaagatggaataaataaatggataatctaattaaaaattgtaatttactatttggaatcaaaaataaataaa caaatcttataatatgtcagcaataaaaataataaaagaacaattgaaagttcaatgtgttgtcaagaaatccattaaagtatcgtcatcaacgg ggtcatcaatttccatgttgttgttattgtcttccataacatctatttccatgaagtcttagagtactgacaatagtttatttagtaaattaattttttgag aaagtttcttgacacattgctttgagactttgattaaatcacaaatgactcactattatcataattttctatccaaaatgttgatttcatttcaatttcca ttgaatcagctattccattacatccatcagttggtttacaaaatgggaccagtggcctcaatatctgtattttcttcctttttttgtgaaaatcgtacttt tgaaaatactaatggattctcgttctgatcgaaatgaggaaactgtgctgttttctaagaacacttgagacgtggattttctttgttgttcttaaata cgaaaatcaaatttactgacaaaatatctaaaacttacaatcacttcgttgctgtagggataatcacaaaaatttgacatgattttctggttttcatt ctgaaaaactgggagcattttaatttgaaaaaaacgaaccgtagtctgccccaattgatttgttggtaaaggaagtgaattaaagcgacaagg aatacatttatctgttgaaagtgaatgcatttttctggaaagacggaataaattgaaattaaaacaatattcagttaaagggaaactgaattatcc caaacccgggttatttcaaaacggaatctacatcttactttaattctgattgtcagccctataacaactatttcatctattcaaaaagatacaaaaa taaaccaattaacattacttcgtagatacctcatcacatgaccaccctctcaagttgatataattaactttctaaattgaccaaaagtgtttgctaat gtgtatagggtatagtaaataggaaggagttcggaagttcgatgagagtaaatatcttttgtgaaatatctattggaaattagcggaaaaaaga taaattttctcctgaagtgcacaactaataacgaatatcttaatgtggaaataaatcaaatcaaatcaatatacatcccaatcatgacatccaag -continued aaccccacaaaaatatgttcctaaaaactaactgataattaatttgaatgtttccaacagaaccttgctcgcttttttgcacatttttccactttgtttc gctctacacgcttgtattttttttaattaattatatttttttcggcctcaataaaaattaaaattccagattgaacacatttaatgtcagaatataattaca gtacctttttatgacaaaacatatttcggtataatctcagatttccacttcttgtttcatggcccaagtttttctcaatgctcacttgtaacggaaaat ggagtcagtgaagctgttcaattctagataatatgatgctatcaaaggtcttaaaatttagataaaatgatgaaaatgacgacattaaagtgtag ccttactgaaaaaaccaattattgaactttaagaaaaaaaacattttggaaaataaaggtaattcatttttcgtacacctaaaatttgaaaaaccg aaatttcagtgagaacgtcttcaactgcatcaaaaaaattgtgaagaaaatcgaattgaaaagagaggctaaattggcttcatatctttaattta gccgattatacacgtcgggccagtctttttttaaatgactgtcatggaggacttgatttcaagattggaagtgatgaactacaaaaaatatcaaa caatttttaactgcataaaaacggtttttctccgggatcaaagatgttttcggtatcaagtcacattcatggttcattaaaacatactatttttctagt cttaaaatgtaatctgtataattttatgttgttgattgaactcataatatgacaggattttttttgtgatttctgtaatgaagtacagtcttacacgaaa actagagtaatacaagtcataaattttattcgtctttttttcccgtagtcctttcaataatgtatgaaaagcatttacaaactacaactctttcaaaaac tagagttcttatcatacaaaccacacatttttttgcagctctatataaaccaactgataatgaggttttgtctactctcattactcaatt ugt-63

SEQ ID NO: 144 gtgaataccacaactgaatgtctcgaatatggagccaatgattcggaaatctatgaggaaatggcatcgatttgcaagtatattgtacgggatt cgagagctcacggggactcggttccagagtgatttttgttgttcgccaattttatgattgtttcttgttgttaagttttctaaaaaataaattctttgat tttaataaatttcgaaaattcaaatattatggggacgccgagggaatcagggtgcaaaggcgctctaacgccaaatgacaaccgagcattg ggtctcgttaggaaatggcggcaaacgagacatttaaatttttttattacgggaacacaaaattctaataatgcgtattgcacaatatatcttacg cgctaagtatctcgtagcgaaaactacagtaatttttttaatgactacgcttgtgtcgatttacgagctcgatttttagagatgaatttattttcgaata gtgtcagcgatatttcgctttaatttcgaatcgagcccgtaaatcgacacaaacgctacagtagtcatttaaagaaattactgtagttttcgctac gagatattttgtgcgtcaaatatgatgcgcaatacgcagtctcagaactttgtgttcccataataaaaagtgagagttttcatgcgccccttggag cgctactgcacctcaatttcaaaaaacgcatttttctgcgtccccataatacaccgggattttcttttctcttcgtctgaaaaacaatcaatcatca ttaaaatcatcatctatcaccaatacagaatccatagatcaaacagatcaaaaaaccaacttgaacgcttgcaggcaactacgataaaaatat attttgtagtgtagtcatcatatcaatcatctagctataataatgcctgccgtataaatacaaaacacgatgatgatctttttgcgaaa gst-5

SEQ ID NO: 145 attagagaacttttcgagaagtctaccgttgtagttttcgaaatagtaatttatttagtgacgtttataaaggtttacatgatttggtttggaaattttttt aggagtttattcataaaaacaaagtaaccatggacattccagaagtctatagtacacgcgatcctaccgtacccttcagtatttctatcagattg atagctttcggtagtcaggtacagcctaaaaaattcctgcttgccttttttgcctacatgtctgcctaccttcagtcataatgcctacataatgatttt ttccaattgaaacttgcagacagaaattcaaatggcaaaaagaaacaaacaccgaaacattaatcacatttcttttcatatcagttttcctgtcaa agcacatttctggagtctgtgtgtattatttgtgtctttatgtgatcggtgttgtgaaatttgtagttgatgttgataacatactttttttttgaaacaaa aagtgattgattaggcttgaattcagagatatgttcgtgatactttgcgattctcgagccaaaaacacggtatccggtctcgacacgacaacttt ttcgcaaaatacaagctgatgtgcgccttgaaagagtactgtaatttcaacctttcgttgttgcggaattttcatagtttctcgttcaaaatatatgt atttattaaacaaaaaactaaaacaaaacaattgagaacacataaattgtgaaaaatcaatgagaccacagcaaaaaaattttgtatctacagta ctctttaaaggcgcacatccgttcttattttcagcaaaaatgtcgcttcgagaccgggtaccgtattttttttttgtgcaaaactttaggtctaggta atattaaaaaaaaattccacaaaactagaatctagagctttccattaaatttttttgatgacatttgaaaattcatgatgattatttccaacaatttcg aaatatccctcttttcacctggtccactgaattctctttccgaaagaccaccacaatttcagggctccgcccatttcgtggtttgtagccttcccg accctacgtttttgatgacaattgtgagagaagtgagaggttcagacacaaaaagcgacgtggtcgaatgagtataaatagagagtgaagtt tccaatttccctcacaattgtttgtttgcaatccactttccaaaaaaacacaacttcaatcaaaaatcatt

T16G1.6

SEQ ID NO: 146

Gctaaactttcgtattcgactgataatgagaacgtggaggagtatcgtgaggttctcactgaaaaagctgaacgtctcatggaagacttaaa gcgatggcacttgtacagtaaagatgtgacaaaggatttagaaacggcggaaaagttgactttatgataagaatacccgataaaattatgaaat ttctcgaaacttttgaattgtgaagcaacttcttaataaagtaactcattgactttaatttttaaaccacggcttagagaaaattaaaaatcaaaca -continued ctgcagctttttgatgcgaaaattcattgatatggaacaaacctcaaatttgataaataatacaataatttgtcaagaaatcacaaaaacgttctt ttgaaatgcaagttataagacatacgcaagatgttatgtcggtggctggttttaactataaaatacgaaacaattgacctcctgacacaaaattt ccgagcttgatttgtctgatatcatttgtgctttggaattattgtttcatgtgcataaaatctacactgtgttcattcacgataagaagaatttcagac agaaaccacaggaggttcatcgatataaaatgctaatcatttgatttaaagaaccatactctttttactctcgtcgttaagaa Cell Division Toxicity Genes mei-1

SEQ ID NO: 147 cagctatcccgaattctcgagcgacatccgtcatctgaaagagatactaatgtcatgtgaagtggtattaaaaatatagtaagcacggtagaa acattaacttataaaattgagatttctgataaataaaatttttccgggagttctgtaaaacttcttacggttttaacttgataattccatagggtttaaa atttccttttgtttcttgagtttcttctcggaatttgaacaaaaataacgcgtttaatctcgaatcagtacaatgatggactacacggcagttttaaa aaaccaattaataataataatcctaaaaaatgagaagaatatttaagaaaatgtaaaagttttccgcggaattccgctaaaattcgaaaattgaa agtgttcaaattgcaagcgattgtgcattcagacgtgacagtgtctggggtgtattgcgtactcgacattttaactgacgacacttgtacttttgc gccatacttccggagctccagctccgcggagccctgagcaattattttttttacttttttatgaaaagctttctatagatatcttttaagaagttacact ataattgtgcaaatcaaactggctccggacaacacaaatttcgtctatacctttatgatcttttttttgttaaacaagtgaaacaattatttccttttca aactgctcttgtttcttctctttattaatcaattattatttttgctttgtgtaaattaattgtttgtcgcggatgagctaattctgaggtttgaccagcag aaatctgttttctgaaaaatcaataactcgccgcttaattttggttttattcaagtgatatgcaattagaaggttctaatcatttatatctcgctgaaa gatctcagatttcaagccttttgctaaggatttaattcctaaaacttttttttgacctatcatttttttgtgtgatctaccgctgtaaatacttgttgttttgc ggctaaactctttcaatgtttccaacaagtgagccaatatcaagtaaaaaaagaaaaaatcgttttctattcaaccattttattctgtaaataatatta aattcatcttcacggtacaatcttcttctcccatctaataaagtccacgcacactccgttccgtcgtttccctattcgttatcattcatcatcttgcca ttttcttctccgccaaatcccattgtcttatactaaatttcatcctctcgtctgtagaagtgtatattattgaaaaattaaagtatattttcag mei-2

SEQ ID NO: 148 cgcttcattttccaacaaaccaagtactggagccatttactataagaactaaattaaatattaaatatatcgtttcaagaattcattggaatgagg caaaagtaaatacttaggattaaaaaatccagctttatattaaaaactttaaaggcgcatatgagatgttattcgggtcccgcagcgctcatgc ggggtacgatagtacttcaaagaattacgcgggaatttcttttatgcgggaaaacggtttttttcttgtttactagttcctttctttcgtctaattttgat atcttgtgtttttttccaattataaaatgtttgtctcttcttaaatttgaaatttttgaaatttttcag mel-26

SEQ ID NO: 149 ctctccttctttcatattctgtgtccacttctcactcattgaatcatacatctctatgttttctcatagtcatcatatattgtcagctgcagaaatctcat catttttccaaacgaaaagctcttaagagaaatgcttgttttctgtggggtacagcgaatggcttctgtgggaatgcagtttgtgaatgtaaata gattgttatgcagtcttgcaaatgtgtcggaggccaaaagtagagtagacatatttgaaatttatagctttgagtgtccttagtctattttgatattt catttctgctttcctcagtctctcattccagctgcaaaaaataaaaataagaaaaaaacacgaatcccgtccattcgccattcaacatagatcata ttcctcagatttttttgcagaatatgtaatttttgctgaatgctcgctctattgtccttcattggttatcaatctttttgcattaatagctttaatttttgatgt tttcgaaagattagggaaaaatttttttaatgtgtcttttgtgacttgagattatatgctacactgaaaaaaattggtcgcataacatttcagagttcaa agtgtttttttctttcgattgtgtaagcggcaaaattctactttatcatgcatttttgtttcaatcaaaaatttgatgtgatttgtacatggcgtcggtttg gtactagttgtccacttcctcagccatgaaaagtgtgagtaagtgataacgtttattatctttttttgaattcattctatgtttaagctacacgtatttaa ctagctgactcatttccaccaaatatgccaaaagacctccgagattttatttgaagataatttcgatttcgcagaaaaaaaaaacatataagtgat gtgggggtgtgtcgccttcttcagctttccatagtgaaagtttcgtaaaaacaagcttgctatttcatttttccccgttctaataccttgtcgccca gaaaaaaatatttatatgatctttttcaactcttttttttgtaaaaatggccaaagattagctaatatttgtataccatcaaagttctgccaaaatctcgtt gaaacatccatcgtagaacactcattgggttccatcaatacattttttgtgtaacatcagtcgattgttatcattcgtatatgcatggtcatctcaac cgccccttacgacgtcttcaaccattttctcttctaactctctttctctcaatttcacttctcactactctagtctattcaattctttgaaaaggcaaaaa aaaatgcataaaaagatgaagaagacattcaacagacgggtgtcttccttatttttattcaaatcaaaacaaatggcgaccttcttattcttctctt -continued ttgcccgatgattcattttctttttccattaattttgttatctattgctgaataacccgctttactgaatgtgtggactggcatttgccacgttgcatttt ggaaaagagccgatgtagttcttccgggtatatgtattcacagaacgattcataagatcagacatatagacataaaattcagcgcattctgcct tgtggtttgtcaactacttccgtctttttctgcatattcatttcccgcttctgctgtcttgttcatgaactcttgaactttgcactttgccctctttttaag tttctctcgattgatgcagcagcagcagactgtcattcatatttgtctagtgatttcgtaggttcaaacaacttattaagcggtttcacctaaaattt cgcatcccaaaataaaagttcaattgcgaactagaagtacccagaagcgaaattatttgcttcaaaaatacggtacccggttttcaacaaaat cgttttcaagtgacatgagcgattttcctttttatggaaaatttctaattcaaaaataaatatttgaaatacctttttttagattattatatttattcttggta ttttctctattcccactaaaatagactgatacgagaacagttcttgtttgcgcaaactcacattttctctctctatctctccgtctcttcttccgtatct ctctgacggtcccatactctctcactcatcgtcagacaccaccacttatcgatctattttcgacgagtgagcggctgttcgtcgcatgttttttat aacttgattcgatcaatttcatcatatcttcttcacttatttgaatttccgttttgaacatcatttttccgtcggaaagttgaagcatttgtttgattttctc ggtggaagattagatttcaaaactttcgaaatttaacaatagaaaaagagaaaaaagtgtagttattaggaaatattttagacaattttgttggca attaattgaaattaatttcttctttctacatattttaaaaatgtatctttttttctatttatatttcctttccggggatgagcgacaattattttcggcagctc tacaaaatgactgcttgagataaaatttctacttaaaatttattgtcgaaagatagaaaaatgttgcctcaaactgtaattttgtcgagttgcccaa aataattgtcgcacacctcagatttttttttctattatttttttaaataattaaaattacagtggaa cul-3

SEQ ID NO: 150 tattttgacttttgaattttggaggttttcaagaataggcaaacgttttggcatctttttgaaaaaatctgatttttttggtagattctatccactttctaa aaattctacatgctctgaacaaagtggaaaatacactgaaaatttcagatcgaagtttcaggtgtttgaatttgtgtaatagtctgaaaaatctga atataagctttcaaatgagacatctcgaagaaaatgaatttgtgaaaaaatccaatttttttctaattcgagcacaaaatgatgtcggtctatcac acctccttgttgttaggtgaataattgttaaattcttaatctttatgatataacaaagataggcttctaactacgtcacgcctacatattcaatgaaat tttgtagtgctactactatttgtgcaagccggaatatgaatgtcctttcattattttcgtcccaaaagtatataaaatatctcacgatatactcagag attgggcaacaaagttcaggagaacttttgatgcacaccggaaataaaagggcttcactgctttttttgttgaattcatattggttttggcggga aatattgaatcattattgatactttgaaacaggaatagacagtatttttcgtacggaaattcgataatttccgaaaatgttcggttgcctccctcg ccccctttgaaattacaggagactaaaattcgaagaatgcgtattacgaaacgtatacgcgcaaaatatctcatagcgaaaactacagtaatt ttttaaattactactgtagcgcttgtgtcgatttatgggctcgattaaaattgagcaaaaaatttagaaaatactatgcaggcgcggaggaaaat aaaatatcgatatcactattcggaaacaaattcatttcaaaaatcgagcacgtaaatcgacacaagcgctacagtagcaattttttaaaaaaatt actgtagttttcgctacgagatattttgcgcgtcaaatttgctgcgcaatacgcattctcagaattttgcgttaccgtaatatacacggtgaagaa cacgagccaccaggagtacggtagccctgactttaattgcaaaaaaagagaaaacagtgaaaaaaatctgtatataattgctattatttttaaa tttcgcaaaaaaaattagaaatgaccacattaatttgaattcctgcgcgaatgaattctatttttttgcgtattcctgcaatatttattggattttctctt agcctaaagcctaaaacgcagaaatttcgaaataataaattgaccatttttgaattattggtgcaaaattgagaaaaattgtgaaaaattatacc atttttttgaacaattacgctcagcttactaattgtaagattactcagatttatggcaaaacacgatttttacgccttcaaaaaatcctagcttttggc aaaacttacaggaaattaaaaaattcagaataaaaagtaataagatccaggaagccatgactcgaatcattgtagttgaactgtatgaatgatt tgatcccagcttcttccgccaccctaaacaccccataatttccgttttccgcttgaataggaaatgttgtatatttctgtactccttcctgaagtatt aaaactcgttttcgtttattaaactgtttctttttttcagatcactcaacttcctcttctcaacgtcaacttcgactcggctaattataattttatttatttttc tgatttttttaaaattcttgtttttttctcaaatttccaatttcaacatcatcttattttcaaataaaaatatttattttgcgactttctattaatttgaaacagc gaatattgttaatttattaagtaaatttaatcattttagatcgttttcaaccgattttcgagggctttccacaaattttgtacttttaaataaatttaaagt ttattctaccgaaaacactatttatttttccacgtggacaccgccaatttctctgaaaattctaaaattctggttgaaaattaatttttaaagcttcct cacgagaaaagcgccaacgcacgaggagcgcgccagcaaacccgcattgacgcagtctcggtgcacttctgaactccaaaacacactg ttcccgttcgatttttctcgcatttttcatagtttttttcgaaattgaagcttttaaaggtgttttagacttgattcgaagtgaaatattgattgattgag ccggaaaataggcaaaaagttctggaaaaacgcgcgaaattaaaattccagtgactttcgagataatgatattgatttttccgagtaattaagt tgatatccagctatttatttttgcgtgacattctaattaccggattttcaaagtttttttcgaaaaaaaaacaaagcaaaatcgatttatttcgaattac tcgcgacttctcaactttgaagctgaaaatagttagttttgtttttttctgttatcagtgcgcgctttttctgcaataataacattccgcagtacgatttt -continued ttcaaatttttttgcttttcgagaacggaaaatcaagtttatttcagtgtgcacgaaaaacgagcgagattctgacttgaccagttcgttcggaatc gactcatttttggag cell cycle toxicity genes cki-1

SEQ ID NO: 151 gatctgttctttccgaaaagaagtagttaacaggtgcggcttcactgggtggtctcatttttcattttaacctgttaatttattccggcttcacctcta atccttaatgacattaacatcttcctaatgtgtctaagcttttcccacggaaagctaatttcctctctcttatttttctcattaccgttctggttgagctt catcttataccgtgaatggtttcataattacgtgctacataatttgttatgctggtcgaggctcaacgtttcgaacatctggctcttttccttcagct aaccacaccactcttcgttacaatcccttctgcgcacacatatcctatctaccagccggacagatgctcgtttctcggtgcaaaacgttgaga gttgagatcgagcagccggttggtagttcttaatgacaaattgccaagactttttctgaattattttaggatttaaaacttttctaaagtattacgat agttcataatttctttcttattaaaaattggctctatttgtaatgtatggtatctaactaaaactaggcctcatttccataactattctttaaattgagtt gagctcaaagagttagacagaactggtgtgaatcatagaacccacctgtgtttttactttctttgaaaaatgtcggtcacttagtcgtctctctgt ctgttcatttcctaatcacaagtaacaacacacagtcttctttcacatatattatttgttgaccaatcgtagggtcaactatctagtactcgagacc gcctatttgaacagagctcctcactgtcaccaaatgtaccgtattgctttccggctgttattgttgttatcactgcttcttcttcctatcatgttaccc atccaactatacaccttagactagtcatcttattgatatacattcctcccatccaacacaacggtattctatttatttatccaattagtcatagtcgta ccaccatccagcacgaaggtgcctctttagtaaagagtagaaagaagaaccggatgggaaatgtttttgttacaaaaaatgacacatattgta gtggacagaaggagtgagacagacatgagcaagccaatttgtttataatttctcttctagaaaaaaatacatttttccatacttcactagtcaaa acctttcacctttctaatacatctcgtaaaccataatcttgatagttctgagcatttcaatacgaaagcttctcactgtctagatctctgactgagtg ccctcatcaaaagtgcaatctgtcatctgtttcctcataatcacggagcactaatttttctctctgcgtctctataatcagatatctctcgtcactaa gaactttccgaaatgtttatgcttctcatctgaccacttcggttccgcacaaaaaaagtacggcattccaaaagaaatctgatccccctccgttca ttcgtggtccgagtcggtgccaccagtcgttgcgcattgaatatttgtttggtccgttccccttcttctccgactgctgacctcgggcactttgat gaccgggccaccacctcagtacccctctattacaccctctttgcctccgcgcatatgactccacccccttctcgtggaaggcgtgtatctcccc tcttttccgctattccctcgatggatatatattcaaatgtatgtgtgttcctgacgggagggcgtctcgcttgagagcatcgtcacatcttttacaa ttttacttatgatttacttcatcttcttcttcttactgcgattttgatatgcattcttatgtaaactattattattccaggtttcctcactcttttcaa cki-2

SEQ ID NO: 152 taggttaacactgataaatcttgcagaactgttttattttattaaatgagacattaccgatctaaataaatttacaatcccatcaaactttctcctttat cctccagaatcccatcattttcatcggcacttcttcaaaagtttaaatgtgagtgaccgcccgtctcgctctactaatcgtatatgcaaattttcttt gatatcatagaacctgtcatacttctccaagtatatgaaagacaattaaaactactgagagaaagaagtagttcgcgataaaaaagtacatat aatacaccttttcacctagaagagatgctttcaacttctacttttctggtcatatgtaaatagttgggtttttttgacagtttgacaggtttacggcagt caagacgacaaaaatggttatcaaaaggagctggcatacagccaataccaccagttctgatctttttacgattatcaaattgtacatgggggg ttaagttgaattttagtttcatttttttcaaaagtttaaactcgaaaaataactgaattgaaatatagtgaagttggcaatataccaagggtagaaaa tcagacgagtgattttatttctagacaatcttaaattgctcaaattgtggtcttttctatatttgaacttttaaatgcagcaatttgtgaaacatacaat tgaaacaaatttcctcaaaaactgccaccagctgaggtatcatgaagccttctgttcacacatgttgccacctaatcggtcacttatcctaatta acattcttccactaaattgtcccctagtcacccccacttgaacgatatacacaccaactgttctcgttcactaatacacttcttccggagggattc aactggttatattctgcagttgtcggcaggtgtgtggtagacggtgacgtaatattgcacagggtgtcggggaatgattatgaagtcgagatg cgcaacagctggtaattgaagccacgagagaaaatggaaaagactatgatgagggcacaaggatagaaaaaattgactgggagtgacca aacaggcgaggtcacaatgaaattggtgaaaatggaaaccctaaaagtaactttagattttagaaaatagttggacgatttttcgttttcaaagt tcaaagcatgcattattatcatctgaagatgcacgatttgacttgtgtgactgatatctcgtcgcgatcttaccgtaacctacagtacttccatatt aactaaagttggttcgcttcgagacatcgggaacgtgagttatgtatttggcattattcgtcattttatattctagaaagatttacattctgtcaagt tggaatattttttcttagccgtgcaatagaacttttgttgaatttctcagagtacaatttttatgaccgccgatttcctctcgataagcattacgttatt tacctatggttttcaactatttaatgagatttatcaggacctcccgtagttttatcttctatttttactcaaattttgagctcaaaaataacaggaaag atttaatcgaaaaaaacatatttctgaaatccaagagcaatcgcgcgctattgataatctggtttgccgcatttctcgcggcaacaacaaagag -continued tttgaatcgaaacgccttttatttgaaaaaaaacctttttgttttaaaatttagtctatacgtgaatctaacacacacaaactgttcactaatttctct ttgttcgtctttttaccatttcatttcgaaactcgctgtcgtctcgtttctctcaccactcttcacttttgccgcctaatcgatcgatcttgccgcg gcgcactcacattttctcttatttcttaccggcaaaaaatgtacgttttaccgcacttttcgcttacattactatttcaaattctcttatcaaaattatt tcagaaacgaagtaacacaa pcn-1

SEQ ID NO: 153 catgaagaaacagtggccgtattgggaaaaatgaacgatttttcggcgggaataatttattatttatgatttctatgcgttttcgggtgattcgg gttgctaagcgattggttgcattttgaatcactagtcttggtattgttgtttctgtgaatgaataattggtttttcgaggtttttttgtcaaacatgcct aaaaaataaattatgacgttttagttgatttgtttgttctttaaacgtctgaaaataaggtttaaatctaatttattaattataaaattcgtcaaaataag ttgcgcgtcaaattatatgtattgtacgcagtgtcaaactccaggcctcagttttcatgaatttaccagcgatttttgttataaatttttttattgaaat ttaaaattttattttcaaccaatttgcctcgaaaattcgttatttccccattaaaaaccgcttttctaaagtgttgcgcgtcaaataaaatgcctgg tacgcaatgcacggagaatgcgcaaaggacgactgctggcgcactttttgaatgcggtaaattgaggcgcgaagtttcattcgaaaacgc gcgcgaaacttcattcatcgcactttctccgttcatttcgtcctattatttgtggatttcgcgatttttttcgcttttctgagtgaaaaaataattttcctt cgtttttttcaatgaaaatccgcggaaaacccatttttttcccgtgaaaatccgcatttttcgctgtatttcataattttttattcagatctcccgtcaaa smo-1

SEQ ID NO: 154 ttgctgttcttaattgatttcataaatatgtataaagcattaaatttgaatatatttttaataaagaaaaatcgatattcacattagagcgcgcttgca atttcacgatgagacctgacgataccgcgcgaattaaatcgatcgctttttggcctaaaatgctcattaacaattgtttttgtagtttttagcttaaa attatattttaaaatccagtttgccttgttacatattggaaaacggtatttttagagtttttcctcaaaaaccaagcgaaaaccttgaattttgttccg aaaacttgttcaaaacattatttcgttgaaaactcaaataattcaccaatttatctattttaggccgaaatctcttattattcagtccaaaaagcacc aaatttggtcaaaaacctgtccaaaatctaccgtaccctcgtgttgctcgtgaaatgcggtgcattgtgtgcaaacaccgcggcgtgaacatg cacactctgcaacgcgggaaatcatttcgaaaaggtattaggcgcgtattgcccgatttttcggctcatttcgtgtgattcatttattttttgccttc tttctccggtcgcgatgcgtttaattaagttttgcttctaaatttcgtcaatttcgctgaaaaaccacgtagaaaacttgataggaactggatatcc taaaaaaaaggatttccttgagaaaaatgggtttttttttctgaatttcgcagtgatattcttgaaattctcagcgcagcgctccccagacaatcga tattcctaatttttcaagcatcttgtggctcagccagctgttctgtaattatcgattttatttgttacagcgtctatataaataccctagaaagtcatca ttctgcactcttaatacctttcactcgtgtgagttgcattctccatagcaactctacctctctccttctatctcttttctcttttcaaatctaatttcgttt cagagactcccgctataaacg rnf-1

SEQ ID NO: 155 ttcgctttaactcctccagaagttgacggtccgccagtgcctccactagtcgtcgggagtttatggttcagtttcgcctttttcatgtcctccggc ttcataatcgtatcatttaggcgtttgtgtttttttacgttccattatttataagattctaaacgagaaactcttaagattttccggaaaataatgataaa aacggttgtgaaattgaatgagaataaaaaaacgaaacaagcacgagtgaggcaggtgcgctccaatgcgaatttctttgcgcggatgttt aaatggttatttttttatgggaatcgacaagtcacatgctacgctagagagagttttacattttacagtctttttggaatttaataatatatatattatc ataaaatcgaataaaaattgtttcgaataatgaatagctttgtttttttcgtcttgacttctgaaataattttaaatttgagaaaaatttgtgtcgcaata tataattattaatattattaataatgtaatttttttataataaactgatttatattttaaaaacaaaaaaggaatgacaattcagtttagttttatgaaaaa ctttgaaaagacaaaaataattacagtaaacgcgctccgctagactccccaaatttgatttgattccaggcttgtgtccaggcaaattccagct ttctttttgtttcagaatttctaggtatttatctccgtgaaa apoptosis toxicity genes

--- egl-1

SEQ ID NO: 156 gaaaacttcgattcttatggttaaaacgagccttgttagtaaaaattattgagtgaataaataaattagatcaagtattttcacttctgccaaaattc aactaaatagaaatggttggaattaagttacaagctaccagtttacaaaacaataattgacaggtaatcggagtgaagacagtttttttgcctttg ataattttacattcacatttaattttacattcacataaaaaaagaatcacacatttttttcaattgacaagtttttgataaagtggaagacatcggag atatgacccgtcaaagttgctcagcagggtgcaaaactaaaagaggaaatactgtgaaacattttgacaatttagagaaatacacagcgaa -continued agaatgaaatctaaaaaagcgtattaactttaactagataaacatactaacttattgaggtaaatctgagcagatcctcttcctattcccaatattt acccaattagtcttctgattgcgcacctgcatatcttaagtactcaaatacaacacacatcttgagaaatgatgactccacactcagaatgcaat tcacactattagaagccatgtgcaatatgaaaacaagcttatcctgaagctgcaaacccatttacctcatcaattatttgcgatgtgccgacctg ttgcatggcttccgacactgtaaggggataatctgtttgtcggcacgcttcaaccgattaattggcgtgtgaaacgatactaatccagtcgatt ctcgactaactgtaaacactttgatgctaaccgacgtgccggctaatatactctctgtgttacgtcagaatcctttaaatatgcaaatatggataa ggtggaatgatctcaagaggtgtgattgggtcaaattggattacgtaattcttaagtgggctaaaggtatactgtaactggggtgcaatttatgt gggaagtgcggcgaagttatattggggttttatagattctataacttgttacattgattttgaatagatttcaattttcagaaaagtgggaaaactg tatttacattttgaaagaaatttaatgcaacagaaaatagtgattggctggaaaagtgcccctatgttataaacttttttgttgaagctttgaaattttt cacaaattattcaactgaagtctcacacgtcgaaaaatggccaaacaaatttttaaaaaatagaggcctgatcatagtttctgccatttcatggc cgtctgtgacgtcacatgaggtttttcgactatttggcttccagggttttacctgtttttaatttcaaaattatatattcttcagtaaatctctgaaagt cacagtcgtttcagcgaactttcaaggccgcgtgtgacgtcacactcttgcaaagaaagctgcacgtggtgtcaggttgtcccataacggttt gctctacgaaaaatgcgggaatttttttcatcaaaaaatgtgacgtcagcacgttcttaaccatgcgaaatcagttgagaagtctgcgtctaagt tcccgcgtttttttgtagatcacaacggaatgggacattctgacaccatgtgaagctggccttgagatagttttgtagattcaaaatatttttaatgt ccaatatttgttttcaaaacattcgttaaaatgtgcagaatatgttaaactgaaggttcctaggtttaaaacttcaagctaaagctttccggctcag ttctcaggttcaggtctgtaatctttctgtaagcttgtaatcttgttagttcctcagacagacttagctgctaaatttatttcatgtctaatattacactt caagagctatgagtttgtcttcataaaagttttggctcccatataggaactttggaacatcatttgatccccgtttcgaaaacgttcgaaaattgtt ttgtttctttatttaaacccgacagttcaaattctttatcttgatcaaacccttttttttcatctgtccattcctcggccttaacctaatttatacagtttcg caataacctcccccgtgcttgctccagtaccagctgttgcgtcacgacttcttattttcaaaactcaaatcttgcatcacacctcatcaattaatc atcctcatcaagcctgcaaacttataccccttctctagacccctctcctgacatttgacactcctgtggtagaggggtgtggccttgcctggg cggggcgtgcaatgagaagctgtgcacgcacaccattcattcacacccaaaacattcacaccgattagtcgtattctaacttctcttttcaattc agttgatatgctggtaagtctagaaattatttattttgatctacatacctgtccaatattgttcgtctccccctccccctcctgagaaacaaattttt gtttttgtctgctcgcctcaccctcaacctctctctctctggatgtgttcgtggtgtagaaacaaaaacagatttttgtttttttgtttttttgtttcttgttt tagaacttgtatcctagtaattgttagacatctccctactatctttcccctatataaaccccccttcaaaaccttactaatttccag cep-1

SEQ ID NO: 157 aacagaactcacccgtttctagaacaacgtttgctatcaactccaccccgaaagaatccaggtggttcgtctgacattatgctgcaattttatg agaatattcagacgcaacaacaacgtgacaaacgacgagataaaaatctatcaaggctgaaacaatgacaaaaaagaaatcccgacaaa tgaaaatggcgcctaaaacaaactttttttaaaggacgtcgggtttcattcacagatgggtctcggaacgaaatcatggagtacggtatcacac acttgaatttgaaagtgaacttctttatttgtttctcttgcaagtttaaacttaagtttttaatttttttctgcttgtttctcaataaaataaaaatattacttg atttgtagcgcaga ced-3

SEQ ID NO: 158 ttctgcgtgaaatgtgatgtttctacagtaacccgtacaaccaaggcatcgaacttcacgacatttacgaattcaaatttgaattgcaaactttttt aattttatcgatttttctttctttttgagctttatcaatagctctaagcgattattcaacagaatttcactttttttacgcctaaatgattgaaaatttgataa aatatcaataatttacggttatcctcttcgtaatcttcgctttcttcccagagtagtgaaaatatcgactttttgatagaaactggatttttttaacttcc ctgttcgaaaaactatttttccttaaatgagatctgaaataaggtgataaattaataaattaagtgtatttctgaggaaatttgactgttttagcaca attaatcagatcagaaaaaaaagtccagattctagattatccgtcttattgtcgaattaatatccctattatcactattcatgctcatcctcgagcg gcagcgtctcaaagaattgtgagagcaaacgcgctccattgacctccacactcagccgccaaaaacaaacgttcgaacattcgtgtgttgt gcctccttttccgttatcttgcagtcatcattgtcgtattactagacttatgagaacgtgagctaagcaattattacatcaattgaagaaaagg ctcgccgatttattgttgccagaaagattctgagattctcgaagtcgattttataatatttaaccttggtttttgcattgtttcgtttaaaaaaaccact gatatgtgaaaaacgattagatactaataaaactactataaaccataccatacctcaccgctccgtgacatggctcatagattacgatactc aaatccaaaaataaatttacgagggcaattaatgtgaaacaaaaacaatcctaagataccacatgatgacctctccggcaccacaccttag ccccaccactccatcacctctttggcggtgttcttcgaaacccacttaggaaagcagtgtgtatctcatttggtatgctcttttcgattttatagct -continued catgtcgcaatttcaatgcataaacaatccaaatcgcattatatagtgcatggaggcaaatgacggggaggaatcttagatgagatcagga gctttcagggtaaacgcccggttcattttgtaccacatttcatcattttcctgtcgtccttggtatcctcaacttgtcccggttttgttttcggtacac tcttccgtgatgccacctgctccgtctcaattatcgtttagaaatgtgaactgtccagatgggtgactcatattgctgctgctacaatccactttct tactcatcggcatgcttacgagcccatcataaactattatccgcgaaatttgcaataaaccggccaaaaactactccaaattgaacgcaata tatacaatccataagaatatcactcaatgatatgatacttcgcagcactactatcgtgtgctaacatcttatttttataatatttccgctaaaattc cgatattgagtattaatttatcgtaaaattatcataatagcaccgaaaactacaaaaaatggtaaagtcattaaatcggctcgacattatcgtatt aaggaatcacaaaattctgagaatgcgtactgcgcaacatatttgacgcgcaaaatatctcgtagcgaaaactacagtaattctttaaatgact actgtagcgcttgtgtcgatttacgggctcaatttttgaaaataatttttttttcgaattttgacaacccgtaaatcgtcacaagcgctacggtagt catttaaaggattactgtagttctagctacgagatattagcgcgccaaatatgatgcgtaatacgcattctctgaattagtgatccgtaataattt cacaagattttggcattcctctttaaaggcgcacggatttattccaatgggtctcggcacgcaaaaagtttgatagacttttaaattctccttgca tattaattcaattactaaaattacgtgaattatctgaaaaattataaaatcagattctaatattaccaggctgacaaacagaaacaaaaacaca acaaacatataaaaatcagattcaaattaaaaataacgatactcattgaaaattgtgattatgatgcgaaaataaaagagaactgattcaaaa caaattaacaaaaaaaaaccccaaaattcgccagaaatcaagataaaaaattcaagagggtcaaaattaccgatatactgactacaccatt tatcgtagacagtgcagagaggagtattgacgaaaactaggaaaaaaatcgataaaaattactcaaatcgagctgaattagaggacaat gtttaaaaaaaaacactatttttccaataatttcactcattttcagactaaatcgaaaatcaaatcgtactctgactacgggtcagtagagaggtc aaccatcagccgaag mev-1

SEQ ID NO: 159 aaattcgaggaattttagatttcatcttgaaatttgcaatggaaaaaataattattcaaagaaaatcacagaaaatgcaacaaaaaaaacaaaa aaagaacaaaaaacaagtcgaaaagtgcgcccgggtcgtttgctgacgcatctcttcaaacgagacgcgctgctggcgcacttctcgtgc cctgtgcgtgcatttccgcaacaaaattcaacacttgttttgaaacgcaccgccctgtttctttttttcaattttgataagaaaatcagcattgtttca gg ced-13

SEQ ID NO: 160 tagaaacatgtttcccgtaagtgacctatccagtgaaacaaaaacatgtttctgtccgccttccttccatcggtggaggtgcatgctagattgc ctcctaaactctaatacctaaaattttaataatttattgacaacatacagtttcaccgataaccgacactcttatttttttctgatcctgactattctgtt cattatttcagctcctatcatagaacgatctttccagatcttggacaagtcacagttacaggtaattttttcaacaggtgtttgtataatgtcttagtt tctgtaaaattgttttatcatgtaaaatatttcagattattcgagggcagaaaaacgtgatattactattggagaggaattgacaaagttgtgtgat aaatttaattttgag bmk-1

SEQ ID NO: 161 cgagtttcttgtgagaaccaaaaactattcctctgcaagaaaaaatttattaatccggcataaaatacttttttattacaataggaacttcacagtc gcttcctccgacgctttgagcggtacatcgatgcttatcaccatgctgattgttacctttcttacccgtttgactttctgcaatttttaactgcaaag atgtttaatgcagatactcgaaagaaacgaaaaaatgataaaaaagtgaaaaaccccaaaaataaatttgaaaactccgcgtaagcttgctc gatcgctgcgagaccattgcataccgtactacttctttaaaggcgcacacatcaaatctagctgtttcgtgacaggacccagcaatgttcagc cgcgaagttttgaatcgccattttttttttaatttctagaatgtttatagttttgctttcgatgagatttttaagcattatgaggaacaaattttttttaaaaa ctttagaagttttaaaatttaattttgcgattatgctttgctttcgcgtgtcctttccgttgttcctcgctccaaatatatcacagtaattaaccactact tatgtagttatcacgtttctaaaaatataaattcatttttatttctctattgattcggtttgttgctcttcttgtctcaatcttgtgctactgccgaataccc tgctaatttttcgttttcagtcattcgattcacttgggttgttgtttaaaatggtaagatttttgcaggttactttctttcccatgaggtaaatgcatttat tgcgggtgcgctctatcgcacgacgccgcgaatcattgtatttcaaattgattttcctgttgcacttttattagttacaatttttattagttatttttagt tggattcgaca -continued rad-51

SEQ ID NO: 162

```
gaaaacctaaaatgaacaaaatttttttgtcattaaataacaacgcttcggttaacgcttgaaattgatattcggaaaataaaaagcctgatttttgt

tcgatttctgaaatatatttcatgctttacccgtttttaattgcgaacaattctaaatttgaaatataattttcaatcaacgaaaaacaattttcaagat

aaaaaattattatataaatttaagctaagtattaataaattaataagtaatagtattcaaaaatcatagaatcttgcaagaaaaaatgttttaaagat

ttaatagttcgagtgattgaaaaacgaatagtactttaaaaaataatgctttaaggcagaaaagtgatataaaaattaagctcaaaagggcaaa

agataaggttaatgtccagttttggttttaaaatggttcggacacaatgtacatagtagacatttgggtgtcctcttccttctcttttccccattgcg

tccactgaccctccttgctgtatgtctgcgcatcgtctttttctacacttttttcctttttccctggcccgttcctatcggtgcctttcacacacgcgag

cggcagtggacgagacgggagggcgaggtgttgaacaagagtacagcaagtgcgcgccatcgaaaaagcggaaaaaaaaatttcaaa

tggcgctactttgaaaattgagaattctgtatttactgccagttttacttgcatttaaatttccatgttttctattctaaaacgaaaatctatctaagaa

aacccttaataaaaacctataaatcataaattgtgattcttaaattcgaaaatatgttcgttcaacttgacgcctagaaatatgtggacttaatcct

gttataaatcagtagttgacgacaaaaatagtagagcagcaaaagcagttctaacttgtgaaaaacatgaaagttcttgttttcgtcaagcgaa

cgggggctcgaggaaggacttggcacgtgtctctaggccatgtttttctcaatttttgttgctctagagaaagcttttgctattgattatgggaca

atcttggggatatgaaggtaacattttaaaaataagtttaggtaaatgtgtagcataatttttgaaaaaaaaagctccactgttaaaaatgccgat

tttagggattgcgaaacgttcactatgtacacataaatggctatataatttgaatttgcattcaataaatcttttccttccaattgtatgttttaactta

aaaataattaattaaaattatctcaggagtcaaaa
```

The invention is a nucleic acid comprising a nucleic acid having a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a isolated nucleic acid comprising a nucleic acid having a sequence 95%, 96%, 97%, 98%, or 99% or more identical to the sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a nucleic acid comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a nucleic acid comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a nucleic acid having a sequence at least 95%, 96%, 97%, 98%, or 99% identical to a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter is and operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a construct comprising a nucleic acid having a sequence at least 95%, 96%, 97%, 98%, or 99% or more identical to a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a construct comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism comprising transgene which is a nucleic acid having a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism comprising transgene which is a nucleic acid having a sequence at least 95%, 96%, 97%, 98%, or 99% identical to a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism having a transgene which is a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism having a transgene which is a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

Inducible promoters for use in the nucleic acids, transgenes, constructs and transgenic organisms of the invention are typically chosen from those present in the host organism and are involved in promoting expression of its cognate gene in response to stimuli or an agent. Examples of stimuli or agents include, but are not limited to, stimuli or agents that cause oxidative stress, stimuli or agents that are genotoxic, stimuli or agents that cause xenobiotic stress.

Exemplary inducible promoters, constructs comprising the inducible promoters, transgenes comprising the inducible promoters, and transgenic organisms comprising the inducible promoters of the invention are described in more detail below.

The invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress, mitochondrial oxidative stress, peroxisomal oxidative stress, endoplasmic reticulum oxidative stress, or nuclear oxidative stress (Zhong, M. et al. PLoS Genet 6, e1000848 (2010)). In a related aspect, the invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress induced by juglone or other quinones or phenazine; mitochondrial oxidative stress induced by paraquat, mitomycin C, antimycin A, or maesanin; peroxisomal oxidative stress induced by aminotriazole or antimycin A; endoplasmic reticulum oxidative stress induced by tunicamycin, menadione or plumbagin; or nuclear oxidative stress induced by belomycin.

The invention is a nucleic acid from a gene involved in oxidative stress whose promoter is used in the transgenic organism, transgene, construct, or nucleic acid of the invention and is chosen from those involved in cytoplasmic oxidative stress that can involve pathways such as heat shock, phase I and phase II xenobiotic response, or proteasome. In one aspect, the gene is hsp-16.41, hsp-16.2, hsp-16.1, hsp-16.11, hsp-16.48, hsp-16.49, sod-1, gcs-1, hpo-15, dhs-18, gst-14, gst-32, W06H8.2, cyp-34A9, or ugt-41, where the promoter for the gene is fused, or operably linked, to a reporter gene.

The invention is a nucleic acid from a gene involved in oxidative stress response whose promoter is used in the transgenic organism, transgene, construct, or nucleic acid of the invention and is chosen from those involved in mitochondrial oxidative stress that can involve pathways such as heat shock or electron transport. In one aspect, the gene is hsp-6, hps-60, mtl-2, mtl-1, cdr-1, sod-3, eat-3, cyp-14A4, cyp-33C8, glrx-10, F56D5.3, B0222.9, F17A9.4, C35B1.5, or gst-4, where the promoter for the gene is fused, or operably linked, to a reporter gene.

The invention is a nucleic acid from a gene involved in oxidative stress whose promoter is used in the transgenic organism, transgene, construct, or isolated nucleic acid of the invention and is chosen from those involved in peroxisomal oxidative stress that can involve pathways such as heat shock or oxidative metabolism. In one aspect, the gene is hps-1, ctl-1, ctl-2, ctl-3, WO1B11.6, F10D7.3, prx-1, prx-5, duox-2, prdx-2, pxn-2, mlt-7, ZK550.6, C28H8.11, or C35B1.5, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in the specification of apoptosis as in endoplasmic reticulum oxidative stress that can involve pathways such as heat shock, ERAD, or disulfide exchange. In one aspect, the gene is hsp-4, dnj-27, dnj-7, Y41C4A.11, arf-1.1, lips-11, srp-7, gale-1, ckb-2, fipr-24, arl-7, F07A11.2, C04F12.1, hke-4.1, or F22E5.6, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in nuclear oxidative stress that can involve pathways such as heat shock or oxidative base damage. In one aspect, the gene is ugt-1, hsp-17, cdr-5, dnj-15, dnj-25, pme-1, pme-2, pme-5, air-2, mlh-1, mlh-2, polq-1, him-6, xpa-1, nth-1, or cep-1, where the promoter for the gene is fused, or operably linked, to a reporter gene.

A promoter region for an oxidative stress response gene (hsp-16.41) has the following DNA sequence (SEQ ID NO:1) and activates transcription of its cognate gene (or a reporter gene fused or operably linked thereto) in response to or by e.g., heat shock. In one embodiment, the invention is an isolated promoter reporter construct nucleic acid comprising SEQ ID NO:1 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-16.2) has the following DNA sequence (SEQ ID NO:2) and activates transcription of its cognate gene (or a reporter gene fused, or operably linked thereto) in response to or by e.g., heat shock. In one embodiment, the invention is an isolated promoter reporter construct nucleic acid comprising SEQ ID NO:2 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (mtl-2) has the following DNA sequence (SEQ ID NO:27) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:27 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (ugt-1) has the following DNA sequence (SEQ ID NO:83) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:83 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP A promoter region for an oxidative stress response gene (hsp-60) has the following DNA sequence (SEQ ID NO:26) and activates transcription of its cognate gene (or a reporter gene fused, or operably linked, thereto) in response to mitochondrial stress by e.g., paraquat. In one embodiment, the invention is an isolated promoter reporter construct nucleic acid comprising SEQ ID NO:26 operably linked, or fused, to a reporter gene. Preferably the reporter gene is one that encodes a fluorescent protein or a luminescent protein. Preferably, the reporter gene is encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-6) has the following DNA sequence (SEQ ID NO:25) and activates transcription of its cognate gene (or a reporter gene fused, or operably linked, thereto) in response to mitochondrial stress by e.g., paraquat exposure. In one embodiment, the invention is an isolated promoter reporter construct nucleic acid comprising SEQ ID NO:25 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-4) has the following DNA sequence (SEQ ID NO:55) and activates transcription of its cognate gene (or a reporter gene fused, or operably linked, thereto) in response to endoplasmic reticulum stress by e.g., exposure to tunicamycin. In one embodiment, the invention is an isolated promoter reporter construct nucleic acid comprising SEQ ID NO:55 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

In another aspect, the invention is an isolated nucleic acid or fragment thereof having 50, 100, 200, 300, 400, or 500 or more nucleotides, which is a promoter for a gene induced by heat shock, heavy metal ion toxicity, mitochondrial oxidative stress, or endoplasmic reticulum oxidative stress which is fused, or operably linked, to a reporter gene. In a specific aspect, the heavy metal ion stress is induced by cadmium or arsenic. In another specific aspect, the mitochondrial stress is induced by paraquat. In yet another specific the endoplasmic reticulum stress is induced by tunicamycin.

In another aspect, the invention is an isolated nucleic acid or fragment thereof having 50, 100, 200, 300, 400, or 500 or more nucleotides, which is a promoter for a gene chosen from hsp-16.41, hsp-16.2, mtl-2, ugt-1, hsp-60, hsp-6, and hsp-4 which is fused, or operably linked, to a reporter gene.

Apoptosis pathway genes: Apoptosis activation is important for understanding toxicology and in the creation of drugs to battle cancer. A compound that activates apoptosis leads to cell death is advantageous for combating cancer. However, activation of cell death would be a detrimental property for apoptosis occurs by either the intrinsic (DNA damage and unfolded protein response) or extrinsic (Ras/MAPK signaling) pathways. Cell death is initiated by activation of the caspase pathway. Caspases activate pathways leading cell corpse engulfment and DNA fragmentation. Thus, the invention relates to transgenic organisms and in particular, nematode strains for monitoring apoptotic gene activation. An apoptotic gene's promoter is used to drive expression of a reporter gene. In one specific aspect the reporter gene is one that expresses a fluorescent protein. Preferred fluorescent proteins are a protein comprising RFP or GFP.

Examples of genes involved in apoptosis whose promoter regions can be used in the transgenic animals, transgenes, constructs, or nucleic acids of the invention are chosen from those involved in the specification of apoptosis as in cep-1, lin-35, jnk-1, prnk-1, mpk-1, ces-2, ces-1, atl-1, atm-1, brc-1, dnj-11, chk-1, cki-1, rad-52, cki-2, dpl-1, ceh-20, efl-1, hlh-2, or daf-16; those involved in the execution of apoptosis as in cps-6, crn-1, crn-2, crn-3, crn-4, crn-5, crn-6, cyn-13, nuc-1, bec-1, ced-1, ced-10, ced-12, ced-2, ced-5, ced-6, ced-7fnta-1, gdi-1, or ggtb-1; or those involved in the core of apoptosis as in drp-1, egl-1, ced-9, ced-4, or ced-3 wherein said promoter is operably linked, or fused, to a reporter gene.

In another aspect, the invention is a nucleic acid or fragment thereof having 50, 100, 200, 300, 400, or 500 or more nucleotides, which is a promoter for a gene induced in apoptosis which is fused, or operably linked, to a reporter gene. In a specific aspect, the gene induced in apoptosis is in the extrinsic pathway. In a specific aspect, the gene induced in apoptosis is in the intrinsic pathway. In another specific aspect, the gene induced in intrinsic apoptosis pathway is a DNA damage gene or unfolded protein response gene). In yet another specific the gene induced in extrinsic apoptosis pathway is a RAS/MAPK pathway gene.

In another aspect, the invention is an isolated nucleic acid or fragment thereof having 50, 100, 200, 300, 400, or 500 or more nucleotides, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, cm-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

In another aspect, the invention is an isolated nucleic acid or fragment thereof having 50, 100, 200, 300, 400, or 500 or more nucleotides, or a nucleotide 95%, 96%, 97%, 98%, or 99% identical thereto, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, cm-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

Genotoxin or Carcinogen Pathway Genes

Genotoxins are compounds that cause DNA damage. Carcinogens are compounds that cause genotoxicity or other procancerous activity such as, stopping cell cycle arrest, stopping cell-cell inhibition signalling, stopping apoptosis induction, etc. The arrays or panels of the invention can include 1 or more representative transgenic organisms, or populations thereof, having a promoter from a genotoxin or carcinogen response pathway gene operably linked, or fused, to a reporter protein.

From the Gene Ontology database, there are 162 genes involved in the *C. elegans* response to DNA damage stimulus (GO:0006974)(Ashburner et al. Nat. Genet 25, 25-29 (2000)) This group was compared to a meta-study cataloging the genes highly expressed after carcinogen exposure (Waters et al. Mutat Res (2010)). 24 genes were identified pathway-specific genes (carcinogen and/or genotoxin responsive genes). In particular, the genes identified corresponded to enyzmes base excision repair, nucleotide excision repair, mismatch repair, recombination controlled repair. Additional genes for inclusion in panels related to carcinogenicity include, but are not limited to, those involved in cell cycle control and apoptosis. To reveal which sections of the promoter contain transcriptional control sequences, data from two sources, 1) the Model Organism ENCyclopedia Of DNA Elements (modENCODE) project, and 2) related species alignments are compared and optimal sequence regions are selected. Once identified, the promoters for these carcinogen and genotoxicity pathway genes can be used to generate the promoter reporter transgenes, contructs, isolated nucleic acids, or transgenic organisms of the invention using genetic engineering technology, such as those described herein.

In one aspect, the invention is an isolated nucleic acid or fragment thereof having 50, 100, 200, 300, 400, or 500 or more nucleotides of a promoter for a carcinogen pathway or genotoxin pathway gene which is fused, or operably linked to a reporter gene. A carcinogen pathway gene is a gene whose expression is altered (e.g., induced) in a cell, tissue or an organism upon exposure to a carcinogen or genotoxin. In another aspect, the invention is an isolated nucleic acid or fragment thereof which is a promoter for a gene induced in base excision repair, nucleotide excision repair, mismatch repair, recombination controlled repair, cell cycle control or apoptosis which is fused, or operably linked, to a reporter gene. In a specific aspect, the promoter for a gene induced in base excision repair is promoter for exo-3, nth-1, pme-1, or ung-1. In a specific aspect, the promoter for a gene induced in nucleotide excision repair is the promoter of xpa-1, mrt-2, ercc-1, or rad-23. In a specific aspect, the promoter for a gene induced in mismatch repair is the promoter for mlh-1, msh-4, msh-5, or msh-6. In a specific aspect, the promoter for a gene induced in recombination controlled repair is the promoter of brc-1, brc-2, rad-50, or cku-70. In a specific aspect, the promoter for a gene induced in cell-cycle control is the promoter for lin-35, mei-1, cki-1, or cki-2. In a specific aspect, the promoter for a gene induced in apoptosis is the promoter for cep-1, ced-3, ced-9, or ced-13.

In another aspect, the invention is an isolated nucleic acid or fragment thereof having 50, 100, 200, 300, 400, or 500 or more nucleotides, which is a promoter for a gene encoding a protein in a DNA damage response pathway that is induced by irradiation with UV or X-ray exposure which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in a DNA damage response pathway that is induced N-ethyl-N-nitrosurea which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in spindle formation that is induced by taxane which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein involved in regulating cell division or checkpoint control which is fused, or operably linked, to a reporter gene.

Endocrine Pathway and/or Xenobiotic Metabolism Genes

In one embodiment, the transgene, transgenic organism, or promoter reporter construct of the invention has a promoter or fragment thereof having 50, 100, 200, 300, 400, or 500 or more nucleotides, derived or obtained from a CYP P450 gene, ABC transporter gene, SDR/Redox gene, GST gene, or a Sol. Transporter gene, which is fused, or operably linked, to a reporter gene.

Examples of CYP P450 genes include, but are not limited to, the following *C. elegans* genes: cyp-13A1, cyp-13A2, cyp-13A3, cyp-13A4, cyp-13A5, cyp-13A6, cyp-13A7, cyp-13A8, cyp-13A10, cyp-13A11, cyp-13A12, cyp-13B2, cyp-14A1, cyp-14A2, cyp-14A3, cyp-14A4, cyp-14A5, cyp-23A1, cyp-25A1, cyp-25A2, cyp-25A3, cyp-25A4, cyp-25A5, cyp-25A6, cyp-29A2, cyp-29A3, cyp-29A4, cyp-31A2, cyp-31A3, cyp-32A1, cyp-32B1, cyp-33A1, cyp-33B1, cyp-33C1, cyp-33C2, cyp-33C3, cyp-33C4, cyp-33C5, cyp-33C6, cyp-33C7, cyp-33C8, cyp-33C9, cyp-33C11, cyp-33C12, cyp-33D1, cyp-33D3, cyp-33E1, cyp-33E2, cyp-33E3, cyp-34A1, cyp-34A2, cyp-34A3, cyp-34A4, cyp-34A5, cyp-34A6, cyp-34A7, cyp-34A8, cyp-34A10, cyp-35A1, cyp-35A2, cyp-35A3, cyp-35A4, cyp-35A5, cyp-35B1, cyp-35B2, cyp-35B3, cyp-35C1, cyp-35D1, cyp-36A1, cyp-37A1, cyp-37B1, cyp-42A1, cyp-43A1, cyp-44A1, dpr-1, coq-6, fmo-1, fmo-2, fmo-3, fmo-4, fmo-5, pah-1, tbh-1, C01H6.4, C46H11.2, F30B5.4, R07B7.4, R07B7.5, T19B4.1, Y47D3A.22, and Y71G12B.4.

Examples of ABC transporter genes include, but are not limited to, the following *C. elegans* genes: abce-1, abcf-1, abcf-2, abcf-3, abch-1, pgp-1, pgp-2, pgp-3, pgp-4, pgp-5, pgp-7, pgp-8, pgp-9, abt-1, abt-2, abt-3, abt-4, abt-5, abt-6, abtm-1, cft-1, haf-1, haf-2, haf-3, haf-4, haf-6, haf-7, haf-8, hmt-1, mrp-2, mrp-3, mrp-4, mrp-6, mrp-7, mrp-8, pgp-10, pgp-11, pgp-12, pgp-13, pgp-14, pmp-1, pmp-2, pmp-3, pmp-4, wht-1, wht-2, wht-3, wht-4, wht-5, wht-6, wht-8, and wht-9.

Examples of SDR/Redox genes include, but are not limited to, the following *C. elegans* genes: dhs-1, dhs-2, dhs-3, dhs-4, dhs-6, dhs-7, dhs-8, dhs-9, dhs-11, dhs-12, dhs-13, dhs-14, dhs-15, dhs-16, dhs-17, dhs-17, dhs-18, dhs-19, dhs-20, dhs-22, dhs-23, dhs-24, dhs-25, dhs-26, dhs-28, dhs-29, dhs-30, dhs-31, ard-1, fasn-1, maoc-1, qdpr-1, sdz-8, C01G12.5, C06E4.3, C06E4.4, C06E4.6, C27D8.4, C30G12.2, C33E10.10, C41A3.1, C55A6.3, C55A6.4, C55A6.6, C55A6.7, D1054.8, DC2.5, E04F6.15, F02C12.2, F12E12.11, F20G2.1, F20G2.2, F25D1.5, F26D2.15, F28H7.2, F32A5.8, F54F3.4, F55E10.6, F59E11.2, H04M03.3, K10H10.6, RO5D8.7, RO5D8.9, R119.3, T01G6.1, T01G6.10, T25G12.2, W03F9.9, Y47G6A.21, Y47G6A.22, ZK697.14, ZK829.1, Y47G6A.21, Y47G6A.22, ZK697.14, ZK829.1, hsd-1, hsd-2, hsd-3, and C32D5.12.

Examples of GST genes include, but are not limited to, the following *C. elegans* genes: gst-1, gst-2, gst-3, gst-4, gst-5, gst-6, gst-8, gst-9, gst-10, gst-12, gst-13, gst-14, gst-15, gst-16, gst-18, gst-19, gst-20, gst-21, gst-23, gst-24, gst-25, gst-26, gst-27, gst-28, gst-29, gst-30, gst-31, gst-33, gst-34, gst-35, gst-37, gst-38, gst-39, gst-40, gst-41, gst-43, K10F12.4, K10F12.4, R11A8.5, W1008.4, Y45G12C.3, Y53G8B.1, Y53G8B.1, F55A11.6, F55A11.6, F56A4.4, gstk-1, and gstk-2.

Examples of Sol. Transporter genes include, but are not limited to, the following *C. elegans* genes: vit-1, vit-2, vit-3, vit-4, vit-5, vit-6, egg-1, egg-2, irp-1, irp-2, lbp-1, lbp-2, lbp-3, lbp-4, lbp-5, lbp-6, lbp-7, lbp-8, lbp-9, nrf-5, cit-1.2, C06G1.1, C05C9.1, F10D11.6, T19C3.5, ZC513.1, ZC513.2, C31H1.1, T10B5.10, D1007.16, C55C3.1, F14D12.1b, F46H5.2a, and ZK616.8.

Specific Panels of Representative Transgenic Organisms or Populations of Representative Organisms In one embodiment, the invention is a panel or array of transgenic organisms as described herein. The panel or array in one aspect is provided in a multiwell plate wherein at least 2 or more (or 3 or more, 4 or more, etc. as described in more detail below) has a transgenic organism or population of transgenic representative organisms representative of one-type of response gene e.g., having a distinct transgene that is distinguishable by the identity of the gene from which the promoter of the transgene was obtained or derived.

Panels or arrays of the invention include 2 or more representative transgenic organisms or populations of representative transgenic organisms. Panels or arrays can include 3 or representative transgenic organisms or populations of representative transgenic organisms. Panels or arrays can include 4 or more representative transgenic organisms or populations of representative transgenic organisms. Panels or arrays can include 5 or more representative transgenic organisms or populations of representative transgenic organisms. Panels or arrays can include 6 or more representative transgenic organisms or populations of representative transgenic organisms. Preferably, the panel or array has a control organism or control population of organisms.

Panels or arrays can include from 2 to 384 representative transgenic organisms or populations of representative transgenic organisms. Panels or arrays can include from 2 to 96 representative transgenic organisms or populations of representative transgenic organisms. Panels or arrays can include from 2 to 48 representative transgenic organisms or populations of representative transgenic organisms. Panels or arrays can include from 2 to 24 representative transgenic organisms or populations of representative transgenic organisms. Panels or arrays can include from 2 to 12 representative transgenic organisms or populations of representative transgenic organisms. Panels or arrays can include from 2 to 6 representative transgenic organisms or populations of representative transgenic organisms. Preferably, the panel or array has a control organism or control population of organisms.

Panels or arrays can include from 3 to 384 representative transgenic organisms or populations of representative transgenic organisms. Panels or arrays can include from 3 to 96 representative transgenic organisms or populations of representative transgenic organisms. Panels or arrays can include from 3 to 48 representative transgenic organisms or populations of representative transgenic organisms. Panels or arrays can include from 3 to 24 representative transgenic organisms or populations of representative transgenic organisms. Panels or arrays can include from 3 to 12 representative transgenic organisms or populations of representative transgenic organisms. Panels or arrays can include from 3 to 6 representative transgenic organisms or populations of representative transgenic organisms. Preferably, the panel or array has a control organism or control population of organisms.

Panels or arrays can include from 4 to 384 representative transgenic organisms or populations of representative transgenic organisms. Panels or arrays can include from 4 to 96 representative transgenic organisms or populations of representative transgenic organisms. Panels or arrays can include from 4 to 48 representative transgenic organisms or populations of representative transgenic organisms. Panels or arrays can include from 4 to 24 representative transgenic organisms or populations of representative transgenic organisms. Panels or arrays can include from 4 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Panels or arrays can include from 5 to 384 representative transgenic organisms or populations of representative transgenic organisms. Panels or arrays can include from 5 to 96 representative transgenic organisms or populations of representative transgenic organisms. Panels or arrays can include from 5 to 48 representative transgenic organisms or populations of representative transgenic organisms. Panels or arrays can include from 5 to 24 representative transgenic organisms or populations of representative transgenic organisms. Panels or arrays can include from 5 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Selected Agents

A "selected agent" refers to a chemical, object, or external stimuli that is contacted with or exposed to the transgenic biosensor organism. The selected agent can be given or exposed to the transgenic organism. In one aspect, the selected agent is dosed in a range at concentrations below a lethal dose and at or above levels where a therapeutic effect is expected to be observed. Such ranges can be determined in dose finding studies. Acute assays can be conducted using the compositions and methods of the invention and can range from about 2 hours to about 24 hours, more preferably from about 2 hours to about 18 hours and more preferably from about 2 hours to about 10 hours.

Typically, chemicals are given to the animal or organism in the range of 1 picomolar to 10 millimolar. In other aspects, the organism are exposed to an agent like a physical object e.g., in their growth medium, lining the vesicle or microwell plate or as a gas.

In one aspect, the selected agent is a chemical. In one aspect, the selected agent is a drug candidate or an agent which is a component of a formulation for a drug product. In one aspect, the selected agent is water. In one aspect, the water is a drinking water. In one aspect, the water is wastewater. In one aspect, the selected agent is a food product or liquid or an additive of either. In a specific aspect, the food product, liquid, or additive of either is intended for human or animal consumption.

Methods for Creating Transgenic Organisms

The transgenic organisms of the invention and for use in the methods of the invention can be produced by any technique. Preferably, the transgenic organisms of the invention have single copy inserts of the desired transgene at defined genomic loci and are stable. The transgenic organisms of the invention have a response element (e.g., promoter) reporter gene construct stably inserted into the host organism's genome.

In one specific aspect, the transgene is an inducible promoter reporter gene construct. The optimal promoter and gene-intron sequences of target genes are identified from publicly or privately available databases. For example, one such public database is found at www.wormbase.org. Gateway-compatible PCR primer sets are created for both the promoter and gene intron regions. PCR reactions are gel purified and cloned into a targeting vector (e.g., a MosSCI targeting vector) containing the desired reporter gene (e.g., tag-RFP, RFP, his-RFP, mCherry, or his-mCherry). Desired construction is verified by PCR and/or restriction enzyme digestion.

MosSCI integration (Frokjaer-Jensen, C. et al., 2008 Nat Genet, 40(11), 1375-83). Plasmid DNA mixtures are injected into MosSCI targeting strains. These strains have a Mos1 element at a specific genomic site on chromosome II and contain the unc-119(ed3) mutation, which is used for positive selection of the transgene. The injection mixes for MosSCI transgenesis contain three types of vectors: 1) the gateway reporter construct containing the unc 119(+) positive selection marker gene and sequences for homologous recombination into the *C. elegans* chromosome, 2) a transposase-producing plasmid, and 3) three plasmids acting as markers for tracking the presence of extrachromosomal arrays. Three injected animals are placed on each plate and transferred to 25° C. for 8 days.

After the 8 days at 25° C., the worms are screened for MosSCI events. Candidate insertion strains are homozygosed by clonally picking 8 Unc-119(+) animals that do not carry mCherry (RFP) arrays to individual plates. MosSCI typically produces one integrated transgene from ten injected animals. Thus, the 25 injections/construct are expected to yield 3-4 independent lines.

Desired insertions are verified by PCR with one primer annealing within the insertion and a second primer in reverse annealing outside the insertion. Outcrossing (2×) of the candidate lines confirms their chromosomal integration by observation of Mendelian segregation of the integration locus.

Validation of reporter construction. Candidate lines are imaged by confocal microscopy to record basal expression profiles. Animals are anesthetized on agarose pads on glass slides with glass coverslips. Laser confocal imaging is performed on a Pascal LMS system. Each worm is imaged with a fixed set of laser intensity settings and the level of RFP expression is quantified with NIH ImageJ.

Kits

The invention relates to a kit having one or more biosensor nematodes and materials for use thereof.

Thus, the kit of the invention has:

One or more transgenic biosensor nematode cultures and reagents necessary to reconstitute healthy populations;

Incubation buffer for delivering agent;

A control nematode culture that is similar to the transgenic biosensor nematode culture but does not have the inducible promoter reporter transgene; and A vesicle or reaction plate for containing and cultureing one or more transgenic biosensor nematode cultures and the control nematode culture.

The reagents necessary to reconstitute healthy populations include a medium. In one aspect, the medium is M9, S-media, or CeMM.

The incubation buffer allows for delivery of the selected agent to the transgenic biosensor nematode culture substantially affecting the nematodes in a negative manner (the incubation buffer minus selected agent desirably does not kill the nematodes). In one aspect, the incubation buffer contains DMSO. In a more specific aspect, the incubation buffer has about 2% DMSO. In another aspect, the incubation buffer has acetone. In a specific aspect, the incubation buffer has about 5% acetone. In another aspect, the incubation buffer has methanol. In a more specific aspect, the incubation buffer has 2% methanol. In some aspect, the incubation buffer comprises 2 components which are a solvent for the selected agent and a buffer. The solvent for the selected agent in is chosen from a solvent comprising DMSO, DMFO, acetone, or methanol. In one aspect, the buffer contains detergent. One detergent for use in the incubation buffer is 0.01% triton x-100. The incubation buffers for use in the kits have capacity to increase uptake of the selected agent compounds.

The vesicle or reaction plate for containing one or more biosensor nematode cultures is of sufficient height, size and depth to contain each transgenic biosenor nematode population separate while allowing for the additional of appropriate reagents for growth and exposure to selected agent. Additionally, the vesicle or plate desirably does not interfere with reporter assay.

Typically, the vesicle or each well in a plate has a number of organisms sufficient to yield an adequate signal of the reporter gene. In one aspect, each vesicle or well has 10 or more organisms. In another aspect each vesicle or well has 50 or more organisms. In another aspect, each vesicle or well has 100 or more organisms. In another aspect, each vesicle or well has from 10 to 1000 organisms. In another aspect, each vesicle or well has from 50 to 1000 organisms. In another aspect, each vesicle or well has from 100 to 1000 organisms. In another aspect, each vesicle or well has from 300 to 1000 organisms. In another aspect, each vesicle or well has from 300 to 800 organisms.

Generally, the nomenclature and the laboratory procedures utilized in the invention include molecular, biochemical, microbiological and recombinant DNA techniques. These techniques are explained in the literature. See, for example, Molecular Cloning: A laboratory Manual Sambrook et al., (1989); Current Protocols in Molecular Biology Volumes I-III Ausubel, R. M., ed. (1994); Ausubel et al., Current Protocols in Molecular Biology, John Wiley and Sons, Baltimore, Md. (1989); Perbal, A Practical Guide to Molecular Cloning, John Wiley & Sons, New York (1988); Watson et al., Recombinant DNA, Scientific American Books, New York; Birren et al. (eds) Genome Analysis: A Laboratory Manual Series, Vols. 1-4, Cold Spring Harbor Laboratory Press, New York (1998); Cell Biology: A Laboratory Handbook, Volumes I-III Cellis, J. E., ed. (1994); Oligonucleotide Synthesis Gait, M. J., ed. (1984); Nucleic Acid Hybridization Hames, B. D., and Higgins S. J., eds. (1985); Transcription and Translation Hames, B. D., and Higgins S. J., Eds. (1984); Animal Cell Culture Freshney, R. I., ed. (1986); Immobilized Cells and Enzymes IRL Press, (1986); A Practical Guide to Molecular Cloning Perbal, B., (1984) and "Methods in Enzymology Vol. 1-317, Academic Press; "PCR Protocols: A Guide To Methods And Applications", Academic Press, San Diego, Calif. (1990); Marshak et al., Strategies for Protein Purification and Characterization—A Laboratory Course Manual" CSHL Press (1996); all of which are incorporated by reference as if fully set forth herein.

Reagents useful in applying such techniques, such as restriction enzymes, coding sequences, fluorescent proteins and the like, are widely known in the art and commercially available from such vendors as New England BioLabs, Boehringer Mannheim, Amersham, Promega Biotec, U.S. Biochemicals, New England Nuclear, Life Technologies, Roche and a number of other sources.

References are provided throughout this document. The procedures therein are believed to be well known in the art. All the information contained in these references is incorporated herein by reference.

EXAMPLES

The examples below describe the construction and use of representative compositions for detecting and screening for response to exposure of whole organisms to selected agents e.g., a chemical or toxin. In these examples, the use of panels of transgenic nematodes as biosensors of toxicity pathway activation is described. The panels are composed of promoters of toxin-responsive genes fused to genes encoding reporter proteins. The promoter-reporter fusion construct is inserted into the nematode genome as a single copy gene insertion (e.g., using single copy or site specific insertion transgenesis techniques) at a defined genomic locus. The result is a set of transgenic nematodes strains or lines where each type of transgenic animal functions as a biosensor for a specific toxin (e.g., a representative transgenic organism). Toxins can be typed e.g., for their class of toxicity by observing which subset of strains show reporter activation.

The unique use of single copy insertion allows direct comparison between strains, where intensity of toxin response is de novo normalized between strains. This allows easier determination of the primary mode of toxicity (or other gene expression effects) when analyzing novel compounds. The transgenic strains or lines can be configured into panel sets (or arrays). It is contemplated that the arrays can be configured to be specific to various types of responses (e.g., toxicity), such as heavy metal, oxidative stress, endocrine disruption, xenobiotic, carcinogenic, genotoxic, neurotoxic, hepatatoxic, nephratoxic, immunotoxic, and others.

Example 1: Studies in *C. elegans* Having a Hsp-16 Promoter-Red Fluorescent Protein Transgene The results described herein demonstrate remarkable responses of the whole organism biosensor to toxic insults (such as: heat shock, cadmium, arsenic, etc). For instance, a protein homeostasis reporter was created by fusing heat shock protein to a nuclear localized red fluorescent protein (hsp-16.42::hRFP)(the materials and methods for the construction of the transgenic organism are described in more detail in the examples below). Exposure to heat toxicity generates induction of nuclear localization. This heat shock gene reporter was screened for gene induction capacity using a heat-shock protocol. The hsp-16::hRFP construct is exposed to a 1 hr incubation at 30 C. Gene induction was screened 4 to 24 hrs after heat shock. Significant red fluorescence is observed in the nuclei of heat-shocked worm relative to control (FIG. 5).

Toxin sensitivity of hsp-16 was confirmed with exposure to heavy metals and metalloids. To develop a rapid screen for the hsp-16::hRFP expression, a fluorescent plate reader assay was developed. To test the sensitivity of this assay, a titrating concentration of nematodes were exposed to heat shock. The worms were transferred to a 96 well plate and red fluorescence was quantified. Good sensitivity for a red fluorescence signal occurs at concentrations of 50 or more worms (FIG. 3A). Next, the toxin dosage sensitivity was measured. The Phsp-16::hRFP reporter shows higher sensitivity to cadmium chloride relative to sodium bis-arsenite (FIG. 3B vs. FIG. 3C). The $EC_{50}$ for cadmium occurs near 0.2 mM while arsenic sensitivity is near 1.5 mM. Thus, the Phsp-16::hRFP reporter shows greater sensitivity to cadmium.

Example 2: Control Reporter

Advantageously, the transgenic animals described in these examples can have a control reporter (e.g., constitutively expressed). Exposure to some selected agents or toxins can lead to shortened life-span, lower brood sizes or other effects that need to be controlled. The problem becomes most pronounced in chronic assays. For instance, exposure to cadmium for 72 hrs leads to significant population effects (FIGS. 4A, B, and C). Thus, it was determined a control for population mass differences between assay wells is desirable. Introduction of a second constitutively expressed reporter gene can be used to control for various population differences.

To create a population control in the fluorescence reader assays, the hsp-16::hRFP was crossed into a line containing a constitutively-expressed neuronal marker (unc-47::GFP). Expression of the control reporter remains constant, while the inducible reporter responds to heat shock (FIGS. 5A and B). The use of a constitutive-expressed reporter allows normalization of induction reporter responses—a toxin's effect on population dynamics is controlled.

Example 3: COPAS Cytometry

The fluorescent expression patterns of individual nematodes was rapidly quantifiable using flow cytometry. The hsp-16::hRFP construct in unc-47::GFP background was sent subjected to COPAS biosorting analysis. Induction of the red fluorescence was observed (FIG. 6A) and COPAS biosorting generated size-dependent profiles for red and green fluorescence expression (FIG. 6B). As expected, the levels of fluorescence increase proportionally with nematode age.

Example 4: Gene Selection and Transgene Construct Construction

The genes chosen for an oxidative stress response panel were the following oxidative response genes (hsp-16.41, hsp16.2, hsp-6 and hsp-60, hsp-4, mlt-2, and ugt-1). To choose the oxidative-response gene promoters, a combination of modENCODE's TF-GFP ChIP-seq data and multi-z 6-species alignment was used to find the extent of conserved genomic regions containing TF sites in front of the oxidative-response gene's start codon. Promoter-reporter fusion constructs were designed for Gibson reaction cloning using APE plasmid editor (biologylabs.utah.edu/jorgensen/wayned/ape). In general, regions ranging from 300 to 4,000 bp upstream of start codon were chosen for promoter selection.

Example 5: Nematode Transgenesis

To make transgenic nematodes, the MosSCI transgenesis procedure was used. Briefly, using the custom transgenesis platform provided by Knudra Transgenics (www.knudra.com/product/custom-transgenics), promoters are positioned in front of a red fluorescent protein fused to histone H2B. The gene is cloned into a vector pNU142, which contains left and right homologous recombination arms of the Mos1 locus (2094 bp and 1825 bp, respectively). The pNU142 plasmid (Ampr) contains CBunc-119 gene obtained from the C. Briggsae genome for use as a positive-selection marker. The resulting construct is inserted as a single copy into the Mos1 ttTi5605 site in *C. elegans* strain COP66, which is homozygous for ttTi5605 and oxIsl2 (unc-47::GFP) alleles. Strains obtained with the MosSCI transgenesis procedure are verified by PCR for single copy insertion at Mos1 locus. Verification oligos for insertion at Mos1 site are forward SEQ ID NO:163 (GATTCCATGATGGTAGCAAACTC) and reverse SEQ ID NO:164 (CAGATGATGAGCCAAGAAGAGTT), which gives a 325 bp product specific to strains homozygous for insertion at Mos1 loci. The resulting nematode is a two-color worm acting as in vivo transcriptional reporter of gene activation. For the results herein, the 7 types of two-color worms used are hsp-4, hsp-6, hsp-60, hsp-16.2, hsp-16.41, mtl-2, and ugt-1.

Example 7: Nematode Preparation

Two-color worms are grown to high density (0.5 ml worm pellet/plate) using Perfect-GROW HB101 plates (www.knudra.com/product/perfect-grow). Worms are recovered from the plate and cleaned by sucrose sedimentation. Animals are distributed on 5 cm NGM plates (seeded with HB101, (www.knudra.com/product/perfect-seed) at densities of 200 adult animals per plate. For heat shock, plates are exposed to 34° C. for 1.5 hr, and then allowed to recover at for 4 hrs at room temperature. For cadmium exposure, fresh seeded NGM plates are pre-incubated for 24 hrs with 700 ul of 10 mM $CdCl_2$. Cleaned nematodes were added at 200 adult animals per plate and incubated for 15 hrs at room temperature.

Example 8: Plate Reader Assay

Each strain is transferred with 1 ml of M9 into a 2 ml deep 96 well plate. Plate is allowed to stand for 5 minutes to settle worms. Excess M9 is siphoned off and a repeat wash/siphon step is performed. Settled worms are transferred (about 200 ul) to a black 96-well-read plate (Corning, Inc. #3651). The plate is read in a fluorescence plate reader (Biotek, Inc., Synergy 4, with optical cubes for GFP detection at ex. 485/20, em. 528/20 and RFP detection at ex. 575/15, em. 620/15 with reading set as endpoint from bottom well at sensitivity of 50). Reads are normalized as RFP/GFP ratio, which adjust for population differences between wells. Fluorescence intensity readings of the reporters in the panel are calculated as ratio of induced RFP/GFP ratio divided by control RFP/GFP ratio.

In conclusion, the oxidative response panel demonstrates the inventive system is feasible for use in testing the effects of external stimuli on gene expression at the whole organism level. As shown herein, the exemplary toxicogenomics studies is remarkably sensitive and selective for detection of oxidative stress toxicity. Furthermore, a simple 7 gene panel can differentiate between different types of oxidative stress e.g., heat shock and metal exposure. The inventive system has advantages over cell culture methods because it is easier to use, less costly to implement, and is believed results more translatable to more complex animal studies like mammalian studies. Importantly, the inventive system is a whole organism approach, which detects cellular response in a native context. The ease of assay implementation makes the system ideal for high-throughput applications. With respect to a specific implementation, toxicogenomics is very valuable in drug discovery. With this invention, pharmaceutical companies will decrease their financial exposure because better toxicology capture at the front end of drug development translates to lower frequency of drugs failing in clinical trials due to unwanted side-effect toxicity.

Those skilled in the art will appreciate that the concepts, specific embodiments, and Examples disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A population of transgenic nematodes divided into two or more physically separated groups, wherein each transgenic nematode of the population comprises in its genome:

a) an inducible promoter region operably linked to a first inducible reporter gene encoding a first fluorescent protein, wherein the inducible promoter region is from a nematode response pathway gene expressed in response to an external stimulus; and, b) a constitutive promoter operably linked to a constitutively expressed reporter gene encoding a second fluorescent protein wherein the constitutively expressed reporter gene normalizes expression of the inducible reporter gene;

whereby the transgenic nematodes are configured as a whole organism biosensor for detecting alteration in gene expression as a response to exposure to an external stimulus and, wherein the first and second fluorescent protein fluoresce at detectably different wavelengths.

2. The population of transgenic nematodes of claim 1, wherein the response pathway gene is selected from a toxicity response pathway gene, an oxidative stress response pathway gene, a carcinogen response pathway gene, an apoptosis pathway gene, an endocrine response pathway gene, a genotoxin response pathway gene, or a xenobiotic metabolism response pathway gene.

3. The population of transgenic nematodes of claim 1, wherein the inducible promoter region operably linked to a first inducible reporter gene is inserted as a single copy into the nematode genome.

4. The population of transgenic nematodes of claim 1, wherein the inducible promoter is selected from SEQ ID NO. 1 to SEQ ID NO. 162, or the inducible promoter is selected from a promoter sequence having 95% or more identical homology to one of SEQ ID NO. 1 to SEQ ID NO. 162.

5. The population of transgenic nematodes of claim 1, wherein the external stimulus is selected from agents that cause oxidative stress, genotoxic stress or xenobiotic stress.

6. The population of transgenic nematodes of claim 1, wherein the external stimulus is a carcinogen, a drug or drug candidate, heat, UV, environmental toxins, chemical agent, or heavy metals.

7. The population of transgenic nematodes of claim 1, wherein the first inducible reporter gene and the constitutively expressed reporter gene are independently selected from green fluorescent protein, red fluorescent protein, cyan fluorescent protein, and spectral variant thereof.

8. The population of transgenic nematodes of claim 1, wherein the nematode is *C. elegans*.

9. A population of transgenic nematodes divided into two or more physically separated groups, wherein each transgenic nematode of the population comprises in its genome:

a) an inducible promoter region operably linked to a red fluorescent protein gene encoding a red fluorescent protein, wherein the inducible promoter region is from a nematode response pathway gene expressed in response to an external stimulus; and, b) a constitutive promoter operably linked to a green fluorescent protein gene encoding a green fluorescent protein wherein the constitutively expressed reporter gene normalizes expression of the inducible reporter gene;

whereby the transgenic nematodes are configured as a whole organism biosensor for detecting alteration in gene expression as a response to exposure to an external stimulus wherein the constitutive promoter normalizes effects of the external stimulus across the population of transgenic nematodes.

10. A method for identify agents that induce a response pathway in a nematode, comprising:

placing the population of transgenic nematodes divided into two or more physically separated groups of claim 1 in a medium comprising a selected agent;

incubating the population of transgenic nematodes with the selected agent for a time period from 2 hours to 24 hours; and, observing the inducible and constitutive reporter gene expression across the population of transgenic nematodes divided into two or more physically separated groups, whereby the agents are identified when the inducible reporter gene is expressed and the constitutive promoter expression normalizes expression of the inducible reporter gene.

11. The method of claim 10, wherein the selected agent is selected from agents that cause oxidative stress, genotoxic stress or xenobiotic stress.

12. The method of claim 10, wherein the selected agent is selected from a carcinogen, a drug or drug candidate, heat, UV, environmental toxins, chemical agent, or heavy metals.

13. The population of transgenic nematodes of claim 1, wherein the inducible promoter region operably linked to a first inducible reporter gene is inserted as more than one copy into the nematode genome.

14. The population of transgenic nematodes of claim 9, wherein the inducible promoter region operably linked to a first inducible reporter gene is inserted as a single copy into the nematode genome.

15. The population of transgenic nematodes of claim 9, wherein the inducible promoter region operably linked to a first inducible reporter gene is inserted as more than one copy into the nematode genome.

16. A method for selective detection of changes in gene expression at a whole organism level when exposed to an external stimulus, comprising:

placing one or more of the populations of transgenic nematodes divided into two or more physically separated groups of claim 1 in a medium;

exposing the populations of the transgenic nematodes to the external stimulus; and, observing the inducible and constitutive reporter gene expression across each of the populations of transgenic nematodes divided into two or more physically separated groups, whereby the changes in gene expression are identified when the inducible reporter gene is expressed and the constitutive promoter expression normalizes expression of the inducible reporter gene.

* * * * *